United States Patent [19]

Figler et al.

[11] Patent Number: 4,653,010

[45] Date of Patent: Mar. 24, 1987

[54] COMPOUNDING SYSTEM

[75] Inventors: Alan A. Figler, Algonquin; Aleandro DiGianfilippo, Crystal Lake, both of Ill.

[73] Assignee: Baxter Travenol Laboratories, Inc., Deerfield, Ill.

[21] Appl. No.: 665,268

[22] Filed: Oct. 26, 1984

[51] Int. Cl.[4] ........................ G06F 15/46; G01F 11/14

[52] U.S. Cl. ........................................ 364/502; 222/2; 222/134

[58] Field of Search ............... 364/502, 148, 152, 153, 364/478, 479; 222/2, 52, 132, 134, 136, 94; 141/1, 83

[56] References Cited

U.S. PATENT DOCUMENTS

| | | | |
|---|---|---|---|
| 3,227,316 | 1/1966 | Webster | 222/134 |
| 3,349,962 | 10/1967 | Levin | 222/2 |
| 3,625,398 | 12/1971 | Tometsko | 222/52 |
| 3,670,923 | 6/1972 | Hawes, Jr. et al. | 222/142 X |
| 3,806,001 | 4/1974 | Pratt | 222/132 |
| 3,904,079 | 9/1975 | Kross | 222/2 |
| 4,314,653 | 2/1982 | Sindoni | 222/41 |
| 4,333,356 | 6/1982 | Bartels et al. | 364/502 X |
| 4,473,884 | 9/1984 | Behl | 364/479 X |
| 4,527,245 | 7/1985 | Axelson, Jr. et al. | 364/479 X |
| 4,545,008 | 10/1985 | Sominin et al. | 364/155 X |

*Primary Examiner*—Parshotam S. Lall
*Assistant Examiner*—H. R. Herndon
*Attorney, Agent, or Firm*—Paul C. Flattery; Kay H. Pierce

[57] ABSTRACT

The present invention provides a fast, efficient and precise method and apparatus for compounding a large number of solutions for use in hyperalimentation therapy. The apparatus includes a host computer which maintains a data base of prescriptions to be compounded, and a high speed compounding apparatus connected to the host computer for compounding mixtures of base solutions in response to information supplied by the host computer from the prescription data base.

Information can be entered concerning patients or prescriptions through a video display tube into the host computer data base. The host computer also includes provisions for a library of prestored standard prescriptions which can be recalled and associated with a given patient. A group of prescriptions to be compounded is first sorted in accordance with the types of specified base solutions and optionally sorted again based on the concentration of base solutions. The prescription information is transmitted to the compounding apparatus in sorted order thereby minimizing the required number of containers of base solution.

97 Claims, 5 Drawing Figures

COMPOUNDING SYSTEM

BACKGROUND OF THE INVENTION

The present invention pertains to a process and apparatus for precisely and rapidly mixing base solutions. More particularly, it pertains to such a process and apparatus especially useful for the compounding of hyperalimentation solutions.

Hyperalimentation therapy is the intravenous feeding of, for example, a protein-carbohydrate mixture to a patient. It is used primarily to meet the patient's protein and caloric requirements which are unable to be satisfied by oral feeding. The protein may be in the form of free-amino acids or protein hydrolysate and the carbohydrate commonly is dextrose. In addition to the protein and carbohydrate, vitamins (water-soluble and fat-soluble) and electrolytes also can be supplied in this therapy.

Each of these parenteral ingredients and the combination thereof are particularly susceptible to the growth of deleterious organisms and it is desirable that they be administered to the patient in a sterile condition. Thus, because these protein and carbohydrate solutions cannot be pre-compounded by the manufacturer, but must be combined at the time of their use, their compounding must be performed under sterile conditions to avoid organism growth.

A known apparatus and process for compounding hyperalimentation solutions utilizes a solution transfer system including a receiving container and a Y-transfer set. The Y-transfer set includes two separate tubes, each having an end attached to a common juncture by which solutions delivered through the tubes will pass through the juncture into the receiving container. The other end of one tube of the set is attached to the protein holding container and of the other tube of the set to the carbohydrate holding container. The desired volume of each solution being transferred to the container is controlled by a clamp placed on each tube. The solutions may be allowed to flow into the receiving container by gravity flow. However, it has been found to be useful to transfer the solutions under the influence of a vacuum applied to the receiving container. When the receiving container is a flexible plastic container, the vacuum is created in a vacuum chamber into which the container is placed.

It has been known in the past that to ensure sterility during the compounding of hyperalimentation solutions, compounding should be performed under a laminar flow hood. Laminar flow hoods are used for reducing the risk of air-borne contamination of such solutions. These units operate by taking room air and passing it through a pre-filter to remove gross contaminates, such as dust and lint. The air is then compressed and channeled through a bacterial retentive filter in the hood in a laminar flow fashion. The purified air flows out over the entire work surface of the hood in parallel lines at a uniform velocity. The bacterial retentive type of filter is designed to remove all bacteria from the air being filtered.

Compounding under a laminar flow hood aids in preventing airborne contamination, but it is relatively cumbersome and expensive and would not be useful for eliminating any other source of contamination, such as contamination caused by handling. When using a hood the operator may inadvertently perform the work at the end or outside of the hood and not within the recommended space, at least six (6) inches within the hood, which insures the benefits of the air being purified. Time must be taken and care must be exercised to maintain a direct open path between the filter and the compounding area. Solution bottles and other non-sterile objects cannot be placed at the back of the hood work area next to the filter because these objects could contaminate everything downstream and disrupt the laminar flow pattern of the purified air. Also, in using a laminar flow hood, it is necessary routinely to clean the work surface of the hood before any compounding is performed.

Other manually controlled devices are known from the prior art for mixing base solutions. These devices use peristaltic pumps to transfer specified quantities of solution to transfer specified quantities of solution to a container. The desired quantities of solution to be transferred are determined in advance and entered by hand into the control unit of the pumping apparatus. The pumping apparatus them delivers the desired quantity of solutions to the mixture container. Such an apparatus and method are disclosed in U.S. patent application Ser. Nos. 391,758 and 391,759, both filed on June 24, 1982 and entitled respectively "Flow Monitoring Method and Apparatus" now U.S. Pat. No. 4,467,844 and "High Speed Bulk Compounder." Said applications have been assigned to the assignee of the present invention.

In order to use the devices and methods disclosed in the above identified applications it is usually necessary to manually translate a prescription from a short-hand designation to a set of parameters that includes the type, concentration and volume of each of the base solutions to be mixed. After the base solutions have been mixed, additives such as trace elements or vitamins can be added to make the final mixture.

The manual translation to a set of volumetric parameters is both time consuming and expensive as the process is usually carried out by a pharmacist. In addition, errors can occur during the calculation process. Further, the manual calculations to a certain extent are only approximations in that the small volumetric additions of the additives are often not taken into consideration.

If a group of prescriptions is to be compounded, once the manual translations have been completed, the order in which the members of the group are compounded becomes important. Compounders of the type disclosed in the above two applications are designed such that a container of base solution that has been partly emptied cannot be removed from the compounder and later reinserted. The containers of base solution which include dextrose, lipids and sterile water are expensive. It is therefore desirable to completely empty each container before removing it from the compounder.

To minimize over-all cost it would be desirable to optimize the compounding of a group of prescriptions by minimizing the needed number of containers of base solution. This requires a careful ordering of all prescriptions to be prepared at one time. Finally, labels must be prepared to identify each mixed prescription.

The process and method of the present invention provide for the translation from a prescription name to a detailed set of parameters without manual calculations. In addition, the compounding of a group of prescriptions can be optimized by the present invention by sorting the prescriptions in accordance with the type of base solution and then compounding them in the sorted order.

SUMMARY OF THE INVENTION

In accordance with the present invention a system and a method are provided for compounding a plurality of selected mixtures from one or more base solutions. The system includes a storage device for storing sets of parameters for a group of mixtures which are to be compounded from the base solutions. A compounder is electrically connected to the storage device, and in combination with the storage device, compounds a selected mixture on receiving a set of parameters which define the base solutions to be used and the amounts thereof. The storage device can be part of a host computer system which transfers information to, and receives information from the compounder by means of a communications link.

A program in the host computer maintains a data base of patient information. Associated with each patient entry are one or more mixtures for the patient which can be compounded from the base solutions. Both patient information and a set of parameters to define a mixture for the patient may be entered through a video display terminal or similar data entry device. The parameters for the base solutions of a mixture may be entered in the form of the volumes of the desired base solutions, the percentages of the total volume of the final mixture that each base solution represents, or as a nutritional contribution of each base solution to the final mixture. Each of the three forms of specifying the base solutions of a given mixture is essentially equivalent to the other two and the other two may be derived therefrom.

Additionally, the system provides a library function whereby a group of standard mixtures may be prestored as sets of parameters with a given name and called up or associated with a selected patient.

A set of parameters which defines a mixture for a given patient, referred to as a bag, is placed in one or more time slots or queues in the host computer to provide for one or more dosages to be given to a patient during a twenty-four hour period. Each queue corresponds to a given time interval within a twenty-four hour day.

The host computer provides facilities for a pharmacist to review each set of parameters, or bags, in a given queue and to authorize the compounding, or creation of the base solution mixture, during an initial part of each time period or shift. The host computer then sorts all of the authorized bags based on the specified base solutions. Compounding the mixtures in their sorted order results in a minimal number of containers of the base solutions being necessary. This results in minimal overall cost.

An important advantage of the present invention that results from sorting the authorized bags is the minimization of changes of tubing in the compounding apparatus. This unexpected result provides for lower overall cost. A further advantage is due to the ability of the host computer to take into account the small volumes of the additives when calculating the desired volumes of base solution.

Once a group of authorized bags has been sorted the system prints a set of labels corresponding to the sorted order of the group.

The types of base solutions and quantities for each authorized set of parameters, or bag, for a given time slot or queue are then presented in sorted order to the compounding apparatus. The compounding apparatus requires that the volumes of the base solutions be specified. Hence, volumetric information for each authorized bag is transmitted to the compounding apparatus in the sorted order. During the compounding process the set of preprinted labels provides a cross-check to ensure that the correct base solutions, amounts, and concentrations are provided for each mixed bag.

A log which keeps track of each operation is also created by the host computer. The log may be in the form of a printed copy or a disk file or both. The logged operations include entering new patient information, entering a new set of parameters, defining a bag, altering a set of parameters, and compounding one or more bags of solution.

Provision is made in the compounding apparatus for operator verification of the type, quantity and concentration of base solution to be compounded into the final mixture. Additionally, provision is made at the compounding apparatus to provide for entry of a patient identification number so that a bag can be prepared out of order should the need arise. Provision is also made in the host computer to inform the compounding apparatus of any change in the type or concentration of solution being used to enable the host computer to monitor the current base solutions being used.

The method of the present invention includes storing parameters for one or more mixtures; transferring base solution information from a storing location to a compounding location and compounding the desired mixtures.

DETAILED DESCRIPTION OF THE PREFERRED EMBODIMENTS

Figure 1:
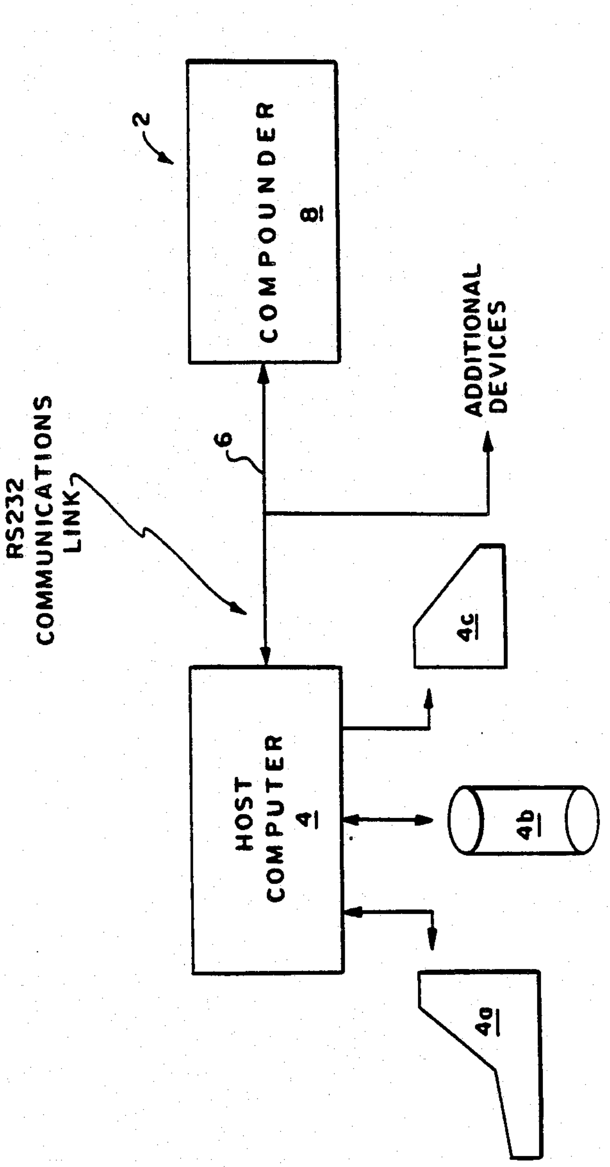
FIG. 1 is a overall block diagram of a system in accordance with the present invention.

Referring now to FIG. 1, a system 2 embodying the present invention is illustrated. The system 2 includes a host computer 4 having at least one cathode ray tube terminal 4*a*, a disk drive 4*b* and a printer 4*c* connected thereto. The host computer 4 can be selected from a variety of small computers including the IBM PC and PCXT or a comparable system. If desired, a larger computer system such as a Digital Equipment Corporation VAX could also be used. The computer 4 can be coupled through an RS 232 communications link 6 to a compounder 8. Additional compounders or other devices may be coupled through communications links to the host computer 4. The communications link 6 provides bidirectional communication between the host computer 4 and compounder 8. Alternately, the computer 4 could be hardwired to the compounder 8.

The host computer stores on its disk drive 4*b* programs for data input, for generating commands to drive the compounder 8, for handling input of authorizations for compounding prescriptions, for scheduling and sorting, for communications, for report generation and for audit trail generation. The host computer 4 also stores on its disk drive 4*b* patient information as well as sets of parameters of mixtures or prescriptions to be prepared for patients. A set of parameters corresponds to a prescription and might be input to the system 2 with only a name of a known standard mixture to be prepared for a patient. Attached hereto as Exhibit A is a copy of an exemplary VAX control program for use with the host computer 4.

Figure 2:
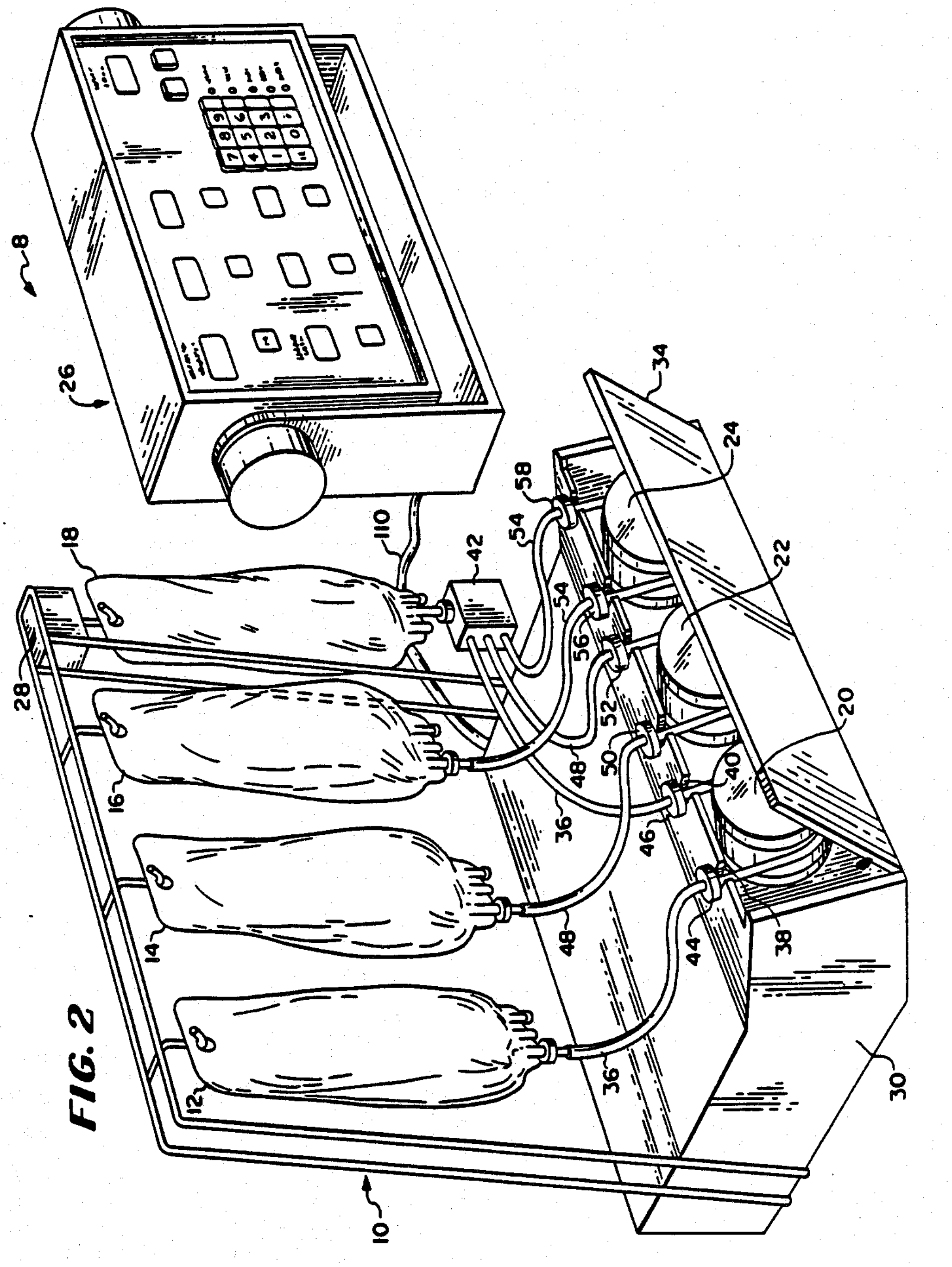
FIG. 2 is a perspective view of a compounding apparatus configured in accordance with the present invention.

FIG. 2 is a perspective view of a portion of the mechanical apparatus of the compounder 8. The compounder 8 includes a framework 10 upon which is hung a plurality of base solution containers 12, 14 and 16. Typical base solutions include amino acids, dextrose, and lipids, all of which are available in different concentrations, as well as sterile water. Base solutions are sometimes referred to as base component solutions. An output bag 18 is supported on the framework 10 and receives solutions from the containers 12 through 16 in quantities determined by the host computer 4 and the information stored therein. Base solutions are transferred from the containers 12 through 16 by means of peristaltic pumps 20 through 24. A control panel 26 is available to provide displays of information from the host computer 4 as well as to provide a means for operator input of control and feedback information concerning the status of the compounder 8. A housing 30 supports the framework 10 as well as the pumps 20 through 24. A front cover 34 covers the pumps.

The supply container 12 is coupled with the collection container 18 by flexible tubing 36. The flexible tubing 36 enters the housing 30 at inlet 38 and is placed around rollers (not shown) of the peristaltic pump 20. The flexible tubing 36 can be connected to another portion of flexible tubing (not shown) for placement around the rollers of the peristaltic pump. The tubing 36 then exits the housing 30 at outlet 40 and enters a junction block 42 coupled to the collection container 18. The junction block 42 provides a channel through which solutions being pumped through a flexible tube can flow to the collection bag 18.

The peristaltic pump 20, in operation, transfers the sterile solution in the supply container 12 to the collection bag 18 by movement of the rollers (not shown) in the pump 20. This movement causes a compression of the walls of the flexible tubing 36 forcing the solution therein forward in a capillary tube action. Retainers 44 and 46 are placed around the flexible tubing 36 at its entrance to and exit from the housing 30 to keep the tubing 36 in place during the operation of the pump 20.

The supply container 14 is coupled with the collection bag 18 by the flexible tubing 48. The sterile solution in the container 14 is delivered to the bag 18 by the peristaltic pump 22 in a similar fashion to the fluid delivered from container 12 caused by the pump 20. The flexible tubing 48 also has retainers 50 and 52 placed in a similar manner to the retainers 44 and 46 of the flexible tubing 36. The supply container 16 is coupled with the collection bag 18 by flexible tubing 54 with the peristaltic pump 24 therebetween. The tubing 54 has retainers 56 and 58 identical in placement and purpose to the retainers 44, 46, 50 and 52.

A manually operable compounder and method of operating same is disclosed in U.S. patent application Ser. No. 391,758, filed June 24, 1982, now allowed as U.S. Pat. No. 4,467,844, entitled "Flow Monitoring Method and Apparatus" and assigned to the assignee of the present invention. A manually operated compounder is also disclosed in U.S. patent application Ser. No. 391,759 filed June 24, 1982 entitled "High Speed Bulk Compounder" assigned to the assignee of the present invention. The above two applications discuss the theory of operation of manually controlled compounders similar mechanically to the compounder 8. The disclosures of said two applications are incorporated herein by reference.

Figure 3:
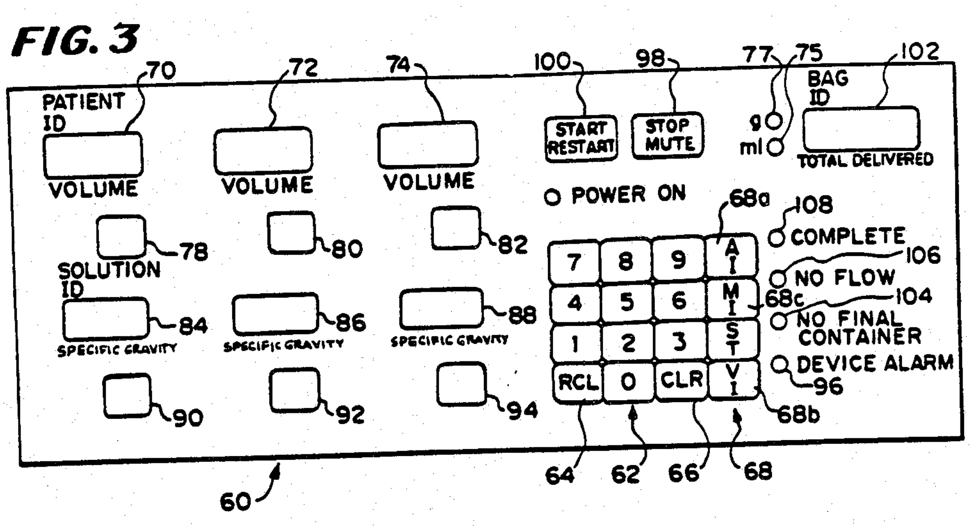
FIG. 3 is a front view of the control panel of the compounding apparatus configured in accordance with the present invention.

FIG. 3 is a view of the control panel 60 of the control unit 26. Panel 60 includes a 16 key keyboard 62 which is manually operable having digits 0 through 9, a recall key 64 a clear keyboard key 66 and 4 keys 68 labeled AI, for Auto I/D, MI, for Manual I/D, ST for standard manual operation and V.I, for Verify I.D. The key switches 68 are used by the operator when the compounder 8 is under control of the host computer 4. Each of the supply containers 12 through 16 is associated with a base solution volume to be delivered which is displayed at various times on the displays 70 through 74. Additionally, patient I/D codes can be displayed thereon. A set of switches 79 through 82 provides for manual entry of volumic parameters of base solutions that are then displayed on display 70 through 74 when the compounder 8 is operating in a manual mode. A specific gravity display 84 through 88 and a set of specific gravity entry switches 90 through 94 are also used for entering respective specific gravity information when operating in a manual mode. A total delivered display 102 provides an indicia of the quantity of solution delivered to the output bag 18 during a given compounding operation. Alternately when operating in connection with the host computer 4 a bag identification number is displayed at times in display unit 102. Lights 96, and 104 through 108 provide manually viewable indicia for the operator of the status of the compounder 8 and can be sensed by the host computer 4 when running in the automatic mode.

Figure 4:
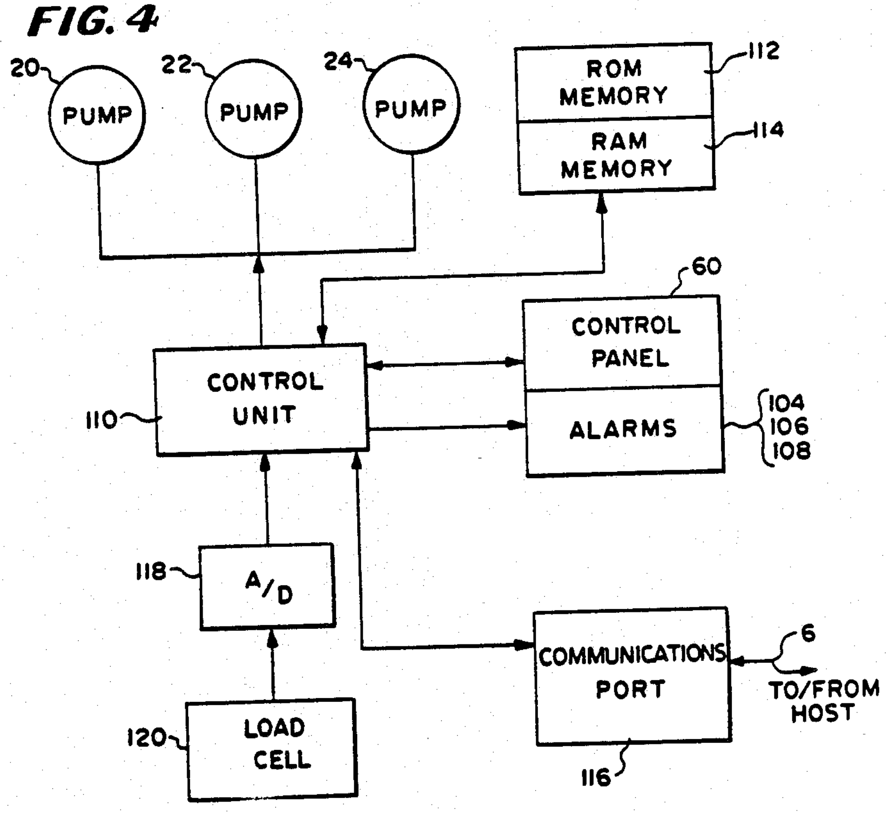
FIG. 4 is a schematic block diagram of the compounding apparatus configured in accordance with the present invention.

FIG. 4 is a schematic block diagram of the electronics of the compounder 8. The compounder 8 includes a control unit 110 which can be a Motorola 6802 microcomputer chip, read only memory 112 (ROM), random access memory 114 (RAM), a communications port 116 an analog to digital converter 118 and a load cell 120. Outputs from the control unit 110 drive the pumps 20 through 24.

The ROM memory 112 of FIG. 4 includes a control program, copy attached hereto as Exhibit B, for operating the compounder 8 in connection with the host computer 4.

Figure 5:
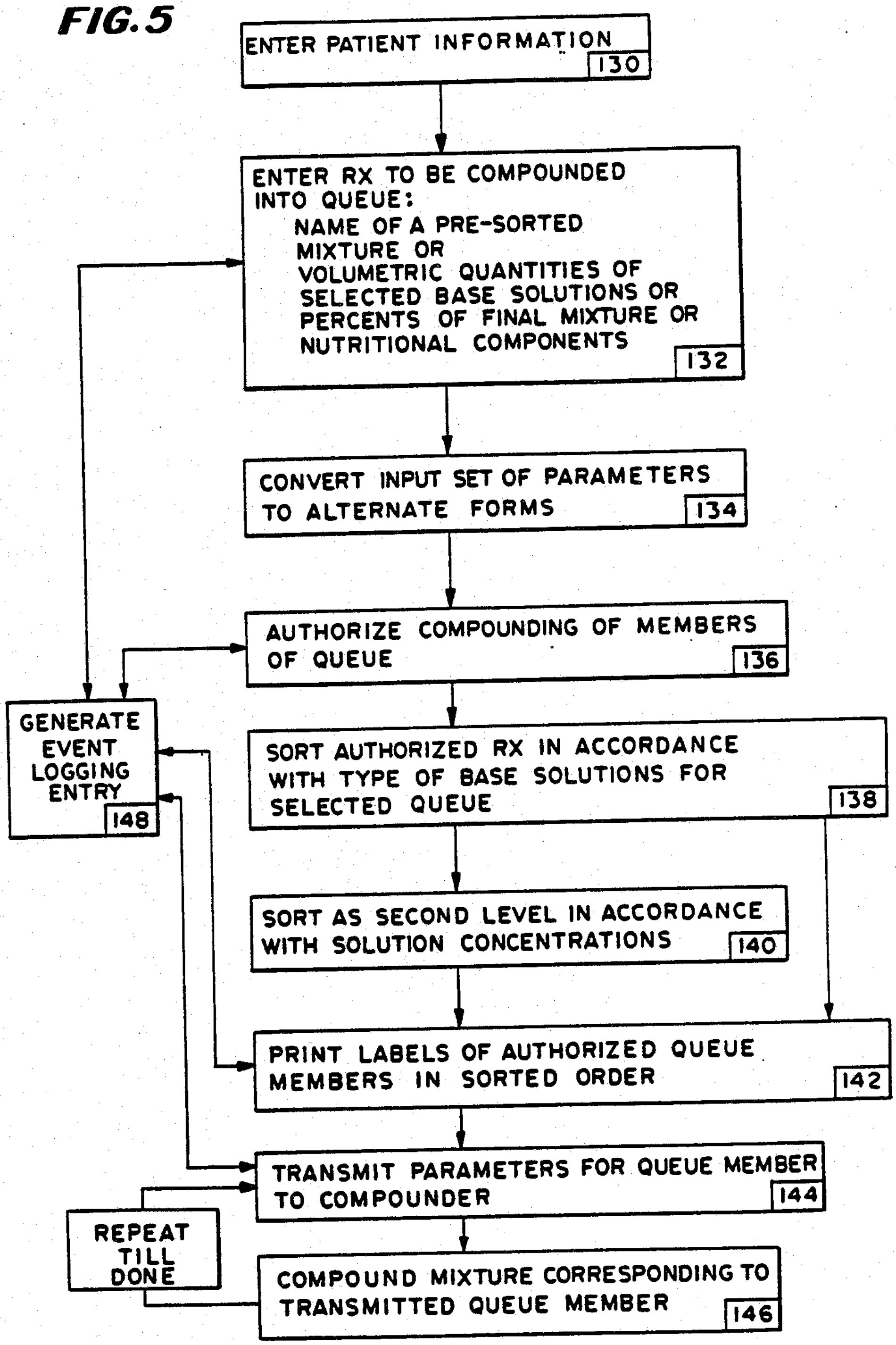
FIG. 5 is an overall flow diagram of the operation of the present invention.

FIG. 5 is an overall flow diagram showing the operation of the system 2. In an initial step 130 patient information is entered by means of cathode ray tube display 4*a*. Typical patient information is shown in Display 1 attached hereto in Exhibit C. The information includes a patient identification number, patient name, room number and related information. Once the patient information has been entered, the next step 132 is to enter a prescription to be compounded. The prescription is entered into one or more available queues. For example, 4 compounding queues can be used and can be allocated to six hour intervals during a twenty-four hour day. Patient information such as shown in Display 1 of Exhibit C attached, as well as prescription information entered in step 132 are all stored on the disk drive 4*b* for subsequent use.

Display 2 of Exhibit C is an exemplary set of parameters for a given prescription. Display 2 attached, in Exhibit C, discloses in the top section 132*a* the parameters for the base solutions for a given bag. The amino acids, dextrose and lipids are specified as a volume to be added to the final mixture. As can be seen from Display 2, the amino acids, dextrose and lipids represent 300 milliliters of the final mixture. In addition to the base solutions, amino acids, dextrose and lipids shown in the top portion of display two, a category of "other" solutions is available. Water is added to provide the desired total volume. Additionally, Display 2 also shows in the upper right 132*b* the concentrations of each of the base solutions to be used in creating the final mixture. The lower part of Display 2, 132*c*, illustrates additives including additional solutions, vitamins, elements or trace minerals to be added once the base solutions have been mixed in the bag 18.

A prescription can be entered by using the name of a prestored mixture and associating it with a given patient. A library of prestored prescriptions is maintained on the disk drive 4*b*. Each member of the library can be accessed merely by using a shorthand name. The library feature enables a short name to be used to define all of the parameters shown in Display 2 of Exhibit C for a given prescription. The standard parameter values can then be altered if necessary. This ability to refer to standard, prestored mixtures eliminates many of the manual calculations now carried out by pharmacists and provides for a substantial increase in the productivity of the person who otherwise would have to transfer a prescription to the detailed set of parameters shown in display 2 of Exhibit C. Standard prescriptions can be added to or deleted from the library maintained on the disk drive 4*b* as needed.

The compounder 8 under control of the host computer 4 receives sets of parameters for the base solutions of a prescription, such as shown in Display 2. The information sent to the compounder 8 defines the volume of amino acid, dextrose, lipids, water and "Other" base solutions. The compounder 8 then fills the bag 18 with required amounts of each of the base solutions corresponding to the parameters of Display 2. The base solution information 132*a, b* shown in Display 2 can also be viewed as a set of parameters for a mixture to be compounded. The additives, the additional solutions, trace elements or vitamins 132*c* of Display 2, Exhibit C such as sodium chloride, or iron are added once the base solutions have been mixed in the bag 18.

Display 3, Exhibit C attached, shows an alternate and substantially equivalent form of representing the base solution parameters of the desired mixture. The form of Display 3 shows the base solutions, the amino acids, dextrose, lipids and "Other" category 133*a*, to be added to the mixture by the compounder 8 in terms of a percent of the desired final mixture. Volumetric information 132*a* of the type shown in Display 2 is the form actually transmitted by the host computer 4 to the compounder 8. A third form 133*b* of the base solution parameters is shown in Display 4 of Exhibit C wherein the nutritional contribution in terms of calories and protein of the various constituent elements of the final solution are shown. The forms of the base solution parameters shown in Displays 2 through 4 are substantially equivalent. The form of the additives 132*c* remains unchanged in Displays 2–4.

An operator may input and/or alter any one of the three forms of base solution parameters and the host computer will automatically update the other two forms. Similarly, in the library of prestored sets of parameters any or all three of the forms of Displays 2–4 can be stored for subsequent recall. Each of the Displays 2–4 represents a set of parameters associated with a given patient identification number and a given bag number. The bag number refers to the identification number to be applied to the mixture bag 18. Further, the bag number also identifies a given prescription with the data base of the host computer 4.

After a set of parameters for a bag had been defined in one of the available forms, the host computer 4 converts the form of the input set into the alternate equivalent forms available, step 134. A given set of parameters for a bag, or a prescription, may be entered into one or more of the available queues which determines how many times during a given twenty-four hour period the prescription or bag is eligible for compounding. Additionally, the host computer 4 also determines how much sterile water needs to be added to the specified base solutions to arrive at the volume ordered. The calculation for water can also take into account the very small volume contributions of the additives which are often ignored when such calculations are manually carried out.

In the next step 136 as shown in FIG. 5, each of the sets of the parameters or members of a given queue is reviewed by a qualified professional, usually a pharmacist, to determine if any changes or corrections need to be made to the defined parameters and also to authorize actual compounding of the mixture in a given time interval. Information for a given set of parameters is not sent to the compounder 8 by the host computer 4 unless compounding of that particular bag or set of parameters has been previously authorized for a given shift or queue. Authorization is carried out by operator intervention through the video display terminal 4*a*. Absent express authorization, a given set of parameters, or bag, will not be compounded.

After all of the members of a given queue have been reviewed for authorization the authorized members of the queue are sorted by the host computer 4 based on the specified types of base solution families a base component solution family includes all concentrations of a given type, for example dextrose, of base component solution.

The sorted sequence of sets of authorized parameters or bags can also be sorted a second time in accordance with the required base solution concentrations. It would also be possible to conduct a third sort based on the size of the needed bag 18 for each set of parameters.

It is a significant and important aspect of the present invention that extensive prescription information can be recalled from a library using a shorthand name for a desired mixture. Additionally, the required mixture bags 18 can now be compounded at a minimum cost since the set of authorized bags has been sorted according to the type of base solutions needed. Minimum cost is achieved by making the fewest number of changes to the base solution containers such as 12 through 16 during the compounding process of a large number of mixture bags 18. The containers 12 through 16, as noted above, cannot be placed back in the compounder 8 if it is necessary to remove them before they are empty. As a result, partly empty base solution containers 12 through 16 are thrown away and increase cost. By sorting the authorized sets of parameters, or bags, as described above, the fewest number of base solution containers 12 through 16 will be required. As a result, wasted base solution will be minimized.

As a further advantage, because the system initially sorts in accordance with base component solution families, the need to flush the lines, such as the lines 36, 48, 54 is minimized. This is important in that it minimizes labor on the part of the operator. It further is important in that it reduces the possibility of contamination of the base component solutions. Finally, it is important in that with respect to some types of solutions, merely flushing the compounder lines is inadequate. In such cases the entire set of lines 36, 48, 52 as well as block 42 must be disposed of and replaced with a new, sterile set which further contributes to the overall cost. Sorting thus minimizes the need to change sets of lines.

Once the authorized sets of parameters or bags have been sorted in a given queue, a print queue is formed in a step 142 and the host computer 4 prints a sequence of labels on the printer 4c in the same sorted order. The labels printed in the step 142 will be used during the actual compounding process for the purpose of assisting the operator and verifying that the proper mixture is being prepared.

Attached hereto as Exhibit D is an exemplary three part label set. Label Part 1 is used by an operator during the compounding process and includes the patient identification number and bag number. Additionally in the "Base Component" Section it discloses the volumic parameters of the base solutions as well as the solution codes, specific gravities and concentrations thereof. Hence, the operator is able to verify that the not only are the proper base solution containers 12 through 16 mounted on the compounder 8 but that base solution containers of the proper concentration are being used. In addition, as will be discussed subsequently, the operator is able to compare each volume parameter shown in milliliters in Label Part 1 of Exhibit D to the quantities shown on the volumetric displays 70 through 74 of the compounder 8 that have been received from the host computer 4. The solution identification codes and specific gravities are also displayed on the display units 84 through 88 of the compounder 8. These additional displays provide an opportunity for the operator to further verify that the proper mixture is being prepared. Part 2 of the printed label, shown in Exhibit D, is attached to the mixture bag 18 for identification and delivery purposes. Part 3 of the label of Exhibit D, contains detailed information of the mixture provided and is designed for insertion into the patient's medical records.

After all of the mixture labels have been printed a Summary Label is prepared, Exhibit E attached, for all bags to be compounded from a given queue. As can be seen from Exhibit E, the Summary Label provides information as to the total volume and concentration of each type of base solution to be provided, and the number of mixture bags, such as bag 18 that will be needed.

After the labels have been printed in step 142, assuming the compounder 8 is available and is ready for receiving data, the operator depresses the AI key, 68a. The AI key signals the host computer 4 that the compounder 8 is ready to proceed. The host computer 4 transmits to the compounder 8 parameters defining the base solutions for the first member of the queue to be compounded. The compounder 8 first displays the patient I/D code in the Displays 70-74, the bag I/D code in display 102 and three solution codes in the displays 84 through 88, respectively. If the patient I/D, bag I/D and solution codes match those present in the Formula, Label Part 1 of Exhibit D, the operator depresses the VI key switch 68b.

To insure that the operator does in fact varify that the displayed patient I/D, bag I/D and base solution codes match those of the corresponding pre-printed label, a delay of, for example, 5 seconds can be built into the control program in the ROM 112 of the compounder 8. A depression of the VI key switch 68b will not be responded to by the compounder 8 until said delay period has passed. Thus the operator must wait for at least the delay period before going on to the next step.

After a depression of the VI key switch has been sensed, the compounder 8 then transmits a verification code to the host computer 4. The host computer 4 then supplies base solution volumetric information to the compounder 8 which is displayed in the display units 70 through 74 as well as specific gravity information which is displayed in the units 84 through 88. Assuming the volume information shown in the displays 70 through 74 and the specific gravity information shown in the displays 84 through 88 matches the information on Label Part 1 of Exhibit D the operator, after a delay period has elapsed, presses the Start key 100 which in turns starts the compounder 8.

The compounder 8 then measures out the base solution volumes as described in the above referenced patent applications. To restart the compounder once the process has been completed the operator again depresses the AI key switch 68a. The host computer 4 continues to send sets of base solution parameters to the compounder 8 until the queue is empty.

In the event that the operator for some reason wishes to temporarily jump ahead to mix a bag which is further down in the queue, perhaps because of some emergency, the operator depresses the MI key switch 68c. The MI key switch alerts the compounder 8 to the fact that the operator wishes to manually enter a patient I/D code through the numeric pad of the key switches 62. Once the patient I/D code has been entered through the numeric pad of the key switches 62 the operator again presses the MI key switch 68c. The compounder 8 then transfers the patient identification code across the communications link 6 to the host computer 4.

When the host computer 4 has sensed the patient identification code, it searches forward in the queue looking for the corresponding set of parameters. It should be noted that only a search forward through the queue can be carried out. The prescription for a patient number corresponding to a prior member of the queue will already have been compounded.

When the corresponding set of parameters or bag has been located in the queue, the host computer 4 then transmits base solution information to the compounder 8 which mixes the identified bag. Once this out of sequence compounding operation has been completed, the operator then depresses the AI key 68a which causes the host computer 4 to return to the prior location in the queue and to send the next member or set of parameters in the queue to the compounder 8.

It should be noted that after each set of parameters or bag has been sent to the compounder 8, the authorization flag for that particular bag is reset by the host computer 4. As a result, that particular prescription or set of parameters will have to be reauthorized to be compounded the next time the respective queue is sorted.

Additionally, in a step 148 an audit trail can be generated by the host computer 4 on the printer 4c or other storage device. An exemplary audit trail is shown in Exhibit F which identifies, at a given time what operation has taken place and by whom.

In a preferred mode of operation the host computer 4 has at least two and preferably three operator authorization levels. The lowest level merely permits an operator to input prescription data through the video display terminal 4*a*. The next level permits an authorized operator to change sets of parameters or bags in the data base on the disk drive 4*b* and to authorize the compounding of mixtures or prescriptions. In a third or maintenance level, prescriptions and other records can be deleted from the system.

Modification and variations of the present invention are possible in the light of the above teachings, for example, different sorting methods may be used. Bag parameters may be stored in groups not organized in queues and different display formats can be used all without departing from the spirit and scope of the present invention. Additionally, the host computer can be used to control a group of compounders or other devices essentially simultaneously. The host computer can also be used to generate accounting or management control reports based on the bags that have been compounded.

EXHIBIT A - HOST PROGRAM

(FORMAT - VMS EXECUTABLE FILE IMAGE AS DEFINED IN VAX-11 LINKER REFERENCE MANUAL NO. AA-D019C-TE)

Virtual block number 1 (00000001), 512 (0200) bytes

```
00000000 FFFFFFFF FFFFFFFF 00000101 34303230 00000000 004C0040 003000B4 ..0.@.L.....0204................ 000000
00000000 00000000 00008200 7FFEDF68 00026C00 00000000 1FA9391F 01000008 .....9.......1..h............... 000020
00002001 00000000 00000000 004E414D 54534806 00000016 00000000 00000128 (............HSTMAN............. 000040
00000000 00003630 2D333005 008D1FA9 391F7720 00000000 00000000 00000000 ............ w.9.....03-06...... 000060
0000008A 00000024 000D0010 00000002 00000080 00000001 00230010 00000000 ......$.................$....... 000080
00000032 00000080 00000041 00F50010 0000008C 00000031 0010000C 00000025 %.......1...........A.......2.... 0000A0
000C0024 FD00008C 003FFFEC 0014000C 00000127 0000040A 00000136 00010010 ....6.......'.........T.....$... 0000C0
00000000 00313030 5F4C5452 534D560A 01000C1C 00000000 03000021 01000000 ....!............VMSRTL_001..... 0000E0
FFFFFFFF FFFFFFFF FFFFFFFF FFFFFFFF FFFFFFFF FFFFFFFF FFFFFFFF FFFF0000 ................................ 000100
FFFFFFFF FFFFFFFF FFFFFFFF FFFFFFFF FFFFFFFF FFFFFFFF FFFFFFFF FFFFFFFF ................................ 000120
FFFFFFFF FFFFFFFF FFFFFFFF FFFFFFFF FFFFFFFF FFFFFFFF FFFFFFFF FFFFFFFF ................................ 000140
FFFFFFFF FFFFFFFF FFFFFFFF FFFFFFFF FFFFFFFF FFFFFFFF FFFFFFFF FFFFFFFF ................................ 000160
FFFFFFFF FFFFFFFF FFFFFFFF FFFFFFFF FFFFFFFF FFFFFFFF FFFFFFFF FFFFFFFF ................................ 000180
FFFFFFFF FFFFFFFF FFFFFFFF FFFFFFFF FFFFFFFF FFFFFFFF FFFFFFFF FFFFFFFF ................................ 0001A0
FFFFFFFF FFFFFFFF FFFFFFFF FFFFFFFF FFFFFFFF FFFFFFFF FFFFFFFF FFFFFFFF ................................ 0001C0
FFFFFFFF FFFFFFFF FFFFFFFF FFFFFFFF FFFFFFFF FFFFFFFF FFFFFFFF FFFFFFFF ................................ 0001E0
```

Virtual block number 2 (00000002), 512 (0200) bytes

```
00000000 00000000 00000000 00000001 00000000 0000004B 1C000102 0000004B H.......H....................... 000000
00000097 00000097 00000008 00000002 00000000 00000002 00000000 00000000 ................................ 000020
C4002008 34001B07 D0001603 E8000000 114E414D 54534806 00000097 00000000 ..........HSTMAN..............4. .. 000040
7603F90C 6C03DC0C 3A03BF0C 3003A20C 26034B0C 1E02FF0C 1C00440B B8002509 .%...D........K.Z...0...:...1...v 000060
4120666F 20646E45 0C055313 2404D410 CC048A10 6804850F A0047D0C 8004680C .h...}.....h..........$.S..End of A 000080
646E4520 2D2D2D20 6E6F6973 73655320 74736F48 2053554C 50205849 4D4F5455 UTOMIX PLUS Host Session --- End 0000A0
2D2D206E 6F697373 65532074 736F4820 53554C50 2058494D 4F545541 20666F20  of AUTOMIX PLUS Host Session -- 0000C0
203E2D2D 2D20392C 382C332C 322C3120 20737365 72503132 3338483F 3130392D -901?H8321Press  1,2,3,8,9 --->. 0000E0
20392D2D 2D2D2D2D 2D2F2020 7C20205C 2D2D2D2D 2D205C20 207C2020 2F202020    /  |  \ -----\  |  /-------9  000100
75412064 6E612073 74726F70 6552202D 2033706C 6548202D 20387469 7845202D - Exit8 - Help3 - Reports and Au 000120
72746E45 20617461 44202D20 31676E69 646E756F 706D6F43 202D2032 73746964 dits2 - Compounding1 - Data Entr 000140
48205355 4C502058 494D4F54 55412D2D 2D20756E 654D206E 69614D20 2D2D2D79 y--- Main Menu ---AUTOMIX PLUS H 000160
1C000202 0000004B 00003030 306D6574 73795320 65726177 74666F53 2074736F ost Software System000..H....... 000180
00000000 00000000 00000000 00000000 00000002 00000000 00000000 0000004B H............................... 0001A0
0000005F 00000000 0000005F 0000005F 00000000 00000001 00000000 00000002 ................_..._........_... 0001C0
00232323 5B3B481B 0C01167D C7001B7D 7800167D 64000000 03455441 434F4C06 .LOCATE....d}..x}...}....H;[###. 0001E0
```

```
Virtual block number 3 (00000003), 512 (0200) bytes

00000000 00000000 00000001 00000001 00000000 00000048 1C000202 0000004B H.......H........................... 000000
00000087 00000087 00000008 00000001 00000000 00000004 00000000 00000000 .................................... 000020
94002075 58001B75 4E001675 30000000 0D504C48 54534806 000000B7 00000000 .........HSTHLP....Ou..Nu..Xu .. 000040
3401D976 2A01C076 02015675 FA015175 F8013A75 D0010575 CB00C775 C6002575 u%..u...u...u!..uO/.uV..v..%v..4 000060
65756E69 746E6F63 206F7420 7265746E 65207373 65727028 0C024776 5B021076 v..[vG..(press enter to continue 000080
75732074 61687420 6E6F2065 6C62616C 69617661 20706C65 68206F4E 20203A29 ):  No help available on that su 0000A0
00000048 3C000302 00000048 00706C68 2E706C68 74734838 39392E74 63656A62 bject.998Hsthlp.hlp.H.......<H... 0000C0
00000001 00000000 00000000 00000000 00000000 00000002 00000004 00000000 .................................... 0000E0
52505503 0000005C 00000000 0000005C 0000005C 00000000 00000001 00000000 ...........\...\........\....UPR 000100
00000048 1C000202 00000048 0000000C 00FA797B 001B792C 00167918 00000003 .....y...y..{y......H.......H... 000120
00000001 00000000 00000000 00000000 00000000 00000001 00000002 00000000 .................................... 000140
54534806 00000073 00000000 00000073 00000073 00000000 00000001 0000000C ..........s...s.........s....HST 000160
FC019C53 98014153 3400FE52 D0002052 6C001B52 0800164E 20000000 0859454B KEY.... N...R..1R ..R..4SA..S... 000180
1C000202 00000048 001B5B4F 414B4250 434D444B 47514952 0C03E055 8C035953 SY.\U...RIQGKDMCPBHAOE..H....... 0001A0
00000000 00000000 00000000 00000000 00000001 00000003 00000000 00000048 H............................... 0001C0
0000045B 00000000 0000045B 000001FB 00000008 00000009 00000000 00000006 ....................[.......[... 0001E0

Virtual block number 4 (00000004), 512 (0200) bytes

B202771B 58002517 70002014 50001B13 EC001613 88000000 6A544E49 54534806 .HSTINTJ...........P. .p.%.X.w.. 000000
DE0B511C B609F31C 8E09B71C 8409A91C 7A07501C 5205411C 2A05051C 2004601B .`.....*.A.R.P.z.............Q... 000020
BA0F1E1D B00ECB1D 7E0E7B1D 560E3F1D 4C0E311D 420D0C1C F20CD01C E80CC21C ..........B.1.L.T.V.{.~......... 000040
3611CB1F 0E11121E E610D61E DC10861E 8210671E 780FC91E 1E0F8D1E 140F3D1D .=.........x.g...................6 000060
28141D37 1F141837 1E141337 15140E37 14140936 B012E423 28129422 6A126C1F .1.J'..(#...6...7...7...7...7...( 000080
50144537 47144037 46143B37 3D143637 3C143137 33142C37 32142737 29142237 7'.)7'.27,.371.<76.=7;.F7@.G7E.P 0000A0
78146D37 6F146837 6E146337 65145E37 64145937 5B145437 5A144F37 51144A37 7J.Q7O.Z7T.[7Y.d7^.e7c.n7h.o7m.x 0000C0
DC149537 97149037 96148B37 8D148637 8C148137 83147C37 82147737 79147237 7r.y7w..7|..7...7...7...7...7... 0000E0
1714BD38 1614B837 FF14B337 FE14AE37 FD14A937 FC14A437 FB149F37 FA149A37 7...7...7...7...7...7...7...8... 000100
2114E538 2014E038 1F14DB38 1E14D638 1D14D138 1C14CC38 1914C738 1814C238 8...8...8...H...8...8...8.. 8..! 000120
29150D38 28150838 27150338 2614FE38 2514F938 2414F438 2314EF38 2214EA38 8..'8..#8..$8..%8..&8..'8..(8..) 000140
31153538 30153038 2F152B38 2E152638 2D152138 2C151C38 2B151738 2A151238 8..*8..+8..,8!.-83..8+./80.085.1 000160
B4155D46 5015583A 97155338 36154E38 35154938 34154438 33153F38 32153A38 8:.28?.38D.48I.58N.6BS..:X.PF]. 000180
3120202C 3033202C 3931202C 3417CA4E 1F171A4A 9C16784A 38164D48 44160346 F..DHM.8Jx..J...N..4, 19, 30,  1 0001A0
3531202C 3931202C 382C3120 2C333420 202C3231 202C3931 202C362C 32202C33 3, 2,6, 19, 12,  43, 1,8, 19, 15 0001C0
202C3131 2C33202C 34372020 2C312020 2C393120 2C30312C 31202C35 3520202C ,  55, 1,10, 19,  1,  74, 3,11,  0001E0

Virtual block number 5 (00000005), 512 (0200) bytes

202C3537 20202C35 20202C39 31202C32 312C3120 2C303720 202C3420 202C3931 19,  4,  70, 1,12, 19,  5,  75,  000000
2C303520 2C393120 2C35312C 36202C30 3820202C 3320202C 3132202C 33312C35 5,13, 21,  3,  80, 6,15, 19, 50, 000020
31202C37 312C3120 2C333331 202C3035 202C3931 202C3631 2C31202C 33382020   83, 1,16, 19, 50, 133, 1,17, 1 000040
31202C36 3332202C 3034202C 3931202C 39312C31 202C3338 31202C30 35202C39 9, 50, 183, 1,19, 19, 40, 236, 1 000060
202C3320 202C3931 202C3232 2C31202C 36373220 2C303420 2C393120 2C30322C ,20, 19, 40, 276, 1,22, 19,  3,  000080
```

```
2C392020 2C332C31 202C3235 33202C34 20202C39 35202C32 322C3120 2C333332 233, 1,22, 59,  4, 352, 1,3,  9, 0000A0
20202C31 31202C36 2C342020 2C323420 2C342C34 20202C38 31202C34 2C342020   4,4, 18,  4,4, 42,  4,6, 11,   0000C0
3420202C 3832202C 30312C34 20202C39 33202C38 2C342020 2C393320 2C372C35 5,7, 39,  4,8, 39,  4,10, 28,  4 0000E0
20202C38 32202C33 312C3420 202C3832 202C3231 2C342020 2C383220 2C31312C ,11, 28,  4,12, 28,  4,13, 28,   000100
202C3832 202C3631 2C342020 2C383220 2C35312C 3420202C 3832202C 34312C34 4,14, 28,  4,15, 28,  4,16, 28,  000120
2C383220 2C39312C 3420202C 3832202C 38312C34 20202C38 32202C37 312C3420  4,17, 28,  4,18, 28,  4,19, 28, 000140
3832202C 32322C34 20202C38 32202C31 322C3420 202C3832 202C3032 2C342020   4,20, 28,  4,21, 28,  4,22, 28 000160
37202C32 312C3420 202C3037 202C3131 2C342020 2C303720 2C30312C 3420202C ,  4,10, 70,  4,11, 70,  4,12, 7 000180
202C3531 2C342020 2C303720 2C34312C 3420202C 3037202C 33312C34 20202C30 0,  4,13, 70,  4,14, 70,  4,15,  0001A0
2C38312C 3420202C 3037202C 37312C34 20202C30 37202C36 312C3420 202C3037 70,  4,16, 70,  4,17, 70,  4,18, 0001C0
31322C34 20202C30 37202C30 322C3420 202C3037 202C3931 2C342020 2C303720  70,  4,19, 70,  4,20, 70,  4,21 0001E0

Virtual block number 6 (00000006), 512 (0200) bytes

646E6120 65746144 202A2A2A 0C342020 2C303720 2C32322C 3420202C 3037202C , 70,  4,22, 70,  4.*** Date and 000000
43594E70 75747261 74732074 61207463 6572726F 636E6920 656D6954 20726F2F /or Time incorrect at startupNYC 000020
20746E65 72727543 2020203A 29274E27 20726F20 27592728 20206D72 69666E6F onfirm  ('Y' or 'N'):   Current  000040
206F7420 7265746E 65207373 65727028 20203A65 6D695420 646E6120 65746144 Date and Time:  (press enter to  000060
6E696E65 704F2072 6F727245 202A2A2A 2A2A2A20 20203A29 65756E69 746E6F63 continue):   ****** Error Openin 000080
6C616974 696E4920 2D207461 642E7773 70747348 6575712E 68637374 73482067 g Hstsch.queHstpsw.dat - Initial 0000A0
7348656C 62615420 6E6F6974 617A6972 6F687475 41207265 73552067 6E697A69 izing User Authorization TableHs 0000C0
6E697A69 6C616974 696E4920 2D207461 642E706D 62747348 7461642E 67616274 tbag.datHstbmp.dat - Initializin 0000E0
7461642E 74617074 73487061 4D206E6F 69747069 72637365 72502067 61422067 g Bag Prescription MarHstpat.dat 000100
6E656974 61502067 6E697A69 6C616974 696E4920 2D207461 642E7269 64747348 Hstdir.dat - Initializing Patien 000120
696C6169 74696E49 202D2074 61642E74 706F7473 4879726F 74636572 69442074 t DirectoryHstopt.dat - Initiali 000140
20746164 2E646461 74734873 6E6F6974 704F2079 63616D72 61685020 676E697A zing Pharmacy OptionsHstadd.dat  000160
62747348 61746144 20657669 74696464 4120676E 697A696C 61697469 6E49202D - Initializing Additive DataHstb 000180
74756C6F 53206573 61422067 6E697A69 6C616974 696E4920 2D207461 642E7361 as.dat - Initializing Base Solut 0001A0
4D4F5455 41202D2D 2D202065 74614420 2D2D2D20 2D2D2D20 61746144 206E6F69 ion Data --- --- Date  --- AUTOM 0001C0
64657472 61745320 302E3120 6E6F6973 72657620 74736F48 2053554C 50205849 IX PLUS Host version 1.0 Started 0001E0

Virtual block number 7 (00000007), 512 (0200) bytes

54474F4C 2E656C69 4620676E 6967676F 4C20676E 696E6570 4F202D20 2D2D2D20  --- - Opening Logging File.LOGT 000000
54542074 726F7020 58415620 6F742067 6E697463 656E6E6F 43202D20 3A545454 TTT: - Connecting to VAX-port TT 000020
43402D2D 2D2D2D2D 2D2F2020 7C20205C 2D2D2D2D 2D205C20 207C2020 2F3A3742 B7:/  |  \ -----\  |  /-------@C 000040
49202C73 62614C20 6C6F6E65 76617254 202D2034 38393120 74686769 7279706F opyright 1984 - Travenol Labs, I 000060
2074736F 48205355 4C502058 494D4F54 5541302E 31206E6F 69737265 562E636E nc.Version 1.0AUTOMIX PLUS Host  000080
00000048 00004A32 5B48313B 315B3031 306D6574 73795320 65726177 74666F53 Software System010[1;1H[2J..H... 0000A0
00000000 00000000 00000000 00000000 00000000 00000000 00000048 1C000202 ....H........................... 0000C0
00000000 0000008F 0000008F 00000008 00000002 00000000 00000002 00000000 ................................ 0000E0
7C002515 18002014 50001B13 EC001613 88000000 0F544E45 54534806 0000008F .....HSTENT...........P.  ...%.| 000100
9E032916 94030C16 6C02EF16 6202D216 58028516 4E025E15 EA021215 E0002A15 .*.......^.N...X...b...l.....).. 000120
2C322C31 20737365 72503132 33343848 3F323039 0C03B517 6603AD16 A7039816 .......f....902?H84321Press 1,2, 000140
34706C65 48202D20 38746978 45202D20 39202020 3E2D2D2D 20392C38 2C342C33 3,4,8,9 --->   9 - Exit8 - Help4 000160
6E656974 61502074 73694C20 2D203373 65697274 6E452065 74656C65 44202D20  - Delete Entries3 - List Patien 000180
```

```
2031736E 6F697470 69726373 65725020 67614220 77656976 6552202D 20327374 ts2 - Review Bas Prescriptions1  0001A0
4D202D2D 2D736E6F 69747069 72637365 72502067 61422F74 6E656974 6150202D - Patient/Bas Prescriptions--- M 0001C0
50205849 4D4F5455 412D2D2D 20756E65 4D207972 746E4520 61746144 206E6961 ain Data Entry Menu ---AUTOMIX P 0001E0

Virtual block number 8 (00000008), 512 (0200) bytes

00000048 00303031 6D657473 79532065 72617774 666F5320 74736F48 2053554C LUS Host Software System100.H... 000000
00000000 00000000 00000000 00000000 00000037 00000000 00000048 1C000202 ....H......7.................... 000020
00000000 00000514 0000042F 00000008 0000000A 00000100 00000025 00000000 ....%.............../........... 000040
38002517 CA002017 8E001B17 84001617 70000000 F7505445 54534806 00000514 .....HSTETP....p..........  ...%.8 000060
4004E61F 3603AD1B 6C03551B 6203501B 5802AE19 0000C618 9C006E18 6A002A18 .*.j.n..........X.P.b.U.1...6...@ 000080
BA076436 B0075823 27064123 23063922 5605D921 3405111F 5404F71F 4A04F21F ...J...T...4!..V'9.$#A.'$X..6d.. 0000A0
E5134C38 E0123B38 D60E0F38 AE0E0A38 A40DFE37 6E07BE37 1E078937 14076936 6i..7...7..n7...8...8...8?..8L.. 0000C0
44162B39 3A157C39 26157039 2114BE39 1214B939 0814AD38 FE149438 F4136438 8d..8...8...9...9..!9p.291.!9+.D 0000E0
A8193A39 9E188B39 8A187F39 8517CD39 7617C839 6C17B139 58171F39 4E163039 90.N9..X9..19..v9...9...9...9!.. 000100
E71C2339 E61C1E39 E51C1239 E41B6039 DA1B5B39 D01AE039 C91ADB39 C6193F39 9?..9...9...9[..9`..9...9...9$.. 000120
EF1C4B39 EE1C4639 ED1C4139 EC1C3C39 EB1C3739 EA1C3239 E91C2D39 E81C2839 9(..9-..92..97..9<..9A..9F..9K.. 000140
3E21CE3A 3421C23A 2F20DE3A 251EBB3A 111C5F3A 021C5A39 F81C5539 F01C5039 9P..9U..9Z..:_..:..%:.  /:.!4:.!> 000160
D4237F3A CA237A3A 9822853A 7A22543A 75221B3A 7022163A 66220A3A 5221D33A :.!R:.'f:.'p:.'u:T'z:.'.:z&.:.#. 000180
3A27FC3E 1C26F63C F025B73C AA255F3C 8C24A43B C424123B 6023FF3A FC23883A :.#.:.$'$.$.$.$.<_%.<.%.<.&.>.': 0001A0
BC2C243E B22BAD3E AD2B773E A8296A3E 8F29613E 8A295C3E 8029503E 7628B33E >.(v>P).>\).>a).>j).>w+.>.+.>$.. 0001C0
5231333F 482FC63E F82F523E EE2F4D3E E42E663E DA2C9B3E D02C683E C62C5B3E >[,.>...>...>f..>M/.>R/.>./H?31R 0001E0

Virtual block number 9 (00000009), 512 (0200) bytes

CA34A93F C034183F B6340F3F AC33643F 9832F53F 8E32A53F 8432553F 7A313C3F ?<1z?U2.?.2.?.2.?d3.?.4.?.4.?.4. 000000
60390D40 56384E40 4236AE40 24367A40 1035C13F E835623F D935263F D434E83F ?.4.?&5.?b5.?.5.@z6$@.6B@8V@.9`.. 000020
543E5D42 4F3C8642 4A3BE642 403AA942 1839A642 0E39A142 04397F40 6A394D40 @M9j@.9.B.9.B.9.B.!@B.#JB.<OBJ>T 000040
EE40B643 DA3FB143 A83FAC43 943FA042 C23EEF42 7C3EEA42 683EDE42 633EB242 B.>cB.>hB.>|B.>.B.?.C.?.C.?.C.@. 000060
77447B45 74446F45 56424545 2E424045 24423444 8E411E44 66411944 5C410D43 C.A\D.AfD.A.D4B$EBB.EEBVEoDtE{Dw 000080
B2467E48 A8467246 19461146 1445F646 0A44F245 F644ED45 EC449945 7E448045 E.D~E.D.E.D.E.D.F.E.F.F.FrF.H~F. 0000A0
66493949 5C490949 52487949 48475449 34471649 2A46FC49 2046F749 0C468348 H.F.I.F I.F*I.C4ITGHIyHRI.I\I9If 0000C0
1F4C8B4A 1A4C2A4A 154BAC4A 1049F549 FC49AE49 F2497C49 E8497749 D4496B49 IkI.IwI.I|I.I.I.I.I.J.K.J*L.J.L. 0000E0
574E9A4E 4D4E4E4E 484DF84E 3E4DF34E 204D914A 2E4D854A 294D6C4A 244CEA4A J.L$J1M)J.M.J.M N.M>N.MHNNNMN.NW 000100
DE52104E D451D24E B651114E 98510C4E 8451004E 6F50A94E 6B502B4E 664FA24E N.OfN+PkN.PoN.Q.N.Q.N.Q.N.Q.N.R. 000120
6054394F 4C53BB4F 2453B64F 1A53AA4F 10536E4F 06529B4E FC52934E E852874E N.R.N.R.N.R.OnS.O.S.O.S$O.SLO9T` 000140
2655B952 1755B452 08555150 1E554C50 1455324F A655264F 9C549E4F 6A543E4F O>TjO.T.O2U.O2U.PLU.PQU.R.U.R.U& 000160
DE59D653 CA594653 B6585353 AC584E53 98584253 8E57B253 3E57AD53 34566B52 RkV4S.W>S.W.SBX.SNX.SSX.SFY.S.Y. 000180
BA5DC354 885D3254 7E5D2554 745D2054 605D0F54 565BE154 065BCC53 F25B4C53 SL[.S.[.T.[VT.]`T ]tT%]"T2].T.]. 0001A0
6E61D555 50612755 3C612255 28611655 1E60EA55 145E6454 D85E5F54 C45E5354 TS^.T_^.Td^.U.`.U.a(U!a<U'aPU.an 0001C0
04661655 F0660A55 E6658B55 C8649055 B462B755 A062B255 8C621955 73621455 U.bsU.b.U.b.U.b.U.d.U.e.U.f.U.f. 0001E0

Virtual block number 10 (0000000A), 512 (0200) bytes

4867D657 E4678157 94677C57 80677057 1C66A356 CC669E56 B8669256 54661B56 V.fTV.f.V.f.V.f.Wg.Wlg.W.g.W.gH 000000
```

```
42697059 1A696B59 1068DE58 F268D958 DE687D58 C0687858 AC67E758 5C67E258 X.a\X.a.Xxh.X}h.X.h.X.h.Yki.YriB 000020
20202020 2020203A 6E65676F 7274694E 2C31202C 366A9261 A76AB061 9E6AB159 Y.J.a.J.a.J6, 1,Nitrogen:         000040
442C3932 2C372C3A 6E696574 6F72502D 73656972 6F6C6143 2C31322C 362C6D67 gm,6,21,Calories-Protein:,7,29,D' 000060
3A6C6174 6F542C32 332C392C 3A646970 694C2C32 332C382C 3A65736F 72747865 extrose:,8,32,Lipid:,9,32,Total: 000080
20202020 2B4B2C37 342C372C 71456D20 20202020 2020202B 414E2C37 342C362C ,6,47,NA+        mEq,7,47,K+      0000A0
342C392C 71456D20 20202020 20202B2B 41432C37 342C382C 71456D20 20202020      mEq,8,47,CA++       mEq,9,4 0000C0
20202020 2020202D 4C432C34 362C362C 71456D20 20202020 20202B2B 474D2C37 7,MG++        mEq,6,64,CL-       0000E0
34362C38 2C6C6F6D 6D202020 20202020 2D2D344F 502C3436 2C372C71 456D2020   mEq,7,64,PO4--        mmol,8,64 000100
646F4320 20202020 656E694C 202F200C 71456D20 20202020 20202020 2D43412C ,AC-         mEq. / Line     Cod 000120
52206575 712E6863 73747348 20676E69 74697257 20726F72 7245202A 2A2A2065 e *** Error Writing Hstsch.que R 000140
74697257 23206365 52206575 712E6863 73747348 20676E69 64616552 23206365 ec #Reading Hstsch.que Rec #Writ 000160
72572320 63655220 67614220 676E6964 61655223 20636552 20676142 20676E69 ing Bag Rec #Reading Bag Rec #Wr 000180
65697461 5020676E 69646165 52232063 65522074 6E656974 61502067 6E697469 iting Patient Rec #Reading Patie 0001A0
23206365 52207061 4D206761 4220676E 69746972 57393939 23206365 5220746E nt Rec #999Writing Bag Map Rec # 0001C0
72637365 72502067 6142202A 2A2A2020 23232320 63655220 70614D20 67611259 YBag Map Rec ###  *** Bag Preser 0001E0

Virtual block number 11 (0000000B), 512 (0200) bytes

69442067 6E697469 72572A2A 2A206465 6C6C6946 20656C69 46206E6F 69747069 iption File Filled ***Writing Di 000000
666E7250 20746E65 69746150 202A2A2A 30202023 20636552 2079726F 74636572 rectory Rec #  0*** Patient Prof 000020
74206B63 61622D27 656D6F48 272A2A2A 2064656C 6C694620 656C6946 20656C69 ile File Filled ***'Home'-back t 000040
74206F74 206B6361 622D2770 55206750 27202C74 65736572 20262070 6F74206F o top 3 reset, 'Pg Up'-back to t 000060
206F7420 7265746E 65207373 65727028 6E776F64 2D276E44 20675027 202C706F op, 'Pg Dn'-down(press enter to  000080
2A204449 20746E65 69746150 20646142 202A2A2A 20203A29 65756E69 746E6F63 continue):  *** Bad Patient ID * 0000A0
704F6E6F 20646567 676F6C20 6465776F 6C6C6120 746F6E20 73736563 63412A2A **Access not allowed logged onOp 0000C0
73483F3F 3F303958 20203A64 726F7773 73615020 7265746E 4520726F 74617265 erator Enter Password:  X90???Hs 0000E0
494C7461 642E6269 6C747348 30203020 30203020 30203020 7461642E 67616274 tbag.dat 0 0 0 0 0 0Hstlib.datLI 000100
2A2A7972 616D6972 70206F6E 202D2064 6E756F66 20746F6E 20494D41 58454450 PDEXAMI not found - no primary** 000120
726F7272 45206573 61422061 74614420 746E656E 6F706D6F 43206573 6142202A * Base Component Data Base Error 000140
202D4220 20202020 2D412020 20746F6C 53206D69 54206D64 6E756F70 6D6F4320  Compound Time Slot   A-     B-  000160
20202020 30202020 2023234D 2D4C2020 2020202D 44202020 2020202D 43202020      C-      D-      L-M##    0   000180
2C73656D 756C6F56 27202C6E 6F697461 72746E65 636E6F43 27202020 20202020        'C'oncentration, 'V'olumes, 0001A0
6D6F6320 65676E61 68632D3E 65636170 733C202C 6E6F6974 69727475 4E272020   'N'utrition, <space>-change com 0001C0
20746F6E 6E61434C 20726F66 20646564 64612067 61422077 654E746E 656E6F70 ponentNew Bag added for LCannot  0001E0

Virtual block number 12 (0000000C), 512 (0200) bytes

2F747865 4E202D2F 2B2B7367 61622064 657A6972 6F687475 61207966 69646F6D modify authorized bags++/- Next/ 000000
77654E20 202C6761 42207972 61726269 4C20726F 66202323 4C20202C 7473614C Last,  L## for Library Bag,  New 000020
4E232323 2E232020 49202020 2323234B 7265626D 754E2067 61422020 726F2020   or  Bag NumberK###   I  #.###N 000040
3F302020 2023232E 23232023 2E232323 23232323 23232E23 23302E30 20514150 PAQ 0.0##.#########.# ##.##    0? 000060
68744F25 5B5D2025 30302E30 2023232E 23233F3F 3F3F206C 6D232323 233F3F3F ????###ml ?????##.## 0.00% ]F%Oth 000080
7942203A 64657A69 726F6874 7541206F 6E696D41 20207865 44646970 694C7265 erLipidDex  Amino Authorized: By 0000A0
75666E49 72682F6C 6D204356 203A6465 7265746E 45203A64 65746164 7055203A : Updated: Entered: VC ml/hrInfu 0000C0
20203A64 65726564 724F2065 6D756C6F 566C6D20 20203A65 74615220 6E6F6973 sion Rate:   mlVolume Ordered:    0000E0
42302029 73286761 42206576 69746341 20202020 64492067 61426576 69746341 ActiveBag Id    Active Bag(s) OB 000100
```

```
676E696C 6C694220 203A6465 7265746E 452D2020 3A646574 61647055 20203A79 y:  Updated:  -Entered: . Billing 000120
20207365 746F4E20 203A2020 20202020 20202020 20202020 203A2065 646F4320  Code :                 :  Notes   000140
65736165 73694420 203A2020 20207365 69677265 6C6C4120 203A2020 20202020         :  Allergies    :  Disease 000160
69202323 23202020 203A2020 20207369 736F6E67 61694420 203A6574 61745320  State:  Diagnosis    :    ### i 000180
20626C20 23232320 20202020 203A2020 20202020 20746867 6965486D 6320206E n  cmHeight|      :    ### lb  0001A0
20202020 20202020 20206567 4120203A 20202020 20202074 68676965 576D674B KgmWeight |    :  Age          0001C0
29657461 6E6F654E 20726F20 63697274 61696465 50202C74 6C756441 2820203A :  (Adult, Pediatric or Neonate) 0001E0

Virtual block number 13 (0000000D), 512 (0200) bytes

20203A20 2020206E 61696369 73796850 20203A20 65707954 20746E65 69746150 Patient Type :  Physician    :   000000
20203A20 656D614E 20746E65 69746150 20203A20 20202020 6E6F6974 61636F4C Location     :  Patient Name :  000020
67614220 746E6569 74615020 67614220 20203A20 20204449 20746E65 69746150 Patient ID   :   Bad Patient Bad 000040
6C69666F 72502074 6E656974 61506465 676E6168 63203231 31585820 726F6620  for XX112 changedPatient Profil 000060
61502077 654E202A 2A64656E 69617465 7220746F 6E203131 31472072 6F662065 e for G111 not retained** New Pa 000080
73736563 63612020 64657461 65726320 20746E65 69746150 2A2A2074 6E656974 tient **Patient  created  access 0000A0
27207473 756A2820 203A4449 20746E65 69746150 20726574 6E45483F 33306465 ed03?HEnter Patient ID:  (Just ' 0000C0
69746150 29756E65 6D206F74 206B6361 62207465 67206F74 20276E72 75746572 return' to get back to menu)Pati 0000E0
1C000202 00000048 39313130 31317972 746E4520 61746144 20676142 2F746E65 ent/Bag Date Entry110119H....... 000100
00000000 00000000 00000000 00000000 00000000 0000002C 00000000 00000048 H............................... 000120
00000478 00000000 00000478 00000393 00000008 0000000A 00000100 00000018 .....................x.......x.. 000140
9C002A18 38002517 CA002017 8E001B17 84001617 70000000 D0525445 54534806 .HSTETR....p..........  ...%.8.*.. 000160
C804A819 64048D19 46041819 32033719 1E02C419 14028D19 00022418 EC006E18 .n...$...........7.2...F...d.... 000180
4A07B71F 4007AB1F 3606721B 6C061A1B 6206151B 5805C51A F405A31A 9004F719 ..........X...b...l.r.6...@...J 0001A0
320AB623 280AAA23 270A7823 26097D23 23097122 56096221 9807D61F 5407BC1F ...T....!h.V'q.##}.&#x.'#..(#..2 0001C0
AE187838 A4136C37 6E0CFC37 1E0CF737 140CD736 BA0CD236 B00CC624 540ABB23 #..T$...6...6...7...7..n71..8x.. 0001E0

Virtual block number 14 (0000000E), 512 (0200) bytes

211A2C39 121A2739 081A1B38 FE1A0238 F418D238 E518BA38 E017A938 D6137D38 8}..8...8...8...8...8...9'..9..! 000000
851D3B39 761D3639 6C1D1F39 581C8D39 4E1B9E39 441B9939 3A1AEA39 261ABE39 9..29..:9..D9..N9..X9..196.v9;.. 000020
E420CE39 DA20C939 D0204E39 C9204939 C61EAD39 A81EAB39 9E1DF939 8A1DED39 9...9...9...9...9I .9N .9. .9. . 000040
EC21A839 EB21A339 EA219E39 E9219939 E8219439 E7218F39 E6218A39 E5217E39 9~!.9.!.9.!.9.!.9.!.9.!.9.!.9.!. 000060
2524273A 1121CB3A 02210639 F821C139 F021BC39 EF21B739 EE21B239 ED21AD39 9.!.9.!.9.!.9.!.9.!.9.!.!.!.!'$% 000080
7A277C3A 7527433A 70273E3A 6627323A 5226FB3A 3E26F63A 3426EA3A 2F264A3A :J&/:.&4:.&>:.&R:2'f:>'p:C'u:|'z 0000A0
AA2A753C 8C29C43B C429343B 6029213A FC28AA3A D428A13A CA289C3A 9827AD3A :.'.:.(.:.(.:.(.:!)`;4).;.).<u*. 0000C0
D02E6B3E 8F2E623E 8A2E5D3E 802E513E 762DB43E 3A2D003E 1C2C003C F02ACB3C <.*.<.,.>.-:>.-v>Q..>].,>b..>k.. 0000E0
8433873F 7A32723F 5232693F 4831003E F8308C3E EE30873E E42FA03E DA2F113E >./.>./.>.0.>.0.>.1H?i2R?r2z?.3. 000100
D936563F D436183F CA35D93F C0354A3F B635413F AC34963F 9834273F 8E33D73F ?.3.?'4.?.4.?A5.?J5.?.5.?.6.?V6. 000120
043AA740 6A3A7540 603A3540 56397740 4237DF40 2437AA40 1036F13F E836923F ?.6.?.6.@.7$@.7B@w9V@5:`@u:j@.:. 000140
5C3CF543 EE3C9E43 DA3B9943 A83B9443 943B8842 C23ADA42 7C3AD542 683AC942 B.:hB.:|B.:.B.;.C.;.C.;.C.<.C.<\ 000160
AB3EA146 193F4046 143F2546 0A3E2B45 F63E2645 EC3E1A44 8E3D0644 663D0144 D.=fD.=.D.>.E&>.E+>.F%?.F@?.F.?. 000180
5C422D49 52419F49 48407C49 34403E49 2A402549 20402049 0C3FB248 B23FAD48 H.?.H.?.I @ I%@*I>@4I|@HI.ARI-B\ 0001A0
1A453D4A 1544C24A 10431649 FC42CF49 F2429F49 E8429A49 D4428E49 66425C49 I\BfI.B.I.B.I.B.I.B.I.C.J.D.J=E. 0001C0
4D47554E 4846FF4E 3E46FA4E 2046984A 2E468C4A 2946744A 2445FA4A 1F45C84A J.E.J.E$JtF)J.F.J.F N.F>N.FHNUGN 0001E0
```

```
Virtual block number 15 (0000000F), 512 (0200) bytes

D44AC84E B64A0C4E 984A074E 8449FB4E 6F49A44E 6B49264E 664BA34E 5747A04E N.GWN.HfN&IkN.IoN.I.N.J.N.J.N.J. 000000
4C4CA94F 244CA44F 1A4C984F 104C5F4F 064B894E FC4B844E E84B784E DE4B024E N.K.NxK.N.K.N.K.O_L.O.L.O.L$O.LL 000020
044EA255 F04E3F50 1E4E3A50 144E204F A64E144F 9C4D8C4F 6A4D2C4F 604D274F O'K O.MJO.M.O.N.O N.P:N.PTN.U.N. 000040
48506257 E4500D57 94500857 804FFC57 1C4F2F56 CC4F2A56 B84F1E56 541EA756 V.NTV.O.V%O.V/O.W.O.W.P.W.P.WbPH 000060
4251FC59 1A51F759 10516A58 F2516558 DE510958 C0510458 AC50735B 5C506E5B XnP\XsP.X.Q.X.Q.XeQ.XJQ.Y.Q.Y.QB 000080
20202020 2020203A 6E65676F 7274694E 2C31202C 36531E61 A7531961 9E530D59 Y.S.a.S.a.S6, 1,Nitrogen:         0000A0
442C3932 2C372C3A 6E696574 6F72502D 73656972 6F6C6143 2C31322C 362C6D67 gm,6,21,Calories-Protein:,7,29,D 0000C0
3A6C6174 6F542C32 332C392C 3A646970 694C2C32 332C382C 3A65736F 72747865 extrose:,8,32,Lipid:,9,32,Total: 0000E0
20202020 2B4B2C37 342C372C 71456D20 20202020 2020202B 414E2C37 342C362C ,6,47,NA+          mEq,7,47,K+    000100
342C392C 71456D20 20202020 20202B2B 41432C37 342C382C 71456D20 20202020      mEq,8,47,CA++       mEq,9,4 000120
20202020 2020202D 4C432C34 362C362C 71456D20 20202020 2020282B 474D2C37 7,MG++        mEq,6,64,CL-        000140
34362C38 2C6C6F6D 6D202020 20202020 2D2D344F 502C3436 2C372C71 456D2020   mEq,7,64,PO4--        mmol,8,64 000160
20202065 6E694C20 2F202323 2323230C 71456D20 20202020 20202020 2D43412C ,AC-             mEq.#### / Line  000180
2E686373 74734820 676E6974 69725720 726F7272 45202A2A 2A206564 6F432020   Code *** Error Writing Hstsch. 0001A0
20636552 20657571 2E686373 74734820 676E6964 61655223 20636552 20657571 que Rec #Reading Hstsch.que Rec   0001C0
65522067 61422067 6E696461 65522320 63655220 67614220 676E6974 69725723 #Writing Bag Rec #Reading Bag Re 0001E0

Virtual block number 16 (00000010), 512 (0200) bytes

20676E69 64616552 23206365 5220746E 65697461 5020676E 69746972 57232063 c #Writing Patient Rec #Reading   000000
20706F74 206F7420 6B636162 2D27656D 6F482723 20636552 20746E65 69746150 Patient Rec #'Home'-back to top  000020
5027202C 706F7420 6F74206B 6361622D 27705520 67502720 2C746573 65722026 & reset, 'Pg Up'-back to top, 'P 000040
6E69746E 6F63206F 74207265 746E6520 73736572 70286E77 6F642D27 6E442067 g Dn'-down(press enter to contin 000060
65636341 2A2A2A20 44492074 6E656974 61502064 6142202A 2A2A2020 3A296575 ue):  *** Bad Patient ID ***Acce 000080
726F7461 7265704F 6E6F2064 6567676F 6C206465 776F6C6C 6120746F 6E207373 ss not allowed logged onOperator 0000A0
6F6E2049 4D415845 4450494C 30582020 3A64726F 77737361 50207265 746E4520  Enter Password:  XOLIPDEXAMI no 0000C0
6D6F4320 65736142 202A2A2A 7972616D 69727020 6F6E202D 20646E75 6F662074 t found - no primary*** Base Com 0000E0
20302020 20202323 4D20726F 72724520 65736142 20617461 4420746E 656F6F70 ponent Data Base Error M##    0  000100
6D756C6F 27562720 2C6E6F69 74617274 6E65636E 6F274327 20202020 20202020         'C'oncentration, 'V'olum 000120
2065676E 6168632D 3E656361 70733C20 2C6E6F69 74697274 75274E27 20207365 es, 'N'utrition, <space>-change  000140
23302E30 2051504E 2323232E 23202049 20202023 23234B74 6E656E6F 706D6F63 componentK###    I  #.###NPQ 0.0# 000160
3F3F3F20 6C6D2323 23233F3F 3F3F3020 20202323 2E232320 232E2323 23232E23 #.####.# ##.##     0????####ml ??? 000180
41202078 65446469 70694C72 6568744F 255B5D20 2530302E 30202323 2E23233F ?##.## 0.00% ][%OtherLipidDex  A 0001A0
6E45203A 64657461 64705520 3A794220 3A64657A 69726F68 74754120 6F6E696D mino Authorized: By: Updated: En 0001C0
6D202020 3A657461 52206E6F 69737566 6E497268 2F6C6D20 56203A64 65726574 tered: V ml/hrInfusion Rate:    m 0001E0

Virtual block number 17 (00000011), 512 (0200) bytes

20206449 20676142 65766974 63412020 3A646572 6564724F 20656D75 6C6F566C lVolume Ordered:  ActiveBag Id    000000
20746E65 69746150 2077654E 202A2A30 20297328 67614220 65766974 63412020   Active Bag(s) 0** New Patient   000020
6C6C6942 20203A64 65726574 6E452D20 203A6465 74616470 5520203A 79422A2A **By:  Updated:  -Entered:  Bill 000040
65746F4E 20203A20 20202020 20202020 20202020 20203A20 65646F43 20676E69 ing Code :                 :  Note 000060
65736944 20203A20 20202073 65696772 656C6C41 20203A20 20202020 20202073 s        :  Allergies     :  Dise 000080
```

```
23232020 20203A20 20202073 69736F6E 67616944 20203A65 74617453 20657361 ase State:  Diagnosis    :     ## 0000A0
20232323 20202020 20203A20 20202020 20207468 67696548 6D632020 6E692023 # in  cmHeight        :    ###  0000C0
20202020 20202065 67412020 3A202020 20202020 74486769 65576D67 4B20626C lb KgmWeight        :  Age      0000E0
616E6F65 4E20726F 20636972 74616964 6550202C 74607564 41282020 3A202020    :  (Adult, Pediatric or Neona 000100
20202020 6E616963 69737968 5020203A 20657079 5420746E 65697461 50296574 te)Patient Type :  Physician    000120
20656D61 4E20746E 65697461 5020203A 20202020 206E6F69 7461636F 4C20203A :  Location      :  Patient Name  000140
61506465 7A69726F 68747561 2020203A 20202044 4920746E 65697461 5020203A :  Patient ID    :   authorizedPa 000160
20274F4E 27202020 2C657A69 726F6874 7561206F 7420274B 4F272074 6E656974 tient 'OK' to authorize,   'NO'  000180
3A796669 646F6D20 6F74203E 6E727574 65723C20 20202C74 63656A65 72206F74 to reject,   <return> to modify: 0001A0
2D422020 2020202D 41202020 746F6C53 20656D69 5420646E 756F706D 6F432020   Compound Time Slot   A-     B- 0001C0
32314B4F 4F4E2067 6142202D 4C202020 20202D44 20202020 202D4320 20202020       C-      D-     L- Bag NOOK12 0001E0

Virtual-block number 18 (00000012), 512 (0200) bytes

206F4E32 32314720 726F6620 67614220 746E6569 74615064 65676E61 68632033 3 changedPatient Bag for G12No   000000
7551206E 6920657A 69726F68 74754120 2F207765 69766552 206F7420 73676142 Bags to Review / Authorize in Qu 000020
2C332C32 2C312073 73657250 31413242 33433444 354C3848 3F353039 20657565 eue 905?H8L5D4C3B2A1Press 1,2,3, 000040
6C654820 202D2038 74697845 20202D20 39202020 3E2D2D2D 20392C38 2C352C34 4,5,8,9 --->   9 -  Exit8 -  Hel 000060
20202D20 34296575 65755120 796C6E4F 20736C65 62614C28 204C2020 2D203570 p5 -  L (Labels Only Queue)4 -   000080
6F687475 41202D2D 2D204120 202D2031 20422020 2D203220 4320202D 20332044 D 3 -  C 2 -  B 1 -  A --- Autho 0000A0
4F545541 2D2D2D20 6E6F6974 63656C65 53206575 65755120 6E6F6974 617A6972 rization Queue Selection ---AUTO 0000C0
3132316D 65747379 53206572 61777466 6F532074 736F4820 53554C50 2058494D MIX PLUS Host Software System121 0000E0
00000000 00000000 00000011 00000000 0000004B 1C000202 0000004B 00303231 120.H.......H.................. 000100
00000103 00000008 00000006 00000194 00000074 00000000 00000000 00000000 ...........t.................... 000120
3A001B2E F900162E E0000000 2C4C5445 54534806 00000103 00000000 00000103 .............HSTETL,...........: 000140
A6057831 9C057031 2E03CC30 0201CC2F 6200AC2F 58002A2F 4E00252F 1400202F / .D/%.N/*.X/..b/...0...1p..1x.. 000160
1A07DB4F 1007A44F 0606CE4E FC06C94E E806BD32 BE05A332 0A059E32 00057D31 1}..2...2...2...N...N...O...O... 000180
1E09B050 14097C4F A609704F 9C08904F 6A086F4F 60086A4F 4C07EC4F 2407E74F O..$O..LOj.'Oo.jO...Op..Ol..P... 0001A0
940B7C57 800B7057 1C0AA456 CC0A9F56 B80A9356 540A1D56 040A1855 F009B550 P...U...V..TV...V...V...Wp..W|.. 0001C0
9E0D8B59 420C7F59 1A0C7A59 100C6E58 AC0BE658 5C0BE158 480BB557 E40B8157 .W...W..HX..\X...Xn..Yz..Y..BY... 0001E0

Virtual block number 19 (00000013), 512 (0200) bytes

2A2A2065 646F4320 20202020 656E694C 202F2023 23232323 0C0D9C61 A70D9761 a...a...##### / Line      Code ** 000000
676E6964 61655223 20636552 20676142 20676E69 74697257 20726F72 7245202A * Error Writing Bag Rec #Reading 000020
20636552 20746E65 69746150 20676E69 74697257 23232320 63655220 67614220  Bag Rec ###Writing Patient Rec  000040
6361622D 27656D6F 48272320 63655220 746E6569 74615020 676E6964 61655223 #Reading Patient Rec #'Home'-bac 000060
74206B63 61622D27 70552067 5027202C 74657365 72202620 706F7420 6F74206B k to top & reset, 'Pg Up'-back t 000080
20726574 6E652073 73657270 28656E6F 642D276E 44206750 27202C70 6F74206F o top, 'Pg Dn'-done(press enter  0000A0
68635320 2D202073 67614220 6C61746F 5420203A 2965756E 69746E6F 63206F74 to continue):  Total Bags  - Sch 0000C0
20303331 64492074 6E656974 6150656D 614E2074 6E656974 61506465 6C756465 eduledPatient NamePatient Id130  0000E0
74634120 29656C62 616C6961 76412028 20202020 20736761 42206576 69746341 Active Bags    ( Available) Act 000100
00000048 1C000202 00000048 00000023 23232820 73746E65 69746150 20657669 ive Patients (###...H.......H... 000120
0000000E 00000000 00000000 00000000 00000000 00000000 00000010 00000000 ................................ 000140
54534806 00000173 00000000 00000173 00000173 00000008 00000006 00000000 ...........s...s.......s...,HST 000160
9C006B18 6A002A18 38002517 CA002017 BE001B17 84001617 70000000 48445445 ETDH...p..........  ...%.8.*.j.k... 000180
```

```
3604991D 4C03C31B BC03711B 6C03191B 6203141B 58030C1A F402AD19 0000C318 ...........X...b...l.a.....L...6 0001A0
480BCF4E 3E0BCA4E 200BBE37 6E054E37 1E054937 14052936 BA052436 B005181F ....6$..6)..7I..7N.n7.. N..>N..H 0001C0
B60ECD4E 980EC84E 840EBC4E 6F0E664E 6B0DEB4E 660D684E 570C6F4E 4D0C244E N$.MNo.WNh.fN..kNf.oN...N...N... 0001E0

Virtual block number 20 (00000014), 512 (0200) bytes

24114F4F 1A11434F 10110C4F 0610364E FC10314E E810254E DE0FBF4E D40FB64E N...N...N%..N1..N6..O...OC..OO.$ 000000
6012E650 1E12E150 1412C74F A612BB4F 9C12364F 6A11D74F 6011D24F 4C11544F OT.LO..`O..JO6..O...O...P...P..` 000020
1E171955 14148C54 D8148754 C4147B54 BA13EC54 88135B54 7E134E54 74134954 TI.ITR.*TE..T...T{..T...T...U... 000040
9418B257 8018A657 1C17DA56 CC17D556 B817C956 54175656 04175155 F0174555 UE..UQ..VV.TV...V...V...W...W... 000060
9E1AC159 4219B559 1A19B059 1019A458 AC191C58 5C191758 48190B57 E418B757 W...W..HX..\X...X...Y...Y..BY... 000080
2A2A2065 646F4320 20202020 656E694C 202F2023 23232323 0C1AD261 A71ACD61 a...a...$$$$$ / Line    Code ** 0000A0
676E6964 61655223 20636552 20676142 20676E69 74697257 20726F72 7245202A * Error Writing Bad Rec $Reading 0000C0
20636552 20746E65 69746150 20676E69 74697257 23232320 63655220 67614220  Bad Rec $$$Writing Patient Rec  0000E0
61422067 6E697469 72572320 63655220 746E6569 74615020 676E6964 61655223 $Reading Patient Rec $Writing Ba 000100
2079726F 74636572 69442067 6E697469 72572323 23232063 65522070 614D2067 g Map Rec $$$$Writing Directory  000120
2C746573 65722026 20706F74 206F7420 6B636162 2D27656D 6F482723 20636552 Rec $'Home'-back to top & reset, 000140
6F642D27 6E442067 5027202C 706F7420 6F74206B 6361622D 27705520 67502720  'Pg Up'-back to top, 'Pg Dn'-do 000160
2A2A2020 3A296575 6E69746E 6F63206F 74207265 746E6520 73736572 7028656E ne(press enter to continue):  ** 000180
6120746F 6E207373 65636341 2A2A2A20 44492074 6E656974 61502044 6142202A * Bad Patient ID ***Access not a 0001A0
7265746E 45205820 726F7461 7265704F 6E6F2064 6567676F 6C206465 776F6C6C llowed logged onOperator X Enter 0001C0
2A2A3020 29732867 61422065 76697463 41202020 20203A64 726F7773 73615020  Password:     Active Bag(s) 0** 0001E0

Virtual block number 21 (00000015), 512 (0200) bytes

452D2020 3A646574 61647055 20203A79 422A2A20 746E6569 74615020 77654E20  New Patient **By:  Updated:  -E 000000
20202020 20202020 203A2065 646F4320 676E696C 6C694220 203A6465 7265746E ntered:  Billing Code :         000020
69677265 6C6C4120 203A2020 20202020 20207365 746F4E20 203A2020 20202020       :  Notes       :  Allergi 000040
736F6E67 61694420 203A6574 61745320 65736165 73694420 203A2020 20207365 es    :  Disease State:  Diagnos 000060
20202020 20746867 6965486D 6320206E 69202323 23202020 203A2020 20207369 is    :     $$$ in  cmHeight     000080
20202020 20202074 68676965 576D674B 20626C20 23232320 20202020 203A2020   :       $$$ lb KgmWeight       0000A0
61696465 50202C74 6C756441 2820203A 20202020 20202020 20206567 4120203A :  Age          :  (Adult, Pedia 0000C0
20203A20 65707954 20746E65 69746150 29657461 6E6F654E 20726F20 63697274 tric or Neonate)Patient Type :   0000E0
20203A20 20202020 6E6F6974 61636F4C 20203A20 2020206E 61696369 73796850 Physician     :  Location     :  000100
20203A20 20204449 20746E65 69746150 20203A20 656D614E 20746E65 69746150 Patient Name :  Patient ID    :  000120
75657551 20687469 7720746E 65697461 50206574 656C6544 20746F6E 6F61434E NCannot Delete Patient with Queu 000140
73696874 20657465 6C654430 20302030 20302030 20302029 73286761 42206465 ed Bag(s) 0 0 0 0 0 0Delete this 000160
3431203A 29274E27 20726F20 27592728 2064726F 63655220 746E6569 74615020  Patient Record ('Y' or 'N'): 14 000180
746F4E20 44492074 6E656974 61505920 746E6569 74615064 6574656C 65442031 1 DeletedPatient YPatient ID Not 0001A0
756A2820 203A4449 20746E65 69746150 20726574 6E45483F 3330646E 756F4620  Found03?HEnter Patient ID:  (ju 0001C0
29756E65 6D206F74 206B6361 62207465 67206F74 20276E72 75746572 27207473 st 'return' to get back to menu) 0001E0

Virtual block number 22 (00000016), 512 (0200) bytes

00000048 00003934 31303431 6E6F6974 656C6544 20676142 2F746E65 69746150 Patient/Bag Deletion140149..H... 000000
00000000 00000000 00000000 00000000 00000045 00000000 00000048 1C000202 ....H.......E................... 000020
```

```
00000000 00000522 000003F7 00000008 00000007 00002354 00000170 00000000 ....r...T$.............'....... 000040
87020817 84002017 70001B13 A6001613 88000000 E94D4F43 54534806 00000522 '....HSTCON...........P. ...... 000060
5803CB18 1003B317 FC033E17 E8031B17 D402F817 C002B517 AC02B217 98025417 .T.................>........X 000080
4807FC1B B207871B AD06A11B 9E06431B 8A05F71B 80058E1B 7B03D81B 6C03D31B ...1...{.........C.............H 0000A0
0A0BE11D F10BC61D E20A841D BA09ED1D B008641D 6008271D 5608221D 4C08161C ...L.'.V.'.`.d.................. 0000C0
A4109C1F 400ECC1E A00E1C1E 960C5D1E 820C581E 780BFA1E 1E0BF51E 140BE91E ...........x.X...].........@.... 0000E0
6C189720 1C173420 08167F1F FE15311F F413CB1F E013B21F D613081F C210A11F .................1...... 4.. ..1 000100
3E1C8D21 341C7D21 161BF421 021A6720 9419DA20 8A196620 8018FD20 7618F820 ..v ... f.. ... g..!...!}.4!..> 000120
88210222 83213C22 7E1FCB22 6A1FC622 601F2E22 061F2921 FC1F1221 661C9221 !..f!...!)..'..`'..j'..^'<!.'.!. 000140
F126C122 EC26B522 E725CD22 C425B122 BA23F422 A623D822 9C21E722 8D21E222 '.!.'.!.'.$.'.$.'.%.'.%.'.&.'.3. 000160
3C2EEC23 322EE723 282EDB23 232EC223 192D4323 052AFC22 FB2AF722 F626C622 '.&.'.*.'.*.$C-.$..$$..($..2$..< 000180
8C34EC23 8B34DC23 82344123 7832FD23 6430BB23 5A30A423 502FD023 462F6C23 $1/F$./F$.O2$.Od$.2x$A4.$.4.$.4. 0001A0
FA38A823 F0389C23 E6387A23 DC37C423 B4376523 AA360623 A034FD23 9634F823 $.4.$.4.$.6.$e7.$.7.$z8.$.8.$.8. 0001C0
29395624 28395124 27394C24 26394724 25394224 24393D24 23393824 2238AD23 $.8'$89$$=9$$B9%$G9&$L9'$Q9($V9) 0001E0
```

Virtual block number 23 (00000017), 512 (0200) bytes

```
263A7925 1C3A6D24 86397424 5E396F24 54396A24 2C396524 2B396024 2A395B24 $[9*$`9+$e9,$j9T$o9^$t9.$m:.%y:& 000000
C03C2F3A AC3C2A3A 983C1E2A F33C172A EE3BE627 243BAA27 1A3BA527 103A7E25 %~:.'.;.'.;$'.;.*.<.*.<.;*<.:/<. 000020
6040283B 563FC93B 533EE13B 513DE13B 243DD13B 103DA03B 063C803A FC3C633A :c<.:.<.;.=.;.=$;.=Q;.>S;.?V;(@` 000040
F8411D3E E441043E D040EA3E BC40CA3E A840BD3E 9440B83E 80405B3B 7440413B ;A@t;[@.>.@.>.@.>.@.>.@.>.A.>.A. 000060
8641CE42 7C41A342 72419E42 6841923F 4841813F 3441683F 20414F3F 0C41363E >6A.?OA ?hA4?.AH?.AhB.ArB.AlB.A. 000080
A8441243 94432343 44431E43 30430D42 A4430542 9A42F542 95427942 90421442 B.B.ByB.B.B.B.C.B.COC.CDC$C.C.D. 0000A0
444B0C47 E04A7447 AE495247 7C477D47 18452B46 B444EE46 6444E946 50441743 C.DPF.DdF.D.F+E.G}G|GRI.GtJ.G.KD 0000C0
0050374A F64F914A EC4E574A CE4DC84A BA4C1F4A 424C1A4A 384C0E4A 2E4BFB48 H.K.J.L8J.LBJ.L.J.M.JWN.J.O.J7P. 0000E0
6F538C4E 6B530C4E 6652834E 57517B4E 4D512F4E 4B50D94E 3E50D44E 2050C84B K.P N.P>N.PHN/QMN{QWN.R?N.SkN.So 000100
06557B4E FC55764E E8556A4E DE54F34E D454B54E B653F44E 9853EF4E 8453E34E N.S.N.S.N.S.N.T.N.T.NjU.NvU.N{U. 000120
A6580B4F 9C57834F 6A57234F 60571E4F 4C569E4F 2456994F 1A568D4F 1056514F OQV.O.V.O.V$O.VLO.W`O$WjO.W.Q.X. 000140
8C599355 73598E55 6E595855 50589E55 3C589955 28583650 1E583150 1458174F O.X.P1X.P6X(U.X<U.XPUXYnU.YsU.Y. 000160
B85E2A56 545DB056 045DAB55 F05D9F55 E65D1C55 C85C1855 B45A3255 A05A2D55 U-Z.U2Z.U.\.U.].U.].U.].V.]TV*^. 000180
AC5F8958 5C5F8458 485F7857 E45F2057 945F1B57 805F0F57 1C5E3B56 CC5E3656 V6^.V;^.W.._.W.._.W _.Wx_HX._\X._. 0001A0
3C624159 D8623559 42612359 1A611E59 10608A58 F2608558 DE602658 C0602158 X!`.X&`.X.`.X.`.Y.a.Y#aBY5b.YAb< 0001C0
CC635C5B 7C63575B 6862E95B 1862E45B 0462955A B462905A A0624B5A 5062465A ZFbPZKb.Z.b.Z.b.[.b.[.bh[Wc|[\c. 0001E0
```

Virtual block number 24 (00000018), 512 (0200) bytes

```
20202020 2C312020 2020202C 3164B461 A764AF61 9E64A35B FE63915B D6638C5B [.c.[.c.[.d.a.d.a.d1,    1,     000000
31202020 20202C31 20202020 2020312C 31202020 20202C30 20202020 20203020  0,     0,     1,1,    ,1,    1 000020
20203120 20202020 2C302020 2020202C 312C3020 20202020 2C302020 2020202C ,    0,    0,1,    0,     1,    000040
2020202C 31202020 20202C31 20202020 20202C30 2C31202020 20202C30 20202020    0,    1,0,    1,    1,    000060
20202020 20203020 20202020 2C312020 2020202C 312C3120 20202020 2C302020  0,    1,1,    1,    0,      000080
2C312020 2020202C 31202020 20202C30 20202020 2020312C 30202020 20202C31 1,    0,1,    0,    1,    1, 0000A0
20202C31 20202020 20203120 20202020 2C312020 2020202C 302C3020 20202020    0,0,    1,    1,    1,    0000C0
20202020 2C312020 2020202C 30202020 20202C30 20202020 2020312C 30202020  0,1,    0,    0,     1,       0000E0
31202020 20202C31 20202020 20203120 20202020 2C302020 2020202C 302C3120 1,0,    0,    1,    1,    1 000100
```

```
2A0C3120 20202020 2C312020 2020202C 30202020 20202C31 20202020 202C302C ,0,      1,      0,      1,      1.* 000120
614C2A2A 2A20736C 6562614C 20676E69 73736563 6F725020 726F7272 45202A2A ** Error Processing Labels ***La 000140
72724520 2A2A2A20 65646F43 20202020 20656E69 4C202F20 6C626C2E 736C6562 bels.lbl / Line     Code *** Err 000160
69646165 52232063 65522065 75712E68 63737473 4820676E 69746972 5720726F or Writing Hstsch.que Rec #Readi 000180
52206761 4220676E 69746972 57232063 65522065 75712E68 63737473 4820676E ng Hstsch.que Rec #Writing Bag R 0001A0
74615020 676E6974 69725723 20636552 20676142 20676E69 64616552 23206365 ec #Reading Bag Rec #Writing Pat 0001C0
20232063 65522074 6E656974 61502067 6E696461 65522320 63655220 746E6569 ient Rec #Reading Patient Rec #  0001E0
```

Virtual block number 25 (00000019), 512 (0200) bytes

```
706F7420 6F74206B 6361622D 27656D6F 48273939 39302030 20302030 20302030 0 0 0 0 0 0999'Home'-back to top 000000
27202C70 6F74206F 74206B63 61622D27 70552067 5027202C 74657365 72202620  & reset, 'Pg Up'-back to top, ' 000020
69746E6F 63206F74 20726574 6E652073 73657270 28656E6F 642D276E 44206750 Pg Dn'-done(press enter to conti 000040
6363412A 2A2A2044 4920746E 65697461 50206461 42202A2A 2A20203A 2965756E nue):  *** Bad Patient ID ***Acc 000060
6F746172 65704F6E 6F206465 67676F6C 20646577 6F6C6C61 20746F6E 20737365 ess not allowed logged onOperato 000080
65746157 20656C69 72657453 20203A64 726F7773 73615020 7265746E 45582072 r XEnter Password:  Sterile Wate 0000A0
202D2065 6D614E20 2D202320 67614220 20202020 20202020 20202020 20202072 r                  Bag # - Name -  0000C0
6620676E 69646E75 6F706D6F 43206465 74617265 6E654720 796C6C61 756E614D Manually Generated Compounding f 0000E0
61572074 61502067 61422020 6D6F7266 20646575 65757165 64202064 4920726F or Id  dequeued from  Bag Pat Wa 000100
2A203A29 4E20726F 20592820 6465646E 756F706D 6F632067 61422065 68742073 s the Bag compounded (Y or N): * 000120
2A2A2A20 65756575 71206465 7463656C 6573206E 6920746F 6E206761 42202A2A ** Bag not in selected queue *** 000140
726F2044 202C4320 2C42202C 41282065 75657551 206D6F72 66206576 6F6D6552 Remove from Queue (A, B, C, D or 000160
69687420 726F6620 67614220 68637573 206F4E20 2A2A2A20 20202020 3A294C20  L):     *** No such Bag for thi 000180
20203A72 65626D75 4E206761 42207265 746E452A 2A2A2074 6E656974 61502073 s Patient ***Enter Bag Number:   0001A0
65746E45 33302A2A 2A206449 20746E65 69746150 20686375 73206F4E 202A2A2A *** No such Patient Id ***03Ente 0001C0
6F742027 6E727574 65722720 7473756A 2820203A 44492074 6E656974 61502072 r Patient ID:  (just 'return' to 0001E0
```

Virtual block number 26 (0000001A), 512 (0200) bytes

```
65757165 4420796C 6C61756E 614D2975 6E656D20 6F74206B 63616220 74656720  get back to menu)Manually Deque 000000
63532073 67614220 6F4E2065 75657551 20273034 32313432 67614220 61206575 ue a Bag241240' Queue No Bags Sc 000020
49207972 746E4520 7473614C 20657565 75512027 27206E49 2064656C 75646568 heduled In '' Queue Last Entry I 000040
20202020 20202073 746E656E 6F706D6F 43206573 61422523 232E2323 2027206E n ' ##.##%Base Components      000060
20303232 32333244 4920746E 65697461 50656D61 4E676142 73656D75 6C6F5620  VolumesBagNamePatient ID232220  000080
4120736C 6562614C 59657565 7551206E 69207367 6142206F 4E302020 23232330 0### ONo Bags in QueueYLabels A 0000A0
28207465 53207765 4E20746E 69725020 2D206465 746E6972 50207964 6165726C lready Printed - Print New Set ( 0000C0
20736569 726F6C61 43202020 206C6174 6F542323 23232320 3A294E20 726F2059 Y or N): #####Total    Calories  0000E0
20202D43 41202020 2B2B474D 20207365 69726F6C 61432020 6E696574 6F725020  Protein  Calories  MG++   AC-   000100
202D4C43 20202020 202B4B20 202D2D34 4F506C6F 6D6D2020 20202B2B 41432020   CA++    mmolPO4--  K+    CL-   000120
20202020 2B414E23 2E232323 2371456D 20202020 20202020 20202020 20202020                 mEq####.#NA+     000140
65736F72 74786544 23232323 20202073 6569726F 6C614320 20202064 6970694C Lipid    Calories   ####Dextrose 000160
6F432020 6E65676F 7274694E 232E2323 23206D67 20202073 6569726F 6C614320  Calories   gm ###.#Nitrogen  Co 000180
69746964 64412D2D 3F3F3F3F 2023232E 2323202D 20252056 20202074 6E65746E ntent   V % - ##.## ????--Additi 0001A0
6F4C2D65 736F442D 20202020 20202020 20202020 20202020 2020202D 2D736576 ves--                     -Dose-Lo 0001C0
67614220 20202020 20202020 20202020 20202020 2020203A 656D614E 203A2063 c : Name:                     Bag 0001E0
```

```
Virtual block number 27 (0000001B), 512 (0200) bytes

6F727463 656C4520 6574616D 69786F72 70704120 2A2A203A 20206449 203A2320  #: Id  : ** Approximate Electro 000000
706D6E43 20202020 20202020 20202020 20202A2A 20736C61 746F5420 6574796C  lyte Totals **             Comp 000020
69726F68 74754120 20202020 20202020 20202020 20203A79 62206465 646E756F  ounded by:               Authori 000040
64657265 746E4520 6E6F6974 70697263 73657250 20676142 203A7962 2064657A  zed by: Bag Prescription Entered 000060
20726576 6F206E75 72206C6C 69772072 682F6C6D 20737275 6F682020 3A796220   by:  hours ml/hr will run over 000080
5F5F5F5F 5F5F5F5F 3A736572 69707845 206E6F69 74756C6F 53207461 206C6D20  ml at Solution Expires:________ 0000A0
7942202E 70657250 5F5F5F5F 5F5F5F5F 5F5F5F5F 5F5F5F5F 5F5F5F5F 5F5F5F5F  ________________________Prep. By 0000C0
6D695420 5F5F5F5F 5F5F5F5F 5F5F5F5F 5F3A6574 6144205F 5F5F5F5F 5F5F5F3A  :________ Date:_____________ Tim 0000E0
20202020 20202020 20202065 6D756C6F 56206C61 746F545F 5F5F5F5F 5F5F3A65  e:_______Total Volume            000100
6C6D4E6E 6F697475 6C6F5320 6E6F6974 69727475 4E206C61 7265746E 65726150  Parenteral Nutrition SolutionNml 000120
30303520 30303031 30303032 30303033 20657355 28296761 42206C61 6E694620   Final Bag)(Use 300020001000 500 000140
656C6972 6574532D 2D2D2D2D 20202020 656D756C 6F56206C 61746F54 30353120   150Total Volume     -----Sterile 000160
2030302E 31202020 20303020 20202020 20202020 20202020 20207265 74615720   Water               00 /  1.00 000180
20202D2D 746E656E 6F706D6F 43206573 61422D2D 23232323 2E232020 20202020        #.####--Base Component--  0001A0
2020202D 6C6D2D20 20202020 20202D67 7053202D 2D65646F 432D2020 20202020        -Code- -Spg-       -ml-    0001C0
20202020 2D2D7365 76697469 6464412D 2D3F3F3F 3F232E23 23202020 20202020         ##.????--Additives--     0001E0

Virtual block number 28 (0000001C), 512 (0200) bytes

2D6C6D2D 20202020 2020202D 65736F44 2D202020 20202020 20202020 20202020                   -Dose-       -ml- 000000
2041204C 2055204D 2052204F 20462020 20202020 20202020 20202020 20202020                    F O R M U L A  000020
202D206C 6D303030 31202D20 2020206C 6D303030 32202D20 6C6D3030 3033202D  - 3000ml - 2000ml    - 1000ml -  000040
65745320 20202023 23232320 20206C6D 30353120 202D2020 20206C6D 30303520   500ml    -   150ml    ####    Ste 000060
23232323 236C6D20 20202020 20202020 20202020 20207265 74615720 656C6972  rile Water                ml##### 000080
6E694620 26206E6F 6974756C 6F53202D 2D2D2020 20202025 23232E23 23202023  #  ##.##%    --- Solution & Fin 0000A0
69746165 72432D2D 2D207365 6972616D 6D755320 72656E69 61746E6F 43206C61  al Container Summaries ---Creati 0000C0
6C206F4E 20726F66 20736C65 62614C64 65746E69 72702073 6C656261 4C20676E  ng Labels printedLabels for No l 0000E0
65757120 73696874 20726F66 20646574 6E697270 20656220 6F742073 6C656261  abels to be printed for this que 000100
35303031 32313132 20657565 7551206E 69207367 61422067 6E697472 6F536575  ueSorting Bags in Queue 21121005 000120
20203E2D 2D2D2039 2C382C35 2C342C33 2C322C31 20737365 72504142 4344354C  L5DCBAPress 1,2,3,4,5,8,9 --->   000140
736C6562 614C2820 4C20202D 2035706C 65482020 2D203874 69784520 202D2039  9 -  Exit8 -  Help5 -  L (Labels 000160
4220202D 20322043 20202D20 33204420 202D2034 29657565 75512079 6C6E4F20   Only Queue)4 -  D 3 -  C 2 -  B 000180
322D2D2D 206E6F69 7463656C 65532065 75657551 202D2D2D 20412020 2D203120   1 -  A --- Queue Selection ---2 0001A0
2D2D2039 2C382C34 2C332C32 2C312073 73657250 31323334 38483F34 30393132  21904?H84321Press 1,2,3,4,8,9 -- 0001C0
796C6C61 756E614D 202D2034 706C6548 202D2038 74697845 202D2039 20203E2D  ->  9 - Exit8 - Help4 - Manually 0001E0

Virtual block number 29 (0000001D), 512 (0200) bytes

6D6F4320 7473694C 202D2033 6574656C 706D6F43 20676142 2061206B 72614D20   Mark a Bag Complete3 - List Com 000000
5020646E 756F706D 6F43202D 20322065 6C756465 68635320 676E6964 6E756F70  pounding Schedule 2 - Compound P 000020
2D2D2D20 736C6562 614C2074 6E697250 202D2031 736E6F69 74706972 63736572  rescriptions1 - Print Labels --- 000040
494D4F54 55412D2D 2D20756E 654D2067 6E69646E 756F706D 6F43206E 69614D20   Main Compounding Menu ---AUTOMI 000060
00003030 326D6574 73795320 65726177 74666F53 2074736F 48205355 4C502058  X PLUS Host Software System200.. 000080
00000000 00000000 00000002 00000039 00000000 00000048 1C000202 00000048  H.......H.......9............... 0000A0
```

```
0000042F 0000042F 00000008 0000000A 000009B0 00000064 00000000 00000000 ........d................/.../... 0000C0
1A002027 10001B13 A6001613 88000000 F7504D41 54534806 0000042F 00000000 ..../....HSTAMP..............'... 0000E0
9C065327 92056A27 8802F527 7402A727 6002A227 56025D27 42018A27 2E002527 '%..'..B'J.V'..''..t'...'J..'S.. 000100
0409F827 F6088A27 E2087227 D8081D27 C407A027 BA074D27 A6073327 A106D227 '...'3..'N..'...'...'r..'...'... 000120
300D742A 1C0CF22A 080C9529 CC0C2E29 900C2929 7C0C1D29 5E0BE229 360AB929 )..6)..^)..|))..)...)...*...*t.0 000140
D00E792A BC0E2C2A A80DE42A 940DA02A 800D8F2A 6C0D8A2A 580D852A 440D802A *..D*..X*..1*...*...*...*...*y.. 000160
7010E32B 5C0F5C2B 480F572B 340F4B2B 200F3B2B 0C0ED62A F80EBF2A E40E9C2A *...*...*...+;. +K.4+W.H+\.\+..p 000180
1012AB2B FC124E2B E812332B D412062B C011C72B AC116A2B 98114F2B 8411222B +"..+0..+J..+...+...+3..+N..+... 0001A0
B0147F2C 9C143E2C 8813FD2C 7413E52C 60138F2C 4C13322C 3813172C 2412EA2C ,..$,..8,2.L,..`,..t,...>,..,.. 0001C0
5016802D 3C16612D 2816512D 14163A2D 0016352C EC16292C D814EA2C C414C02C ,........)..,5..-:..-Q.(-a.<-..P 0001E0
```

Virtual block number 30 (0000001E), 512 (0200) bytes

```
F0178F2D DC175A2D C817292D B417102D A017002D 8C16FB2D 7816EF2D 6416CA2D -..d-..x-..-...-...-)..-Z..-... 000000
9018452E 7C18392E 68181F2E 5417EE2E 4017D52E 2C17C52E 1817C02E 0417B42D -............,...@...T...h.9.I.E.. 000020
3019222F 1C19092F 0818F02E F418D72E E018AE2E CC18962E B818862E A4184A2E .J......................./.../'.0 000040
D01AD12F BC1AC12F A81AAC2F 941A6B2F 801A2A2F 6C19E92F 5819922F 44193B2F /;.D/..X/..1/*..,/k../.../.../... 000060
C01B9430 AC1B7430 981B6730 841B6230 341B5630 0C1B3D2F F81B362F E41B132F /.../6../=..0V.40b..0d..0t..0... 000080
601D3231 4C1CFA31 381C9131 241C7931 101C5B30 FC1C0830 E81BCC30 D41BB430 0...0...0...0[..1y.$1..81..L12.` 0000A0
001EBD31 EC1EB131 D81E9531 C41E3B31 B01D8131 9C1D7831 881D7331 741D5731 1W.1;s..1x..1..1;..1...1...1... 0000C0
A0203532 8C203032 78202B32 64201F32 50200532 3C1F3D32 281F0132 141EC232 2...2..(2=.<2. P2. d2+ x20 .25 . 0000E0
2C217733 19217233 18215833 04210B32 F520BE32 F020B932 DC20B432 C8208432 2. .2. .2. .2. .2.!.3X!.3r!.3w!, 000100
CC22BD33 B822A333 A4225233 90220233 7C21DA33 6821BF33 54218833 40218333 3.!@3.!T3.!h3.!|3.".3R".3.".3.". 000120
6C248E34 58240F34 4423A034 30238534 1C232734 0822F833 F422F333 E022E733 3.".3.".3.".4'$.4.$04.$D4.$X4.$1 000140
0C25F134 F825CA34 E425A234 D0259D34 BC259134 A8257734 94256234 8024CE34 4.$.4b%.4w%.4.%.4.%.4.%.4.%.4.%. 000160
AC26A035 98268735 84266E35 70265535 5C263C35 48262335 34260A35 2025FD35 5.% 5.&45&H5<&\5U&p5n&.5.&.5.&. 000180
4C276836 38274F36 24273636 10271D35 FC270435 E826EB35 D426D235 C026B935 5.&.5.&.5.&.5.'.5.'.66'$60'86h'L 0001A0
CE29F24A BA2B494A 42284444 38283836 9C279736 88279236 74278D36 60278136 6.'`6.'t6.'.6.'.68(BJD(BJI(.J.). 0001C0
782FF64B 6E2FA94B 642CE34B 0A2CDE4B 002CD24A FB2C414A F62B9B4A EC2A814A J.*.J.+.JA,.J,,.K,..K,.dK./nK./x 0001E0
```

Virtual block number 31 (0000001F), 512 (0200) bytes

```
FA336A4B DC33374B D232F04B C832D74B A031E34B 9631CA4B BC30D74B B230BE4B K.0.K.0.K.1.K.1.K.2.K.2.K73.KJ3. 000000
2435EF4F 1A35E34F 1035A74F 0634D14E FC34CC4E E833A04C 31339B4C 2C338F4B K.3,L.31L.3.N.4.N.4.O.5.O.5.O.5$ 000020
50378A55 3C378555 28376B4F A6375F4F 9C36D74F 6A36774F 6036724F 4C35F44F O.5LOr6`Ow6JO.6.O_7.Ok7(U.7<U.7P 000040
F03C7055 E63BEF55 C83AF355 B4391955 A0391455 8C387B55 73387655 6E384155 UA8nUv8sU(8.U.9.U.9.U.:.U.;.Up<. 000060
E43DE757 943DE257 803DD657 1C3D0956 CC3D0456 B83CF856 543C8156 043C7C55 UI<.V.<TV.<.V.=.V.=.W.=.W.=.W.=. 000080
1A3FD159 103F4458 F23F3F58 DE3EE358 C03EDE58 AC3E4D58 5C3E4858 483E3C57 W<>HXH>\XN>.X.>.X.>.X??.XD?.Y.?. 0000A0
20202020 656E694C 202F2023 23232323 0C40F861 A740F361 9E40E759 423FD659 Y.?BY.@.a.@.a.@.##### / Line      0000C0
712E6863 73747348 20676E69 74697257 20726F72 7245202A 2A2A2065 646F4320  Code *** Error Writing Hstsch.q 0000E0
23206365 52206575 712E6863 73747348 20676E69 64616552 23206365 52206575 ue Rec #Reading Hstsch.que Rec # 000100
63655220 67614220 676E6964 61655223 20636552 20676142 20676E69 74697257 Writing Bag Rec #Reading Bag Rec 000120
5020676E 69646165 52232063 65522074 6E656974 61502067 6E697469 72572320  #Writing Patient Rec #Reading P 000140
39393930 20203020 30203020 30203020 30203020 23206365 5220746E 65697461 atient Rec # 0 0 0 0 0 0 0   0999 000160
72657453 20203A29 65756E69 746E6F63 206F7420 7265746E 65207373 65727028 (press enter to continue):  Ster 000180
```

```
20202025 23232E23 23202020 20202020 20202020 20202072 65746157 20656C69 ile Water           $$.$$%   0001A0
74754120 2D20656D 614E202D 20232067 61422020 3F3F3F3F 232E2323 20202020     $$.$????  Bag $ - Name - Aut 0001C0
39414244 45462064 4920726F 6620676E 69646E75 6F706D6F 43206369 74616D6F omatic Compounding for Id FEDBA9 0001E0

Virtual block number 32 (00000020), 512 (0200) bytes

64616548 206F4E40 6D75736B 68432072 64486570 79542072 64482064 61423738 87Bad Hdr TypeHdr Chksum@No Head 000000
67617373 654D2064 61420D34 33303034 3030406D 75736B68 43206773 4D347265 er4Msg Chksum@0040034.Bad Messag 000020
40313030 40303230 31353032 30323031 30313030 30303030 30323536 30304065 e@00652000000010102020510200010 000040
51564D30 30303131 32313833 54524F42 41797274 6552330D 0D333330 30333030 0030033..3RetryABORT38121100PMVQ 000060
524F4853 204F4F54 23232D2D 30303030 30312020 31302020 20204A43 594E4B4F OKNYCJ    01  100000--##TOO SHOR 000080
2D2D2D30 30313020 20202323 23232323 234D5241 50204441 42444920 4E414D54 THAN IDBAD PARM#######   0100--- 0000A0
64657463 656A6552 20676142 20454E4F 442D2D2D 2D2D2D2D 2D2D2D2D 2D2D2D2D ---------------DONE Bag Rejected 0000C0
20646E61 6D6D6F43 20205845 4F484445 5443454A 45522064 49202D20 67614220  Bag - Id REJECTEDHOEX  Command  0000E0
7463656A 65523A67 6E696E69 616D6552 203A2974 69584520 726F2064 6C4F4B28 (HOld or EXit): Remaining:Reject 000100
65766974 63412020 3A644920 20206F74 75413A64 6574656C 706D6F43 3A206465 ed :Completed:Auto   Id:  Active 000120
65755120 656C7564 65686353 20676E69 73736563 6F725020 2D2D2020 3A644920  Id:  -- Processing Schedule Que 000140
69207367 6162206F 4E206575 65755164 65646E75 6F706D6F 63203232 32206575 ue 222 compoundedQueue No bags i 000160
6C616974 696E4920 2D2D2D2D 20646E75 6F706D6F 63206F74 20657565 7571206E n queue to compound ---- Initial 000180
58494D4F 54554120 65756575 5120656C 75646568 63532072 6F662067 6E697A69 izing for Schedule Queue AUTOMIX 0001A0
0000004B 1C000202 00000048 31323267 6E69646E 756F706D 6F432053 554C5020  PLUS Compounding221H.......H... 0001C0
00000037 00000000 00000000 00000000 00000000 00000000 0000001E 00000000 ...........................7... 0001E0

Virtual block number 33 (00000021), 512 (0200) bytes

54534806 00000247 00000000 00000247 00000247 00000008 00000006 000006A0 ............G...G.......G....HST 000000
84004B17 70002A15 1A002515 18002014 50001B13 EC001613 88000000 7D545052 RPT}.........P. ...%...*.p..K... 000020
6203411B 5803391B 10032317 FC02B417 E8029317 AC027217 98021B17 8701CF17 .........r..........#...9.X.A.b 000040
E406231B D006021B BC05E11B A805C01B 94059F1B 8005481B 6F04FC1B 6C03461B .F.l...o.H..................#.. 000060
EA07E51F D607561F C207141F A406C01F 4A06BB1F 4006AF1C E806A71B F806921B ...........@...J........V........ 000080
A60BF827 9C0A9727 88097D27 7E08F727 7408A327 1A089E27 10089221 3408751F .u.4!...'...';;t'..~'}..'...'... 0000A0
0412572B 0A106E28 000FAF27 EC0F5727 E20EBB27 D80EA227 C40E7327 B00D1227 '...'s..'...'...'W..'...(n..(W.. 0000C0
EC14782B 6613B22B 5C137F2B 2013652B 0C12E92B 02129A2A F812SE2A C6127129 )q..*...*...+...+e.. +..\+..f+x... 0000E0
6616C04E 5715C74E 4D157C4E 4815274E 3E15224E 2015164A 3815113A 9815052C ....:..BJ.., N'.>N'.HN!.MN..WN..f 000100
E8198E4E DE19184E D418DF4E B618264E 9818214E 8418154E 6F17BF4E 6817434E NC.kN..oN...N!..N3..N...N...N... 000120
6A1B404F 601B3B4F 4C1ABD4F 241AB84F 1A1AAC4F 101A754F 06199F4E FC199A4E N...N...Ou..O...O..$O..LO..^OE.J 000140
6E1D6C55 501CBB55 3C1CB655 281C5350 1E1C4E50 141C344F A61C284F 9C1BA04F O...O(..O4..PN..PS.(U..<U..PUl.n 000160
04219C55 F0219055 E6211155 C8201755 B41E4155 A01E3C55 8C1DA455 731D9F55 U..sU...U<..UA..U. .U.!.U.!.U.!. 000180
4822F757 E422A257 94229D57 80229157 1C220756 CC220256 B821F656 5421A156 V.!TV.!.V.".V.".W.".W.".W.".W."H. 0001A0
42249159 1A248C59 1023FF58 F223FA58 DE239E58 C0239958 AC230858 5C230358 X.#\X.#.X.#.X.#.X.#.X.#.Y.$.Y.$B 0001C0
6826555B 1826505B 0426025A B425FD5A A025B85A 5025B35A 3C25AE59 D825A259 Y.%.Y.%<Z.%PZ.%.Z.%.Z.3.[P3.[U3h 0001E0

Virtual block number 34 (00000022), 512 (0200) bytes

202A2A2A 0C281F61 A7281A61 9E280E5B FE26FD5B D626F85B CC26C85B 7C26C35B [.&I[.&.[.&.[.&.[.(.a.(.a.(.*** 000000
6C656261 4C2A2A2A 20736C65 62614C20 676E6973 7365636F 72502072 6F727245 Error Processing Labels ***Label 000020
```

```
45202A2A 2A206564 6F432020 20202065 6E694C20 2F202323 2323236C 626C2E73 s.lbl##### / Line     Code *** E 000040
52232323 20636552 20657571 2E686373 74734820 676E6974 69725720 726F7272 rror Writing Hstsch.que Rec ###R 000060
4220676E 69746972 57232063 65522065 75712E68 63737473 4820676E 69646165 eading Hstsch.que Rec #Writing B 000080
676E6974 69725723 20636552 20676142 20676E69 64616552 23206365 52206761 ag Rec #Reading Bag Rec #Writing 0000A0
65522074 6E656974 61502067 6E696461 65522320 63655220 746E6569 74615020  Patient Rec #Reading Patient Re 0000C0
27656D6F 48273939 39232323 30202030 20302030 20302030 20302030 20232063 c # 0 0 0 0 0 0 0 0  0###999'Home' 0000E0
61622D27 70552067 5027202C 74657365 72202620 706F7420 6F74206B 6361622D -back to top & reset, 'Pg Up'-ba 000100
6E652073 73657270 28656E6F 642D276E 44206750 27202C70 6F74206F 74206B63 ck to top, 'Pg Dn'-done(press en 000120
65697461 50206461 42202A2A 2A20203A 2965756E 69746E6F 63206F74 20726574 ter to continue):  *** Bad Patie 000140
67676F6C 20646577 6F6C6C61 20746F6E 20737365 6363412A 2A2A2044 4920746E nt ID ***Access not allowed logg 000160
20203A64 726F7773 73615020 7265746E 45582072 6F746172 65704F6E 6F206465 ed onOperator XEnter Password:   000180
20644920 67614220 676E6979 66697265 5620726F 72724520 79726F6D 654D5930 0YMemory Error Verifying Bag Id  0001A0
65564E20 64492067 61422067 6E697966 69726556 20726F72 7245206B 73694420  Disk Error Verifying Bag Id NVe 0001C0
72452079 726F6D65 4D6E6F69 74616D72 6F666E49 20676142 20676E69 79666972 rifying Bag InformationMemory Er 0001E0
```

Virtual block number 35 (00000023), 512 (0200) bytes

```
7245206B 73694420 64492074 6E656974 61502067 6E697966 69726556 20726F72 ror Verifying Patient Id Disk Er 000000
69796669 72655620 64492074 6E656974 61502067 6E697966 69726556 20726F72 ror Verifying Patient Id Verifyi 000020
342C332C 322C3120 73736572 50333431 33732744 4920746E 65697461 5020676E ng Patient ID's3143Press 1,2,3,4 000040
73657565 7551206C 6C612079 66697265 56202D20 3420203E 2D2D2D20 392C382C ,8,9 --->  4 - Verify all Queues 000060
6556202D 20326E6F 6974616D 726F666E 49206761 42207966 69726556 202D2033 3 - Verify Bag Information2 - Ve 000080
64754120 6C6C6120 6E755220 2D203173 27444920 746E6569 74615020 79666972 rify Patient ID's1 - Run all Aud 0000A0
483F3033 39737469 64754120 74736F48 2053554C 50205849 4D4F5455 41737469 itsAUTOMIX PLUS Host Audits930?H 0000C0
38746978 45202D20 3920203E 2D2D2D20 392C382C 322C3120 73736572 50313238 821Press 1,2,8,9 --->  9 - Exit8 0000E0
2D2D2D20 73746964 7541202D 20317374 726F7065 52202D20 32706C65 48202D20  - Help2 - Reports1 - Audits --- 000100
726F7065 52205355 4C502058 494D4F54 55412D2D 2D20756E 654D206E 69614D20  Main Menu ---AUTOMIX PLUS Repor 000120
00000000 00000048 1C000202 00000048 30303373 74696475 4120646E 61207374 ts and Audits300H.......H........ 000140
00000014 00000000 00000000 00000000 00000000 00000000 00000001 00000005 ................................ 000160
074D4954 54534806 0000006F 00000000 0000006F 0000006F 00000000 00000003 ........o...o.......o....HSTTIM. 000180
0C020D55 8C018353 FC00C453 34007752 D0002052 6C001B52 0800164E 20000000 ....N...R..lR ..Rw.4S...S...U... 0001A0
00000000 00000002 00000006 00000000 00000048 3C000302 00000048 58454F48 HOEXH......<H................... 0001C0
00000060 00000000 00000006 00000000 00000000 00000000 00000000 00000000 ............................`... 0001E0
```

Virtual block number 36 (00000024), 512 (0200) bytes

```
00207D1E 001B7D0A 00167D00 00000004 58454803 00000060 00000000 00000060 `.......`....HEX.....}...}...} . 000000
00000000 00000000 00000046 45444342 41393837 36353433 3231300C 01297D63 c})..0123456789ABCDEF........... 000020
00000000 00000000 00000000 00000000 00000000 00000000 00000000 00000000 ................................ 000040
00000000 00000000 00000000 00000000 00000000 00000000 00000000 00000000 ................................ 000060
00000000 00000000 00000000 00000000 00000000 00000000 00000000 00000000 ................................ 000080
00000000 00000000 00000000 00000000 00000000 00000000 00000000 00000000 ................................ 0000A0
00000000 00000000 00000000 00000000 00000000 00000000 00000000 00000000 ................................ 0000C0
00000000 00000000 00000000 00000000 00000000 00000000 00000000 00000000 ................................ 0000E0
00000000 00000000 00000000 00000000 00000000 00000000 00000000 00000000 ................................ 000100
00000000 00000000 00000000 00000000 00000000 00000000 00000000 00000000 ................................ 000120
```

```
00000000 00000000 00000000 00000000 00000000 00000000 00000000 00000000 ................................ 000140
00000000 00000000 00000000 00000000 00000000 00000000 00000000 00000000 ................................ 000160
00000000 00000000 00000000 00000000 00000000 00000000 00000000 00000000 ................................ 000180
00000000 00000000 00000000 00000000 00000000 00000000 00000000 00000000 ................................ 0001A0
00000000 00000000 00000000 00000000 00000000 00000000 00000000 00000000 ................................ 0001C0
00000000 00000000 00000000 00000000 00000000 00000000 00000000 00000000 ................................ 0001E0

Virtual block number 37 (00000025), 512 (0200) bytes

00000000 00000000 00000000 00000000 00000000 00000000 00000000 00000000 ................................ 000000
00000000 00000000 00000000 00000000 00000000 00000000 00000000 00000000 ................................ 000020
00000000 00000000 00000000 00000000 00000000 00000000 00000000 00000000 ................................ 000040
00000000 00000000 00000000 00000000 00000000 00000000 00000000 00000000 ................................ 000060
00007C28 010E000A 00000000 00000000 00000000 00000000 00000000 00000000 ..............................(|.. 000080
00000353 010E000E 00000361 010E0011 00000372 010E0021 00000393 010E0003 ........!...r.......a.......S... 0000A0
0000031E 010E0008 00000326 010E0008 0000032E 010E0016 00000344 010E000F ....D..............&............ 0000C0
00000303 010E0007 0000030A 010E0006 00000310 010E0007 00000317 010E0007 ................................ 0000E0
000003FE 010E0001 00000298 010E0020 000002B8 010E0029 000002EA 010E0019 ........)....................... 000100
000003FA 010E0001 000003FB 010E0001 000003F8 010E0001 000003FC 010E0002 ................................ 000120
000004CB 010E0001 00007C28 010E000A 000004C9 010E000A 000003F9 010E0001 ...................(|........... 000140
000005B6 010E0001 00004800 010E0014 00000488 010E001C 000004A4 010E0022 ......................H......... 000160
00000CAF 010E0003 00007C28 010E000A 00000CB2 010E0005 00000CB7 010E0003 ...................(|........... 000180
00000C57 010E0007 00000C5E 010E0025 00000C83 010E000B 00000C8E 010E0021 !...............%..^.......W... 0001A0
00000C24 010E001A 00000C43 010E0007 00000C4A 010E0006 00000C50 010E0007 ....F.......J.......C.......$... 0001C0
00000BD6 010E002E 00000C04 010E0017 00000C1B 010E0004 00000C21 010E0003 ....!........................... 0001E0

Virtual block number 38 (00000026), 512 (0200) bytes

00000B9C 010E000A 00000BA6 010E0022 00000BC8 010E0004 00000BCC 010E000A ................................ 000000
00000000 010E0001 00000000 010E0001 00000000 010E0012 00000000 010E0005 ................................ 000020
00000B75 010E000A 00000B7F 010E001D 00000000 010E0001 00000000 010E0001 ............................u... 000040
00000B55 010E0020 00000000 010E000C 00000000 010E0006 00000000 010E0018 ............................U... 000060
0000725E 010E0001 00007236 010E0028 0000720E 010E0028 00000B4B 010E000A ....K...(....r..(...6r......Kr.. 000080
00000B2A 010E0021 0000726F 010E0001 0000726E 010E0001 0000725F 010E000B ...._r.......nr.......or..!...*... 0000A0
00000AE8 010E000A 00000AF2 010E0024 00000B16 010E000A 00000B20 010E000A ..................$............. 0000C0
00000000 010E000A 00000AAC 010E000A 00000AB6 010E0028 00000ABE 010E000A ........(....................... 0000E0
00000A8C 010E0004 00000A90 010E0012 00000AA2 010E000A 00000000 010E000F ................................ 000100
00000A3F 010E0018 00000A57 010E0001 00000A58 010E0018 00000A70 010E001C ....P.......X.......W.......?... 000120
00000DF7 010E0021 00000E18 010E0003 00007C28 010E000A 00000A14 010E0029 )...........(|..........!....... 000140
00000D91 010E0011 00000DA2 010E001C 00000DBE 010E001D 00000DDB 010E001C ................................ 000160
00000D56 010E0019 00000D6F 010E0008 00000D77 010E0008 00000D7F 010E0012 ............W.......o.......V... 000180
000018D9 010E0023 000018FC 010E0016 00001912 010E0003 00007C28 010E000A ....(|...................#...... 0001A0
00001887 010E0003 0000188A 010E000D 000018A8 010E0008 000018C6 010E0013 ................................ 0001C0
0000186A 010E0008 00001872 010E0014 00007C41 010E000C 00007D87 010E0008 .....}......DI.......r.......J... 0001E0
```

```
Virtual block number 39 (00000027), 512 (0200) bytes

000062B2 010E0008 00007D9E 010E0002 00007DA0 010E0003 00001867 010E0003 ....a.........}.......}.......b.. 000000
00001840 010E0010 000061E2 010E0004 00001850 010E0005 00001855 010E0010 ....U.......P.......a.......@... 000020
00007C6E 010E000C 00001820 010E0010 00007C50 010E001E 00001830 010E0010 ....0.......P|..............n|.. 000040
00007C8D 010E0001 00001800 010E0010 00007C7A 010E000F 00001810 010E0010 ............z|...............|.. 000060
000017C3 010E0010 00007C89 010E0004 000017D3 010E0010 000017E3 010E001D ........................|....... 000080
000017A5 010E0012 000017B7 010E0008 000017BF 010E0004 00007C8E 010E0005 ....|........................... 0000A0
000017B9 010E0010 00001799 010E0008 000017A1 010E0004 00007C93 010E0003 ....|........................... 0000C0
00001769 010E0010 00007CC8 010E0032 00001779 010E0010 00007C96 010E0032 2...|.......y...2...|.......i... 0000E0
00001749 010E0010 00007D2F 010E0028 00001759 010E0010 00007CFA 010E0032 2...|.......Y...(.../}......I... 000100
0000172F 010E000A 00007D2C 010E0003 00001739 010E0010 00007D57 010E0028 (..W}.......9.......}......./... 000120
0000171F 010E0005 00001724 010E000A 0000172E 010E0001 00007D7F 010E0008 ....}...............$........... 000140
000061B8 010E000C 0000170D 010E0010 0000171D 010E0002 00007D8F 010E000F ....}.......................a.. 000160
000016EF 010E0010 000016FF 010E0007 00001706 010E0007 000061C4 010E001E ....a........................... 000180
000061EA 010E0004 000016DC 010E0010 000016EC 010E0003 000061E6 010E0004 ....a.......................a.. 0001A0
000016C2 010E0009 000062AA 010E0008 000016CB 010E0009 000016D6 010E0006 ......................b......... 0001C0
000062C9 010E000F 000016B2 010E000C 000062BA 010E000F 000016BE 010E0001 ............b...............b.. 0001E0

Virtual block number 40 (00000028), 512 (0200) bytes

0000169C 010E0001 00000000 010E0006 000016B1 010E0001 00000000 010E0018 ................................ 000000
00001693 010E0005 000061EE 010E0020 00001698 010E0003 0000169B 010E0001 .....................a.......... 000020
00001683 010E0004 00001687 010E0002 00001689 010E0005 0000168E 010E0005 ................................ 000040
00001675 010E0006 00000000 010E0012 0000167B 010E0004 0000167F 010E0004 ............{...............u... 000060
00001651 010E0003 0000166B 010E0005 0000620E 010E009C 00001670 010E0005 ....p.......b.....k.......Q... 000080
000062DB 010E0003 000062FC 010E0003 00001617 010E0039 00007C44 010E0163 c...DT..9...............b.......b.. 0000A0
000061B8 010E014E 000015E6 010E0012 000015F9 010E001D 000062D8 010E0003 ....b...................N....a... 0000C0
00001561 010E0033 00001595 010E0002 00001597 010E0005 000015A5 010E0041 A.......................3....a... 0000E0
00000000 010E0005 00001531 010E000D 0000153E 010E0023 000062DE 010E000C .....b..#...>.......1........... 000100
000014FB 010E0003 000014FE 010E000A 00001514 010E000A 00001527 010E000A ....'........................... 000120
000014F8 010E0001 000014E7 010E0011 000014F9 010E0001 000014FA 010E0001 ................................ 000140
000014AC 010E0016 000014C2 010E0012 000014D4 010E000A 000014DE 010E0009 ................................ 000160
00000000 010E0064 00001416 010E0017 00001453 010E003D 00001490 010E001C ........=...S...........d....... 000180
000013E0 010E0001 00000000 010E0064 000013E1 010E000D 000013FE 010E0004 ................d............... 0001A0
00000000 010E0064 000013CB 010E0015 00000000 010E0064 00000000 010E0064 d.......d...............d....... 0001C0
00007DA9 010E0003 00000000 010E0064 00000000 010E0064 0000165F 010E0001 ...._...d.......d...........}.. 0001E0

Virtual block number 41 (00000029), 512 (0200) bytes

000013B3 010E0015 00007DAF 010E0003 0000142D 010E0003 00007DAC 010E0003 ....}.......-.......}........... 000000
00001364 010E0018 0000137C 010E0011 0000139D 010E0011 0000139E 010E0015 ....................|.......d... 000020
00001331 010E0008 00001339 010E0009 00001342 010E000A 0000134C 010E0018 ....L.......B.......9.......1... 000040
000022B7 010E0025 000022DC 010E0021 000022FD 010E0003 00007C28 010E000A ....(|.......'..!....'..%....'.. 000060
0000229B 010E0007 000022A2 010E0007 000022A9 010E0007 000022B0 010E0007 ....'.......'.......'.......'.. 000080
00002254 010E001B 0000226F 010E0009 00002278 010E0009 00002281 010E001A ....'.......x'......o'......T'.. 0000A0
```

```
0000221D 010E0027 000062FC 010E0003 000061B8 010E014E 00007DA9 010E0003 .....}..N....a........b..'....'.. 0000C0
00002209 010E0010 00007C44 010E000C 00007D87 010E0008 0000221A 010E0003 .....'.........}......D|........'.. 0000E0
000062B2 010E0008 00007D9E 010E0002 000021FE 010E0003 00002201 010E0008 .....'.......!.......}.......b.. 000100
000062DE 010E000C 000021C2 010E0033 000061E2 010E0004 000021F5 010E0005 .....!........a..3....!........b.. 000120
00002163 010E0010 00002173 010E000B 0000217E 010E000B 00002186 010E003C <....!......~!......s!......c!.. 000140
00007C6E 010E000C 00002143 010E0010 00007C50 010E001E 00002153 010E0010 ....S!.......P|......C!......n|.. 000160
00007C8D 010E0001 00002123 010E0010 00007C7A 010E000F 00002133 010E0010 ....3!......z|.......!.......|.. 0001B0
000020E6 010E0010 00007C89 010E0004 000020F6 010E0010 00002106 010E001D .....!........ .......|........ .. 0001A0
000020CB 010E0012 000020DA 010E0008 000020E2 010E0004 00007CBE 010E0005 .....|........ ....... ........ .. 0001C0
000020AC 010E0010 000020BC 010E0008 000020C4 010E0004 00007C93 010E0003 .....|........ ....... ........ .. 0001E0

Virtual block number 42 (0000002A), 512 (0200) bytes

0000208C 010E0010 00007CC8 010E0032 0000209C 010E0010 00007C96 010E0032 2....|........ ..2....|........ .. 000000
0000206C 010E0010 00007D2F 010E0028 0000207C 010E0010 00007CFA 010E0032 2....|.......| ..(.../}.....l .. 000020
00002052 010E000A 00007D2C 010E0003 0000205C 010E0010 00007D57 010E0028 (...W}......\ .......}......R .. 000040
00002042 010E0005 00002047 010E000A 00002051 010E0001 00007D7F 010E0008 .....}......Q ......G ......B .. 000060
000061B8 010E000C 0000201F 010E0010 0000202F 010E0002 00007D8F 010E000F .....}......./ ....... ........e.. 000080
00002001 010E0010 00002011 010E0007 00002018 010E0007 000061C4 010E001E .....a........ ....... ....... .. 0000A0
000061EA 010E0004 00001FEE 010E0010 00001FFE 010E0003 000061E6 010E0004 ....a.........................a.. 0000C0
00001FD5 010E0009 000062AA 010E0008 00001FDE 010E0009 00001FE8 010E0006 ......................b.......... 0000E0
000062C9 010E000F 00001FC5 010E000C 000062BA 010E000F 00001FD1 010E0004 .............b...............b.. 000100
00001FAF 010E0001 00000000 010E0006 00001FC4 010E0001 00000000 010E0018 ................................ 000120
00001FA6 010E0005 000061EE 010E0020 00001FAB 010E0003 00001FAE 010E0001 .................. ....a......... 000140
00001F96 010E0004 00001F9A 010E0002 00001F9C 010E0005 00001FA1 010E0005 ................................ 000160
00001F88 010E0006 00000000 010E0012 00001F8E 010E0004 00001F92 010E0004 ................................ 000180
00007D44 010E0163 00001F6A 010E0003 0000620E 010E009C 00001F83 010E0005 ..............b......j...c...D|.. 0001A0
00001EF4 010E0023 00001F18 010E0002 00001F1A 010E0005 00001F2B 010E0041 A...(....................$....... 0001C0
00001ED3 010E0001 00001EDD 010E000A 00000000 010E0005 00001EE7 010E000D ................................ 0001E0

Virtual block number 43 (0000002B), 512 (0200) bytes

00001EB8 010E0009 00001ED2 010E0001 00001EC1 010E0011 00002244 010E0001 ....D'.......................... 000000
00001E6A 010E001C 00001E86 010E0016 00001E9C 010E0012 00001EAE 010E000A ...........................j.... 000020
00001E03 010E0015 00007DA0 010E0003 00001E18 010E0015 00001E2D 010E003D =...-..................}.......... 000040
00001DB1 010E0018 00001DC9 010E0018 00001DE1 010E0011 00001DF2 010E0011 ................................ 000060
00001D91 010E0005 00001D96 010E0008 00001D9E 010E0009 00001DA7 010E000A ................................ 000080
000062DB 010E0003 000062DE 010E000C 00007DA0 010E0003 00007D9E 010E0002 .....}........}.......b.......b.. 0000A0
0000251C 010E0012 0000252E 010E0003 00007C50 010E001E 00007C44 010E000C ....D|.......P|.......%.......%.. 0000C0
000024FC 010E0003 00007C28 010E000A 000024FF 010E0012 00002511 010E000B .....%.......$.......(|.......$.. 0000E0
000024B3 010E001C 000024CF 010E0017 000024E6 010E000C 000024F2 010E000A .....$.......$........$.......$.. 000100
0000244A 010E0002 0000244C 010E0015 00002461 010E0015 00002476 010E003D =...v$.......a$.......L$......J$.. 000120
00002415 010E0009 0000241E 010E000A 00002428 010E0011 00002439 010E0011 ....9$......($........$.......$.. 000140
00002A14 010E0003 00007C28 010E000A 00002408 010E0005 0000240D 010E0008 .....$.......$.......(|........*.. 000160
000029B2 010E0014 000029CA 010E0013 000029DD 010E0023 00002A00 010E0014 .....*..*.....).......).......).. 000180
00002975 010E0029 0000299E 010E0003 000029A1 010E0008 000029A9 010E0008 .....).......).......)..)...u).. 0001A0
```

```
00002941 010E0028 000062D8 010E0003 00007D9E 010E0002 00007DA0 010E0003 .....).......).......b..(...A).. 0001C0
00007C50 010E001E 00002920 010E0010 00007C41 010E000C 00002930 010E0010 ....0)......D|...... )......P|.. 0001E0

Virtual block number 44 (0000002C), 512 (0200) bytes

00007C7A 010E000F 00002900 010E0010 00007C6E 010E000C 00002910 010E0010 .....)......n|.......)......z|.. 000000
000028C3 010E0010 000028D3 010E001D 00007C8D 010E0001 000028F0 010E0010 .....(.......|.......(.......(.. 000020
000028AF 010E0004 00007C8E 010E0005 000028B3 010E0010 00007C89 010E0004 .....|.......(.......|.......(.. 000040
00002891 010E0004 00007C93 010E0003 00002895 010E0012 000028A7 010E0008 .....(.......(.......|.......(.. 000060
00002869 010E0010 00007C96 010E0032 00002879 010E0010 00002889 010E0008 .....(......y(..2....|......i(.. 000080
00002849 010E0010 00007CFA 010E0032 00002859 010E0010 00007CC8 010E0032 2....|......Y(..2....|......I(.. 0000A0
00002829 010E0010 00007D57 010E0028 00002839 010E0010 00007D2F 010E0028 (../)......9(..(...W)......)(.. 0000C0
0000281E 010E0001 00007D7F 010E0008 0000281F 010E000A 00007D2C 010E0003 .....).......(.......).......(.. 0000E0
00007D8F 010E000F 0000280F 010E0005 00007D87 010E0008 00002814 010E000A .....(.......).......(.......).. 000100
000027DA 010E0001 000027DB 010E0011 000027EC 010E0010 000027FC 010E0002 .....'.......'.......'.......'.. 000120
000027B4 010E0012 000027C6 010E000A 000027D0 010E0009 000027D9 010E0001 .....'.......'.......'.......'.. 000140
0000272B 010E0003 00002745 010E003D 00002782 010E001C 0000279E 010E0016 .....'.......'.......E'......+'.. 000160
00002940 010E0001 00000000 010E0064 00002716 010E0015 0000272E 010E0017 .....'.......'..d...........@).. 000180
00002701 010E0015 000062D8 010E0003 00000000 010E0064 00000000 010E0064 d.......d...............b......'.. 0001A0
000026C8 010E0011 000026D9 010E0011 000026EA 010E0002 000026EC 010E0015 .....&.......&.......&.......&.. 0001C0
000026A8 010E0005 000026AD 010E0008 000026B5 010E0009 000026BE 010E000A .....3.......3.......3.......3.. 0001E0

Virtual block number 45 (0000002D), 512 (0200) bytes

0000385D 010E001D 0000387A 010E0021 0000389B 010E0003 00007C28 010E000A ....(|.......8..!...z8......J8.. 000000
000037F4 010E0020 00003814 010E001E 00003832 010E001A 0000384C 010E0011 ....L8......28.......8.......7.. 000020
000037BF 010E0003 000037CC 010E0018 000037E4 010E0008 000037EC 010E000B .....7.......7.......7.......7.. 000040
00003793 010E0007 0000379A 010E0007 000037A1 010E0007 000037A8 010E0017 .....7.......7.......7.......7.. 000060
00003760 010E0009 00003769 010E0009 00003772 010E001A 0000378C 010E0007 .....7......r7......i7......`7.. 000080
00007DA9 010E0003 00003722 010E0016 00003738 010E0003 00003746 010E001A ....F7......87......'7.......).. 0000A0
000036E9 010E0008 000036F1 010E000B 000036FC 010E0026 00007DAF 010E0003 .....)..&....6.......6.......6.. 0000C0
000061B8 010E014E 000062DE 010E000C 000062FC 010E0003 000036DA 010E000F .....6.......b.......b..N....a.. 0000E0
000036A3 010E0006 000036A9 010E0001 000036AA 010E0004 00000000 010E0012 .............6.......6.......6.. 000100
00003679 010E001F 00003698 010E0003 0000369B 010E0006 000036A1 010E0002 .....6.......6.......6......y6.. 000120
00003654 010E0009 0000365D 010E000C 00003669 010E000C 00003675 010E0004 ....u6......i6......J6......T6.. 000140
000035E0 010E0007 0000620E 010E009C 0000363F 010E0009 00003648 010E000C ....H6......?6.......b.......5.. 000160
000061EE 010E0020 000035DD 010E0003 00000000 010E0006 00000000 010E0018 .....................5.......a.. 000180
000061E6 010E0004 000035A6 010E0004 000035AA 010E0002 00000000 010E0012 .............5.......5.......a.. 0001A0
0000354B 010E0005 00003564 010E0010 00003574 010E0005 00003579 010E002D -...y5......t5......d5......K5.. 0001C0
000061EA 010E0004 00003509 010E000D 0000725F 010E000B 0000353E 010E000D ....>5......_r.......5.......a.. 0001E0

Virtual block number 46 (0000002E), 512 (0200) bytes

000062BA 010E000F 00003485 010E0006 0000348B 010E0015 000034A0 010E0007 .....4.......4.......4.......b.. 000000
0000342E 010E001D 0000344B 010E001D 000062C9 010E000F 00003468 010E001D ....h4.......b......K4.......4.. 000020
```

```
000061E2 010E0004 000033EA 010E001A 00003404 010E0006 00007C44 010E000C ....D!.......4.......3........a.. 000040
000033DE 010E0006 00007C6E 010E000C 000033E4 010E0006 00007C50 010E001E ....P!.......3......n!.......3.. 000060
00000000 010E0012 000033AE 010E0005 00000000 010E0006 00000000 010E0018 ........................3......... 000080
0000338E 010E0006 00000000 010E0012 000033A9 010E0002 000033AB 010E0003 .....3.......3...............3.. 0000A0
0000337B 010E0013 00003373 010E0005 0000338B 010E0003 00003394 010E0014 .....3.......3......s3......x3.. 0000C0
0000334F 010E0004 00003359 010E0007 00003353 010E0006 00003340 010E0013 ....`3......S3......Y3......03.. 0000E0
0000332E 010E0007 00003335 010E0007 0000333C 010E0007 00003343 010E000C ....C3......<3......53.......3.. 000100
00003314 010E0007 0000331B 010E0007 00003322 010E0007 00003329 010E0005 ....)3......'3.......3.......3.. 000120
000032B8 010E0031 000032EE 010E0013 000032E9 010E0005 00003301 010E0013 .....3.......2.......2..1....2.. 000140
00003299 010E0003 0000329F 010E0002 000032A1 010E0003 000032A7 010E0010 .....2.......2.......2.......2.. 000160
0000326A 010E001E 00003288 010E0003 0000328B 010E0004 0000328F 010E000A .....2.......2.......2......J2.. 000180
00003263 010E0007 00000000 010E0012 000061C4 010E001E 000061B8 010E000C .....a.......a...............c2.. 0001A0
000062ED 010E0003 000062EA 010E0003 0000324C 010E0008 00003254 010E000F ....T2......L2.......b.......b.. 0001C0
000062F9 010E0003 000062F6 010E0003 000062F3 010E0003 000062F0 010E0003 .....b.......b.......b.......b.. 0001E0
```

Virtual block number 47 (0000002F), 512 (0200) bytes

```
00003228 010E0003 0000322E 010E0007 00003235 010E0017 00007DAC 010E0003 .....}......52.......2......(2.. 000000
000031C0 010E001A 000031DC 010E0013 000031EF 010E0023 00003212 010E0016 .....2..$....1.......1.......1.. 000020
000062D8 010E0003 00007D9E 010E0002 00007DA0 010E0003 000031AD 010E0013 .....1.......}.......}.......b.. 000040
0000311E 010E0021 0000313F 010E0021 00003160 010E0029 00003189 010E0024 $....1..)...`1..!...?1..!....1.. 000060
000030E0 010E0026 00003106 010E000F 00003115 010E0005 0000311A 010E0004 .....1.......1.......1..&....0.. 000080
00000000 010E0006 00000000 010E0018 000030CF 010E000A 000030D9 010E0007 .....0.......0.................. 0000A0
000030A2 010E0001 000030A3 010E0011 000030B4 010E001B 00000000 010E0012 .............0.......0.......0.. 0000C0
00003067 010E0016 0000307D 010E0012 0000308F 010E000A 00003099 010E0009 .....0.......0......}0......a0.. 0000E0
00002FEA 010E0015 000032A4 010E0003 0000300E 010E003D 0000304B 010E001C ....K0..=....0.......2......./.. 000100
00002F9B 010E0018 00002FB3 010E0011 00002FC4 010E0011 00002FD5 010E0015 ...../......./......./......./.. 000120
00002F68 010E0008 00002F70 010E0009 00002F79 010E000A 00002F83 010E0018 ...../......y/......P/......h/.. 000140
00003FB9 010E0018 00003FD1 010E0003 00007C28 010E000A 00002F5E 010E000A ....^/......(|.......?.......?.. 000160
00007DAF 010E0003 00007DA9 010E0003 00003F93 010E0003 00003F96 010E0023 &....?.......?.......}.......}.. 000180
00003F71 010E0006 00003F77 010E001C 000061B8 010E014E 000062FC 010E0003 .....b..N....a......w?......a?.. 0001A0
00003F3A 010E000C 00003F46 010E001D 00003F63 010E0003 00003F66 010E000B ....f?......c?......F?......!?.. 0001C0
00003F10 010E000A 00003F1A 010E000A 00003F24 010E000A 00003F2E 010E000C .....?......$?.......?.......?.. 0001E0
```

Virtual block number 48 (00000030), 512 (0200) bytes

```
00003ED8 010E0012 000061B8 010E000C 000062DE 010E000C 00003EF8 010E001B .....>.......b.......a.......>.. 000000
00003EAF 010E0003 00003EB2 010E0004 000061E2 010E0004 00003EB3 010E0005 .....>.......a.......>.......>.. 000020
00003E84 010E0001 00003E85 010E0001 00003E8C 010E0001 00003E96 010E0002 .....>.......>.......>.......>.. 000040
00003E41 010E0003 00003E68 010E0001 00003E5B 010E0004 00003E47 010E0014 ....G>......[>......h>......A>.. 000060
00003DD6 010E0007 000061C4 010E001E 00003DDD 010E001D 00003E2D 010E0009 ....->.......=.......a.......=.. 000080
00000000 010E0018 00003DBD 010E0007 0000620E 010E009C 00003DCC 010E000A .............b.......=.......... 0000A0
00003DB7 010E0006 00000000 010E0012 000061EE 010E0020 00000000 010E0006 .............a...............=.. 0000C0
00003D80 010E001C 00003D9C 010E001B 000061E6 010E0004 00003EF6 010E0002 .....>.......a.......=.......=.. 0000E0
00003D57 010E0015 00003D7B 010E0002 00003D7A 010E0003 00007DAC 010E0003 .....}.......z=......x=......W=.. 000100
00003D31 010E0011 00003D42 010E0015 00007DA0 010E0003 00007D9E 010E0002 .....}.......}......B=.......1=.. 000120
```

```
00003CE6 010E000A 00003CF0 010E0018 00003D08 010E0018 00003D20 010E0011 ....=.......=.......<.......<.. 000140
00007C28 010E000A 00003CD0 010E0005 00003CD5 010E0008 00003CDD 010E0009 .....<.......<.......<......(I.. 000160
00004512 010E000B 0000451D 010E0011 0000452E 010E001F 0000454D 010E0003 ....ME.......E.......E.......E.. 000180
000044E3 010E0014 000044F7 010E0008 000044FF 010E0008 00004507 010E000B .....E.......D.......D.......D.. 0001A0
00004480 010E001A 0000449A 010E0017 000044B1 010E0012 000044C3 010E0018 .....D.......D.......D.......D.. 0001C0
00007C44 010E000C 00004439 010E0016 00004453 010E0018 0000446B 010E0015 ....kD......SD......9D......DI.. 0001E0
```

Virtual block number 49 (00000031), 512 (0200) bytes

```
00007BB0 010E0064 000043DE 010E0019 000043F7 010E0022 00004419 010E0020 ....D..".....C.......C..d....{.. 000000
000061E2 010E0004 000043C0 010E0001 000043C1 010E001C 000061B8 010E000C .....a.......C.......C.......a.. 000020
00000000 010E0064 000043A2 010E001E 00000000 010E0064 000043DD 010E0001 .....C..d............C..d....... 000040
00000000 010E0064 000043A1 010E0001 00000000 010E0064 00000000 010E0064 d.......d............C..d....... 000060
00007DA0 010E0003 00000000 010E0064 00000000 010E0064 00000000 010E0064 d.......d.......d...........}.. 000080
000062DB 010E0003 000062D8 010E0003 000062FC 010E0003 00007D9E 010E0002 .....}.......b.......b.......b.. 0000A0
0000437B 010E000A 00004385 010E0009 0000438E 010E0001 0000438F 010E0011 .....C.......C.......C......{C.. 0000C0
000042FA 010E003D 00004337 010E001C 00004353 010E0016 00004369 010E0012 ....iC......SC.......7C..=....B.. 0000E0
000061B8 010E014E 00007DAC 010E0003 00007DA9 010E0003 000042F4 010E0003 .....B.......}.......}..N....a.. 000100
00007DAF 010E0003 000042EF 010E0002 000062DE 010E000C 000042F1 010E0003 .....B.......b.......B.......}.. 000120
00004297 010E0011 000042A8 010E0011 000042B9 010E0015 000042CE 010E0015 .....B.......B.......B.......B.. 000140
0000425B 010E000A 00004265 010E0018 0000427F 010E0013 0000427D 010E0002 ....}B.......B......eB......[B.. 000160
0000423B 010E000A 00004245 010E0005 0000424A 010E0006 00004252 010E0009 ....RB......JB......EB......;B.. 000180
00000000 00000000 00004625 010E0010 00004800 010E0084 00004884 010E0014 .....H.......H......%F.......... 0001A0
00000000 00000000 00000000 00000000 00000000 00000000 00000000 00000000 ................................ 0001C0
00000000 00000000 00000000 00000000 00000000 00000000 00000000 00000000 ................................ 0001E0
```

Virtual block number 50 (00000032), 512 (0200) bytes

```
FCADFDAF 9EFCADFD AF9E0001 EAB2FF16 5150D050 FFFF7FF4 EF9E52FB AF9ECFFC .....R......F.FQ................ 000000
120000C0 808E5C51 5C77AB4E 00000DD4 EF01FB77 ABDFFCAD FDAF9EFC ADFDAF9E ..............W........N.w\Q\..... 000020
FB0001EA 9DFF01FB FFFFC640 EF9F0001 EAB2FF01 FB00DDFC ADFDAF9E 04413103 .1A..................@.......... 000040
DD000004 EDEF02FB F8A9DFF8 A918D0FC A9DFFCA9 0000004D 8FD00001 EA7EFF00 ..~.....M....................... 000060
FCA916D0 0001EA48 FF00FB00 01EA6FFF 01FBFFFF C612EF9F 0001EA4C FF01FB00 ....L...............O.......H... 000080
FFFFC5E8 EF9F0001 EA1AFF01 FB00DD00 0004BBEF 02FBF8A9 DFF8A905 D0FCA9DF ................................ 0000A0
89EF02FB F8A9DFF8 A908D0FC A9DFFCA9 1ED00001 EA16FF00 FB0001EA 35FF01FB ...5............................ 0000C0
0001E9E4 FF00FB00 01EA03FF 01FBFFFF C5BEEF9F 0001E9E8 FF01FB00 DD000004 ................................ 0000E0
EF9F0001 E9B6FF01 FB00DD00 000457EF 02FBF8A9 DFF8A90B D0FCA9DF FCA914D0 ..................W............. 000100
F8A9DFF8 A90CD0FC A9DFFCA9 14D00001 E9B2FF00 FB0001E9 D1FF01FB FFFFC594 ................................ 000120
FF00FB00 01E99FFF 01FBFFFF C56AEF9F 0001E984 FF01FB00 DD000004 25EF02FB ...%...............j............ 000140
E952FF01 FB00DD00 0003F3EF 02FBF8A9 DFF8A90D D0FCA9DF FCA914D0 0001E980 ..............................R. 000160
A90FD0FC A9DFFCA9 14D00001 E94EFF00 FB0001E9 6DFF01FB FFFFC540 EF9F0001 ....@.......m.......N........... 000180
01E93BFF 01FBFFFF C516EF9F 0001E920 FF01FB00 DD000003 C1EF02FB F8A9DFF8 ............................;... 0001A0
FB00DD00 0003BFEF 02FBF8A9 DFF8A910 D0FCA9DF FCA914D0 0001E91C FF00FB00 ................................ 0001C0
00000049 8FD00001 E8EAFF00 FB0001E9 09FF01FB FFFFC1EC EF9F0001 E8EEFF01 ............................I... 0001E0
```

```
Virtual block number 51 (00000033), 512 (0200) bytes

C4BEEF9F 0001E8B8 FF01FB00 DD000003 59EF02FB F8A9DFF8 A913D0FC A9DFFCA9 ..............Y................ 000000
FBF8A9DF F8A914D0 FCA9DFFC A9C9AFD0 0001E8B4 FF00FB00 01E8D3FF 01FBFFFF ................................ 000020
81FF00FB 0001E8A0 FF01FBFF FFC493EF 9F0001E8 85FF01FB 00DD0000 0326EF02 ..&............................. 000040
E852FF01 FB00DD00 0002F3EF 02FBF8A9 DFF8A915 D0FCA9DF FCA996AF D00001E8 ..............................R. 000060
A9DFFCA9 00000049 8ED00001 E84EFF00 FB0001E8 6DFF01FB FFFFC468 EF9F0001 ...h......m......N.....I...J.... 000080
01FBFFFF C43AEF9F 0001E81C FF01FB00 DD000002 BDEF02FB F8A9DFF8 A916D0FC ................................ 0000A0
02BAEF02 FBF8A9DF F8A917D0 FCA9DFFC A9C9AFD0 0001E818 FF00FB00 01E837FF .7.............................. 0000C0
9E0001E7 E5FF00FB 0001E804 FF01FBFF FFC3EFEF 9F0001E7 E9FF01FB 00DD0000 ................................ 0000E0
E7B2FF01 FB00DD00 000253EF 02FBF8A9 DFF8A914 D0FCA9DF FCA914D0 FCADFDAF ....................S........... 000100
A914D0FC A9DFFCA9 2AD00001 E7AEFF00 FB0001E7 CDFF01FB FFFFC3B8 EF9F0001 ....................*........... 000120
AB7E5167 AB7E0000 06B6EF01 FB67AB7F FCADFDAF 9E000002 21EF02FB F8A9DFF8 .......!..........g........~.gQ~. 000140
00A97F6F AB7F01DD D3110212 FFFF7D76 EF002073 BB6FAB2D 0001E728 FF16506F oP..(...-.o.s ..v}.............o... 000160
E6EEFF16 506FAB7E 5108A97E 0000056C EF02FB08 A97F00A9 7F0001E3 E1EF03FB ...............l...~..Q~.oP.... 000180
9EFC8531 0000222C EF00FB0A 12FFFF7D 36EF0120 73BB6FAB 2DFCADFD AF9E0001 .......-.o.s ..6}.........1.... 0001A0
ADFDAF9E FC683100 010C53EF 00FB0A12 FFFF7D18 EF012073 BB6FAB2D FCADFDAF ....-.o.s ...}.......S...1h..... 0001C0
AB2DFCAD FDAF9EFC 4B310001 B212EF00 FB0A12FF FF7CFAEF 012073BB 6FAB2DFC .-.o.s ...|............1K......-. 0001E0

Virtual block number 52 (00000034), 512 (0200) bytes

13FFFF7C C6EF0120 73BB6FAB 2D5C01CE 03115CD4 0413FFFF 7CDCEF01 2073BB6F o.s ...|.....\....\-.o.s ...|... 000000
5801CE03 1158D404 13FFFF7C ADEF0120 73BB6FAB 2D5C58C8 5801CE03 1158D404 ..X....X.XX-.o.s ...|.....X....X 000020
01FB00A9 7F0001E6 31FF1650 00A97E52 FFFF7C92 EF9E5102 3221135C D55C58C8 .X\.\.!2.Q...|..R~..P..1......... 000040
FDAF9E08 110212FF FF7C68EF 012073BB 6FAB2DFC ADFDAF9E FBDC3100 000233EF .3...1.......-.o.s ..h|.......... 000060
11021200 0000008F 5C515CFF FFF58FEF 4EFCADFD AF9EFCAD FDAF9EFE 7A31FCAD ..12.............N......\Q\....... 000080
0001E644 FF01FB00 A97F0001 DEAFEF02 FB00A97F 00DD0001 E62AFF01 FB02DD33 3.....*.....................D... 0000A0
E5F2FF01 FB00DDFC ADFDAF9E 0001E610 FF00FB00 01E62FFF 01FBFFFF C242EF9F ..B...../....................... 0000C0
A902D0FC A9DFFCA9 05B00001 E5EEFF00 FB0001E6 0DFF01FB FFFFC1B0 EF9F0001 ................................ 0000E0
01E5DBFF 01FBFFFF C1F6EF9F 0001E5C0 FF01FB00 DD000000 61EF02FB F8A9DFF8 ........a....................... 000100
01E55BFF 01FB02DD 0001E5AC FF00FB00 01E5A3FF 01FB00DD 0001E5BC FF00FB00 ..............................[.. 000120
1650FFFF 7AA2EF9E FCADFDAF 9E0001E5 49FF01FB 07DD0001 E552FF01 FB0ADD00 .....R.........I...........z..P.. 000140
E546FF16 5150D050 FFFF7C20 EF9E52FB AF9ECFFC 00000004 5001D000 01E53FFF .?.....P.........R.. |..P.PQ..F. 000160
7F7E73BB 6EFFFFC1 7DEF9F24 18225C51 5C73BB4E FCADFDAF 9EFCADFD AF9E0001 ............N.s\Q\'.$..}....n.s~. 000180
6EFFFFC1 61EF9F22 110001E4 D9FF1650 63AB7E51 00A97E00 01E129EF 04FB00A9 .....)...~..Q~.cP.........a..... 0001A0
515C77BB 4E0001E4 B5FF1650 63AB7E51 00A97E00 01E105EF 04FB00A9 7F7E73BB .s~..........~..Q~.cP......N.w\Q 0001C0
506BAB7E 5100A97E 0001E0DA EF04FB00 A97F7E77 BB6EFFFF C12EEF9F 2418225C \".$.......n.w~...........~..Q~.kP 0001E0

Virtual block number 53 (00000035), 512 (0200) bytes

5100A97E 0001E0B6 EF04FB00 A97F7E77 BB6EFFFF C112EF9F 22110001 E48AFF16 ......."......n.w~..........~..Q 000000
0001E4C4 FF01FBFF FFC0EEEF 9F0001E4 A1FF01FB 00DD0001 E466FF16 506BAB7E ~.kP..f.......................... 000020
FF01FBFF FFC0DBEF 9F0001E4 ADFF01FB 63AB7F00 01E4B7FF 01FBFFFF C0EAEF9F ..............c................. 000040
E462FF00 FB0001E4 89FF01FB FFFFC0CC EF9F0001 E496FF01 FB6BAB7F 0001E4A0 ......k.......................b. 000060
EF9E52FB AF9ECFFC 045001D0 0001E410 FF1650FF FF7B0BEF 9EFCADFD AF9E0001 ..........{..P.........P......R.. 000080
```

```
FDAF9EFC ADFDAF9E FCADFDAF 9EFCADFD AF9E0001 E41AFF16 5150D050 FFFF7B5C \{..P.PQ...................... 0000A0
AE01D008 AEFFFFC0 6DEF9E37 DD000020 008FDD6E 2B006E00 2C5E2BC2 00DDFCAD ......+^..n.+n.....7..m........ 0000C0
F9FF01FB FFFFC054 EF9F0001 E3DEFF01 FB00DD5E 37C00001 E3FEFF01 FB5EDD2C ..^.......7^..........T........ 0000E0
49EF02FB F8A9DFF8 A91BD0FC A9DFFCA9 0000004D BFD00001 E3DAFF00 FB0001E3 ...........M..................I 000100
C1FF01FB 73BB7F00 01E3CBFF 01FBFFFF C026EF9F 0001E3A8 FF01FB00 DDFFFFFE ..............&.............s.... 000120
9EFFFFFE 0DEF02FB F8A9DFF8 A901D0FC A9DFFCA9 01D00001 E39AFF00 FB0001E3 ................................ 000140
AB3C0001 E366FF00 FB0001E3 A5FF01FB 53AB7F00 01E36FFF 01FB01DD FCADFDAF ........o.....S..........f...<. 000160
FDAF9E00 01DFDFEF 04FB5BAB 7F53AB7F 01DD02DD 77AB5C4A 5C14425C 5B4E5853 SXNX\B.\J\.w......S..[.......... 000180
FFBF9FEF 9F0001E3 19FF01FB 00DD2011 0213FFFF 7B18EF02 205FBB5B AB2DFCAD ..-.[._ ...{......... ........ 0001A0
5FBB5BAB 2D5C73BB 7EFCADFD AF9E009F 310001E3 15FF00FB 0001E334 FF01FBFF ....4..........1.......~.s\-.[._ 0001C0
DD77ABDD 0001E2D8 FF01FB00 DDFCADFD AF9EFCAD FDAF9EFF 74310313 04BC6C20 1....1v......................w. 0001E0
```

Virtual block number 54 (00000036), 512 (0200) bytes

```
DD0001E2 C5FF00FB 0001E2E4 FF01FB00 A97F0001 DF6EEF04 FB00A97F 53AB7F03 ...S.......n..................... 000000
5C5B4E58 53AB3C00 01E2ABFF 00FB0001 E2EAFF01 FB53AB7F 0001E2B4 FF01FB01 ..........S...............<.SXNX\ 000020
73BB7EFC ADFDAF9E 0001DF24 EF04FB5B AB7F53AB 7F01DD02 DD77AB5C 4A5C1442 B.\J\.w......S..[...$.........~.s 000040
A918D0FC A9DFFCA9 05D0FCAD FDAF9E00 11FF7A31 0312048C 6C205FBB 5BAB2D5C \-.[._ 1....1z..................... 000060
01E263FF 01FBFFFF BEGEEF9F 0001E240 FF01FB00 DDFFFFFC E1EF02FB F8A9DFF8 ................@................ 000080
16506BAB 7E5163AB 7E000001 59EF01FB 63AB7FFC ADFDAF9E 0001E23C FF00FB00 ....<...........c....Y...~.cQ~.kP. 0000A0
9EC91102 1304B900 A9206FBB 6BAB2D00 01E1C7FF 02FB00A9 7F0DDD00 01E1CBFF .................-.k.o .......... 0000C0
00000450 01D00001 E1AAFF16 50FFFF79 0DEF9E00 01E1AFFF 01FB01DD FCADFDAF ................y..P.........P... 0000E0
FCADFDAF 9EFCADFD AF9E0001 E1B2FF16 5150D050 FFFF79C8 EF9E52FB AF9ECFFC .....R....y..P.PQ............... 000100
AB6BABD0 6BAB5CD0 5C67BB3C 0001E158 FF16505B AB7E52FF FF7A08EF 9E510032 2.Q...z..R~.EP..X...<.g\.\.k..k. 000120
67BB7F6F ABDD01DD FCADFDAF 9E009431 00036FAB 0173ABF1 6FABD76F AB01D073 s...o..o..s..o..1............o..s 000140
AB504A00 01E054EF 1650504E 0001DF70 EF01FB00 A97F0001 DE12EF04 FB00A97F ..............p...NPP..T....JP. 000160
58D40419 000043F6 8F575157 77AB4E5C 01CE0311 5CD40414 3C585158 77AB4E77 wN.wXQX<....\....\N.wWQW..C......X 000180
00A97F77 ABDD77AB 5C4A5C30 425C77AB 4E0B135C D55C58CA 5858D258 01CE0311 ....X.XX.X\.\...N.w\B0\J\.w...w... 0001A0
0173ABF1 FCADFDAF 9E0001E0 B1FF03FB 5BAB7F5B AB7F00A9 7F0001E0 D1FF02FB ............[..[...............s. 0001C0
9EFCADFD AF9E0001 E096FF16 5063BB7E 515BAB7E FCADFDAF 9E6FABD7 FF6F6FAB .oo....o......~.[Q~.cP............ 0001E0
```

Virtual block number 55 (00000037), 512 (0200) bytes

```
5150D050 FFFF7918 EF9E52FB AF9ECFFC 00000004 0001E098 FF1650FF FF78CFEF ..x..P...............R...y..P.PQ 000000
74EF0020 FFFFBBD8 EF012DFC ADFDAF9E FCADFDAF 9EFCADFD AF9E0001 E0A2FF16 .......................-.........t 000020
03115BD4 0413FFFF 795DEF00 20FFFFBB C2EF012D 5C01CE03 115CD404 12FFFF79 y.....\.....\-....... ..Jy......X.. 000040
01E00BFF 16506FBB 7E52FFFF BB9EEF9E 51013225 135CD55C 58CA5858 D25801CE ..X.XX.X\.\.X2.Q.......R~.oP..... 000060
FFFFBB75 EF0120FF FF791EEF 002C035E 31FFFFBB 85EF0120 FFFF792F EF002C00 ...../y.. ......1^.....y.......... 000080
0001E00C FF01FB02 B0CF9F73 AB000002 008F5CC9 5C000000 408F0000 00318FC9 ..1.....@...\.\.......s........... 0000A0
7E0001DC 89EF03FB 00A97FFF FFBC9BEF 9F01DD22 12000000 008F5C51 5C61AB4D M.a\Q\......'....................~ 0000C0
0001DF98 FF02FB00 A97F7E5C 325C61AB B01F1100 01DFA3FF 16506FBB 7E5100A9 ..Q~.oP...........a\2\~............ 0000E0
5C50D000 01DDC7EF 01FB6FBB 7FFCADFD AF9E0001 DF82FF16 506FBB7E 5100A97E ~..Q~.oP..................o.........P\ 000100
D1EF0120 FFFF787B EF002C11 13585CD1 5850D000 01DDB7EF 01FBFFFF BC52EF9F ..R...........PX.\X......{x.. ... 000120
012004B8 682D586F BB7EFCAD FDAF9E00 01DF7BFF 01FB021F CF9F02AA 31FFFFBA ...1.........{.........~.oX-h..... 000140
D40412FF FF7837EF 012004B7 672D576F BB7E5C01 CE03115C D40412FF FF7850EF .Px.....\.....\~.oW-g.. ..7x..... 000160
4F31FFFF BA76EF01 20FFFF78 20EF002C 11135CD5 5C58CA58 58D25801 CF031158 X....X.XX.X\.\.... x.. ..v...10 000180
```

```
2D0001DE D1FF1650 67AB7E51 6FBB7EFC ADFDAF9E 0001DF20 FF01FB01 C4CF9F02 ................~.oQ~.dP......- 0001A0
00DDFFFF BA36EFFF FF77D9EF 0128FCAD FDAF9E2E 12FFFF77 EBEF0120 6BBB67AB .d.k ...w.........(...w...6..... 0001C0
6BBB67AB 2D016631 0001DE98 FF16506F BB7E5100 A97E0001 DEAEFF02 FB00A97F ..........~..Q~.oP......1f.-.d.k 0001E0

Virtual block number 56 (00000038), 512 (0200) bytes

FB00A97F 00DDFFFF B9FAEFFF FF779BEF 0128FCAD FDAF9E2E 12FFFF77 AAEF0120 ...w..........(...w............. 000000
6CEF0120 6BBB67AB 2D012A31 0001DE5C FF16506F BB7E5100 A97E0001 DE72FF02 ..n...~..Q~.oP..\...1*.-.d.k ...1 000020
DE36FF02 FB00A97F 00DDFFFF B9BEEFFF FF775DEF 0128FCAD FDAF9E2E 12FFFF77 w.........(..]w................6. 000040
12FFFF77 2EEF0120 6BBB67AB 2D00EE31 0001DE20 FF16506F BB7E5100 A97E0001 ..~..Q~.oP.. ...1..-.d.k ...w... 000060
A97E0001 DDFAEF02 FB00A97F 00DDFFFF B982EFFF FF771FEF 0128FCAD FDAF9E2E ......(...w.....................~. 000080
FDAF9E2E 12FFFF76 F5EF0120 6BBB67AB 2D00B231 0001DDE4 FF16506F BB7E5100 .Q~.oP......1..-.d.k ...v....... 0000A0
BB7E5100 A97E0001 DDBEFF02 FB00A97F 00DDFFFF B946EFFF FF76E2EF 0128FCAD ..(...v...F...............~..Q~. 0000C0
0128FCAD FDAF9E2D 12FFFF76 B3EF0120 6BBB67AB 2D007631 0001DDA8 FF16506F oP.......1v.-.d.k ...v.........(. 0000E0
FF16506F BB7E5100 A97E0001 DDB2FF02 FB00A97F 00DDFFFF B90AEFFF FF76A4EF ..v...................~..Q~.oP.. 000100
FFFF766A EF0128FC ADFDAF9E 2D12FFFF 7676EF01 206BBB67 AB2D3B11 0001DD6C l....;-.d.k ..vv...-......(..Jv.. 000120
110001DD 31FF1650 6FBB7E51 00A97E00 01DD47FF 02FB00A9 7F00DDFF FFB8CFEF .............G...~..Q~.oP..1..... 000140
00DDFFFF B882EF9F 01DD00DD 00DD00DD 00DDFCAD FDAF9E00 8731FCAD FDAF9E00 ......1......................... 000160
515C61AB 4D77AB50 D07FFEDE 009F0CFB 00DDFFFF ECA4EFDD 73ABDD5D AB3F00DD ..T.J..s..................P.wM.a\Q 000180
BB7E5100 A97E0001 D9AEEF03 FB00A97F FFFFB9C0 EF9F01DD 22120000 00008F5C \.......'...............~..Q~. 0001A0
7E5100A9 7E0001DC BDFF02FB 00A97F7E 5C325C61 ABB01F11 0001DCC8 FF16506F oP..........a\2\~.........~..Q~ 0001C0
DCA2FF16 50FFFF75 39EF9EFC ADFDAF9E 040001DC B9FF1600 01DCA7FF 16506FBB .oP....................9u..P.... 0001E0

Virtual block number 57 (00000039), 512 (0200) bytes

AF9E0001 DCAAFF16 5150D050 FFFF75A4 EF9E52FB AF9ECFFC 00000450 01D00001 ....P.........R...u..P.PQ........ 000000
EF9E0001 DC5AFF02 FB18A97F 1BDDFCAD FDAF9EFC ADFDAF9E FCADFDAF 9EFCADFD ..........................Z...... 000020
08A97F00 01DC3BFF 02FB08A9 7F1BDD00 01DC37FF 03FB10A9 7F18A97F FFFFB93C <............7.................. 000040
05FF03FB FFFFB914 EF9F00A9 7FFFFFB9 15EF9F00 01DC1BFF 03FB00A9 7F10A97F ................................ 000060
0001DC44 FF00FB00 01DC63FF 01FBFFFF B8FEEF9F 0001DC48 FF01FB00 DD0001DC ........H...........c......D.... 000080
DC12FF01 FB00DDFF FFF6B3EF 02FBF8A9 DFF8A918 D0FCA9DF FCA90000 004D8FD0 ..M............................. 0000A0
CF9E6BBB 00000000 8F4A0001 DC0EFF00 FB0001DC 35FF01FB FFFFB8D0 EF9F0001 ............5..........J.......k.. 0000C0
DBD2FF01 FB00DDFF FFF673EF 02FBF8A9 DFF8A905 D0FCA9DF FCA916D0 7FAB1483 ........................s........ 0000E0
A907D0FC A9DFFCA9 1ED00001 DBCEFF00 FB0001DB EDFF01FB FFFFB898 EF9F0001 ................................ 000100
01DBBBFF 01FBFFFF B86EEF9F 0001DBA0 FF01FB00 DDFFFFF6 41EF02FB F8A9DFF8 .......A...............n......... 000120
FB00DDFF FFF60FEF 02FBF8A9 DFF8A909 D0FCA9DF FCA914D0 0001DB9C FF00FB00 ................................ 000140
00000049 8FD00001 DB6AFF00 FB0001DB 89FF01FB FFFFB844 EF9F0001 DB6EFF01 ..n......D...............J......I... 000160
B816EF9F 0001DB38 FF01FB00 DDFFFFF5 D9EF02FB F8A9DFF8 A913D0FC A9DFFCA9 ........................8........ 000180
FBF8A9DF F8A914D0 FCA9DFFC A9C9AFD0 0001DB34 FF00FB00 01DB53FF 01FBFFFF .....S.......4.................. 0001A0
01FF00FB 0001DB20 FF01FBFF FFB7EBEF 9F0001DB 05FF01FB 00DDFFFF F5A6EF02 ................................ 0001C0
DAD2FF01 FB00DDFF FFF573EF 02FBF8A9 DFF8A915 D0FCA9DF FCA996AF D00001DB ..........................s........ 0001E0

Virtual block number 58 (0000003A), 512 (0200) bytes

A9DFFCA9 00000049 8FD00001 DACEFF00 FB0001DA EDFF01FB FFFFB7C0 EF9F0001 ..........................I....... 000000
01FBFFFF B792EF9F 0001DA9C FF01FB00 DDFFFFF5 3DEF02FB F8A9DFF8 A916D0FC ................................ 000020
```

```
F50AEF02 FBFBA9DF FBA917D0 FCA9DFFC A9C9AFD0 0001DA98 FF00FB00 01DAB7FF ................................ 000040
9E0001DA 65FF00FB 0001DA84 FF01FBFF FFB747EF 9F0001DA 69FF01FB 00DDFFFF .......i.....G...............@.... 000060
D0FCA9DF FCA901D0 0001D9E4 FF16503B AB7E52FF FF79B1EF 9E510532 FCADFDAF ....2.Q...v..R^.;P............... 000080
41FF01FB FFFFB71C EF9F0001 DA1EFF01 FB00DDFF FFF4BFEF 02FBF8A9 DFF8A90C ...............................A 0000A0
DD6E2B00 6E002C5E 2BC200DD 0001DA10 FF00FB00 01DA2FFF 01FB3BAB 7F0001DA .....;.../.......%.....+^..n.+n. 0000C0
DD5E37C0 0001D9EC FF01FB5E DD2CAE0A D008AEFF FFB6F3EF 9E37DD00 0020008F .. ...7..............^.......7^. 0000E0
FF01FB5E DD2CAE09 D008AE3B AB7E37DD 00001000 8FDD6E2B 006E002C 5E2BC200 ..+^..n.+n.......7^.;.......^... 000100
01FBFFFF E8FCEFDF 6FAB50D0 0001D960 FF01FBFF FFE909EF DF5E37C0 0001D9C4 .....7^.........`....P.o........ 000120
00A97E52 FFFF78C3 EF9E5102 32FFFFE8 DFEFDF00 DD00DD6F AB50D000 01D94FFF .0.....P.o...........2.Q...x..R^.. 000140
7FFFFFE8 BFEFDF00 DD00DD6F AB50D07F FEDE509F 04FB00A9 7F0001D9 25FF1650 P..%.........P....P.o............ 000160
A97F38A9 7F02DD00 01D007EF 02FB38A9 7F00DD6F AB50D07F FEDE509F 04FB3BAB .;...P....P.o....8............8.. 000180
04FB20A9 7F28A97F 04DD03DD 0001CFEC EF02FB28 A97F000D 0001D5C0 EF03FB30 0...........(............(....... 0001A0
01CFBFEF 02FB10A9 7F00DD00 01D8B3FF 03FB18A9 7F30A97F 20A97F00 01D5B7EF ....... ..0...................... 0001C0
D886FF03 FB00A97F 18A97F08 A97F0001 D58AEF04 FB08A97F 10A97F08 DD02DD00 ................................ 0001E0
```

Virtual block number 59 (0000003B), 512 (0200) bytes

```
EF9F0001 D8B6FF01 FB00DD00 01D873FF 03FB43AB 7F00A97F FFFFB5E0 EF9F0001 ..........;.....C...s............... 000000
0001D850 FF16504B AB7E5143 AB7E0001 D8B2FF00 FB0001D8 D1FF01FB FFFFB5CC ..................^.CQ^;KP..P... 000020
01FB5EDD 2CAE02D0 08AE43AB 7E000500 37BFDD00 DD6E2B00 6E002C5E 2BC200DD ...+^..n.+n....7...^.C.......^.. 000040
EF144A13 55310312 0000C080 8F5C515C 6BBB4EFC ADFDAF9E 5E37C000 01D883FF ......7^.....N.k\Q\.........1U.J.. 000060
61FF01FB 00A97F00 01D0CCEF 02FB00A9 7F00DD00 01D847FF 01FB02DD FFFFE7A0 .........C.......................@ 000080
0001D814 FF01FB02 DD0001D8 2DFF00FB 0001D84C FF01FBFF FFB54FEF 9F0001D8 .....0......L.......-........... 0000A0
21FF01FB FFFFB524 EF9F0001 D82EFF01 FB08A97F 0001D099 EF02FB08 A97F00DD .......................$.......! 0000C0
FBFFFFB5 09EF9F00 01D80BFF 01FB00A9 7F0001CE B1EF02FB 00A97F00 DD000108 ................................ 0000E0
01D7B3FF 01FB00DD 7FAB104F CF9EFCAD FDAF9E00 01D7D7FF 00FB0001 D7F6FF01 ......................0.......... 000100
7E52FFFF 765EEF9E 510A3200 01D7AFFF 00FB0001 D7CEFF01 FBFFFFB4 E9EF9F00 ......................2.Q..^v..R^ 000120
00DD1274 31031200 00C0808F 5C515C6B BB4EFCAD FDAF9E00 01D743FF 16504BAB .KP..C.........N.k\Q\........1t... 000140
FB5EDD2C AE01D008 AEFFFFB4 A1EF9E37 DD000020 008FDD6E 2B006E00 2C5E2BC2 .+^..n.+n... ...7.............^. 000160
0AFCADFD AF9E01A6 31000373 AB0113F1 73ABD773 AB01D05E 37C00001 D762FF01 ..b.....7^....s..s.....s..1........ 000180
75DAEF00 2C5C0005 130073AB 0AFFFFCD 55EF4C00 0000008F 4A5C0001 130073AB .s.....\J......L.U........s....\....u 0001A0
FFCDDBEF 4C1220FF FF75C3EF 002C5C00 12130073 AB0AFFFF CB8EEF4C 0520FFFF .. .L........s....\....u.. .L.... 0001C0
71EF4CAC AF505C00 01130073 AB0AFFFF CF32EF4C BDAF505C 00011300 73AB0AFF ...s.....\P..L.2.......s.....\P..L.a 0001E0
```

Virtual block number 60 (0000003C), 512 (0200) bytes

```
4C8AAF50 5C000113 0073AB0A FFFFCFB0 EF4C9BAF 505C0001 130073AB 0AFFFFCF .....s....\P..L.........s....\P..L 000000
00011300 73AB0AFF FFD02BEF 4C000000 008F505C 00011300 73AB0AFF FFCFEFEF ........s....\P.....L.+.......s.... 000020
130073AB 0AFFFFD0 A9EF4CDA AF505C00 01130073 AB0AFFFF D06AEF4C EBAF505C \P..L.J........s....\P..L.........s.. 000040
73AB0AFF FFD127EF 4C8BAF50 5C000113 0073AB0A FFFFD0E8 EF4CC9AF 505C0001 ..\P..L.........s....\P..L.'......s 000060
0AFFFFD1 A5EF4C96 AF505C00 01130073 AB0AFFFF D166EF4C A7AF505C 00011300 ....\P..L.f.........s....\P..L...... 000080
EF4C0000 00008F4A 5C000113 0073AB0A FFFFD1E4 EF4CB5AF 505C0001 130073AB .s.....\P..L..........s....\J......L. 0000A0
EF002C5C 00011300 73AB0AFF FFD25FEF 4CEBAF4A 5C000113 0073AB0A FFFFD220  ......s....\J..L._.......s......\... 0000C0
95EF4C01 20FFFF74 A1EF002C 5C000113 0073AB0A FFFFD298 EF4C0120 FFFF74B8 .t.. .L.........s....\.....t.. .L.. 0000E0
01130073 AB0AFFFF D292EF4C 0120FFFF 74BAEF00 2C5C0001 130073AB 0AFFFFD2 .....s....\.....t.. .L........s... 000100
73ABD7FE 5D73AB01 13F1FCAD FDAF9EFF FFD28FEF 4C0120FF FF7473EF 002C5C00 .\....st.. .L...................s]...s 000120
```

```
FDAF9EFC ADFDAF9E 77ABF7AF 4A73AB00 0000008F 4A7FAB0F 0CCF9EFC ADFDAF9E ...........J......sJ...w......... 000140
55FF01FB 01DD73AB 5C4A5C08 405C73AB 4E023D31 0313E3AF 5C515C77 AB4EFCAD ..N.w\Q\....1=.N.s\@.\J\.s.....U 000160
00051300 73AB0A00 01D58BFF 01FBFFFF CB76EF4C DF5C0001 130073AB 0A0001D5 .....s....\.L.v.............s.... 000180
12130073 AB0A0001 D562FF01 FBFFFFB2 6DEF9FFF FFB277EF FFFFCBB0 EF4C9E5C \.L.......w......m.......b......s... 0001A0
130073AB 0A0001D5 41FF01FB FFFFB254 EF9FFFFF B25EEFFF FFCBF3EF 4C9E5C00 .\.L.......^.....T.......A.....s.. 0001C0
FFFFCD74 EF4CDF5C 00011300 73AB0A00 01D52FFF 01FBFFFF CD3AEF4C DF5C0001 ..\.L.:......./.....s....\.L.t... 0001E0
```

Virtual block number 61 (0000003D), 512 (0200) bytes

```
73AB0A00 01D503FF 01FBFFFF CDAEEF4C DF5C0001 130073AB 0A0001D5 19FF01FB ..........s....\.L..............s 000000
CE22EF4C DF5C0001 130073AB 0A0001D4 EDFF01FB FFFFCDE8 EF4CDF5C 00011300 ....\.L...............s....\.L.?.. 000020
0A0001D4 C1FF01FB FFFFCE5C EF4CDF5C 00011300 73AB0A00 01D4D7FF 01FBFFFF ............s....\.L.\.......... 000040
EF4CDF5C 00011300 73AB0A00 01D4ABFF 01FBFFFF CE96EF4C DF5C0001 130073AB .s....\.L...............s....\.L. 000060
01D47FFF 01FBFFFF CE0AEF4C DF5C0001 130073AB 0A0001D4 95FF01FB FFFFCED0 .............s....\.L............ 000080
DF5C0001 130073AB 0A0001D4 69FF01FB FFFFCF44 EF4CDF5C 00011300 73AB0A00 ...s....\.L.D......i.....s....\. 0000A0
3DFF01FB FFFFCFB8 EF4CDF5C 00011300 73AB0A00 01D453FF 01FBFFFF CF7EEF4C L.^......S.......s....\.L.........= 0000C0
00011300 73AB0A00 01D42BFF 01FBFFFF CFF2EF4C DF5C0001 130073AB 0A0001D4 .....s....\.L.........+......s.... 0000E0
11EFFFFF D066EF4C 9E5C0001 130073AB 0A0001D4 15FF01FB FFFFD02C EF4CDF5C \.L.................s....\.L.f..... 000100
EFFFFFD0 B9EF4C9E 5C000113 0073AB0A 0001D3EC FF01FBFF FFB107EF 9FFFFFB1 ....................s....\.L.Y.... 000120
FFFFD04C EF4C9E5C 00011300 73AB0A00 01D3CBFF 01FBFFFF B0EEEF9F FFFFB0F8 .....................s....\.L.L.... 000140
FFD03FEF 4C9E5C00 01130073 AB0A0001 D3AAFF01 FBFFFFB0 D5EF9FFF FFB0DFEF ......................s....\.L.?.. 000160
5C515C73 AB4E0001 D34AFF00 FB0001D3 89FF01FB FFFFB0BC EF9FFFFF B0C6EFFF ......................J...N.s\Q\ 000180
9E0001D2 DDFF01FB 01DDFCAD FDAF9EFC ADFDAF9E FDB13108 11021200 0042988F ..B.......1....................... 0001A0
0001D31C FF01FBFF FFB077EF 9F0001D3 01FF01FB 00DD7FAB 0B9DCF9E FCADFDAF .......................w......... 0001C0
FCADFDAF 9E0001D2 91FF1650 4BAB7E52 FFFF7185 EF9E510A 320001D2 FDFF00FB ........2.Q...q..R~.KP........... 0001E0
```

Virtual block number 62 (0000003E), 512 (0200) bytes

```
0020008F DD6E2B00 6E002C5E 2BC200DD 0DC23103 120000C0 B08F5C51 5C6BBB4E N.k\Q\........1.....+^..n.+n.... . 000000
D773AB01 D05E37C0 0001D2B0 FF01FB5E DD2CAE01 D008AEFF FFB02FEF 9E37DD00 ..7../..........^........7^....s. 000020
4C000000 008F4A5C 00011A00 73AB0AFC ADFDAF9E 00F83100 0373AB01 1AF173AB .s....s..1..........s....\J.....L 000040
0073AB0A FFFFCFC4 EF4C1820 FFFF7128 EF002C5C 00181A00 73AB0AFF FFCF6FEF .o......s....\...(q.. .L........s. 000060
EF4C0620 FFFF7100 EF002C5C 00061A00 73AB0AFF FFD23BEF 4CD4AF50 5C00011A ...\P..L.;......s....\....a.. .L. 000080
1A0073AB 0AFFFFD3 1BEF4C0C 20FFFF70 E9EF002C 5C000C1A 0073AB0A FFFFD290 .r.....s....\....p.. .L........s.. 0000A0
73AB0AFF FFD4A9EF 4C84AF50 5C00011A 0073AB0A FFFFD44E EF4C95AF 505C0001 ..\P..L.N......s....\P..L........s 0000C0
D55CEF4C EBAF505C 00011A00 73AB0AFF FFD501EF 4C000000 006F505C 00011A00 ....\P.....L........s....\P..L.\./ 0000E0
EF4CC9AF 505C0001 1A0073AB 0AFFFFD5 B7EF4CDA AF505C00 011A0073 AB0AFFFF .....s....\P..L.........s....\P..L. 000100
0B73AB01 1AF1FCAD FDAF9EFF FFD66DEF 4CB8AF50 5C00011A 0073AB0A FFFFD612 .......s....\P..L.m.............s. 000120
AF9EFCAD FDAF9E77 AB90AF4A 73AB95AF 4A7FAB0B 0BCF9EFC ADFDAF9E 73ABD7FF ...s.............J....sJ...w....... 000140
01DD73AB 5C4A5C08 405C73AB 4E015231 03130000 00008F5C 515C77AB 4EFCADFD ...N.w\Q\.......1R.N.s\@.\J\.s.. 000160
73AB0A00 01D187FF 01FBFFFF CE3EEF4C DF5C0001 1A0073AB 0A0001D1 51FF01FB ...Q......s....\.L.>.............s 000180
AB0A0001 D15EFF01 FBFFFFAE A9EF9FFF FFAEB3EF FFFFCE94 EF4C9E5C 00181A00 ....\.L..................^..... 0001A0
51EF4C9E 5C00061A 0073AB0A 0001D14C FF01FBFF FFD0FBEF 4CDF5C00 011A0073 s....\.L...........L.....s....\.L.Q 0001C0
EF4C9E5C 000C1A00 73AB0A00 01D127FF 01FBFFFF AE7AEF9F FFFFAE84 EFFFFFD1 ...............z.......'.......s....\.L. 0001E0
```

```
Virtual block number 63 (0000003F), 512 (0200) bytes

 4CDF5C00 011A0073 AB0A0001 D106FF01 FBFFFFAE 61EF9FFF FFAE6BEF FFFFD1D2 .....K.....8..............s....\.L 000000
 D0DEFF01 FBFFFFD3 4BEF4CDF 5C00011A 0073AB0A 0001D0F4 FF01FBFF FFD2F5EF ..................s....\.L.K........ 000020
 5C00011A 0073AB0A 0001D0C8 FF01FBFF FFD3A1EF 4CDF5C00 011A0073 AB0A0001 ....s....\.L.................s....\ 000040
 FF01FBFF FFD44DEF 4CDF5C00 011A0073 AB0A0001 D0B2FF01 FBFFFFD3 F7EF4CDF .L...............s....\.L.M....... 000060
 011A0073 AB0A0001 D086FF01 FBFFFFD4 A3EF4CDF 5C00011A 0073AB0A 0001D09C .......s....\.L.................s... 000080
 02122F5C 315C73AB 4E0001D0 2DFF00FB 0001D070 FF01FBFF FFD4F9EF 4CDF5C00 .\.L...........p.......-...N.s\Q\/.. 0000A0
 84CF9EFC ADFDAF9E 0001CFC4 FF01FB01 DDFCADFD AF9EFCAD FDAF9EFE 99310811 ..1............................. 0000C0
 0001CFE4 FF00FB00 01D003FF 01FBFFFF AD86EF9F 0001CFE8 FF01FB00 DD7FAB08 ................................ 0000E0
 8F5C515C 6BBB4EFC ADFDAF9E 0001CF78 FF16504B AB7E52FF FF6E42EF 9E510A32 2.Q..Bn..R^.KP..x..........N.k\Q\. 000100
 AD3EEF9E 37DD0000 20008FDD 6E2B006E 002C5E2B C200DD0A A9310312 0000C080 ........1......+^,.n.+n...  ...7..>. 000120
 25EF9F00 01CF7FFF 01FB01DD 5E37C000 01CF97FF 01FB5EDD 2CAE01D0 08AEFFFF .........,.^..........7^.........% 000140
 FFFFAD10 EF9F0001 CF62FF01 FB01DD00 01CF73FF 00FB0001 CFB2FF01 FBFFFFAD ...................s.........b.......... 000160
 FF01FBFF FFACFBEF 9F0001CF 41FF01FB 01DD0001 CF56FF00 FB0001CF 95FF01FB ...........V.........A.............. 000180
 01CF5BFF 01FBFFFF ACE6EF9F 0001CF24 FF01FB01 DD0001CF 39FF00FB 0001CF78 x.......9.........$...............[.. 0001A0
 00FB0001 CF46FF01 FBFFFFD4 93EFDF00 01CF07FF 01FB01DB 0001CF1C FF00FB00 ..........................F...... 0001C0
 CEE2FF00 FB0001CF 21FF01FB FFFFACB4 EF9F0001 CEEAFF01 FB01DD00 01CEFFFF ...........................!......... 0001E0

Virtual block number 64 (00000040), 512 (0200) bytes

 DD0001CE C5FF00FB 0001CF04 FF01FBFF FFAC9FEF 9F0001CE CDFF01FB 01DD0001 ................................ 000000
 01DDFCAD FDAF9E00 01CEABFF 00FB0001 CEEAFF01 FB53AB7F 0001CEB0 FF01FB01 ............S....................... 000020
 FFAC57EF 9F0001CE 79FF01FB 00DD7FAB 0715CF9E FCADFDAF 9E0001CE 55FF01FB ...U.......................y......W.. 000040
 09FF1650 4BAB7E52 FFFF6CA8 EF9E510A 320001CE 75FF00FB 0001CE94 FF01FBFF ..............u...2.Q...1..R^.KP... 000060
 2BC20000 0F008FDD 093A3103 120000C0 808F5C51 5C6BBB4E FCADFDAF 9E0001CE ..........N.k\Q\..........1:..........+ 000080
 FFDD53EF 9E08AEFF FFAC07EF 9E010103 378FDD00 0020068F DD6E2B00 6E002C5E ^,.n.+n...  ....7................S.. 0000A0
 F173ABD7 73AB01D0 FCADFDAF 9E5E37C0 0001CE18 FF01FB5E DD2CAE03 D010AEFF .........,.^..........7^............s..s. 0000C0
 73AB0A00 01CDC7FF 02FB03DD 73ABDDFC ADFDAF9E 35110002 73AB0100 0000648F .d......s....5..........s................s 0000E0
 ABD7CE73 ABC6AFF3 FCADFDAF 9EFFFFD6 4EEF4CFF FFDD07EF 0C285C00 OCDEAF00 ......\(.......L.O...................s... 000100
 16504BAB 7E52FFFF 6BDCEF9E 510A327F AB0636CF 9EFCADFD AF9EFCAD FDAF9E73 s.................6...2.Q..'.k..R^.KP. 000120
 00016300 8FDD0878 31031200 00C0808F 5C515C6B BB4EFCAD FDAF9E00 01CD47FF .G...........N.k\Q\.........1x......c.. 000140
 C1EF9E08 AEFFFFAB 4DEF9E01 0103378F DD000020 068FDD6E 2B006E00 2C5E2BC2 .+^,.n.+n...  ....7......M.......... 000160
 7FAB05C7 CF9EFCAD FDAF9E5E 37C00001 CD56FF01 FB5EDD2C AE04D010 AEFFFFDC ...........,.^....V....7^............. 000180
 510A3200 01CD27FF 00FB0001 CD46FF01 FBFFFFAB 21EF9F00 01CD2BFF 01FB00DD ......+.......!.........F........'....2.Q 0001A0
 00C0808F 5C515C6B BB4EFCAD FDAF9E00 01CCBBFF 16504BAB 7E52FFFF 6B22EF9E ..."k..R^.KP.................N.k\Q\.... 0001C0
 0103378F DD000020 068FDD6E 2B006E00 2C5E2BC2 00006400 8FDD07EC 31031200 ...1......d...+^,.n.+n...  ....7.. 0001E0

Virtual block number 65 (00000041), 512 (0200) bytes

 37C00001 CCCAFF01 FB5EDD2C AE05D010 AEFFFFDB A1EF9E08 AEFFFFAA D1EF9E01 ........................,.^........7 000000
 CC82EE02 FB05DD73 ABDDECAD EDAF9E39 11000273 AB0103F1 73ABD773 AB01D05E ^....s....s.....s.....9.......s........ 000020
 FDAF9EFF FFD9C1EF 4CFFFFDB 59EF0064 8F285C00 00000064 8F030073 AB0A0001 ....s....d.....\(.d..Y...L....... 000040
 5BEF9E51 0A327FAB 04EDCF9E FCADFDAF 9EFCADFD AF9E73AB D7CA73AB 03F3FCAD .....s....s......................2.Q..[ 000060
 03120000 C0808F5C 515C6BBB 4EFCADFD AF9E0001 CBFEFF16 504BAB7E 52FFFF6A j..R^.KP............N.k\Q\......... 000080
```

```
EF9E0101 03378FDD 00002006 8FDD6E2B 006E002C 5E2BC200 014E008F DD072F31 1/....N...+^..n.+n... ....7..... 0000A0
AF9E5E37 C00001CC 0DFF01FB 5EDD2CAE 06D010AE FFFFC0EC EF9E08AE FFFFAA1C ......................^........7^.. 0000C0
FB0001CB FDEF01FB FEEFA9F0 EF9F0001 CBE2FF01 FB00DD7F AB047ECF 9EFCADFD ......"........................ 0000E0
4EFCADFD AF9E0001 CB72FF16 504BAB7E 52FFFF69 9DEF9E51 0A320001 CBDEFF00 ......2.Q...i..R".KP..r.........N 000100
00002000 8FDD6E2B 006E002C 5E2BC200 DD06A331 03120000 C0808F5C 515C6BBB .k\Q\.......1.....+^..n.+n.... .. 000120
ABD773AB 01D05E37 C00001CB 91FF01FB 5EDD2CAE 01D008AE FFFFA9A8 EF9E37DD ..7.....................^.........7^....s.. 000140
0A20FFFF 6A1EEF00 2C5C000A 190073AB 0AFCADFD AF9E5411 000273AB 0119F173 s....s...T.......s.....\.....J.. . 000160
73AB0AFF FFD1D7EF 4C0F20FF FF6A07EF 002C5C00 0F190073 AB0AFFFF D0EAEF4C L........s.....\.....J.. .L........s 000180
AF9E73AB D7AF73AB 19F3FCAD FDAF9EFF FFD349EF 4C000000 008F4A5C 00011900 ....\J.....L.I...............s....s.. 0001A0
77AB4EFC ADFDAF9E FCADFDAF 9E77ABD6 AF4A73AB DBAF4A7F AB048ECF 9EFCADFD ..........J....sJ....w...........N.w 0001C0
AB0A0001 CADAFF01 FB01DD73 AB5C4A5C 08405C73 AB4E0085 310313C2 AF5C515C \Q\.....1..N.s\@.\J\.s.............. 0001E0
```

Virtual block number 66 (00000042), 512 (0200) bytes

```
0A0001CA FDFF01FB FFFFA8E0 EF9FFFFF A8EAEFFF FFD063EF 4C9E5C00 0A190073 s.....\.L.c........................ 000000
0001CADC FFD1FBFF FFA8C7EF 9EFFFFA8 D1EFFFFF D146EF4C 9E5C000F 190073AB .s.....\.L.F....................... 000020
73AB4E00 01CA87FF 00FB0001 CACEFF01 FBFFFFD2 ABEF4CDF 5C000119 0073AB0A ..s.....\.L....................N.s 000040
CA1AFF01 FB01DDFC ADFDAF9E FCADFDAF 9EFF6931 08110212 000042C8 8F5C515C \Q\..B......1i.................... 000060
ADFDAF9E 0001C9F0 FF16504B AB7E52FF FF6811EF 9E510A32 7FAB02DF CF9E0001 ........2.Q...h..R".KP........... 000080
6E2B006E 002C5E2B C200000A 008FDD05 21310312 0000C0A0 8F5C515C 6BBB4EFC .N.k\Q\........1!.........+^..n.+n 0000A0
2CAE07D0 10AEFFFF DACEEF9E 08AEFFFF A836EF9E 01010337 8FDD0000 20068FDD ... .....7.....6................. 0000C0
31000373 AB010EF1 73ABD773 AB01D0FC ADFDAF9E 5E37C000 01C9FFFF 01FB5EDD .^........7^..........s...s....s...1 0000E0
FF01FBFF FFDA97EF 4CDF5C00 012E0073 AB0A0001 C9D2FF00 FBFCADFD AF9E0090 ....................s.....\.L........ 000100
012E0073 AB0A0001 C9EAFF01 FBFFFFDB 3DEF4CDF 5C00012E 0073AB0A 0001CA00 .......s.....\.L.=..............s... 000120
FBFFFFDC B9EF4CDF 5C00010E 0073AB0A 0001C9D4 FF01FBFF FFDBE3EF 4CDF5C00 .\.L.................s.....\.L...... 000140
61FF00FB 0001C9A8 FF01FBFF FFDCAFEF 4CDF5C00 010E0073 AB0A0001 C9BEFF01 .........s.....\.L...............a 000160
2EF173AB D773AB0F D0FCADFD AF9E73AB D7FF7373 AB010EF1 FCADFDAF 9E0001C9 .............ss...s...........s..s.. 000180
D9F2EF4C DF5C0001 2E0073AB 0A0001C9 2DFF00FB FCADFDAF 9E621100 0273AB01 ..s....b.........-.....s.....\.L... 0001A0
0A0001C9 45FF01FB FFFFDA98 EF4CDF5C 00012E00 73AB0A00 01C95BFF 01FBFFFF .....[.....s.....\.L.........E.... 0001C0
ADFDAF9E 0001C8E8 FF00FB00 01C92FFF 01FBFFFF DB3EEF4C DF5C0001 2E0073AB .s.....\.L.>......./............... 0001E0
```

Virtual block number 67 (00000043), 512 (0200) bytes

```
FCADFDAF 9EFCADFD AF9EFCAD FDAF9E02 6F31FCAD FDAF9E73 ABD7A173 AB2EF3FC ....s....s......1o................. 000000
AF9EFCAD FDAF9EFC ADFDAF9E FCADFDAF 9EFCADFD AF9EFCAD FDAF9EFC ADFDAF9E ................................ 000020
ADFDAF9E FCADFDAF 9EFCADFD AF9EFCAD FDAF9EFC ADFDAF9E FCADFDAF 9EFCADFD ................................ 000040
9EFCADFD AF9EFCAD FDAF9EFC ADFDAF9E FCADFDAF 9EFCADFD AF9EFCAD FDAF9EFC ................................ 000060
FDAF9EFC ADFDAF9E FCADFDAF 9EFCADFD AF9EFCAD FDAF9EFC ADFDAF9E FCADFDAF ................................ 000080
FCADFDAF 9EFCADFD AF9EFCAD FDAF9EFC ADFDAF9E FCADFDAF 9EFCADFD AF9EFCAD ................................ 0000A0
AF9EFCAD FDAF9EFC ADFDAF9E FCADFDAF 9EFCADFD AF9EFCAD FDAF9EFC ADFDAF9E ................................ 0000C0
ADFDAF9E FCADFDAF 9EFCADFD AF9EFCAD FDAF9EFC ADFDAF9E FCADFDAF 9EFCADFD ................................ 0000E0
9EFCADFD AF9EFCAD FDAF9EFC ADFDAF9E FCADFDAF 9EFCADFD AF9EFCAD FDAF9EFC ................................ 000100
FDAF9EFC ADFDAF9E FCADFDAF 9EFCADFD AF9EFCAD FDAF9EFC ADFDAF9E FCADFDAF ................................ 000120
FCADFDAF 9EFCADFD AF9EFCAD FDAF9EFC ADFDAF9E FCADFDAF 9EFCADFD AF9EFCAD ................................ 000140
DDFFFFE1 EDEF02FB F8A9DFF8 A917D0FC A9DFFCA9 05D0FCAD FDAF9EFC ADFDAF9E ................................ 000160
```

```
FB0001C7 61FF01FB 4BAB7F00 01C76FFF 01FBFFFF A582EF9F 0001C74C FF01FB00 ....L.............o.....K...a.... 000180
01FB5CDD 5C50D000 01C6FBFF 00FB0001 C762FF01 FB5CDD5C 50D00001 C70AFF00 .......P\.\...b...........P\.\.. 0001A0
FCA9DFFC A905D000 01C70BFF 00FB0001 C72AFF01 FBFFFFA5 4DEF9F00 01C753FF .S.....M......*................. 0001C0
FF01FBFF FFA523EF 9F0001C6 DDFF01FB 00DDFFFF E17EEF02 FBF8A9DF F8A918D0 ..........~.............$...... 0001E0

Virtual block number 68 (00000044), 512 (0200) bytes

AB7E515B AB7EFFFF E5F6EF01 FB5BAB7F FCADFDAF 9E0001C6 D9FF00FB 0001C700 ................[.......~.[Q~. 000000
021304B9 00A92067 BB63AB2D 0001C664 FF02FB00 A97F0DDD 0001C668 FF165063 cP..h............d...-.c.d ...... 000020
01C64FFF 00FBFCAD FDAF9E00 01C66BFF 01FB0184 CF9F6BBB 0000C080 8F4AC911 ..J......k.......k...........D.. 000040
7FABD400 01C63BFF 00FB0A11 0001C648 FF00FB77 AB084A0D 12235C51 5C504E00 .HP\Q\$..J..w...H.......#...... 000060
31FF01FB 00DDFFFF E0D2EF02 FBF8A9DF F8A917D0 FCA9DFFC A905D0FC ADFDAF9E ..............................1 000080
FB08A97F 0001BCE4 EF02FB08 A97F00DD 0001C654 FF01FBFF FFA47FEF 9F0001C6 ..........T..................... 0000A0
7F0001BE 86EF02FB 00A97F00 DD0001C6 31FF01FB FFFFA464 EF9F0001 C63EFF01 ..>.....d......1................. 0000C0
02FBF8A9 DFF8A918 D0FCA9DF FCA905D0 0001C5F4 FF00FB00 01C613FF 01FB00A9 ................................ 0000E0
C5C2FF00 FB0001C5 E9FF01FB FFFFA424 EF9F0001 C5C6FF01 FB00DDFF FFE067EF .d.............$................ 000100
2D0001C5 51FF1650 63AB7E51 5BAB7EFF FFE4DFEF 01FB5BAB 7FFCADFD AF9E0001 .........[.......~.[Q~.cP..Q...- 000120
5140A97E FFFFE3A4 EF02FB40 A97F63AB 7FD31102 12FFFF64 51EF0020 67BB63AB .c.d ..Qd.........c..@.......~.@Q 000140
2067BB63 AB2D5811 0212FFFF 62C8EF01 2067BB63 AB2D0001 C526FF16 5063AB7E ~.cP..3...-.c.d ...b.....X-.c.d 000160
FFA217EF 9F0001C5 39FF01FB 02DD6BBB 0000C080 8F4A9811 0213FFFF 62B7EF01 ...b......J......k.....9........ 000180
EF9F0001 C546FF01 FB00A97F 0001C214 EF02FB00 A97F09DD 0001C55C FF01FBFF ....\......................F..... 0001A0
FF1650FF FF5DDBEF 9EFCADFD AF9E0001 C512FF00 FB0001C5 31FF01FB FFFFA37C |......1....................].P.. 0001C0
AF9E0001 C4CAFF16 5150D050 FFFF64C8 EF9E52FB AF9ECFFC 045001D0 0001C4C0 ......P......R...d..P.PQ........ 0001E0

Virtual block number 69 (00000045), 512 (0200) bytes

0001C4B4 FF01FB00 DDFCADFD AF9EFCAD FDAF9EFC ADFDAF9E FCADFDAF 9EFCADFD ................................ 000000
D0FCA9DF FCA90000 004D8FD0 0001C4B0 FF00FB00 01C4CFFF 01FBFFFF A322EF9F .."....................N......... 000020
A1FF01FB FFFFA2F4 EF9F0001 C47EFF01 FB00DDFF FFDF1FEF 02FBF8A9 DFF8A918 ......................~.......... 000040
DDFFFFDE EDEF02FB F8A9DFF8 A905D0FC A9DFFCA9 16D00001 C47AFF00 FB0001C4 ......z......................... 000060
FCA919D0 0001C448 FF00FB00 01C467FF 01FBFFFF A2CAEF9F 0001C44C FF01FB00 ....L..............d.......H...... 000080
FFFFA2A0 EF9F0001 C41AFF01 FB00DDFF FFDEBBEF 02FBF8A9 DFF8A908 D0FCA9DF ................................ 0000A0
89EF02FB F8A9DFF8 A90BD0FC A9DFFCA9 14D00001 C416FF00 FB0001C4 35FF01FB ...5............................ 0000C0
0001C3E4 FF00FB00 01C403FF 01FBFFFF A276EF9F 0001C3E8 FF01FB00 DDFFFFDE ..................v.............. 0000E0
EF9F0001 C3B6FF01 FB00DDFF FFDE57EF 02FBF8A9 DFF8A90C D0FCA9DF FCA914D0 ..................W............. 000100
F8A9DFF8 A90DD0FC A9DFFCA9 14D00001 C3B2FF00 FB0001C3 D1FF01FB FFFFA24C L............................... 000120
FF00FB00 01C39FFF 01FBFFFF A222EF9F 0001C384 FF01FB00 DDFFFFDE 25EF02FB ...%..............'............. 000140
C352FF01 FB00DDFF FFDDF3EF 02FBF8A9 DFF8A90E D0FCA9DF FCA914D0 0001C380 ..............................R. 000160
A910D0FC A9DFFCA9 14D00001 C34EFF00 FB0001C3 6DFF01FB FFFFA1F8 EF9F0001 ............m......N............ 000180
01C33BFF 01FBFFFF A1CEEF9F 0001C320 FF01FB00 DDFFFFDD C1EF02FB F8A9DFF8 ............................... 0001A0
FB00DDFF FFDDBFEF 02FBF8A9 DFF8A911 D0FCA9DF FCA914D0 0001C31C FF00FB00 ..........................'...... 0001C0
D0FCADFD AF9E0001 C2EAFF00 FB0001C3 09FF01FB FFFFA1A4 EF9F0001 C2EEFF01 ................................ 0001E0

Virtual block number 70 (00000046), 512 (0200) bytes

75EF9F00 01C2B7FF 01FB00DD FFFFDD58 EF02FBF8 A9DFF8A9 14D0FCA9 DFFCA914 ...............X...............u 000000
```

```
FBF8A9DF F8A914D0 FCA9DFFC A92BD000 01C2B3FF 00FB0001 C2D2FF01 FBFFFFA1 .................+............ 000020
2DFF1650 73AB7E51 6BAB7EFF FFE1BBEF 01FB6BAB 7FFCADFD AF9EFFFF DD26EF02 ..&..........k........~.kQ~.sP..- 000040
BEE6EF03 FB00A97F 73AB7F01 DDD31102 12FFFF62 E7EF0020 77BB73AB 2D0001C2 ...-.s.w ...b..........s....... 000060
FDAF9E00 01C1F3FF 165073AB 7E5108A9 7EFFFFE0 71EF02FB 08A97F00 A97F0001 ...........Q...~..Q~.sP........ 000080
2DFCADFD AF9EFD58 31000000 FDEF00FB 0A12FFFF 62A7EF01 2077BB73 AB2DFCAD ..-.s.w ...b.........1X......- 0000A0
BB73AB2D FCADFDAF 9EFD3B31 00006B88 EF00FB0A 12FFFF62 89EF0120 77BB73AB .s.w ...b........k..1;.......-.s. 0000C0
012077BB 73AB2DFC ADFDAF9E FD1E3100 00BE9FEF 00FB0A12 FFFF626B EF012077 w ..kb............1........-.s.w . 0000E0
622FEF01 2077BB73 AB2DFCAD FDAF9EFD 01310000 CC36EF00 FB0A12FF FF624DEF .Kb.......6...1........-.s.w ../b 000100
5801CE03 1158D404 13FFFF62 19EF0120 77BB73AB 2D5C01CE 03115CD4 0413FFFF .....\....\-.s.w ...b../..X....X 000120
3221135C D55C58C8 5801CE03 1158D404 13FFFF62 00EF0120 77BB73AB 2D5C58C8 .X\-.s.w ...b.....X....X.X\.\.!2 000140
FC9231FF FFDD1BEF 01FB00A9 7F0001C1 19FF1650 00A97E52 FFFF61E5 EF9E5102 .Q....a..R~..P...............1.. 000160
FDAF9EFE 5D31FCAD FDAF9E08 110212FF FF61BBEF 012077BB 73AB2DFC ADFDAF9E .....-.s.w ...a.............1J.... 000180
FFFF625C EF9E52FB AF9ECFFC 00045001 D00001C0 F5FF1650 FFFF6114 EF9EFCAD ......a..P........P........R..\b.. 0001A0
AF9EFCAD FDAF9EFC ADFDAF9E FCADFDAF 9EFCADFD AF9E0001 C0FEFF16 5150D050 P.PQ............................ 0001C0
0001C08C FF1650FE 97CB7E52 FFFF6D21 EF9E5103 329FAB00 0000008F 4AFCADFD ...J........2.Q..!m..R~...P...... 0001E0
```

Virtual block number 71 (00000047), 512 (0200) bytes

```
310312FF FF6CF8EF 0020FEA3 DBFE9FCB 2D0001C0 BDFF01FB 4D9FCF9F A3AB084A J.......M.......-....... ....1.....1 000000
FF00FB00 01C0BFFF 01FBEFFE 9F6AEF9F 0001C0A4 FF01FB00 DDFCADFD AF9E05CB ...................j............. 000020
FB00DDFF FFDB0FEF 02FBF8A9 DFF8A918 D0FCA9DF FCA90000 004D8FD0 0001C0A0 ......M.......................... 000040
D0FCADFD AF9E0001 C06AFF00 FB0001C0 91FF01FB FFFF9F3C EF9F0001 C06EFF01 ..n......<..............j......... 000060
0DEF9F00 01C037FF 01FB00DD FFFFDAD8 EF02FBF8 A9DFF8A9 08D0FCA9 DFFCA90A ..........................7...... 000080
FBF8A9DF F8A90BD0 FCA9DFFC A90AD000 01C033FF 00FB0001 C052FF01 FBFFFF9F ......R.......3................. 0000A0
01FF00FB 0001C020 FF01FBFF FF9EE3EF 9F0001C0 05FF01FB 00DDFFFF DAA6EF02 ...................... ....... 0000C0
01BED7FF 01FB0ADD FFFFDA74 EF02FBF8 A9DFF8A9 0AD0FCA9 DFFCA90A D00001C0 .........................t........ 0000E0
0001BFC4 FF00FB00 01C003FF 01FBFEA7 CB7F0001 BFF6FF01 FBFFFF9E B9EF9F00 ................................ 000100
EF03FBFE AFCB7FFE A7CB7F01 DD04BA31 0312FFFF 6BE7EF00 20FEABDB FEA7CB2D -....... ...k.....1............... 000120
01BF2FFF 1650FEAF CB7E5138 A97EFFFF DDAEEF02 FB38A97F FEA7CB7F 0001BC24 $..........8........~.8Q~...P../.. 000140
20FEB3DB FEAFCB2D 5C01CE03 115CD404 13FFFF6B 56EF0120 FEB3DBFE AFCB2D00 .-....... ..Vk......\.....\-....... 000160
52FFFF6B 23EF9E51 02322113 5CD55C58 C85801CE 031158D4 0413FFFF 6B3EEF01 ..>k......X.....X.X\.\.!2.Q..#k..R 000180
BF0AFF01 FB4F05CF 9FFE6B31 FFFFDAE4 EF01FB00 A97F0001 BEE2FF16 5000A97E ~..P.................1k.....O..... 0001A0
7E52FFFF 6ADBEF9E 510932FE 4D310312 FFFF6B45 EF0020FE ABDBFEA7 CB2D0001 ..-....... ..Ek.....1M.2.Q....j..R~ 0001C0
AF9E2F11 0002A7AB 01000000 648FF1A7 ABD7A7AB 01D00001 BEA2FF16 50FEB7CB ...P.................d........../.. 0001E0
```

Virtual block number 72 (00000048), 512 (0200) bytes

```
9E431102 12FEABDB FEA7CB20 FFFFC74E EF4C0C2D 5C000CEA AF00A7AB 0AFCADFD ............\-.L.N... .........C. 000000
FEB7CB7E 52FFFF6A 75EF9E51 0932FCAD FDAF9EA7 ABD7D4A7 ABCCAFF3 FCADFDAF .................2.Q..uJ..R~..... 000020
31031300 0000008F 5C515CAB AB4E0001 BE7AFF01 FB531DCF 9F0001BE 45FF1650 P..E......S...z...N..\Q\........1 000040
7FFEB7CB 7F0001BE 0DFF03FB 00A97FFF FF9D57EF 9FFEA7CB 7FFCADFD AF9E038B ..............W.................. 000060
29FF01FB 0068CF9F 0001BE34 FF01FB51 5CCF9F00 01BDFBFF 03FBFE7F CB7F00A9 ...............\Q...4.....h.....) 000080
0313FFFF 69D9EF11 20FFFFCD 99EF1E2D 67963103 13AEAF5C 515CABAB 4E0001BE ...N...\Q\.....1.g-....... .....i..... 0000A0
BDA6FF03 FB00A97F FFFF9CF0 EF9FFEA7 CB7F0001 BDFEFF01 FB5A0DCF 9F01E331 1.....Z.......................... 0000C0
01BDCBFF 01FB50F3 CF9F0001 BD92FF03 FBFE7FCB 7F00A97F FFFF9CE8 EF9F0001 ..........................P....... 0000E0
```

```
FF01FBFF FF9C83EF 9F0001BD BDFF01FB 00DDFCAD FDAF9EFC ADFDAF9E FB1E3100 .1.............................. 000100
EF02FBF8 A9DFF8A9 18D0FCA9 DFFCA900 00004D8F D000013D B9FF00FB 0001BDD8 .............N.................. 000120
01BD83FF 00FB0001 BDAAFF01 FBFFFF9C 85EF9F00 01BD87FF 01FB00DD FFFFD828 (............................... 000140
19310313 00000000 8F5C515C ABAB4E00 01BD5BFF 01FB03AE CF9FFCAD FDAF9E00 .............[...N..\Q\.......1. 000160
E9FF1650 FEBFCB7E 52FFFFCC ADEF9E51 01638F32 0001BD40 FF01FB51 7BCF9F01 ...{Q...@...2.c.Q.......R^...P... 000180
A1110212 FFFF68CA EF0120FE B3DBFEAF CB2D0001 BD1EFF01 FB1F87CF 9F0001BC .................-........h...... 0001A0
CDADEF0F 20FEA3DB FE9FCB2C 00C63103 12FFFFCC 75EFC4AF 20FEC3DB FEBFCB2D -........u.....1................ 0001C0
7F00DD00 01B96BEF 03FB28A9 7F30A97F 02DD0001 B3B2EF02 FB30A97F 00DDFFFF ......0............0..(...k...... 0001E0
```

Virtual block number 73 (00000049), 512 (0200) bytes

```
28A97F18 A97F0001 B962EF04 FB18A97F 20A97F04 DD03DD00 01B397EF 02FB20A9 .....................b.........( 000000
00A97F08 A97F08DD 02DD0001 B36AEF02 FB08A97F 00DD0001 BC5EFF03 FB10A97F ........^........J............... 000020
01FB61F4 CF9F0001 BC2EFF03 FBFFFF9B 8DEF9F10 A97F00A9 7F0001B9 35EF04FB ...5..........................a.. 000040
EF9B77EF 9F0001BC 0DFF03FB 00A97FFF FF9B7FEF 9FFFFF9B 7DEF9F00 01BC67FF .a.....}.....................w... 000060
16FCADFD AF9E0001 BC32FF01 FB4F5ACF 9F0001BB F9FF03FB FE7FCB7F 00A97FFF ..................ZO...2......... 000080
1650FEAF CB7E52FF FF685CEF 9E510032 FCADFDAF 9EFCADFD AF9E0400 01BC03FF ..................2.Q..\h..R^...P. 0000A0
0001BC1C FF01FBFF FF9AC7EF 9F0001BC 01FF01FB 00DDFCAD FDAF9E00 01BBC7FF ................................. 0000C0
FFFFD66C EF02FBF8 A9DFF8A9 18D0FCA9 DFFCA900 00004D8F D00001BB FDFF00FB ..........N..................1... 0000E0
008F4A00 01BBC7FF 00FB0001 BBEEFF01 FBFFFF9A F1EF9F00 01BBCBFF 01FB00DD ..............................J.. 000100
E5FF01FB FFFF9AD4 EF9FAFAB 504A0001 BBF6FF01 FBFFFF9A DDEF9F9F AB000000 ..................JP............. 000120
32008E31 0313C5AF 5C515CAB AB4E0001 BB7AFF01 FB61E5CF 9FB3AB50 4A0001BB ...JP.....a...z...N..\Q\....1..2 000140
B042EFFF FFCAD3EF 1E280001 BB16FF16 50FEC7CB 7E52FFFF B04EEF9E 51014E8F .N.O..N....R^...P......(........B. 000160
6FCF9F00 01BB2FFF 01FB4F6A CF9FFCAD FDAF9E00 01BB3FFF 01FB0838 CF9FFFFF ....B....?...........JO.../......o 000180
2D5C01CE 03115CD4 0413FFFF 66D0EF01 20FEB3DB FEAFCB2D 0001BB24 FF01FB23 $...$...-...........f.....\.....\- 0001A0
FEE53103 135CD55C 58C85801 CE031158 D40413FF FF6698EF 0220FEB3 DBFEAFCB ...........f.....X....X.X\.\..1.. 0001C0
CBDBFEC7 CB2DFCAD FDAF9E64 5131FCAD FDAF9EFA 35310001 BAE2FF01 FB12AF9F ...........15.......1Qd.....-..... 0001E0
```

Virtual block number 74 (0000004A), 512 (0200) bytes

```
7F00DDFF FFB09DEF 0F20FEA3 DBFE9FCB 2C00FD31 0312FFFF AFAEEF01 4E8F20FE ..N.........1......................  000000
EF02FB20 A97F00DD 0001B730 EF03FB28 A97F30A9 7F02DD00 01B177EF 02FB30A9 .0...w........0..(...0............ 000020
03FB10A9 7F28A97F 18A97F00 01B727EF 04FB18A9 7F20A97F 04DD03DD 0001B15C \......................'.......(..... 000040
B6FAEF04 FB00A97F 08A97F08 DD02DD00 01B12FEF 02FB08A9 7F00DD00 01BA23FF .$................/................. 000060
BA86FF01 FBFFFF99 6DEF9F00 01B9F3FF 03FBFFFF 99BAEF9F 10A97F00 A97F0001 ..............................m......... 000080
10A97FFF FF9963EF 9FFFFF99 31EF9F00 01BA1BFF 01FB60EC CF9FAFAB 504A0001 ..JP.....`..........1.......c........ 0000A0
FFFF9950 EF9F0001 B9AEFF03 FB08A97F 10A97FFF FF995BEF 9F0001B9 C1FF03FB ..........[.....................P... 0000C0
01B987FF 03FBFE7F CB7F00A9 7FFFFF99 05EF9F00 01B99BFF 03FB00A9 7F08A97F ................................. 0000E0
FDAF9EFC ADFDAF9E 040001B9 91FF16FC ADFDAF9E 0001B9C0 FF01FB4C EBCF9F00 ....L............................. 000100
FDAF9E06 75310313 00000000 8F5C515C ABAB4E00 01B99FFF 01FB5EA4 CF9FFCAD .....^.......N..\Q\.......1u...... 000120
01FB00DD FFFFD410 EF02FBF8 A9DFF8A9 02D0FCA9 DFFCA903 D0FCADFD AF9EFCAD ................................. 000140
FB0001B9 7DFF01FB FFFF9870 EF9F0001 B992FF01 FBFFFF98 CDEF9F00 01B96FFF .o.....................p.......}.... 000160
FF01FB00 DDFFFFD3 D1EF02FB F8A9DFF8 A904D0FC A9DFFCA9 03D00001 B95EFF00 ..^............................... 000180
00FB0001 B93EFF01 FBFFFF98 91EF9F00 01B953FF 01FBFFFF 9896EF9F 0001B930 0..............S...........>..... 0001A0
F1FF01FB 00DDFFFF D392EF02 FBF8A9DF F8A906D0 FCA9DFFC A903D000 01B91FFF ................................. 0001C0
FF00FB00 01B8FFFF 01FBFFFF 9862EF9F 0001B914 FF01FBFF FF9867EF 9F0001B8 .....a..............b.............. 0001E0
```

```
Virtual block number 75 (0000004B), 512 (0200) bytes

BBB2FF01 FB00DDFF FFD353EF 02FBF8A9 DFF8A908 D0FCA9DF FCA903D0 0001B8E0 ......................S......... 000000
A1FF00FB 0001B8C0 FF01FBFF FF9833EF 9F0001B8 D5FF01FB FFFF9838 EF9F0001 ....8...........3............... 000020
01B873FF 01FB00DD FFFFD314 EF02FBF8 A9DFF8A9 0AD0FCA9 DFFCA903 D00001B8 ..............................s. 000040
B862FF00 FB0001B8 81FF01FB FFFF9804 EF9F0001 B896FF01 FBFFFF98 09EF9F00 ..............................b. 000060
0001B834 FF01FB00 DDFFFFD2 D5EF02FB F8A9DFF8 A90AD0FC A9DFFCA9 28D00001 ...(........................4... 000080
DFF8A90B D0FCA9DF FCA903D0 0001B830 FF00FB00 01B84FFF 01FBFFFF 97DAEF9F .........0.......0.............. 0000A0
9F0001B8 25FF01FB FFFF97B0 EF9F0001 B802FF01 FB00DDFF FFD2A3EF 02FBF8A9 ............................%... 0000C0
A9DFF8A9 0CD0FCA9 DFFCA903 D00001B7 F1FF00FB 0001B810 FF01FBFF FF97ABEF ................................ 0000E0
EF9F0001 B7E6FF01 FBFFFF97 81EF9F00 01B7C3FF 01FB00DD FFFFD264 EF02FBF8 ....d........................... 000100
9F0001B7 A5FF00FB 0001B7CC FF01FBFF FF9777EF 9F0001B7 D9FF01FB FFFF977C |...........w.................... 000120
8F445C50 500001B7 CDFF01FB FFFF974C EF9F0001 B782FF02 FB00DDFF FF976BEF .k..............L.........PP\D. 000140
61FF00FB 0001B78C FF01FB7E 5C505C50 500001B6 62EF1650 005C415C 182B410D .A+.\A\.P..b...PP\P\^.........a 000160
01B733FF 01FB00DD FFFFD1D4 EF02FBF8 A9DFF8A9 0DD0FCA9 DFFCA903 D00001B7 .............................3.. 000180
FF9707EF 9F0001B7 49FF01FB FFFF970C EF9F0001 B756FF01 FBFFFF97 11EF9F00 ..........V.............I........ 0001A0
EF9F0001 B6F2FF02 FB00DDFF FF96FBEF 9F0001B7 15FF00FB 0001B73C FF01FBFF ....<........................... 0001C0
500001B5 D2EF1650 005C415C 93083FC9 8F445C50 500001B7,3DFF01FB FFFF96DC .........=...PP\D..?..\A\.P......P 0001E0

Virtual block number 76 (0000004C), 512 (0200) bytes

A9DFF8A9 0FD0FCA9 DFFCA903 D00001B6 D1FF00FB 0001B6FC FF01FB7E 5C505C50 P\P\^........................... 000000
EF9F0001 B6C6FF01 FBFFFF96 A1EF9F00 01B6A3FF 01FB00DD FFFFD144 EF02FBF8 ....D........................... 000020
F8A9DFF8 A910D0FC A9DFFCA9 03D00001 B692FF00 FB0001B6 B1FF01FB FFFF969C ................................ 000040
6DEF9F00 01B687FF 01FBFFFF 9672EF9F 0001B664 FF01FB00 DDFFFFD1 05EF02FB m...........d.....r.............m 000060
FBF8A9DF F8A911D0 FCA9DFFC A903D000 01B653FF 00FB0001 B672FF01 FBFFFF96 .......r......S................. 000080
963EEF9F 0001B648 FF01FBFF FF9643EF 9F0001B6 25FF01FB 00DDFFFF D0C6EF02 ...........%.....C......H.....>. 0000A0
02FBF8A9 DFF8A913 D0FCA9DF FCA903D0 0001B614 FF00FB00 01B633FF 01FBFFFF .....3.......................... 0000C0
FF960FEF 9F0001B6 09FF01FB FFFF9614 EF9F0001 B5E6FF01 FB00DDFF FFD087EF ................................ 0000E0
EF02FBF8 A9DFF8A9 14D0FCA9 DFFCA903 D00001B5 D5FF00FB 0001B5F4 FF01FBFF ................................ 000100
FFFF95E0 EF9F0001 B5CAFF01 FBFFFF95 E5EF9F00 01B5A7FF 01FB00DD FFFFD048 H............................... 000120
09EF02FB F8A9DFF8 A916D0FC A9DFFCA9 03D00001 B596FF00 FB0001B5 B5FF01FB ................................ 000140
FBFFFF95 B1EF9F00 01B58BFF 01FBFFFF 95B6EF9F 0001B568 FF01FB00 DDFFFFD0 ..........h..................... 000160
CFCAEF02 FBF8A9DF F8A902D0 FCA9DFFC A937D000 01B557FF 00FB0001 B576FF01 ..v.......W....7................ 000180
FFFF9580 EF9F02DD 0001B54C FF01FBFF FF9587EF 9F0001B5 29FF01FB 00DDFFFF .........)............L......... 0001A0
FF01FB00 DD0001B5 09FF00FB 0001B530 FF01FB00 A97F0001 B19EEF03 FB00A97F .................0.............. 0001C0
04FB08A9 7FFFFF95 45EF9F03 DD03DD00 01B513FF 01FBFFFF 955EEF9F 0001B4F0 ......^...................E..... 0001E0

Virtual block number 77 (0000004D), 512 (0200) bytes

06DD02DD 0001B4E8 FF01FBFF FF9533EF 9F0001B4 F5FF01FB 08A97F00 01B177EF .w................3............. 000000
01B4A3FF 00FB0001 B4C2FF01 FB00A97F 0001B14C EF04FB00 A97FFFFF 951AEF9F ............L................... 000020
9F0001B4 75FF01FB 00DDFFFF CF16EF02 FBF8A9DF F8A903D0 FCA9DFFC A937D000 ..7.........................u... 000040
A97F0001 B0EAEF03 FB00A97F FFFF936C EF9F02DD 0001B498 FF01FBFF FF94EBEF ...................l............ 000060
01FBFFFF 94AAEF9F 0001B43C FF01FB00 DD0001B4 55FF00FB 0001B47C FF01FB00 ....|.......U........<.......... 000080
```

```
41FF01FB 08A97F00 01B0C3EF 04FB08A9 7FFFFF93 31EF9F03 DD03DD00 01B45FFF .-.........1...................A 0000A0
EF04FB00 A97FFFFF 9306EF9F 06DD02DD 0001B434 FF01FBFF FF947FEF 9F0001B4 ...........4.................... 0000C0
F8A904D0 FCA9DFFC A93CD000 01B3EFFF 00FB0001 B40EFF01 FB00A97F 0001B098 ........................<....... 0000E0
0001B3E4 FF01FBFF FF943FEF 9F0001B3 C1FF01FB 00DDFFFF CE62EF02 FBF8A9DF .....b..................T....... 000100
DFF8A906 D0FCA9DF FCA93CD0 0001B3B0 FF00FB00 01B3CFFF 01FBFFFF 943AEF9F ..!.....................<....... 000120
B372FF01 FB00DD1F 12FFFF5F 40EF1120 FFFFC300 EF1E2DFF FFCE23EF 02FBF8A9 .....4...-........@_..........r. 000140
01B353FF 01FB00DD 1D110001 B36EFF00 FB0001B3 95FF01FB FFFF9400 EF9F0001 .......................n......S.. 000160
EF9F0001 B336FF01 FB00DD00 01B34FFF 00FB0001 B376FF01 FBFFFF92 B9EF9F00 ...........v......O.......6..... 000180
AF9E0400 01B2EBFF 16FCADFD AF9E0001 B332FF00 FB0001B3 51FF01FB FFFF93CC .......Q.......2................ 0001A0
FB00DDFF FFCDBFEF 02FBF8A9 DFF8A901 D0FCA9DF FCA902D0 FCADFDAF 9EFCADFD ................................ 0001C0
0001B2FC FF01FBFF FF937FEF 9F0001B3 11FF01FB FFFF924C EF9F0001 B2EEFF01 ........L....................... 0001E0
```

Virtual block number 78 (0000004E), 512 (0200) bytes

```
01FB00DD FFFFCD50 EF02FBF8 A9DFF8A9 02D0FCA9 DFFCA902 D00001B2 DDFF00FB .......................P........ 000000
FB0001B2 BDFF01FB FFFF9348 EF9F0001 B2D2FF01 FBFFFF92 15EF9F00 01B2AFFF .......................H........ 000020
FF01FB00 DDFFFFCD 11EF02FB F8A9DFF8 A903D0FC A9DFFCA9 02D00001 B29EFF00 ................................ 000040
00FB0001 B286FF01 FBFFFF91 B9EF9F00 01B293FF 01FBFFFF 931EEF9F 0001B270 p............................... 000060
FF01FB00 A97F0001 AF2EEF02 FB00A97F 20DD0001 B246FF01 FB00DD00 01B25FFF .-.......F...................... 000080
00FB0001 B23EFF01 FBFFFF92 D9EF9F00 01B253FF 01FBFFFF 9166EF9F 0001B260 `.....f......S..............>.... 0000A0
F1FF01FB 00DDFFFF CC92EF02 FBF8A9DF F8A904D0 FCA9DFFC A902D000 01B21FFF ................................ 0000C0
A5EF9F00 01B207FF 01FBFFFF 92AAEF9F 0001B214 FF01FBFF FF92AFEF 9F0001B1 ................................ 0000E0
FBF8A9DF F8A904D0 FCA9DFFC A91AD000 01B1D3FF 00FB0001 B1F2FF01 FBFFFF92 ................................ 000100
9276EF9F 0001B1C8 FF01FBFF FF927BEF 9F0001B1 A5FF01FB 00DDFFFF CC46EF02 ..F.............{............v. 000120
EF012900 01B187FF 00FB0001 B1A6FF01 FBFFFF92 71EF9F00 01B1BBFF 01FBFFFF ...........q.................).. 000140
5B52EFFF FFB6E1EF 01290001 B156FF01 FB04FECF 9F0B12FF FF5B6CEF FFFFB6FA .....1[..........V...)........R[ 000160
6ECF9F0B 12FFFF5C EBEFFFFF B6C8EF01 290001B1 3DFF01FB 07F4CF9F 0B12FFFF ..............=...)........\......n 000180
FB00DDFF FFCBAFEF 02FBF8A9 DFF8A901 D0FCA9DF FCA938D0 0001B124 FF01FB0B ....$....8...................... 0001A0
03FB00A9 7FFFFF91 F5EF9F02 DD0001B1 31FF01FB FFFF91FC EF9F0001 B10EFF01 ...............1................ 0001C0
9F0001B0 D5FF01FB 00DD0001 B0EEFF00 FB0001B1 15FF01FB 00A97F00 01AD83EF ................................ 0001E0
```

Virtual block number 79 (0000004F), 512 (0200) bytes

```
0001AD5C EF04FB08 A97FFFFF 91BAEF9F 03DD03DD 0001B0F8 FF01FBFF FF9143EF .C..........................\... 000000
FF918FEE 9F06DD02 DD0001B0 CDFF01FB FFFF9118 EF9F0001 B0DAFF01 FB08A97F ................................ 000020
FCA938D0 0001B088 FF00FB00 01B0A7FF 01FB00A9 7F0001AD 31EF04FB 00A97FFF .......1....................8.. 000040
FFFF9158 EF9F0001 B05AFF01 FB00DDFF FFCAFBEF 02FBF8A9 DFF8A902 D0FCA9DF .......................Z.....X... 000060
61FF01FB 00A97F00 01ACCEEF 03FB00A9 7FFFFF8F 89EF9F02 DD0001B0 7DFF01FB ...}...........................a 000080
0001B044 FF01FBFF FF908FEF 9F0001B0 21FF01FB 00DD0001 B03AFF00 FB0001B0 ......!........!..........D..... 0000A0
EF9F0001 B026FF01 FB08A97F 0001ACAB EF04FB08 A97FFFFF 8F4EEF9F 03DD03DD ......N...................&..... 0000C0
7F0001AC 7DEF04FB 00A97FFF FF8F23EF 9F06DD02 DD0001B0 19FF01FB FFFF9064 d...............#.........}..... 0000E0
02FBF8A9 DFF8A903 D0FCA9DF FCA93DD0 0001AFD4 FF00FB00 01AFF3FF 01FB00A9 ................=............... 000100
FF90A7EF 9F0001AF C9FF01FB FFFF90AC EF9F0001 AFA6FF01 FB00DDFF FFCA47EF .G.............................. 000120
EF02FBF8 A9DFF8A9 04D0FCA9 DFFCA935 D00001AF 95FF00FB 0001AFB4 FF01FBFF ...................5............ 000140
FFFF9078 EF9F0001 AF8AFF01 FBFFFF90 7DEF9F00 01AF67FF 01FB00DD FFFFCA08 ..........g.....}..........x.... 000160
```

```
ABD7BFAB 01D0BBAB 00000000 8F4AB7AB 2C4A0001 AF56FF00 FB0001AF 75FF01FB ...y......V...J...J.............. 000180
013200B7 AB0AB7AB 5C4A5C08 405CB7AB 4EFCADFD AF9E5711 0002BFAB 011AF1BF .........W.....N..\@.\J\......2. 0001A0
FFFF5B35 EF0020FF FFAC67EF 4C182D5C 00181A00 BFAB0AFD 77CB4CCF AF4A5C00 .\J..L.w........\-.L.g... ..5[.. 0001C0
ABD7ACBF AB1AF3FC ADFDAF9E FCADFDAF 9EBBAB5C 1A5C0840 5CBBAB4E 0B110212 ....N..\@.\J\................... 0001E0

Virtual block number 80 (00000050), 512 (0200) bytes

18585C51 5BBBAB4E 5C10445C C3AB4EC3 AB5C4A5C 10465CBB AB4EFCAD FDAF9EBF ......N..\F.\J\..N..\D.\N..XQ\X. 000000
8F4AC7AB 5C4A5C21 405C1046 5C255843 58C3AB4E C3AB5C4A 5C08405C C3AB4E0B .N..\@.\J\..N..XCX%\F.\@!\J\...J. 000020
00BFAB0A FCADFDAF 9E020531 0003BFAB 011AF1BF ABD7BFAB 01D0CBAB 00000000 ....................1........... 000040
4A5C0840 5CCBAB4E 01D03103 12FFFF5A A2EF0020 FFFFABD4 EF4C182D 5C00181A ...\-.L...... ...Z....1..N..\@.\J 000060
F1CFABD6 CFAB18D0 0001ADF4 FF1650FE CFCB7E52 FFFF5A89 EF9E5100 32CBAB5C \..2.Q...Z..R~...P.............. 000080
9ECFABDD 01DD5C00 181A00BF AB0AFCAD FDAF9E00 83310003 CFABFFFF FFFF8F01 .........1..............\...... 0000A0
FECFCB2D 0001AAA0 EF04FBFE AFCB7FFF FF8F2FEF 9FFFFF8F 39EFFFFF AB7AEF4C L.2...:9...../.................. 0000C0
18110212 FFFF57B5 EF0120FE B3DBFEAF CB2D1211 0213FFFF 5A2BEF00 20FED3DB ... ..+Z.......-.........W....... 0000E0
FDAF9EFC ADFDAF9E 0001AD70 FF03FBFE CFCB7FFE AFCB7FFE CFCB7FFC ADFDAF9E ...................P........... 000100
D7AB104A D3ABC7AB CBABC1FC ADFDAF9E CFABD6FF 80CFABFF FFFFFF8F 01F1FCAD ..........................J... 000120
0D12105C 515CD7AB 4ED7AB33 4AD3AB5C C3ABC35C C7ABCBAB C11015C3 ABCBABD1 ...........\...\..J3..N..\Q\.... 000140
5C000132 00B7AB0A B7AB5C4A 5C2C405C D3AB4E0B 11B7AB5C 4A5C2340 5CD3AB4E N..\@.\J\....N..\@.\J\......2..\ 000160
CFCB7F00 01AD37FF 01FB00DD FFFFC7D8 EF02FBD3 ABDFD7AB DFFD77CB 4CBFABD0 ...L.w..................7...... 000180
4A580000 42G88F5C 435G584E 58FECFCB 3C0001AD 35FF00FB 0001AD5C FF01FBFE ....\......5...<...XNX\C\..B..XJ 0001A0
A97FDBAB DD2EDD00 01ACFBFF 01FB00DD 3C150000 00008F5C 515CDBAB 4EDBAB58 X..N..\Q\......<................ 0001C0
01FB00A9 7F0001AC 8DFF03FB 00A97FFF FF8E17EF 9F08A97F 0001A9BC EF03FB08 ................................ 0001E0

Virtual block number 81 (00000051), 512 (0200) bytes

0001ACB4 FF01FB00 DD0001AC B5FF01FB 0DBACF9F 0001ACD8 FF00FB00 01ACFFFF ................................ 000000
01ACBBFE 01EBFFFE 8DD6EF9E FEFF8DE0 EFFFFFAD 05EF4C9E 5C00061A 00BFAB0A .......\.L....................... 000020
ADFDAF9E BFABD7FD FEBFAB01 1AF1FCAD FDAF9EFC ADFDAF9E 0001AC9C FF00FB00 ................................ 000040
FFFF5655 EF9E5101 32FCADFD AF9EFCAD FDAF9E04 0001AC3C FF16FCAD FDAF9EFC ........<..............2.Q..UV.. 000060
FFFF560C EF9E5105 320001AC 35FF01FB 0CF2CF9F 0001AC00 FF1650FE D7CB7E52 R~...P..............5...2.Q...V.. 000080
EF9E5105 320001AC 11FF01FB 007CCF9F D3AB1C4A 0001ABE0 FF1650FE DFCB7E52 R~...P......J.....|........2.Q.. 0000A0
05320001 ABEEFF01 FB59AF9F D3AB1E4A 0001ABBC FF1650FE DFCB7E52 FFFF55E3 .U..R~...P......J.....Y.......2. 0000C0
01ABCBFF 01FB36AF 9FD3AB20 4A0001AB 99FF1650 FEDFCB7E 52FFFF55 BBEF9E51 Q...U..R~...P......J ....6...... 0000E0
FF01FB13 AF9FD3AB 214A0001 AB76FF16 50FEDFCB 7E52FFFF 5593EF9E 51053200 .2.Q...U..R~...P..v...J!........ 000100
FBD3ABDF FCA9DFFC A909D0FC ADFDAF9E 040001AB 79FF16FC ADFDAF9E 0001ABA8 ..........y..................... 000120
FB10A97F 17DD0001 ABAAFF01 FBFEDFCB 7F0001AB B5FF01FB 00DDFFFF C626EF02 ..&........................... 000140
7F28DD00 01AB87FF 01FBFFFF 8CA2EF9F 0001AB94 FF01FB10 A97F0001 A862EF02 ..b..........................(. 000160
0001AB64 FF01FBFE FF8C87EF 9F0001AB 71FF01FB 08A97F00 01AB3FEF 03FB08A9 .....?.................d... 000180
FFFF8C68 EF9F0001 AB4AFF01 FB00A97F 0001A818 EF02FB00 A97F0000 00428FDD ..B.....................J.....h.... 0001A0
9E040001 AACAFF16 0001AAF4 FF01FB0E AF9F0001 AB16FF00 FB0001AB 35FF01FB ...5............................ 0001C0
10405CDF AB4EDFAB 5C4A5C08 405C2044 5C1C425C D3AB4EFC ADFDAF9E FCADFDAF .........N..\B.\D \@.\J\..N..\@. 0001E0
```

```
Virtual block number 82 (00000052), 512 (0200) bytes

AB06FF01 FB00A97F 0001A764 EF04FB00 A97FFFFF 8C22EF9F 5CDD02DD 5C5C4A5C \J\\...\..'.........d........... 000000
02DD0001 AA8EFF01 FB2867CF 9F0B1200 0000008F 5C515CE3 AB4EE3AB 504A0001 ..JP..N..\Q\........a(.......... 000020
AB504A00 01AACBFF 01FB00A9 7F0001A7 29EF04FB 00A97FFF FF8BE7EF 9FDFABDD ..............)............JP. 000040
7F0001A6 FDEF04FB 00A97FFF FF8BBBEF 9F5CDD04 DD5C5C4A 5C18405C DFAB4EE7 .N..\@.\J\\...\................. 000060
AF5C515C 50500001 AA8EFF01 FBFFFF8B 0DEF9FEB AB504A00 01AA9FFF 01FB00A9 .........JP..............PP\Q\. 000080
EF9F58FF FFA267EF 4C4458EB AB4E5C00 011300E3 AB0A2911 EFAB87AF 5007128C ...P.....).......\N..XDL.a...X.. 0000A0
DFFCA9DF FCA915D0 FCADFDAF 9EEFAB58 5C475C50 500001AA 5DFF01FB FFFF8ADC ........J...PP\G\X.............. 0000C0
8B36EF9F 0001A9D8 FF01FB00 DD1F1200 0000008F EFAB51FF FFC483EF 02FBD3AB .........Q.....................6. 0000E0
E5EF4CE7 ABD15C00 011300E3 AB0A5311 0001A9D4 FF00FB00 01A9F3FF 01FBFFFF ................S.......\...L.. 000100
FB0001A9 C9FF01FB 7EEFAB50 0001A99C FF02FB00 DDFFFF8B 15EF9F23 12FFFF9F ....#..............P..~........ 000120
00FB0001 A99EFF01 FBFFFF8A F1EF9F00 01A983FF 01FB00DD 1D110001 A99EFF00 ................................ 000140
ADFDAF9E 040001A9 2DFF1600 01A957FF 01FB0321 CF9FFCAD FDAF9E00 01A97FFF ...........!....W.....-........ 000160
FB09E3CF 9F0001A8 F1FF1650 FED7CB7E 52FFFF53 45EF9E51 0132FCAD FDAF9EFC ......2.Q..ES..R~...P........... 000180
9FD3AB1C 4A0001A8 D1FF1650 FEDFCB7E 52FFFF52 FDEF9E51 05320001 A926FF01 ..&...2.Q...R..R~...P......J.... 0001A0
4A0001A8 ADFF1650 FEDFCB7E 52FFFF52 D4EF9E51 05320001 A902FF01 FB007CCF .!........2.Q...R..R~...P......J 0001C0
A88AFF16 50FEDFCB 7E52FFFF 52ACEF9E 51053200 01A8DFFF 01FB59AF 9FD3AB1E .....Y.......2.Q...R..R~...P.... 0001E0

Virtual block number 83 (00000053), 512 (0200) bytes

1650FEDF CB7E52FF FF5284EF 9E510532 0001A8BC FF01FB36 AF9FD3AB 204A0001 ..J ....6.......2.Q...R..R~...P. 000000
9E040001 A86AFF16 FCADFDAF 9E0001A8 99FF01FB 13AF9FD3 AB214A00 01A867FF .a...J!.....................J..... 000020
CB7F0001 A876FF01 FB00DDFF FFC317EF 02FBD3AB DFFCA9DF FCA909D0 FCADFDAF .......................v..... 000040
9F0001A8 85FF01FB 10A97F00 01A553EF 02FB10A9 7F16DD00 01A89BFF 01FBFEDF ................S............. 000060
A862FF01 FB08A97F 0001A530 EF02FB08 A97F28DD 0001A878 FF01FBFF FF89CBEF ........x....(......0.........b. 000080
7F0001A5 09EF02FB 00A97F00 0000428F DD0001A8 55FF01FB FFFF8978 EF9F0001 ....x......U.....B.............. 0000A0
0EAF9F00 01A807FF 00FB0001 A826FF01 FBFFFF89 59EF9F00 01A83BFF 01FB00A9 .....f.....Y......&............. 0000C0
445C1C42 5CD3AB4E FCADFDAF 9EFCADFD AF9E0400 01A7BBFF 160001A7 E5FF01FB ......................N..\B.\D 0000E0
00A97FFF FF8913EF 9F5CDD02 DD5C5C4A 5C10405C DFAB4EDF AB5C4A5C 08405C20 \@.\J\..N..\@.\J\\...\........ 000100
00000000 8F5C515C E3AB4EE3 AB504A00 01A7F7FF 01FB00A9 7F0001A4 55EF04FB ...U.............JP..N..\Q\..... 000120
A41AEF04 FB00A97F FFFF88D8 EF9FDFAB DD02DD00 01A77FFF 01FB2558 CF9F0B12 ....X%........................... 000140
EF9F5CDD 04DD5C5C 4A5C1840 5CDFAB4E E7AB504A 0001A7BC FF01FB00 A97F0001 ............JP..N..\@.\J\\...\.. 000160
FCA915D0 EBAB504A 0001A790 FF01FB00 A97F0001 A3EEEF04 FB00A97F FFFF88AC ...........................JP...... 000180
AB0A5C01 CE03115C D4041287 AF585158 EBAB4EFF FFC1BFEF 02FBD3AB DFFCA9DF .............N..XQX.....\.....\.. 0001A0
5CD55C57 CA5757D2 5701CE03 1157D404 13FFFF9D 39EF48E7 ABD15800 011300E3 .....X...H.9......W....W.WW.W\.\ 0001C0
A6E2FF00 FB0001A7 15FF01FB EBABDD00 01A6DFFF 02FB00DD FFFF8870 EF9F2013 ...P............................ 0001E0

Virtual block number 84 (00000054), 512 (0200) bytes

ABD15800 011300E3 AB0A5C01 CE03115C D4041200 0000008F 585158EB AB4E0001 ..N..XQX.........\....\.......X.. 000000
91FF01FB 00DD1D13 5CD55C57 CA5757D2 5701CE03 1157D404 12FFFF9C E1EF48E7 .H.........W....W.WW.W\.\........ 000020
12AAAF5C 515CEBAB 4E0001A6 8DFF00FB 0001A6AC FF01FBFF FF8817EF 9F0001A6 ........................N..\Q\... 000040
AF9F0001 A666FF00 FB0001A6 85FF01FB FFFF87F8 EF9F0001 A66AFF01 FB00DD1D .....J......................f..... 000060
FCA9DFFC A92DD0FC ADFDAF9E FCADFDAF 9E040001 A61AFF16 0001A644 FF01FB0E ....D.......................-...... 000080
```

```
9CFAEF4C 9E5C0012 1300E3AB 0A0001A6 21FF01FB 00DDFFFF C0C2EF02 FBD3ABDF ...............!..........\.L...  0000A0
FF8797EF 9F0001A6 09FF00FB 0001A630 FF01FBFF FF87A3EF 9FFFFF87 ADEFFFFF ................0...............  0000C0
01A607FF 01FB7EFF FF9E2BEF 4C505C00 011300E3 AB0A0001 A5E6FF02 FB00DDFF .................\PL.+...........  0000E0
5164EF9E 510132FC ADFDAF9E FCADFDAF 9E040001 A59AFF16 0001A5DC FF00FB00 .........................2.Q..dQ  000100
BFABD7BF AB01D000 01A593FF 01FB0650 CF9F0001 A55EFF16 50FED7CB 7E52FFFF ..R"...P..^.....P...............  000120
DF0001A5 C5FF01FB F3ABBF00 01A58BFF 00FBFCAD FDAF9E67 110002BF AB010CF1 ........g.......................  000140
ABDFF7AB DF0001A5 69FF00FB 0001A5A8 FF01FBFE E7CB7F00 01A5BBFF 01FBF7AB ..........................i.....  000160
41FF00FB 0001A560 FF01FBFE E7CB7F00 01A543FF 01FB00DD FFFFBFE4 EF02FBF3 ............C...........`......A  000180
FB0001A5 0DFF01FB 56AF9FFC ADFDAF9E BFABD79C BFAB0CF3 FCADFDAF 9E0001A5 ..........................V.....  0001A0
ADFDAF9E FCADFDAF 9EFCADFD AF9E0400 01A4D7FF 16FCADFD AF9E0001 A52AFF00 ..*.............................  0001C0
9EFCADFD AF9EFCAD FDAF9EFC ADFDAF9E FCADFDAF 9EFCADFD AF9EFCAD FDAF9EFC ................................  0001E0
```

Virtual block number 85 (00000055), 512 (0200) bytes

```
FF5065EF 9E510132 FCADFDAF 9EFCADFD AF9EFCAD FDAF9EFC ADFDAF9E FCADFDAF ........................2.Q..eP.  000000
4BCBF1AF 50FE47CB F7AF50FB AB000000 008F5000 01A45FFF 1650FED7 CB7E52FF .R"...P..-..P.......P...G.P...K  000020
00BFAB0A FCADFDAF 9E211100 02BFAB01 07F1BFAB D7BFAB01 D0FE4FCB EBAF50FE .P...O.................!.........  000040
AB01D0FC ADFDAF9E BFABD7E2 BFAB07F3 FCADFDAF 9EFE57CB 4CC8AF50 5C000107 ...\P..L.W.......................  000060
5C08405C 20445C08 425CBFAB 4EFCADFD AF9E01F5 310003BF AB0104F1 BFABD7BF ...........1.......N..\B.\D \@.\  000080
01A467FF 01FB00A9 7F0001A0 C5EF04FB 00A97FFF FF8583EF 9F5CDD02 DD5C5C4A J\\...\.......................g..  0000A0
7FFFFF85 51EF9F5C DD02DD5C 5C4A5C14 405C2044 5C08425C BFAB4EE7 AB504A00 .JP..N..\B.\D \@.\J\\...\..Q....  0000C0
20445C08 425CBFAB 4EE3AB50 4A0001A4 35FF01FB 00A97F00 01A093EF 04FB00A9 ...............5...JP..N..\B.\D  0000E0
01FB00A9 7F0001A0 61EF04FB 00A97FFF FF851FEF 9F5CDD04 DD5C5C4A 5C1A405C \@.\J\\...\..........a.........  000100
0A013031 0313FFFF 99CEEF4C E7ABD15C 00011300 E3AB0AEB AB504A00 01A403FF .....JP.........\...L.......10..  000120
4E5C0001 1300E3AB 0AFBAB58 4058FFFF 9C22EF4C 4458EBAB 4E5C0001 1300E3AB .......\N..XDL."...X@X..........\N  000140
4458EBAB 4E5C0001 1300E3AB 0AFE47CB FE47CB58 4158FFFF 9C5AEF4C 4458EBAB ..XDL.Z...XAX.G..G........\N..XD  000160
9CC2EF4C 4458EBAB 4E5C0001 1300E3AB 0AFE4BCB FE4BCB58 4158FFFF 9CBEEF4C L.....XAX.K..K........\N..XDL...  000180
4158FFFF 9CF6EF4C 4458EBAB 4E5C0001 1300E3AB 0AFE4FCB FE4FCB58 4158FFFF ..XAX.O..O.........\N..XDL.....XA  0001A0
FE5FCB58 4158FFFF 9D2AEF4C 4458EBAB 4E5C0001 1300E3AB 0AFE5BCB FE5BCB58 X.[..[........\N..XDL.*....XAX.._.  0001C0
0AFE63CB FE63CB58 4158FFFF 9D5EEF4C 4458EBAB 4E5C0001 1300E3AB 0AFE5FCB ._.........\N..XDL.^...XAX.c..c..  0001E0
```

Virtual block number 86 (00000056), 512 (0200) bytes

```
1300E3AB 0AFE67CB FE67CB58 4158FFFF 9D92EF4C 4458EBAB 4E5C0001 1300E3AB ......\N..XDL.....XAX.g..g......  000000
4E5C0001 1300E3AB 0AFE6BCB FE6BCB58 4158FFFF 9DC6EF4C 4458EBAB 4E5C0001 ..\N..XDL.....XAX.k..k........\N  000020
4458EBAB 4E5C0001 1300E3AB 0AFE6FCB FE6FCB58 4158FFFF 9DFAEF4C 4458EBAB ..XDL.....XAX.o..o........\N..XD  000040
FE0EBFAB 0104F1FC ADFDAF9E FCADFDAF 9EFE73CB FE73CB58 4158FFFF 9E2EEF4C L.....XAX.s..s..................  000060
D0FCA9DE ECA90BD0 FE53CBFE 4FCB5C41 5CFE4BCB FE47CB41 FCADFDAF 9EBFABD7 ........A.C..K.\A\.O..S..........  000080
7EFBAB50 0001A214 FF02FB00 DDFFFF83 CDEF9FFF FFBCBFEF 02FBF8A9 DFF8A906 ..........................P..~  0000A0
AF9E5911 0002BFAB 0104F1BF ABD7BFAB 01D00001 A216FF00 FB0001A2 41FF01FB ...A.........................Y..  0000C0
9FFFFFBC 6DEF02FB F8A9DFF8 A95C4A5C 1A405CBF AB4EFCA9 DFFCA927 D0FCADFD .....'.....N..\@.\J\.........m....  0000E0
E5FF01FB 7EFE43CB 4C505C00 010400BF AB0A0001 A1C2FF02 FB00DDFF FF8353EF .S..................\PL.C."....  000100
BFAB01D0 FCADFDAF 9EBFABD7 AABFAB04 F3FCADFD AF9E0001 A1BAFF00 FB0001A1 ................................  000120
9EDEEF4C 182D5C00 181A00BF AB0AFCAD FDAF9E01 59310003 BFAB011A F1BFABD7 ..........1Y.............\-.L...  000140
FFA147EF 4C515C00 011A00BF AB0A5801 CE031158 D40413FF FF4DACEF 0020FFFF .. ...N.....X....X........\QL.G..  000160
5C08425C BFAB4E00 F9310313 58D55857 C85701CE 031157D4 04130000 0000BFFF .........W....W.WX.X..1..N..\B.\  000180
```

```
00A97F00 019DBFEF 04FB00A9 7FFFFF82 D3EF9F5C DD04DD5C 5C4A5C14 405C1C44 D.\@.\J\\...\.................. 0001A0
00BFAB0A FFAB5CFF FFA0EFEF 48475800 011A00BF AB0A5C50 500001A1 61FF01FB ...a...PP\.......XGH.....\...... 0001C0
4C455C00 011A00BF AB0AFE5B CBFE5BCB 584158FF ABFFFFA3 2FEF4C45 5C00011A ...\EL./.....XAX.[..[........\EL 0001E0

Virtual block number 87 (00000057), 512 (0200) bytes

ABFFFFA3 D3EF4C45 5C00011A 00BFAB0A FE5FCBFE 5FCB5841 58FFABFF FFA381EF .......XAX._.!._.........\EL..... 000000
67CB5841 58FFABFF FFA425EF 4C455C00 011A00BF AB0AFE63 CBFE63CB 584158FF .XAX.a..c.......\EL.%.....XAX.a 000020
AB0AFE6B CBFE6BCB 584158FF ABFFFFA4 77EF4C45 5C00011A 00BFAB0A FF67CBFE ..a........\EL.w.....XAX.k..k... 000040
5C00011A 00BFAB0A FE6FCBFE 6FCB5841 58FFABFF FFA4C9EF 4C455C00 011A00BF .....\EL.......XAX.o..o.........\ 000060
AB011AF1 FCADFDAF 9EFCADFD AF9EFE73 CBFE73CB 584158FF ABFFFFA5 1BEF4C45 EL.......XAX.s..s............... 000080
03BFAB01 07F1BFAB D7BFAB01 D0D7AB35 4AD3AB1C 4AFCADFD AF9EBFAB D7FEAABF ..........J...J5............... 0000A0
4C515C00 010700BF AB0AFFFF BA96EF02 FBD3ABDF D7ABDFFC ADFDAF9E 00AD3100 .1.........................\QL 0000C0
00010700 BFAB0A00 019FD7FF 02FB00DD FFFF8190 EF9F2D18 0000457A 8FFE57CB .W..zE..-....................... 0000E0
FB00DDFF FF8173EF 9F2B1100 019FCFFF 00FB0001 9FFAFF01 FB7EFE57 CB4C505C \PL.W.~..............+..s....... 000100
9FA2FF00 FB00019F CDFF01FB 7EFE57CB 4C505C00 010700BF AB0A0001 9FAAFF02 .............\PL.W.~........... 000120
00000046 8FD0D3AB 1C4A0C15 215C515C D3AB4ED3 AB5C4A5C 08405CD3 AB4E0001 ..N..\@.\J\..N..\Q\!..J.....F... 000140
019F27FF 16FCADFD AF9EFCAD FDAF9EBF ABD7FF56 BFAB0107 F1FCADFD AF9ED7AB ...........V...............'.. 000160
ADFDAF9E 1D110002 03AB0109 F103ABD7 03AB06D0 FCADFDAF 9EFCADFD AF9E0400 .............................. 000180
AF9EFCAD FDAF9E03 ABD7E603 AB09F3FC ADFDAF9E 00019F20 FF01FB31 C5CF9FFC ....1........................ 0001A0
08405C1C 445C0842 5CBFAB4E FCADFDAF 9EFCADFD AF9E0400 019EDFFF 16FCADFD .................N..\B.\D.\@. 0001C0
FF01FB00 A97F0001 9B82EF04 FB00A97F FFFF8098 EF9F07AB DD02DD07 AB5C4A5C \J\........................... 0001E0

Virtual block number 88 (00000058), 512 (0200) bytes

FF8067EF 9F5CDD04 DD5C5C4A 5C10405C 07AB4EFC ADFDAF9E 0BAB50D0 00019F28 (....P.......N..\@.\J\\...\..a.. 000000
AB0AFCAD FDAF9E0F AB505000 019EF3FF 01FB00A9 7F00019B 51EF04FB 00A97FFF .......Q.............PP......... 000020
EF9E5104 32171800 0043C88F 0FAB5155 12FFFF9B 85EF4C0B ABD15C00 011A00BF ....\...L......UQ....C....2.Q.. 000040
FEEFCB7E 52FFFF48 08EF9E51 04321511 00019E1C FF1650FE EFCB7E52 FFFF4803 .H..R~...P.........2.Q...H..R~... 000060
FB00019E 6DFF01FB 7E0FAB50 00019E3C FF02FB00 DDFEEFCB 7F00019E 05FF1650 P..............<...P..~...m.... 000080
0000008F 0FAB5151 13FFFF9B 1DEF4C0B ABD15C00 011A00BF AB0A0001 9E3EFF00 ..>...........\...L......QQ...... 0000A0
9CEF9E51 04321511 00019DB4 FF1650FE EFCB7E52 FFFF4797 EF9E5104 32171200 ...2.Q...G..R~...P........2.Q... 0000C0
01FF01FB FEEFCB7F 00019DDC FF01FB00 DD00019D 9DFF1650 FEEFCB7E 52FFFF47 G..R~...P...................... 0000E0
00019DE4 FF01FBFF FF7EEFEF 9F00019D C1FF01FB 00DD0001 9DDAFF00 FB00019E ...................~.......... 000100
ADFDAF9E B7AB084A FCADFDAF 9EFCADFD AF9E0400 019D7BFF 1600019D BDFF00FB ...............{.........J........ 000120
012E00B7 AB0A05AA 31031525 5C515CB7 AB4EB7AB 084A0418 085C515C B7AB4EFC .N..\Q\...J...N..\Q\%..1......... 000140
00B7AB0A F7ABFFFF AEF6EF4C D05C0001 2E00B7AB 0AF3ABFF FFAE4BEF 4CD05C00 .\.L.K.............\.L........... 000160
00150501 FFFFB088 EF4CCF5C 00010E00 B7AB0A13 ABFFFFAF A1EF4CD0 5C00012E ...\.L...............\.L......... 000180
09FF01FB 22EFCF9F FCADFDAF 9E00019C F9FF01FB 3ADD030C 01750015 00BA0028 (.....u..:.................... 0001A0
EF0120FE B3DBFEAF CB2D0001 9CF6FF01 FB22DCCF 9FFCADFD AF9E03EA 3100019D ...1..........-.......... .. 0001C0
1158D404 13FFFF46 67EF0120 FEB3DBFE AFCB2D5C 01CE0311 5CD40413 FFFF48A2 .H.....\....\-....... ..aF.....X. 0001E0

Virtual block number 89 (00000059), 512 (0200) bytes

5CD40413 FFFF487B EF1120FF FFAC3BEF 1E2D04F6 3103135C D55C58C8 5801CE03 ...X.X\.\..1..-..;... ..{H.....\ 000000
1304B900 A920FEFB DBFEF7CB 2D000199 71EF03FB 00A97F1E DD20DD5C 01CE0311 ....\. ........q...-...... ...... 000020
```

```
4ACF9FFC ADFDAF9E 035831FF 71310313 5CD55C58 CA5858D2 5801CE03 1158D404 ..X....X.XX.X\.\..1a.1X.........J 000040
295C01CE 03115CD4 0413FFFF 463BEF01 20FEFB0B FEF7CB2D 00019C64 FF01FB22 °...d...-.......3F.....\....\) 000060
0F310313 5CD55C58 CA5858D2 5801CE03 1158D404 12FFFF46 26EFFFFF AC07EF01 .......&F.....X....X.XX.X\.\..1. 000080
CB2D0001 9BD2FF16 50FEF7CB 7E5138A9 7EFFFFBA 51EF02FB 38A97FFE F7CB7F03 .......8...Q...".8Q"...P......-. 0000A0
7DEF0120 FEFBDBFE F7CB2D5C 01CE0311 5CD40413 FFFF4595 EF0120FE FBDBFEF7 ..... ...E....\....\-...... ..} 0000C0
D40413FF FF4562EF 0120FEFB DBFEF7CB 2D5C58C8 5801CE03 1158D404 13FFFF45 E.....X....X.X\-...... ..bE..... 0000E0
EFFFFFAB 6EEF0129 FCADFDAF 9EFF4531 02A03103 135CD55C 58C85801 CE031158 X....X.X\.\..1..1E......)..n.... 000100
5105322E 1100019B 51FF1650 FEEFCB7E 52FFFF45 2BEF9E51 05321712 FFFF453B ;E....2.Q..+E..R"...P.:Q.....2.Q 000120
0B12FFFF 4502EFFF FFA116EF 01290001 9B3AFF16 50FEEFCB 7E52FFFF 452AEF9E ..*E..R"...P..!...)........E.... 000140
DBFEF7CB 2D00019B 51FF01FB 23B7CF9F FCADFDAF 9EF7AB5C 4A5C2140 5CF7AB4E N..\@!\J\..........#...Q...-.... 000160
03115CD4 0413FFFF 44C6EFFF FFA0DAEF 012902D9 310312FF FF44CFEF 0220FEFB .. ...D....1..).........D.....\.. 0001A0
5CD55C58 CA5858D2 5801CE03 1158D404 12FFFF44 B0EFFFFF AAE3EF01 295C01CE ..\)........D.....X.....X.XX.X\.\ 0001A0
50FEEFCB 7F583CF3 3FE8BF5C 455C0040 5C505000 019B5BFF 01FBFEF7 CB7F3B13 .;........[...PP\@.\E\..?.<X....P 0001C0
F7CB7F2E 1100019A 95FF1650 FEF7CB7E 5138A97E 000196CC EF03FB38 A97F7E58 X"..8.......".8Q"...P............ 0001E0
```

Virtual block number 90 (0000005A), 512 (0200) bytes

```
5138A97E 0001969C EF03FB38 A97F7E5C 50FEEFCB 7F5C5050 00019B20 FF01FBFE .... ...PP\....P\"..8........".8Q 000000
FFFFB52C EF02FBF8 A9DFF8A9 0CD0FCA9 DFFCA913 D000019A 65FF1650 FEF7CB7E "...P..e......................... 000020
019AA3FF 01FBFFFF 7A4EEF9F 00019AB0 FF01FBFE F7CB7F00 019A8BFF 01FB00DD .....................Nz......... 000040
9AA6FF01 FBFEF7CB 7F00019A 59FF02FB 00DDFFFF 7A42EF9F 00019A7C FF00FB00 ....!.....Bz.......Y............ 000060
00019A68 FF01FB7E 5C505C50 50000199 3EEF1650 5C182B41 0D8F455C 50500001 ..PP\E..A+.\P..>...PP\P\"...h... 000080
F7AB4E0B 12FFFF43 9CEFFFFF 9FB8EF01 29FCADFD AF9E0106 3100019A 3DFF00FB ...=...1.......).........C....N.. 0000A0
FF4373EF 0320FEFB DBFEF7CB 2D000199 F9FF01FB 225FCF9F F7AB5C4A 5C21405C \@!\J\...._'.......-..:.... ..sC. 0000C0
5000019A 29FF01FB FEF7CB7F 3B12FFFF 4365EFFF FF9F81EF 01290181 310312FF ...1..)........eC...;.......)...P 0000E0
0001959B EF03FB38 A97F7E58 50FFFF7B 85EF9F58 005C415C 8F5C4122 8F445C50 P\D.'A\.\A\.X....{..PX"..8....... 000100
EF02FBF8 A9DFF8A9 0DD0FCA9 DFFCA915 D0000199 61FF1650 FEF7CB7E 5138A97E ".8Q"...P..a..................... 000120
01FBFFFF 796AEF9F 000199AC FF01FBFE F7CB7F00 019987FF 01FB00DD FFFFB428 (.........................jy.... 000140
FBFEF7CB 7F000199 55FF02FB 00DDFFFF 795EEF9F 00019978 FF00FB00 01999FFF ........x.....^y.......U........ 000160
7E5C505C 50500001 9837EF16 50005C41 5C930C3F C98F445C 50500001 99A2FF01 ......PP\D..?..\A\.P..7...PP\P\" 000180
EF03FB00 A97F13AB DD20DDFC ADFDAF9E 00110001 9936FF00 FB000199 61FF01FB ...a......6...................... 0001A0
EF4C4E5C 00010E00 B7AB0A00 92310312 04B900A9 20FEFBDB FEF7CB2D 000195E0 ....-...........1..........\NL. 0001C0
F7CB7F00 01956BEF 03FB10A9 7FFFFF7A ADEF9F5C DD5C584A 58084258 FFFFAC04 ....XB.XJX\.\...z........k....... 0001E0
```

Virtual block number 91 (0000005B), 512 (0200) bytes

```
5C13ABFF FFABCBEF 4CC15C00 010E00B7 AB0A0001 987AFF03 FB08A97F 10A97FFE ..........z..........\.L.......\ 000000
58584A58 000044B2 8E574357 574E5713 ABFFFFAB B9EF48C1 5800010E 00B7AB0A .......X.H.......WNWWCW..D..XJXX 000020
FFFF7A40 EF9F08A9 7F00A97F 00019528 EF04FB00 A97FFFFF 7A56EF9F 5CDD58DD .X.\..Vz........(.............@z.. 000040
2DFAB431 0312FFFF 41DDEF01 20FEB3DB FEAFCB2D FCADFDAF 9E000198 21FF03FB ...!........-....... ...A....1..- 000060
EF0120FE B3DBFEAF CB2D5C01 CE03115C D40413FF FF4438EF 0120FEB3 DBFEAFCB ...... ..8D....\....\-......-.. 000080
2DB7AB5C 4A5C1042 5CB7AB4E 0B135CD5 5C58C858 01CE0311 58D40413 FFFF41AC .A.....X....X.X\.\..N..\B.\J\..- 0000A0
EF0120FE B3DBFEAF CB2D5C01 CE03115C D40413FF FF43B9EF 0120FEB3 DBFEAFCB ...... ...C.....\....\-...... .. 0000C0
AB5C4A5C 08405CB7 AB4E0E11 02135CD5 5C58C858 01CE0311 58D40413 FFFF417E "A.....X....X.X\.\....N..\@.\J\. 0000E0
AF9EB7AB 274AFCAD FDAF9EFC ADFDAF9E 04000197 99FF16FC ADFDAF9E FA3831B7 .18.......................J'.... 000100
```

```
ABFFFFA8 75EF4CD0 5C00012E 00B7AB0A B7AB274A 0418275C 515CB7AB 4EFCADFD ...N..\Q\'..J'.........\.L.u.... 000120
FFA9CBEF 4CD05C00 012ED0B7 AB0AF7AB FFFFA920 EF4CD05C 00012E00 B7AB0AF3 ........\.L. ............\.L.... 000140
4E17AB00 00433C8F 4A000197 55FF01FB 1FBBCF9F 2B15275C 515CB7AB 4E13ABFF ...N..\Q\'.+.......U...J.<C....N 000160
D017AB00 00432C8F 4A02B831 17AB0000 434C8F4A 08120000 42888F5C 515CB7AB ..\Q\..B....J.LC....i..J.,C..... 000180
E5EF9F00 019717FF 01FB00DD FFFFB1B8 EF02FBF8 A9DFF8A9 17D0FCA9 DFFCA903 ................................ 0001A0
42B88F4A 000196F0 FF01FB1C D6CF9F00 019713FF 00FB0001 9732FF01 FBFFFF7B x.....2....................J..B 0001C0
7F000193 69EF03FB 00A97FFE F7CB7F01 DD000196 DDFF01FB 2982CF9F 03AB0000 .......)...................i.... 0001E0

Virtual_block number 92 (0000005C), 512 (0200) bytes

FF788FEF 9F000196 75FF1650 FEE7CB7E 5138A97E FFFFB4F4 EF02FB38 A97F00A9 ....8.......".8Q"...P..u.......x. 000000
7876EE9E 1412FFFF 3FDCEF01 20FEEBDB FEE7CB2D A7AB504A 00019700 FF01FBFF ........JP..-...... ...?......vx 000020
1412FFFF 40D0EF01 20FEEBDB FEE7CB2D 0188311B AB504A00 0196DFFF 01FBFFFF .........JP..1..-...... ...@.... 000040
3FDDEF01 20FEEBDB FEE7CB2D 0164311B AB504A00 0196BBFF 01FBFFFF 785AEF9F ..Zx.........JP..1d.-...... ...? 000060
AB4E5C01 CE03115C D40413FF FF4280EF 0020FFFF 8C3BEF0F 2D00DA31 0312FFFF ....1..-..;... ...B.....\....\N. 000080
20FEB3DB FEAFCB2D 00733103 135CD55C 58C85801 CE031158 D4041408 575157A3 .WQW....X....X.X\.\..1s.-...... 0000A0
FFFFB08C EF02FBF8 A9DFF8A9 17D0FCA9 DFFCA903 D013C731 0312FFFF 3F9CEF01 ...T....1....................... 0000C0
46CF9F00 0195E7FF 00FB0001 9606FF01 FBFFFF77 D9EF9F00 0195EBFF 01FB00DD ............w..................F 0000E0
AFCB7E52 FFFF416A EF9E5101 32000195 B9FF01FB 29F4CF9F 000195C4 FF01FB27 '..........).......2.Q..JA..R".. 000100
0312FFFF 3EBAEF01 20FEEBDB FEE7CB2D FCADFDAF 9E02EF31 00019564 FF1650FE .P..d...1.......-....... ...>.... 000120
B43100F1 31031200 0000008F 5C515C1F AB4E0001 957EFF01 FB195ACF 9F00F931 1....Z....."...N..\Q\........1..1. 000140
50500001 95AAFF01 FBFFFF74 99EF9F00 01955BFF 01FBDA8B CF9FFCAD FDAF9EFD ..............[......t.........PP 000160
01FBFFFF 746AEF9F FD7D3100 019537FF 01FB18BF CF9F0E12 000043C6 8F5C515C \Q\..C...........7...1}...Jt.... 000180
FFFF7710 EF9FFFFF 742EEF9F 00019518 FF01FB2C 55CF9F23 AB504A00 019583FF .....JP.#..U...........t.....w.. 0001A0
14CF9FFC ADFDAF9E 37110001 94F6FF01 FB281ECF 9F000194 BDFF03FB FF7FCB7F ..............(.........7........ 0001C0
B5EF9E51 014E8F32 000194D4 FF01FB3B 3FCF9FAF AB1BABD0 000194E4 FF01FBDA ...............?;........2.N.Q... 0001E0

Virtual block number 91 (0000005B), 512 (0200) bytes

5C13ABFF FFABCBEF 4CC15C00 010E00B7 AB0A0001 987AFF03 FB08A97F 10A97FFE .........2..........\.L.......\ 000000
58584A58 000044B2 8F574357 574E5713 ABFFFFAB B9EF48C1 5800010E 00B7AB0A .......X.H.......WNWWCW..D..XJXX 000020
FFFF7A40 EF9F08A9 7F00A97F 00019528 EF04FB00 A97FFFFF 7A56EF9F 5CDD58DD .X.\..Vz........(...........@z.. 000040
2DFAB431 0312FFFF 41DDEF01 20FEB3DB FEAFCB2D FCADFDAF 9E000198 21FF03FB ...!........-...... ...A....1..- 000060
EF0120FE B3DBFEAF CB2D5C01 CE03115C D40413FF FF4438EF 0120FEB3 DBFEAFCB ...... ..8D....\....\-.......-.. 000080
2DB7AB5C 4A5C1042 5CB7AB4E 0B135CD5 5C58C858 01CE0311 58D40413 FFFF41AC .A.....X....X.X\.\..N..\B.\J\..- 0000A0
EF0120FE B3DBFEAF CB2D5C01 CE03115C D40413FF FF43B9EF 0120FEB3 DBFEAFCB ...... ...C....\....\-...... .. 0000C0
AB5C4A5C 08405CB7 AB4E0E11 02135CD5 5C58C858 01CE0311 58D40413 FFFF417E "A.....X....X.X\.\....N..\@.\J\. 0000E0
AF9EB7AB 274AFCAD FDAF9EFC ADFDAF9E 04000197 99FF16FC ADFDAF9E FA3831B7 .18.......................J'.... 000100
ABFFFFA8 75EF4CD0 5C00012E 00B7AB0A B7AB274A 0418275C 515CB7AB 4EFCADFD ...N..\Q\'..J'.........\.L.u.... 000120
FFA9CBEF 4CD05C00 012ED0B7 AB0AF7AB FFFFA920 EF4CD05C 00012E00 B7AB0AF3 ........\.L. ............\.L.... 000140
4E17AB00 00433C8F 4A000197 55FF01FB 1FBBCF9F 2B15275C 515CB7AB 4E13ABFF ...N..\Q\'.+.......U...J.<C....N 000160
D017AB00 00432C8F 4A02B831 17AB0000 434C8F4A 08120000 42888F5C 515CB7AB ..\Q\..B....J.LC....i..J.,C..... 000180
E5EF9F00 019717FF 01FB00DD FFFFB1B8 EF02FBF8 A9DFF8A9 17D0FCA9 DFFCA903 ................................ 0001A0
42B88F4A 000196F0 FF01FB1C D6CF9F00 019713FF 00FB0001 9732FF01 FBFFFF7B x.....2....................J..B 0001C0
7F000193 69EF03FB 00A97FFE F7CB7F01 DD000196 DDFF01FB 2982CF9F 03AB0000 .......)...................i.... 0001E0
```

```
Virtual_block number 92 (0000005C), 512 (0200) bytes

FF788FEF 9F000196 75FF1650 FEE7CB7E 5138A97E FFFFB4F4 EF02FB38 A97F00A9 ....8.......^.8Q^...P..u.......x. 000000
7876EE9E 1412FFFF 3FDCEF01 20FEEBDB FEE7CB2D A7AB504A 00019700 FF01FBFF ........JP..-......  ...?......vx 000020
1412FFFF 40D0EF01 20FEEBDB FEE7CB2D 0188311B AB504A00 0196DFFF 01FBFFFF .........JP..1..-......  ...@.... 000040
3FDDEF01 20FEEBDB FEE7CB2D 0164311B AB504A00 0196BBFF 01FBFFFF 785AEF9F ..Zx.........JP..1d.-......  ...? 000060
AB4E5C01 CE03115C D40413FF FF4280EF 0020FFFF 8C3BEF0F 2D00DA31 0312FFFF ....1..-..;....  ...B.....\....\N. 000080
20FEB3DB FEAFCB2D 00733103 135CD55C 58C85801 CE031158 D4041408 575157A3 .WQW....X....X.X\.\..1s.-...... 0000A0
FFFFB08C EF02FBF8 A9DFF8A9 17D0FCA9 DFFCA903 D013C731 0312FFFF 3F9CEF01 ...?....1..................... 0000C0
46CF9F00 0195E7FF 00FB0001 9606FF01 FBFFFF77 D9EF9F00 0195EBFF 01FB00DD ..........w.................F 0000E0
AFCB7E52 FFFF416A EF9E5101 32000195 B9FF01FB 29F4CF9F 000195C4 FF01FB27 '..........).......2.Q..JA..R^.. 000100
0312FFFF 3EBAEF01 20FEEBDB FEE7CB2D FCADFDAF 9E02EF31 00019564 FF1650FE .P..d...1.......-......  ...>.... 000120
B43100F1 31031200 0000008F 5C515C1F AB4E0001 957EFF01 FB195ACF 9F00F931 1....Z....^...N..\Q\.......1...1. 000140
50500001 95AAFF01 FBFFFF74 99EF9F00 01955BFF 01FBDA8B CF9FFCAD FDAF9EFD .............[......t.........PP 000160
01FBFFFF 746AEF9F FD7D3100 019537FF 01FB18BF CF9F0E12 000043C6 8F5C515C \Q\..C...........7...1}...Jt...: 000180
FFFF7710 EF9FFFFF 742EEF9F 00019518 FF01FB2C 55CF9F23 AB504A00 019583FF .....JP.#..U..........t......w.. 0001A0
14CF9FFC ADFDAF9E 37110001 94F6FF01 FB281ECF 9F000194 BDFF03FB FF7FCB7F .............(.......7........ 0001C0
B5EF9E51 014E8F32 000194D4 FF01FB3B 3FCF9FAF AB1BABD0 000194E4 FF01FBDA ...............?;........2.N.Q... 0001E0

Virtual_block number 94 (0000005E), 512 (0200) bytes

2DFCADFD AF9E0001 92B2FF01 FBECPCCF 9F0B12FF FF3C52EF 0120FEDB DBFED7CB ......  ..R<...................- 000000
FFFF3E46 EF0120FE B3DBFEAF CB2DFAE3 310312FF FF3C2AEF 0120FEB3 DBFEAFCB ......  ..*<....1..-..........F>.. 000020
5801CE03 115BD404 13FFFF3C 0BEF0120 FEB3DBFE AFCB2D5C 01CE0311 5CD40413 ...\....\-......  ...<.....X....X 000040
FFFF7320 EF9F5C01 CE03115C D4041328 58515BB7 AB4E0AEB 3103135C D55C58C8 .X\.\..1..N..XQX(...\....\.. s.. 000060
5C58CA58 58D25801 CE031158 D4041300 0000008F 58515850 50000192 A1FF01FB .......PPXQX........X....X.XX.X\ 000080
CB2D5C01 CE03115C D40413FF FF3E10EF 0120FEB3 DBFEAFCB 2DFA7731 03135CD5 .\..1w.-......  ...>.....\....\-. 0000A0
5CB7AB4E 0E135CD5 5C58C858 01CE0311 58D40413 FFFF3B84 EF0120FE B3DBFEAF .....  ...;.....X....X.X\.\..N..\ 0000C0
1D310318 295C515C B7AB4EB7 AB5C4A5C 08405CB7 AB4EFA34 31B7AB5C 4A5C0842 B.\J\..14.N..\@.\J\..N..\Q\)..1. 0000E0
03D00001 91AEFF01 FB2453CF 9F03AB00 0042BBBF 4AFCADFD AF9EFCAD FDAF9EFA ...........J..B......S$......... 000100
739EEF9F 00019198 FF01FB00 DDFFFFAC 39EF02FB F8A9DFF8 A917D0FC A9DFFCA9 ...............9...............s 000120
0312FFFF 3B76EF01 20FEDBDB FED7CB2D 00019194 FF00FB00 0191B3FF 01FBFFFF ..............-......  ..v;..... 000140
4EFCADFD AF9EBFAB 084A044D 310312FF FF3D15EF 0120FEDB DBFED7CB 2D018431 1..-......  ...^....1M.J.........N 000160
01912BFF 01FB1698 CF9F13AB 1A4AF7AB 000042AB 8F4AF3AB 5C4A5C1A 405CBFAB ..\@.\J\..J..B....J..........+.. 000180
3B13EF01 20FEDBDB FED7CB2D 03643103 12FFFF3B 02EF0120 FEEBDBFE E7CB2D00 .-......  ...;....1d.-......  ...; 0001A0
0B425CBF AB4E022F 310312FF FF39CBEF 0520FEFB DBFEF7CB 2DFF3A31 0313FFFF ....1:.-......  ...9....1/.N..\B. 0001C0
A97F0001 8D7EEF04 FB00A97F FFFF723C EF9F5CDD 02DD5C5C 4A5C1440 5C20445C \D \@.\J\\...\..<r.........^..... 0001E0

Virtual_block number 93 (0000005D), 512 (0200) bytes

FF01FB3A 35CF9F27 ABAFABD0 FCADFDAF 9E000194 7DFF1650 FEC7CB7E 52FFFF89 ...R^...P..}............'..5:... 000000
ADFDAF9E 12563100 019453FF 1650FEAF CB7E52FF FF4038EF 9E510232 000194A8 ....2.Q..8Q..R^...P..S...1V...... 000020
41EF03FB 00A97F13 ABDD20DD FCADFDAF 9EFCC631 00019480 FF01FB15 AFCF9FFC ............1........  ........A 000040
0194A7FF 01FBFFFF 7526EF9F 01A63103 1204B900 A920FEFB DBFEF7CB 2D000191 ...-......  ......1....&u........ 000060
0190C7EF 03FB10A9 7FFFFF76 41EF9F5C DD5C5C4A 5C08425C 17AB4E2B AB504A00 .JP.+N..\B.\J\\.\..Av........... 000080
```

```
584E5813 AB17ABC1 5C13AB17 ABC10001 93D6FF03 FB08A97F 10A97FFE F7CB7F00 .......................\.....XNX 0000A0
0001909C EF04FB00 A97FFFFF 7602EF9F 5CDD58DD 58574A57 800044A7 8F584358 XCX..D..WJWX.X.\...v............ 0000C0
03120000 00008F5C 515C2BAB 4E000193 95FF03FB FFFF75EC EF9F08A9 7F00A97F ........u.........N.+\Q\........ 0000E0
D000FB31 0312585C 51582BAB 4E5C5050 00019418 FF01FBFF FF7497EF 9F011731 1.....t.........PP\N.+XQ\X..1... 000100
405C2044 5C08425C BFAB4EFC ADFDAF9E 00943100 03BFAB01 04F1BFAB D7BFAB01 ............1.......N..\B.\D \@ 000120
9006EF03 FB10A97F FFFF74D8 EF9F5CDD 5C5C4A5C 08425C2F AB4E2FAB 5C4A5C1A .\J\./N./\B.\J\\.\...t.......... 000140
4E5C5C4A 5C18405C 2FAB4E00 019313FF 03FB08A9 7F10A97F FFFF7500 EF9F0001 ....u...............N./\@.\J\\N 000160
8FDAEF04 FB00A97F FFFF7498 EF9F5CDD 58DD5858 4A580000 42E88F57 43572FAB ./WCW..B..XJXX.X.\...t.......... 000180
6FBFAB01 04F1FCAB FDAF9E00 0192D3FF 03FBFFFF 7482EF9F 08A97F00 A97F0001 ...........t....................o 0001A0
FF01FBE6 90CF9F0B 12FFFF3C FEEF0120 FEDBDBFE D7CB2DFC ADFDAF9E BFABD7FF ........-.......<............... 0001C0
2D000192 CDFF01FB E984CF9F 0B12FFFF 3CE2EF01 20FEDBDB FED7CB2D 000192E8 ....-.........<................- 0001E0
```

Virtual block number 95 (0000005F), 512 (0200) bytes

```
5C01CE03 115CD404 13000042 988F5851 58E3AB4E E3AB504A 00019120 FF01FB00 ........JP..N..XQX..B.....\....\ 000000
135CD55C 57C85701 CE031157 D40414FF FF88F3EF 4833AB51 58000113 00E3AB0A .......XQ.3H........W....W.W\.\. 000020
A97F0001 903AFF02 FB00A97F 07DD0001 9082FF01 FB00DD33 AB000000 008F502E .P......3....................... 000040
71BEEF9F FFFFAAF0 EF02FBF3 ABDFF7AB DF000190 75FF00FB 00019094 FF01FB00 ............u...................u 000060
33AB5100 019047FE 00EB0001 9072FF01 FB7E33AB 50000190 45FF02FB 00DDFFFF .......E...P.3"..P.......G...Q.3 000080
46580001 1300E3AB 0A5C5050 00019074 FF01FBFF FF70F3EF 9FFED331 0312A1AF ....1.....P.....t...PP\.......XF 0000A0
FF01FB0F F0CF9F33 AB505000 018EFCEF 1650005C 415C33AB 445CFFFF 885EEF48 H.^...\D.3\A\.P.V....PP.3....... 0000C0
F3AB5C4A 5C1A405C BFAB4EFC ADFDAF9E BFAB084A FCADFDAF 9E012231 00018FE8 ....1'......J........N..\@.\J\.. 0000E0
FF3990EF 0120FEEB DBFEE7CB 2D00018F B9FF01FB 1526CF9F 13AB1A4A F7AB2A4A J*..J.....&.......-.........9. 000100
FEFBDBFE F7CB2DFD C8310313 FFFF39A0 EF0120FE DBDBFED7 CB2D01F2 310312FF ...1.-..........9....1.-........ 000120
5CDD02DD 5C5C4A5C 14405C20 445C0842 5CBFAB4E 00BD3103 12FFFF38 55EF0420 ...U8....1..N..\B.\D \@.\J\\....\ 000140
AB4EE3AB 504A0001 8FAEFF01 FB00A97F 00018C0C EF04FB00 A97FFFFF 70CAEF9F ..P.........................JP..N. 000160
5000018F 89FF01FB FFFF7008 EF9F5C01 CE03115C D4041200 0042988F 585158E3 .XQX..B.....\....\...P.........P 000180
FF01FB0F 10CF9F0D 135CD55C 58CA5858 D25801CE 031158D4 04155833 AB515850 PXQ.3X....X....X.XX.X\.\......... 0001A0
7106EF9F 00018EF8 FF01FB00 DDFFFFA9 99EF02FB F3ABDFF7 ABDF4311 00018F08 .....C..........................u 0001C0
FB00018E FDFF01FB 00A97F00 018EA3FF 02FB00A9 7F07DD00 018F1BFF 01FBFFFF ................................ 0001E0
```

Virtual block number 96 (00000060), 512 (0200) bytes

```
F4310312 FFFF383B EF0120FE B3DBFEAF CB2DFCAD FDAF9EFE E7310001 8EDEFF00 ......1.......-....... ..;8....1. 000000
20FEB3DB FEAFCB2D 5C01CE03 115CD404 13FFFF3A 57EF0120 FEB3DBFE AFCB2DF6 .-...... ..W:.....\.....\-....... 000020
CB2DFCAD FDAF9E06 FC310313 5CD55C58 C85801CE 031158D4 0413FFFF 381CEF01 ...8.....X....X.X\.\..1........-. 000040
42EF0120 FEB3DBFE AFCB2D5C 01CE0311 5CD40413 FFFF37E4 EF0120FE B3DBFEAF ..... ...7.....\....\-...... ..B 000060
AB4EBFAB 5C4A5C10 425CBFAB 4E0B135C D55C58C8 5801CE03 1158D404 13FFFF3A :.....X....X.X\.\..N..\B.\J\..N. 000080
CE03115C D4041400 0000008F 585158BF AB4EFCAD FDAF9EBF AB5C4A5C 08405CBF .\@.\J\........N..XQX........\... 0000A0
FED7CB2D 16135CD5 5C58CA58 58D25801 CE031158 D404191A 575157BF AB4E5C01 .\N..WQW....X....X.XX.X\.\..-... 0000C0
01FB206C CF9F03AB 000042B8 8F4AFDFE 31FC8B31 0312FFFF 37EBEF01 20FEDBDB ... ...7....1..1..J..B......1 .. 0000E0
BFABD0FC ADFDAF9E 031631F6 0931B7AB 284A0718 085C515C BFAB4E00 018DC7FF .....N..\Q\...J(..1..1.......... 000100
FB00A97F FFFF6EF4 EF9F5CDD 02DD5C5C 4A5C1440 5C20445C 08425CBF AB4E37AB .7N..\B.\D \@.\J\\...\...n...... 000120
9E510532 5C000513 00E3AB0A E3AB504A 00018DD8 FF01FB00 A97F0001 8A36EF04 ..6..............JP.........\2.Q. 000140
37ABD000 018D4FFF 01FB0BEA CF9F0001 8D1AFF16 50FEDFCB 7E52FFFF 83F2EF4C L.....R"...P..............O.....7 000160
```

```
3ECF9F0D 12FFFF37 3AEF0120 FEDBDBFE D7CB2DD3 AB5C4A5C 1A405CBF AB4EBFAB ..N..\@.\J\..-....... ..!7......> 000180
00018D0C FF01FBE6 D6CF9F00 018D17FF 01FBE540 CF9F0B11 00018D24 FF01FBE2 ....$.......@................. 0001A0
FFFF9DD4 EF4CD05C 00012E00 B7AB0AFC ADFDAF9E B7AB294A FCADFDAF 9EFEE631 1.......J)............\.L..... 0001C0
9F2AEF4C D05C0001 2E00B7AB 0AF7ABFF FF9E7FEF 1CD05C00 012E00B7 AB0AF3AB .........\.L..............\.L.*. 0001E0

Virtual block number 97 (00000061), 512 (0200) bytes

310313FF FF3B69EF 0120FEDB DBFED7CB 2D00018C BDFF01FB 122ACF9F 13ABFFFF ......*.........-...... ..i8....1 000000
31031204 B900A920 EEFBDBFE F7CB2D00 018973EF 03FB00A9 7F13ABDD 20DDFADF ..........&...-..............1- 000020
FDAF9EEF 4D310086 00480009 02015CCF 5C5C4A5C 00004288 8F425CB7 AB4E0133 3.N..\B..B..\J\\.\....H...1M.... 000040
00018CA8 FF01FB00 A97F0001 8906EF04 FB00A97F FFFF6DC4 EF9F03DD 02DDFCAD .........m..................... 000060
ADFDAF9E 007A31BF AB084A33 ABFFFF84 E1EF4C46 5C000113 00E3AB0A E3AB504A JP.........\FL......3J....12.... 000080
4A00018C 69FF01FB 00A97F00 0188C7EF 04FB00A9 7FFFFF4D 85EF9F0B DD02DDFC .........m.................i...J 0000A0
DDFCADFD AF9E3C11 BFAB104A 33ABFFFF 8542EF4C 465C0001 1300E3AB 0AE3AB50 P..........\FL.B....3J....<...... 0000C0
AB504A00 018C2BFF 01FB00A9 7F000188 89EF04FB 00A97FFF FF6D47EF 9F13DD02 .....Gm..................+...JP. 0000E0
FF6C7FEF 9FFCADFD AF9EBFAB 144A33AB FFFF8554 EF4C465C 00011300 E3AB0AE3 .........\FL.T....3J...........1. 000100
8B92FF01 FB00DD33 AB000000 008F502E 155C33AB 515C5050 00018C00 FF01FBFF .........PP\Q.3\..P......3....... 000120
9F00018B 85FF00FB 00018BA4 FF01FB00 A97F0001 8B4AFF02 FB00A97F 07DD0001 ...........J..................... 000140
B3DBFEAF CB2DFCAD FDAF9E00 018B57FF 01FBE6A0 CF9F0001 8B62FF01 FB0B6ACF .J.....W..........W........-..... 000160
115CD404 13FFFF36 EBEF0120 FEB3DBFE AFCB2DF3 88310312 FFFF34CF EF0120FE . ...4....1..-...... ...6......\. 000180
5CD55C58 C85801CE 031158D4 0413FFFF 34B0EF01 20FEB3DB FEAFCB2D 5C01CE03 ...\-....... ...4.....X....X.X\.\ 0001A0
FEAFCB2D 5C01CE03 115CD404 13FFFF36 F2EF0120 FEB3DBFE AFCB2D03 90310313 ..1..-...... ....6.....\.....\-... 0001C0
10425CB7 AB4E0B13 5CD55C58 C85801CE 031158D4 0413FFFF 3466EF01 20FEB3DB ... ..?4.....X....X.X\.\..N..\B. 0001E0

Virtual block number 98 (00000062), 512 (0200) bytes

5CB7AB4E F3023103 18295C51 5CB7AB4E B7AB5C4A 5C08405C B7AB4EB7 AB5C4A5C \J\..N..\@.\J\..N..\Q\)..1..N..\ 000000
03AB0000 42B88F4A B7ABEDAF 4AFCADFD AF9E0011 FDA03103 18000042 A88F5C51 Q\..B....1..........J....J..B.... 000020
00018A2C FF1650FE AFCB7E52 FFFF345D EF9E5101 3200018A B1FF01FB 1D26CF9F ..&........2.R..J4..R"...P...... 000040
00012E00 B7AB0AF3 ABFFFF9B 3DEF4CD0 5C00012E 00B7AB0A FCADFDAF 9E02D031 1.............\.L=.............. 000060
FB128CCF 9F13ABFF FF9C93EF 4CD05C00 012E00B7 AB0AF7AB FFFF9BE8 EF4CD05C \.L.............\.L.............. 000080
00013200 B7AB0A01 4A310312 FFFF32E8 EF0420FE FBDBFEF7 CB2D0001 8A26FF01 ..2...-....... ....2....1J.....2.. 0000A0
A97F7EFF FF86F7EF 4C6EFFFF 6C1AEF9F 5C00011A 00BFAB0A BFABFD77 CB4CD05C \.L.w...........\...1..nL......".. 0000C0
FFCB7F00 A97FFEF7 CB7F0001 899AFF16 5000A97E 5138A97E 000185EA EF04FB38 8........".8Q"..P................ 0000E0
5C08425C 2FAB4E2F AB5C4A5C 08405C1C 445C0842 5CBFAB4E 00018980 FF03FBFE .........N..\B.\D.\@.\J\./N./\B.\ 000100
FB08A97F 10A97FFE FFCB7F00 018633EF 03FB10A9 7FFFFF6B 5DEF9F5C DD5C5C4A J\\.\..Jk.........3............. 000120
DD58584A 58000044 2EBF5743 572FAB4E 5C5C4A5C 1C405C2F AB4E0001 8942FF03 ..B...N./\@.\J\\N./WCW..D..XJXX. 000140
FBFFFF6B 09EF9F08 A97F00A9 7F000186 09EF04FB 00A97FFF FF6B1FEF 9F5CDD58 X.\...k......................k... 000160
51043217 18000043 C8BF33AB 51FFFFA3 D9EF02FB F3ABDFF7 ABDF0001 8902FF03 ..................Q.3..C.....2.Q 000180
CB7E52FF FF32C6EF 9E510432 15110001 88DAFF16 50FEEFCB 7E52FFFF 32C1EF9E ...2..R"...P.........2.Q...2..R". 0001A0
018927FF 01FB7E33 AB500001 88FAFF02 FB00DDFE EFCB7F00 0188C3FF 1650FEEF ..P..................P.3"...'.. 0001C0
C9FF01FB E412CF9F 0B12FFFF 3490EF01 20FEDBDB FED7CB2D 000188FC FF00FB00 ........-...... ...4............ 0001E0
```

Virtual block number 99 (00000063), 512 (0200) bytes

```
DBFEAFCB 2DF0FA31 0312FFFF 3241EF01 20FEB3DB FEAFCB2D FCADFDAF 9F000188 ........-....... ..A2....1..-.... 000000
FFFF3222 EF0120FE B3DBFEAF CB2D5C01 CE03115C D40413FF FF345DEF 0120FEB3 .....J4.....\....\=...........2.. 000020
FF3464EF 0120FEB3 DBFEAFCB 2D010231 03135CD5 5C58C858 01CE0311 58D40413 ...X....X.X\.\..1..-....... ..d4. 000040
41110212 FFFF31D4 EF0120FE B3DBFEAF CB2DB7AB 5C4A5C10 425CB7AB 4E0B12FF ...N..\B.\J\..-....... ...1.....A 000060
AB4EB7AB 5C4A5C08 405CB7AB 4E006E31 0312FFFF 3106EF01 20FEB3DB FEAFCB2D -....... ...1....1n.N..\@.\J\...N. 000080
72310097 31031500 0043388F 5C515CB7 AB4EF658 31031800 0042A88F 5C515CB7 .\Q\..B....1X.N..\Q\.8C....1..1r 0000A0
8F4AB7AB 5C4A5C25 425CB7AB 4EF63331 0312D7AF 5C515CB7 AB4EFCAD FDAF9E00 ......N..\Q\....13.N..\B%\J\..J. 0000C0
11B7AB5C 4A5C0000 42C88F40 5CB7AB4E 0F18B7AF 5C515CB7 AB4E3BAB 0000C080 .....$N..\Q\....N..\@..B..\J\.... 0000E0
B7AB4EB7 AB5C4A5C 25405CB7 AB4E4311 0212A7AF 5C515CB7 AB4EFCAD FDAF9E32 2.....N..\Q\.....CN..\@%\J\..N.. 000100
5C000132 00B7AB0A FCADFDAF 9EB7AB5C 4A5CC8AF 425CB7AB 4E0C1590 AF5C515C \Q\....N..\B..\J\...........2..\ 000120
2DFCADFD AF9EFCAD FDAF9EFE AE31FD11 31031300 0000008F 585158FD 77CB4C4E NL.w.XQX........1..1............- 000140
FF07CB7E 52FFFF7D 63EF9E51 0C320520 310312FF FF3319EF 0120FEB3 DBFEAFCB ...... ...3....1 .2.Q..c}..R".... 000160
A9DFFCA9 03D00001 8732FF01 FB19D7CF 9F03AB00 0042B88F 4A000187 05FF1650 P......J..B............2......... 000180
01FBFFFF 693AEF9F 0001871C FF01FB00 DDFFFFA1 BDEF02FB F8A9DFF8 A917D0FC ...........................!..... 0001A0
ADFDAF9E 6C110002 BFAB0104 F1BFABD7 BFAB00D0 00018718 FF00FB00 018737FF .7.........................1.... 0001C0
FFFFA16C EF02FBFC A9DFFCA9 17D0F7AB DFF7AB5C 4A5C2D40 5C1E445C BFAB4EFC .N..\D.\@-\J\...............1... 0001E0
```

Virtual block number 100 (00000064), 512 (0200) bytes

```
FFFF68E0 EF9F5CDD 02DD5C5C 4A5C0840 5C10445C BFAB4E00 0186CBFF 01FB00DD ..........N..\D.\@.\J\\...\...h.. 000000
FCADFDAF 9E000186 A9FF00FB 000186C8 FF01FB00 A97F0001 8352EF04 FB00A97F ......R......................... 000020
FDAF9ECB AB084A13 AB104AF3 AB000042 B88F4AFC ADFDAF9E BFABD797 BFAB04F3 .............J..B....J...J...... 000040
01864BFF 01FB0EB1 CF9FF7AB 5C4A5C2D 405C1E44 5C10465C 08425CCB AB4EFCAD ..N..\B.\F.\D.\@-\J\.........K.. 000060
0FCB7FFF 07CB7FCB ABDD02DD 01063103 12FFFF2F C9EF0220 FEFBDBFE F7CB2D00 .-...... .../....1............... 000080
D4041400 0000008F 5C515C50 50000186 75FF01FB FF0FCB7F 000182D4 EF04FBFF ..............u...PP\Q\......... 0000A0
01CE0311 58D40413 E1AF5851 58505000 018657FF 01FBFEF7 CB7F5C01 CE03115C \....\........W...PPXQX.....X..... 0000C0
0185D3FF 01FB00DD FFFFA074 EF02FBF3 ABDFF7AB DF46135C D55C58CA 5858D258 X.XX.X\.\.F.........t........... 0000E0
A97F0001 856AFF03 FB00A97F FF0FCB7F 08A97F00 01858BFF 02FB08A9 7F07DD00 ........................J...... 000100
BDEF9F5C DD5C5C4A 5C08425C CBAB4E69 11000185 B5FF00FB 000185D4 FF01FB00 .................iN..\B.\J\\.\... 000120
AB4E0001 852AFF03 FB0BA97F 10A97FFE F7CB7F00 01821BEF 03FB10A9 7FFFFF67 ..........................*...N. 000140
00A97FFF FF6783EF 9F5CDD58 DD58584A 58235743 57CBAB4E 5C5C4A5C 10405CCB .\@.\J\\N..WCW#XJXX.X.\......... 000160
2DFCADFD AF9E0001 84EEFF03 FBFFFF67 6DEF9F08 A97F00A9 7F000181 F5EF04FB ................ms..............- 000180
FFFF30C6 EF0120FE B3DBFEAF CB2D0088 310312FF FF2EAAEF 0120FEB3 DBFEAFCB ...... .........1..-....... ...O.. 0001A0
0120FEB3 DBFEAFCB 2D631102 12FFFF2E BFEF0120 FEB3DBFE AFCB2D02 CB310312 ..1..-...... ..........c-...... . 0001C0
58D40413 FFFF2E54 EF0120FE B3DBFEAF CB2D5C01 CE03115C D40413FF FF30E0EF ..O......\....\-....... ..T......X 0001E0
```

Virtual block number 101 (00000065), 512 (0200) bytes

```
5C4A5C10 405CCBAB 4ECBAB5C 4A5C1842 5CCBAB4E 0B135CD5 5C58C858 01CE0311 ....X.X\.\..N..\B.\J\..N..\@.\J\ 000000
9FFCADFD AF9EFE23 31031822 5C515CCB AB4EFA00 31031808 5C515CCB AB4ECBAB ..N..\Q\...1..N..\Q\'..1#....... 000020
19310003 3FAB0106 F13FABD7 3FAB01D0 AFAB504A 000184DC FF01FBFF FF63C3EF ..c.........JP.....?..?.....?..1. 000040
667EEF9F CBABDD02 DDCBAB5C 4A5C0840 5C10445C 08425C3F AB4EFCAD FDAF9E02 ......N.?\B.\D.\@.\J\.........~f 000060
7FCBABDD 02DD43AB 504A0001 8492FF01 FB00A97F 000180F0 EF04FB00 A97FFFFF ....................JP.C...... 000080
```

```
5158A3AB 4E47AB50 4A000184 71FF01FB 00A97F00 0180CFEF 04FB00A9 7FFF07CB ....................Q...JP.GN..XQ 0000A0
C85801CE 03115BD4 04130000 00008F57 515743AB 4E5C01CE 03115CD4 0419105B X....\....\N.CWQW........X....X. 0000C0
B5EF014E 8F2D5C01 CE03115C D40413E1 AF585158 47AB4E01 28310313 5CD55C58 X\.\..1(.N.GXQX.....\.....\.N... 0000E0
75CF9F00 F4310313 5CD55C58 C85801CE 03115BD4 0413FECB DBFEC7CB 20FFFF78 x.. ........X....X.X\.\..1.....u 000100
0001838C FF01FB25 2DCF9F01 5D310313 A2AF5C51 5CABAB4E 00018344 FF01FB2A %.......N..\Q\....1]...-%....... 000120
01836BFF 01FB29D6 CF9FAFAB 504A0001 83D6FF01 FBFFFF62 BDEF9F47 ABBFAF4A J...G...b.........JP.....)....k.. 000140
FEC7CB7E 52FFFF78 3DEF9E51 98AF3201 21310313 00000000 8F5C515C ABAB4E00 .N..\Q\.......1!.2..Q..=x..R"... 000160
C5EF03FB 18A97FFF FF6567EF 9F5CDD5C 5C4A5C08 425CCBAB 4E000183 05FF1650 P......N..\B.\J\\.\..ge.......... 000180
165010A9 7E5138A9 7E00017F 1BEF04FB 38A97F7E 43AB6EFF FF6547EF 9F00017F .....Ge..n.C"..8........".8Q"..P. 0001A0
4E5C5C4A 5C10405C CBAB4E00 0182B3FF 03FB08A9 7F18A97F 10A97F00 01B2CBFF ......................N..\@.\J\\N 0001C0
A97F0001 7F7EEF04 FB00A97F FFFF650C EF9F5CDD 58DD5858 4A582337 4357CBAB ..WCW#XJXX.X.\...e.........."..... 0001E0
```

Virtual block number 102 (00000066), 512 (0200) bytes

```
0000008F 58515847 AB4EFCAD FDAF9E00 018277FF 03FBFFFF 64F6EF9F 08A97F00 .......d.....w.........N.GXQX.... 000000
5CD55C58 C85801CE 031158D4 0413EBAF 57515743 AB4E5C01 CE03115C D4041200 ....\.....\N.CWQW.....X....X.X\.\ 000020
FB2277CF 9FFFFF78 6EEF0F20 FEA3DBFE 9FCB2C0E 15085C51 5CA3AB4E 22110213 ..."N..\Q\..........nx.....w". 000040
2DFCADFD AF9E3FAB D7FDEA3F AB0106F1 FCADFDAF 9EFCADFD AF9E0001 8266FF01 ..f...................?.....?......- 000060
AF9E0400 01820BFF 16FCADFD AF9EEAB3 310312FF FF2BCAEF 0120FEB3 DBFEAFCB ...........+.....1................. 000080
36110002 CBAB0113 F1CBABD7 CBAB01D0 E3AB0000 00008F4A FCADFDAF 9EFCADFD ........J.........................6 0000A0
FFFF7EE0 EF4C0129 5C000113 00E3AB0A 000181FC FF01FB00 97CF9FFC ADFDAF9E .........................\).L..".. 0000C0
9FFEDFCB 7FFCADFD AF9ECBAB D7CDCBAB 13F3FCAD FDAF9E6B 110212FF FF2B7BEF .{+.....k.......................... 0000E0
65FF03FB FE7FCB7F 00A97FFF FF63FBEF 9F000181 79FF03FB 00A97FFF FF6403EF ..d...........y.......c...............e 000100
CF9F0001 81A6FF00 FB000181 C5FF01FB FE7FCB7F 000181A8 FF01FB00 DD000181 ................................... 000120
04000181 49FF16FC ADFDAF9E 0001817B FF01FB12 FACF9F00 018183FF 01FB14AB .................x...........I.... 000140
5000A97E 5138A97E FFFF9F88 EF02FB38 A97FFEDF CB7FFCAD FDAF9EFC ADFDAF9E ................8........".8Q"..P 000160
0113F1BF ABD7BFAB 01D00001 7DD2EF03 FBFEDFCB 7F00A97F 03DD0001 B10AFF16 .................}............... 000180
0042988F 5C515CE3 AB4EE3AB 504A5C08 405CE3AB 4EFCADFD AF9E6411 0002BFAB .....d......N..\@.\J\..N..\Q\..B. 0001A0
35EF9FFF FF633FEF FFFF7780 F4C9E03 DD5C0005 1300E3AB 0AE3AB08 4A041500 ...J...........\....L...w....Tc.....5 0001C0
FDAF9E6D 110212FE E3DBFED B2004B9 00A92D00 017D7BEF 03FB00A9 7FFFFF63 c..........{}..-.... ..........m.... 0001E0
```

Virtual block number 103 (00000067), 512 (0200) bytes

```
65FF03FB 00A97FFF FF62EFEF 9FFEDFCB 7FFCADFD AF9EBFAB D79FBFAB 13F3FCAD ......................b..........c 000000
00018094 FF01FB00 DD000180 51FF03FB FE7FCB7F 00A97FFF FF62F7EF 9F000180 ......b.............Q............. 000020
E6CF9F00 01806FFF 01FB1397 CF9F0001 8092FF00 FB000180 B1FF01FB FE7FCB7F ............................o....... 000040
FF28A3EF 0320FEE3 DBFEDFCB 2DBFAB18 4AFCADFD AF9E5711 00018064 FF01FB11 ....d.....W.....J....-........ ....(. 000060
DBFEDFCB 2DBFAB10 4A0412FF FF288CEF 0320FEE3 DBFEDFCB 2DBFAB08 4A0412FF ...J...-......  ...(.....J...-...... 000080
01800BFF 01FB13AF 9F33AB00 0000008F 50BFAB14 4A0412FF FF2875EF 0320FEE3 ..  ..u(.....J....P.......3......... 0000A0
9F5C0001 1300E3AB 0AFCADFD AF9EFCAD FDAF9E04 00017FDC FF16FCAD FDAF9E00 ..............................\. 0000C0
165018A9 7E5138A9 7E00017B DBEF04FB 38A97F7E FFFF761C EF4C6EFF FF620BEF ..b...nL...v..."..8.....{.."..8Q"..P. 0000E0
10A97E51 40A97E00 017BB9EF 04FB40A9 7F7EE3AB 6EFFFF61 E5EF9F00 017F8BFF ...........a...n..."..@.....{..".@Q".. 000100
33AB50FF FF611BEF 9F00017F 51FF03FB 08A97F18 A97F10A9 7F00017F 69FF1650 P..i....................Q.......a..P.3 000120
7F08A97F 00A97F00 017F37FF 165000A9 7E5148A9 7E00017B 6DEF03FB 48A97F7E "..H....m{..".HQ"..P..7........... 000140
425C2FAB 4E2FAB5C 4A5C0840 5C20445C 08425CBF AB4E0001 7F1EFF03 FBFEFFCB ..........N..\B.\D \@.\J\./N./\B 000160
```

```
A97F10A9 7FFEFFCB 7F00017B D1EF03FB 10A97FFF FF60A3EF 9F5CDD5C 5C4A5C08 .\J\\.\...`.........{........... 000180
584A5800 0042C88F 5743572F AB4E5C5C 4A5C2040 5C2FAB4E 00017EE0 FF03FB08 .....~..N./\@ \J\\N./WCW..B..XJX 0001A0
FF604FEF 9F08A97F 00A97F00 017BA7EF 04FB00A9 7FFFFF60 65EF9F5C DD58DD5B X.X.\..e`.........{...........O`. 0001C0
CF9EFCAD FDAF9EFC ADFDAF9E 0400017E B5FF16FC ADFDAF9E 00017EA0 FF03FBFF .....~..........~............... 0001E0

Virtual block number 104 (00000068), 512 (0200) bytes

00017F08 FF01FB00 A97F0001 7B66EF04 FB00A97F FEF7CB7F 02DD02DD 7FAB022D -.................f{............ 000000
1158D404 142F5751 574BAB4E 5C01CE03 115CD404 19085851 584BAB4E 4BAB504A JF.KN.KXQX....\....\N.KWQW/...X. 000020
7E3AFF01 FB06DD01 CA310001 7E76FF01 FB01FECF 9F0E135C D55C58CB 5801CE03 ...X.X\.\..........v~..1........!~ 000040
A5EF9E01 0103378F DD000020 068FDD6E 2B006E00 2C5E2BC2 00014E00 8FDD0001 ......N...+^,.n.+n... ....7...... 000060
AFABD05E 37C00001 7E4EFF01 FB5EDD2C AE06D010 AEFFFF73 2DEF9E08 AEFFFF60 `.......-s..........,.^...N~...7^... 000080
FFFF72F8 EF9E510C 3200017D D5FF1650 FF17CB7E 52FFFF73 37EF9E51 04324FAB .02.Q..7s..R~...P...}..2.Q...r.. 0000A0
017DABFF 1650FF27 CB7E52FF FF72EFEF 9E511E32 00017DC0 FF1650FF 1FCB7E52 R~...P...}..2.Q...r..R~.'.P...}. 0000C0
52FFFF73 D9EF9E51 03320001 7D96FF16 50FF2FCB 7E52FFFF 73C0EF9E 51083200 .2.Q...s..R~./.P...}..2.Q...s..R 0000E0
00017D6C FF1650FF 3FCB7E52 FFFF73C7 EF9E5103 3200017D 81FF1650 FF37CB7E ~.7.P...}..2.Q...s..R~.7.P..1}.. 000100
01FB23F2 CF9FAFAB 4BABD000 017D57FF 1650FF47 CB7E52FF FF73D3EF 9E510332 2.Q...s..R~.G.P..W}....K.....$.. 000120
20FF23DB FF1FCB2C FFFF728A EF0420FF 1BDBFF17 CB2CAFAB 4FABD000 017D87FF .'.}....O..,........ ...r..,.....$. 000140
7328EF08 20FF33DB FF2FCB2C FFFF7250 EF1E20FF 2BDBFF27 CB2CFFFF 7252EF0C ..Rr...,.'..+. ..Pr...,/..3. ..(s 000160
CB2CFFFF 733AEF03 20FF3BDB FF37CB2C FFFF7322 EF0820FF 33DBFF2F CB2CFFFF ...,/..3. ..'s...,7..;. ..:s...,. 000180
FF2547EF 0C28FFFF 7342EF03 20FF4BDB FF47CB2C FFFF732F EF0320FF 43DBFF3F ?..C. ../s...,G..K. ..Bs..(..G%. 0001A0
008FDD00 017CBFFF 01FB06DD FFFF72E6 EF0F20FE A3DBFE9F CB2CFFFF 7318EFFF ...s.,........ ...r..........|..... 0001C0
08AEFFFF 5F32EF9E 01010337 8FDD0000 20068FDD 6E2B006E 002C5E2B C200014E N...+^,.n.+n... ....7.....2_.... 0001E0

Virtual block number 105 (00000069), 512 (0200) bytes

A9FF01FB C9A2CF9F 5E37C000 017CD3FF 01FB5EDD 2CAE06D0 10AEFFFF 71B2EF9E ...a........,.^....|...7^......... 000000
89FF01FB 11AF9FFC ADFDAF9E FCADFDAF 9E040001 7C7AFF16 FCADFDAF 9E00017C |...........z|.......................... 000020
FBA9DFF8 A903D0FC A9DFFCA9 09D0FCAD FDAF9E00 017C73FF 01FBDDAF 9F00017C |...........s|.......................... 000040
7F07DD00 017C87FF 01FBFFFF 5EC2EF9F 00017C64 FF01FB00 DDFFFF97 05EF02FB ...............d|......^.......|...... 000060
00017C08 FF160001 7C4AFF00 FB00017C 69FF01FB 00A97F00 017C0FFF 02FB00A9 .......|...........i|......J|......|.. 000080
FF24DBEF 0420FEFB DBFEE7CB 2D1FAB00 000000BF 4AFCADFD AF9EFCAD FDAF9E04 ...............J.........-....... ...$. 0000A0
D25801CE 031158D4 0413FFFF 24C6EFFF FF7111EF 04295C01 CE03115C D40413FF ....\.....\)...a.....$......X.....X. 0000C0
FDAF9E00 C1310003 CFAB0104 F1CFABD7 CFAB01D0 00D93103 135CD55C 58CA5858 XX.X\.\..1....................1...... 0000E0
EF0120FF 53DBFF4F CB2D0001 7866EF04 FBFF4FCB 7FFEF7CB 7FCFABDD 01DDFCAD ..................O.....fx..-.O..S. .. 000100
1158D404 13FFFF25 F3EF0120 FF53DBFF 4FCB2D5C 01CE0311 5CD40413 FFFF258D .%......\.....\-.O..S. ...%......X. 000120
FF5DDFEF 9F5C50D0 0001798C EF01FBFF 4FCB7F5D 1102135C D55C58C8 5801CE03 ...X.X\.\....J..O......y...F\....J. 000140
7962EF01 FBFF4FCB 7F5C01CE 03115CD4 0419585C D15850D0 0001797C EF01FBFF ....|y...PX.\X....\......\..O.....by 000160
01CE0311 58D40414 5758D157 50D00001 7952EF01 FBFFFF5D BDEF9F58 50D00001 ....PX....J......Ry....PW.XW....X..... 000180
AF9ECFAB D7FF42CF AB0104F1 FCADFDAF 9EFCADED AF9E1B11 02135CD5 5C58C858 X.X\.\...........................B....... 0001A0
B7AB0AFF FF8C93EF 4CDF5C00 012E00B7 AB0A1FAB 084AFCAD FDAF9E61 11FCADFD .....a......J...............\.L.......... 0001C0
5C5EEF9F 00017AD8 FF01FB00 DDFFFF95 79EF02FB FFFF8BC8 EF4CDF5C 00012E00 ....\.L...........y................z.....^\ 0001E0
```

```
Virtual block number 106 (0000006A), 512 (0200) bytes

FB00017A DDFF01FB 00A97F00 017A83FF 02FB00A9 7F07DD00 017AFBFF 01FBFFFF ......z.............z.........z... 000000
9FAB084A FCADEDAF 9EFCADED AF9E0400 017A77FF 16FCADFD AF9E0001 7ABEFF00 ...z.........wz..............J... 000020
FBCE0ECF 9F0B12FF FF247CEF 0120FEEB DBFEE7CB 2D00017A 81FF01FB 02E7CF9F ........z..-......  ..|$.......... 000040
017A4BFF 01FBD102 CF9F0B12 FFFF2460 EF0120FE EBDBFEE7 CB2D0001 7A66FF01 ..fz..-.......  ..`$............Kz. 000060
00008F4A 00017A30 FF01FBD4 7ACF9F0B 12FFFF23 D0EF0120 FEEBDBFE E7CB2D00 .-........$.......z.....0z...J... 000080
03FBFEF7 CB7F13AB DD20DDFC ADFDAF9E FCADFDAF 9E040001 79FEFF16 9FAB0000 .......y..............  ......... 0000A0
EF02FBF8 A9DFF8A9 01D0FCA9 DFFCA901 D0FCADFD AF9E53AB D6AF4A00 0176DFEF ..v..J...S......................... 0000C0
ABDFFCA9 DFFCA953 ABF7ABC1 000179F0 FF00FB00 0179E7FF 01FB00DD FFFF9488 ..........y.......y.......S....... 0000E0
AFCB7E51 FF57CB7E FFFF98F8 EF01FBFF 57CB7FFC ADFDAF9E FFFF9464 EF02FBF3 ....d..........W.........~.W.Q~.. 000100
DBFEAFCB 2D00F231 0312FFFF 237BEF01 20FEB3DB FEAFCB2D 00017968 FF1650FE .P..hy..-......  ..{$.....1..-.... 000120
FEB3DBFE AFCB2D00 01793FFF 02FB00A9 7F0DDDBB 110212FF FF25CCEF 0020FEB3 ..  ...%...............?y..-...... 000140
00A920FE B3DBFEAF CB2D0001 7922FF02 FB00A97F 00DD01B5 31031204 B900A920  ......1...........'y..-....... .. 000160
A920FEB3 DBFEAFCB 2D000179 01FF02FB 08A97F00 00007F8F DD016631 031204B9 ....1?..............y..-....... . 000180
20FEB3DB FEAFCB2D 000178E0 FF02FB00 A97F08DD 5C01CE03 115CD404 120CB908 .......\.....\..........x..-....... 0001A0
BF5C515C 53AB4E54 1102135C D55C58CA 5858D258 01CE0311 58D40412 04B900A9 .......X.....X.XX.X\.\...TN.S\Q\. 0001C0
03FB08A9 7FFEF7CB 7F53ABDD 53AB5C4A 5C08425C 53AB4EFF 1F310312 00000000 ......1..N.S\B.\J\.S..S.......... 0001E0

Virtual block number 107 (0000006B), 512 (0200) bytes

7F08A97F 00A97F00 01758BEF 03FB00A9 7F5CDD20 DD5C13AB 53ABC300 017563EF .cu....S..\.  .\.........u......... 000000
7892FF01 FB00DD29 1213AB53 ABD1FCAD FDAF9E00 90310001 785EFF03 FBFEF7CB .......^x..1...........S...)......x 000020
31000178 85FF00FB 000178A4 FF01FB00 A97F0001 784AFF02 FB00A97F 07DD0001 ..........Jx...........x.......x...1 000040
10A97FFE F7CB7F5C DD5C5C4A 5C08425C 53AB4E53 AB5C4A5C 08405C53 AB4EFE68 h.N.S\@.\J\.SN.S\B.\J\\.\........ 000060
20DD5C13 AB53ABC3 000177F0 FF03FB08 A97F10A9 7FFEAFCB 7F000174 E1EF03FB ....t.....................w....6..\. 000080
FDAF9E00 0177CBFF 03FBFEF7 CB7F08A9 7F00A97F 000174F8 EF03FB00 A97F5CDD .\.......t......................w..... 0000A0
19FF01FB FEF7CB7F 000177FC FF01FB00 DDFFFF92 9DEF02FB F3ABDFF7 ABDFFCAD ..........................w.......... 0000C0
57CB7EFF FF9713EF 01FBFF57 CB7FFCAD FDAF9EFD DD310001 77FAFF00 FB000178 x......w..1..........W.........~.W 0000E0
9ECE1102 12FFFF23 FAEF0020 FEB3DBFE AFCB2D00 01778 3FF 1650FEAF CB7E51FF .Q~...P...w..-.......  ...3........ 000100
03FBFEF7 CB7F13AB DD20DDFC ADFDAF9E FCADFDAF 9E040001 777EFF16 FCADFDAF ......~w..............  .......... 000120
772AFF16 50FEE7CB 7E52FFFF 1FA2EF9E 51013253 AB000000 008F4A00 01745FEF ._t..J......S2.Q......R^...P..*w 000140
01FB00DD FFFF91F0 EF02FBF8 A9DFF8A9 01D0FCA9 DFFCA901 D0FCADFD AF9E0001 ................................ 000160
DFFCA9DF FCA95C4A 5C08425C 5C4E5C13 ABF7ABC1 00017758 FF00FB00 01774FFF .Dw.....Xw........\N\\B.\J\...... 000180
CB7E51FF 57CB7EFF FF9657EF 01FBFF57 CB7FFCAD FDAF9EFF FF91C3EF 02FBF3AB ..................W.....W...~.W.Q~. 0001A0
50FEE7CB 7E5138A9 7EFFFF95 29EF02FB 38A97FFE AFCB7F00 0176C7FF 1650FEAF ..P....v.........8....)....~.8Q~...P 0001C0
EF0120FE EBDBFEE7 CB2D5C01 CE03115C D4041308 5851589F AB4E0001 76AAFF16 ....v...N...XQX.....\.....\-....... .. 0001E0

Virtual block number 108 (0000006C), 512 (0200) bytes

1157D404 13FFFF20 B9EF0120 FEEBDBFE E7CB2D58 01CE0311 58D40413 FFFF20D1 . .....X.....X-......  ...  .....W. 000000
57C85701 CE031157 D40413FF FF202AEF 0120FEEB DBFEE7CB 2D5857C8 5701CE03 ...W.WX-.......  ..*  ......W.....W.W 000020
58CA5858 D25857C8 5701CE03 1157D404 13FFFF20 62EF0120 FEEBDBFE E7CB2D58 X-.......  ..b  ......W.....W.WX.XX.X 000040
92EF0020 FEB3DBFE AFCB2D02 C4310001 7626FF02 FBFEAFCB 7F0DDD10 135CD55C \.\...........2v..1..-.......  ... 000060
04B900A9 20FEB3DB FEAFCB2D 00017604 FF02FB00 A97F0DDD FF213103 12FFFF22 ".....1!.............v..-......... 000080
```

```
31031204 B900A920 FEB3DBFE AFCB2D00 0175E7FF 02FB00A9 7F00DD02 7B310312 ..1{..........u..-...... ......1. 0000A0
04120CB9 08A920FE B3DBFEAF CB2D0001 75C6FF02 FB08A97F 0000007F BFDD01AA ...............u..-...... ...... 0000C0
1204B900 A920FEB3 DBFEAFCB 2D000175 A5FF02FB 00A97F08 DD5C01CE 03115CD4 .\....\..........u..-........... 0000E0
12000000 008F5C51 5C53AB4E 4C110213 5CD55C58 CA5858D2 5801CE03 1158D404 ..X....X.XX.X\.\...LN.S\Q\...... 000100
7FFEF7CB 7F5CDD5C 5C4A5C08 425C13AB 4E53AB5C 4A5C0842 5C53AB4E FE853103 .1..N.S\B.\J\.SN..\B.\J\\.\..... 000120
007E3100 01752BFF 03FBFEF7 CB7FFFFF 56B6EF9F 00A97F00 01721FEF 03FB00A9 ......r.........V..........+u..1". 000140
017517FF 02FB00A9 7F07DD00 0175SFFF 01FB00DD 291213AB 53ABD1FC ADFDAF9E .......S...).....u...........,u. 000160
53AB5C4A 5C08405C 53AB4EFD CD310001 7552FF00 FB000175 71FF01FB 00A97F00 .......au.....Ru..1..N.S\@.\J\.S 000180
FEAFCB7F 000171C0 EF04FB00 A97FFEF7 CB7F02DD 5CDD5C5C 4A5C0842 5C13AB4E N..\B.\J\\.\..............a...... 0001A0
AF9E0001 74B2FF16 50FEE7CB 7E51FEAF CB7E0001 74BAFF03 FBFEF7CB 7F00A97F ...........t.."...Q"...P...t.... 0001C0
2D000171 A5EF03FB 00A97F13 ABDD20DD FFFF8F7C EF02FBF3 ABDFF7AB DFFCADFD ............|.... ..........a..- 0001E0
```

Virtual block number 109 (0000006D), 512 (0200) bytes

```
5C5C4A5C 08425C13 AB4E0001 74BEFF01 FB00DD41 1204B900 A920FEFB DBFEF7CB ...... .....A.......t..N..\B.\J\\ 000000
01FBFFFF 5702EF9F 000174CC FF01FB00 A97F0001 7176EF03 FB00A97F 5CDD20DD . .\......va...........t.....W.... 000020
749AFF01 FBFEF7CB 7F000174 7DFF01FB 00DD1B11 00017498 FF00FB00 0174B7FF ..t.......t..........}t..........t 000040
FF57CB7E FFFF9394 EF01FBFF 57CB7FFC ADFDAF9E FCF63100 01747BFF 00FB0001 .....{t..1..........W.........".W. 000060
AF9ECE11 0212FFFF 207BEF00 20FEB3DB FEAFCB2D 00017404 FF1650FE AFCB7E51 Q"...P...t..-...... ..{ ........ 000080
FFFF9240 EF02FB38 A97FFEE7 CB7F6E11 02120000 00008F5C 515C9FAB 4EFCADFD ...N..\Q\.........n......8...@... 0000A0
D40413FF FF1DFBEF 0120FEEB DBFEE7CB 2D000173 C1FF1650 FEE7CB7E 5138A97E ".8Q"...P...s..-...... .......... 0000C0
5C58C858 01CE0311 58D40413 FFFF1DE0 EF0120FE EBDBFEE7 CB2D5C01 CE03115C \....\-...... .........X....X.X\ 0000E0
19110213 5CD55C58 C85801CE 031158D4 0413FFFF 1D51EF01 20FEEBDB FEE7CB2D -....... ..Q.......X....X.X\.\.... 000100
FF16FCAD FDAF9E33 AB505000 0173F3FF 01FBFEF7 CB7F7FAB 1DAF9EFC ADFDAF9E ...................s..PP.3........ 000120
00017374 FF01FB00 DDFFFF8E 15EF02FB F3ABDFF7 ABDFFCAD FDAF9E04 00017364 ds..........................ts.. 000140
A97F08A9 7F000173 1DFF02FB 08A97F07 DD000170 35EF03FB 10A97F13 ABDD3FDD .?..........5p...........s...... 000160
FB90CF9F 00017348 FF00FB00 017367FF 01FB00A9 7F000172 FDFF03FB 00A97F10 .........r.........gs.....Hs...... 000180
FFFF51E0 EF9F0001 731AFF01 FB00DDFC ADFDAF9E FCADFDAF 9E000173 19FF01FB ....s......................s.....Q.. 0001A0
FBA9DFFB A918D0FC A9DFFCA9 0000004D 8FD00001 7316FF00 FE000173 35FF01FB ...5s.......s....M................ 0001C0
72E2FF00 FB000173 01FF01FB FE97CB7F 000172E4 FF01FB00 DDFFFF8D 85EF02FB ..............r...............s.......r 0001E0
```

Virtual block number 110 (0000006E), 512 (0200) bytes

```
01FB00DD FFFF8D50 EF02FBF8 A9DFF8A9 05D0FCA9 DFFCA90A D0FCADFD AF9E0001 ..........................P....... 000000
1ED3EF9E 51003200 0172ABFF 00FB0001 72D2FF01 FBFFFF55 25EF9F00 0172AFFF ..r.....%U......r........r..2.Q.... 000020
CB7EFFFF 91B2EF01 FBFF57CB 7FFCADFD AF9E0001 723EFF16 50FF5FCB 7E52FFFF ..R"._.P..>r...........W.........". 000040
CE110212 FFFF1E99 EF0020FE B3DBFEAF CB2D0001 7222FF16 50FEAFCB 7E51FF57 W.Q"...P..'r..-...... .......... 000060
CB3C6B12 04B900A9 20FEB3DB FEAFCB2D 00017208 FF02FB00 A97F0000 007F8FDD ..............r..-..............k<.. 000080
FB00DD00 016EABEF 03FBFF5F CB7FFF5F CB7F5CDD 5C5C4A5C 08425C58 4E58FF5F _.XNX\B.\J\\.\..._......n..... 0000A0
5326EF9F 00017228 FF01FB08 A97F0001 71C6FF02 FB08A97F 08DD0001 720EFF01 ...r...............q.........(r.....&S 0000C0
FB000172 05FF01FB 00A97F00 0171A3FF 02FB00A9 7F08DD00 01721BFF 01FBFFFF ......r...............q..........r..... 0000E0
B900A920 FEB3DBFE AFCB2D00 017183FF 02FB00A9 7F0DDDFF 45310001 71DEFF00 ...q...1E...........q..-....... ... 000100
9F000171 95FF01FB 00DD0001 7152FF03 FBFF5FCB 7FFF5FCB 7FFEAFCB 7F331304 ..3......._......_....Rq.........q... 000120
DBFF5FCB 2DFCADFD AF9EFEF8 31000171 91FF00FB 000171B8 FF01FBFF FF5413EF ..T........q.......q..1........-..... 000140
A97F0001 6DEAEF03 FB00A97F FF5FCB7F 0ADDFE94 310312FF FF1DACEF 0020FF63 c. .........1......._..........m..... 000160
ADD7BFAB 01D00001 70F6FF16 50FF5FCB 7E5138A9 7EFFFF8F 75EF02FB 38A97F00 ...8....u....".8Q"._.P....p........ 000180
```

```
0A20FF63 DBFF5FCB 2D5C000A 1900BFAB 0AFCADFD AF9E2D11 0002BFAB 0119F1BF .........-............\-.._..e. . 0001A0
9E007E31 FCADFDAF 9EBFABD7 D6BFAB19 F3FCADFD AF9E1511 0212FFFF 76AAEF4C L..V.......................1".. 0001C0
00011900 BFAB0A64 110215FF FF7905EF 4CA3ABD1 5C000119 00BFAB0A FCADFDAF ...........\...L..y......d....... 0001E0
Virtual block number 111 (0000006F), 512 (0200) bytes

9FCB7E52 FFFF7758 EF4C9E51 0F325C00 0F1900BF AB0AA3AB FFFF78F2 EF4CD05C \.L..x.............\2.Q.L.Xw..R".. 000000
5326EE9F 0001704C FE03FB00 A97FFFFF 532EEF9F FE9FCB7F 00017064 FF1650FE .P..dp...........S.........L.....2S 000020
FDAF9E57 11000170 71FF01FB 0399CF9F 00017038 FF03FBFE 7FCB7F00 A97FFFFF ...........Bp.........ap...W... 000040
00017054 FF01FB00 DDFFFF8A F5EF02FB F8A9DFF8 A90AD0FC A9DFFCA9 0AD0FCAD ..........................Tp.. 000060
CB7E52FF FF1C78EF 9E510032 00017050 FF00FB00 01706FFF 01FBFFFF 52EAEF9F ...R;....op.....Pp..2.Q..x...R".. 000080
0400016F E9FF16FC ADFDAF9E 00017018 FF01FB01 9ACF9F00 016FE3FF 1650FE9F ..P...o.........p..........o... 0000A0
5CFEA7CB 3C00016C 8DEF03FB FEA7CB7F FEA7CB7F 0CDDFCAD FDAF9EFC ADFDAF9E .......................1..<...\ 0000C0
BFABD7BF AB01D000 016F93FF 1650FF67 CB7E52FF FF1C28EF 9E510032 57AB5CD0 .\.W2.Q..(...R".g.P.....o......... 0000E0
52FFFF19 92EF9E51 01321715 57ABBFAB D1FCADFD AF9E00A3 310003BF AB010CF1 .......1...........W..2.Q......R 000100
016C3BEF 04FBFEAF CB7FFEA7 CB7FBFAB DD01DD59 1100016F 61FF1650 FEAFCB7E "...P..ao...Y..................;1. 000120
34585158 5BAB4E5B AB504A00 016E7CEF 1650504E 00016D98 EF01FBFE AFCB7F00 .........m..NPP..ln..JP.[N.[XQX4 000140
5C58C858 01CE0311 58D40414 00004364 8F575157 5BAB4E5C 01CE0311 5CD40419 ...\.....\N.[WQW.dC.....X.....X.X\ 000160
AF9E0001 6EEAFF03 FBFF67CB 7FFF67CB 7FFEAFCB 7FFCADFD AF9E3E11 02135CD5 .\...>..............g...g......n..... 000180
6ECEFF16 50FEA7CB 7E51FF67 CB7EFCAD FDAF9EBF ABD7FF60 BFAB010C F1FCADFD ........`..........".g.Q"...P....n 0001A0
6EF2FF01 FB00DD00 016F0BFF 00FB0001 6F02FF01 FB00DDFC ADFDAF9E 77110001 ...w...........o.........o.........n 0001C0
A97F0001 6BCAEF02 FB00A97F 0ADD0001 6EE2FF01 FB00DD00 016EFBFF 00FB0001 ......n............n............k..... 0001E0
Virtual block number 112 (00000070), 512 (0200) bytes

FB28AF9F 00016EC8 FF00FB00 016EE7FF 01FBFFFF 516AEF9F 00016EFC FF01FB00 .....n....JQ.......n.........n.....(. 000000
FCADFDAF 9E00016E 51FE1650 FEA7CB7E 52FFFF1A E6EF9E51 00320001 6EA6FF01 ...n..2.Q.......R"...P..Qn........ 000020
FBF8A9DF F8A918D0 FCA9DFFC A901D0FC ADFDAF9E FCADFDAF 9E040001 6E62FF16 ..bn............................... 000040
00A97F00 016B27EF 03FB00A9 7F28DD20 DD00016E 65FF01FB 00DDFFFF 8906EF02 ...............en.... .(......'k...... 000060
C9EF02FB F8A9DFF8 A918D0FC A9DFFCA9 29D00001 6E56FF00 FB00016E 7DFF01FB ...)n......Vn...)................ 000080
FF01FB00 A97F0001 6AEAEF03 FB00A97F 24DD20DD 00016E28 FF01FB00 DDFFFF88 .........(n.... .$.......J......... 0000A0
FFFF888C EF02FBF8 A9DFF8A9 01D0FCA9 DFFCA901 D000016E 19FF00FB 00016E40 @n.......n........................... 0000C0
02FBF8A9 DFF8A918 D0FCA9DF FCA905D0 00016DF4 FF00FB00 016DEBFF 01FB00DD .......m.........m.................. 0000E0
6DC2FF00 FB00016D E9FF01FB FFFF506C EF9F0001 6DC6FF01 FB00DDFF FF8867EF .g...........m.....lP.......m........m 000100
6D4EFF16 50FEE7CB 7E51FF57 CB7EFFFF 8CDEEF01 FBFF57CB 7FFCADFD AF9E0001 .........W.........".W.Q"...P..Nm 000120
AF9EC411 021304B9 00A920FE EBDBFEE7 CB2D0001 6D4AFF02 FB00A97F 0DDD0001 ...........Jm..-......  .......... 000140
02FB03AB DFFCA9DF FCA901D0 FCADFDAF 9EFCADFD AF9E0400 016D3FFF 16FCADFD .....?m........................... 000160
FB00A97F 00016A08 EF03FB00 A97F28DD 20DD0001 6D46FF01 FB00DDFF FF87E7EF ...........Fm....  .(.......J....... 000180
00DDFFFF 87AEEF02 FB03ABDF FCA9DFFC A929D000 016D37FF 00FB0001 6D56FF01 ...Vm......7m...)................ 0001A0
FB00016D 1DFF01FB 00A97F00 0169CFEF 03FB00A9 7F28DD2C DD00016D 0DFF01FB ....m.... .(........i..........m... 0001C0
21EF4E7F AB00EBCF 9EFCADFD AF9EFCAD FDAF9E04 00016CBC FF160001 6CFEFF00 ...l......l......................N.! 0001E0
Virtual block number 113 (00000071), 512 (0200) bytes

02FB00A9 7F00DD00 016CBBFF 01FB02DD 00CA3103 12000000 008F5C51 5CFFFF7C |..\Q\.........1.........1........ 000000
FE7FCB7F 00016CC8 FE01FBFE FF4DD3EF 9F00016C D5FF01FB 00A97F00 016540EF .@e...........l.....M......l...... 000020
325C0001 03005FAB 0AFCADFD AF9E5FAB 084A0001 6C96FF00 FB00016C B5FF01FB ....l.......l..J.._.............\2 000040
```

```
5FAB5C4A 5C08405C 5FAB4E00 016C17FF 1650FE77 CB4C7E52 FFFF18AD EF9E5100 .Q......R"L.w.P...1..N._\@.\J\._ 000060
FB02DD3D 110212FF FE187CEF 002004BC 6C2D5CFE 77CB4C7E 5C000103 005FAB0A ..._....\"L.w.\-1.. ..l........... 000080
005FAB0A 00016C48 FF01FB00 A97F0001 6916EF02 FB00A97F 0ADD0001 6C2EFF01 ...l..........i.........Hl...._. 0000A0
16FCADFD AF9EFF78 3100016C 0DFF00FB 00016C2C FF01FBFE 77CB4C7F 5C000103 ...\.L.w....1......l..1x........ 0000C0
00016BC0 FF01FBE1 AF9FFFFF 7B2EEF00 0000008F 4AFCADFD AF9E0400 016BC3FF ..k.........J.......{.........k.. 0000E0
DDFFFF86 4DEF02FB FBA9DFFB A91BD0FC A9DFFCA9 03D0FCAD FDAF9EFC ADFDAF9E .........................M.... 000100
FCA901D0 00016BA8 FF00FB00 016BCFFF 01FBFFFF 4E5AEF9F 00016BAC FF01FB00 .....k....ZN......k.....k...... 000120
016B83FF 00FB0001 6B7AFF01 FB00DDFF FF861BEF 02FBF8A9 DFF8A901 D0FCA9DF .........................zk.....k. 000140
ABD7A7AB 01D0ABAB 00000000 8F4AFCAD FDAF9EFC ADFDAF9E 0400016B 41FF1600 ...Ak...........J............ 000160
EF4C0C2D 5C000CEA AF00A7AB 0AFCADFD AF9E2F11 0002A7AB 01000000 64BFF1A7 ...d........./...........\-.L. 000180
FDAF9EA7 ABD7D4A7 ABCCAFF3 FCADFDAF 9E701102 12FFFF17 6AEF0020 FFFF73BE .s.. ..J........................ 0001A0
00016AF4 FF01FB00 DD00016A B5FF1650 FE7FCB7E 52FFFF12 65EF9E51 2332FCAD ..2#Q..e...R"...P...J.........J.. 0001C0
6AE2FF00 FB00016B 01FF01FB FE7FCB7F 00016AE4 FF01FB00 DD00016A FDFF00FB ....J........J..........k.......J 0001E0

Virtual block number 114 (00000072), 512 (0200) bytes

9E01D731 ABAB084A 00016AB4 FF01FBFC 36CF9F00 016ABFFF 01FBFDE7 CF9F0001 ..........J....6.....J..J...1... 000000
7A02EF0C 20FEABDB FEA7CB2C FFFF7A10 EF01638F 20FFFF16 EAEF002C FCADFDAF .................c..z..............z 000020
20FEA3DB FE9FCB2C FFFF79F8 EF1E20FF FF1646EF 112CB3AB 00000000 8F4AFFFF ..J.........F.... ...y.......... 000040
0166E7EF 03FB28A9 7F30A97F 02DD0001 612EEF02 FB30A97F 00DDFFFF 7B29EF0F ..){......0....a.......0..(....f. 000060
A97F0001 66DEEF04 FB18A97F 20A97F04 DD03DD00 016113EF 02FB20A9 7F00DD00 ........a........................f.... 000080
A97F08DD 02DD0001 60E6EF02 FB08A97F 0ODD0001 69DAFF03 FB10A97F 28A97F18 ...(........i.............`........ 0000A0
08280001 69AAFF03 FBFFFF4A 69EF9F10 A97F00A9 7F000166 B1EF04FB 00A97F08 .........f.............iJ.......i..(. 0000C0
798CEFFF FF129AEF 0528FFFF 7997EFFF FF1370EF 0128FFFF 7A9DEFFF FF7A9AEF ...z.....z...(..p........y..(.........y 0000E0
0169ABFF 01FB00EB CF9F23AB 00000000 8F4AFFFF 7985EFFF FF1124EF 0328FFFF ..(..$......y..J.......$.........i. 000100
AF5C515C ABAB4E00 016993FF 01FB0F20 CF9F00C8 310313E7 AF5C515C ABAB4E00 .N..\Q\....1....  .....i..N..\Q\. 000120
FF7201EF 4C0C20FE ABDBFEA7 CB2C5C00 0C000000 648F00A7 AB0A00B0 310313CF ...1........d.....\r........L..r. 000140
7E000165 53EF04FB 38A97F7E A7AB6EFF FF4B27EF 9FFCADFD AF9EFCAD FDAF9EFF ..............'K..n.."..8...Se.." 000160
0168E7FF 03FBFE7F CB7FFFFF 4BFAEF9F 00A97F00 016903FF 165000A9 7E5138A9 .BQ"..P....i.........K..........h. 000180
FEA7CB2C 000168E4 FF01FB03 DD000169 11FF02FB 03DDA7AB DD7FAB11 7ACF9E00 ...z................i..........h...... 0001A0
A92C0001 64F4EF04 FB38A97F 7EAFAB6E FFFF4AC8 EF9FFFFF 784AEF0C 20FEABDB ... ..Jx.....J..n.."..8....d..... 0001C0
0168A7FF 16FCADFD AF9E0001 68F6FF02 FB03DDA7 ABDDFFFF 7836EF03 203CB938 8.< ..6x............h...........h. 0001E0

Virtual block number 115 (00000073), 512 (0200) bytes

FDAF9E00 7B310003 CBAB0103 F1CBABD7 CBAB01D0 FCADFDAF 9EFCADFD AF9E0400 ...........................1{.... 000000
0300CBAB 0AFCADFD AF9E4E11 0002BFAB 01000000 648FF1BF ABD7BFAB 01D0FCAD ...........d..........N............ 000020
04FB00A9 7FFFFF4B 3DEF9FFF FF4B47EF FFFF75CE EF4C9EBF ABDD01DD 5C00E9AF ...\......L..u...GK....=K........ 000040
BFABADAF F3FCADFD AF9E0084 310312FF FF11EEEF 012004B9 00A92D00 016517EF ..e..-.... ........1............. 000060
512432FC ADFDAF9E CBABD7FF 88CBAB01 03F1FCAD FDAF9EFC ADFDAF9E BFABD7B5 ..............................2$Q 000080
6822FF00 FB000168 19FF01FB 00DD0001 67DAFF16 50FE7FCB 7E52FFFF 0F4CEF9E ..L...R"...P...g........h......"h 0000A0
0CCF9F00 016807FF 00FB0001 6826FF01 FBFE7FCB 7F000168 09FF01FB 00DD0001 .........h.........&h.......h...... 0000C0
4EFCADFD AF9E03C9 31ABAB08 4A000167 D9FF01FB F95BCF9F 000167E4 FF01FBFB .....g....[.....g..J...1........N 0000E0
AB6EFFFF 497AEF9F 63AB584A 585C4058 BFAB4E5C 000043C8 8F445C08 425CCBAB ..\B.\B..C..\N..X@\XJX.c..zI..n. 000100
515C23AB 4E000167 55FF1650 FF6FCB7E 5138A97E 000163A6 EF04FB38 A97F7E63 c"..8....c..~.8Q".o.P..Ug..N.#\Q 000120
2C000167 2DFF1650 FF77CB7E 52FFFF5D 88EF9E51 03324011 02120000 00008F5C \.........@2.Q...J..R".w.P..-g... 000140
```

```
ABAB4E00 01674FFF 01FB0E20 CF9FAFAB 23ABD0FF FF5D6EEF 0320FF73 DBFF6FCB .o..s. ..n].....$..... ....Os..N.. 000160
9FFFFF5C 19EF014E 8F20FFFF 137FEF00 2CFCADFD AF9E0339 310313BD AF5C515C \Q\.....19............ .N...\... 000180
FB38A97F 7E5850FF FF49E7EF 9F58085C 415C5050 0001677C FF01FBFF FF466BEF .kF......Ia..PP\A\.X...I..PX"..8. 0001A0
EF9FFFFF 5BDAEFFF FF766BEF 0C28FFFF 5C10EF04 203CB938 A92C0001 62F2EF03 ....b....8.< ...\..(..kv....[.... 0001C0
CB2CFFFF 5CFEEF03 203CB938 A92C0001 62E0EF04 FB38A97F 7EA7AB6E FFFF48B4 .H..n..."..8....b....8.< ...\.... 0001E0
```

Virtual block number 116 (00000074), 512 (0200) bytes

```
28A97F30 A97F02DD 00015D88 EF02FB30 A97F00DD FFFF5CAE EF0F20FE A3DBFE9F ...... ...\......0.....]........0..( 000000
EF04FB18 A97F20A9 7E04DD03 DD00015D 6DEF02FB 20A97F00 DD000163 41EF03FB ...Ac......... ...m]................. 000020
00015D40 EF02FB08 A97F00DD 00016634 FF03FB10 A97F28A9 7F18A97F 00016338 8c........(........Af..............@].. 000040
FF03FBFF FF4753EF 9F10A97F 00A97F00 01630BEF 04FB00A9 7F08A97F 08DD02DD ..................c.............SG...... 000060
0BB2CF9F FFFF5C42 EFFFFF0E 71EF0C28 FFFF5C22 EFFFFF5C 1FEF0828 00016604 .f..(...\...."\...(..G.....B\........ 000080
5C19EF03 20FF73DB FF6FCB2C 1E120000 00008F5C 515C23AB 4E000166 25FF01FB ...%f..N.#\Q\............o..s. ....\ 0000A0
FFFF5BFB EF0320FF 7BDBFF77 CB2C2E11 FFFF5C08 EF0320FF 73DBFF6F CB2CFFFF ....o..s. ...\.......w..{. ...[.. 0000C0
FFFF5BD8 EF03203C B938A92C 000161DE EF04FB38 A97F7E23 AB6EFFFF 47B2EF9F ....G..n.#"..8.......8.<.....[.. 0000E0
31031391 AF5C515C ABAB4E00 0165B7FF 01FB0C88 CF9FAFAB 63ABD0FC ADFDAF9E .........c...............e..N..\Q\.....1 000100
9FAFAB50 4A000165 EDFF01FB FFFF4784 EF9F5211 021284AF 5C515C23 AB4E01A1 ..N.#\Q\......R...G........e..JP... 000120
73DBFF6F CB2C0169 31031300 0000008F 5C515CAB AB4E0001 6582FF01 FB0BEDCF ..........e..N..\Q\.........li....o... 000140
01433103 13D6AF5C 515CABAB 4E000165 59FF01FB 0C2ACF9F FFFF5B70 EF0320FF . ..p[.....*.....Ye..N..\Q\.....1C. 000160
FFFF46F8 EF9FFCAD FDAF9E27 AB63ABD0 B3AB5D4A 5C08405C B3AB4EFC ADFDAF9E ......N..\@.\J\......c.'..........F.. 000180
9F00A97F 000164D4 FF165000 A97E5138 A97E0001 6124EF04 FB38A97F 7EA7AB6E n.."..8....$a.."..8Q"..P....d........ 0001A0
64E2FF02 FB05DDCB ABDD7FAB 0D4BCF9E 000164B8 FE03FBFE 7FCB7FFF FF47E3EF ..C..............d.....K.................d 0001C0
584A5808 4258BFAB 4E5C0000 0000648F 0300CBAB 0A000164 B5FF01FB 05DD0001 ..........d...........d.....\N..XB.XJX 0001E0
```

Virtual block number 117 (00000075), 512 (0200) bytes

```
9F000161 49EF03FB 10A97FFF FF479BEF 9FFFFF47 A5EFFFFF 7214EF4C 9E5BDD58 X.X.L..r.....G......G..........Ie.... 000000
4058BEAB 4E5C00B8 AE0300CB AB0A0001 6456FF03 FB08A97F 10A97FFF FF4793EF ..G..............Vd..............\N..XQ 000020
EFFFFF71 BFEF4C9E 58DD57DD 57574A57 000043C8 8F564356 BFAB4E5B 584A5808 .XJXXN..VCV..C..WJWW.W.X.L...a.... 000040
5C000000 00648F03 00CBAB0A 00016108 EF04FB00 A97FFFFF 4756EF9F FFFF4760 `G.....VG..............a............d.....\ 000060
0A000163 E9FF03FB FFFF4730 EF9FFFFF 473AEFFF FF7191EF 4C9E08A9 7F00A97F .........L...a....!G.....OG.........c.... 000080
29FF02FB 05DDCBAB DDFFFF72 F9EFFFFF 716CEF4C 00648F28 5C00D4AF 0300CBAB ..........\(.d.L:la.....r..............) 0000A0
8F4AFCAD FDAF9EFC ADFDAF9E 04000163 D5FF16AF AB63ABD0 FCADFDAF 9E000164 d............c.......c....................J. 0000C0
0113CF9F AFAB504A 00016430 FF01FBFF FF4317EF 9FFCADFD AF9EABAB 00000000 ......................C......Od..JP....... 0000E0
016407FF 01FBFFFF 42F6EF9F 00F33103 13D1AF5C 515CABAB 4E000163 C5FF01FB .....c...N..\Q\.....1.......B.........d. 000100
0912CF9F FFFF7308 EF01638F 20FFFF0F E2EF002C BA110213 B8AF5C51 5C505000 .PP\Q\................ .c.....s...... 000120
5C000C00 0000648F 00A7AB0A 00B33103 1391AF5C 515CABAB 4E000163 B5FF01FB .....c.'N..\Q\.....1..........d.......\ 000140
4516EF9F FCADFDAF 9EAFAB00 0000008F 4AFFFF6B F3EF4C0C 20FFFF0F AEEF002C .......... .L...k..J.....................E 000160
A97F0001 62F2FF16 5000A97E 5138A97E 00015F42 EF04FB38 A97F7EA7 AB6EFFFF ..n.."..8....B_..."..8Q"..F....b..... 000180
FF02FB03 DDA7ABDD 7FAB0B69 CF9E0001 62D6FF03 FBFE7FCB 7FFFFF45 E9EF9F00 .....E..............b......i.................. 0001A0
FF44B7EF 9FFFFF72 39EF0C20 FFFF0F41 EF002C00 0162D3FF 01FB03DD 00016300 .c...........b.....A.... ..9r......D. 0001C0
03DDA7AB DDFFFF72 25EF0320 3CB938A9 2C00015E E3EF01FB 38A97F7E AFAB6EFF .n.."..8.....^....8.< ..%r.......... 0001E0
```

```
Virtual block number 118 (00000076), 512 (0200) bytes

0FCF9FFC ADFDAF9E FCADFDAF 9E040001 6296FF16 FCADFDAF 9E000162 E5FF02FB ....b..........b................ 000000
AB6EFFFF 445AEF9F 02923103 13000000 008F5C51 5CABAB4E 000162A4 FF01FB09 .....b..N..\Q\........1....ZD..n. 000020
6DEF9F00 A97F0001 6236FF16 5000A97E 5138A97E 00015E86 EF04FB38 A97F7EA7 .~..B.....~..~.8Q~...P..6b.......m 000040
0043C88F 475C0842 5CAFAB4E 7FAB0AAD CF9E0001 621AFF03 FBFE7FCB 7FFFFF45 E..........b........N..\B.\G..C. 000060
AB4E5CE0 AF445C08 425CCBAB 4ECBAB5C 4A5C0840 5C505000 016148EF 16505C00 .\P..Ha..PP\@.\J\..N..\B.\D./\N.- 000080
DD58584A 58084258 BFAB4E5C 00000000 648F0300 CBAB0ABF AB584A58 5C4258AF .XB\XJX........d....\N..XB.XJXX. 0000A0
FDEF9F00 015E8BEF 03FB10A9 7FFFFF45 05EF9FFF FF450FEF FFFF6F56 EF4C9E58 X.L.Vo....E.....E.........^..... 0000C0
58084058 BFAB4E5C 00B8AF03 00CBAB0A 00016198 FF03FB08 A97F10A9 7FFFFF44 D............a..........\N..XQ.X 0000E0
44CAEFFF FF6F01EF 4C9E58DD 57DD5757 4A570000 43C88F56 4356BFAB 4E58584A JXXN..VCV..C..WJWW.W.X.L..o....D 000100
A97F5C00 00000064 8F0300CB AB0A0001 5E4AEF04 FB00A97F FFFF14C0 EF9FFFFF .....D........J^........d....\.. 000120
CBABDD00 01612BFF 03FBFFFF 449AEF9F FFFF44A4 EFFFFF6E D3EF4C9E 08A97F00 .....L..n.....D.....D.....+a..... 000140
4C00648F 285C00BF AF0300CB AB0A0001 612EFF01 FB05DD00 01615BFF 02FB05DD .....Ca.........a...........\(.d.L 000160
85FF01FB FFFF4324 EF9F0001 6156FF02 FB05DDCB ABDDFFFF 7026EFFF FF6E99EF ..n...Sp...........Va.....$C...... 000180
20FFFF0D 56EF002C 6BAB504A 00016174 FF01FBEF FF430BEF 9F67AB50 4A000161 a..JP.a...C......ta..JP.k...V... 0001A0
0001614B FF01FBFF FF4037EF 9F000160 F9FF01FB 07CACF9F FFFF55F0 EF014EBF .N...U..........`....7@.....Ha.. 0001C0
C9FF01FB 0734CF9F AFAB67AB D000AB31 6BAB0000 00008F4A 0B12085C 515C5050 PP\Q\...J......k1.....a.....4..... 0001E0
Virtual block number 119 (00000077), 512 (0200) bytes

EF04FB38 A97F7E6B AB6EFFFF 4282EF9F 00BA3103 13DFAF5C 515CABAB 4E000160 `..N..\Q\....1.....B..n.k~..8... 000000
515CABAB 4E000160 91EE01FB 0762CF9F FFFF56AB EE03203C B938A92C 00015CAE .\....8.< ...V.....b.........N..\Q 000020
BAAF5C51 5CABAB4E 00016074 FF01FB06 DFCF9FAF AB6BABD0 00823103 13A7AF5C \....1....k..........t`..N..\Q\.. 000040
EF03203C B938A92C 00015C5A EF04FB38 A97F7E67 AB6EFFFF 422EEF9F 66110213 ...f....B..n.g~..8....Z\....8.< .. 000060
AF9E2C11 02130000 00008F5C 515CABAB 4E000160 3DFF01FB 070ECF9F FFFF5654 TV..........`..N..\Q\.......... 000080
9F27AB6B ABD0B3AB 5C4A5C08 425C5050 00016078 FF01FBFF FF3F67EF 9FFCADFD .....g?......x`..PP\B.\J\.....k.'. 0000A0
FCADFDAF 9EFCADFD AF9E0400 015FD3FF 16FCADFD AF9E0001 6002FF01 FB058FCF .......`........................ 0000C0
00015F8C FF1650FF 7FCB7E52 FFFF06D4 EF9E5103 3200015F E1FF01FB 0748CF9F ..H.......2.Q......R~...P....... 0000E0
7E00015B B3EF04FB 38A97F7E AFAB6EFF FF4187EF 9F00015F C1FF01FB 00C4CF9F ..............A..n...~..8.....[..~ 000100
8F5C515C 50500001 5FEEFF01 FBFFFF42 C5EF9F00 015F63FF 165087AB 7E5138A9 .8Q~..P..c_.......B........PP\Q\. 000120
015FC7FF 01FBFFFF 42A6EF9F 3511FFFF 7057EF03 208BBB87 AB2C0E12 00000000 ................Wp...5...B........ 000140
9F00015F 11FF1650 FF7FCB7E 5187AB7E 00015F5C FF01FB05 C7CF9FAF AB504A00 .JP..........\_...~..Q~...P....... 000160
01FB06EF CF9FFFFF 7012EF03 208BBB87 AB2CFCAD FDAF9E00 015F43FF 01FB46AF .F...C_...............P......... 000180
015F0BFF 01FB0576 CF9FAFAB 504A0001 5F76FF01 FBFFFF3E 5DEF9F00 015F27FF .'_.....]>......v_..JP.....v......_. 0001A0
44998F40 5C14445C 08425C3F AB4EFCAD FDAF9EFC ADFDAF9E 0400015E E1FF1600 ....^...............N.T\B.\D.\@..D 0001C0
65EF03FB 10A97FFF FF40DFEF 9F5CDD5C 5C4A5C08 425C2FAB 4E2FAB5C 4A5C8000 ..\J\./N./\B.\J\\.\...@..........e 0001E0
Virtual block number 120 (00000078), 512 (0200) bytes

AB4E5C5C 4A5C1440 5C2FAB4E 00015E74 FF03FB08 A97F10A9 7FFF7FCB 7F00015B [................t^..N./\@.\J\\N. 000000
015B3BEF 04FB00A9 7FFFFF40 A1EF9F5C DD58DD58 584A5880 0044A76F 5743572F /WCW..D..XJXX.X.\....@.........#[. 000020
1600015E 6DFF01FB 053ECF9F 00015E34 FF03FBFF FF408BEF 9F08A97F 00A97F00 ..........@.....4^....>.....m^... 000040
80004499 8F405C14 445C0842 5C3FAB4E FCADFDAF 9EFCADFD AF9E0400 015E43FF .C^..............N.?\B.\D.\@..D.. 000060
00000000 8F5C515C ABAB4E00 015E37FF 01FB04A2 CF9F73AB AFABD06F AB5C4A5C \J\.o.....s.......7^..H..\Q\...... 000080
425C6FAB 4E00015A C1EF04FB FF6FCB7F FFFF4028 EF9F6FAB DD03DD03 19310313 ..1.......o...(@.....o.....Z..N.o\B 0000A0
10A97FFF FF412BEF 9F00015A 91EF03FB 10A97FFF FF400BEF 9F5CDD5C 5C4A5C08 .\J\\.\...@..........Z.....+A...... 0000C0
```

```
58800044 A78F5743 576FAB4E 5C5C4A5C 14405C6F AB4E0001 5D9EFF03 FB08A97F .......J..N.o\@.\J\\N.oWCW..D..X 0000E0
B5EF9F08 A97F00A9 7F00015A 65EF04FB 00A97FFF FF3FCBEF 9F5CDD5B DD585B4A JXX.X.\...T........eZ........... 000100
425CCBAB 4ECBAB5C 4A5C0840 5C10445C 08425C3F AB4E0001 5D5EFF03 FBFFFF3F ?.....^J..N.?\B.\D.\@.\J\..N.,\B 000120
10A97FFF FF3E0BEF 9F00015A 11EF03FB 10A97FFF FF3FB3EF 9F5CDD5C 5C4A5C08 .\J\\.\...T.........Z.....>...... 000140
DD58584A 58235743 57CBAB4E 5C5C4A5C 10405CCB AB4E0001 5D1EFF03 FB08A97F .......J..N..\@.\J\\N..WCW$XJXX. 000160
FBFFFF3F 61EF9F08 A97F00A9 7F000159 E9EFQ4FB 00A97FFF FF3F77EF 9F5CDD5B X.\..w?..........Y...........a?... 000180
5307EF0F 20FFFF09 5AEF002C 0E12FFFF 0556EFFF FF5331EF 0C290001 5CE2FF03 ...\..)..1S...V........Z... ...S 0001A0
4BCF9F01 E1310313 00000000 8F5C515C ABAB4E00 015CFFFF 01FB03D0 CF9FFFFF ..........\..N..\Q\.......1....K 0001C0
7E52FFFF 042FEF9E 51033201 C9310313 E4AF5C51 5CABAB4E 00015CE4 FF01FB04 .....\..N..\Q\....1..2.Q../...R" 0001E0
Virtual block number 121 (00000079), 512 (0200) bytes

5C585158 73AB4E5C 50500001 5D12FF01 FBFFFF3F E9EF9F00 015C83FF 16508FAB ..P...\.....T.......J..PP\N.sXQX\ 000000
00015CE8 FF01FBFF EF3EBFEE 9F010C31 FFFF6D79 EF0320FF 73DBFF6F CB2C1112 ........um..1.....?......\. 000020
13000000 008F5C51 5CABAB4E 00015C78 FF01FB02 E3CF9FFC ADFDAF9E AFAB504A JP...............x\.N..\Q\...... 000040
A5FF01FB 00A97F00 015903EF 04FB00A9 7FFFFF3E 69EF9F4F A3DD03DD 015A3103 .1Z.....o...i>.........Y......... 000060
7F7EAFAB 6EFFFF3D EDEF9FAF 11AFAB77 ABD00713 73AB77AB D177AB50 4A00015C \..JP.w..w.s.....w..........n..". 000080
5C4A5C08 425C6FAB 4E00015B D9FF1650 8FAB7E51 38A97E00 015829EF 04FB38A9 .8...)X..".8Q"..P...C..N.o\B.\J\ 0000A0
FF03FB08 A97F10A9 7FFF6FCB 7F000158 95EF03FB 10A97FFF FF3E0FEF 9F5CDD5C \.\...>..........X.....o......... 0000C0
DD58DD58 584A5880 0044A78F 5743576F AB4E5C5C 4A5C1440 5C6FAB4E 00015BA4 .C..N.o\@.\J\\N.oWCW..D..XJXX.X. 0000E0
FF03FBFF FF3DBBEF 9F08A97F 00A97F00 015B6BEF 04FB00A9 7FFFFF3D D1EF9F5C \...=...........kX..............=..... 000100
9E007F31 03130000 00008F5C 515CABAB 4E00015B 9DFF01FB 026ECF9F 00015B64 dC....n......C..N..\Q\........1... 000120
EF03280C 12C00045 798F5C51 5C505000 015BD7FF 01FBFFFF 3EAEEF9F FCADFDAF ......>.......C..PP\Q\.yE.....(.. 000140
585C5158 73AB4E5C 50500001 5BB2FF01 FBFFFF3E 91EF9FFF FF6C40EF FFFF02C9 .....@1.....>.......C..PP\N.sXQ\X 000160
AB4E5C50 5000015B 8DFF01FB FFFF3E7C EF9FFFFF 6C1EEF03 2093BB8F AB2C0C12 ..............1.....l>.......C..PP\N. 000180
AF9E0001 5B0EFF01 FB02D6CF 9FFFFF6B FCEF0320 93BB8FAB 2C0C1258 5C515873 sXQ\X.........k...........C..... 0001A0
3CB6EF9F ABAB0000 00008F4A FCADFDAF 9EFCADFD AF9E0400 015ADFFF 16FCADFD ......Z...............J.........< 0001C0
A97F0001 5A92FF16 5000A97E 5138A97E 000156E2 EF04FB38 A97F7EA7 AB6EFFFF ..n..."..8....V..".8Q"..P...Z.... 0001E0
Virtual block number 122 (0000007A), 512 (0200) bytes

FF02FB04 DDA7ABDD 7FAB0309 CF9E0001 5A76FF03 FBFE7FCB 7FFFFF3E 11EF9F00 ....>..........vZ................ 000000
5AEAFF01 FBFFFF39 CDEF9FB3 AB50D000 015AFBFF 01FBFFFF 39E6EF9F 00015AA0 .Z.....9.......Z...P.....9......Z 000020
00008F4A FCADFDAF 9EFCADFD AF9E0400 015A57FF 16FCADFD AF9E27AB 50D00001 ...P.'........WZ..............J... 000040
5000A97E 5138A97E 0001565A EF04FB38 A97F7EA7 AB6EFFFF 3C2EEF9F ABAB0000 .......<..n..."..8...ZV..".8Q"..P 000060
7FAB0281 CF9E0001 59EEFF03 FBFE7FCB 7FFFFF3D 91EF9F00 A97F0001 5A0AFF16 ...Z.........=...........Y........ 000080
FFFF6ADE EF02203C B938A92C 0001561E EF04FB38 A97F7EB3 AB6EFFFF 3C4AEF9F ..J<..n..."..8....V....8.< ...J.. 0000A0
FFFF6AC0 EF03203C B938A92C 000155FE EF04FB38 A97F7E27 AB6EFFFF 3BD2EF9F ......n.'"..8....U....8.< ...J.. 0000C0
59C2FF02 FB04DDA7 ABDD0001 5996FF16 5097AB7E 52FFFF69 59EF9E51 01638F32 2.c.Q..Yi..R"..P...Y.............Y 0000E0
FF02FB04 DDA7ABDD FFFF692C EFCFAF20 9BBB97AB 2C000159 95FF01FB 04DD0001 ........Y...... ....i........... 000100
00000000 8F4AFCAD FDAF9EFC ADFDAF9E 04000159 79FF16FC ADFDAF9E 000159C8 .Y.............yY............J...... 000120
FF165000 A97E5138 A97E0001 557CEF04 FB38A97F 7EAFAB6E FFFF3B50 EF9FABAB ....P...n..."..8...|U..".8Q"..P.. 000140
ABDD7FAB 01A3CF9E 00015910 FF03FBFE 7FCB7FFF FF3CBBEF 9F00A97F 0001592C .Y........<............Y.......... 000160
FCADFDAF 9EFCADFD AF9E0400 015913FF 16FCADFD AF9E0001 593AFF02 FB06DDAF ........:Y..........Y............ 000180
00A97E51 38A97E00 015519EF 04FB38A9 7F7EA7AB 6EFFFF3A EDEF9FAB AB99AF4A J.......:..n..."..8....U..".8Q".. 0001A0
AB0140CF 9E000158 ADFF03FB FE7FCB7F FFFF3C60 EF9F00A9 7F000158 C9FF1650 P...X.......`<..........X....@.. 0001C0
C1FF02FB 06DDAFAB DD000158 95FF1650 97AB7E52 FFFF4DCC EF9E5101 4E8F327F .2.N.Q...M..R"..P...X........... 0001E0
```

```
Virtual block number 123 (0000007B), 512 (0200) bytes

02FB06DD AFABDDFF FF4D9FEF CFAF209B BB97AB2C 00015894 FF01FB06 DD000158 X........X.............M.......... 000000
EF9FABAB 00000000 8F4AFCAD FDAF9EFC ADFDAF9E 04000158 7DFF1600 0158C7FF ..X....}X...............J......... 000020
00015830 FF165000 A97E5138 A97E0001 5480EF04 FB38A97F 7E3FAB6E FFFF3AAC .:..n.T"..8....1..".8Q"..F:.0X.. 000040
FB07DD3F ABDD7FAB 00A7CF9E 00015814 FF03FBFE 7FCB7FFF FF3BCFEF 9F00A97F ......!..........X.........?... 000060
3A4EEF9F ABAB9EAF 4AFCADFD AF9EFCAD FDAF9E04 0001581C FF160001 5B3EFF02 .:>X.....X...............J......N: 000080
A97F0001 57D2FF16 5000A97E 5138A97E 00015422 EF04FB38 A97F7E3F AB6EFFFF ..n.?"..8...'T..".8Q"..P...W.... 0000A0
FFFF68C8 EF95510A 327FAB4A AF9E0001 57B6FF03 FBFE7FCB 7FFFFF3B 79EF9F00 ...y!..........W....J..2.Q...h.. 0000C0
000157A0 FF01FB07 DD000157 CDFF02FB 07DD3FAB DD000157 A1FF1650 97AB7E52 R"..P...W....?......W.........W.. 0000E0
9E040001 578AFF16 000157D4 FF02FB07 DD3FABDD FFFF689C EF0A209B BB97AB2C ........h....?......W.....W.... 000100
7FCB7FAB AB084A00 0157ABFF 00FB0001 57A2FF01 FB00DDFC ADFDAF9E FCADFDAF ...............W......W..J...... 000120
3936EF9F 5C50D000 015757FF 00FB0001 5736FF03 FBFE7FCB 7FFFFF3B 01EF9FFE ....!..........6W......WW...P\..69 000140
18A97F00 015713FF 165018A9 7E5138A9 7E000153 63EF04FB 38A97F7E 5C6EFFFF ..n\"..8...cS..".8Q"..P...W..... 000160
E5FF03FB 08A97F10 A97FFFFF 3AC2EF9F 000156F8 FF03FB10 A97FFFFF 3ACAEF9F ...!.........V.....!............ 000180
00015312 EF04FB40 A97F7E5C 6EFFFF38 DDEF9F5C 50D00001 570AFF00 FB000156 V......W...P\...8..n\"..@....S.. 0001A0
DD000156 A9FF03FB FE87CB7F 08A97F00 A97F0001 56C2FF16 5000A97E 5140A97E ".@Q"..P...V................V... 0001C0
D1FF01FB 00DD0001 56EAFF00 FB000157 09FF01FB FE7FCB7F 000156EC FF01FB00 .....V..........W......V........ 0001E0

Virtual block number 124 (0000007C), 512 (0200) bytes

000156AC FF01FBE9 D4CF9F00 0156CFFF 00FB0001 56EEFF01 FBFE87CB 7F000156 V..........V......V..........V.. 000000
00015668 FE16FCAD FDAF9E00 01568BFF 01FB07AF 9F000156 A1FF01FB E823CF9F ..$.....V.........V..........hV.. 000020
AF9ECFFC 045001D0 0001564C FF1650FF FEF7CBEF 9FFCADFD AF9EFCAD FDAF9E04 .................P..LV....P..... 000040
ADFDAF9E FCADFDAF 9EFCADFD AF9E0001 5656FF16 5150D050 FFFF02B0 EF9E52FB .R......P.PQ..VV................ 000060
2BCB7E52 FFFF0C64 EE9E5103 32CBAB00 0000008F 4AFCADFD AF9EFCAD FDAF9EFC ..........J.......2.Q..d...R"..+ 000080
0020FF37 DBFF33CB 2D000156 15FF01FB 46A6CF9F CFAB104A 000155E4 FF1650FF .P...U..J......F....V..-.3..7. . 0000A0
01FBFFFF 3982EF9F 000155FC FF01FB00 DDFCADFD AF9E52B0 310312FF FF0C3BEF .!.....1.R.........U.....9.... 0000C0
02FBF8A9 DFF8A918 D0FCA9DF FCA90000 004D8FD0 000155F8 FF00FB00 015617FF ..V......U....M.................. 0000E0
55C2FF00 FB000155 E9FF01FB FFFF3954 EF9F0001 55C6FF01 FB00DDFF FF7067EF .dp.........U....T9......U.......U 000100
00015594 FF01FB00 DDFFFF70 35EF02FB F8A9DFF8 A905D0FC A9DFFCA9 16D00001 ......................5p.........U.. 000120
DFF8A907 D0FCA9DF FCA914D0 00015590 FF00FB00 0155AFFF 01FBFFFF 392AEF9F ..*9.......U.......U............. 000140
FB000155 7DFF01FB FFFF3900 EF9F0001 5562FF01 FB00DDFF FF7003EF 02FBF8A9 .......p.........bU.....9......}U... 000160
FF01FB00 DDFFFF6F D1EF02FB F8A9DFF8 A90AD0FC A9DFFCA9 14D00001 555EFF00 ..^U.........................o........ 000180
D0FCA9DF FCA914D0 0001552C FF00FB00 01554BFF 01FBFFFF 38D6EF9F 00015530 0U.....8.....KU......U.......... 0001A0
19FF01FB FFFF38AC EF9F0001 54FEFF01 FB00DDFF FF6F9FEF 02FBF8A9 DFFBA90B .........o.........T.....8...... 0001C0
DDFFFF6F 6DEF02FB F8A9DFF8 A90CD0FC A9DFFCA9 14D00001 54FAFF00 FB000155 U......T.......................mo... 0001E0

Virtual block number 125 (0000007D), 512 (0200) bytes

FCA914D0 000154C8 FF00FB00 0154E7FF 01FBFFFF 3882EF9F 000154CC FF01FB00 .....T.....8......T......T...... 000000
FEFF3858 EF9F0001 549AFF01 FB00DDFF FF6F3BEF 02FBF8A9 DFF8A90D D0FCA9DF ..............!o........T....X8.. 000020
09EF02FB F8A9DFF8 A90ED0FC A9DFFCA9 14D00001 5496FF00 FB000154 B5FF01FB ....T.......T..................... 000040
00015464 FF00FB00 015483FF 01FBFFFF 382EEF9F 00015468 FF01FB00 DDFFFF6F o........hT.....8.......T.....dT.. 000060
31FF01FB 00DDFFFF 6ED2EF02 FBF8A9DF F8A911D0 FCA9DFFC A914D0FC ADFDAF9E .........................n.........1 000080
12D0FCA9 DFFCA914 D0000154 2DFF00FB 0001544C FF01FBFF FF37FFEF 9F000154 T.....7.....LT......-T............ 0000A0
```

```
541AFF01 FBFFFF37 D5EF9F00 0153FFFF 01FB00DD FFFF6EA0 EF02FBF8 A9DFF8A9 .........n........S.....7.......T 0000C0
69EF02FB F8A9DFF8 A914D0FC A9DFFCA9 14D0FCAD FDAF9E00 0153FBFF 00FB0001 ......S.........................i 0000E0
000153C4 FF00FB00 0153E3FF 01FBFFFF 37A6EF9F 000153C8 FF01FB00 DDFFFF6E n........S.....7......S......S.. 000100
01FBFF3B CB7FFFFF 6E32EF02 FBF8A9DF F8A914D0 FCA9DFFC A92DD0FC ADFDAF9E .....-.................2n....;... 000120
9DEF0020 FF47DBFF 43CB2D00 01533BFF 1650FF43 CB7E51FF 3BCB7EFF FF72CBEF ..r..^.;.Q^.C.P..;S..-.C..C. ... 000140
EF02FB38 A97F00A9 7F00014F F1EF03FB 00A97FFF 43CB7F01 DDB91102 12FFFF09 ..........C........O.......8... 000160
20FF47DB FF43CB2D FCADFDAF 9E000152 FDFF1650 FF43CB7E 5138A97E FFFF717C 1@..^.BQ^.C.P...R.......-.C..G. 000180
0152CBFF 1650FF4B CB7E52FF FF089DEF 9E510132 D3AB084A 1C12FFFF 08ADEF01 ........J...2.Q......R^.K.P...R. 0001A0
FF086FEF 9E510132 D3AB104A 1C12FFFF 087FEF01 20FF47DB FF43CB2D 01403100 .1@.-.C..G. ........J...2.Q..o.. 0001C0
1C12FFFF 0851EF01 20FF47DB FF43CB2D 01143100 01529FFF 1650FF4B CB7E52FF .R^.K.P...R..1..-.C..G. ..Q..... 0001E0
Virtual block number 126 (0000007E), 512 (0200) bytes

FF43CB2D 00E83100 015273FF 1650FF4B CB7E52FF FF0841EF 9E510132 D3AB144A J...2.Q..A...R^.K.P..sR..1..-.C. 000000
1650FF4B CB7E52FF FF0813EF 9E510132 D3AB184A 1C12FFFF 0823EF01 20FF47DB .G....$.....J...2.Q......R^.K.P. 000020
9E510132 D3AB1A4A 1C12FFFF 07F5EF01 20FF47DB FF43CB2D 00BC3100 015247FF .CR..1..-.C..G. ........J...2.Q. 000040
FF47DBFF 43CB2DFC ADFDAF9E 00903100 01521BFF 1650FF4B CB7E52FF FF07E5EF .....R^.K.P...R..1.......-.C..G. 000060
0413FFFF 07AAEF01 20FF47DB FF43CB2D 5C01CE03 115CD404 13FFFF07 C2EF0120 .........\....\-.C..G. ......... 000080
01CE0311 58D40413 FFFF078F EF0120FF 47DBFF43 CB2D5C58 C85801CE 031158D4 .X....X.X\-.C..G. .........X.... 0000A0
FB00A97F 000151B0 FF165000 A97E52FF FF0774EF 9E510232 21135CD5 5C58C858 X.X\.\.!2.Q..t...R^..P...Q...... 0000C0
79310312 FFFF0748 EF0120FF 47DBFF43 CB2DFCAD FDAF9EFB E131FFFF 6DB2EF01 ...m..1........-.C..G. ..H.....1y 0000E0
13000000 008F5C51 5CD7AB4E 000151B8 FF01FB4C 53CF9FFC ADFDAF9E FDE5314E N1.........SL....Q..N..\Q\....... 000100
DBAF4A00 E4310312 E3AF5C51 5C505000 0151F7FF 01FBFFFF 3596EF9F FBA63103 '.1.....5.......Q..PP\Q\....1..J.. 000120
03CF9FE3 ABDFABD0 FCADFDAF 9EDFAB50 4A000151 D9FF01FB FFFF3578 EF9FDBAB ....x5.......Q..JP............... 000140
405C1444 5C08425C D3AB4EFB 55310313 ABAF5C51 5CD7AB4E 00015164 FF01FB4B K...dQ..N..\Q\....1U.N..\B.\D.\@ 000160
00A97F00 014DDFEF 04FB00A9 7FFFFF35 35EF9F5C DD03DD5C 5C4A5C80 0044998F ..D..\J\\...\..55.........M..... 000180
DBAB4E42 110213FF FF0747EF 0020FFFF 4717EF0F 2DDFAB50 4A000151 81FF01FB ....Q..JP..-...G... ..G......BN.. 0001A0
FF01FB00 94CF9FE7 AB504A00 015153FF 01FBFFFF 3502EF9F DBAB5C4A 5C08405C \@.\J\......5.....SQ..JP.......... 0001C0
9E000150 CDFF01FB 021BCF9F FAD63103 13000000 008F5C51 5CD7AB4E 000150E8 .P..N..\Q\........1..........P... 0001E0
Virtual block number 127 (0000007F), 512 (0200) bytes

A9310315 CFAF5C51 5CDBAB4E FF3F3103 13C00045 798F5C51 5CDFAB4E FCADFDAF ....N..\Q\.yE....1?.N..\Q\....1. 000000
FF01FB00 DDFFFF6B 31EF02FB F8A9DFF8 A917D0FC A9DFFCA9 03D0FCAD FDAF9EFA ........................1k........ 000020
81FF00FB 000150A0 FF01FBFF 4BCB7F00 0150B3FF 01FBFFFF 34BEEF9F 00015090 .P.....A.......P....K.....P...... 000040
FF01FB00 DDFCADFD AF9EFCAD FDAF9EFA 59310001 505EFF01 FB4579CF 9F000150 P....yE...^P..1Y................ 000060
FCA90000 004D8FD0 0001504C FF00FB00 01506BFF 01FBFFFF 33D6EF9F 00015050 PP.....3.....kP......LP.....M...... 000080
FFFF3420 EF9F0001 501AFF01 FB00DDFF FF6ABBEF 02FBF8A9 DFF8A918 D0FCA9DF ...............J........P.... 4.. 0000A0
AB4E0001 4FEEFF01 FB0657CF 9FFCADFD AF9E0001 5016FF00 FB000150 3DFF01FB ...P........P........W.....D..N. 0000C0
EF9E5101 638F3200 014FD3FF 01FB47A4 CF9F0119 31031300 0000008F 5C515CD7 .\Q\........1......G....O..2.c.Q.. 0000E0
DBFF43CB 2D00014F B1FF01FB 21E4CF9F 00014F7C FF1650FF 53CB7E52 FFFF5F40 @....R^.S.P..!O.....!....D..-.C.. 000100
C6310312 FFFF5F08 EFC4AF20 FF57DBFF 53CB2DA1 110212FF FF04F0EF 0120FF47 G. ..........-.S..W. .........1. 000120
30A97F02 DD000146 45EF02FB 30A97F00 DDFFFF60 40EF0F20 FF37DBFF 33CB2C00 ...3..7. ..@`.......O...EF.......O 000140
18A97F20 A97F04DD 03DD0001 462AEF02 FB20A97F 00DD0001 4BFEEF03 FB28A97F ..(.....K....... ....*F......... ... 000160
FDEF02FB 08A97F00 DD00014E F1FF03FB 10A97F28 A97F18A9 7F00014B F5EF04FB ....K.......(........N............ 000180
FFFF3328 EF9F10A9 7F00A97F 00014BC8 EF04FB00 A97F08A9 7F08DD02 DD000145 E..................K...........(3.. 0001A0
A97FFFFF 331AEF9F FFFF3318 EF9F0001 4EFAFF01 FB47BBCF 9F00014E C1FF03FB ....N.....G.....N.....3.....3.... 0001C0
4583CF9F 00014E8C FF03FBFF 13CB7F00 A97FFFFF 3312EF9F 00014EA0 FF03FB00 .....N.....3..............N.....E 0001E0
```

```
Virtual block number 128 (00000080), 512 (0200) bytes

510032FC ADFDAF9E FCADFDAF 9E040001 4E96FF16 FCADFDAF 9E00014E C5FF01FB ....N...........N.............2.Q 000000
00014E94 FF01FB00 DDFCADFD AF9E0001 4E5AFF16 50FF43CB 7E52FFFF 04DAEF9E ......R^.C.P..ZN.............N.. 000020
D0FCA9DF FCA90000 004D8FD0 00014E90 FF00FB00 014EAFFF 01FBFFFF 321AEF9F ...2......N......N....K......... 000040
81FF01FB FFFF328C EF9F0001 4E5EFF01 FB00DDFF FF68FFEF 02FBF8A9 DFF8A918 ..........h......^N.....2....... 000060
4A00014E 89FF01FB FFFF3278 EF9FCBAB 00000000 8F4A0001 4E5AFF00 FB00014E N.....ZN..J.........x2......N..J 000080
5D8EEF1E 28011231 0313D6AF 5C515CD7 AB4E0001 4E1EFF01 FB47BDCF 9FEBAB50 P.......G....N..N..\Q\....1..(...] 0000A0
CB7E52FF FF42DBEF 9E51014E 8F320001 4DFAFF01 FB0B09CF 9FFFFF42 FDEFFFFF ....B..........M..2.N.Q...B..R^. 0000C0
02FAEF02 20FF67DB FF63CB2D 00014DD8 FF01FB02 25CF9F00 014DA3FF 1650FF5B [.P...N....%.....N..-.c..d. .... 0000E0
CE031158 D40413FF FF02E1EF 0220FF67 DBFF63CB 2D5C01CE 03115CB4 0413FFFF ....\....\-.c..d. .........X... 000100
4DBAFF01 FBFFFF31 25EF9F00 014D9FFF 01FB00DD 00923103 135CD55C 58C85801 .X.X\.\..1.........N....%1......M 000120
680AEF02 FBF8A9DF F8A918D0 FCA9DFFC A9000000 4D6FD000 014D9BFF 00FB0001 .......M....M....................h 000140
9F00014D 65FF00FB 00014D8C FF01FBFF FF3197EF 9F00014D 69FF01FB 00DDFFFF ........iM.....1.......N.....eM... 000160
00014D2C FF01FB25 20CF9F00 014D37FF 01FB4508 CF9F0001 4D42FF01 FB0A51CF .Q....BN.....E...7M.... %....M.. 000180
AF9E0001 4D0EFF01 FB015BCF 9FFE7F31 0312FFFF 026BEF01 20FF47DB FF43CB2D -.C..G. ..k......1....[.....M.... 0001A0
CB2DFCAD FDAF9E04 00014CD0 FF16FCAD FDAF9E00 014CFFFF 01FB13AF 9FFCADFD ...........L..........L.........-. 0001C0
FF42B9EF 0F20FF37 DBFF33CB 2C00E131 0312FFFF 41CAEF01 4E8F20FF 5FDBFF5B [..._. .N...A.....1....3..7. ...B. 0001E0
Virtual block number 129 (00000081), 512 (0200) bytes

A97F00DD 0001494C EF03FB28 A97F30A9 7F02DD00 014393EF 02FB30A9 7F00DDFF .....O....C.......O..(...LI....... 000000
7F28A97F 18A97F00 014943EF 04FB18A9 7F20A97F 04DD03DD 00014378 EF02FB20 ...xC.................CI.......(.. 000020
FB00A97F 08A97F08 DD02DD00 01434BEF 02FB08A9 7F00DD00 014C3FFF 03FB10A9 ......TL...........KC............. 000040
9FFFFF30 71EF9F00 014C0FFF 03FBFFFF 30A6EF9F 10A97F00 A97F0001 4916EF04 ...I...........O.......L.....uO... 000060
4BE6FF03 FB08A97F 10A97FFF FF308BEF 9F00014B F9FF03FB 10A97FFF FF3073EF .sO..........K......O.............K. 000080
CB7F00A9 7FFFFF30 45EF9F00 014BD3FF 03FB00A9 7F08A97F FFFF3080 EF9F0001 .....O...............K.....EO....... 0000A0
FF67DBFF 63CB2DFC ADFDAF9E 00014BF8 FF01FB42 B6CF9F00 014BBFFF 03FBFF13 ......K......B.....K.......-.c..d. 0000C0
FB45CBCF 9F0B1102 11FFFF41 D2EF0F20 FF37DBFF 33CB2C10 12FFFF01 15EF0220 ...........3..7. ...A............E. 0000E0
42B8BF4A FCADFDAF 9EFCADFD AF9E0400 014B97FF 16FCADFD AF9E0001 4BC6FF01 ...K...........K...............J..B 000100
EF02FBF8 A9DFF8A9 17D0FCA9 DFFCA903 D000014B 9DFF01FB 41D8CF9F EFAB0000 ........A.....K..................... 000120
014B83FF 00FB0001 4BA2FF01 FBFFFF2F DDEF9F00 014B87FF 01FB00DD FFFF6628 (f.........K....../.......K.......K. 000140
5C2D405C 1E445CF3 AB4EFCAD FDAF9E6C 110002F3 AB0104F1 F3ABD7F3 AB00D000 ...................1......N..\D.\@-\ 000160
AB4E0001 4B36FF01 FB00DDFF FF65D7EF 02FBFCA9 DFFCA917 D0F7ABDF F7AB5C4A J\...................e........6K..N. 000180
7F000147 BDEF04FB 00A97FFF FF2F83EF 9F5CDD02 DD5C5C4A 5C08405C 10445CF3 .\D.\@.\J\\...\..../..........G... 0001A0
FDAF9EF3 ABD797F3 AB04F3FC ADFDAF9E 00014B14 FF00FB00 014B33FF 01FB00A9 ......3K.......K.................... 0001C0
00014AD8 FF01FB0A DDFFFF65 75EF02FB F8A9DFF8 A918D0FC A9DFFCA9 04D0FCAD ......................ue........J.. 0001E0
Virtual block number 130 (00000082), 512 (0200) bytes

DD00014A C5FF00FB 00014B04 FF01FBFF 63CB7F00 014AF7FF 01FBFFFF 2F3AEF9F ..!/.......J.....c.......K.......J... 000000
5138A97E FFFF68C4 EF02FB38 A97F00A9 7F000147 39EF03FB 00A97FFF 63CB7F02 ...c.........9G..........8.....h..^.8Q 000020
CE03115C D40412FF FEFFA3EF 0220FF67 DBFF63CB 2D00014A 45FF1650 FF63CB7E ^.c.P...EJ..-.c..d. ..........\... 000040
2D5C58CA 5858D258 01CE0311 58D40412 FFFEFF8A EF0220FF 67DBFF63 CB2D5C01 .\-.c..d. ..........X.....X.XX.X\- 000060
15135CD5 5C58CA58 58D25801 CE031158 D40412FF FF0073EF 0020FF67 DBFF63CB .c..d. ..s.......X.....X.XX.X\.\.. 000080
39EF0220 FF67DBFF 63CB2D00 0149D7FF 1650FF63 CB7E52FF FEFF51EF 9E510232 2.Q...Q....R^.c.F....I..-.c..d. ..9 0000A0
3DEF9F00 0149ABFF 03FB10A9 7FFFFF2E 75EF9FFF FF2E23EF 9F5B1102 13FFFEFF .......[..#......u............I..... 0000C0
```

```
85FF03FB 00A97F08 A97FFFFF 2E32EF9F 00014998 FF03FB08 A97F10A9 7FFFFF2E ..............I.....2.............. 0000E0
49AAFF01 FB4068CF 9F000149 71FF03FB FF13CB7F 00A97FFF FF2E47EF 9F000149 I....C...............aI.....hG....I 000100
89FF01FB 41C2CF9F FCADFDAF 9EFCADFD AF9E0400 01497BFF 16FCADFD AF9E0001 .........{I...............A....  000120
A903D0FC ADFDAF9E FCADFDAF 9E067531 03130000 00008F5C 515CD7AB 4E000149 I..N..\Q\.......1u.............. 000140
FF2DD7EF 9F000149 59FF01FB 00DDFFFF 63FAEF02 FBF8A9DF F8A902D0 FCA9DFFC ..............c.......YI......-. 000160
FCA903D0 00014948 FF00FB00 014967FF 01FBFFFF 2D62EF9F 0001497C FF01FBFF ....|I....b-......sI......HI..... 000180
FFFF2DA0 EF9F0001 491AFF01 FB00DDFF FF63BBEF 02FBF8A9 DFF8A904 D0FCA9DF ..............c.........I.....-.. 0001A0
DFFCA903 D0000149 09FF00FB 00014928 FF01FBFF FF2D9BEF 9F000149 3DFF01FB ...#I......-.....(I.......I........ 0001C0
FBFFFF2D 71EF9F00 0148DBFF 01FB00DD FFFF637C EF02FBF8 A9DFF8A9 06D0FCA9 .............|c.........H.....a-.... 0001E0
Virtual block number 131 (00000083), 512 (0200) bytes

A9DFFCA9 03D00001 48CAFF00 FB000148 E9FF01FB FFFF2D6C EF9F0001 48FEFF01 ...H.....1-.......H.......H......... 000000
01FBFFFF 2D42EF9F 0001489C FF01FB00 DDFFFF63 3DEF02FB F8A9DFF8 A908D0FC ..........=c........H.....B-..... 000020
FCA9DFFC A903D000 01488BFF 00FB0001 48AAFF01 FBFFFF2D 3DEF9F00 0148BFFF ..H.....=-.......H.......H......... 000040
FF01FBFF FF2D13EF 9F000148 5DFF01FB 00DDFFFF 62FEEF02 FBF8A9DF F8A90AD0 ...........b.........]H......-..... 000060
D0FCA9DF FCA928D0 0001484C FF00FB00 01486BFF 01FBFFFF 2D0EEF9F 00014880 .H.....-......kH......LH....(...... 000080
39FF01FB FFFF2CE4 EF9F0001 481EFF01 FB00DDFF FF62BFEF 02FBF8A9 DFF8A90A ..........;b.........H...........9 0000A0
DDFFFF62 8DEF02FB F8A9DFF8 A90BD0FC A9DFFCA9 03D00001 481AFF00 FB000148 H......H......................b... 0000C0
47FAFF01 EBEFFF2C B5EF9F00 01480FFF 01FBFFFF 2CBAEF9F 000147EC FF01FB00 .....G.............H.............G 0000E0
00DDFFFF 624EEF02 FBF8A9DF F8A90CD0 FCA9DFFC A903D000 0147DBFF 00FB0001 ......C......................Nb..... 000100
0147C3FF 01FBFFFF 2C86EF9F 000147D0 FF01FBFF FF2C8BEF 9F000147 ADFF01FB ....G...............G.............G. 000120
FF02FB00 DDFFFF2C 75EF9F00 01478FFF 00FB0001 47B6FF01 FBFFFF2C 81EF9F00 ............G......G....u......... 000140
1650005C 415C182B 410D8F44 5C505000 0147B7FF 01FBFFFF 2C56EF9F 0001476C 1G....V........G..PP\D..A+.\A\.P. 000160
FCA9DFFC A903D000 01474BFF 00FB0001 4776FF01 FB7E5C50 5C505000 01464CEF .LF...PP\P\~....vG.....KC.......... 000180
FF01FBFF FF2C1BEF 9F000147 1DFF01FB 00DDFFFF 61BEEF02 FBF8A9DF F8A90DD0 ...........a.........G............ 0001A0
00FB0001 4726FF01 FBFFFF2C 11EF9F00 014733FF 01FBFFFF 2C16EF9F 00014740 &G...........3G...........&G.... 0001C0
014727FF 01FBFFFF 2BE6EF9F 000146DC FF02FB00 DDFFFF2C 05EF9F00 0146FFFF ..F...............F......+......'G. 0001E0
Virtual block number 132 (00000084), 512 (0200) bytes

46E6FF01 FB7E5C50 5C505000 0145BCEF 1650005C 415C930C 3FC98F44 5C505000 .PP\D..?..\A\.P...E..PP\P\~.....F 000000
00DDFFFF 612EEF02 FBF8A9DF F8A90FD0 FCA9DFFC A903D000 0146BBFF 00FB0001 ......F............................ 000020
01469BFF 01FBFFFF 2BA6EF9F 000146B0 FF01FBFF FF2BABEF 9F000146 8DFF01FB ....F......+....\.F......+.......F. 000040
FB00DDFF FF60EFEF 02FBF8A9 DFF8A910 D0FCA9DF FCA903D0 0001467C FF00FB00 ....|F......................`...... 000060
0001465C FF01FBFF FF2B77EF 9F000146 71FF01FB FFFF2B7C EF9F0001 464EFF01 ..NF.....|+......qF.....w+......\F.. 000080
01FB00DD FFFF60B0 EF02FBF8 A9DFF8A9 11D0FCA9 DFFCA903 D0000146 3DFF00FB ...=F.....................`...... 0000A0
FB000146 1DFF01FB FFFF2B48 EF9F0001 4632FF01 FBFFFF2B 4DEF9F00 01460FFF ..F.....H+.....2F.....H+.......F... 0000C0
FF01FB00 DDFFFF60 71EF02FB F8A9DFF8 A913D0FC A9DFFCA9 03D00001 45FEFF00 ...E....................a`...... 0000E0
00FB0001 45DEFF01 FBFFFF2B 19EF9F00 0145F3FF 01FBFFFF 2B1EEF9F 000145D0 .F......+.......E.......+.......E.... 000100
91FF01FB 00DDFFFF 6032EF02 FBF8A9DF F8A914D0 FCA9DFFC A903D000 0145BFFF ..E.......................2`........ 000120
FF00FB00 01459FFF 01FBFFFF 2AEAEF9F 000145B4 FF01FBFF FF2AEFEF 9F000145 E......*.......E......*.......E..... 000140
4552FF01 FB00DDFF FF5FF3EF 02FBF8A9 DFF8A916 D0FCA9DF FCA903D0 00014580 .E.........................-........RE 000160
41FF00FB 00014560 FF01FBFF FF2ABBEF 9F000145 75FF01FB FFFF2AC0 EF9F0001 .....*......uE......*......`E.....A 000180
014513FF 01FB00DD FFFFBFB4 EF02FBF8 A9DFF8A9 02D0FCA9 DFFCA937 D0000145 E...7.................-..........E. 0001A0
00014188 EF03FB00 A97FFFFF 2A8AEF9F 02DD0001 4536FF01 FBFFFF2A 91EF9F00 ....*......6E.......*..........A.. 0001C0
FFFF2A68 EF9F0001 44DAFF01 FB00DD00 0144F3FF 00FB0001 451AFF01 FB00A97F .......E.......D..........D....h*.. 0001E0
```

```
Virtual block number 133 (00000085), 512 (0200) bytes

01FB08A9 7F000141 61EF04FB 08A97FFF FF2A4FEF 9F03DD03 DD000144 FDFF01FB ....D.........D%..........aA....... 000000
FB00A97E FFFF2A24 EF9F06DD 02DD0001 44D2FF01 FBFFFF2A 3DEF9F00 0144DFFF ..D....=%.......D..........$%...... 000020
03D0FCA9 DFFCA937 D0000144 8DFF00FB 000144AC FF01FB00 A97F0001 4136EF04 ..6A..........D.......D...7........ 000040
4482FF01 FBFFFF29 F5EF9F00 01445FFF 01FB00DD FFFF5F00 EF02FBF8 A9DFF8A9 .................D.....)......D 000060
00FB0001 4466FF01 FB00A97F 000140D4 EF03FB00 A97FFFFF 285EEF9F 02DD0001 ......^(..........@.........fD..... 000080
9F03DD03 DD000144 49FF01FB FFFF29B4 EF9F0001 4426FF01 FB00DD00 01443FFF .?D.......3D.....)......ID....... 0000A0
FBFFFF29 89EF9F00 01442BFF 01FB08A9 7F000140 ADEF04FB 08A97FFF FF2823EF .$(..........@..........+D.....).... 0000C0
FF01FB00 A97F0001 4082EF04 FB00A97F FFFF27F8 EF9F06DD 02DD0001 441EFF01 ...D..........'..........@......... 0000E0
FFFF5E4C EF02FBF8 A9DFF8A9 04D0FCA9 DFFCA93C D0000143 D9FF00FB 000143F8 .C......C...<..................L^.. 000100
B9FF01FB FFFF2944 EF9F0001 43CEFF01 FBFFFF29 49EF9F00 0143ABFF 01FB00DD ......C....I)........C....D)....... 000120
2DFFFF5E 0DEF02FB F8A9DFFB A906D0FC A9DFFCA9 3CD00001 439AFF00 FB000143 C.......C...<..................^.. 000140
01FBFFFF 290AEF9F 0001435C FF01FB00 DD1F12FF FEF6C4EF 1120FFFF 52EAEF1E ...R.. ..............\C.......).... 000160
FF01FBFF FF2773EF 9F000143 3DFF01FB 00DD1D11 00014358 FF00FB00 01437FFF ..C......XC...........=C.....s'..... 000180
01433BFF 01FBFFFF 28D6EF9F 00014320 FF01FB00 DD000143 39FF00FB 00014360 `C......9C........ C.....(......;C. 0001A0
02D0FCAD FDAF9EFC ADFDAF9E 04000142 D5FF16FC ADFDAF9E 0001431C FF00FB00 .....C...............B.............. 0001C0
2756EF9F 000142D8 FF01FB00 DDFFFF5D 79EF02FB F8A9DFF8 A901D0FC A9DFFCA9 ..................y].........B.....V' 0001E0
Virtual block number 134 (00000086), 512 (0200) bytes

A902D000 0142C7FF 00FB0001 42E6FF01 FBFFFF28 89EF9F00 0142FBFF 01FBFFFF .......B......(.......B.......B...... 000000
FF271FEF 9F000142 99FF01FB 00DDFFFF 5D3AEF02 FBF8A9DF F8A902D0 FCA9DFFC .................:]..........B....... 000020
FCA902D0 00014288 FF00FB00 0142A7FF 01FBFFFF 2852EF9F 000142BC FF01FBFF ......B....R(.......B.......B....... 000040
FFFF2828 EF9F0001 425AFF01 FB00DDFF FF5CFBEF 02FBF8A9 DFF8A903 D0FCA9DF ................\........ZB....((.. 000060
FF01FB00 DD000142 49FF00FB 00014270 FF01FBFF FF269BEF 9F000142 7DFF01FB ...}B......&......pB.....IB........ 000080
FFFF2650 EF9F0001 424AFF01 FB00A97F 00013F18 EF02FB00 A97F20DD 00014230 0B..............?.........JB.....P3.. 0000A0
DFFCA902 D0000142 09FF00FB 00014228 FF01FBFF FF22E3EF 9F000142 3DFF01FB ...=B......'......(B.......B........ 0000C0
FBFFFF27 B9EF9F00 0141DBFF 01FB00DD FFFF5C7C EF02FBF8 A9DFF8A9 04D0FCA9 ..............|\.........A.......'.. 0000E0
000141DC FF01FBFF FF27AFEF 9F000141 F1FF01FB FFFF27B4 EF9F0001 41FEFF01 ...A......'.......A......'.......A.. 000100
01FB00DD FFFF5C30 EF02FBF8 A9DFF8A9 04D0FCA9 DFFCA91A D0000141 BDFF00FB ....A......................0\...... 000120
9F000141 A5FF01FB FFFF2780 EF9F0001 41B2FF01 FBFFFF27 85EF9F00 01418FFF ..A......'.......A......'.......A... 000140
12FFFEF6 CFEFFFFF 46E4EF01 29000141 71FF00FB 00014190 FF01FBFF FF277BEF .{'.......A......qA..)....F......... 000160
01FB07F4 CF9F0B12 FFFEF44F EFFFFF46 CBEF0129 00014140 FF01FB04 FECF9F0B ........@A..)....F....O............ 000180
38D00001 410EFF01 FB0B6ECF 9F0B12FF FEF668EF FFFF46B2 EF012900 014127FF .'A..)....F....h.........n......A...8 0001A0
2706EF9F 000140F8 FF01FB00 DDFFFF5B 99EF02FB F8A9DFF8 A901D0FC A9DFFCA9 ..........................[........@......' 0001C0
01FB00A9 7F00013D 6DEF03FB 00A97FFF FF26FFEF 9F02DD00 01411BFF 01FBFFFF ........A.........=.........m-........ 0001E0
Virtual block number 135 (00000087), 512 (0200) bytes

40E2FF01 FBFFFF26 4DEF9F00 0140BFFF 01FB00DD 000140D8 FF00FB00 0140FFFF ..@.......@..........@....M&.......@ 00000C
000140C4 FF01FB08 A97F0001 3D46EF04 FB08A97F FFFF26C4 EF9F03DD 03DD0001 ..........=.........F&...........@.. 00002C
013D1BEF 04FB00A9 7FFFFF26 99EF9F06 DD02DD00 0140B7FF 01FBFFFF 2622EF9F ..'&.......@.........&............". 00004C
F8A9DFF8 A902D0FC A9DFFCA9 38D00001 4072FF00 FB000140 91FF01FB 00A97F00 .........@.......r@....8............ 00006C
9F02DD00 014067FF 01FBFFFF 2662EF9F 00014044 FF01FB00 DDFFFF5A E5EF02FB ....Z........D@.....b&.......g@..... 00008C
00014024 FF00FB00 01404BFF 01FB00A9 7F00013C B9EF03FB 00A97FFF FF2473EF .s$..........<..........K@......$@.. 0000AC
FFFF2438 EF9F03DD 03DD0001 402EFF01 FBFFFF25 99EF9F00 01400BFF 01FB00DD ......@......%.........@.........B$.. 0000CC
```

```
014003FF 01FBFFFF 256EEF9F 00014010 FF01FB08 A97F0001 3C92EF04 FB08A97F .......<.........Q....n%......@. 0000E0
FB00013F DDFF01FB 00A97F00 013C67EF 04FB00A9 7FFFFF24 0DEF9F06 DD02DD00 ........$.........d<.........?... 000100
FF01FB00 DDFFFF5A 31EF02FB F8A9DFF8 A903D0FC A9DFFCA9 3DD00001 3FBEFF00 ...?..=.................1Z...... 000120
00FB0001 3F9EFF01 FBFFFF25 B1EF9F00 013FB3FF 01FBFFFF 25B6EF9F 00013F90 .?.....%......?.....%......?.... 000140
51FF01FB 00DDFFFF 59F2EF02 FBF8A9DF F8A904D0 FCA9DFFC A935D000 013F7FFF ..?...5................Y.......Q 000160
FF00FB00 013F5FFF 01FBFFFF 2582EF9F 00013F74 FF01FBFF FF2587EF 9F00013F ?.....%.....t?.....%....._?..... 000180
57110002 F3AB011A F1F3ABD7 F3AB01D0 FFAB0000 00008F4A FBAB2C4A 00013F40 Q?..J...J......................W 0001A0
0AFE0BCB 4CCFAF4A 5C000132 00FBAB0A FBAB5C4A 5C08405C FBAB4EFC ADFDAF9E .....N..\@.\J\......2..\J..L.... 0001C0
08405CFF AB4E0B11 0212FFFE F50AEF00 20FFFF3C 51EF4C18 2D5C0018 1A00F3AB .......\-.L.Q<.. ..........N..\@. 0001E0
Virtual block number 136 (00000088), 512 (0200) bytes

5CFFAB4E FCADFDAF 9EF3ABD7 ACF3AB1A F3FCADFD AF9EFCAD FDAF9EFF AB5C4A5C \J\.........................N..\ 000000
5C4A5C08 405C03AB 4E0B1858 5C5158FF AB4E5C10 445C03AB 4E03AB5C 4A5C1046 F.\J\..N..\D.\N..XQ\X..N..\@.\J\ 000020
F3AB01D0 0BAB0000 00008F4A 07AB5C4A 5C21405C 10465C25 58435803 AB4E03AB ..N..XCXX\F.\@!\J\..J........... 000040
3BBEEF4C 182D5C00 181A00F3 AB0AFCAD FDAF9E02 05310003 F3AB011A F1F3ABD7 ..........1..............\-.L..; 000060
F45EEF9E 5100320B AB5C4A5C 08405C0B AB4E01D0 310312FF FEF477EF 0020FFFF .. ..w.....1..N..\@.\J\..2.Q..?. 000080
00030FAB FFFFFFFF 8F01F10F ABD60FAB 18D00001 3DDEFF16 50FF6BCB 7E52FFFE ..R^.k.P...=.................... 0000A0
FF2443EF FFFF3B64 EF4C9E0F ABDD01DD 5C00181A 00F3AB0A FCADFDAF 9E008331 1.............\......L.d!...C$. 0000C0
FFFEF400 EF0020FF 6FDBFF6B CB2D0001 3A8AEF04 FBFF43CB 7FFFFF24 39EF9FFF ...9$....C.....!..-.k..o. ...... 0000E0
7FFF6BCB 7FFCADFD AF9E1811 0212FFFE F0B2EF01 20FF47DB FF43CB2D 12110213 ....-.C..C. ..................k.. 000100
ABFFFFFF FF8F01F1 FCADFDAF 9EFCADFD AF9E0001 3D5AFF03 FBFF6BCB 7FFF43CB .C...k....Z=.................... 000120
0BABC110 1503AB0B ABD117AB 104A13AB 07AB0BAB C1FCADFD AF9E0FAB D6FF800F ................J............... 000140
AB5C4A5C 23405C13 AB4E0D12 105C515C 17AB4E17 AB334A13 AB5C03AB C35C07AB ..\...\..J3..H..\Q\...N..\@$\J\. 000160
17ABDFFE 0BCB4CF3 ABD05C00 013200FB AB0AFBAB 5C4A5C2C 405C13AB 4E0B11FB ...N..\@.\J\......2..\...L...... 000180
00FB0001 3D46FF01 FBFF6BCB 7F00013D 21FF01FB 00DDFFFF 57C2EF02 FB13ABDF .......W........!=....k....F=.... 0001A0
8F5C515C 1BAB4E1B AB584A58 000042C8 8F5C435C 584E58FF 6BCB3C00 013B1FFF ..=..<.k.XNX\C\..B..XJX..N..\Q\. 0001C0
A97F0001 39A6EF03 FB08A97F 1BABDD2E DD00013C E5FF01FB 00DD3C15 00000000 .....<......<..............9.... 0001E0
Virtual block number 137 (00000089), 512 (0200) bytes

3CC2FF00 FB00013C E9FF01FB 00A97F00 013C77FF 03FB00A9 7FFFFF23 21EF9F08 ...!#........w<..........<......< 000000
4C9E5C00 061A00F3 AB0A0001 3C9EFF01 FB00DD00 013C9FFF 01FB0074 CF9F0001 ....t.....<.........<.........\.L 000020
AF9E0001 3C86FF00 FB00013C A5FF01FB FFFF22E0 EF9FFFFF 22EAEFFF FF3CEFEF ..<....'.....'......<.......<.... 000040
3C26FF16 FCADFDAF 9EFCADFD AF9EF3AB D7FDFEF3 AB011AF1 FCADFDAF 9EFCADFD ...............................3< 000060
3BEAFF16 50FF73CB 7E52FFFE F1B8EF9E 510132FC ADFDAF9E FCADFDAF 9E040001 ............2.Q......R^.s.P...; 000080
3BCAFF16 50FF7BCB 7E52FFFE EF09EF9E 51053200 013C1FFF 01FB0CAC CF9F0001 .?........<..2.Q......R^.{.P...; 0000A0
50FF7BCB 7E52FFFE EEE0EF9E 51053200 013BFBFF 01FB007C CF9F13AB 1C4A0001 ..J......|.....;..2.Q......R^.{.P 0000C0
CB7E52FF FEEEB8EF 9E510532 00013BD8 FF01FB59 AF9F13AB 1E4A0001 3BA6FF16 ...;..J.....Y....;..2.Q......R^. 0000E0
FFFEEE90 EF9E5105 3200013B B5FF01FB 36AF9F13 AB204A00 013B83FF 1650FF7B {.P...;..J ....6....;..2.Q...... 000100
16FCADFD AF9E0001 3B92FF01 FB13AF9F 13AB214A 00013B60 FF1650FF 7BCB7E52 R^.{.P..`;..J!.........;........ 000120
01FB00DD FFFF5610 EF02FB13 ABDFFCA9 DFFCA909 D0FCADFD AF9E0400 013B63FF .c;.......................V...... 000140
FB10A97F 0001384C EF02FB10 A97F17DD 00013B94 FF01FBFF 7BCB7F00 013B6FFF .o;....{.....;...........L8...... 000160
7F000138 29EF02FB 08A97F28 DD00013B 71FF01FB FFFF21AC EF9F0001 3B7EFF01 ..^;......!.....q;....(.......)8... 000180
FB00A97F 00000042 8FDD0001 3B4EFF01 FBFFFF21 91EF9F00 013B5BFF 01FB08A9 .....[;.....!.....N;....B....... 0001A0
FF00FB00 013B1FFF 01FBFFFF 2172EF9F 00013B34 FF01FB00 A97F0001 3B02EF02 ...B........4;....r!.......;..... 0001C0
4EFCADFD AF9EFCAD FDAF9E04 00013AB4 FF160001 3ADEFF01 FB0EAF9F 00013B00 .;........:......:..............N 0001E0
```

```
Virtual block number 138 (0000008A), 512 (0200) bytes

EF9F5CDD 02DD5C5C 4A5C1040 5C1FAB4E 1FAB5C4A 5C08405C 20445C1C 425C13AB ..\B.\D \@.\J\..N..\@.\J\\...\.. 00000C
5C23AB4E 23AB504A 00013AF0 FF01FB00 A97F0001 374EEF04 FB00A97F FFFF212C .!........N7..........!..JF.$N.$\ 00002C
7FFFFF20 F1EF9F1F ABDD02DD 00013A78 FF01FB1E E4CF9F0B 12000000 008F5C51 Q\..............x!............ ... 00004C
5C4A5C18 405C1FAB 4E27AB50 4A00013A B5FF01FB 00A97F00 013713EF 04FB00A9 ......7..........!..JP.'N..\@.\J\ 00006C
4A00013A 89FF01FB 00A97F00 0136E7EF 04FB00A9 7FFFFF20 C5EF9F5C DD04DD5C \...\... .........6.........!..J 00008C
29112FAB 87AF5007 128CAF5C 515C5050 00013A78 FF01FBFF FF2017EF 9F2BAB50 P.+... '.....x!..PP\Q\....P.../.) 0000AC
013A47FF 01FBFFFF 1FE6EF9F 58FFFF32 51EF4C44 582BAB4E 5C000113 0023AB0A ..$....\N.+XDL.Q2..X.........G!. 0000CC
51FFFF54 6DEF02FB 13ABDFFC A9DFFCA9 15D0FCAD FDAF9E2F AB585C47 5C505000 .PP\G\X./....................mT..Q 0000EC
FB000139 DDFF01FB FFFF2040 EF9F0001 39C2FF01 FB00DD1F 12000000 008F2FAB ./............9....@ ......9... 00010C
FF201FEF 9F2312FF FF2FCFEF 4C27ABD1 5C000113 0023AB0A 53110001 39BEFF00 ...9...S..$....\..'L../...$... . 00012C
00DD1D11 00013988 FF00FB00 0139B3FF 01FB7E2F AB500001 3986FF02 FB00DDFF .......9..P./"...9......9....... 00014C
FCADFDAF 9E000139 69FF00FB 00013988 FF01FBFF FF1FFBEF 9F000139 6DFF01FB ...m9............9.....i9....... 00016C
9E510132 FCADFDAF 9EFCADFD AF9E0400 013917FF 16000139 41FF01FB 0321CF9F ..!....A9.....9.............2.Q. 00018C
9E510532 00013910 FF01FB09 9DCF9F00 0138DBFF 1650FF73 CB7E52FF FEEC42EF .B...R".s.P...8...........9..2.Q. 0001AC
000138EC FF01FB00 7CCF9F13 AB1C4A00 0138BBFF 1650FF7B CB7E52FF FEEBFAEF .....R".{.P...8..J.....!.....8.. 0001CC
C9FF01FB 59AF9F13 AB1E4A00 013897FF 1650FF7B CB7E52FF FEEBD1EF 9E510532 2.Q......R".{.P...8..J.....Y.... 0001EC

Virtual block number 139 (0000008B), 512 (0200) bytes

FB36AF9F 13AB204A 00013874 FF1650FF 7BCB7E52 FFFEEBA9 EF9E5105 3200013B 8..2.Q......R".{.P..t8..J ....6. 000000
9E13AB21 4A000138 51FF1650 FF7BCB7E 52FFFEEB 81EF9E51 05320001 38A6FF01 ...8..2.Q......R".{.P..Q8..J!... 000020
A9DFFCA9 09D0FCAD FDAF9E04 00013854 FF16FCAD FDAF9E00 013883FF 01FB13AF ......8.........T8.............. 000040
DD000138 85FF01FB FF7BCB7F 00013860 FF01FB00 DDFFFF53 01EF02FB 13ABDFFC ........S........'8....{.....8... 000060
3862FF01 FBFFFF1E D5EF9F00 01386FFF 01FB10A9 7F000135 3DEF02FB 10A97F16 .......=5.........o8...........b8 000080
01FBFFFF 1E82EF9F 0001384C FF01FB08 A97F0001 351AEF02 FB08A97F 28DD0001 ...(.......5........L8.......... 0000A0
9F000138 25FF01FB 00A97F00 0134F3EF 02FB00A9 7F000000 428FDD00 01383FFF .?8....B...........4.........%8... 0000C0
A5FF1600 0137CFFF 01FB0EAF 9F000137 F1FF00FB 00013810 FF01FBFF FF1E63EF .c.......8......7.........7..... 0000E0
4E1FAB5C 4A5C0840 5C20445C 1C425C13 AB4EFCAD FDAF9EFC ADFDAF9E 04000137 7.............N..\B.\D \@.\J\..N 000100
00A97F00 01343FEF 04FB00A9 7FFFFF1E 1DEF9F5C DD02DD5C 5C4A5C10 405C1FAB ..\@.\J\\...\.............?4..... 000120
69FF01FB 1BD5CF9F 0B120000 00008F5C 515C23AB 4E23AB50 4A000137 E1FF01FB ....7..JP.$N.$\Q\...............i 000140
37A6FF01 FB00A97F 00013404 EF04FB00 A97FFFFF 1DE2EF9F 1FABDD02 DD000137 7.........................4.........7 000160
EF04FB00 A97FFFFF 1DB6EF9F 5CDD04DD 5C5C4A5C 18405C1F AB4E27AB 504A0001 ..JP.'N..\@.\J\\...\............ 000180
A9EF02FB 13ABDFFC A9DFFCA9 15D02BAB 504A0001 377AFF01 FB00A97F 000133D8 .3........z7..JP.+.............. 0001A0
4827ABD1 58000113 0023AB0A 5C01CE03 115CD404 1287AF58 51582BAB 4EFFFF51 Q..N.+XQX.....\.....\..$.....X..'H 0001C0
00DDFFFF 1D7AEF9F 20135CD5 5C57CA57 57D25701 CE031157 D40413FF FF2D23EF .$-.....W....W.WW.W\.\. ..z..... 0001E0

Virtual block number 140 (0000008C), 512 (0200) bytes

008F5851 582BAB4E 000136CC FF00FB00 0136FFFF 01FB2BAB DD000136 C9FF02FB ....6....+....6.......6..N.+XQX.. 000000
D40412EF EF2CCBEF 4827ABD1 58000113 0023AB0A 5C01CE03 115CD404 12000000 ......\....\..$....X..'H........ 000020
FBFFFF1D 21EF9F00 01367BFF 01FB00DD 1D135CD5 5C57CA57 57D25701 CE031157 W....W.WW.W\.\........{6....!.... 000040
00013654 FF01FB00 DD1D12AA AF5C515C 2BAB4E00 013677FF 00FB0001 3696FF01 ...6......w6..N.+\Q\.........T6.. 000060
FF160001 362EFF01 FB0EAF9F 00013650 FF00FB00 01366FFF 01FBFFFF 1D02EF9F ..........o6.....P6...........6..... 000080
FFFF50AC EF02FB13 ABDFFCA9 DFFCA92D D0FCADFD AF9EFCAD FDAF9E04 00013604 .6.............-.............P.. 0000A0
```

```
ADEF9FFF FF1CB7EF FFFF2CE4 EF4C9E5C 00121300 23AB0A00 01360BFF 01FB00DD ......6....$....\.L............... 0000C0
000135D0 FF02FB00 DDFFFF1C A1EF9F00 0135F3FF 00FB0001 361AFF01 FBFFFF1C ........6......5..............5.. 0000E0
FF160001 35C6FF00 FB000135 F1FF01FB 7EFFFF2E 15EF4C50 5C000113 0023AB0A ..$....\FL.....^....5......5.... 000100
FF1650FF 73CB7E52 FFFEEAE1 EF9E5101 32FCADFD AF9EFCAD FDAF9E04 00013584 .5.............2.Q......R^.s.P.. 000120
9E651100 02F3AB01 0CF1F3AB D7F3AB01 D0000135 7DFF01FB 060ACF9F 00013548 H5.........}5.................e. 000140
7F000135 A5FF01FB F7ABDF00 0135AFFF 01FB33AB DF000135 75FF00FB FCADFDAF ........u5....3....5.........5.. 000160
FB00DDFF FF4FCFEF 02FB33AB DFF7ABDF 00013554 FF00FB00 013593FF 01FB83AB ......5.....T5.......3.....D..... 000180
F3AB0CF3 FCADFDAF 9E000135 2DFF00FB 0001354C FF01FB83 AB7F0001 352EFF01 ...5........L5.....-5............ 0001A0
16FCADFD AF9E0001 3516FF00 FB000134 F9FF01FB 56AF9FFC ADFDAF9E F3ABD79E ............V....4......5........ 0001C0
9EFCADFD AF9EFCAD FDAF9EFC ADFDAF9E FCADFDAF 9EFCADFD AF9E0400 0134C3FF ..4.............................. 0001E0
```

Virtual block number 141 (0000008D), 512 (0200) bytes

```
FDAF9EFC ADFDAF9E FCADFDAF 9EFCADFD AF9EFCAD FDAF9EFC ADFDAF9E FCADFDAF ................................ 000000
01344BFF 1650FF73 CB7E52FF FEE9E4EF 9E510132 FCADFDAF 9EFCADFD AF9EFCAD ...........2.Q......R^.s.P..K4.. 000020
D7F3AB01 D0FEE3CB EBAF50FE DFCBF1AF 50FEDBCB F7AF5037 AB000000 008F5000 .P......7P.....P.....P.......... 000040
9EFEEBCB 4CC8AF50 5C000107 00F3AB0A FCADFDAF 9E211100 02F3AB01 07F1F3AB ..........!...........\P..L..... 000060
310003F3 AB0104F1 F3ABD7F3 AB01D0FC ADFDAF9E F3ABD7E2 F3AB07F3 FCADFDAF ...............................1 000080
FF1A8FEF 9F5CDD02 DD5C5C4A 5C08405C 20445C08 425CF3AB 4EFCADFD AF9E01F5 .......N..\B.\D \@.\J\\...\..... 0000A0
5C08425C F3AB4E27 AB504A00 013453FF 01FB00A9 7F000130 B1EF04FB 00A97FFF ........0........S4..JP.'N..\B.\ 0000C0
00A97F00 01307FEF 04FB00A9 7FFFFF1A 5DEF9F5C DD02DD5C 5C4A5C14 405C2044 D \@.\J\\...\..].........0..... 0000E0
9F5CDD04 DD5C5C4A 5C1A405C 20445C08 425CF3AB 4E23AB50 4A000134 21FF01FB ...!4..JP.$N..\B.\D \@.\J\\...\. 000100
23AB0A2B AB504A00 0133EFFF 01FB00A9 7F000130 4DEF04FB 00A97FFF FF1A2BEF .+.........M0.........3..JP.+..$ 000120
44582BAB 4E5C0001 130023AB 0A013031 0313FFFF 29BAEF4C 27ABD15C 00011300 ....\..'L..)....10...$....\N.+XD 000140
4158FFFF 2C46EF4C 44582BAB 4E5C0001 130023AB 0A37AB58 4058FFFF 2C0EEF4C L.....X@X.7..$....\N.+XDL.F...XA 000160
FEDFCB58 4158FFFF 2C7AEF4C 44582BAB 4E5C0001 130023AB 0AFEDBCB FEDBCB58 X........$....\N.+XDL.z...XAX... 000180
0AFEE3CB FEE3CB58 4158FFFF 2CAEEF4C 44582BAB 4E5C0001 130023AB 0AFEDFCB .....$....\N.+XDL.....XAX....... 0001A0
130023AB 0AFEEFCB FEEFCB58 4158FFFF 2CE2EF4C 44582BAB 4E5C0001 130023AB .$....\N.+XDL.....XAX........$.. 0001C0
4E5C0001 130023AB 0AFEF3CB FEF3CB58 4158FFFF 2D16EF4C 44582BAB 4E5C0001 ..\N.+XDL..-..XAX........$....\N 0001E0
```

Virtual block number 142 (0000008E), 512 (0200) bytes

```
44582BAB 4E5C0001 130023AB 0AFEF7CB FEF7CB58 4158FFFF 2D4AEF4C 44582BAB .+XDL.J-..XAX........$....\N.+XD 000000
2D82EF4C 44582BAB 4E5C0001 130023AB 0AFEFBCB FEFBCB58 4158FFFF 2D7EEF4C L.^-..XAX........$....\N.+XDL.~. 000020
4158FFFF 2DE6EF4C 44582BAB 4E5C0001 130023AB 0AFEFFCB FEFFCB58 4158FFFF ..XAX........$....\N.+XDL..-..XA 000040
FF07CB58 4158FFFF 2E1AEF4C 44582BAB 4E5C0001 130023AB 0AFF03CB FF03CB58 X........$....\N.+XDL.....XAX... 000060
FEDBCB41 FCADFDAF 9EF3ABD7 FE0EF3AB 0104F1FC ADFDAF9E FCADFDAF 9EFF07CB ..............................A. 000080
FF4CABEF 02FBF8A9 DFF8A906 D0FCA9DF FCA90BD0 FEE7CBFE E3CB5C41 5CFEDFCB ...\A\.........................L. 0000A0
3202FF00 FB000132 2DFF01FB 7E37AB50 00013200 FF02FB00 DDFFFF18 D9EF9FFF .............2..P.7^...-2......2 0000C0
AB4EFCA9 DFFCA927 D0FCADFD AF9E5911 0002F3AB 0104F1F3 ABD7F3AB 01D00001 .................Y......'.....N. 0000E0
31AEFF02 FB00DDFF FF185FEF 9FFFFF4C 59EF02FB F8A9DFF8 A95C4A5C 1A405CF3 .\@.\J\..........YL....-.......1 000100
AF9E0001 31A6FF00 FB000131 D1FF01FB 7EFED7CB 4C505C00 010400F3 AB0A0001 .........\FL...^....1......1.... 000120
59310003 F3AB011A F1F3ABD7 F3AB01D0 FCADFDAF 9EF3ABD7 AAF3AB04 F3FCADFD ..............................1Y 000140
D40413FF FEE783EF 0020FFFF 2ECAEF4C 182D5C00 181A00F3 AB0AFCAD FDAF9E01 ..............\-.L.............. 000160
031157D4 04130000 00008FFF FF3133EF 4C515C00 011A00F3 AB0A5801 CL031158 X....X........\QL.31..........W.. 000180
DD04DD5C 5C4A5C14 405G1C44 5C08425C F3AB4E00 F9310313 58D55857 C85701CE ..W.WX.X..1..N..\B.\D.\@.\J\\.... 0001A0
```

```
ABOA5C50 50000131 4DFF01FB 00A97F00 012DABEF 04FB00A9 7FFFFF17 E1EF9F5C \.............-.........K1..PP\.. 0001C0
ABFFFF33 1BEF4C45 5C00011A 00F3AB0A 3BAB5CFF FF30DBEF 48475800 011A00F3 .....XGH..0..\.;........\EL..3... 0001E0

Virtual block number 143 (0000008F), 512 (0200) bytes

F3CB5841 583BABFF FF336DEF 4C455C00 011A00F3 AB0AFEEF CBFEEFCB 5841583B ;XAX.............\EL.m3...;XAX.. 000000
AB0AFEE7 CBFEF7CB 5841583B ABFFFF33 BFEF4C45 5C00011A 00F3AB0A FEF3CBFE ...........\EL..3...;XAX........ 000020
5C00011A 00F3AB0A FEFBCBFE FBCB5841 583BABFF FF3411EF 4C455C00 011A00F3 .....\EL..4...;XAX.............\ 000040
FF34B5EF 4C455C00 011A00F3 AB0AFEFF CBFEFFCB 5841583B ABFFFF34 63EF4C45 EL.c4...;XAX.............\EL..4. 000060
5841583B ABFFFF35 07EF4C45 5C00011A 00F3AB0A FF03CBFF 03CB5841 583BABFF ..;XAX.............\EL..5...;XAX 000080
4AFCADFD AF9EF3AB D7FEAAF3 AB011AF1 FCADFDAF 9EFCADFD AF9EFF07 CBFF07CB ...............................J 0000A0
DF17ABDF FCADFDAF 9E6A1100 02F3AB01 07F1F3AB D7F3AB01 D017AB35 4A13AB1C ...J5...................J....... 0000C0
5C000107 00F3AB0A 00012FD8 FF02FB00 DDFFFF16 B1EF9FFF FF4A83EF 02FB13AB ......J...................../.........\ 0000E0
4E13AB5C 4A5C0840 5C13AB4E 00012FD0 FF00FB00 012FFBFF 01FB7EFE EBCB4C50 PL...~..../....../..N..\@.\J\..N 000100
ABD799F3 AB07F3FC ADFDAF9E 17AB0000 00468FD0 13AB1C4A 0C15215C 515C13AB ..\Q\!..J.....F................. 000120
EFAB06D0 FCADFDAF 9EFCADFD AF9E0400 012F57FF 16FCADFD AF9EFCAD FDAF9EF3 .............W/................. 000140
ADFDAF9E 00012F50 FF01FB25 8BCF9FFC ADFDAF9E 1D110002 EFAB0109 F1EFABD7 ...................%...P/....... 000160
9EFCADFD AF9E0400 012F0FFF 16FCADFD AF9EFCAD FDAF9EEF ABD7E6EF AB09F3FC ......................./......... 000180
FFFF15E8 EF9F3FAB DD02DD3F AB5C4A5C 08405C1C 445C0842 5CF3AB4E FCADFDAF ....N..\B.\D.\@.\J\.?....?...... 0001A0
3FAB4EFC ADFDAF9E 43AB50D0 00012F5B FF01FB00 A97F0001 2DB2EF04 FB00A97F .......+.........X/...P.C.....N.? 0001C0
01FB00A9 7F00012B 81EF04FB 00A97FFF FF15B7EF 9F5CDD04 DD5C5C4A 5C10405C \@.\J\\...\..............+....... 0001E0

Virtual block number 144 (00000090), 512 (0200) bytes

12FFFF2B B5EF4C43 ABD15C00 011A00F3 AB0AFCAD FDAF9E47 AB505000 012F23FF .#/..PP.G............\..CL..+... 000000
1100012E 4DFF1650 8BAB7E52 FFFEE14B EF9E5104 32161800 0043C88F 47AB5152 RQ.G..C....2.Q..K...R~..P..M.... 000020
012E6FFF 02FB00DD 8BAB7F00 012E37FF 16508BAB 7E52FFFE E14CEF9E 51043214 .2.Q..L...R~..P..7............o.. 000040
EF4C43AB D15C0001 1A00F3AB 0A00012E 71FF00FB 00012EA0 FF01FB7E 47AB5000 .P.G~..........o...........\..CL. 000060
FF16508B AB7E52FF FEE0E2EF 9E510432 16120000 00008F47 AB514E13 FFFF2B50 P+...NQ.G.......2.Q.......R~..P.. 000080
11FF01FB 00DD0001 2DD2FF16 508BAB7E 52FFFEE0 E3EF9E51 04321411 00012DE8 .-....2.Q......R~..P...-........ 0000A0
45EF9F00 012DF7FF 01FB00DD 00012E10 FF00FB00 012E37FF 01FB8BAB 7F00012E .........7.....................-.....E 0000C0
FDAF9EFC ADFDAF9E 0400012D B1FF1600 012DF3FF 00FB0001 2E1AFF01 FBFFFF14 .............-.....-............. 0000E0
15255C51 5CFBAB4E FBAB084A 0418085C 515CFBAB 4EFCADFD AF9EFBAB 084AFCAD ..J.........N..\Q\...J...N..\Q\%. 000100
EF4CD05C 00012E00 FBAB0A33 ABFFFF3E 81EF4CD0 5C00012E 00FBAB0A 05893103 .1.........\.L..>...3.......\.L. 000120
6F5C0001 0E00FBAB 0A4BABFF FF3FD7EF 4CD05C00 012E00FB AB0AF7AB FFFF3F2C ,?..........\.L..?...K.......\. 000140
FDAF9E00 012D2FFF 01FB3ADD 02F40169 001500B8 00280015 0501FFFF 40BEEF4C L..@......(......i.....!..../-...... 000160
00012B2C FF01FB16 E3CF9FFC ADFDAF9E 03CC3100 012D3FFF 01FB16F6 CF9FFCAD ........?-..1.................-.. 000180
0120FF47 DBFF43CB 2B5C01CE 03115CD4 0413FFFE E26BEF01 20FF47DB FF43CB2D -.C..G. ..k.......\....\-.C..G. . 0001A0
20FFFF3C 71EF1E2D 04D53103 135CD55C 58C85801 CE031158 D40413FF FEDFB5EF ........X....X.X\.\..1..-..a<.. 0001C0
93AB2D00 0129A7EF 03FB00A9 7F1EDD20 DD5C01CE 03115CD4 0413FFFE E04BEF11 ..K.......\.....\. ..........)..-.. 0001E0

Virtual block number 145 (00000091), 512 (0200) bytes

033C31FF 73310313 5CD55C58 CA5858D2 5801CE03 1158D404 1304B900 A92097BB .. .......X....X.XX.X\.\..1s.1<. 000000
5CD40413 FFFEDF88 EF012097 BB93AB2D 00012C9C FF01FB16 53CF9FFC ADFDAF9E .......S.........-.... .........\ 000020
5C58CA58 58D25801 CE031158 D40412FF FEDF73EF FFFF3C41 EF01295C 01CE0311 ....\)..A<...s.......X....X.XX.X\ 000040
```

```
2C0EFF16 5093AB7E 5138A97E FFFF4A8C EF02FB38 A97F93AB 7F02F531 03135CD5 .\..1.......8....J..".8Q"..P.... 000060
D6EF0120 97BB93AB 2D5C01CE 03115CD4 0413FFFE E1C4EF01 2097BB93 AB2D0001 ..-.... .........\....\-.... ... 000080
1158D404 13FFFEDE BDEF0120 97BB93AB 2D5C58C8 5801CE03 1158D404 13FFFEDE ......X....X.X\-.... .........X. 0000A0
DE96EFFF FF3BB0EF 0129FCAD FDAF9EFF 4F31028E 3103135C D55C58C8 5801CE03 ...X.X\.\..1..1O......)......... 0000C0
80EF9E51 05322D11 00012B94 FF16508B AB7E52FF FEDE86EF 9E510532 1612FFFE ....2.Q......R"..P...+....-2.Q... 0000E0
5CF7AB4E 0B12FFFE DE5FEFFF FF315AEF 01290001 2B7EFF16 508BAB7E 52FFFEDE ...R"..P.."+..)..Z1.........R..\ 000100
2EEF0220 97BB93AB 2D00012B 95FF01FB 17C6CF9F FCADFDAF 9EF7AB5C 4A5C2140 @!\J\...............+..-.... ... 000120
EF01295C 01CE0311 5CD40413 FFFEDE25 EFFFFF31 20EF0129 02C83103 12FFFEDE .....1..).. 1...%......\....\).. 000140
FB93AB7F 38135CD5 5C58CA58 58D25801 CE031158 D40412FF FEDE0FEF FFFF3B29 );..........X....X.XX.X\.\.8.... 000160
EF03FB38 A97F7E58 508BAB7F 583CF33F E88F5C45 5C00405C 50500001 2BA2FF01 ...+..PP\@.\E\..?.<X...PX"..8... 000180
50500001 2B6AFF01 FB93AB7F 2B110001 2ADEFF16 5093AB7E 5138A97E 00012714 .'..".8Q"..P...*...+......J+..PP 0001A0
D000012A B1FF1650 93AB7E51 38A97E00 0126E7EF 03FB38A9 7F7E5C50 8BAB7F5C \...P\"..8....&..".8Q"..P....*.... 0001C0
93AB7F00 012AD7FF 01FB00DD FFFF4578 EF02FBF8 A9DFF8A9 0CD0FCA9 DFFCA913 ................xE.........*..... 0001E0
```

Virtual block number 146 (00000092), 512 (0200) bytes

```
FF0FAFEF 9F00012A C9FF00FB 00012AF0 FF01FBFF FF0FBBEF 9F00012A FDFF01FB ....*............*......*....... 000000
16505C18 2B410D8F 455C5050 00012AF4 FF01FB93 AB7F0001 2AA6FF02 FB00DDFF .......*.........*..PP\E..A+.\P. 000020
ADFDAF9E 01003100 012ABBFF 00FB0001 2AB6FF01 FB7E5C50 5C505000 01298CEF ..)..PP\P\"....*.......*..1...... 000040
01FB1678 CF9FF7AB 5C4A5C21 405CF7AB 4E0B12FF FEDD03EF FFFF3006 EF0129FC .)...0.........N..\@!\J\.....x... 000060
DCCEEFFF EF2FD1EF 0129017A 310312FF FEDCDCEF 032097BB 93AB2D00 012A47FF .G%..-.... .........1z.)..../..... 000080
10EEEF9F 58005C41 5C8F5C41 228F445C 50500001 2A7AFF01 FB93AB7F 3912FFFE ...9.......z*..PP\D."A\.\A\.X.... 0000A0
A915D000 0129B3FF 165093AB 7E5138A9 7E000125 E9EF03FB 38A97F7E 5850FFFF ..PX"..8....%..".8Q"..P...)..... 0000C0
01FB93AB 7F000129 D9FF01FB 00DDFFFF 447AEF02 FBF8A9DF F8A90DD0 FCA9DFFC ...............zD........)....... 0000E0
DDFFFF0E D1EF9F00 0129CBFF 00FB0001 29F2FF01 FBFFFF0E DDFF9F00 0129FFFF ..)............)......)......... 000100
50005C41 5C9300 3F C98F445C 50500001 29F6FF01 FB93AB7F 000129A8 FF02FB00 .....).........)..PP\D..?..\A\.P 000120
ADFDAF9E 00110001 298AFF00 FB000129 B5FF01FB 7E5C505C 50500001 288BEF16 ...(..PP\P\"....).......)........ 000140
0A009131 031204B9 00A92097 BB93AB2D 00012634 EF03FB00 A97F4BAB DD20DDFC .. ..K.....42..-.... .......1... 000160
10A97FFF FF101BEF 9F5CDD5C 584A5808 4258FFFF 3C5AEF4C 4E5C0001 0E00FBAB ........\NL.Z<..XB.XJX\.\........' 000180
C15C0001 0E00FBAB 0A000128 D1FF03FB 08A97F10 A97F93AB 7F000125 C1EF03FB ....%..................(..........\. 0001A0
57435757 4E574BAB FFFF3C10 EF48C158 00010E00 FBAB0A5C 4BABFFFF 3C22EF4C L."<...K\........X.H..<...KWNWWCW 0001C0
00A97F00 01257FEF 04FB00A9 7FFFFF0F C5EF9F5C DD58DD58 584A5800 0044B28F ..D..XJXX.X.\..............%..... 0001E0
```

Virtual block number 147 (00000093), 512 (0200) bytes

```
4DEF0120 FF47DBFF 43CB2DFC ADFDAF9E 00012878 FF03FBFF FF0FAFEF 9F08A97F ............x(.......-.C..G. ..K 000000
2D5C01CE 03115CD4 0413FFFE DE12EF01 20FF47DB FF43CB2D FAD53103 12FFFEDB .....1..-.C..G. .........\....\-- 000020
FBAB4E0B 135CD55C 58C85801 CE031158 D40413FF FEDB1CEF 0120FF47 DBFF43CB .C..C. .........X....X.X\.\..N.. 000040
2D5C01CE 03115CD4 0413FFFE DDA3EF01 20FF47DB FF43CB2D FBAB5C4A 5C10425C \B.\J\..-.C..G. .........\....\- 000060
4E0E1102 135CD55C 58C85801 CE031158 D40413FF FEDAEDEF 0120FF47 DBFF43CB .C..G. .........X....X.X\.\.....N 000080
AF9EFCAD FDAF9E04 000127F0 FF16FCAD FDAF9EFA 5931FBAB 5C4A5C08 405CFBAB ..\@.\J\..1Y........'.......... 0000A0
00012E00 FBAB0AFB AB274A04 18275C51 5CFBAB4E FCADFDAF 9EFBAB27 4AFCADFD ...J'.......N..\Q\'..J'......... 0000C0
2E00FBAB 0AF7ABFF FF3977EF 4CD05C00 012E00FB AB0A33AB FFFF38CC EF4CD05C \.L..8...3.......\.L.w9......... 0000E0
000127AC FF01FB13 DDCF9F2A 15275C51 5CFBAB4E 4BABFFFF 3A22EF4C D05C0001 ..\.L.":...KN..\Q\'.*.........'.. 000100
4A2E114F AB000043 4C8F4A08 12000042 888F5C51 5CFBAB4E 4FAB0000 433C8F4A J.<C...ON..\Q\..B....J.LC...O..J 000120
53AB4E00 01276FFF 01FB0F2C CF9F0001 277AFF01 FB1131CF 9F4FAB00 00432C8F ..C...O..1....z'..........o'..N.S 000140
```

```
012423EF 03FB00A9 7F4BABDD 20DDFCAD FDAF9EFF 51310313 00000000 8F5C515C \Q\........1Q........ ..K......$$. 000180
FF0B27EF 9F5CDD5C 5C4A5C08 425C4FAB 4E6D1102 1204B900 A92097BB 93AB2D00 .-.... ........mN.O\B.\J\\.\..'.. 0001B0
4BAB4FAB C1000126 CDFF03FB 08A97F10 A97F93AB 7F000123 BDEF03FB 10A97FFF ........$...............2....O.K 0001A0
7FFFFF0A E9EF9F5C DD58DD58 574A57B0 0044A78F 58435858 4E584BAB 4FABC15C \..O.KXNXXCX..D..WJWX.X.\....... 0001C0
ADFDAF9E 0001268C FF03FBFF FF0AD3EF 9F08A97F 00A97F00 012393EF 04FB00A9 ......$..................&...... 0001E0

Virtual block number 148 (00000094), 512 (0200) bytes

DBF7EF01 20FF47DB FF43CB2D FEAA3103 12FFFED9 61EF0120 FF47DBFF 43CB2DFC .-.C..G. ..a.....1..-.C..G. .... 000000
CE031158 D40413FF FED941EF 0120FF47 DBFF43CB 2D5C01CE 03115CD4 0413FFFE .....\....\-.C..G. ..A......X.... 000020
0C5EEF9F 5C01CE03 115CD404 13285851 58FBAB4E 0AD93103 135CD55C 58C85801 .X.X\.\..1..N..XQX(...\....\..^. 000040
CA5858D2 5801CE03 1158D404 13000000 008F3851 58505000 0126BFFF 01FBFFFF ......&..PPXQX........X....X.XX. 000060
5C01CE03 115CD404 13FFFEDB B1EF0120 FF47DBFF 43CB2DFE 3E310313 5CD55C58 X\.\..1>.-.C..G. .........\....\ 000080
AB4E0E13 5CD55C58 C85801CE 031158D4 0413FFFE D8BBEF01 20FF47DB FF43CB2D -.C..G. .........X....X.X\.\..N. 0000A0
0318295C 515CFBAB 4EFBAB5C 4A5C0840 5CFBAB4E FDFB31FB AB5C4A5C 08425CFB .\B.\J\..1..N..\@.\J\..N..\Q\).. 0000C0
000125CC EF01FB1C 07CF9FEF AB000042 B8BF4AFC ADFDAF9E FCADFDAF 9EFDE431 1............J..B............%.. 0000E0
EF9F0001 25B6FF01 FB00DDFF FF4057EF 02FBF8A9 DFFBA917 D0FCA9DF FCA903D0 ................W@.........%.... 000100
FFFED8A7 EF0120FF 77DBFF73 CB2D0001 25B2FF00 FB000125 D1FF01FB FFFF0C9C ........%......%..-.s..w. ...... 000120
ADFDAF9E F3AB084A 04453103 12FFFEDA C6EF0120 FF77DBFF 73CB2D01 80310312 ..1..-.s..w. ........1E.J....... 000140
49FF01FB 0E8DCF9F 4BAB1A4A F7AB0000 42A88F4A 33AB5C4A 5C1A405C F3AB4EFC .N..\@.\J\.3J..B....J..K.......I 000160
DAACEF01 20FF77DB FF73CB2D 035E3103 12FFFED8 35EF0120 87BB83AB 2D000125 %..-.......5.....1^.-.s..w. .... 000180
445C0842 5CF3AB4E 022B3103 12FFFED7 70EF0520 97BB93AB 2DFF3C31 0313FFFE ....1<.-.... ..p.....1+.N..\B.\D 0001A0
FB00A97F 000121A0 EF04FB00 A97FFFFF 0B7EEF9F 5CDD02DD 5C5C4A5C 14405C20 \@.\J\\...\..".........!...... 0001C0
AB0A5C01 CE03115C D4041300 0042988F 58515823 AB4E23AB 504A0001 2542FF01 ..B%..JP.$N.$XQX..B.....\....\.. 0001E0

Virtual block number 149 (00000095), 512 (0200) bytes

502E135C D55C57C8 5701CE03 1157D404 14FFFF1D 15EF4857 AB515800 01130023 $....XQ.WH........W....W.W\.\..P 000000
EB00A97E 0001245C FE02EB00 A97E07DD 000124A4 FF01FB00 DD57AB00 0000008F ......W......$..........\$...... 000020
FFFF0B00 EF9FFFFF 3F12EF02 FB33ABDF F7ABDF00 012497FF 00FB0001 24B6FF01 ...$......$.......3....?........ 000040
A1AF57AB 51000124 69FF00FB 00012494 FF01FB7E 57AB5000 012467FF 02FB00DD .....$$..P.W"....$......i$..Q.W.. 000060
EF484658 00011300 23AB0A5C 50500001 2496FF01 FBFFFF0A 35EF9FFE D7310312 ..1....5........$..PP\..$....XFH. 000080
240AFF01 FB0AA2CF 9F57AB50 50000123 1EEF1650 005C415C 57AB445C FFFF1C80 ....\D.W\A\.P...$..PP.W........$ 0000A0
2A4A33AB 5C4A5C1A 405CF3AB 4EFCADFD AF9EF3AB 084AFCAD FDAF9E01 1E310001 ..1.......J........N..\@.\J\.3J* 0000C0
310312FF FED6C7EF 012087BB 83AB2D00 0123DBFF 01FB0D1F CF9F4BAB 1A4AF7AB ..J..K........$..-.... ........1 0000E0
FED5FEEF 042097BB 93AB2DFD CE310313 FFFED6D7 EF0120FF 77DBFF73 CB2D01F0 ..-.s..w. ........1..-.... ..... 000100
FFFF0A10 EF9F5CDD 02DD5C5C 4A5C1440 5C20445C 08425CF3 AB4E008D 310312FF ...1..N..\B.\D \@.\J\\....\...... 000120
98BF5851 5823AB4E 23AB504A 000123D4 FF01FB00 A97F0001 2032EF04 FB00A97F ......2 ..........$..JP.$N.$XQX.. 000140
5857AB51 58505000 0123AFFF 01FBFFFF 094EEF9F 5C01CE03 115CD404 12000042 B....\....\..N.......$..PPXQ.WX 000160
43110001 232EFF01 FB09C6CF 9F0D135C D55C58CA 5858D258 01CE0311 58D40415 ...X....X.XX.X\.\...........$...C 000180
41FF01FB FFFF0A0C EF9F0001 231EFF01 FB00DDFF FF3DBFEF 02FB33AB DFF7ABDF .....3......=.........$.........A 0001A0
00012304 FF00FB00 012323FF 01FB00A9 7F000122 C9FF02FB 00A97F07 DD000123 $..........'..........$$......$.. 0001C0
DBFF43CB 2DFAC331 0312FFFE D57AEF01 20FF47DB FF43CB2D FCADFDAF 9EFEEB31 1........-.C..G. ..z.....1..-.C.. 0001E0

Virtual block number 150 (00000096), 512 (0200) bytes

FFFED55A EF0120FF 47DBFF43 CB2D5C01 CE03115C D40413FF FED810EF 0120FF47 G. .........\....\-.C..G. ..Z... 000000
```

```
20FF47DB FF43CB2D FCADFDAF 9E06F231 03135CD5 5C58C858 01CE0311 58D40413 ...X....X.X\.\..1........-.C..G.  000020
D40413FF FED7EBEF 0120FF47 DBFF43CB 2D5C01CE 03115CD4 0413FFFE D523EF01 ..$.......\....\-.C..G. .......... 000040
4A5C0840 5CF3AB4E F3AB5C4A 5C10425C F3AB4E0B 135CD55C 58C85801 CE031158 X....X.X\.\..N..\B.\J\..N..\@.\J 000060
57F3AB4E 5C01CE03 115CD404 14000000 008F5851 58F3AB4E FCADFDAF 9EF3AB5C \.......N..XQX........\....\N..W 000080
EF0120FF 77DBFF73 CB2D1613 5CD55C58 CA5858D2 5801CE03 1158D404 191A5751 QW....X....X.XX.X\.\..-.s..w. .. 0000A0
4E000121 EDFF01FB 1828CF9F EFAB0000 42B88F4A FE0231FC 93310312 FFFED78A ......1..1..J..B......(.....!..N 0000C0
5CF3AB4E 5BABF3AB D0FCADFD AF9E0314 31F9D831 FBAB284A 0718085C 515CF3AB ..\Q\...J(..1..1...........[N..\ 0000E0
00011E5C EF04FB00 A97FFFFF 083AEF9F 5CDD02DD 5C5C4A5C 14405C20 445C0842 B.\D \@.\J\\...\..:..........\... 000100
FFFF1918 EF4C9E51 05325C00 05130023 AB0A23AB 504A0001 21FEFF01 FB00A97F .......!..JP.$..$....\2.Q.L..... 000120
5CF3AB4E F3AB5BAB D0000121 75FF01FB 06A0CF9F 00012140 FF1650FF 7BCB7E52 R~.{.P..@!.........u!....[..R..\ 000140
214AFF01 FBE67ACF 9F0D12FF FED6D9EF 0120FF77 DBFF73CB 2D13AB5C 4A5C1A40 @.\J\..-.s..w. ..........z....J! 000160
FDAF9EFE E6310001 2132FF01 FBEB12CF 9F000121 3DFF01FB E97CCF9F 0B110001 ......!....=!.........2!..1..... 000180
00FBAB0A 33ABFFFF 31FAEF4C D05C0001 2E00FBAB 0AFCADFD AF9EFBAB 294AFCAD ..J).............\.L..1...3.... 0001A0
CF9F4BAB FFFF3350 EF4CD05C 00012E00 FBAB0AF7 ABFFFF32 A5EF4CD0 5C00012E ...\.L..2............\.L.P3...K.. 0001C0
ABDD20DD FAE73103 13FFFED6 22EF0120 FF77DBFF 73CB2D00 0120E3FF 01FB0A27 '..... ..-.s..w. ..".....1... .. 0001E0

Virtual block number 151 (00000097), 512 (0200) bytes

8F425CFB AB4E0133 31031204 B900A920 97BB93AB 2D00011D 99EF03FB 00A97F4B K..........-.... ......13.N..\B. 000000
EF9E03DD 02DDECAD FDAE9EF3 3E310086 00480009 02015CCF 5C5C4A5C 00004288 .B..\J\\.\....H...17............ 000020
0023AB0A 23AB504A 000120D0 FF01FB00 A97F0001 1D2EEF04 FB00A97F FFFF070C ...................... ..JP.$..$. 000040
CDEF9F0B DD02DDFC ADFDAF9E 007A31F3 AB084A57 ABFFFF19 09EF4C46 5C000113 ...\FL......WJ...1z.............. 000060
130023AB 0A23AB50 4A000120 91FF01FB 00A97F00 011CEFEF 04FB00A9 7FFFFF06 ..................... ..JP.$..$.. 000080
FF068FEF 9F13DD02 DDFCADFD AF9E3C11 F3AB104A 57ABFFFF 196AEF4C 465C0001 ..\FL.J....WJ....<............... 0000A0
00011300 23AB0A23 AB504A00 012053FF 01FB00A9 7F00011C B1EF04FB 00A97FFF .................S ..JP.$..$.... 0000C0
00012028 FF01FBFF EF05C7EF 9FFCADFD AF9EF3AB 144A57AB FFFF197C EF4C465C \FL.!....WJ................( .. 0000E0
FB00A97F 07DD0001 1FBAFF01 FB00DD57 AB000000 008F502E 155C57AB 515C5050 PP\Q.W\..P......W.............. 000100
1F8AFF01 FB0622CF 9F00011F ADFF00FB 00011FCC FF01FB00 A97F0001 1F72FF02 ..r............................ 000120
FFFED210 EF0120FF 47DBFF43 CB2DFCAD FDAF9E00 011F7FFF 01FBEADC CF9F0001 .................-.C..G. ...... 000140
FF43CB2D 5C01CE03 115CD404 13FFFED4 A6EF0120 FF47DBFF 43CB2DF7 59310312 ..1Y.-.C..G. .........\....\-.C. 000160
43CB2D03 88310313 5CD55C58 C85801CE 031158D4 0413FFFE D1F0EF01 20FF47DB .C. ..........X....X.X\.\..1..-.C 000180
D1A7EF01 20FF47DB FF43CB2D 5C01CE03 115CD404 13FFFED4 9DEF0120 FF47DBFF ..G. ..........\....\-.C..G. .... 0001A0
FBAB4EFB AB5C4A5C 10425CFB AB4E0B13 5CD55C58 C85801CE 031158D4 0413FFFE .....X....X.X\.\..N..\B.\J\..N.. 0001C0
18000042 A88F5C51 5CFBAB4E F6D33103 18295C51 5CFBAB4E FBAB5C4A 5C08405C \@.\J\..N..\Q\)..1..N..\Q\..B... 0001E0

Virtual block number 152 (00000098), 512 (0200) bytes

A9FF01FB 14E4CF9F EFAB0000 42B88F4A FBABEDAF 4AFCADFD AF9E0011 FDA23103 .1.........J....J..B............. 000000
FCADFDAF 9E02C831 00011E54 FF1650FF 43CB7E52 FFFED198 EF9E5101 3200011E ...2.Q......R~.C.P..T...1........ 000020
FFFF3010 EF4CD05C 00012E00 FBAB0A33 ABFFFF2F 65EF4CD0 5C00012E 00FBAB0A .......\.L.e/...3.......\.L..0.. 000040
AB2D0001 1E4EFF01 FB0A7FCF 9F4BABFF FF30BBEF 4CD05C00 012E00FB AB0AF7AB .........\.L..0...K.......N...-. 000060
AB0AF3AB FE0BCB4C D05C0001 3200FBAB 0A014431 0312FFFE D095EF04 2097BB93 ... .........1D.....2..\.L....... 000080
A97E0001 1A14EF04 FB38A97F 7EFFFF1B 21EF4C6E FFFF0524 EF9F5C00 011A00F3 .....\..$...nL.!...~..8.......~. 0000A0
5CF3AB4E 00011DAC FF03FB9B AB7F00A9 7F93AB7F 00011DC4 FF165000 A97E5138 8Q~..P......................N..\ 0000C0
7FFFFF04 A9EF9F5C DD5C5C4A 5C08425C 5FAB4E5F AB5C4A5C 08405C1C 445C0842 B.\D.\@.\J\._N._\B.\J\\.\....... 0000E0
5C1C405C 5FAB4E00 011D6FFF 03FB0BA9 7F10A97F 9BAB7F00 011A5FEF 03FB10A9 ....._...................o...N._\@.\ 000100
```

```
FB00A97F FFFF046C EF9F5CDD 58DD5858 4A580000 442E8F57 43575FAB 4E5C5C4A J\\N._WCW..D..XJXX.X.\..1....... 000120
FB33ABDF F7ABDF00 011D2FFF 03FBFFFF 0456EF9F 08A97F00 A97F0001 1A36EF04 ..6...........V....../.........3. 000140
FF16508B AB7E52FF FED006EF 9E510432 16180000 43C88F57 AB51FFFF 3806EF02 ...8..Q.W..C....2.Q......R^..P.. 000160
FB00DD8B AB7F0001 1CF2FF16 508BAB7E 52FFFED0 07EF9E51 04321411 00011D08 ......2.Q......R^..P............ 000180
20FF77DB FF73CB2D 00011D2C FF00FB00 011D57FF 01FB7E57 AB500001 1D2AFF02 ..*...P.W^...W..........-.s..w.  0001A0
20FF47DB FF43CB2D FCADFDAF 9E00011C F9FF01FB E856CF9F 0B12FFFE D253EF01 ..S.......V.............-.C..G.  0001C0
CE03115C D40413FF FED220EF 0120FF47 DBFF43CB 2DF4D331 0312FFFE CF8AEF01 ........1..-.C..G. .. ......\... 0001E0
```

Virtual block number 153 (00000099), 512 (0200) bytes

```
03135CD5 5C58C858 01CE0311 58D40413 FFFECF6A EF0120FF 47DBFF43 CB2D5C01 .\-.C..C. ..J......X....X.X\.\.. 000000
CB2DFBAB 5C4A5C10 425CFBAB 4E0B12FF FED217EF 0120FF47 DBFF43CB 2D010231 1..-.C..G. ........N..\B.\J\..-.. 000020
0312FFFE CEB9EF01 20FF47DB FF43CB2D 41110212 FFFECF1D EF0120FF 47DBFF43 C..C. .........A-.C..G. ........ 000040
AB4EF66A 31031800 0042A88F 5C515CFB AB4EFBAB 5C4A5C08 405CFBAB 4E006E31 1n.N..\@.\J\..N..\Q\..B....1J.N. 000060
0312D7AF 5C515CFB AB4EFCAD FDAF9E00 72310097 31031500 0043388F 5C515CFB .\Q\.8C....1..1r......N..\Q\.... 000080
0F18B7AF 5C515CFB AB4E63AB 0000C080 8F4AFBAB 5C4A5C25 425CFBAB 4EF64531 1E.N..\B%\J\..J......cN..\Q\.... 0000A0
0212A7AF 5C515CFB AB4EFCAD FDAF9E32 11FBAB5C 4A5C0000 42C88F40 5CFBAB4E N..\@..B..\J\...2.....N..\Q\.... 0000C0
4A5CC8AF 425CFBAB 4E0C1590 AF5C515C FBAB4EFB AB5C4A5C 25405CFB AB4E4311 .CN..\@%\J\..N..\Q\....N..\B..\J 0000E0
31031300 0000008F 5B5158FE 0BCB4C4E 5C000132 00FBAB0A FCADFDAF 9EFBAB5C \...........2..\NL...XQX........1 000100
23ABDBAF 4AFCADFD AF9EFCAD FDAF9E04 00011B78 FF16FCAD FDAF9EFE AE31FD19 ..1.........x..............J....# 000120
00011B6C FF01FB00 97CF9FFC ADFDAF9E 36110002 0BAB0113 F10BABD7 0BAB01D0 ...............6..............1.... 000140
13F3FCAD FDAF9E6B 110212FF FECE04EF FFFF1850 EF4C0129 5C000113 0023AB0A ..#....\).L.P...........k....... 000160
9F00011A E9FF03FB 00A97FFF FF0243EF 9FFF7BCB 7FFCADFD AF9E0BAB D7CD0BAB .............{...C.............. 000180
FF13CB7F 00011B18 FF01FB00 DD00011A D5FF03FB FF13CB7F 00A97FFF FF023BEF .#.............................. 0001A0
FF01FB10 03CF9F00 011AF3FF 01FB11B1 CF9F0001 1B16FF00 FB00011B 35FF01FB ...5............................ 0001C0
A97FFF7B CB7FFCAD FDAF9EFC ADFDAF9E 0400011A B9FF16FC ADFDAF9E 00011AE8 ............................{... 0001E0
```

Virtual block number 154 (0000009A), 512 (0200) bytes

```
FBFF7BCB 7F00A97F 03DD0001 1A7AFF16 5000A97E 5138A97E FFFF38F8 EF02FB38 8....8..^.8Q^..P..z...........{.. 000000
405C23AB 4EFCADFD AF9E6411 0002F3AB 0113F1F3 ABD7F3AB 01D00001 1742EF03 ..B....................d.....N.#\@ 000020
DD5C0005 130023AB 0A23AB08 4A041500 0042988F 5C515C23 AB4E23AB 5C4A5C0B .\J\.#N.#\Q\..B....J..#..#....\. 000040
00A92D00 0116EBEF 03FB00A9 7FFFFF01 75EF9FFF FF017FEF FFFF10F0 EF4C9E03 ..L.............u.............-.. 000060
7FFCADFD AF9EF3AB D79FF3AB 13F3FCAD FDAF9E6D 110212FF 7FDBFF7B CB2004B9 .. .{.......m.......................  000080
FF13CB7F 00A97FFF FF0137EF 9F000119 D5FF03FB 00A97FFF FF012FEF 9FFF7BCB .{.../..............7........... 0000A0
1A02FF00 FB00011A 21FF01FB FF13CB7F 00011A04 FF01FB00 DD000119 C1FF03FB ........................!........ 0000C0
4AFCADFD AF9E5711 000119D4 FF01FB0E EFCF9F00 0119DFFF 01FB109D CF9F0001 ........................W......J 0000E0
0320FF7F DBFF7BCB 2DF3AB0B 4A0412FF FECBC9EF 0320FF7F DBFF7BCB 2DF3AB18 ...-.{.... ........J...-.{.... . 000100
50F3AB14 4A0412FF FECB9BEF 0320FF7F DBFF7BCB 2DF3AB10 4A0412FF FECBB2EF .......J...-.{.... ........J...P 000120
FDAF9E04 0001194C FF16FCAD FDAF9E00 01197BFF 01FB13AF 9F57AB00 0000008F ......W.......{...........L....... 000140
38A97F7E FFFF0F8C EF4C6EFF FF005BEF 9F5C0001 130023AB 0AFCADFD AF9EFCAD .........#....\...nL.....^..8 000160
7F7E23AB 6EFFFF00 35EF9F00 0118FBFF 165018A9 7E5138A9 7E000115 4BEF04FB ...K...^.8Q^..P.........5...n.#^. 000180
08A97F18 A97F10A9 7F000118 D9FF1650 10A97E51 40A97E00 011529FF 04FB40A9 .@...)...^.@Q^..P................ 0001A0
7E5148A9 7E000114 DDEF03FB 48A97F7E 57AB50FF FEFFABEF 9F000118 C1FF03FB ..............P.W^..H........^.HQ^ 0001C0
5C08425C F3AB4E00 01188FFF 03FB9BAB 7F08A97F 00A97F00 0118A7FF 165000A9 ..P.......................N..\B.\ 0001E0
```

```
Virtual block number 155 (0000009B), 512 (0200) bytes

FB10A97F FFFEFF34 EF9F5CDD 5C5C4A5C 08425C5F AB4E5FAB 5C4A5C08 405C2044 D \@.\J\._N._\B.\J\\.\..4....... 000000
5C5C4A5C 20405C5E AB4E0001 1852FF03 FB08A97F 10A97F9B AB7F0001 1542EF03 ..B...............R...N._\@ \J\\ 000020
19EF04FB 00A97FFF FEFEF7EF 9F5CDD58 DD5858AA 58000042 C88F5743 575FAB3E N._WCW..B..XJXX.X.\............. 000040
011827FF 16FCADFD AF9E0001 1812FF03 FBFFFEFE E1EF9F08 A97F00A9 7F000115 ..............................'.. 000060
EFFECA7F EF042097 BB93AB2D 53AB0000 00008F4A FCADEDAF 9EFCADFD AF9E0400 ............J......S=........... 000080
58D25801 CE031158 D40413FF FECA6AEF FFFF0D32 EF04295C 01CE0311 5CD40413 ...\....\)..2....J.......X....X.X 0000A0
ADFDAF9E 00B93100 030FAB01 04F10FAB D70FAB01 D000D131 03135CD5 5C58CA58 X.X\.\..1.................1...... 0000C0
13FFFECA C5EF0120 A7BBA3AB 2D000114 89EF04FB A3AB7F93 AB7F0FAB DD01DDFC ................................ 0000E0
5C58C858 01CE0311 58D40413 FFFECB3D EF0120A7 BBA3AB2D 5C01CE03 115CD404 .\....\-..........X.....X.X\. 000100
000115A4 EF01FBFF FEFEBFEF 9F5C50D0 00011584 EF01FBA3 AB7F5B11 02135CD5 .\...[..........P\.............. 000120
FE9EEF9F 5850D000 01158BEF 01FBA3AB 7F5C01CE 03115CD4 0419585C D15850D0 .PX.\X...\....\...........PX..... 000140
1102135C D55C58C8 5801CE03 1158D404 145758D1 5750D000 01157BEF 01FBFFFE .....{....PW.XW...X....X.X\.\... 000160
ADFDAF9E 6111FCAD FDAF9E0F ABD7FF4A 0FAB0104 F1FCADFD AF9EFCAD FDAF9E1B ...............J..........a..... 000180
E1EF4CDE 5C00012E 00FBAB0A FFFF28BC EF4CDF5C 00012E00 FBAB0A53 AB084AFC .J..S........\.L..(.........\.L.. 0001A0
00011724 FF01FBFF FEFDA7EF 9F000117 01FF01FB 00DDFFFF 31A2EF02 FBFFFF27 '......1.....................$... 0001C0
FDAF9E00 0116E7FF 00FB0001 1706FF01 FB00A97F 000116AC FF02FB00 A97F07DD ................................ 0001E0

Virtual block number 156 (0000009C), 512 (0200) bytes

16AAFF01 FB02DBCF 9FCBAB08 4AFCADFD AF9EFCAD FDAF9E04 000116A0 FF16FCAD ..................J............. 000000
87BB83AB 2D000116 91FF01FB DA4FCF9F 0B12FFFE CC20EF01 2087BB83 AB2D0001 ..-.... .. .......O.............. 000020
FFFEC918 EF012087 BB83AB2D 00011678 FF01FBDD 45CF9F0B 12FFFEC9 A0EF0120 ...........E....x............... 000040
ADFDAF9E 04000116 2DFF16CB AB000000 008F4A00 01165FFF 01FBE0BF CF9F0B12 ..............J.......-......... 000060
D0FCADFD AF9E67AB D7AF4A00 01130FEF 03FB93AB 7F4BABDD 20DDFCAD FDAF9EFC .......' ..K..........J...g...... 000080
FF00FB00 011617FF 01FB00DD FFFF30B8 EF02FBF8 A9DFF8A9 01D0FCA9 DFFCA901 ..........................O........ 0000A0
3BCB7FFC ADFDAF9E FFFF3094 EF02FB33 ABDFFCA9 DFFCA967 ABF7ABC1 00011620 .......g.......3....O.........; 0000C0
20FF47DB FF43CB2D 00011598 FF1650FF 43CB7E51 FF3BCB7E FFFF3528 EF01FBFF ....(5..".$.O".C.P.......-.C..G. 0000E0
7F0DDDBB 110212FF FECBE7EF 0020FF47 DBFF43CB 2D00F031 0312FFFE C8BEEF01 .........1..-.C..G. ........... 000100
FB00A97F 00DD01B0 31031204 B900A920 FFA7DBFF 43CB2D00 01156FFF 02FB00A9 .....o...-.C..G. ......1......... 000120
08A97F00 00007F8F DD016131 031204B9 00A920FF 47DBFF43 CB2D0001 1552FF02 ..R....-.C..C. ......1a.......... 000140
A97F08DD 5C01CE03 115CD404 120CB908 A920FF47 DBFF43CB 2D000115 31FF02FB ...1...-.C..G. ........\.....\.... 000160
5858D258 01CE0311 58D40412 04B900A9 20FFA7DB FF43CB2D 00011510 FF02FB00 .........-.C..C. .......X....X.XX 000180
5C08425C 67AB4EFF 1F310312 00000000 8F5C515C 67AB4E52 1102135C D55C58CA .X\.\...RN.g\Q\.......1..N.g\B.\ 0001A0
A97F5CDD 20DD5C4B AB67ABC3 00011194 EF03FB08 A97F93AB 7F67ABDD 67AB5C4A J\.g..g..................g.K\. .\.. 0001C0
FCADFDAF 9E008E31 00011490 FF03FB93 AB7F08A9 7F00A97F 000111BC EF03FB00 ..........................1....... 0001E0

Virtual block number 157 (0000009D), 512 (0200) bytes

FB00A97F 0001147C FF02FB00 A97F07DD 000114C4 FF01FB00 DD29124B AB67ABD1 ..g.K.)..................1....... 000000
425C67AB 4E67AB5C 4A5C0840 5C67AB4E FE6A3100 0114B7FF 00FB0001 14D6FF01 ..............1J.N.g\@.\J\.gN.g\B 000020
03FB08A9 7F10A97F FF43CB7F 00011114 EF03FB10 A97F93AB 7F5CDD5C 5C4A5C08 .\J\\.\...............C.........; 000040
7F08A97F 00A97F00 01112BEF 03FB00A9 7F5CDD20 DD5C4BAB 67ABC300 011423FF .#.....g.K\. .\......+.......... 000060
FF01FB00 DDFFFF2E D1EF02FB 33ABDFF7 ABDFFCAD FDAF9E00 0113FFFF 03FB93AB ..................3............. 000080
3BCB7FFC ADFDAF9E FDE23100 01142FFF 00FB0001 144EFF01 FB93AB7F 00011430 0.........N....../...1.........; 0000A0
```

```
20FF47DB FF43CB2D 000113B8 FF1650FF 43CB7E51 FF3BCB7E FFFF3348 EF01FBFF ....H3..^.;.Q^.C.P......-.C..C.  0000C0
FCADFDAF 9EFCADFD AF9E0400 0113B3FF 16FCADFD AF9ECE11 0212FFFE CA1AEF00 ................................ 0000E0
FFFEC5B2 EF9E5101 3267AB00 0000008F 4A000110 95EF03FB 93AB7F4B ABDD20DD . ..K..........J......#2.Q...... 000100
02FBF8A9 DFF8A901 D0FCA9DF FCA901D0 FCADFDAF 9E000113 61FF1650 83AB7E52 R^..P..a........................ 000120
08425C5C 4E5C4BAB F7ABC100 0113BFFF 00FB0001 1386FF01 FB00DDFF FF2E27EF .'.......................K\N\\B. 000140
328EEF01 FBFF3BCB 7FFCADFD AF9EFFFF 2DFAEF02 FB33ABDF FCA9DFFC A95C4A5C \J\.......3....-.........;.....2 000160
FFFF3160 EF02FB38 A97FFF43 CB7F0001 12FEFF16 50FF43CB 7E51FF3B CB7EFFFF ..^.;.Q^.C.P........C...8...`1.. 000180
AB2D5C01 CE03115C D4041308 585158CB AB4E0001 12E2FF16 5083AB7E 5138A97E ^.8Q^..P......N..XQX....\.....\-. 0001A0
13FFFEC6 08EF0120 87BB83AB 2D5801CE 031158D4 0413FFFE C884EF01 2087BB83 ... ..........X....X-.... ....... 0001C0
5701CE03 1157D404 13FFFEC5 81EF0120 87BB83AB 2D5857C8 5701CE03 1157D404 ..W....W.WX-.... .........W....W 0001E0
```

Virtual block number 158 (0000009E), 512 (0200) bytes

```
58CA5858 D25857C8 5701CE03 1157D404 13FFFEC5 B5EF0120 87BB83AB 2D5857C8 .WX-.... .........W....W.WX.XX.X 000000
BDEF0020 FF47DBFF 43CB2D02 B3310001 1266FF02 FBFF43CB 7F0DDD10 135CD55C \.\.......C....f...1..-.C..G. .... 000020
04B900A9 20FF47DB FF43CB2D 00011244 FF02FB00 A97F0DDD FF2A3103 12FFFEC8 .....1%.........D...-.C..C. .... 000040
31031204 B900A920 FF47DBFF 43CB2D00 011227FF 02FB00A9 7F00DD02 6B310312 ..1k.........'...-.C..G. ......1 000060
04120CB9 08A920FF 47DBFF43 CB2D0001 1206FF02 FB08A97F 0000007F BFDD01A2 .................-.C..G. ....... 000080
1204B900 A920FF47 DBFF43CB 2D000111 E5FF02FB 00A97F08 DD5C01CE 03115CD4 .\....\..............-.C..G. ..... 0000A0
12000000 008F5C51 5C67AB4E 4A110213 5CD55C58 CA5858D2 5801CE03 1158D404 ..X....X.XX.X\.\...JN.#\Q\...... 0000C0
A97F93AB 7F5CDD5C 5C4A5C08 425C4BAB 4E67AB5C 4A5C0842 5C67AB4E FE8E3103 .1..N.#\B.\J\.#N.K\B.\J\\.\..... 0000E0
AF9E007B 31000111 6DFF03FB 93AB7FFF FEF817EF 9F00A97F 00010E60 EF03FB00 ....`..................m...1(... 000100
7F000111 59FF02FB 00A97F07 DD000111 A1FF01FB 00DD2912 4BAB67AB D1FCADFD .....#.K.)................Y.... 000120
AB4E67AB 5C4A5C08 405C67AB 4EFDD831 00011194 FF00FB00 0111B3FF 01FB00A9 ................1..N.#\G.\J\.#N. 000140
00A97FFF 43CB7F00 010E03EF 04FB00A9 7F93AB7F 02DD5CDD 5C5C4A5C 08425C4B K\B.\J\\.\..................C.... 000160
ABDFFCAD FDAF9E00 0110F7FF 165083AB 7E51FF43 CB7E0001 10FEFF03 FB93AB7F ..........^.C.Q^..P.............. 000180
2097BB93 AB2D0001 0DEAEF03 FB00A97F 4BABDD20 DDFFFF2B C1EF02FB 33ABDFF7 ...3....+.... ..K..........-.... 0001A0
00A97F5C DD20DD5C 5C4A5C08 425C4BAB 4E000111 05FF01FB 00DD4112 04B900A9 .....A..........N.K\B.\J\\. .\... 0001C0
00FB0001 10FEFF01 FBFFFEF8 01EF9F00 011113FF 01FB00A9 7F00010D BDEF03FB ................................ 0001E0
```

Virtual block number 159 (0000009F), 512 (0200) bytes

```
0110C3FF 00FB0001 10E2FF01 FB93AB7F 000110C4 FF01FB00 DD1A1100 0110DFFF ................................ 000000
FF1650FF 43CB7E51 FF3BCB7E FFFF2FDC EF01FBFF 3BCB7FFC ADFDAF9E FD073100 .1.........;....../..^.;.Q^.C.P.. 000020
515CCBAB 4EFCADFD AF9ECE11 0212FFFE C6AEEF00 20FF47DB FF43CB2D 0001104C L...-.C..C. ...............N..\Q 000040
165083AB 7E5138A9 7EFFFF2E 89EF02FB 38A97F83 AB7F4611 02120000 00008F5C \.........f.....8........^.8Q^..P. 000060
2087BB83 AB2D5C01 CE03115C D40413FF FEC5BDEF 012087BB 83AB2D00 01100BFF ......-.... ..........\.....\-..... 000080
0413FFFE C2BAEF01 2087BB83 AB2D5C58 C85801CE 031158D4 0413FFFE C341EF01 ..A.......X.....X.X\-.... ........ 0000A0
FF01FB93 AB7F7FAB 1CAF9EFC ADFDAF9E 18110213 5CD55C58 C85801CE 03115BD4 .X.....X.X\.\.................... 0000C0
FB33ABDF F7ABDFFC ADFDAF9E 0400010F B5FF16FC ADFDAF9E 57AB5050 00011044 D...PP.W.....................3. 0000E0
07DD0001 0C86EF03 FB10A97F 4BABDD3F DD00010F C5FF01FB 00DDFFFF 2A66EF02 ..f%.............?..K............ 000100
FF01FB00 A97F0001 0F4EFF03 FB00A97F 10A97F08 A97F0001 0F6EFF02 FB08A97F ........n..............N......... 000120
FCADFDAF 9EFCADFD AF9E0001 0F6AFF01 FBFBACCF 9F00010F 99FF00FB 00010FB8 ...................J............. 000140
4D8FD000 010F67FF 00FB0001 0F86FF01 FBFFFEF2 F1EF9F00 010F6BFF 01FB00DD ......k..................a.....M 000160
7F00010F 35FF01FB 00DDFFFF 29D6EF02 FBF8A9DF FBA918D0 FCA9DFFC A9000000 ........................).......5.... 000180
A905D0FC A9DFFCA9 0AD0FCAD FDAF9E00 010F33FF 00FB0001 0F52FF01 FBFF2BCB .+....R.......3.................. 0001A0
```

```
010F23FF 01FBFFFE F62EEF9F 00010F00 FF01FB00 DDFFFF29 A1EF02FB FBA9DFF8 ........)...................$.. 0001C0
ADFDAF9E 00010E90 FF1650AB AB7E52FF FEC50FEF 9E510032 00010EFC FF00FB00 ........2.Q......R^..P.......... 0001E0

Virtual block number 160 (000000A0), 512 (0200) bytes

FF43CB2D 00010E74 FF1650FF 43CB7E51 FF3BCB7E FFFF2E04 EF01FBFF 3BCB7FFC ..;........^.;.Q^.C.P..t...-.C. 000000
CB2D0001 0E5AFF02 FB00A97F 0000007F 8FDDCE11 0212FFFE CAD6EF00 20FF47DB .G......................Z...-. 000020
AB7FABAB 7F5CDD5C 5C4A5C08 425C584E 5BABAB3C 6B1204B9 00A920FF 47DBFF43 C..C. .....h<..XNX\B.\J\\.\..... 000040
08A97F00 010E1BFF 02FB08A9 7F08DD00 010E63FF 01FB00DD 00010B00 EF03FBAB ..........c..................... 000060
00010DF8 FF02FB00 A97F08DD 00010E70 FF01FBFF FFF49BEF 9F00010E 7DFF01FB ..}...........p................ 000080
00010DD8 FF02FB00 A97F0DDD FF483100 010E33FF 00FB0001 0E5AFF01 FB00A97F ......Z......3...1H............. 0000A0
DD00010D A9FF03FB ABAB7FAB AB7FFF43 CB7F3113 04B900A9 20FF47DB FF43CB2D -.C..C. .....1..C............... 0000C0
9EFEFD31 00010DE8 FF00FB00 010E0FFF 01FBFFFE F522EF9F 00010DEC FF01FB00 .........."...................1... 0000E0
EF03FB00 A97FABAB 7F0ADDFE 9C310312 FFFEC3F0 EF0020AF BBABAB2D FCADFDAF ....-.... ........1............. 000100
D000010D 51FF1650 ABAB7E51 38A97EFF FF2BCFEF 02FB38A9 7F00A97F 00010A44 D........8....+..^.8Q^..P..Q.... 000120
BBABAB2D 5C000A19 00F3AB0A FCADFDAF 9E2B1100 02F3AB01 19F1F3AB D7F3AB01 .............+...........\-... 000140
31FCADFD AF9EF3AB D7D8F3AB 19F3FCAD FDAF9E15 110212FF FF1307FF 4C0A20AF . .L.........................1 000160
00F3AB0A 64110215 FFFF1562 EF4CCFAB D15C0001 1900F3AB 0AFCADFD AF9E007E ^.............\...L.b.......d.... 000180
52FFFF13 B5EF4C9E 510F325C 000F1900 F3AB0ACF ABFFFF15 4FEF4CD0 5C000119 ...\.L.Q.............\2.Q.L.....R 0001A0
9F00010C A9FF03FB 00A97FFF FEF443EF 9FFF33CB 7F00010C C1FF1650 FF33CB7E ^.3.P........3...C.............. 0001C0
57110001 0CCEFF01 FB038CCF 9F00010C 95FF03FB FF13CB7F 00A97FFF FEF43BEF .;..............................W 0001E0

Virtual block number 161 (000000A1), 512 (0200) bytes

B1FF01FB 00DDFFFF 2752EF02 FBFBA9DF F8A90AD0 FCA9DFFC A90AD0FC ADFDAF9E .....................R'......... 000000
FFFEC2C0 EF9E5100 3200010C ADFF00FB 00010CCC FF01FBFF FEF3FFEF 9F00010C ......................2.Q....... 000020
0C46FF16 FCADFDAF 9E00010C 75FF01FB 0190CF9F 00010C40 FF1650FF 33CB7E52 R^.3.P..@.........u.........F. 000040
5CB3AB3C 000108EC EF03FBB3 AB7FB3AB 7F0CDDFC ADFDAF9E FCADFDAF 9E040001 ......\....................<..\ 000060
F1F3ABD7 F3AB01D0 00010BF4 FF1650BB AB7E52FF FEC273EF 9E510032 6BAB5CD0 .\.k2.Q...s...R^..P.............. 000080
7E52FFFE BF06EF9E 51013217 156BABF3 ABD1FCAD FDAF9E00 A0310003 F3AB010C ......1...........k...2.Q......R^ 0000A0
7F000108 9DEF04FB FF43CB7F B3AB7FF3 ABDD01DD 58110001 0BC2FF16 50FF43CB .C.P.......X...........C......... 0000C0
04193458 51586FAB 4E6FAB50 4A00010A DEEF1650 504E0001 09FAEF01 FBFF43CB .C.........NPP......JP.oN.oXQX4.. 0000E0
5CD55C58 C85801CE 031158D4 04140000 43648F57 51576FAB 4E5C01CE 03115CD4 .\....\N.oWQW.dC.....X....X.X\.\ 000100
F1FCADFD AF9E0001 0B4EFF03 FBBBAB7F BBAB7FFF 43CB7FFC ADFDAF9E 3A110213 ..:.......C...........N......... 000120
AF9E7611 00010BB4 FF1650B3 AB7E51BB AB7EFCAD FDAF9EF3 ABD7FF63 F3AB010C ....v..........^..Q^..P..4....v.. 000140
61FF00FB 00010B58 FF01FB00 DD00010B 71FF00FB 00010B68 FF01FB00 DDFCADFD ........h.......q.........X......a 000160
0B62FF01 FB00A97F 00010B30 EF02FB00 A97F0ADD 00010B48 FF01FB00 DD00010B ........H...........0..........b. 000180
00010B0C FF01FB27 AF9F0001 0B2EFF00 FB00010B 4DFF01FB FFFEF288 EF9F0001 ............N...............'...... 0001A0
0400010A C9FF16FC ADFDAF9E 00010AB8 FF1650B3 AB7E52FF FEC137EF 9E510032 2.Q..7...R^..P.................. 0001C0
DDFFFF25 6DEF02FB F8A9DFF8 A918D0FC A9DFFCA9 01D0FCAD FDAF9EFC ADFDAF9E ...........................m%... 0001E0

Virtual block number 162 (000000A2), 512 (0200) bytes

00010AE4 FF01FB00 A97F0001 078EEF03 FB00A97F 28DD20DD 00010ACC FF01FB00 .......... .(..................... 000000
01FB00DD FFFF2530 EF02FBF8 A9DFF8A9 18D0FCA9 DFFCA929 D000010A BDFF00FB ........)................0%...... 000020
FF00FB00 010AA7FF 01FB00A9 7F000107 51EF03FB 00A97F24 DD20DD00 010A8FFF ...... .$......Q................. 000040
```

```
0A52FF01 FB00DDFF FF24F3EF 02FBF8A9 DFF8A901 D0FCA9DF FCA901D0 00010A80 ......................$.......R. 000060
00DDFFFF 24CEEF02 FBF8A9DF F8A918D0 FCA9DFFC A905D000 010A5BFF 00FB0001 .....[...................$..... 000080
FCADFDAF 9E00010A 29FF00FB 00010A50 FF01FBFF FEF18BEF 9F00010A 2DFF01FB ...-...........P......)......... 0000A0
FB00A97F 0DDD0001 09B6FF16 5083AB7E 51FF3BCB 7EFFFF29 45EF01FB FF3BCB7F ..;....E)..^.;.Q~..P............ 0000C0
04000109 A9FF16FC ADFDAF9E C7110213 04B900A9 2087BB83 AB2D0001 09B2FF02 .....-.......................... 0000E0
FF01FB00 DDFFFF24 51EF02FB EFABDFFC A9DFFCA9 01D0FCAD FDAF9EFC ADFDAF9E ......................Q$........ 000100
A1FF00FB 000109C0 FF01FB00 A97F0001 0672EF03 FB00A97F 28DD20DD 000109B0 ......(......P.................. 000120
DD20DD00 010977FF 01FB00DD FFFF2418 EF02FBEF ABDFFCA9 DFFCA929 D0000109 ....)...........$.......w....... 000140
0926FF16 00010968 FF00FB00 010987FF 01FB00A9 7F000106 39EF03FB 00A97F28 (......9................h......&. 000160
0000008F 5C515CFF FF188BEF 4E7FAB00 EBCF9EFC ADFDAF9E FCADFDAF 9E040001 ..................N....\Q\....... 000180
01FB00A9 7F000101 AAEF02FB 00A97F00 DD000109 25FF01FB 02DD00CA 31031200 ...1.......%..................... 0001A0
FF00FB00 01091FFF 01FBFF13 CB7F0001 0932FF01 FBFFFEEF 5DEF9F00 01093FFF .?.....J......2.................. 0001C0
7E52FFFE BF02EF9E 5100325C 00010300 73AB0AFC ADFDAF9E 73AB084A 60010900 ....J.............s....\2.Q......R~ 0001E0
```

Virtual block number 163 (000000A3), 512 (0200) bytes

```
4C7E5C00 01030073 AB0A73AB 5C4A5C08 405C73AB 4E000108 81FF1650 FF0BCB4C L...P......N.s\@.\J\.s..s....\^L 000000
A97F0ADD 00010898 FF01FB02 DD3D1102 12FFFEBE D1EF0020 04BC6C2D 5CFF0BCB ...\-1.......................... 000020
FBFF0BCB 4C7F5C00 01030073 AB0A0001 08B2FF01 FB00A97F 00010580 EF02FB00 ......................s....\.L.... 000040
ADFDAF9E 04000108 2DFF16FC ADFDAF9E FF783100 010877FF 00FB0001 0896FF61 .........w...1x.........-....... 000060
FCADFDAF 9EFCADFD AF9E0001 082AFF01 FBE1AF9F FFFF1798 EF000000 008F4AFC .J...................*.......... 000080
EF9F0001 0816FF01 FB00DDFF FF22B7EF 02FBF8A9 DFF8A918 D0FCA9DF FCA903D0 .................'.............. 0000A0
F8A9DFF8 A901D0FC A9DFFCA9 01D00001 0812FF00 FB000108 39FF01FB FFFEEF7C |......9......................... 0000C0
AF9E0400 0107ABFF 16000107 EDFF00FB 000107E4 FF01FB00 DBFFFF22 85EF02FB ....'........................... 0000E0
EF04FB38 A97F7EE7 AB6EFFFE EE9AEF9F D7AB0000 00008F4A FCADFDAF 9EFCADFD ........J.............n..~..B... 000100
FBFF13CB 7FFFFEEF 0DEF9F00 A97F0001 075EFF16 5000A97E 5138A97E 000103AE ....~.8Q~..P..^................. 000120
01FBFFFE EBB2EF9F 0001076C FF02FB04 DDE7ABDD 7FAB0309 CF9E0001 0742FF03 ..B...............1............. 000140
16FCADFD AF9E77AB 50D00001 07B6FF01 F8FFFEEE E1EF9FEB AB50D000 0107C7FF ......P.................P.w...... 000160
AB6EFFFE EE12EF9F D7AB0000 00008F4A FCADFDAF 9EFCADFD AF9E0400 010723FF .&...............J.............n. 000180
95EF9F00 A97F0001 06D6FF16 5000A97E 5138A97E 00010326 EF04FB38 A97F7EE7 .~..8...&...~.8Q~..P............ 0001A0
A97F7EEB AB6EFFFE EDF6EF9F 7FAB0281 CF9E0001 06BAFF03 FBFF13CB 7FFFFEEE ......................n..~.. 0001C0
A97F7E77 AB6EFFFE EDB6EF9F FFFF17AA EF02203C B938A92C 000102EA EF04FB38 8.........8.<...............n.w~.. 0001E0
```

Virtual block number 164 (000000A4), 512 (0200) bytes

```
52FFFF16 25EF9E51 01638F32 FFFF178C EF03203C B938A92C 000102CA EF04FB38 8.........B.<.......2.c.Q..%...R 000000
2C000106 61FF01FB 04DD0001 068EFF02 FB04DDE7 ABDD0001 0662FF16 50C3AB7E ~..P..b......................... 000020
45FF16FC ADFDAF9E 00010694 FF02FB04 DDE7ABDD FFFF15F8 EFCFAF20 C7BBC3AB ...............................E 000040
7EE3AB6E FFFEED34 EF9FD7AB 00000000 8F4AFCAD FDAF9EFC ADFDAF9E 04000106 ...............J.........4...n..~ 000060
FEEDBFEF 9F00A97F 000105F8 FF165000 A97E5138 A97E0001 0248EF04 FB38A97F ..8...H...~.8Q~..P.............. 000080
AF9E0001 0606FF02 FB06DDE3 ABDD7FAB 01A3CF9E 000105DC FF03FBFF 13CB7FFF ................................ 0000A0
6EFFFEEC D1EF9FD7 AB99AF4A FCADFDAF 9EFCADFD AF9E0400 0105DFFF 16FCADFD ...................J..........n 0000C0
EF9F00A9 7F000105 95FF1650 00A97E51 38A97E00 0101E5EF 04FB38A9 7F7EE7AB ..~..8........~.8Q~..P.......... 0000E0
FFFEFA98 EF9E5101 4E8F327F AB0140CF 9E000105 79FF03FB FF13CB7F FFFEED64 d............@...2.N.Q........ 000100
00010560 FF01FB06 DD000105 8DFF02FB 06DDE3AB DD000105 61FF1650 C3AB7E52 R~..P...a...................`... 000120
04000105 49FF1600 010593FF 02FB06DD E3ABDDFF FEFA6BEF CFAF20C7 BBC3AB2C ..........k..................I.... 000140
```

```
FB38A97F 7ED3AB6E FFFEEC58 EF9FD7AB 00000000 8F4AFCAD FDAF9EFC ADFDAF9E ............J..........X...n..~..8. 000160
13CB7FFF FEECD3EF 9F00A97F 000104FC FF165000 A97E513B A97E0001 014CEF04 ..L...^.8Q^..P.................. 000180
000104E8 FF160001 050AFF02 FB07DDD3 ABDD7FAB 00A7CF9E 000104A0 FF03FBFF ................................ 0001A0
EF04FB38 A97F7ED3 AB6EFFFE EBFAEF9F D7AB9EAF 4AFCADFD AF9EFCAD FDAF9E04 ............J..........n.~..8... 0001C0
FBFF13CB 7FFFFEEC 7DEF9F00 A97F0001 019EFF16 5000A97E 5138A97E 000100EE ....~.8Q~..P.............}........ 0001E0

Virtual block number 165 (000000A5), 512 (0200) bytes

DD000104 6DFF1650 C3AB7E52 FFFF1594 EF9E510A 327FAB4A AF9E0001 0482FF03 ..........J..2.Q.......R~..P..m..... 000000
FFFF1568 EF0A20C7 BBC3AB2C 0001046C FF01FB07 DD000104 99FF02FB 07DDD3AB ......................l........h... 000020
FB00DDFC ADFDAF9E FCADFDAF 9E040001 0456FF16 000104A0 FF02FB07 DDD3ABDD ................V................. 000040
FBFF13CB 7FFFFEEC 05EF9FFF 13CB7FD7 AB084A00 010477FF 00FB0001 046EFF01 ..n.......w...J..................... 000060
2FEF04FB 38A97F7E 5C6EFFFE EB1AEF9F 5C50D000 010423FF 00FB0001 0402FF03 ...........8....P\.........n\~..8.../ 000080
FF03FB10 A97FFFFE EBCEEF9F 18A97F00 0103DFFF 165018A9 7E5138A9 7E000100 ...~.8Q~..P....................... 0000A0
50D00001 03D6FF00 FB000103 B1FF03FB 0BA97F10 A97FFFFE EBC6EF9F 000103C4 ...............................P 0000C0
038EFF16 5000A97E 5140A97E 0000FFDE EF04FB40 A97F7E5C 6EFFFEFB B1EF9F5C \.......n\~..@........~.@Q~..P.... 0000E0
FF13CB7F 000103B8 FF01FB00 DD000103 75FF03FB FF1BCB7F 08A97F00 A97F0001 ...................u............... 000100
03BAFF01 FBFF1BCB 7F000103 9DFF01FB 00DD0001 03B6FF00 FB000103 D5FF01FB ................................ 000120
9F000103 6DFF01FB F888CF9F 00010378 FF01FBFA 36CF9F00 01039BFF 00FB0001 .............6.....x..........m..... 000140
9EFCADFD AF9EFCAD FDAF9E04 00010334 FF16FCAD FDAF9E00 010357FF 01FB07AF ......W............4................ 000160
5150D050 FFFEB968 EF9E52FB AF9ECFFC 04500100 00010318 FF1650FF FEAF93EF ......P.........P.......R..h...P.PQ 000180
4AFCADFD AF9EFCAD FDAF9EFC ADFDAF9E FCADFDAF 9EFCADFD AF9E0001 0322FF16 ..".............................J 0001A0
8FF13FAB D73FAB01 D0000102 F5FF01FB 055ECF9F 3BABF7AF 4A37AB00 0000008F .......?J...f..^................T..T.. 0001C0
01E1AF00 3FAB0A5C 000CEAAF 003FAB0A FCADFDAF 9E4C1100 023FAB01 00000064 d......?...L.........?......\..?.... 0001E0

Virtual block number 166 (000000A6), 512 (0200) bytes

01C1AF00 3FAB0A00 010273FF 1650FC97 CB487E52 FFFF0B56 EF4C9E51 0C325800 .X2.Q.L.V...R^H...P..s.......T..... 000000
ADFDAF9E FCADFDAF 9E3FABD7 B73FABAF AFF3FCAD FDAF9EFB 03CB4C3F ABD05C00 .\...?L................?...?.......... 000020
0B43AB41 FCADFDAF 9E013731 000343AB 08000043 C68F4F43 AB084243 AB0850FC .P..CB..CO..C.....C..17.........A.C. 000040
5C47AB4A FCADFDAF 9E00FE31 000347AB 08000043 C88F4F47 AB084247 AB5C505C \P\.GB..GO..C.....G..1.........J.G\ 000060
CB487E5C FC97CB4C 7E580001 F0AF0058 0A5843AB 4A5C0001 00000064 8F005C0A .\..d.......\J.CX.X.......X^L...\^H. 000080
97CB4C7E 5C0001CB AF005C0A 5C43AB4A 00AC3103 1A04BC6C 2004B848 2D58FC97 ..X-h.. 1.....1..J.C\.\.......\^L.. 0000A0
AF00580A 5843AB4A 5C0001AF AF005C0A 5C47AB4A 000101C4 FF165017 AB7E51FC .Q^..P........J.G\.\.......\J.CX.X.. 0000C0
0185AF00 5C0A5C47 AB4A0001 019AFF16 50FC97CB 487E51FC 97CB4C7E 580001A3 ...X^L...Q^H...P......J.G\.\...... 0000E0
00010000 00648F00 5C0A5C43 AB4A0001 017EFF16 50FC97CB 4C7E5117 AB7E5C00 .\^...Q^L...P..^.....J.C\.\..d...... 000100
580001DD AF00580A 5843AB4A 5C0001E9 AF005C0A 5C47AB4A 4BABFB03 CB4CD05C \.L.....KJ.G\.\.......\J.CX.X......X 000120
ADFDAF9E FB03CB4C 4BABD05C 0001C8AF 005C0A5C 47AB4AFB 03CB48FB 03CB4CD0 .L...H...J.G\.\........\..KL........ 000140
4FFCADFD AF9EFCAD FDAF9E47 AB0842FF 0647AB08 000043C8 8F4FFCAD FDAF9EFC .......O..C.....G..B..G............O 000160
00000064 8FF14FAB D74FAB01 D0FCADFD AF9E43AB 0842FECD 43AB0800 0043C68F ..C.....C..B..C.........O..O..d... 000180
04BC6C2D 5CFC97CB 4C7E5C00 01E9AF00 4FAB0AFC ADFDAF9E 01CC3100 034FAB01 ..O..1............O......\^L...\-1.. 0001A0
5C0001BF AF004FAB 0A37AB5C 4A5C0840 5C37AB4E 01903103 12FFFEB9 6AEF0020 ..j......1..N.7\@.\J\.7..O......\ 0001C0
50000101 29FF01FB FFFEE8A8 EF9F0001 00DAFF01 FB07BDCF 9F3FABFB 03CB4CD0 .L....?.........................)...P 0001E0

Virtual block number 167 (000000A7), 512 (0200) bytes

0106FF01 FBFFFEE8 8DEF9F53 AB000000 008F4A3B AB584A58 5C40583B AB4E5C50 P\N.;X@\XJX.;J......S............ 000000
```

```
ABD75BAB 01D05FAB 5C4A5C50 50000100 F5FF01FB FFFEE874 EF9F57AB 504A0001  ..JP.W..t..........PP\J\.....[..  000020
FEE84FEF 9F000100 71FF01FB 08B8CF9F FCADFDAF 9E501100 025BAB01 5FABF15B  [.....[...P...............O..  000040
E836EF9F 53AB5C4A 5C08405C 53AB4E0B 13A0AF5C 515C5050 00010000 FF01FBFF  ........PP\Q\....N.S\Q.\J\.S..6.  000060
FCADFDAF 9E5BABD7 B35BAB5F ABF3FCAD FDAF9E57 AB504A00 01009FFF 01FBFFFE  .........JP.W........[...[.....  000080
9F000100 45FF01FB 18A97F00 00FD13EF 02FB18A9 7F05D000 01002BFF 01FB00DD  ....................E....  0000A0
0022FF01 FB10A97F 0000FCF0 EF02FB10 A97F14DD 00010038 FF01FBFF FEE7FBEF  ........8......................  0000C0
01FB08A9 7F0000FC CDEF02FB 08A97F3C DD000100 15FF01FB FFFEE7E0 EF9F0001  ..............<.................  0000E0
FCA6EF02 FB00A97F 00000049 BFDD0000 FFF2FF01 FBFFFEE7 95EF9F00 00FFFFFF  ....................I...........  000100
63AB4E00 00FFA7FF 00FB0000 FFDAFF01 FB53ABDD 0000FFD8 FF01FB00 A97F0000  ................S............N.c  000120
ADFDAF9E 0000FF70 FF01FB01 B3CF9F0B 152B5C51 5C63AB4E 63AB5C4A 5C08405C  \@.\J\.cN.c\Q\+.................  000140
2A5C515C 63AB4EFC ADFDAF9E 4FABD7FE 371FAB01 00000064 8FF1FCAD FDAF9EFC  ........d.....07...O.....N.c\Q\*  000160
FB00DD00 00FF47FF 00FB0000 FF3EFF01 FB00DD00 00FF3FFF 01FB0182 CF9F0B15  ...........?.........>......G......  000180
21FF00FB 0000FF48 FF01FB00 A97F0000 FC16EF02 FB00A97F 14DD0000 FF2EFF01  ........................H.......!  0001A0
01FF00FB 0000FF3C FF01FB37 ABDD0000 FEFEFF02 FB00DDFF FEE707EF 9F0000FF  ......................?...<.......  0001C0
0000FEE4 FF00FB00 00FF0BFF 01FBFFFE E6E6EF9F 0000FEE8 FF01FB00 DD0000FF  ................................  0001E0
```

Virtual block number 168 (000000A8), 512 (0200) bytes

```
01FB7E5C 505C0000 43C88F58 435837AB 4E0000FE C1FF02FB 00DDFFFE E6CAEF9F  ...............N.7XCX..C..\P\~..  000000
FEBAFF01 FBFFFEE6 A5EF9F00 00FE9FFF 01FB00DD 0000FEB8 FF00FB00 00FEE7FF  ................................  000020
A97F0000 FB6AEF02 FB00A97F 14DD0000 FE82FF01 FB00DD00 00FE9BFF 00FB0000  ...........................J.....  000040
ABDD0000 FE52FF02 FB00DDFF FEE65BEF 9F0000FE 75FF00FB 0000FE9C FF01FB00  ...........u.....[........R.....  000060
01FBFFFE E64AEF9F 0000FE3C FF01FB00 DD0000FE 55FF00FB 0000FE90 FF01FB3B  ;..........U.........<......J....  000080
43583BAB 4E0000FE 15FF02FB 00DDFFFE E61EEF9F 0000FE38 FF00FB00 00FE5FFF  ._.......8.................N.;XC  0000A0
00FDF3FF 01FB00DD 0000FE0C FF00FB00 00FE3BFF 01FB7E5C 505C0C00 44968F58  X..D..\P\~...;..................  0000C0
0000FDCC FF01FB01 60CF9F00 00FDEFFF 00FB0000 FE0EFF01 FBFFFEE5 F9EF9F00  .............................  0000E0
0EAF9F00 00FDAFFF 01FB0143 CF9FFCAD FDAF9EFC ADFDAF9E 082431FC ADFDAF9E  .....1$..............C...........  000100
00FD93FF 01FB00DD FCADFDAF 9EFCADFD AF9E0400 00FD7BFF 16000CFD A5FF01FB  ..........{......................  000120
FCA9DFFC A9000000 4DBFD000 00FDBFFF 00FB0000 FDAEFF01 FBFFFEE5 A9EF9F00  ..........................M.........  000140
FF01FBFF FEE57BEF 9F0000FD 5DFF01FB 00DDFFFF 17FEEF02 FBF8A9DF F8A918D0  ...........................]......{......  000160
FFFF17CC EF02FBF8 A9DFF8A9 01D0FCA9 DFFCA901 D00000FD 59FF00FB 0000FDB0  .......Y.........................  000180
02FB08A9 7F05DD00 00FD1BFF 01FB00DD 0000FD34 FF00FB00 00FD2BFF 01FB00DD  .....+......4...................  0001A0
A97F19DD 0000FD28 FF01FBFF FEE52BEF 9F0000FD 35FF01FB 08A97F00 00FA03EF  ............5.....+.......(........  0001C0
FB0000FD 05FF01FB FFFEE510 EF9F0000 FD12FF01 FB00A97F 0000F9E0 EF02FB00  ................................  0001E0
```

Virtual block number 169 (000000A9), 512 (0200) bytes

```
01FB00A9 7F0000F9 ADEF02FB 00A97F38 DD0000FC C5FF01FB 00DD0000 FCDEFF00  ................8...............  000000
FC92FF01 FB00DD00 00FCABFF 00FB0000 FCCAFF01 FBFFFEE4 E5EF9F00 00FCDFFF  ................................  000020
AF9EFCAD FDAF9E04 0000FC50 FF16FCAD FDAF9E63 AB144A00 00FC9BFF 00FB0000  ..........J..c........P..........  000040
00FC53FF 01FB00DD FFFF16F4 EF02FBF8 A9DFF8A9 18D0FCA9 DFFCA901 D0FCADFD  ..............................S..  000060
0000FC4A EF00FB00 00FC6BFF 01FB00A9 7F0000F9 15EF03FB 00A97F28 DD20DD00  ..(...............k......D...  000080
20DD0000 FC16FF01 FB00DDFF FF16B7EF 02FBF8A9 DFF8A918 D0FCA9DF FCA929D0  .)..............................  0000A0
A901D000 00FC07FF 00FB0000 FC2EFF01 FB00A97F 0000F8D8 EF03FB00 A97F24DD  .$..............................  0000C0
FBE2FF00 FB0000FB D9FF01FB 00DDFFFF 167AEF02 FBF8A9DF F8A901D0 FCA9DFFC  ..................z.............  0000E0
0000FBB4 FF01FB00 DDFFFF16 55EF02FB F8A9DFF8 A918D0FC A9DFFCA9 05D00000  .........................U.........  000100
```

```
CDEF01FB 1FAB7FFC ADFDAF9E 0000FBB0 FF00FB00 00FBD7FF 01FBFFFE E3F2EF9F ................................ 000120
27AB2D00 00FB3BFF 02FB00A9 7F0DDD00 00FB3FFF 165027AB 7E511FAB 7FFFFF1A ...^..Q^.'P..T............$...-.' 000140
ADFDAF9E FCADFDAF 9E040000 FB32FF16 FCADFDAF 9EC91102 1304BD00 A9202BDB .+ ..............2............ 000160
7F28DD20 DD0000FB 39FF01FB 00DDFFFF 15DAEF02 FB67ABDF FCA9DFFC A901D0FC .........g...........9.... .(. 000180
A9DFFCA9 29D00000 FB2AFF00 FB0000FB 49FF01FB 00A97F00 00F7FBEF 03FB00A9 ...............I......*....)..... 0001A0
F7C2EF03 FB00A97F 28DD20DD 0000FB00 FF01FB00 DDFFFF15 A1EF02FB 67ABDFFC ...g................ .(......... 0001C0
9EFCADFD AF9E0400 00FAAFFF 160000FA F1FF00FB 0000FB10 FF01FB00 A97F0000 ................................ 0001E0

Virtual block number 170 (000000AA), 512 (0200) bytes.

FCADFDAF 9E00E031 00036BAB 0128F16B ABD76BAB 01D07FAB 0104CF9E FCADFDAF .............k..k.(..k..1........ 000000
D40413EF FEB2E4EF 002004BC 6C2D5CBF AB4C7E5C 00010A00 6BAB0AFC ADFDAF9E ........k....\^L..\-1.. ......... 000020
585CC85C 01CE0311 5CD40413 00000000 8F575157 FFFF09D8 EF4E5801 CE031158 X....XN.....WQW........\....\.\X 000040
02FB00A9 7F00DD00 00FA5BFF 01FB02DD 2612085C 515C6BAB 4E009931 031358D5 .X..1..N.k\Q\..3.....[.......... 000060
DD0000FA 35FF01FB 02DD0000 FA4EFF00 FB0000FA 75FF01FB 00A97F00 00F2E0EF ...........u......N........5.... 000080
AB4C7F5C 00010A00 6BAB0A00 00FA4FFF 01FB00A9 7F0000F7 1DEF02FB 00A97F09 .................O.....k....\.L. 0000A0
FFFEB251 EF9E5100 325C0001 0A006BAB 0A0000FA 15FF00FB 0000FA34 FF01FBBF ....4..............k.....\2.Q..Q... 0000C0
FCADFDAF 9E6BABD7 FF236BAB 0128F1FC ADFDAF9E 0000F9A0 FF165CBF AB4C7E52 R^L..F............(..k$...k..... 0000E0
0902EF5C 4A5C0842 5CFFFF09 0DEF4EFC ADFDAF9E 040000F9 9DFF16FC ADFDAF9E ...............N......\B.\J\... 000100
0000F97C FF00FB00 00F983FF 00FB0712 00000000 8F5C515C FFFF0EFC EF4EFFFF ..N.....\Q\.................!... 000120
DDFFFF14 0DEF02FB FBA9DFF8 A918D0FC A9DFFCA9 03D0FCAD FDAF9EFC ADFDAF9E ................................ 000140
FCA901D0 0000F968 FF00FB00 00F98FFF 01FBFFFE E1B2EF9F 0000F96C FF01FB00 ....1.....................h....... 000160
00F943FF 00FB0000 F93AFF01 FB00DDFF FF13DBEF 02FBF8A9 DFF8A901 D0FCA9DF ..........................:......C.. 000180
FFFEE110 EF9F6FAB 00000000 8F4AFCAD FDAF9EFC ADFDAF9E 040000F9 01FF1600 ..................J......o....... 0001A0
9F00A97F 0000F8B4 FF165000 A97E5120 A97E0000 F504EF04 FB20A97F 7E3FAB6E n.?^.. ........^. Q^..P.......... 0001C0
00F8C3FF 02FB04DD 3FABDD7F AB0217CF 9E0000F8 99FF03FB C7AB7FFF FEE143EF .C.......................?........ 0001E0

Virtual block number 171 (000000AB), 512 (0200) bytes

D00000F9 0DFF01FB FFFEE090 EF9F73AB 50D00000 F91EFF01 FBFFFEE0 99EF9F00 ...............P.s.............. 000000
AB000000 008F4AFC ADFDAF9E FCADFDAF 9E040000 F87AFF16 FCADFDAF 9E77AB50 P.w.......z...............J........ 000020
2DFF1650 00A97E51 20A97E00 00F47DEF 04FB20A9 7F7E3FAB 6EFFFEE0 89EF9F6F o......n.?^.. ...}...^. Q^..P..- 000040
E0B6EF9F 7FAB0190 CF9E0000 F812FF03 FBC7AB7F FFFEE0C4 EF9F00A9 7F0000F8 ................................ 000060
E02EEF9F FFFF0902 EF022024 B920A92C 0000F442 EF04FB20 A97F7E73 AB6EFFFE ..n.s^.. ...B..... .$.............. 000080
01638F32 FFFF08E4 EF032024 B920A92C 0000F422 EF04FB20 A97F7E77 AB6EFFFE ..n.w^.. ...".... .$ .......2.c. 0000A0
04DD0000 F7E6FF02 FB04DD3F ABDD0000 F7BAFF16 502FAB7E 52FFFF07 7DEF9E51 Q..)...R^./P........T............ 0000C0
0000F7EC FF02FB04 DD3FABDD FFFF0750 EFCFAF20 33BB2FAB 2C0000F7 B9FF01FB ........./.3 ...P.....?.......... 0000E0
EF9F6FAB 00000000 8F4AFCAD FDAF9EFC ADFDAF9E 040000F7 9DFF16FC ADFDAF9E .......................J.......o.. 000100
0000F750 FF165000 A97E5120 A97E0000 F3A0EF04 FB20A97F 7E57AB6E FFFEDFAC .....n.W^.. ........^. Q^..P..P... 000120
02FB06DD 57ABDD7F AB00B3CF 9E0000F7 35FF03FB C7AB7FFF FEDFF7EF 9F00A97F ...................5...........W.... 000140
6FAB9AAF 4AFCADFD AF9EFCAD FDAF9E04 0000F738 FF16FCAD FDAF9E00 00F75FFF .-...........8.............J....o 000160
F6EEFF16 5000A97E 5120A97E 0000F33E EF04FB20 A97F7E3F AB6EFFFE DF4AEF9F ..J....n.?^.. ...>...^. Q^..P.... 000180
9E51014E 8F327FAB 52AF9E00 00F6D3FF 03FBC7AB 7FFFFEDF 9DEF9F00 A97F0000 ...........................R..2.W.Q. 0001A0
01FB06DD 0000F6E8 FF02FB06 DD57ABDD 0000F6BC FF16502F AB7E52FF FFEBF3EF .....R^./P........W............. 0001C0
AF9E0000 F6EEFF02 FB06DD57 ABDDFFFE EBC6EFCF AF2033BB 2FAB2C00 00F6B3FF ......./.3 .........W.......... 0001E0
```

```
Virtual block number 172 (000000AC), 512 (0200) bytes

FF00FB00 00F6B7FF 01FB00DD FCADFDAF 9EFCADFD AF9E0400 00F69FFF 16FCADFD ................................ 000000
F66EFF00 FB0000F6 4DFF03FB C7AB7FFF FEDF1FEF 9FC7AB7F 6FAB084A 0000F6C0 ....J..o..................M......n. 000020
5018A97E 5120A97E 0000F27A EF04FB20 A97F7E5C 6EFFFEDE 85EF9F5C 55D00000 ...P\......n\~.. ...z....~. Q~..P 000040
7FFFFEDE E1EF9F00 00F60FFF 03FB10A9 7FFFFEDE E9EF9F18 A97F0000 F62AFF16 ..a............................. 000060
7F7E5C6E FFFEDECC EF9F5C50 D00000F6 21FF00FB 0000F5FC FF03FB08 A97F10A9 ..............!....P\.......n\~. 000080
CFAB7F08 A97F00A9 7F0000F5 D9FF1650 00A97E51 28A97E00 00F229EF 04FB28A9 .(...)...~.(Q~..P............... 0000A0
00F603FF 00FB0000 F622FF01 FBC7AB7F 0000F604 FF01FB00 DD0000F5 C1FF03FB ................................ 0000C0
FBFAFBCF 9F0000F5 E9FF00FB 0000F608 FF01FBCF AB7F0000 F5EAFF01 FB00DD00 ................................ 0000E0
FCADFDAF 9E0000F5 A5FF01FB 07AF9F00 00F5BBFF 01FBF94F CF9F0000 F5C6FF01 ........O....................... 000100
01D00000 F566FF16 50FFFEAB CDEF9EFC ADFDAF9E FCADFDAF 9E040000 F582FF16 ..........................P..f..... 000120
9EFCADFD AF9E0000 F56EFF16 5150D050 FFFEADE4 EF9E52FB AF9ECFFC 00000450 P........R.....P.PQ..n.......... 000140
EF9E5103 323BAB00 0000008F 4AFCADFD AF9EFCAD FDAF9EFC ADFDAF9E FCADFDAF .....................J......;2.Q.. 000160
AB2D0000 F52EFF01 FB0B77CF 9F3FAB14 4A0000F4 FDFF1650 EBAB7E52 FFFEB293 ....R~..P......J..?..w.........-. 000180
ADEF9F00 00F517FF 01FB00DD FCADFDAF 9E02A131 0312FFFE B26DEF00 20F7BBF3 .....m.....1.................... 0001A0
F8A918D0 FCA9DFFC A9000000 4DBFD000 00F513FF 00FB0000 F532FF01 FBFFFEDD ......2............M............ 0001C0
0000F504 FF01FBFF FEDD7FEF 9F0000F4 E1FF01FB 00DDFFFF 0F82EF02 FBF8A9DF ................................ 0001E0

Virtual block number 173 (000000AD), 512 (0200) bytes

FF0F4BEF 02FBF8A9 DFF8A908 D0FCA9DF FCA90AD0 FCADFDAF 9E0000F4 DDFF00FB ...........................K.. 000000
0AD00000 F4A6FF00 FB0000F4 C5FF01FB FFFEDD50 EF9F0000 F4AAFF01 FB00DDFF ...........P................... 000020
DD26EF9F 0000F47B FF01FB00 DDFFFF0F 19EF02FB F8A9DFF8 A90BD0FC A9DFFCA9 ..........................x.....&. 000040
02FBF8A9 DFF8A90A D0FCA9DF FCA90AD0 0000F474 FF00FB00 00F493FF 01FBFFFE ..........t..................... 000060
01FBFBAB 7F0000F4 69FF01FB FFFEDCFC EF9F0000 F44AFF01 FB0ADDFF FF0EE7EF ..........J.........i........... 000080
7F01DD01 93310312 FFFEB15F EF0020FF BBFBAB2D 0000F438 FF00FB00 00F477FF .w.......8..-.... ..-.....1...... 0000A0
03AB7E51 20A97EFF FF1227EF 02FB20A9 7FFBAB7F 0000F09C EF03FB03 AB7FFBAB ..................'...~. Q~.. 0000C0
BB03AB2D 5C01CE03 115CD404 13FFFEB0 D6EF0120 07BD03AB 2D0000F3 A9FF1650 P.......-..... .........\.....\-... 0000E0
FEB0A5EF 9E510232 21135CD5 5C58C858 01CE0311 58D40413 FFFEB0C0 EF012007 . .........X.....X.X\.\.!2.Q..... 000100
FF01FB0C CFCF9FFE 7631FFFF 0F62EF01 FB00A97F 0000F360 FF165000 A97E52FF .R~..P..`.........b...1v........ 000120
0064BFF1 43ABD743 AB01D0FE 5A310312 FFFEB0C7 EF0020FF BBFBAB2D 0000F388 ....-.... .........1Z.....C..C..d. 000140
20FFFEFB E3EF4C0C 2D5C000C EAAF0043 AB0AFCAD FDAF9E2D 11000243 AB010000 ....C...-.........C......\-.L...... 000160
DFFCA905 D0FCADFD AF9E43AB D7D643AB CEAFF3FC ADFDAF9E 69110212 FFBBFDAB ........i..........C...C.......... 000180
FBFFFEDB D9EF9F00 00F31BFF 01FB00DD FFFF0DBC EF02FBF8 A9DFF8A9 17D0FCA9 ................................ 0001A0
01FF00FB 0000F320 FF01FB00 A97F0000 F2C6FF02 FB00A97F 07DD0000 F33EFF01 ..>...................... ....... 0001C0
0000F2CC FF01FB5F AF9FFCAD FDAF9EFD BE310000 F2DEFF01 FB0D9ECF 9F0000F3 ................1........_....... 0001E0

Virtual block number 174 (000000AE), 512 (0200) bytes

9FFBAB7F 0000F2B0 FF01FB10 7BCF9FFD 9E310313 FFFEAFA5 EF012007 BB03AB2D -.... .........1....x............. 000000
F246FF03 FBD3AB7F 00A97FFF FEDB73EF 9F0000F2 59FF03FB 00A97FFF FEDB7BEF .{..........Y.....s..............{F. 000020
FDAF9EFC ADFDAF9E 17BE31FC ADFDAF9E FD5F3100 00F27FFF 01FB0ED0 CF9F0000 .............1_.......1........... 000040
D00000F2 65FF00FB 0000F284 FF01FBFF FEDAFFEF 9F0000F2 69FF01FB 00DDFCAD ........i...................e.... 000060
00F233FF 01FB00DD FEFF0CD4 EF02FBF8 A9DFF8A9 18D0FCA9 DFFCA900 00004D8F .M...........................3.. 000080
01FB01AA CF9FFCAD FDAF9E00 00F22FFF 00FB0000 F256FF01 FBFFFEDB 09EF9F00 ..........V......./............... 0000A0
```

```
F8A918D0 FCA9DFFC A903D001 87310313 00000000 8F5C515C 47AB4E00 00F207FF .....N.G\Q\.......1............. 0000C0
0000F204 FF01FBFF FEDABFEF 9F0000F1 E1FF01FB 00DDFFFF 0C82EF02 FBF8A9DF ................................ 0000E0
FF165003 AB7E510B AB7EFFFF 10FAEF01 FB0BAB7F FCADFDAF 9E0000F1 DDFF00FB ......................^..Q^..F.. 000100
FF0FBFEF 02FB20A9 7F03AB7F D3110212 FFFEAEE7 EF002007 BB03AB2D 0000F16C 1...-........................... 000120
00FC3103 13FFFEAE 56EF0120 07BB03AB 2D0000F1 41FF1650 03AB7E51 20A97EFF .^. Q^..P..A...-.......V.....1.. 000140
50500000 F1AAFF01 FBFFFEDA 51EF9F4B AB504A00 00F1BBFF 01FBFFFE DA5AEF9F ..Z..........JP.K..Q..........PP 000160
FB1457CF 9FFCADFD AF9E3F11 00024FAB 0153ABF1 4FABD74F AB01D053 AB5C4A5C \J\.S...O..O..S..O...T.......W.. 000180
65FF01FB FFFEDA14 EF9F2711 0213FFFE ADB7EFFF FEE731EF 0C290090 F126FF01 ..Z...)..1............'........e 0001A0
FDAF9E00 7F31FCAD FDAF9E4F ABD7C44F AB53ABF3 FCADFDAF 9E4BAB50 4A0000F1 ...JP.K.......S.O...O.....1..... 0001C0
F8A917D0 FCA9DFFC A903D000 00F0D7FF 01FB0CA5 CF9F57AB 000042B8 8F4AFCAD ..J..B...W...................... 0001E0

Virtual block number 175 (000000AF), 512 (0200) bytes

0000F0E4 FF01FBFF FED9BFEF 9F0000F0 C1FF01FB 00DDFFFF 0B62EF02 FBF8A9DF ......b......................... 000000
34CF9F00 00F0A7FE 00FB0000 F0C6FF01 FB00A97F 0000F06C FF02FB00 A97F07DD ........1.......................4 000020
ADFDAF9E 0000F030 FF165003 AB7E52FF FEACEFEF 9E510132 0000F084 FF01FB0B ........2.Q......R^..P..O....... 000040
47AB4E00 00F04FFF 01FB121F CF9FFCAD FDAF9EFC ADFDAF9E 040000F0 41FF16FC ...A....................O...N.G 000060
02D0FCA9 DFFCA903 D0FCADFD AF9EFCAD FDAF9E06 75310313 0000000C 8F5C515C \Q\........1u................... 000080
F042FF01 FBFFFED9 25EF9F00 00F01FFF 01FB000D FFFF0AC0 EF02FBF8 A9DFF8A9 .....................%.......B. 0000A0
A904D0FC A9DFFCA9 03D00000 F00EFF00 FB0000F0 2DFF01FB FFFED920 EF9F0000 ...........-.................... 0000C0
00F003FF 01FBFFFE D8F6EF9F 0000EFE0 FF01FB00 DDFFFF0A 81EF02FB F8A9DFF8 ................................ 0000E0
F8A906D0 FCA9DFFC A903D000 00EFCFFF 00FB0000 EFEEFF01 FBFFFED8 F1EF9F00 ................................ 000100
0000EFC4 FF01FBFF FED8C7EF 9F0000EF A1FF01FB 00DDFFFF 0A42EF02 FBF8A9DF ......B......................... 000120
DFF8A908 D0FCA9DF FCA903D0 0000EF90 FF00FB00 00EFAFFF 01FBFFFE DBC2EF9F ................................ 000140
9F0000EF 85FF01FB FFFED898 EF9F0000 EF62FF01 FB00DDFF FF0A03EF 02FBF8A9 ............b................... 000160
A9DFF8A9 0AD0FCA9 DFFCA903 D00000EF 51FF00FB 0000EF70 FF01FBFF FED893EF ..............Q................. 000180
EF9F0000 EF46FF01 FBFFFED8 69EF9F00 00EF23FF 01FB00DD FFFF09C4 EF02FBF8 ..............#.....i......F..... 0001A0
F8A9DFF8 A90AD0FC A9DFFCA9 28D00000 EF12FF00 FB0000EF 31FF01FB FFFED864 d......1..........(.............. 0001C0
FF00FB00 00EEFFFF 01FBFFFE D83AEF9F 0000EEE4 FF01FB00 DDFFFF09 85EF02FB ..................:............. 0001E0

Virtual block number 176 (000000B0), 512 (0200) bytes

EEB2FF01 FB00DDFF FF0953EF 02FBF8A9 DFF8A90B D0FCA9DF FCA903D0 0000EEE0 ....................S.......... 000000
A1FE00EB 0000EEC0 FF01FBFF FED80BEF 9F0000EE D5FF01FB FFFED810 EF9F0000 ................................ 000020
00EE73FF 01FB00DD FFFF0914 EF02FBF8 A9DFF8A9 0CD0FCA9 DFFCA903 D00000EE .............................s.. 000040
FED7D7EF 9F0000EE 89FF01FB FFFED7DC EF9F0000 EE96FF01 FBFFFED7 E1EF9F00 ................................ 000060
EF9F0000 EE32FF02 FB00DDFF FED7CBEF 9F0000EE 55FF00FB 0000EE7C FF01FBFF ....1......U..............2...... 000080
500000ED 12EF1650 005C415C 182B410D 8F445C50 500000EE 7DFF01FB FFFED7AC ........}...PP\D..A+.\A\.P......P 0000A0
A9DFF8A9 0DD0FCA9 DFFCA903 D00000EE 11FF00FB 0000EF3C FF01FB7E 5C505C50 P\P\^...<....................... 0000C0
EF9F0000 EE06FF01 FBFFFED7 71EF9F00 00EDE3FF 01FB00DD FFFF0884 EF02FBF8 ...............q............... 0000E0
9F0000ED C5FF00FB 0000EDEC FF01FBFF FED767EF 9F0000ED F9FF01FB FFFED76C 1..............g................ 000100
8F445C50 500000ED EDFF01FB FFFED73C EF9F0000 EDA2FF02 FB00DDFF FED75BEF .[..............<.........PP\D. 000120
81FF00FB 0000EDAC FF01FB7E 5C505C50 500000EC 82EF1650 005C415C 930C3FC9 .?..\A\.P......PP\P\^........... 000140
00ED53FF 01FB00DD FFFF07F4 EF02FBF8 A9DFF8A9 0FD0FCA9 DFFCA903 D00000ED ..............................S.. 000160
ED42FF00 FB0000ED 61FF01FB FFFED6FC EF9F0000 ED76FF01 FBFFFED7 01EF9F00 ...........v..........a......B. 000180
0000ED14 FF01FB00 DDFFFF07 B5EF02FB F8A9DFF8 A910D0FC A9DFFCA9 03D00000 ................................ 0001A0
```

```
00ED03FF 00FB0000 ED22FF01 FBFFFED6 CDEF9F00 00ED37FF 01FBFFFE D6D2EF9F .........7.............'.........  0001C0
9F0000EC D5FF01FB 00DDFFFF 0776EF02 FBF8A9DF F8A911D0 FCA9DFFC A903D000 ...............V................  0001E0

Virtual block number 177 (000000B1), 512 (0200) bytes

0000ECC4 FF00FB00 00ECE3FF 01FBFFFE D69EEF9F 0000ECF8 FF01FBFF FFD6A3EF ................................  000000
EF9F0000 EC96FF01 FB00DDFF FF0737EF 02FBF8A9 DFF8A913 D0FCA9DF FCA903D0 ..............7.................  000020
D00000EC 85FF00FB 0000ECA4 FF01FBFF FED66FEF 9F0000EC B9FF01FB FFFED674 t.............o.................  000040
45EF9F00 00EC57FF 01FB00DD FFFF06F8 EF02FBF8 A9DFF8A9 14D0FCA9 DFFCA903 ..........................W.....E  000060
03D00000 EC46FF00 FB0000EC 65FF01FB FFFED640 EF9F0000 EC7AFF01 FBFFFED6 ......z.....@.....e......F.......  000080
D616EF9F 0000EC18 FF01FB00 DDFFFF06 B9EF02FB F8A9DFF8 A916D0FC A9DFFCA9 ................................  0000A0
A937D000 00EC07FF 00FB0000 EC26FF01 FBFFFED6 11EF9F00 00EC3BFF 01FBFFFE .....;..........&...........7.  0000C0
FED5E7EF 9F0000EB D9FF01FB 00DDFFFF 067AEF02 FBF8A9DF F8A902D0 FCA9DFFC ...................z............  0000E0
FF01FB00 A97F0000 EB4EEF03 FB00A97F FFFED5E0 EF9F02DD 0000EBFC FF01FBFF ........................N.........  000100
00EBC3FF 01FBFFFE D5BEEF9F 0000EBA0 FF01FB00 DD0000EB B9FF00FB 0000EBE0 ................................  000120
9F0000EB A5FF01FB 08A97F00 00E827EF 04FB08A9 7FFFFED5 A5EF9F03 DD03DD00 ..................'.............  000140
0000E7FC EF04FB00 A97FFFFE D57AEF9F 06DD02DD 0000EB98 FF01FBFF FED593EF ...................z..............  000160
FBF8A9DF F8A903D0 FCA9DFFC A937D000 00EB53FF 00FB0000 EB72FF01 FB00A97F ........r......S....7.............  000180
EF9F02DD 0000EB48 FF01FBFF FED54BEF 9F0000EB 25FF01FB 00DDFFFF 05C6EF02 ..........%.....K.......H.........  0001A0
DD0000EB 05FF00FB 0000EB2C FF01FB00 A97F0000 E79AEF03 FB00A97F FFFED544 D...............................  0001C0
7FFFFED5 09EF9F03 DD03DD00 00EB0FFF 01FBFFFE D50AEF9F 0000EAEC FF01FB00 ................................  0001E0

Virtual block number 178 (000000B2), 512 (0200) bytes

0000EAE4 FF01FBFF FED4DFEF 9F0000EA F1FF01FB 08A97F00 00E773EF 04FB08A9 ....s...........................  000000
00FB0000 EABEFF01 FB00A97F 0000E748 EF04FB00 A97FFFFE D4DEEF9F 06DD02DD ....................H...........  000020
71FF01FB 00DDFFFF 0512EF02 FBF8A9DF F8A904D0 FCA9DFFC A93CD000 00EA9FFF ......<........................q  000040
FF00FB00 00EA7FFF 01FBFFFE D4A2EF9F 0000EA94 FF01FBFF FED4A7EF 9F0000EA ................................  000060
FFFEF9B0 EF1E2DFF FF04D3EF 02FBF8A9 DFF8A906 D0FCA9DF FCA93CD0 0000EA60 `....<...................-.......  000080
FB0000EA 45FF01FB FFFED468 EF9F0000 EA22FF01 FB00DD1F 12FFFEA5 57EF1120 ..W.........".....h......E....  0000A0
00FB0000 EA26FF01 FBFFFED2 F1EF9F00 00EA03FF 01FB00DD 1D110000 EA1EFF00 .......................&........  0000C0
E9E2FF00 FB0000EA 01FF01FB FFFED434 EF9F0000 E9E6FF01 FB00DD00 00E9FFFF ....................4...........  0000E0
00E9B3FF 01FB00DD FCADFDAF 9EFCADFD AF9E0400 00E99BFF 16FCADFD AF9E0000 ................................  000100
FCA9DFFC A9000000 4D8FD000 00E9AFFF 00FB0000 E9CEFF01 FBFFFED2 49EF9F00 ...I......................M........  000120
00E99BFF 01FBEBAB 7F0000E9 7DFF01FB 00DDFFFF 041EEF02 FBF8A9DF F8A918D0 .........................}............  000140
03EAEF02 FBF8A9DF F8A905D0 FCA9DFFC A90AD0FC ADFDAF9E 0000E97C FF00FB00 ....|...........................  000160
320000E9 45FF00FB 0000E96C FF01FBFF FED39FEF 9F0000E9 49FF01FB 00DDFFFF .......I..........l......E...2  000180
084EEF01 FB0BAB7F FCADFDAF 9E0000E8 D9FF1650 13AB7E52 FFFEA66F EF9E5100 .Q..o....R~..P...................N.  0001A0
D3110212 FFFEA63B EF002007 BB03AB2D 0000E8C0 FF165003 AB7E510B AB7EFFFF ..^..Q^..P.....-.......;........  0001C0
5813AB3C 681204B9 00A92007 BB03AB2D 0000E8A8 FF02FB00 A97F0000 007F8FDD ...............-..........h<..X  0001E0

Virtual block number 179 (000000B3), 512 (0200) bytes

00E8B3FF 01FB00DD 0000E550 EF03FB13 AB7F13AB 7F5CDD5C 5C4A5C0B 425C5B4E N\\B.\J\\.\.........P..........  000000
EE01EBFE FED2FBEF 9E0000E8 CDFF01FB 08A97F00 00E86BFF 02FB08A9 7F08DD00 .........k......................  000020
00E883FF 00FB0000 E8AAFF01 FB00A97F 0000E848 FF02FB00 A97F08DD 0000E8C0 ...........H....................  000040
```

```
7F03AB7F 301304B9 00A92007 BB03AB2D 0000E828 FF02FB00 A97F0DDD FF4F3100 .10.........(...-.... .....0.... 000060
EB62FF01 FBFFFED2 A5EF9E00 00E83FFF 01FB00DD 0000E7FC FF03FB13 AB7F13AE ...................T...........b. 000080
310312FF FEA55AEF 002017BB 13AB2DFC ADFDAF9E FF073100 00E83BFF 00FB0000 .......1.......-..... ..Z.....1 0000A0
A97EFFFF 0622EF02 FB20A97F 00A97F00 00E497EF 03FB00A9 7F13AB7F 0ADDFEA6 ........................ ...."....". 0000C0
ADFDAF9E 2B110002 4FAB0119 F14FABD7 4FAB01D0 0000E7A4 FF163013 AB7E5120 0".P.........0..0....0...+.... 0000E0
F3FCADFD AF9E1511 0212FFFE ED5AEF4C 0A2017BB 13AB2D5C 000A1900 4FAB0AFC ...0....\-....  .L.Z............. 000100
4C3FABD1 5C000119 004FAB0A FCADFDAF 9E007B31 FCADFDAF 9E4FABD7 D84FAB19 ..0...0.....1(........0....\..?L 000120
0F19004F AB0A3FAB FFFEEFA2 EF4CD05C 00011900 4FAB0A61 110215FF FEEFB5EF ........e..0....\.L......?..0... 000140
FFFED1C8 EF9FF3AB 7F0000E7 15FF1650 F3AB7E52 FFFEEE08 EF4C9E51 0F325C00 .\2.Q.L.....R"..P............... 000160
75CF9F00 00E6EBFF 03FBD3AB 7F00A97F FFFED1C0 EF9F0000 E6FEFF03 FB00A97F .........................u 000180
EF02FBF8 A9DFF8A9 0AD0FCA9 DFFCA90A D0FCADFD AF9E5611 0000E724 FF01FB03 ....$....V...................... 0001A0
00E703FF 00FB0000 E722FF01 FBFFFED1 85EF9F00 00E707FF 01FB00DD FFFF01A8 ..........................'........ 0001C0
0000E6CC FF01FB01 7CCF9F00 00E697FF 1650F3AB 7E52FFFE A42DEF9E 51003200 .2.Q..-...R"..P.........!........ 0001E0
```

Virtual block number 180 (000000B4), 512 (0200) bytes

```
03FBFBAB 7FFBAB7F 0CDDFCAD FDAF9EFC ADFDAF9E 040000E6 9DFF16FC ADFDAF9E ................................ 000000
00E64BFF 16501BAB 7E52FFFE A3E1EF9E 5100325B AB5CD05C FBAB3C00 00E343EF .C...<..\.\.[2.Q......R"L.P..K..- 000020
01321615 5BAB4FAB D1FCADFD AF9E009C 3100034F AB010CF1 4FABD74F AB01D000 ....0..0....0..1..........0.[..2. 000040
FB03AB7F FBAB7F4F ABDD01DD 56110000 E61AFF16 5003AB7E 52FFFEA1 73EF9E51 Q..s...R"..P.......V....0....... 000060
5FAB4E5F AB504A00 00E538EF 1650504E 0000E454 EF01FB03 AB7F0000 E2F6EF04 ............T...NPP..8....JP..N.= 000080
01CE0311 58D40414 00004364 8F575157 5FAB4E5C 01CE0311 5CD40419 34585158 XOX4...\.....\N._WQW.dC.....X.... 0000A0
9E0000E5 A9FF03FB 1BAB7F1B AB7F03AB 7FFCADFD AF9E3911 02135CD5 5C58C85B X.X\.\...9....................... 0000C0
00E58FFF 1650FBAB 7E511BAB 7EFCADFD AF9E4FAB D7FF674F AB010CF1 FCADFDAF ........0g...0......"..Q"..P..... 0000E0
00E5B3FF 01FB00DD 0000E5CC FF00FB00 00E5C3FF 01FB00DD FCADFDAF 9E661100 ..f............................. 000100
FF01FBFF FED023EF 9F0000E5 CDFF01FB 00A97F00 00E29BEF 02FB00A9 7F0ADD00 .........................$...... 000120
7E52FFFE A2B9EF9E 51003200 00E577FF 01FB27AF 9F0000E5 99FF00FB 0000E5B8 ............'...w...2.Q......R" 000140
D0FCADFD AF9EFCAD FDAF9E04 0000E534 FF16FCAD FDAF9E00 00E523FF 1650FBAB ..P..$.........4................ 000160
DD20DD00 00E537FF 01FB00DD FFFEFFD8 EF02FBF8 A9DFF8A9 18D0FCA9 DFFCA901 ........................7.... . 000180
FCA929D0 0000E528 FF00FB00 00E54FFF 01FB00A9 7F0000E1 F9EF03FB 00A97F28 (..............0.......(.....).. 0001A0
A97F24DD 20DD0000 E4FAFF01 FB00DDFF FEFF9BEF 02FBF8A9 DFF8A918 D0FCA9DF ........................ .$.. 0001C0
FCA9DFFC A901D000 00E4EBFF 00FB0000 E512FF01 FB00A97F 0000E1BC EF03FB00 ................................ 0001E0
```

Virtual block number 181 (000000B5), 512 (0200) bytes

```
05D00000 E4C6FF00 FB0000E4 BDFF01FB 00DDFFFE FF5EEF02 FBF8A9DF FBA901D0 ..........^..................... 000000
CF26EF9E 0000E498 EE01FB00 DDFFFEFF 39EF02FB F8A9DFF8 A918D0FC A9DFFCA9 ...............9..............3. 000020
7EFFFF03 B1EF01FB 0BAB7FFC ADFDAF9E 0000E494 FF00FB00 00E4BBFF 01FBFFFE ...............................~ 000040
A92027BB 23AB2D00 00E41FFF 02FB00A9 7F0DDD00 00E423FF 165023AB 7E510BAB ..Q".#P..$..............-.$.' . 000060
A901D0FC ADFDAF9E FCADFDAF 9E040000 E416FF16 FCADFDAF 9EC91102 1304B900 ................................ 000080
03FB00A9 7F28DD20 DD0000E4 1DFF01FB 00DDFFFE FEBEEF02 FB57ABDF FCA9DFFC ......W................ .(...... 0000A0
57ABDFFC A9DFFCA9 29D00000 E40EFF00 FB0000E4 2DFF01FB 00A97F00 00E0DFEF .............-..........).......W 0000C0
A97F0000 E0A6EF03 FB00A97E 28DD20DD 0000E3E4 FF01FB00 DDFFFEFE 85EF02FB ................ .(.............. 0000E0
FCADFDAF 9EFCADFD AF9E0400 00E393FF 160000E3 D5FF00FB 0000E3F4 FF01FB00 ................................ 000100
E392FF01 FB02DD00 C6310312 00000000 8F5C515C FFFEF2F8 EF4E7FAB 00E7CF7E ......N.....\Q\.......1......... 000120
01FBFFFE CDDAEF9F 0000E3AC FF01FB00 A97F0000 DC17EF02 FB00A97F 00DD0000 ................................ 000140
```

```
0AFGADFD AF9E63AB 084A0000 E36EFF00 FB0000E3 8DFF01FB D3AB7F00 00E39FFF ..................n...J..c...... 000160
5C63AB4E 0000E2F0 FF1650CB AB4C7E52 FFFE6087 EF9E5100 325C0001 030063AB .c....\2.Q......R^L..F......N.c\ 000180
12FFFEA0 58EF0020 04BC6C2D 5CCBAB4C 7E5C0001 030063AB 0A63AB5C 4A5C0840 @.\J\.c..c....\^L..\-1.. ..X.... 0001A0
E322FF01 FB00A97F 0000DFF0 EF02FB00 A97F0ADD 0000E308 FF01FB02 DB3C1102 ..<............................. 0001C0
9EFF7B31 0000E2E8 FF00FB00 00E307FF 01FBCBAB 4C7F5C00 01030063 AB0A0000 ....c....\.L................1(.. 0001E0
```

Virtual block number 182 (000000B6), 512 (0200) bytes

```
01FBE1AF 9FFFFEF2 09EF0000 00008F4A FCADFDAF 9E040000 E29EFF16 FCADFDAF ................J............... 000000
EF02FBF8 A9DFF8A9 18D0FCA9 DFFCA903 D0FCADFD AF9EFCAD FDAF9E00 00E29BFF ................................ 000020
00E283FF 00FB0000 E2AAFF01 FBFFFECD 1DEF9F00 00E287FF 01FB00DD FFFEFD28 (............................... 000040
FB0000E2 55FF01FB 00DDFFFE FCF6EF02 FBF8A9DF F8A901D0 FCA9DFFC A901D000 ...........................U.... 000060
9E47AB00 0000008F 4AFCADFD AF9EFCAD FDAF9E04 0000E21C FF160000 E25EFF00 ..^.....................J......G. 000080
0000E20C FF01FB01 12CF9F4B AB504A00 00E277FF 01FBFFFE CB16EF9F FCADFDAF ..............w...JP.K.......... 0000A0
AF5C515C 50500000 E24EFF01 FBFFFECA F5EF9F00 F2310313 D1AF5C51 5C47AB4E N.G\Q\....1...........N...PP\Q\. 0000C0
0000E1CC FF01FB04 20CF9FFF FEF14FEF 01638F20 FFFE9F2B EF002CBA 110213B8 ........+.....c..0.............. 0000E0
FFFE9EF7 EF002C5C 000C0000 00648F00 43AB0A00 B2310313 91AF5C51 5C47AB4E N.G\Q\....1....C..d......\...... 000100
7F7E43AB 6EFFFECC 3DEF9FFC ADFDAF9E 4BAB0000 00008F4A FFFEEA3A EF4C0C20 .L.:...J.......K..........n.C^. 000120
FFFECC20 EF9F00A9 7F0000E1 39FF1650 00A97E51 20A97E00 00DDB9EF 04FB20A9 . .......^. Q^..P..9.......... 000140
01FB03DD 0000E148 FF02FB03 DD43ABDD 7FAB0586 CF9E0000 E11EFF03 FBD3AB7F .................C.....H........ 000160
20A97F7E 4BAB6EFF FECBDFEF 9FFFFEF0 81EF0C20 FFFE9E8B EF002C00 00E11BFF ..........................n.K^.. 000180
9E0000E1 2DFF02FB 03DD43AB DDFFFEF0 6DEF0320 24B920A9 2C0000DD 2BEF04FB ...+..... .$ ..m.....C......-..... 0001A0
0000E0EC FF01FB04 1DCF9FFC ADFDAF9E FCADFDAF 9E040000 E0DFFF16 FCADFDAF ................................ 0001C0
EF04FB20 A97F7E43 AB6EFFFE CB82EF9F 02993103 13000000 008F5C51 5C47AB4E N.G\Q\.......1.........n.C^..... 0001E0
```

Virtual block number 183 (000000B7), 512 (0200) bytes

```
03FBD3AB 7FFFFECB 6DEF9F00 A97F0000 E07EFF16 5000A97E 5120A97E 0000DCCE ....^. Q^..P..^........m........ 000000
0000DF91 EF16505C 000043C8 8F475C08 425C4BAB 4E7FAB04 CBCF9E00 00E063FF .c.........N.K\B.\G..C..\P...... 000020
4FAB584A 585C4258 4BAB4E5C E0AF445C 08425C67 AB4E67AB 5C4A5C08 405C5050 PP\@.\J\.gN.g\B.\D..\N.KXB\XJX.@ 000040
EFFFFEED 9FEF4C9E 58DD5858 4A580842 584FAB4E 5C000000 00648F03 00670B0A ..g...d....\N.OXB.XJXX.X.L...... 000060
08A97F10 A97FFFFE CAFEEF9F 0000DCD4 EF03FB10 A97FFFFE CB06EF9F FFFFECB10 ................................ 000080
5643564F AB4E5858 4A580840 584FAB4E 5C00B8AF 030067AB 0A0000DF E1FF03FB ..........g.....\N.OX@.XJXXN.OVCV 0000A0
7FFFFECA C1EF9FFF FECACBEF FFFEED4A EF4C9E58 DD57DD57 574A5700 0043C88F ..C..WJWW.W.X.L.J............... 0000C0
ED1CEF4C 9E08A97F 00A97F5C 00000000 648F0300 67AB0A00 00DC93EF 04FB00A9 ...........g....d....\.......L... 0000E0
0000DFA4 FF02FB05 DD67ABDD 0000DF74 FF03FBFF FECA9BEF 9FFFFECA A5EFFFFE .................t.....g......... 000100
7E52FFFE ECE0EF4C 9E510064 8F325C00 BFAF0300 67AB0A00 00DF77FF 01FB05DD .....w.....g......\2.d.Q.L.....R^ 000120
DFC6FF01 FBFFFECB 75EF9F00 00DF97FF 02FB05DD 67ABDD00 00DF43FF 16502BAB .+P..C.....g.............u....... 000140
8F20FFFE 9C99EF00 2C6FAB50 4A0000DF B5FF01FB FFFECA44 EF9F6BAB 504A0000 ..JP.k..D...........JP.o........ 000160
500000DF 89FF01FB FFFEC830 EF9F0000 DF3AFF01 FB02D0CF 9FFFFED4 31EF014E N..1........:......O..........P 000180
DF0AFF01 FB023BCF 9F4BAB6B AB D000AB 316FAB00 0000006F 4A0B1208 5C515C50 P\Q\...J.......o1....k.K..+...... 0001A0
EFEF04FB 20A97F7E 6FAB6EFF FEC9A3EF 9F00BA31 0313DFAF 5C515C47 AB4E0000 ..N.G\Q\....1.........n.o^...... 0001C0
5C515C47 AB4E0000 DED2FF01 FB0268CF 9FFFFED4 ECEF0320 24B920A9 2C0000DA ..... .$ ........h.........N.G\Q\ 0001E0
```

```
Virtual block number 184 (000000B8), 512 (0200) bytes

13BAAF5C 515C47AB 4E0000DE B5FF01FB 01E6CF9F 4BAB6FAB D000B231 0313A7AF ....1....o.K...........N.C\Q\... 000000
95EF0320 24B920A9 2C0000DA 9BEF04FB 20A97F7E 6BAB6EFF FEC94FEF 9F661102 ..f..O...n.k~.. ........ .$ ... 000020
FDAF9E2C 11021300 0000008F 5C515C47 AB4E0000 DE7EFF01 FB0214CF 9FFFFED4 ..........~...N.C\Q\........... 000040
CF9F77AB 6FABD073 AB5C4A5C 08425C50 500000DE B9FF01FB FFFEC760 EF9FFCAD ....`..........PP\B.\J\.s..o.w.. 000060
4AFCADFD AF9EFCAD FDAF9E04 0000DE14 FF16FCAD FDAF9E00 00DE43FF 01FB0097 .....C..........................J 000080
5000A97E 5120A97E 0000DA1A EF04FB20 A97F7E43 AB6EFFFE C8CEEF9F 47ABB3AF ...G......n.C~.. .......~. Q~..P 0000A0
DD7FAB02 17CF9E00 00DDAFFF 03FBD3AB 7FFFFEC8 E9EF9F00 A97F0000 DDCAFF16 ................................ 0000C0
C6BEEF9F 73AB50D0 0000DE34 FF01FBFF FEC6D7EF 9F0000DD D9FF02FB 04DD43AB .C.................4....P.s.... 0000E0
AF9EFCAD FDAF9E04 0000DD90 FF16FCAD FDAF9E77 AB50D000 00DE23FF 01FBFFFE ....4....P.w.................... 000100
7E0000D9 93EF04FB 20A97F7E 43AB6EFF FEC847EF 9F47AB00 0000005F 4AFCADFD ...J......G..G....n.C~.. .......~ 000120
0000DD28 FF03FBD3 AB7FFFFE C86AEF9F 00A97F00 00DD43FF 165000A9 7E5120A9 . Q^..P..C.........J..........(... 000140
2024B920 A92C0000 D958EF04 FB20A97F 7E73AB6E FFFEC85C EF9F7FAB 0190CF9E .........\....n.s~.. ...X..... .$ 000160
2024B920 A92C0000 D938EF04 FB20A97F 7E77AB6E FFFEC7EC EF9FFFFE EE18EF02 .............n.w~.. ...8..... .$ 000180
DD43ABDD 0000DCD0 FF165033 AB7E52FF FEEC93EF 9E510163 8F32FFFE EDFAEF03 ......2.c.Q......R~.3P........C. 0001A0
ABDDFFFE EC66EFCF AF2037BB 33AB2C00 00DCCFFF 01FB04DD 0000DCFC FF02FB04 .................r.3.7 ....f..... 0001C0
FCADFDAF 9EFCADFD AF9E0400 00DCB3FF 16FCADFD AF9E0000 DD02FF02 FB04DD43 C............................... 0001E0

Virtual block number 185 (000000B9), 512 (0200) bytes

5120A97E 0000D8B6 EF04FB20 A97F7E4B AB6EFFFE C76AEF9F 47AB0000 0000BF4A J......C..J....n.K~.. .......~. Q 000000
B3CF9E00 00DCABFF 03FBD3AB 7FFFFEC7 9DEF9F00 A97F0000 DC66FF16 5000A97E ~..P..f.................K....... 000020
FCADFDAF 9E040000 DC4EFF16 FCADFDAF 9E0000DC 75FF02FB 06DD4BAB DD7FAB00 .....K.....u..........N......... 000040
A97E0000 D854EF04 FB20A97F 7E43AB6E FFFEC708 EF9F47AB 9AAF4AFC ADFDAF9E .....J...G......n.C~.. ...T...~. 000060
9E0000DB E9FF03FB D3ABZFFF FEC743EF 9F00A97F 0000DC04 FF165000 A97E5120  Q^..P...........C............. 000080
FB06DD4B ABDD0000 DBD2FF16 5033AB7E 52FFFED1 09EF9E51 014E8F32 7FAB52AF .R..2.N.Q......R~.3P........K... 0000A0
DD4BABDD FFFEDODC EFCFAF20 37BB33AB 2C0000DB D1FF01FB 06DD0000 DBFEFF02 .................r.3.7 .........K. 0000C0
00DDFCAD FDAF9EFC ADFDAF9E 040000DB B5FF16FC ADFDAF9E 0000DC04 FF02FB06 ................................ 0000E0
03FBD3AB 7FFFFEC6 C5EF9FD3 AB7F47AB 084A0000 DBD6FF00 FB0000DB CDFF01FB ................J..G............. 000100
D790EF04 FB20A97F 7E5C6EFF FEC643EF 9F5C50D0 0000DB84 FF00FB00 00DB63FF .c............P\..C...n\~.. ..... 000120
25FF03FB 10A97FFF FEC68FEF 9F18A97F 0000DB40 FF165018 A97E5120 A97E0000 ...^. Q^..P..@.................% 000140
5C50D000 00DB37FF 00FB0000 DB12FF03 FB08A97F 10A97FFF FEC687EF 9F0000DB ........................7....P\ 000160
00DAEFFF 165000A9 7E5128A9 7E0000D7 3FEF04FB 28A97F7E 5C6EFFFE C672EF9F ..r....n\~..(...?...~.(Q~..P..... 000180
FF01FBD3 AB7F0000 DB1AFF01 FB00DD00 00DAD7FF 03FBDBAB 7F08A97F 00A97F00 ................................ 0001A0
00FB0000 DB1EFF01 FBDBAB7F 0000DB00 FF01FB00 DD0000DB 19FF00FB 0000DB38 8............................... 0001C0
01FB07AF 9F0000DA D1FF01FB F581CF9F 0000DADC FF01FBF7 2DCF9F00 00DAFFFF ......-......................... 0001E0

Virtual block number 186 (000000BA), 512 (0200) bytes

FE9313EF 9EFCADFD AF9EFCAD FDAF9E04 0000DA98 FF16FCAD FDAF9E00 00DABBFF ................................ 000000
DA86FF16 5150D050 FFFE97E4 EF9E52FB AF9ECFFC 045001D0 0000DA7C FF165OFF .P..l.....P......R......P.PQ.... 000020
FFFEC5A0 EF9F0000 DA7AFF01 FB00DDFC ADFDAF9E FCADFDAF 9EFCADFD AF9E0000 ..........................z........ 000040
F8A9DFF8 A918D0FC A9DFFCA9 0000004D 8FD00000 DA76FF00 FB0000DA 95FF01FB ..........v.....M.............. 000060
FF00FB00 00DA67FF 01FBFFFE C572EF9F 0000DA44 FF01FB00 DDFFFEF4 E5EF02FB ..............D.....r.......8...... 000080
DA12FF01 FB00DDFF FEF4B3EF 02FBF8A9 DFF8A905 D0FCA9DF FCA916D0 0000DA40 @............................... 0000A0
```

```
A908D0FC A9DFFCA9 19D00000 DA0EFF00 FB0000DA 2DFF01FB FFFEC548 EF9F0000 ....H.......-................... 0000C0
00D9FBFF 01FBFFFE C51EEF9F 0000D9E0 FF01FB00 DDFFFEF4 81EF02FB F8A9DFF8 ................................ 0000E0
FB00DDFF FEF44FEF 02FBF8A9 DFF8A90B D0FCA9DF FCA914D0 0000D9DC FF00FB00 .........................D...... 000100
A9DFFCA9 14D00000 D9AAFF00 FB0000D9 C9FF01FB FFFEC4F4 EF9F0000 D9AEFF01 ................................ 000120
01FBFFFE C4CAEF9F 0000D97C FF01FB00 DDFFFEF4 1DEF02FB F8A9DFF8 A90CD0FC ..................|............. 000140
FEF3EBEF 02FBF8A9 DFF8A90D D0FCA9DF FCA914D0 0000D978 FF00FB00 00D997FF .......x........................ 000160
14D00000 D946FF00 FB0000D9 65FF01FB FFFEC4A0 EF9F0000 D94AFF01 FB00DDFF ......J............e......F..... 000180
C476EF9F 0000D918 FF01FB00 DDFFFEF3 B9EF02FB F8A9DFF8 A90ED0FC A9DFFCA9 .............................v.. 0001A0
02FBF8A9 DFF8A910 D0FCA9DF FCA914D0 0000D914 FF00FB00 00D933FF 01FBFFFE .....3.......................... 0001C0
D8E2FF00 FB0000D9 01FF01FB FFFEC44C EF9F0000 D8E6FF01 FB00DDFF FEF387EF ................L............... 0001E0
```

Virtual block number 187 (000000BB), 512 (0200) bytes

```
0000D8B4 FF01FB00 DDFFFEF3 55EF02FB F8A9DFF8 A911D0FC A9DFFCA9 14D00000 ......................U......... 000000
FCA9DFFC A914D0FC ADFDAF9E 0000D8B0 FF00FB00 00D8CFFF 01FBFFFE C122EF9F ................................ 000020
FF01FBFF FEC3F3EF 9F0000D8 7DFF01FB 00DDFFFE F31EEF02 FBF8A9DF F8A914D0 ......................}......... 000040
FFFEF2EC EF02FBF8 A9DFF8A9 14D0FCA9 DFFCA92B D00000D8 79FF00FB 0000D898 ........y.....+................. 000060
0000D7F0 FF1650FE 9ECB7E51 FE97CB7E FFFEF780 EF01FBFE 97CB7FFC ADFDAF9E ...................~...Q~...P... 000080
D4A6EF03 FB00A97F FE9FCB7F 01DDCE11 0212FFFE A31EEF00 20FEA3DB FE9FCB2D -............................... 0000A0
AF9E0000 D7B2FF16 50FE9FCB 7E5128A9 7EFFFEF6 31EF02FB 28A97F00 A97F0000 ........(....1...~.(Q~...P...... 0000C0
4B310000 D7CEFF01 FB0557CF 9F0E12FF FEA2DAEF 0120FEA3 DBFE9FCB 2DFCADFD ...-....................W......1K 0000E0
00D7ABFF 01FB38B7 CF9F0E12 FFFEA2B6 EF0120FE A3DBFE9F CB2DFCAD FDAF9EFD ......-.................8....... 000100
FF01FB39 19CF9F0E 12FFFEA2 92EF0120 FEA3DBFE 9FCB2DFC ADFDAF9E FD283100 .1(.........-................9... 000120
41B5CF9F 0E12FFFE A26EEF01 20FEA3DB FE9FCB2D FCADFDAF 9EFD0531 0000D7B8 ....1.........-..........n.......A 000140
D40413FF FEA24AEF 0120FEA3 DBFE9FCB 2DFCADFD AF9EFCE2 310000D7 65FF01FB ...e...1.......-.........J....... 000160
5C58C858 01CE0311 58D40413 FFFEA232 EF0120FE A3DBFE9F CB2D5C01 CE03115C \....\-...........2.......X....X.X\ 000180
02322113 5CD55C58 C85801CE 031158D4 0413FFFE A217EF01 20FEA3DB FE9FCB2D -.................X....X.X\.\.12. 0001A0
9EFC6D31 FFFEF2BC EF01FB00 A97F0000 D6BAFF16 5000A97E 52FFFEA1 FCEF9E51 Q......R^..P................1m.. 0001C0
9EFE3531 FCADFDAF 9E60E931 0312FFFE A1D0EF01 20FEA3DB FE9FCB2D FCADFDAF ....-...................1.`.....15.. 0001E0
```

Virtual block number 188 (000000BC), 512 (0200) bytes

```
FB0000D6 DDFF01FB FFFEC1E8 EF9F0000 D6C2FF01 FB00DDFC ADFDAF9E FCADFDAF ................................ 000000
DDFFFEF1 2DEF02FB F8A9DFF8 A918D0FC A9DFFCA9 0000004D 8FD00000 D6BEFF00 .........M...................... 000020
FCA916D0 0000D688 FF00FB00 00D6AFFF 01FBFFFE C20AEF9F 0000D6BC FF01FB00 ................................ 000040
FFFEC190 EF9F0000 D65AFF01 FB00DDFF FEF0FBEF 02FBF8A9 DFF8A905 D0FCA9DF ........................Z....... 000060
C9EF02FB F8A9DFF8 A907D0FC A9DFFCA9 1AD00000 D656FF00 FB0000D6 75FF01FB ...u......V..................... 000080
0000D624 FF00FB00 00D643FF 01FBFFFE C1AEEF9F 0000D628 FF01FB00 DDFFFEF0 .........(.........C.....$...... 0000A0
EF9F0000 D5F6FF01 FB00DDFF FEF097EF 02FBF8A9 DFF8A90A D0FCA9DF FCA914D0 ................................ 0000C0
F8A9DFF8 A90BD0FC A9DFFCA9 14D00000 D5F2FF00 FB0000D6 11FF01FB FFFEC184 ................................ 0000E0
FF00FB00 00D5DFFF 01FBFFFE C15AEF9F 0000D5C4 FF01FB00 DDFFFEF0 65EF02FB ....e..................Z........ 000100
D592FF01 FB00DDFF FEF033EF 02FBF8A9 DFF8A90C D0FCA9DF FCA914D0 0000D5C0 .........................3...... 000120
A90DD0FC A9DFFCA9 14D00000 D5BEFF00 FB0000D5 ADFF01FB FFFEC130 EF9F0000 ....0........................... 000140
00D57BFF 01FBFFFE C106EF9F 0000D560 FF01FB00 DDFFFEF0 01EF02FB F8A9DFF8 ......................`.......{.. 000160
FB00DDFF FEEFCFEF 02FBF8A9 DFF8A90E D0FCA9DF FCA914D0 0000D55C FF00FB00 ....\........................... 000180
D0FCADFD AF9E0000 D52AFF00 FB0000D5 49FF01FB FFFEC0DC EF9F0000 D52EFF01 ................I.......*....... 0001A0
```

```
ADEF9F00 00D4F7FF 01FB00DD FFFEEF98 EF02FBF8 A9DFF8A9 11D0FCA9 DFFCA914 ................................ 0001C0
FBF8A9DF F8A912D0 FCA9DFFC A914D000 00D4F3FF 00FB0000 D512FF01 FBFFFEC0 ................................ 0001E0

Virtual block number 189 (000000BD), 512 (0200) bytes

C1FF00FB 0000D4E0 FF01FBFF FEC083EF 9F0000D4 C5FF01FB 00DDFFFE EF66EF02 ..f............................. 000000
FB00DDFF FEEF2FEF 02FBF8A9 DFF8A914 D0FCA9DF FCA914D0 FCADFDAF 9E0000D4 ........................./...... 000020
A9DFFCA9 2DD00000 D48AFF00 FB0000D4 A9FF01FB FFFEC054 EF9F0000 D48FFF01 ........T....................... 000040
7EFFFEF3 91EF01FB FE97CB7F FCADFDAF 9EFFFEEE FDEF02FB F8A9DFF8 A914D0FC ...............................~ 000060
110212FF FE9F2FEF 0020FEA3 DBFE9FCB 2D0000D4 01FF1650 FE9FCB7E 51FE97CB ...Q^...P......-.......... /.......~ 000080
A97EFFFE F242EF02 FB28A97F 00A97F00 00D0B7EF 03FB00A9 7FFE9FCB 7F01DDCE ......................(...B...~. 0000A0
FFFE9EEB EF0120FE A3DBFE9F CB2DFCAD FDAF9E00 00D3C3FF 1650FE9F CB7E512B (Q^...P..........-............ 0000C0
2D014331 0000D390 FF1650FE A7CB7E52 FFFE9E55 EF9E5101 32FF67CB 084A1D12 ..J..g.2.Q..U...R^...P......1C.- 0000E0
CB7E52FF FE9E27EF 9E510132 FF67CB10 4A1D12FF FE9EBDEF 0120FEA3 DBFE9FCB ..................J..g.2.Q..'...R^. 000100
67CB144A 1D12FFFE 9E8FEF01 20FEA3DB FE9FCB2D 01163100 00D363FF 1650FEA7 ..P..c...1..-.............J..g 000120
FEA3DBFE 9FCB2D00 E9310000 D336FF16 50FEA7CB 7E52FFFE 9DF9EF9E 510132FF .2.Q......R^...P..6...1..-...... 000140
09FF1650 FEA7CB7E 52FFFE9D CBEF9E51 0132FF67 CB184A1D 12FFFE9E 61EF0120 ..a.....J..g.2.Q......R^...P... 000160
EF9E5101 32FF67CB 1A4A1D12 FFFE9DAD EF0120FE A3DBFE9F CB2D00BC 310000D3 ...1..-.........J..g.2.Q.. 000180
20FEA3DB FE9FCB2D FCADFDAF 9E008F31 0000D2DC FF1650FE A7CB7E52 FFFE9D9C ....R^...P......1.......-...... 0001A0
D40413FF FE9DE9EF 0120FEA3 DBFE9FCB 2D5C01CE 03115CD4 0413FFFE 9E01EF01 ..........\....\-............... 0001C0
5801CE03 1158D40A 13FFFE9D CEEF0120 FEA3DBFE 9FCB2D5C 58C85301 CE031158 X....X.X\-...............X....X 0001E0

Virtual block number 190 (000000BE), 512 (0200) bytes

01FB00A9 7F0000D2 71FF1650 00A97E52 FFFE9D2E EF9E5102 3221135C D55C58C8 .X\.\.!2.Q......R^..P..a.......... 000000
31031102 12FFFE9D 87EF0120 FEA3DBFE 9FCB2DFC ADFDAF9E FBDC31FF FEEE73EF .s...1.......-.................1 000020
FE9CDAEF 9E510332 FCADFDAF 9EFCADFD AF9E0400 00D25BFF 16FCADFD AF9EFE2D -........[...............2.Q..... 000040
B7CB2D00 00D24FFF 01FB488A CF9FFF6B CB084A00 00D21FFF 1650FEAF CB7E52FF .R^...P......J..k....H...O...-.. 000060
0000D22C FF01FBFB 66CF9FFC ADFDAF9E 03853103 12FFFE9D 41EF0020 FEBBDBFE ......A.....1..........f........ 000080
BD3EEF9F 0000D218 FF01FB00 DD036231 0312FFFE 9D14EF01 20FEA3DB FE9FCB2D -..............1b...........>. 0000A0
DFF8A917 D0FCA9DF FCA90000 004D8FD0 0000D214 FF00FB00 00D233FF 01FBFFFE .....3............M........... 0000C0
FB0000D1 FDFF01FB FFFEBDB0 EF9F0000 D1E2FF01 FB00DDFF FEEC83EF 02FBF8A9 ................................ 0000E0
FF01FB00 DDFFFEEC 51EF02FB F8A9DFF8 A90AD0FC A9DFFCA9 0AD00000 D1DEFF00 .........................Q........ 000100
A1FF00FB 0000D1C0 FF01FBFE A7CB7F00 00D1D3FF 01FBFFFE BD86EF9F 0000D1B0 ................................ 000120
9F02AE31 03130000 00008F5C 515CFF6F CB4E0000 D17EFF01 FB25CCCF 9F0000D1 ......Z...^...N.o.\Q\.......1... 000140
01FBFFFE BD3AEF9F 02953103 13E3AF5C 515CFF6F CB4E0000 D162FF01 FB56EACF ..V...b...N.o.\Q\....1....:..... 000160
BD1EEF9F 5C01CE03 115CD404 12C3AF58 515BFF73 CB4EFF73 CB504A00 00D1A3FF .....JP.s.N.s.XQX.....\....\.... 000180
D55C58CA 5858D258 01CE0311 58D40412 A6AF5851 58505000 00D17FFF 01FBFFFE .........PPXQX.....X....X.XX.X\. 0001A0
FCA9DFFC A90AD000 00D0F3FF 01FB4CF3 CF9FFF77 CB000042 B88F4A54 1102135C \...TJ..B...w....L............... 0001C0
FF01FBFF FEBCCBEF 9F0000D0 DDFF01FB 00DDFFFE EB7EEF02 FBF8A9DF F8A917D0 ..........~...................... 0001E0

Virtual block number 191 (000000BF), 512 (0200) bytes

CB7FFCAD FDAF9E01 F4310000 D0B6FF01 FB4B93CF 9F0000D0 D9FF00FB 0000D0F8 ...............K.......1.......... 000000
FBFD57CB 7F00A97F FEFEBCA0 EE9F0000 D056FF03 FB00A97F FFFEBCA8 EF9FFEA7 ...............V..............W.. 000020
FCA90AD0 0000D070 FF01FB01 CCCF9F00 00D07BFF 01FB4D00 CF9F0000 D042FF03 ..B.......M...{...........B....... 000040
```

```
FFFEBC60 EF9F0000 D05AFF01 FB00DDFF FEEAFBEF 02FBF8A9 DFF8A90C D0FCA9DF ......................Z.....`... 000060
08425CFF 67CB4E00 00D033FF 01FB57E0 CF9F0000 D056FF00 FB0000D0 75FF01FB ...u......V......W...3...N.a.\B. 000080
0000D00C FF01FB54 8ECF9FFC ADFDAF9E FF7BCB5C 4A5C8000 44998F40 5C14445C \D.\@..D..\J\.{.........T....... 0000A0
504A0000 D04AFF01 FBFFFEBC 11EF9F01 3C310313 00000000 8F5C515C FF6FCB4E N.o.\Q\.......1<...........J...JF 0000C0
FF67CB4E 01113103 13D1AF5C 515CFF6F CB4E0000 CFDEFF01 FB52F0CF 9FFF7FCB ......R.......N.o.\Q\....1..N.a. 0000E0
00CC5BEF 04FB00A9 7FFFFEBB D9EF9F5C DD02DD5C 5C4A5C08 405C1044 5C08425C \B.\D.\@.\J\\...\.............[.. 000100
0283AB01 87ABF183 ABD783AB 01D087AB 5C4A5C50 500000CF FDFF01FB 00A97F00 ...........PP\J\................ 000120
ABD7E583 AB87ABF3 FCADFDAF 9E0000CF 79FF01FB 057CCF9F FCADFDAF 9E1E1100 ..........|....a................ 000140
FB00A97F 0000CC00 EF04FB00 A97FFFFE BB86EF9F FF7BCBDD 03DDFCAD FDAF9E83 ..........{..................... 000160
9F0000CF 2DFF01FB 4EC1CF9F 0B121A5C 515CFF67 CB4E8BAB 504A0000 CFA2FF01 ......JP..N.a.\Q\......N...-.... 000180
5801CE03 1158D404 135C5751 57FF73CB 4E5C5050 0000CF7C FF01FBFF FEBB1BEF ........|...PP\N.s.WQW\...X....X 0001A0
5C01CE03 115CD404 13000000 008F5C51 5C505000 00CF5BFF 01FBFFFE BAFAEF9F ..........[...PP\Q\........\....\ 0001C0
CECAFF01 FB0089CF 9FFCADFD AF9EFEBE 31FF73CB 8BABD009 11021358 D5585CC8 .\X.X.........s.1............... 0001E0
```

Virtual block number 192 (000000C0), 512 (0200) bytes

```
0000CE88 FF16FCAD FDAF9EFC 7B31FCAD FDAF9E00 00CEBFFF 01FB577D CF9F0000 ....>W.............1{............ 000000
FCADFDAF 9E211100 028FAB01 13F18FAB D78FAB01 D0FCADFD AF9EFCAD FDAF9E04 ........................!..... 000020
ADFDAF9E 8FABD7E2 8FAB13F3 FCADFDAF 9EF2BBCB 4C88AF4A 5C000113 008FAB0A .......\J..L.................... 000040
25FF16A3 ABE8AF4A 9FABEDAF 4A9BABF2 AF4A97AB F7AF4A93 AB000000 008F4AFC .J.......J....J....J....J......% 000060
FF01FBFF FEB963EF 9F0000CE 3DFF01FB 00DDFCAD FBAF9EFC ADFDAF9E 040000CE ..................".....c....... 000080
0000CDCC FF1650FE BFCB7E52 FFFE97FA EF9E512C 320000CE 39FF00FB 0000CE58 X......9...2,Q......R~...P...... 0000A0
7F0000CE 25FF01FB 00A97F00 00CAF3EF 02FB00A9 7F0ADD00 00CE0BFF 01FB00DD ........................%.... 0000C0
8FAB01D0 0000CDD0 FF01FB55 C7CF9F00 00CDF3FF 00FB0000 CE12FF01 FBFEBFCB ....................U........... 0000E0
58F2BBCB 4C4E5C00 0113008F AB0AFCAD FDAF9E01 4F310003 8FAB0112 F18FABD7 ...........10..............\NL...X 000100
FFFEB9C4 EFFFFEC4 81EF4C9E 5C001213 008FAB0A 011C3103 12000000 008F5851 QX.......1..........\.L.......... 000120
7F10A97F FFFEB9B4 EF9F0000 CD32FF03 FB10A97F FFFEB9BC EF9FFFFE B9BAEF9F ....................2........... 000140
7F7EFFFE C5A6EF4C 50FFFEB9 A1EF9F5C 00011300 8FAB0A00 00CD1FFF 03FB08A9 ...............\.......PL.....~. 000160
BFCB7F08 A97F00A9 7F0000CC F9FF1650 00A97E51 28A97E00 00C92FEF 03FB2BA9 .(.../...^.(Q~\.P............... 000180
008FAB0A 0000CCCC FF03FB10 A97FFEBF CB7FFFFE B972EF9F 0000CCE0 FF03FBFE ..........r..................... 0001A0
A97E5128 A97E0000 C8F8EF04 FB28A97F 7EF2BBCB 4C6EFFFE B95EEF9F 5C000113 ...\..^...nL...^..(........~.(Q^. 0001C0
A97FFFFE B932EF9F 0000CC90 FF03FB00 A97F10A9 7F08A97F 0000CCA8 FF165008 .P.........................2.... 0001E0
```

Virtual block number 193 (000000C1), 512 (0200) bytes

```
00C9A7EF 02FB00A9 7F0ADD00 00CCBFFF 01FB00DD 0000CC7C FF03FBFE BFCB7F00 .........|...................... 000000
7BCF9F00 00CCA7FF 00FB0000 CCC6FF01 FBFEBFCB 7F0000CC D9FF01FB 00A97F00 ...............................{ 000020
ADFDAF9E 8FABD7FE B48FAB01 12F1FCAD FDAF9EFC ADFDAF9E 0000CC84 FF01FB54 T............................... 000040
28A97F7E F307CB6E FFFEB8B0 EF9F0086 31031200 0000008F 5C515CF3 07CB4EFC .N...\Q\.......1........n....~..( 000060
A97FFFFE BB9AEF9F 0BA97F00 00CBFBFF 165008A9 7E512BA9 7E0000C8 4BEF04FB ...K...~.(Q~..P................. 000080
01FB00DD 0000CBCC FF03FBFE BFCB7F00 A97FFFFE B882EF9F 0000CBE0 FF03FB00 ................................ 0000A0
FBFEBFCB 7F0000CC 29FF01FB 00A97F00 00C8F7EF 02FB00A9 7F0ADD00 00CC0FFF ......................).......... 0000C0
3DEF9FFC ADFDAF9E 0000CBD4 FF01FB53 CBCF9F00 00CBF7FF 00FB0000 CC16FF01 .................S.............= 0000E0
9F0000CB 71FF1650 00A97E51 28A97E00 00C7C1EF 04FB28A9 7F7E93AB 6FFFFEBB ...n..~..(........~.(Q~..P..o.... 000100
28A97F7E 97AB6EFF FEB807EF 9F0000CB 55FF03FB FEBFCB7F 00A97FFF FEB823EF .#.............U.........n..~..( 000120
FB00A97F FEBFCB7F 08A97F00 00CB3BFF 165008A9 7E5128A9 7E0000C7 8BEF04FB .......~.(Q~..P..;.............. 000140
```

```
FFFEB7C0 EF9F0000 CB0EFF03 FBFEBFCB 7F00A97F FFFEB7E4 EF9F0000 CB22FF03 ................................ 000160
7F08A97F 0000CAF4 FF165008 A97E5128 A97E0000 C744EF04 FB28A97F 7E9BAB6E n..~..(...D...~.(Q~..P.......... 000180
00CAC7FF 03FBFEBF CB7F00A9 7FFFFEB7 A5EF9F00 00CADBFF 03FB00A9 7FFEBFCB ................................ 0001A0
0000CB24 FF01FB00 A97F0000 C7F2EF02 FB00A97F 0ADD0000 CB0AFF01 FB00DD00 ............................$... 0001C0
3DEF9F00 00CACFFF 01FB52C6 CF9F0000 CAF2FF00 FB0000CB 11FF01FB FEBFCB7F ......................R.........= 0001E0
```

Virtual block number 194 (000000C2), 512 (0200) bytes

```
9F0000CA 71FF1650 00A97E51 28A97E00 00C6C1EF 04FB28A9 7F7E9FAB 6EFFFEB7 ...n..~..(.......~.(Q~..P..a.... 000000
28A97E7E A3AB6EFF FEB707EF 9F0000CA 55FF03FB FEBFCB7F 00A97FFF FCB73BEF ..............U.........n..~..( 000020
FB00A97F FEBFCB7F 08A97F00 00CA3BFF 165008A9 7E5128A9 7E0000C6 8BEF04FB .......~.(Q~..P................ 000040
51FF01FB 00DD0000 CA0EFF03 FBFEBFCB 7F00A97F FFFEB6FC EF9F0000 CA22FF03 ...............................Q 000060
FF01FBFE BFCB7F00 00CA6BFF 01FB00A9 7F0000C7 39EF02FB 00A97F0A DD0000CA ..........9.........E........... 000080
00CA0BFF 01FB44E8 CF9F0000 CA16FF01 FB520DCF 9F0000CA 39FF00FB 0000CA58 X......9......R...........D...... 0000A0
0000C6C4 EF03FB08 A97F27DD 20DDFCAD FDAF9EFC ADFDAF9E 0A0000C9 E1FF1600 .................. .'........... 0000C0
BBCF9F00 00C98BFF 03FBFEBF CB7F08A9 7F00A97F 0000C0B4 EF02FB00 A97F00DD ................................ 0000E0
9BCF9F00 00C96FFF 1650FEBF CB7E52FF FE930FEF 9E511F32 0000C9D4 FF01FB51 Q.......2.Q.......R~...P..o...... 000100
00320000 C98EFF01 FB10D7CF 9F0000C9 99FF01FB 0E29CF9F 0000C9A4 FF01FB51 Q.........)..................2., 000120
8F500000 C96EFF01 FB5165CF 9F0000C9 39FF1650 FEBFCB7E 52FFFE94 85EF9E51 Q......R~..\P..9......eQ...n...P. 000140
FB513DCF 9F0000C9 11FF1650 FEBFCB7E 52FFFE92 80EF9E51 3132A7AB 00000000 ......21Q......R~...P.........=Q. 000160
5C8FAB4E FCADFDAF 9E025B31 00038FAB 011AF18F ABD78FAB 01D00000 C946FF01 ..F.................1E......N..\ 000180
C5BAEF04 FB00A97F FFFEB5B8 EF9FABAB DD02DDAB AB5C4A5C 08405C1C 445C0842 B.\D.\@.\J\...................... 0001A0
EF9F5CDD 04DD5C5C 4A5C1040 5CABAB4E AFAB50D0 0000C960 FF01FB00 A97F0000 ........`....P..N..\@.\J\\...\.. 0001C0
8FB3AB51 B3AB5050 0000C930 FF01FB00 A97F0000 C58EEF04 FB00A97F FFFEB58C ...................0...PP..Q... 0001E0
```

Virtual block number 195 (000000C3), 512 (0200) bytes

```
031158D4 0412FFFE C5BAEF4C AFABD15C 00011A00 8FAB0A01 D5310312 00000000 ......1..........\...L.........X.. 000000
5857C857 01CE0311 57D40413 CCAFFFFE C896EF4C 515C0001 1A008FAB 0A5801CE ..X.......\QL...........W....W.WX 000020
9189EF9E 51043200 00C833FF 1650FEC7 CB7E52FF FE919EEF 9E510432 2013S8D5 .X.-2.Q......R~...P..3...2.Q.... 000040
EF9E5104 32171800 0043C88F B3AB5100 C3310000 C81EFF16 50FECFCB 7E52FFFE ..R~...P......1..Q....C....2.Q.. 000060
FED7CB7E 52FFFE91 DAEF9E51 04321511 0000C7FC FF1650FE D7CB7E52 FFFE9163 c...R~...P.........2.Q......R~... 000080
C7CB7E51 28A97E00 00C3FFEF 03FB28A9 7F7EB3AB 50FED7CB 7F0000C7 E5FF1650 P..........P..~..(........~.(Q~.. 0000A0
95AFB7AB 51B7ABB3 ABFFFEC7 F1EF4C47 5C00011A 008FAB0A 0000C7C8 FF1650FE .P.............\QL.........Q.... 0000C0
9173EF9E 51043215 110000C7 95FF1650 FED7CB7E 52FFFE70 FCEF9E51 04321718 ..2.Q.......R~...P.........2.Q..s. 0000E0
03FB28A9 7F7EB7AB 50FED7CB 7FA7ABB7 AB400000 C77EFF16 50FED7CB 7E52FFFE ..R^...P..^...@.........P..^..(.. 000100
00181A00 8FAB0AFC ADFDAF9E 0000C75C FF1650FE CFCB7E51 28A97E00 00C393EF .....~.(Q~...P..\................ 000120
25FF03FB 20A97FFF FEB427EF 9FFFFEB4 31EFFFFE C4F2EF4C 9EFFFEB4 31EF9F5C \..1....L......1.....'.........X 000140
10A97F18 A97FFFFE B396EF9F 0000C714 FF03FB18 A97F20A9 7FFEC7CB 7F0000C7 ................................ 000160
FEB3E7EF 9FFFFEB3 F1EFFFFE C79EEF4C 9E5C0006 1A008FAB 0A0000C7 01FF03FB ..............\.L................ 000180
00C6C7FF 03FB00A9 7F08A97F FFFEB3DC EF9F0000 C6DAFF03 FB08A97F 10A97FFF ................................ 0001A0
AF9E0000 C6EEFF01 FB4EE5CF 9F0000C6 B5FF03FB FEBFCB7F 00A97FFE CFCB7F00 ..........................N....... 0001C0
9E510032 FCADFDAF 9EFCADFD AF9E8FAB D7FDA88F AB011AF1 FCADFDAF 9EFCADFD ..........................2.Q. 0001E0
```

```
Virtual block number 196 (000000C4), 512 (0200) bytes

9E513132 0000C6B0 FF01FB4E A7CF9F00 00C67BFF 1650FEBF CB7E52FF FE91C7EF .....R^...P..C......N........21Q. 000000
8FAB01D0 0000C690 FF01FB4E 87CF9F00 00C65BFF 1650FEBF CB7E52FF FE8F87EF .....R^...P..C......N............ 000020
4A5C0840 5C20445C 08425C8F AB4EFCAD FDAF9E02 72310003 8FAB0104 F18FABD7 ..........1r......R..\B.\D \@.\J 000040
C6AAFF01 FB00A97F 0000C304 EF04FB00 A97FFFFE B32AEF9F ABABDD02 DDABAB5C \.........*...................... 000060
EF04FB00 A97FFFFE B2FEEF9F 5CDD02DD 5C5C4A5C 10405CAB AB4EBBAB 50D00000 ...P..R..\@.\J\\...\............. 000080
5CDD04DD 5C5C4A5C 18405CAB AB4EBFAB 50D00000 C67EFF01 FB00A97F 0000C2D8 ..........^....P..N..\Q.\J\\...\ 0000A0
AB0AB7AB 50500000 C64EFF01 FB00A97F 0000C2AC EF04FB00 A97FFFFE B2D2EF9F .....................N...PP..... 0000C0
AB51F2BB CB48574A 57B7AB40 57F2BBCB 4C4E5800 011300BF AB0A5C00 011300BF .....\.......XNL....W@..WJWH...Q. 0000E0
04321713 FFFEBBEC EF4CBBAB D15C0001 1300BFAB 0A01A031 03120000 00008FB7 ..........1.........\...L.......2. 000100
FFFEB200 EF9FA7AB B7AB4028 110000C5 59FF1650 FECFCB7E 52FFFE8E C4EF9E51 Q......R^...P..Y....(@........... 000120
FDAF9E00 00C533FF 1650FECF CB7E5128 A97E0000 C16AEF03 FB28A97F 7FB7AB50 P..^..(...J...^.(Q^...P..3...... 000140
B21EEF9F FFFEB228 EFFFFEBC 45EF4C9E FFFEB1A0 EF9F5C00 121300BF AB0AFCAD .................\.......L.E....(....... 000160
FEBDB3EF 4C50FFFE B17EEF9F 5C000113 00BFAB0A 0000C4FC FF03FB08 A97FFFFE ....................\..^...PL.... 000180
08A97F00 A97F0000 C4D6FF16 5000A97E 5128A97E 0000C10C EF03FB28 A97F7EFF .^..(.........^.(Q^..P........... 0001A0
0A0000C4 A9FF03FB 08A97FFE BFCB7FFF FEB1BFEF 9F0000C4 BDFF03FB FFBFCB7F ................................ 0001C0
7E0000C0 D3EF04FB 28A97F7E FFFEC140 EF4C6EFF FEB1BBEF 9F5C0001 1300BFAB ......\.......nL.Q...^..(........^ 0001E0

Virtual block number 197 (000000C5), 512 (0200) bytes

EF9F0000 C46AFF03 FBFEBFCB 7F08A97F 00A97F00 00C4B3FF 165000A9 7E5128A9 .(Q^..P...................J...... 000000
FEC0A3EF 4C4E5C00 011300BF AB0A0000 C436FF03 FB18A97F FEBFCB7F FFFEB0E4 ..............V..........\NL.... 000020
28A97E00 00C05BEF 03FB28A9 7F7E5C50 FFFEB160 EF9F5C58 000043C8 8F475BFF .XG..C..X\..`...P\^..(...C...^.( 000040
FEB0F7EF 9F0000C4 0DFF03FB 08A97F18 A97F10A9 7F0000C4 25FF1650 10A97E51 O^..P..%......................... 000060
0000C3E8 FF03FBFE BFCB7F00 A97FFECF CB7F0000 C3FAFF03 FB00A97F 08A97FFF ................................ 000080
9E8FABD7 FD918FAB 0104F1FC ADFDAF9E FCADFDAF 9E0000C4 21FF01FB 4C18CF9F ...L...!........................ 0000A0
D5EF9F00 83310319 5CA7AB51 5C505000 00C457FF 01FBFFFE BOEFEF9F FCADFDAF ..........W...PP\Q..\..1..... 0000C0
03FB28A9 7F7E5850 FFFEB048 EF9F585C A7AB435C 50500000 C43EFF01 FBFFFEB0 ......>...PP\C..\X..H...PX^..(.. 0000E0
CB7FFFFE B0A2EF9F FECFCB7F 0000C37C FF1650FE CFCB7E51 28A97E00 00BFB3EF .....^.(Q^...P..|.............. 000100
4A585C40 58F307CB 4E5C5050 0000C3F4 FF01FBFE CFCB7F00 00C35FFF 03FBFEBF .....-.............PP\N...X@\XJ 000120
A7AB5050 0000C3CC FF01FBFF FEB063EF 9F0000C3 7DFF01FB 4B74CF9F F307CB58 X.....tK...}.....c..........PP.. 000140
FEBFCB7F 00A97FFF FEB04FEF 9F0000C0 31EF03FB 00A97F2C DD20DDFC ADFDAF9E ......,.......1.....O........... 000160
0000C004 EF03FB10 A97F1DDD 20DD0000 C33AEF01 FB4B31CF 9F0000C3 01FF03FB ..........1K...:................ 000180
28A97F7E A7AB50FF FEAF87EF 9F0000C2 D5FF03FB 08A97F10 A97FFFFE B02AEF9F ..*.....................P..^..( 0001A0
FBFEBFCB 7F08A97F 00A97F00 00C2BBFF 165000A9 7E5128A9 7E0000BE F1EF03FB ........^.(Q^..P................ 0001C0
405C93AB 4E231800 0044668F A7AB5100 00C2DBFF 01FB4AD2 CF9F0000 C2A2FF03 .........J.......Q...fD...#N..\@ 0001E0

Virtual block number 198 (000000C6), 512 (0200) bytes

AB5100A5 310000C2 71FF1650 FEDFCB7E 52FFFEBB 51EF9E51 0432930AB 5C4A5C08 .\J\..2.Q..Q...R^...P..q....1..Q. 000000
DFCB7E52 FFFE8B20 EF9E5104 3297AB5C 4A5C0840 5C97AB4E 23180000 45118FA7 ...E...#N..\@.\J\..2.Q.. ...R^.. 000020
9BAB5C4A 5C08405C 9BAB4E22 18000045 878FA7AB 51007831 0000C244 FF1650FE .P..D...1x.Q....E...'N..\@.\J\.. 000040
18000046 028FA7AB 514C1100 00C217FF 1650FEDF CB7E52FF FE8AEFEF 9E510432 2.Q......R^...P.......LQ....F... 000060
00C1EBFF 1650FEDF CB7E52FF FE8ABFEF 9E510432 9FAB5C4A 5C08405C 9FAB4E22 'N..\@.\J\..2.Q......R^...P..... 000080
C9FF1650 FEDFCB7E 52FFFE8A 99EF9E51 0432A3AB 5C4A5C08 405CA3AB 4E201100 .. N..\@.\J\..2.Q......R^...P... 0000A0
```

```
7F10A97F FFFEAEFC EF9F0000 BECEEF03 FB10A97F 1BDD20DD FCADFDAF 9E0000C1 ................................ 0000C0
FFFEAEE0 EF9F0000 C18EFF03 FB00A97F 08A97FFE DFCB7F00 00C19FFF 03FB08A9 ................................ 0000E0
FF01FB49 F3CF9F00 00C1B3FF 01FB49AA CF9F0000 C17AFF03 FBFEBFCB 7F00A97F ..........I..........I... 000100
BE3AEF04 FB00A97F FFFEAEB0 EF9F01DD 01DDFCAD FDAF9EFC ADFDAF9E 0000C1A8 ..............................!. 000120
FEBFCB7E 52FFFEC6 B3EF9E51 28324011 0212FFFE B9EFEF01 2004B900 A92D0000 ..-.............@2(Q......R^... 000140
FEBFCB7E 52FFFEC6 BBEF9E51 28320000 C15AFF01 FB4951CF 9F0000C1 25FF1650 P..%.....QI...Z...2(Q......R^... 000160
FFFE8976 EF9E5127 32FCADFD AF9E0000 C13AFF01 FB4931CF 9F0000C1 05FF1650 P........1I...!........2'Q..v... 000180
C10AFF01 FB059ACF 9F0000C1 15FF01FB 490CCF9F 0000C0E0 FF1650FE BFCB7E52 R^...P.........I................ 0001A0
895BEF01 2004B900 A92D0000 BDA6EF04 FB00A97F FFFEAE1C EF9F07DD 01DD0000 ..........................-.....E. 0001C0
FB48BDCF 9F0000C0 91FF1650 FEBFCB7E 52FFFED0 D9EF9E51 32322011 0212FFFE ..... 22Q......R^...P.........H. 0001E0

Virtual block number 199 (000000C7), 512 (0200) bytes

EF03FB18 A97F1DDD 20DD0000 C0B6FF01 FB07FFCF 9FFCADFD AF9E0000 C0C6FF01 ................................ 000000
A7AB50EF EEAD03EF 9F0000C0 51FF03FB 10A97F18 A97FFFFE ADC6EF9F 0000BD30 ..................Q.........P.. 000020
7F10A97F 08A97F00 00C037FF 16500 8A9 7E5128A9 7F0000BC 6DEF03FB 28A97F7E ^..(...m...^.(Q^..P..7.......... 000040
3BCF9F00 00C00BFF 03FBFEBF CB7F00A9 7FFFFEAC C1EF9F00 00C01FFF 03FB00A9 ...............................; 000060
FE8B2BEF 9E510032 FCADFDAF 9E0000C0 39FF01FB 0566CF9F 0000C044 FF01FB48 H...D.....f....9.........2.Q..+.. 000080
FE8817EF 9E513132 0000C014 FF01FB48 0BCF9F00 00BFDFFF 1650FEBF CB7E52FF .R^...P..........H........21Q..... 0000A0
FEBAEBEF 9E510032 0000BFF4 FF01FB47 EBCF9F00 00BFBFFF 1650FEBF CB7E52FF .R^...P..........G........2.Q..... 0000C0
FE87A6EF 9E513132 0000BFD4 FF01FB47 CBCF9F00 00BF9FFF 1650FEBF CB7E52FF .R^...P..........G........21Q..... 0000E0
ACC6EF9F 05DD01DD 0000BFB4 FF01FB47 ABCF9F00 00BF7FFF 1650FEBF CB7E52FF .R^...P..........G................ 000100
B5EF9F00 E3310312 FFFE8805 EF012004 B900A92D 0000BC30 EF01FB00 A97FFFFE ........P..-.............1..... 000120
FBFFFEAC 99EF9F00 C7310312 00000000 8F5C515C 50500000 BFDEFF01 FBFFFEAC ..........PP\Q\.......1......... 000140
FB28A97F 7EA7AB50 FFFEABC8 EF9FC3AB 58A A58A7 AB5C475C 50500000 BFC2FF01 ......PP\G\..XJX........P..^..(. 000160
00A97F08 A97FFFFE AC66EF9F 0000BEFC FF165008 A97E5128 A97E0000 BB32EF03 ..2...^.(Q^..P.........f......... 000180
FEAC47EF 9F0000BE CDFF03FB FEBFCB7F 00A97FFF FEAC4BEF 9F0000BE E1FF03FB .........K.....................G.. 0001A0
EFEF04FB 28A97F7E C3AB6EFF FEABD3EF 9F0000BE B9FF03FB 10A97FFE BFCE7FFF ........................n..^..(.... 0001C0
00BE87FF 03FB00A9 7F10A97F 08A97F00 00BE9FFF 165008A9 7E5128A9 7E0000BA ...^.(Q^..P....................... 0001E0

Virtual block number 200 (000000C8), 512 (0200) bytes

0000BEAC FF01FB46 A3CF9F00 00BE73FF 03FBFEBF CB7F00A9 7FFFFEAC 09EF9F00 ..................s......F........ 000000
012004B9 00A92D00 00BB43EF 04FB00A9 7FFFFEAB B9EF9F08 DD01DDFC ADFDAF9E ..................C............... 000020
CF9F0000 BE2EFF16 50FEBFCB 7E52FFFE 897AEF9E 51003260 110212FF FE86FBCF ........`2.Q..z...R^...P......... 000040
CF9F0000 BE0EFF16 50FEBFCB 7E52FFFE CEBDEF9E 51283200 00BE63FF 01FB465A ZF...c...2(Q......R^...P......... 000060
CF9F0000 BDEEFF16 50FEBFCB 7E52FFFE CEC5EF9E 51283200 00BE43FF 01FB463A :F...C...2(Q......R^...P......... 000080
AF9EFCAD FDAF9E00 00BE13FF 01FB465E CF9FFCAD FDAF9E00 00BE23FF 01FB461A .F...^...........^F.......#...... 0000A0
00A97F00 00B4C3EF 02FB00A9 7F00DD00 00BAD3EF 03FB08A9 7F27DD20 DDFCADFD ....'........................... 0000C0
EF01FB02 58CF9F00 00BDD3FF 01FB45CA CF9F0000 BD9AFF03 FBFEBFCB 7F08A97F ................E.........X...... 0000E0
FB459DCF 9F0000BD 6DFF03FB FEBFCB7F FFFEAB10 EF9FFFFE AB0EEF9F 0000BDC8 ......................m.......E. 000100
7BCF9F00 00BD4BFF 03FBFEBF CB7FFFFE AAFEEF9F FFFEAAFC EF9F0000 BDA6FF01 ........................K......{ 000120
5BCF9F00 00BD2BFF 03FBFEBF CB7FFFFE AAE6EF9F FEB7CB7F 0000BD84 FF01FB45 E.......................+......[ 000140
00BA23EF 03FB18A9 7F1DDD20 DD0000BD 59FF01FB 04A2CF9F 0000BD64 FF01FB45 E...d..........Y.........$.. 000160
A97F7EA7 AB50FFFE A9A6EF9F 0000BCF4 FF03FB10 A97F18A9 7FFFFEAA 69EF9F00 ...i......................P..^.. 000180
FB00A97F 10A97F08 A97F0000 BCDAFF16 5008A97E 5128A97E 0000B910 EF03FB28 (.......^.(Q^..P................. 0001A0
```

```
01FB44DE CF9F0000 BCAEFF03 FBFEBFCB 7F00A97F FFFEA964 EF9F0000 BCC2FF03 ........d.....................D.. 0001C0
1650FEBF CB7E52FF FE87D3EF 9E510032 0000BCDC FF01FB02 09CF9F00 00BCE7FF ...............2.Q......R"...P. 0001E0

Virtual block number 201 (000000C9), 512 (0200) bytes

1650FEBF CB7E52FF FE83F1EF 9E512432 0000BCBC FF01FB44 B3CF9F00 00BCB7FF ........D.......2$Q......R"...P. 000000
EF9E5100 320000BC 91FF01FB 08B9CF9F 0000BC9C FF01FB44 93CF9F00 00BC67FF .u......D..................2.Q.. 000020
FEA997EF 9F0000BC 71FF01FB 4468CF9F 0000BC3C FF1650FE BFCB7E52 FFFE8788 ....R"...P..<.....hD............ 000040
FF01FBFF FEA97BEF 9F00C731 03120000 00008F5C 515C5050 0000BCC0 FF01FBFF ........PP\Q\.......1.....{...... 000060
EF03FB28 A97F7EA7 AB50FFFE ABAAEF9F C3AB5B4A 5BA7AB5C 475C5050 0000BCA4 ....PP\C\..XJX........P.."..(... 000080
03FB00A9 7F08A97F FFFEA948 EF9F0000 BBDEFF16 5008A97E 5128A97E 0000B814 ....".(Q"..P.......H............ 0000A0
7FFFFEA9 29EF9F00 00BBAFFF 03FBFEBF CB7F00A9 7FFFFEA9 2DEF9F00 00BBC3FF ......-..................)...... 0000C0
00B7D1EF 04FB28A9 7F7EC3AB 6EFFFEA8 B5EF9F00 00BB9BFF 03FB10A9 7FFEBFCB ......................n..."..(....... 0000E0
9F0000BB 69FF03FB 00A97F10 A97F08A9 7F0000BB 81FF1650 08A97E51 28A97E00 ."(Q"..P.....................i.... 000100
AF9E0000 BB8EFF01 FB4385CF 9F0000BB 55FF03FB FEBFCB7F 00A97FFF FEA8EBEF ...............U......C.......... 000120
9FF6ADFD AF9EFCAD FDAF9E04 0000BB54 FF160000 BB7EFF01 FB43C9CF 9FFCADFD ......C...".....T............... 000140
A97F08A9 7FFFFEA8 D5EF9F00 00BB13FF 03FB08A9 7FFFFEA8 DDEF9FFF FEA8DBEF ................................ 000160
431CCF9F 0000BAEC FF03FBFE BFCB7F00 A97FFFFE A8CAEF9F 0000BB00 FF03FB00 ...............................C 000180
CF9F0000 BACAFF03 FBFEBFCB 7FFFFEA8 B5EF9FFF FEA8B3EF 9F0000BB 25FF01FB ...%............................ 0001A0
0000BAA8 FF03FBFE BFCB7FFF FEABA3EF 9FFFFEA8 A1EF9F00 00BB03FF 01FB42FA .B.............................. 0001C0
9E510032 FCADFDAF 9EFCADFD AF9E0400 00BAB7FF 160000BA E1FF01FB 42D8CF9F ...B.........................2.Q. 0001E0

Virtual block number 202 (000000CA), 512 (0200) bytes

9E512632 0000BAB0 FF01FB42 A7CF9F00 00BA7BFF 1650FEBF CB7E52FF FE85C7EF .....R"...P..{......B.......2&Q. 000000
8FAB01D0 0000BA90 FF01FB42 87CF9F00 00BA5BFF 1650FEBF CB7E52FF FE8193EF .....R"...P..[......B........... 000020
4A5C0840 5C1C445C 08425C8F AB4EFCAD FDAF9E01 B5310003 8FAB011A F1BFABD7 ..........1.......N..\B.\D.\@.\J 000040
BAAAFF01 FB00A97F 0000B704 EF04FB00 A97FFFFE A702EF9F ABABDD02 DDABAB5C \............................... 000060
EF04FB00 A97FFFFE A6D6EF9F 5CDD04DD 5C5C4A5C 10405CAB AB4EAFAB 50D00000 ...P..N..\@.\J\\...\............ 000080
0A012F31 03120000 00008FB3 AB51B3AB 50500000 BA7AFF01 FB00A97F 0000B6D8 ..........z...PP..Q.........1/.. 0000A0
00011A00 8FAB0A58 01CE0311 58D40412 FFFEB704 EF4CAFAB D15C0001 1A008FAB ......\...L........X.....X...... 0000C0
E8EF9E51 04321713 58D55857 C85701CE 03115704 0413CCAF FFFEB9E0 EF4C515C \QL.........W.....W.WX.X..2.Q... 0000E0
EF9E5104 32171800 0043C88F B3AB5157 110000B9 7DFF1650 FEC7CB7E 52FFFE82 ...R"...P..>....WQ.....C.....2.Q.. 000100
FED7CB7E 52FFFE83 3AEF9E51 04321511 0000B95C FF1650FE D7CB7E52 FFFE82C3 ....R"...P..\.....2.Q.....R"... 000120
C7CB7E51 28A97E00 00B55FEF 03FB28A9 7F7EB3AB 50FED7CB 7F0000B9 45FF1650 P..E.......P.."..(...._....".(Q".. 000140
B6BEEF4C 9EFFFEA5 FDEF9F5C 00181A00 8FAB0AFC ADFDAF9E 0000B928 FF1650FE .P..(...............\.......L... 000160
A97F10A9 7FFEC7CB 7F0000B8 F1FF03FB 10A97FFF FEA6F3EF 9FFFFEA6 FDEFFFFE ................................ 000180
1A008FAB 0A0000B8 CDFF03FB 00A97F08 A97FFFFE A562EF9F 0000B8EQ FF03FB08 ..........b..................... 0001A0
A5FF03FB FEBFCB7F 00A97FFF FEA6B3EF 9FFFFEA6 BDEFFFFE B96AEF4C 9E5C0006 ..\.L.J......................... 0001C0
D7FE4E8F AB011AF1 FCADFDAF 9EFCADFD AF9E0000 B8DEFF01 FB40D5CF 9F0000B8 .....@......................N.. 0001E0

Virtual block number 203 (000000CB), 512 (0200) bytes

FE83ABEF 9E510032 FCADFDAF 9EFCADFD AF9E0400 00BB9BFF 16FCADFD AF9E8FAB ........................2.Q..... 000000
EFFFFEBE 1FEF0129 0000B894 FF01FB40 8BCF9F00 00B85FFF 1650FEBF CB7E52FF .R"...P._........@.......)....... 000020
4EFCADFD AF9E01BE 3100038F AB0104F1 8FABD78F AB01D001 D7310313 FFFE82FF ......1..................1.......N 000040
```

```
04FB00A9 7FFFFEA5 1DEF9FAB ABDD02DD ABAB5C4A 5C08405C 20445C08 425C8FAB ..\B.\D \@.\J\................... 000060
DD02DD5C 5C4A5C10 405CABAB 4EBBAB50 D00000B8 9DFF01FB 00A97F00 00B4F7EF ...............P..N..\@.\J\\.... 000080
4EBFAB50 D00000B8 71FF01FB 00A97F00 00B4CBEF 04FB00A9 7FFFFEA4 F1EF9F5C \....................@....P..N 0000A0
00A97F00 00B49FEF 04FB00A9 7FFFFEA4 C5EF9F5C DD04DD5C 5C4A5C18 405CABAB ..\@.\J\\...\................... 0000C0
A4B6EF9F 5C01CE03 115CD404 13000000 008FB7AB 51B7AB50 500000B8 41FF01FB ...A...PP..Q.........\....\..... 0000E0
03135CD5 5C58C858 01CE0311 58D40413 DFAF5851 58505000 00B81FFF 01FBFFFE .........PPXQX.....X....X.X\.\.. 000100
B7E6FF01 FBFFFEA4 7DEF9F58 FFFEAFF0 EF4CB7AB 455C0001 1300BFAB 0A00E131 1.........\E..L.....X.:}........ 000120
51053217 13FFFEAD ADEF4CBB ABD15C00 011300BF AB0AC7AB 585C475C 50500000 ..FP\G\X..........\...L.......2.Q 000140
A97F7EC7 AB50FFFE A516EF9F 23110000 B71AFF16 50FEE7CB 7E52FFFE 7E4DEF9E ..M~..R~...P.........P..~.. 000160
9F5C0012 1300BFAB 0A0000B6 F9FF1650 FEE7CB7E 5128A97E 0000B330 EF03FB28 (...O...~.(Q~...P.............\. 000180
00B6C7FF 03FB10A9 7FFFFEA4 E1EF9FFF FEA4EBEF FFFEAE10 EF4C9EFF FEA36BEF .k....L......................... 0001A0
03FB00A9 7F08A97F FEE7CB7F 0000B6B4 FF03FB08 A97F10A9 7FFFFEA4 D9EF9F00 ................................ 0001C0
FF01FB3E BFCF9F00 00B68FFF 03FBFEBF CB7F00A9 7FFFFEA4 BDEF9F00 00B6A3FF ............................>... 0001E0
```

Virtual block number 204 (000000CC), 512 (0200) bytes

```
02C131FC ADFDAF9E 8FABD7FE 458FAB01 04F1FCAD FDAF9EFC ADFDAF9E 0000B6C8 ..................E.........1.. 000000
0104F18F ABD78FAB 01D001C3 310313FF FE7D77EF FFFEBC32 EF0129FC ADFDAF9E .....)..2....w}....1............ 000020
DD02DDAB AB5C4A5C 08405C20 445C0842 5C8FAB4E FCADFDAF 9E01AA31 00038FAB ....1.......N..\B.\D \@.\J\..... 000040
BBAB50D0 0000B6B0 FF01FB00 A97F0000 B30AEF04 FB00A97F FFFEA330 EF9FABAB ....O.........................P.. 000060
A97F0000 B2DEEF04 FB00A97F FFFEA304 EF9F5CDD 02DD5C5C 4A5C1040 5CABAB4E N..\@.\J\\...\.................. 000080
FFFEA2D8 EF9F5CDD 04DD5C5C 4A5C1840 5CABAB4E BFAB50D0 0000B684 FF01FB00 .........P..N..\@.\J\\...\...... 0000A0
00000000 8FB7AB51 B7AB5050 0000B654 FF01FB00 A97F0000 B2B2EF04 FB00A97F ................T...PP.Q........ 0000C0
FE7EEAEF 9E510432 1713FFFE AC12EF4C BBABD15C 00011300 BFAB0A00 FB310312 ..1.........\...L.......2.Q...~. 0000E0
95EF03FB 28A97F7E B7AB50FF FEA22BEF 9F231100 00B57FFF 1650FECF CB7E52FF .R~...P........+...P..~..(.... 000100
FFFEA1D0 EF9F5C00 121300BF AB0A0000 B55EFF16 50FECFCB 7E5128A9 7E0000B1 ...~.(Q~...P..^...........\...... 000120
00BFAB0A 0000B52C FF03FB20 A97FFFFE A35EEF9F FFFEA368 EFFFFEAC 75EF4C9E .L.u....h.....^................. 000140
5128A97E 0000B13C EF03FB28 A97F7EFF FEADB3EF 4C50FFFE A1AEEF9F 5C000113 ...\.......PL......~..(...<...~.(Q 000160
FFFEA300 EF9F0000 B4EEFF03 FB10A97F 20A97F18 A97F0000 B506FF16 5018A97E ~..P............................ 000180
EF9F0000 B4CAFF03 FB00A97F 08A97FFE CFCB7F00 00B4DBFF 03FB08A9 7F10A97F ................................ 0001A0
FDAF9E00 00B4EFFF 01FB3CE6 CF9F0000 B4B6FF03 FBFEBFCB 7F00A97F FFFEA16C 1.....................<.......... 0001C0
CF9FFCAD FDAF9E00 E831FCAD FDAF9E8F ABD7FE59 8FAB0104 F1FCADFD AF9EFCAD ............Y.........1......... 0001E0
```

Virtual block number 205 (000000CD), 512 (0200) bytes

```
2BA97E00 00B09BEF 03FB28A9 7F7ECBAB 50FFFEA2 A9EF9F00 00B4C3FF 01FB0521 !..............P..~..(.......~.( 000000
EF9F0000 B44AFF03 FB00A97F FFFEA28C EF9F08A9 7F0000B4 65FF1650 08A97E51 Q~..P..e....................J...... 000020
6DEF9F00 00B46FFF 01FB3C66 CF9F0000 B436FF03 FBFEBFCB 7F00A97F FFFEA284 ..............6.....f<....o.....m 000040
0000B410 FF165000 A97E5128 A97E0000 B046EF03 FB28A97F 7EF28FCB 50FFFEA2 ...P...~..(...F...~.(Q~..P....... 000060
9F0000B4 2DFF01FB 3C24CF9F 0000B3F4 FF03FBFE BFCB7FFF FEA24FEF 9F00A97F .....O................$<..-...... 000080
B3CEFF16 5000A97E 5128A97E 0000B004 EF03FB28 A97F7EF2 93CB50FF FEA22BEF .+...P...~..(.........~.(Q~..P.... 0000A0
00B3EBFF 01FB3BE2 CF9F0000 B3B2FF03 FBFEBFCB 7FFFFEA2 15EF9F00 A97F0000 ............................;... 0000C0
B3CAFF01 FB0428CF 9FFCADFD AF9EFCAD FDAF9E04 0000B35C FF16FCAD FDAF9E00 .........................(...... 0000E0
165010A9 7E5128A9 7E0000AF A1EF03FB 28A97F7E F29FCB50 FFFEA150 EF9F0000 ........P...~..(........~.(Q~..P. 000100
A97FFFFE A1BAEF9F 0000B350 FF03FB08 A97FFFFE A1C2EF9F 10A97F00 00B36BFF .k........................P:..... 000120
9F0000B3 29FF03FB FEBFCB7F 00A97FFF FEA1AFEF 9F0000B3 3DFF03FB 00A97F08 .......=....................)..... 000140
```

```
A97F7EF2 AFCB50FF FEA16FEF 9E0000B3 15FF03FB 10A97FFE BFCB7FFF FEA1A3EF ......................O...P...~.. 000160
FB00A97F 10A97F08 A97F0000 B2FAFF16 5008A97E 5128A97E 0000AF30 EF03FB28 (...O...~.(Q~..P................ 000180
01FB3AFE CF9F0000 B2CEFF03 FBFEBFCB 7F00A97F FFFEA14C EF9F0000 B2E2FF03 ........L.....................{.. 0001A0
A97E5128 A97E0000 AEDEEF03 FB28A97F 7EF2A3CB 50FFFEA1 1DEF9F00 00B307FF ...........P...~..(........~.(Q~. 0001C0
FEA0F7EF 9F0000B2 8DFF03FB 08A97FFF FEA11FEF 9F10A97F 0000B2A8 FF165010 .P.............................. 0001E0
```

Virtual block number 206 (000000CE), 512 (0200) bytes

```
B266FF03 FBFEBFCB 7F00A97F FFFEA0EC EF9F0000 B27AFF03 FB00A97F 08A97FFF ...........2...................f! 000000
F2B3CB50 FFFEA0AC EE9E0000 B252FF03 FB10A97F FEBFCB7F FFFEA0F0 EF9F0000 ......................R.........P... 000020
7F10A97F 08A97F00 00B237FF 16500BA9 7E5128A9 7E0000AE 6DEF03FB 28A97F7E ~..(...m...~.(Q~..P..7........... 000040
3BCF9F00 00B20BFF 03FBFEBF CB7F00A9 7FFFFEA0 B1EF9F00 00B21FFF 03FB00A9 ................................; 000060
28A97E00 00AE1BEF 03FB28A9 7F7EF2A7 CB50FFFE A05AEF9F 0000B244 FF01FB3A :...D.....Z...P...~..(........~.( 000080
EF9F0000 B1CAFF03 FB08A97F FFFEA074 EF9F10A9 7F0000B1 E5FF1650 10A97E51 Q~..P.............t.............. 0000A0
03FBFEBF CB7F00A9 7FFFFEA0 29EF9F00 00B1B7FF 03FB00A9 7F08A97F FFFEA034 4...................)............ 0000C0
50FFFE9F E9EF9F00 00B18FFF 03FB10A9 7FFEBFCB 7FFFFEA0 45EF9F00 00B1A3FF ........E.......................P 0000E0
7F08A97F 0000B174 FF165008 A97E5128 A97E0000 ADAAEF03 FB28A97F 7EF2B7CB ...~..(.........^.(Q~..P..t....... 000100
0000B148 FF03FBFE BFCB7F00 A97FFFFE 9FC6EF9F 0000B15C FF03FB00 A97F10A9 ..........\....................H... 000120
0000AD58 EF03FB28 A97F7EF2 ABCB50FF FE9F97EF 9F0000B1 81FF01FB 397BCF9F ..x9...............P...~..(...X.... 000140
00B107FF 03FB00A9 7FFFFE9F C1EF9F08 A97F0000 B122FF16 5008A97E 5128A97E ~.(Q~..P.."....................... 000160
0000B12C FF01FB39 23CF9F00 00B0F3FF 03FBFEBF CB7F00A9 7FFFFE9F 71EF9F00 ...@....................#9....... 000180
0000B10C FF01FB39 03CF9F00 00B0D7FF 1650FEBF CB7E52FF FE7C23EF 9E510032 2.Q..|..R~...P.........9........ 0001A0
B0AEFF16 5008A97E 5128A97E 0000ACE4 EF03FB28 A97F7ECB AB50FFFE 9EF2EF9F .......P...~..(........~.(Q~..P.... 0001C0
CB7F00A9 7FFFFE9E CDEF9F00 00B093FF 03FB00A9 7FFFFE9E D5EF9F08 A97F0000 ................................ 0001E0
```

Virtual block number 207 (000000CF), 512 (0200) bytes

```
7F7EF28B CB50FFFE 9EB6EF9F 0000B0B8 FF01FB38 AFCF9F00 00B07FFF 03FBFEBF ...............8...............P...~. 000000
FFFE9F00 EF9F00A9 7E0000B0 59FF1650 00A97E51 28A97E00 00AC8FEF 03FB28A9 .(.........~.(Q~..P..Y.............. 000020
F28FCB50 FFFE9E74 EF9F0000 B076FF01 FB386DCF 9F0000B0 3DFF03FB FEBFCB7F ..................m8...v......t...P... 000040
9E56EF9F 00A97F00 00B017FF 165000A9 7E5128A9 7E0000AC 4DEF03FB 28A97F7E ~..(...M...~.(Q~..R..............V. 000060
CB50FFFE 9E32EF9F 0000B034 FF01FB38 2BCF9F00 00AFFBFF 03FBFEBF CB7FFFFE ....................+8...4.....2...P. 000080
EF9F00A9 7F0000AF D5FF1650 00A97E51 28A97E00 00AC0BEF 03FB28A9 7F7EF293 ..~..(........~.(Q~..P............. 0000A0
FFFE9E68 EF9F0000 AFF2FF01 FB37E9CF 9F0000AF B9FF03FB FEBFCB7F FFFE9E1C ......................7..........h... 0000C0
00A97F00 00AF93FF 165000A9 7E5128A9 7E0000AB C9EF03FB 28A97F7E F297CB50 P...~..(........~.(Q~..P.......... 0000E0
AF86FF16 0000AFB0 FF01FB37 A7CF9F00 00AF77FF 03FBFEBF CB7FFFFE 9E4AEF9F ..J.............w.......7............. 000100
8FCBF1AF 50F28BCB F7AF50CB AB000000 008F50FC ADFDAF9E FCADFDAF 9E010000 .................P........P......P.... 000120
008FAB0A FCADFDAF 9E211100 028FAB01 07F18FAB D78FAB01 D0F293CB EBAF50F2 .P.........................!......... 000140
AB01D0FC ADFDAF9E 8FABD7E2 8FAB07F3 FCADFDAF 9EF29BCB 4CC8AF50 5C000107 ...\P..L........................... 000160
5C08405C 20445C08 425C8FAB 4EFCADFD AF9E01F5 3100038F AB0104F1 8FABD78F .............1........N..\B.\D \@.\ 000180
00AF67FF 01FB00A9 7F0000AB C5EF04FB 00A97FFF FE9BEBEF 9F5CDD02 DD5C5C4A J\\...\...........................g.. 0001A0
7FFFFE9B B9EF9F5C DD02DD5C 5C4A5C14 405C2044 5C08425C 8FAB4EBB AB504A00 .JP..N..\B.\D \@.\J\\...\......... 0001C0
20445C08 425C8FAB 4EBFAB50 4A0000AF 35FF01FB 00A97F00 00AB93EF 04FB00A9 ..................5...JP..N..\B.\D 0001E0
```

```
Virtual block number 208 (000000D0), 512 (0200) bytes

 01FB00A9 7E0000AB 61EF04FB 00A97FFF FE9BB7EF 9F5CDD04 DD5C5C4A 5C1A405C \@.\J\\...\.............a........ 000000
 0A013031 0313FFFE A4CEEF4C BBABD15C 00011300 BFAB0ACF AB504A00 00AF03FF .....JP.........\...L......10.. 000020
 4E5C0001 1300BFAB 0ACBAB58 4058FFFE A722EF4C 4458CFAB 4E5C0001 1300BFAB ......\N..XDL.°...X@X.........\N 000040
 4458CFAB 4E5C0001 1300BFAB 0AF28BCB F28BCB58 4158FFFE A75AEF4C 4458CFAB ..XDL.Z...XAX.............\N..XD 000060
 A7C2EF4C 4458CFAB 4E5C0001 1300BFAB 0AF28FCB F28FCB58 4158FFFE A78EEF4C L.....XAX.............\N..XDL... 000080
 4158FFFE A7F6EF4C 4458CFAB 4E5C0001 1300BFAB 0AF293CB F293CB58 4158FFFE ..XAX.............\N..XDL.....XA 0000A0
 F2A3CB58 4158FFFE A82AEF4C 4458CFAB 4E5C0001 1300BFAB 0AF29FCB F29FCB58 X.............\N..XDL.*...XAX... 0000C0
 0AF2A7CB F2A7CB58 4158FFFE A85EEF4C 4458CFAB 4E5C0001 1300BFAB 0AF2A3CB ..........\N..XDL.^...XAX....... 0000E0
 1300BFAB 0AF2ABCB F2ABCB58 4158FFFE A892EF4C 4458CFAB 4E5C0001 1300BFAB ......\N..XDL.....XAX........... 000100
 4E5C0001 1300BFAB 0AF2AFCB F2AFCB58 4158FFFE A8C6EF4C 4458CFAB 4E5C0001 ..\N..XDL.....XAX.............\N 000120
 4458CFAB 4E5C0001 1300BFAB 0AF2B3CB F2B3CB58 4158FFFE A8FAEF4C 4458CFAB ..XDL.....XAX.............\N..XD 000140
 FE0E8FAB 0104F1FC ADFDAF9E FCADFDAF 9EF2B7CB F2B7CB58 4158FFFE A92EEF4C L.....XAX....................... 000160
 F18FABD7 8FAB01D0 F297CBF2 93CB5C41 5CF2BBCB F2BBCB41 FCADFDAF 9E8FABD7 ........A......\A\.............. 0001A0
 0020FFFE AA82EF4C 182D5C00 181A008F AB0AFCAD FDAF9E01 59310003 8FAB011A ......1Y.............\-.L....... 0001A0
 0008FFFF FEACEBEF 4C515C00 011A008F AB0A5801 CE031158 D40413FF FF7B07EF ........X....X.......\QL........ 0001C0
 405C1C44 5C08425C 8FAB4E00 F9310313 58D55857 C85701CE 03115704 01130000 .....W....W.WX.X..1..H..\B.\D.\@ 0001E0

Virtual block number 209 (000000D1), 512 (0200) bytes

 05FF01FB 00A97F00 00A963EF 04FB00A9 7FFFFE99 61EF9F5C DD04DD5C 5C4A5C14 .\J\\...\..a..........c......... 000000
 5C00011A 008FAB0A D3AB5CFF FEAC93EF A8475800 011A008F AB0A5C50 500000AD ...PP\........XGH....\.........\ 000020
 FEAF25EF 4C455C00 011A008F AB0AF29F CBF29FCB 584158D3 ABFFFEAE D3EF4C45 E|........XAX.............\EL.%.. 000040
 584158D3 ABFFFEAF 77EF4C45 5C00011A 008FAB0A F2A3CBF2 A3CB5841 58D3ABFF ...XAX.............\EL;w.....XAX 000060
 F2ABCBF2 ABCB5841 58D3ABFF FEAFC9EF 4C455C00 011A008F AB0AF2A7 CBF2A7CB ..............\EL.......XAX..... 000080
 011A008F AB0AF2AF CBF2AFCB 584158D3 ABFFFEB0 1BEF4C45 5C00011A 008FAB0A .......\EL.......XAX............ 0000A0
 BFEF4C45 5C00011A 008FAB0A F2B3CBF2 B3CB5841 58D3ABFF FEB06DFF 4C455C00 .\EL.m.....XAX..............\EL.. 0000C0
 D7FEAA8F AB011AE1 FCADFDAF 9EFCADFD AF9EF2B7 CBF2B7CB 584158D3 ABFFFEB0 .....XAX........................ 0000E0
 2CCF9FFC ADFDAF9E FCADFDAF 9E040000 AB96FF16 FCADFDAF 9EFCADFD AF9E8FAB ................................ 000100
 FBFFFE97 81EF9F05 DF310313 00000000 8F5C515C FF6FCB4E 0000ABA4 FF01FB31 1.......H.o.\Q\.......1.......... 000120
 FB2766CF 9FFF77CB 000042BB 8F4A00AA 310312E3 AF5C515C 50500000 ABE2FF01 ......PP\Q\....1..J..B...w...f'. 000140
 FF01FB00 DDFFFEC5 F1EF02FB F8A9DFF8 A917D0FC A9DFFCA9 0AD00000 AB66FF01 ..f............................. 000160
 97CB7FFC ADFDAF9E 0000AB4C FF00FB00 00AB73FF 01FBFFFE 99CEEF9F 0000AB50 P...........s.....L............. 000180
 20FEA3DB FE9FCB2D 0000AAD8 FF1650FE 9FCB7E51 FE97CB7E FFFECA68 EF01FBFE ....h...~...Q~..P.....-...... 0001A0
 5000A97E 5128A97E FFFEC928 EF02FB28 A97FFE9F CB7FCE11 0212FFFE 7606EF00 ...v...........(...(...~.(Q~..P 0001C0
 ADFDAF9E 051C31FF 6FCB084A 0813FFFE 70C5EF01 2004B900 A92D0000 AAAAFF16 ........-.......p....J..o.1...... 0001E0

Virtual block number 210 (000000D2), 512 (0200) bytes

 EAAF008F AB0AFCAD FDAF9E26 110002BF AB010000 012C8FF1 8FABD78F AB01D0FC .....................&.......... 000000
 FCADFDAF 9E8FABD7 DD8FABD5 AFF3FCAD FDAF9ED0 93CB4C00 0000008F 4A5C0001 ..\J.....L...................... 000020
 4A5C8000 44998F40 5C14445C 08425CFF 67CB4EDB AB000043 C88F4AD7 ABE2AF4A J....J..C....N.g.\B.\D.\@..D..\J 000040
 42B88F4A 54110213 ADAF5C51 5C505000 00AAB7FF 01FBFFFE 964EEF9F FF7BCB5C \.(...N..........PP\Q\.....TJ..B 000060
 02FBF8A9 DFF8A917 D0FCA9DF FCA90AD0 0000AA3C FF01FB26 3CCF9FFF 77CB0000 ...w....<&...<.................. 000080
 AA22FF00 FB0000AA 41FF01FB FFFE98AC EF9F0000 AA26FF01 FB00DDFF FEC4C7EF ...........3............A......". 0000A0
```

```
AA46FF01 FBFFFE95 DDEF9FFC ADFDAF9E 04483100 00A9FFFF 01FB24DC CF9F0000 ......$.........1H..............F. 0000C0
008F5C51 5CFF6FCB 4E0000A9 D5FF01FB 2E57CF9F FCADFDAF 9EFF73CB 504A0000 ..JF.s..........W..........N.o.\Q\.. 0000E0
00012C8F 00DBAB0A 2212FFFE 74B6EF00 20FFFE9F BAEF0F2D 04103103 13000000 .....1..-....... ...t...'........ 000100
08405CD7 AB4E01EF 31DBAB5C 4A5C0842 5CDBAB4E D093CB4C FF73CBD0 5C000100 ...\..s.L...N..\B.\J\..1..N..\@. 000120
AF00D7AB 0ADFABA6 AF4AD093 CB4CFF73 CBD05C00 01D2AF00 D7AB0AD7 AB5C4A5C \J\..............\..s.L...J.......... 000140
ABD7E3AB 01D00000 A912FF16 50F3E7CB 4C7E52FF FE745FEF 9E510032 5C0001BC ...\2.Q..._t..R~L...F............... 000160
5C5C4A5C 1A405C20 445C0842 5CE3AB4E FCADFDAF 9E00BE31 0003E3AB 0104F1E3 ..........1........N..\B.\D \@.\J\\ 000180
5C000600 00012C8F 00D7AB0A 0000A5C8 EF04FB00 A97FFFFE 95EEEF9F 5CDD04DD ...\...........................\ 0001A0
0006DBAF 00D7AB0A D547CB4C 504A0000 A956FF01 FB00A97F 5C5C0105 00E3AB0A .......\\........V...JFL.G.......... 0001C0
5C5C4A5C 14405C20 445C0842 5CE3AB4E DFABD547 CB4CC05C 5C010500 E3AB0A5C \........\\.L.G...N..\B.\D \@.\J\\ 0001E0
```

Virtual block number 211 (000000D3), 512 (0200) bytes

```
D7AB0A5C 00019FAF 00D7AB0A 0000A568 EF04FB00 A97FFFFE 958EEF9F 5CDD02DD ...\..................h..............\... 000000
F1ECADED AE9E0000 A84EFF03 FBE3E7CB 487FF3E7 CB4C7F00 A97F5800 0196AF00 ......X.....L.....H........N.......... 000020
AF9E7411 0002E3AB 011AF1E3 ABD7E3AB 01D0FCAD FDAF9EE3 ABD7FF45 E3AB0104 .....E............................t... 000040
5C08425C E3AB4E4C 13000000 008FFFFE A856EF4C 515C0001 1A00E3AB 0AFCADFD ............\QL.V...........LN..\B.\ 000060
00A97F00 00A4DFEF 04FB00A9 7FFFFE94 DDEF9F5C DD04DD5C 5C4A5C14 405C1C44 D.\@.\J\\...\......................... 000080
5C4058DF AB4E5CFF FEA80FEF 48465800 011A00E3 AB0A5C50 500000A8 81FF01F8 .........PP\..........XFH.....\N..X@\ 0000A0
0000012C 8F00D7AB 0AFCADFD AF9EE3AB D78FE3AB 1AF3FCAD FDAF9EDF AE584A58 XJX................................ 0000C0
585158DF AB4E5C50 500000A8 31FF01FB FFFE94C8 EF9FD55B CB4C8DAF 4A5C0004 ..\J..L.[............1...PP\N..XQX 0000E0
57DFAB4E 580006C3 AF00D7AB 0A5C5050 0000A818 FF01FBFF FE94AFEF 9F26185C \.&................PP\..........XN..W 000100
EF04FB00 A97FFFFE 93BEEF9F FF7BCBDD 03DDFCAD FDAF9ED5 5BCB485C 4A5C5742 BW\J\H.[...............(.............. 000120
13C00045 798F5C51 5CFF73CB 4EFF73CB 504A0000 A7DAFF01 FB00A97F 0000A438 B..................JP.s.N.s.\Q\.uE.... 000140
6D22EF03 28FFFEB8 2EEFFFFE 6D2EEF03 280000A7 5DFF01FB 01BCCF9F FD833103 .1............].....(....m...........(...m 000160
CB4E0000 A72EFF01 FB2D1ACF 9FFFFEB8 1CEFFFFE 6D16EF03 28FFFEB8 25EFFFFE ...%....(....m.............-.........N. 000180
ABD7ABD0 00B13103 12EFAF5C 515CD7AB 4E016931 03130000 00008F5C 515CFF4F o.\Q\............1i.N..\Q\.....1....... 0001A0
0000012C 8F008FAB 0AFCADFD AF9E5911 00028FAB 01E7ABF1 8FABD78F AB01D0E7 ....................Y................. 0001C0
13A7AF5C 515CFF6F CB4E0000 A6D6FF01 FB2B58CF 9FFF73CB D093CB4C D05C0001 ..\.L.......s....X+..........N.o.\Q\... 0001E0
```

Virtual block number 212 (000000D4), 512 (0200) bytes

```
FDAF9E00 FB310313 8EAF5C51 5CFF6FCB 4E0000A6 BDFF01FB 24BDCF9F 01143103 .1......$..........N.o.\Q\.....1...... 000000
04FB28A9 7E7EFF73 CB6EFFFE 9532EF9F FCADFDAF 9E8FABD7 AA8FABE7 ABF3FCAD .........................2...n.s.~..(.. 000020
FF6FCB4E 0000A670 FF01FB2C 5CCF9FFF FEB75EEF 03202CB9 28A92C00 00A28DEF .......,.(.r ..^......\r....P....N.o. 000040
31031200 0043C88F 5C515CDB AB4EFCAD FDAF9E00 AB310313 00000000 8F5C515C \Q\..........1..........N..\Q\..C.....1 000060
FFFFFFFF 8FEBABF1 8FABD68F AB000000 648FD0EB AB5C4A5C 08405CDB AB4E0086 ..R...\@.\J\.....d...................... 000080
9FFF73CB D093CB4C D05C0001 0000012C 8F008FAB 0AFCADFD AF9E5D11 00028FAB ......]........................\.L.....s.. 0000A0
A5EAFF01 FB23EACF 9F411102 1391AF5C 515CFF6F CB4E0000 A602FF01 FB2A84CF ..*.........N.o.\Q\......A....$...... 0000C0
FFA68FAB A0AFEBAB F1FCADFD AF9E2611 02130000 00008F5C 515CFF6F CB4E0000 ..N.o.\Q\..........3................... 0000E0
85FF16FC ADFDAF9E 0000A5B4 FF01FB2B A0CF9FFC ADFDAF9E FCADFDAF 9E8FABD6 ......................+................... 000100
8FABD78F AB01D000 00A593FF 01FB03A2 CF9FFCAD FDAF9EFC ADFDAF9E 040000A5 ........................................ 000120
03E3AB01 05F1E3AB D7E3AB01 D0FCADFD AF9E0273 3100038F AB010000 012C8FF1 ..r...........1s.......................... 000140
58D547CB 4C4E5C5C 010500E3 AB0A5C00 06D3AF00 8FAB0AFC ADFDAF9E 00E23100 .1......................\.......\\HL.G.X 000160
4C000000 008F4A5C 5C010500 E3AB0A5C 0006B4AF 008FAB0A 00AA3103 192A5851 QX*...1...............\........\\J......L 000180
F3E7CB4C 7F58DD58 584A5810 44580842 58E3AB4E 5C000199 AF008FAB 0AD547CB .G..............\N..XB.XD.XJXX.X.L.... 0001A0
```

```
8FAB0A00 00A4ABFF 03FB08A9 7F10A97F FFFE93A0 EF9F0000 A19EEF03 FB10A97F ................................ 0001C0
20574357 104457E3 AB4E5858 4A580840 58104458 E3AB4E5C 00010000 012C8F00 ........\N..XD.X@.XJXXN..WD.WCW  0001E0
```

Virtual block number 213 (000000D5), 512 (0200) bytes

```
5C0001C5 AF008FAB 0A0000A1 65EF04FB 00A97FF3 E7CB4C7F 58DD57DD 57564A56 VJVW.W.X.L.........e...........\ 000000
AB0105E1 FCADFDAF 9EFCADFD AF9E0000 A456FF03 FBF3E7CB 4C7F08A9 7F00A97F .......L......V................. 000020
01493100 03E3ABFF FFFFFF8F 01F1E3AB D6E3AB05 D0FCADFD AF9EE3AB D7FF21E3 .!............................1I. 000040
FDAF9E4D 110002F3 AB0105F1 F3ABD7F3 AB01D0EF AB000000 008F4AFC ADFDAF9E ....J.....................N... 000060
0A580006 EBAF008F AB0A5C5C 010500F3 AB0A5C00 06000001 2C8F008F AB0AFCAD ..............\......\\......X.. 000080
FDAF9EEF AB5C4A5C 08405CEF AB4E0B15 D547CB4C D547CB48 D1585801 0500E3AB .....XX.H.G.L.G...N..\@.\J\..... 0000A0
AF008FAB 0A00B631 0319105C 515CEFAB 4EFCADFD AF9EF3AB D7B6F3AB 05F3FCAD ...............N..\Q\...1....... 0000C0
3103121A 5C515CF3 AB4ED547 CB4C0000 00008F4A 5C5C0105 00E3AB0A 5C0006A6 ...\.......\\J.....L.G.N..\Q\...1 0000E0
CB4C7F58 DD58584A 58104458 084258E3 AB4E5C00 01000001 2C8F008F AB0A008F ............\N..XB.XD.XJXX.X.L. 000100
0A0000A3 49FF03FB 08A97F10 A97FFFFE 923EEF9F 0000A03C EF03FB10 A97FF3E7 ........<.....>.............I.... 000120
56205743 57104457 E3AB4E58 584A5808 40581044 58E3AB4E 5C0001C2 AF008FAB .......\N..XD.X@.XJXXN..WD.WCW-V 000140
7F5C0001 8BAF008F AB0A0000 A006EF04 FB00A97F F3E7CB4C 7F58DD57 DD57564A JVW.W.X.L.....................\. 000160
FFFF8F01 F1FCADFD AF9EFCAD FDAF9E00 00A2F7FF 03FBF3E7 CB4C7F08 A97F00A9 .....L.......................... 000180
ABD7FD90 8FAB0100 00012C8F F1FCADFD AF9EFCAD FDAF9EE3 ABD6FEBA E3ABFFFF ................................ 0001A0
FCADFDAF 9E00E831 0003F7AB 010AF1F7 ABD7F7AB 01D08FAB 084AFCAD FDAF9E8F .....J.................1........ 0001C0
5C515C5C 4E5C8FAB FBABC3FC ADFDAF9E 0000A2DC FF01FB01 B2CF9FFB AB8FABD0 ..........................\N\\Q\ 0001E0
```

Virtual block number 214 (000000D6), 512 (0200) bytes

```
4A008231 03120000 00008F5C 515CFFAB 4EFCADFD AF9EFFAB 084A00A0 31031814 ...1..J.........N..\Q\.......1..J 000000
11000203 AB0107AB F103ABD7 03ABFBAB D007AB5C 4A5C1042 5C8FAB4E FFABF4AF ....N..\B.\J\................... 000020
03AB0A5C 00010000 012C8F00 0BAB0A0B AB5C4A5C 08405C03 AB4EFCAD FDAF9E58 X.....N..\@/\J\...............\... 000040
0225CF9F 0F1B04BC 6C2004B8 682D58F3 E7CB487E 5CF3E7CB 4C7E5800 01F3AF00 .....X"L...\"H...X-h.. 1......%. 000060
6931FCAD FDAF9E03 ABD7AB03 AB07ABF3 FCADFDAF 9EFFAB08 4A0000A2 45FF01FB ...E...J.......................1i 000080
FF1BF7AB 010AF1FC ADFDAF9E 14110215 D7AB8FAB D1FCADFD AF9EFCAD FDAF9EFF ................................ 0000A0
01D0FCAD FDAF9EFC ADFDAF9E 040000A1 D5FF16FC ADFDAF9E FCADFDAF 9EF7ABD7 ................................ 0000C0
02F3AB01 05F1F3AB D7F3AB01 D0FCADFD AF9E6311 0002F7AB 010AF1F7 ABD7F7AB ................c............... 0000E0
DF5C5C01 0500F3AB 0A5C0006 0A00F7AB 0A0000A1 D1FF00FB FCADFDAF 9E3C1100 ..<...................\.......\\. 000100
9EF3ABD7 C7F3AB05 F3FCADFD AF9E0000 A1B2FF00 FB0000A1 F9FF01FB F17FCB4C L............................... 000120
45FF1600 00A193FF 00FBFCAD FDAF9EF7 ABD7A0F7 AB0AF3FC ADFDAF9E FCADFDAF ...............................E 000140
FDAF9EFC ADFDAF9E FCADFDAF 9EFCADFD AF9EFCAD FDAF9EFC ADFDAF9E 040000A1 ................................ 000160
FCADFDAF 9EFCADFD AF9EFCAD FDAF9EFC ADFDAF9E FCADFDAF 9EFCADFD AF9EFCAD ................................ 000180
FDAF9E00 D7310003 E3AB010F ABF1E3AB D7E3AB8F ABD00FAB D7ABD0FC ADFDAF9E ..........................1..... 0001A0
FCADFDAF 9E007331 0003F3AB 0105F1F3 ABD7F3AB 01D0EFAB 00000000 8F4AFCAD ..J.......................1s...... 0001C0
031158D4 0413CAAF 575157F1 7FCB4C4E 5C5C0105 00F3AB0A 5C00060A 00F7AB0A .......\.......\\NL...WQW.....X.. 0001E0
```

Virtual block number 215 (000000D7), 512 (0200) bytes

```
AF565156 D547CB4C 4E5C5C01 0500F3AB 0A5C0006 0000012C 8F00E3AB 0A5B01CE ..X...........\.......\\NL.G.VQV. 000000
9EEFAB5C 4A5C0840 5CEFAB4E 0B1358D5 5857CA57 57D25701 CE031157 D10413A3 ....W....W.WW.WX.X..N..\@.\J\... 000020
EFAB4E0B ABE3ABD0 03AB8FAB D0FCADFD AF9EF3AB D7FF90F3 AB0105F1 FCADFDAF ...........................N.. 000040
```

```
D7AB8FAB D18FAB5C 4A5C0840 5C8FAB4E 0000A05C FF01FB3C AF9F1519 105C515C \Q\.....<...\...N..\@.\J\....... 000060
FF16FCAD FDAF9EFC ADFDAF9E E3ABD7FF 2CE3AB01 0FABF1FC ADFDAF9E 15110215 ................................ 000080
D093CB4C D05C0001 0000012C 8F0003AB 0AFCADFD AF9EFCAD FDAF9E04 0000A004 .........................\.L... 0000A0
0BAB0AD0 93CB48D0 93CB4CD0 580001E3 AF0003AB 0A5C0001 ECAF000B AB0A13AB ..........\.........X.L...H...... 0000C0
FEEFCB7E 51F3E7CB 4C7E5C00 01C1AF00 03AB0AD0 93CB4C13 ABD05C00 01D1AF00 .....\...L...........\^L...Q^... 0000E0
7E51F3E7 CB4C7E58 00019EAF 0003AB0A 5C0001A7 AF000BAB 0A00009F 89FF1650 P..............\........X^L...Q^ 000100
1650F3E7 CB4C7E51 FEEFCB7E 5C000183 AF000BAB 0A00009F 65FF1650 F3E7CB48 H...P..e............\^...Q^L...P. 000120
2C8F0003 AB0AFCAD FDAF9E70 110002F3 AB0105F1 F3ABD7F3 AB01D000 009F4BFF .K.................P.........., 000140
AB0A5C00 06E4AF00 0BAB0A13 ABD547CB 4CD05C5C 010500F3 AB0A5C00 06000001 .....\......\\.L.G...........\.. 000160
D547CB48 D547CB4C D0585801 0500F3AB 0A580006 D3AF0003 AB0A5C5C 010500F3 ....\\.........X;.....XX.L.C.H.C. 000180
AB05F3FC ADFDAF9E D547CB4C 13ABD05C 5C010500 F3AB0A5C 0006B9AF 000BAB0A ........\......\\...L.G......... 0001A0
EF9E5103 32FCADFD AF9EFCAD FDAF9E04 00009ED8 FF16FCAD FDAF9EF3 ABD793F3 ..........................2.Q.. 0001C0
00009ECC FF01FB15 07CF9FFF 6BCB084A 00009E9C FF1650FE AFCB7E52 FFFE64B8 .J..R^...P.....J..k............. 0001E0

Virtual block number 216 (000000D8), 512 (0200) bytes

9EAAFF01 FBC7E4CF 9FFCADFD AF9E3811 0212FFFE 69BEEF00 20FEBBDB FFB7CB2D -.......  ...i......8.............. 000000
B5EF02FB EF67CBDF F5A7CB7F 16110212 FFFE6992 EF0120FE A3DBFE9F CB2D0000 ..-......  ...i...........g...... 000020
FCADFDAF 9EFCADFD AF9E0400 009E53FF 16FCADFD AF9EC811 FCADFDAF 9E00002B (...............S............... 000040
20FEA3DB FE9FCB2D 00009E54 FF01FBC7 8ECF9F1B ABF7AF50 17AB0000 0000SF4A J.......P............T...-...... 000060
4E00009E 2DFF01FB 0532CF9F FCADFDAF 9E040000 9E1AFF16 0712FFFE 693CEF01 ..<i.....................2....-...N 000080
FFFE8940 EF9F0000 9E1AFF01 FB00DDFC ADFDAF9E AF110211 0213065C 515C1FAB ..\Q\........................@... 0000A0
F8A9DFF8 A918D0FC A9DFFCA9 0000004D 8FD00000 9E16FF00 FB00009E 35FF01FB ...S..............M............. 0000C0
FF00FB00 009E07FF 01FBFFFE 8C82EF9F 00009DE4 FF01FB00 DDFFFE88 85EF02FB ................................ 0000E0
9DB2FF01 FB00DDFF FEB853EF 02FBF8A9 DFF8A902 D0FCA9DF FCA901D0 00009DE0 ........................S......... 000100
A902D0FC A9DFFCA9 0ED00000 9DAEFF00 FB00009D CDFF01FB FFFE8C58 EF9F0000 ....X........................... 000120
009D9BFF 01FBFFFE 8C2EEF9F 00009D80 FF01FB00 DDFFFEB8 21EF02FB F8A9DFF8 .......!........................ 000140
FB00DDFF FEB7EFEF 02FBF8A9 DFF8A902 D0FCA9DF FCA92DD0 00009D7C FF00FB00 ....|....-...................... 000160
A9DFFCA9 32D00000 9D4AFF00 FB00009D 69FF01FB FFFE8C04 EF9F0000 9D4EFF01 ..N...............i.....J....2.... 000180
01FBFFFE 8BDAEF9F 00009D1C FF01FB00 DDFFFE87 BDEF02FB F8A9DFF8 A902D0FC ................................ 0001A0
27ABF18F ABD78FAB 01D027AB 23ABD0FC ADFDAF9E 00009D18 FF00FB00 009D37FF .7................#.'.........' 0001C0
FDAF9EFF 73CBF30B CB4CD05C 00010A00 8FAB0AFC ADFDAF9E 029A3100 038FAB01 .....1...............\.L....s.... 0001E0

Virtual block number 217 (000000D9), 512 (0200) bytes

A901D000 009CAFFF 01FB0534 CF9FFCAD FDAF9E00 009CBFFF 01FB2141 CF9FFCAD ....A!...............4............ 000000
FFFEB72C EF02FBF8 A9DFF8A9 584A585C 405817AB 4E5C1440 5C8FAB4E FCA9DFFC ....N..\@.\N..X@\XJX.............. 000020
A90ED000 009C87FF 00FB0000 9CA6FF01 FBFFFE8B 51EF9F00 009C8BFF 01FB00DD ............Q.................... 000040
FFFEB6EC EF02FBF8 A9DFF8A9 584A585C 405817AB 4E5C1440 5C8FAB4E FCA9DFFC ....N..\@.\N..X@\XJX............ 000060
A92DD000 009C47FF 00FB0000 9C66FF01 FBFFFE8B 19EF9F00 009C4BFF 01FB00DD .....K............f......G....-.. 000080
FFFEB6AC EF02FBF8 A9DFF8A9 584A585C 405817AB 4E5C1440 5C8FAB4E FCA9DFFC ....N..\@.\N..X@\XJX............ 0000A0
AB01D000 009C07FF 00FB0000 9C26FF01 FBFFFE89 89EF9F00 009C0BFF 01FB00DD ...................&............ 0000C0
F337CB4C 4E5C0001 0A002BAB 0AFCADFD AF9E017A 3100032B AB0104F1 2BAB072B +..+....+..1z.........+....\NL.7. 0000E0
5C14405C 8FAB4EFC A9DFFCA9 32D0FCAD FDAF9E01 47310312 00000000 8F585158 \Q\........1G.......2.....N..\@.\ 000100
AB0A0000 9B96FF01 FB00DDFF FEB637EF 02FBF8A9 DFF8A958 4A585C40 5817AB4E N..X@\XJX........7............... 000120
```

```
8A4EEF9F FFFE8A58 EFFFFE92 65EF4C9E 5C001213 00F363CB 4C0A5C00 010A002B +....\.L.c.....\.L.e....X.....N. 000140
0A00009B 51FF02FB 00DDFFFE 8A42EF9F 00009B74 FF00FB00 009B9BFF 01FBFFFE ............t.....B........Q.... 000160
00009B6C FF01FB7E FFFE93BC EF4C505C 00011300 F363CB4C 0A5C0001 0A002BAB .+....\.L.c.....\FL.....^...1... 000180
4CDD5C00 010A002B AB0A0000 9B1AFF02 FB00DDFF FE8923EF 9F00009B 3DFF00FB ..=.....$..............+....\.L 0001A0
5C8FAB4E 17AB5C4A 5C08405C 17AB4E00 009B13FF 00FB0000 9B46FF01 FBF337CB .7....F..........N..\@.\J\..N..\ 0001C0
5843588F AB4EFCAD FDAF9E5F 11021800 0042988F 5851585C 405817AB 4E5C1440 @.\N..X@\XQX..B......_.....N..XCX 0001E0

Virtual block number 218 (000000DA), 512 (0200) bytes

FF77CB01 14F1FF77 CBD7FF77 CB04D000 009ABBFF 01FB1598 CF9F17AB 5C4A5C08 .\J\.................w...w......w. 000000
D7E5FF77 CB14F3FC ADFDAF9E 00009A98 FF01FB16 98CF9FFC ADFDAF9E 1F110002 ...........................w... 000020
04F1FCAD FDAF9EFC ADFDAF9E FDB93103 13185C51 5C2BAB4E FCADFDAF 9EFF77CB .w......N.+\Q\...1.............. 000040
D7FD698F AB0127AB F1FCADFD AF9EFCAD FDAF9EFC ADFDAF9E 2BABD7FE 892BAB01 ..+....+................'....i.. 000060
FEB4CBEF 02FBF8A9 DFF8A916 D0FCA9DF FCA905D0 FCADFDAF 9EFCADFD AF9E8FAB ................................ 000080
9A42FF01 FBFEA7CB 7F00009A 4DFF01FB FFFE8910 EF9F0000 9A2AFF01 FB00DDFF ......*..........M..........B. 0000A0
0099EBFF 01FB14C8 CF9F0000 9A0EFF00 FB00009A 2DFF01FB FFFE8900 EF9F0000 ...........-.................... 0000C0
01FF67CB CFFCADFD AF9E2FAB 00000000 8F50FCAD FDAF9EFC ADFDAF9E FB773100 .1w...........P....../.......g.. 0000E0
FE88AFEF 9FFCADFD AF9E0000 9996FF01 FB3ADD00 93007A00 61004800 2F001505 .../.H.a.z....{................. 000100
99E6FF01 FBFFFE88 9DEF9FFC ADFDAF9E 007D31FF 73CB504A 00009A00 FF01FBFF ........JP.s.1}................. 000120
FF73CB50 4A000099 CDFF01FB FFFE888C EF9FFCAD FDAF9E64 11FF73CB 504A0000 ..JP.s..d.................JP.s. 000140
FCADFDAF 9E3211FF 73CB504A 000099B4 FF01FBFF FE887BEF 9FFCADFD AF9E4B11 .K.......{..........JP.s..2..... 000160
FBFFFE88 59EF9FFC ADFDAF9E 1911FF73 CB504A00 00999BFF 01FBFFFE 886AEF9F ..j..........JP.s...........Y.... 000180
AF9E2FAB 08500412 33ABFF73 CBD1FCAD FDAF9E00 11FF73CB 504A0000 9982FF01 ......JP.s............s..3..P../.. 0001A0
ABF7AF4A 8FAB0000 00008F4A FCADFDAF 9EFCADFD AF9E0400 0098DFFF 16FCADFD ........................J.......J... 0001C0
DDFCADFD AF9E3BAB 5C4A5C08 425C1044 5CFF67CB 4E2FABED AF501FAB F2AF4A37 7J....P.../N.g.\D.\B.\J\.;...... 0001E0

Virtual block number 219 (000000DB), 512 (0200) bytes

DDEF9F3F AB504A00 00990FFF 01FBFFFE 84A6EF9F 000098B8 FF02FB07 DDFF67CB .g........................JP.T... 000000
65110213 9AAF5C51 5C3FAB4E FF73CB3F ABD033AB 504A0000 98FEFF01 FBFFFE87 ..........JP.3..?.s.N.?\Q\......e 000020
00DDFFFE B30EEF02 FBF8A9DF F8A916D0 FCA9DFFC A905D01F AB084AFC ADFDAF9E .....J.......................... 000040
9F000098 85FF01FB FEA7CB7F 00009890 FF01FBFF FE879BEF 9F000098 6DFF01FB ...m............................ 000060
FF160000 982EFF01 FB130BCF 9F000098 51FF00FB 00009870 FF01FBFF FE878BEF ........p......Q................ 000080
0000980C FF01FB1C 8ECF9F8F AB5C4A5C 08405C8F AB4EFCAD FDAF9E04 00009804 ..........N..\@.\J\.............. 0000A0
50000098 49FF01FB 00A97F00 0094A7EF 04FB00A9 7FFFFE84 25EF9F3B ABDD02DD ....;..%....................I...P 0000C0
2FAB51F3 0BCB4CFF 73CBD05C 00010A00 8FAB0A37 AB584A58 5C405837 AB4E5C50 P\N.7X@\XJX.7.......\..s.L...Q./ 0000E0
1102135C D55C58C8 5801CE03 115BD404 1333AB3F ABD15C01 CE03115C D4041308 ....\....\..T.3...X....X.X\.\... 000100
ABD0FCAD FDAF9EFF 6C31FCAD FDAF9E00 00979BFF 01FBFDBA CF9FFCAD FDAF9E18 ........................11........ 000120
43AB08C2 43AB01D0 2BAB084A FCADFDAF 9EFCADFD AF9E0400 00975FFF 1623ABBF ..$.._...............J..+...C...C 000140
04FBFEF7 CB7FFFFE 841EEF9F 43ABDD08 DDFCADFD AF9E00C8 31000343 AB0820F1 . ..C..1............C............ 000160
7F5C0001 0A002BAB 0A000093 E5EF04FB 00A97FFE F7CB7F01 DD02DD00 0093F7EF ........................+....\. 000180
0093BBEF 04FB00A9 7FFEF7CB 7F03DD02 DDF38FCB 4C504A00 00977FFF 01FB00A9 .........JPL...................... 0001A0
F7CB7F05 DD04DDF3 63CB4C50 4A000097 55FF01FB 00A97F5C 00010A00 2BAB0A00 ...+....\......U...JPL.c......... 0001C0
4C504A00 00972BFF 01FB00A9 7F5C0001 0A002BAB 0A000093 91EF04FB 00A97FFE ..............+....\......+...JPL 0001E0
```

```
Virtual block number 220 (000000DC), 512 (0200) bytes

 5C4A5C08 405C2BAB 4E1BAB1B AB584158 F337CB4C 4E5C0001 0A002BAB 0AF337CB .7...+....\RL.7.XAX....R.+\@.\J\ 000000
 AF9E0400 00966BFF 16FCADFD AF9E43AB 08C2FF3C 43AB0820 F1FCADFD AF9E2BAB .+...... ..C<....C.......k....... 000020
 009C8FF1 43AB06C2 43AB01D0 47AB0000 00008F50 2BAB084A FCADFDAF 9EFCADFD ..........J..+P......C...C...C.... 000040
 04FBFEFF CB7FFFFE 82F6EF9F 43ABDD06 DDFCADFD AF9E009F 31000343 AB060000 ....C..1..............C............ 000060
 7F5C0001 1A002BAB 0A000092 E5EF04FB 00A97FFE FFCB7F01 DD02DD00 0092F7EF .........................+....\. 000080
 B9EF04FB 00A97FFE FFCB7F03 DD04DDFF FE9323EF 4C504A00 00967FFF 01FB00A9 ..........JPL.#................... 0000A0
 0A002BAB 0AF3BBCB 4C505000 009653FF 01FB00A9 7F5C0001 0A002BAB 0A000092 .....+....\.......S...PPL.....+.. 0000C0
 0000009C 8FF1FCAD FDAF9E2B AB5C4A5C 08405C2B AB4E47AB F3BBCB4C 405C0001 ..\@L....GN.+\@.\J\.+............ 0000E0
 32FCADFD AF9EFCAD FDAF9E04 00009594 FF16FCAD FDAF9E43 AB06C2FF 6543AB06 ..Ce....C.......................2 000100
 FF01FB0B C3CF9FFF 6BCB144A 00009558 FF1650FE AFCB7E52 FFFE5B03 EF9E5103 .Q...[..R^...P..X...J..k......... 000120
 01FB00DD FCADFDAF 9E06E331 0312FFFE 607AEF00 20FEBBDB FEB7CB2D 000095B8 ....-........ ..z`....1.......... 000140
 A9000000 4D8FD000 00956BFF 00FB0000 958AFF01 FBFFFE80 95EF9F00 00956FFF .o......................k.....M.... 000160
 FE8477EF 9F000095 39FF01FB 00DDFFFE AFDAEF02 FBF8A9DF F8A918D0 FCA9DFFC ..........................9.....w.. 000180
 EF02FBF8 A9DFF8A9 08D0FCA9 DFFCA90A D0000095 35FF00FB 0000955C FF01FBFF ....\.......5...................... 0001A0
 009503FF 00FB0000 9522FF01 FBFFFE84 4DEF9F00 009507FF 01FB00DD FFFFAFAB ...............M.......'.......... 0001C0
 9F000094 D5FF01FB 00DDFFFE AF76EF02 FBF8A9DF F8A90BD0 FCA9DFFC A90AD000 ......................v............ 0001E0

Virtual block number 221 (000000DD), 512 (0200) bytes

 A9DFF8A9 0AD0FCA9 DFFCA90A D0000094 D1FF00FB 000094F0 FF01FBFF FE8423EF .#.............................. 000000
 CB7F0000 94C6FF01 FBEFEE83 F9EE9F00 0094A7FF 01FB0ADD FFFEAF44 EF02FBF8 ....D........................... 000020
 0312FFFE 5F6EEF00 20FF0BDB FF07CB2D 00009494 FF00FB00 0094D3FF 01FBFF07 ..................-....... ..D_.... 000040
 B27EEF02 FB28A97F FF07CB7F 000090F4 EF03FBFE 9FCB7FFF 07CB7F01 DD05D731 1.........................(...~. 000060
 13FFFE5F 27EF0120 FEA3DBFE 9FCB2D00 0093FFFF 1650FE9F CB7E5128 A97EFFFE ..^.(Q^...P.......-....... ..'-.... 000080
 C85801CE 031158D4 0413FFFE 5F0FEF01 20FEA30B FE9FCB2D 5C01CE03 115CD404 ..\.....\-....... ..._......X....X. 0000A0
 EF01FB00 A97F0000 93B2FF16 5000A97E 52FFFE59 0BEF9E51 02322113 5CD55C58 X\.\.!2.Q...Y..R^..P............ 0000C0
 FFFE5ECC EF0020FF 0BDBFF07 CB2D0000 93DAFF01 FB0D30CF 9FFE7031 FFFEAFB4 ....1p...0.........-....... ...^.. 0000E0
 ADFDAF9E 32110002 FF7FCB01 00000064 8FF1FF7F CBD7FF7F CB01D0FE 52310312 ..1R................d.............2.... 000100
 AF9E6B11 0212FF0B DBFF07CB 20FFFE9C 2FEF4C0C 2D5C000C E8AF00FF 7FCB0AFC ..........\-.L./... ..........k.. 000120
 A9DFF8A9 17D0FCA9 DFFCA90A D0FCADFD AF9EFF7F CBD7D2FF 7FCBCAAF F3FCADFD ................................ 000140
 07DD0000 9386FF01 FBFFFE82 C1EF9F00 009363FF 01FB00DD FFFEAE04 EF02FBF8 ...............c.................. 000160
 FB0E03CF 9F000093 49FF00FB 00009368 FF01FB00 A97F0000 930EFF02 FB00A97F ....................h.......I........ 000180
 A9EF02FB F8A9DFF8 A90DD0FC A9DFFCA9 0AD0FCAD FDAF9EFD AE310000 9326FF01 ..2...1........................... 0001A0
 FF01FBFF 0FCB7F00 00932BFF 01FBFFFE 826EEF9F 0000930C FF01FB0A DDFFFEAD ..................n.......+.......... 0001C0
 05EF9FAC 110212FF FE5DD3EF 0020FF13 DBFF0FCB 2D000092 F9FF00FB 00009338 8.............-....... ...].......... 0001E0

Virtual block number 222 (000000DE), 512 (0200) bytes

 008F47EF 03FBFF17 CB7F00A9 7F04DD00 009277FF 03FB00A9 7FFF0FCB 7FFFFE7F .............w...............G.. 000000
 05EF9F03 FD310313 00000000 8F5C515C FF6FCB4E 000092A0 FF01FB15 B2CF9F00 ............N.o.\Q\.......1..... 000020
 4A5C5050 000092CC FF01FBFF FE81FBEF 9FFF73CB 504A0000 920EFF01 FBFFFE82 ...........JP.s...............PP\J 000040
 01FB16C9 CF9FFCAD FDAF9E00 AE310003 8FAB014B ABF18FAB D78FAB01 D04BABSC \.K.........K.....1............. 000060
 EDFF1650 FF0FCB7E 51FF17CB 7E03A731 0313A6AF 5C515CFF 6FCB4E00 009247FF .G...N.o.\Q\....1..^...Q^...P... 000080
```

```
20FF13DB FF0FCB2D FCADFDAF 9E491100 02E3AB01 03F1E3AB D7E3AB01 D0000091 ................I....-...... 0000A0
EF9F00A9 7F00008E 8DEF03FB 00A97FFF 0FCB7F03 DD00B331 0312FFFE 671CEF04 ........1................... 0000C0
ADFDAF9E E3ABD7BA E3AB03F3 FCADFDAF 9E000091 99FF03FB FF0FCB7F FFFE7E2C ,~.......................... 0000E0
FF558FAB 014BABF1 FCADFDAF 9EFF73CB 504A0000 921AFF01 FBFFFE81 51EF9FFC ...Q.........JP.s........K...U. 000100
FB00DDFF FEAC2FEF 02FBF8A9 DFF8A917 D0FCA9DF FCA90AD0 FCADFDAF 9E8FABD7 ........................./...... 000120
7F000091 39FF02FB 00A97F07 DD000091 B1FF01FB FFFE8114 EF9F0000 918FFF01 ...........................9.J... 000140
AF9EFBD9 31000091 51FF01FB 0C2ECF9F 00009174 FF00FB00 009193FF 01FB00A9 ............t.........Q...1.... 000160
009133FF 01FB00DD FFFEABD4 EF02FBF8 A9DFF8A9 0FD0FCA9 DFFCA90A D0FCADFD ..........................3.. 000180
F8A90FD0 FCA9DFFC A92FD000 00912FFF 00FB0000 914EFF01 FBFFFE80 C1EF9F00 ..........N....../..../........ 0001A0
00FB0000 913EFF01 FBFF1FCB 7F000091 05FF01FB 0ADDFFFE ABA2EF02 FBFBA9DF ..........................>..... 0001C0
908EFF16 50FF1FCB 7E5128A9 7EFFFEAF 0DEF02FB 28A97FFF 1FCB7F00 0090FFFF ..........(.......~.(Q~...P.... 0001E0
```

Virtual block number 223 (000000DF), 512 (0200) bytes

```
23DBFF1F CB2D0086 31FF67CB 084A0812 FFFE5B35 EF0120FF 23DBFF1F CB2D0000 ..-....#. ..5[....J..g.1..-....# 000000
FFFE5B03 EF0120FF 23DBFF1F CB2D006E 31FF67CB 104A0812 FFFE5B1C EF0120FF . ...[....J..g.1n.-....$. ...[.. 000020
4011FF67 CB184A07 12FFFE5A EBEF0120 FF23DBFF 1FCB2D57 11FF67CB 144A0712 ..J..g..W-....#. ...Z....J..g..@ 000040
0000905A FF01FB00 DD2911FF 67CB1A4A 0712FFFE 5AD2EF01 20FF23DB FF1FCB2D -....$. ...Z....J..g..).....T... 000060
FEDE3100 009047FF 00FB0000 9066FF01 FB00A97F 0000900C FF02FB00 A97F07DD ..............f.......C...1.. 000080
FFFE7C30 EF9F5CDD 02DD5C5C 4A5C0840 5C10445C 08425CFF 67CB4EFC ADFDAF9E .....N.g.\B.\D.\@.\J\\...\..0|.. 0000A0
02130000 00008F5C 515C5050 00009054 FF01FB00 A97F0000 8CB2EF04 FB00A97F ...............T...PP\Q\........ 0000C0
00008FD4 FF01FB00 DDFFFEAA 75EF02FB F8A9DFF8 A917DCFC A9DFFCA9 0AD05611 .V.................u............ 0000E0
D9FF01FB 00A97F00 008F7FFF 02FB00A9 7F07DD00 008FF7FF 01FBFFFE 7F6AEF9F ..j............................ 000100
A90AD0FC ADFDAF9E FA1F3100 008F97FF 01FB0A74 CF9F0000 8FBAFF00 FB00008F ............t.........1......... 000120
FE7F17EF 9F00008F 7DFF01FB 0ADDFFFE AA1AEF02 FBF8A9DF F8A911D0 FCA9DFFC ........................}........ 000140
EF9FFF07 CB7F0000 8F6AFF00 FB00008F A9FF01FB FE9FCB7F 00008F9C FF01FBFF .........................j.....«/. 000160
008EE7FF 03FB10A9 7F18A97F FFFE7EF4 EF9F0000 8EFAFF03 FB18A97F FFFE7EFC .~..............~.............. 000180
00A97F08 A97FFFFE 7ED6EF9F 00008ED4 FF03FB08 A97F10A9 7FFFFE7C B1EF9F00 ....|................~........ 0001A0
FF01FB0B 6DCF9F00 008EAFFF 03FBFD57 CB7F00A9 7FFF1FCB 7F00008E C1FF03FB ................W..........m.... 0001C0
FEACFFEF 02FB28A9 7F08A97F 00008B74 EF03FB08 A97FFE9F CB7F01DD 00008EF8 ................t........(...... 0001E0
```

Virtual block number 224 (000000E0), 512 (0200) bytes

```
26AF9F0A 12FFFE54 9CEF0120 04B900A9 2D00008E B1FF1650 00A97E51 28A97EFF .~.(Q~..P......-.... ...T......& 000000
16FCADFD AF9EF91D 3100008E 95FF01FB 0E29CF9F FCADFDAF 9E00008E A5FF01FB ..............)........1........ 000020
FD57CB7F FFFE7E3C EF9FFFFE 7D4AEF9F FCADFDAF 9EFCADFD AF9E0400 008E63FF .c..................J}....<~....W. 000040
25EF9F00 008E0BFF 03FB08A9 7FFFFE7E 2DEF9FFF FE7D3BEF 9F00008E 21FF03FB ...!.....;}....-~...............% 000060
FF03FBFD 5FCB7F00 A97FFFFE 7BC2EF9F 00008DF8 FF03FB00 A97F08A9 7FFFFE7E ~.................{.......-..... 000080
D6310003 8FAB011A F18FABD7 8FAB01D0 A7AB0000 00008F50 F3AB114A 00008DE4 ....1...P.......................1. 0000A0
7A8EEF9F ABABDD02 DDABAB5C 4A5C0840 5C1C445C 08425C8F AB4EFCAD FDAF9E01 ......N..\B.\D.\@.\J\...........z 0000C0
10405CAB AB4EAFAB 50D00000 8E36FF01 FB00A97F 00008A90 EF04FB00 A97FFFFE .................6....P..N..\@. 0000E0
8E06FF01 FB00A97F 00008A64 EF04FB00 A97FFFFE 7A62EF9F 5CDD04DD 5C5C4A5C \J\\...\..bz........d........... 000100
EF4CAFAB D15C0001 1A008FAB 0A015031 03120000 00008FB3 AB51B3AB 50500000 ..PP..Q..........1P........\...L. 000120
0413CCAF FFFE8D6C EF4C515C 00011A00 8FAB0A58 01CE0311 58D40412 FFFE8A90 .......X....X.......\QL.1....... 000140
09FF1650 FEC7CB7E 52FFFE56 74EF9E51 04321713 58D55857 C85701CE 031157D4 .W....W.WX.X..2.Q..tV..R~...P... 000160
FF1650FE D7CB7E52 FFFE564F EF9E5104 32171800 0043C88F B3AB516F 1100008D ....oQ....C....2.Q..OV..R~...P.. 000180
```

```
50FED7CB 7F00008C D1FF1650 FED7CB7E 52FFFE56 C6EF9E51 04321511 00008CE8 ......2.Q...V..R^...P...........P 0001A0
008FAB0A 00008CB4 FF1650FE C7CB7E51 28A97E00 0088EBEF 03FB28A9 7F7EB3AB ..^..(........^.(Q^...P........... 0001C0
00181A00 8FAB0AFC ADFDAF9E A7ABB7AB 40B7AB83 ABFFFE8C DDEF4C47 5C00011A ...\GL.........@.................. 0001E0

Virtual block number 225 (000000E1), 512 (0200) bytes

65FF03FB 10A97FFF FE7C97EF 9FFFFE7C A1EFFFFE 8A32EF4C 9EFFFE79 71EF9F5C \..ay...L.2.....|.....|.........e 000000
00A97F08 A97FFFFE 78D6EF9F 00008C54 FF03FB08 A97F10A9 7FFEC7CB 7F00008C ...............T......x.......... 000020
59EFFFFE 8CD6EF4C 9E580001 2800F3AB 0A5C0006 1A008FAB 0A00008C 41FF03FB ...A..........\....(..X.L......Y 000040
4A5C0840 5CF3AB4E 00008C10 FF03FBFD 4FCB487F 00A97FFF FE7C4FEF 9FFFFE7C |....O|......H.O.........N..\@.\J 000060
8FAB01D0 FCADFDAF 9E8FABD7 FE2D8FAB 011AF1FC ADFDAF9E FCADFDAF 9EF3AB5C \................-............... 000080
4A5C0840 5C20445C 08425C8F AB4EFCAD FDAF9E01 CA310003 8FAB0104 F18FABD7 ..........1.......N..\B.\D \@.\J 0000A0
8C4AFF01 FB00A97F 000088A4 EF04FB00 A97FFFFE 78CAEF9F ABABDD02 DDABAB5C \.........x.......................J. 0000C0
EF04FB00 A97FFFFE 789EEF9F 5CDD02DD 5C5C4A5C 10405CAB AB4EBBAB 50D00000 ...P..N..\@.\J\\....\...x......... 0000E0
5CDD04DD 5C5C4A5C 18405CAB AB4EBFAB 50D00000 8C1EFF01 FB00A97F 00008878 x..............P..N..\@.\J\\....\ 000100
AB0AB7AB 50500000 8BEEFF01 FB00A97F 0000884C EF04FB00 A97FFFFE 7872EF9F ..PX.........L..............PP.... 000120
AB51F2BB CB48574A 57B7AB40 57F2BBCB 4C4E5800 011300BF AB0A5C00 011300BF .....\........XNL...WG..WJWH...Q. 000140
04321713 FFFE818C EF4CBBAB D15C0001 1300BFAB 0A00F831 03120000 00008FB7 ........1..........\...L........2. 000160
FFFE77A0 EF9FA7AB B7AB4028 1100008A F9FF1650 FECFCB7E 52FFFE54 64EF9E51 Q..dT..R^...P.......(@.......w.. 000180
FDAF9E00 008AD3FF 1650FECF CB7E5128 A97E0000 870AEF03 FB28A97F 7EB7AB50 P..^..(........^.(Q^...P......... 0001A0
7ADEEF9F FFFE7AE8 EFFFFE81 E5EF4C9E FFFE7740 EF9F5C00 121300BF AB0AFCAD ..........\..@w...L.......z.....z 0001C0
FE8323EF 4C50FFFE 771EEF9F 5C000113 00BFAB0A 00008A9C FF03FB18 A97FFFFE ..................\....w..PL.$.. 0001E0

Virtual block number 226 (000000E2), 512 (0200) bytes

18A97F10 A97F0000 8A76FF16 5010A97E 5128A97E 000086AC EF03FB28 A97F7EFF .^..(........^.(Q^..P..v.......... 000000
F3AB0A00 008A4BFF 03FB00A9 7F08A97F FFFE76F0 EF9F0000 8A5EFF03 FB08A97F ......^.....v...............K...... 000020
4A5C0840 5CF3AB4E 00008A30 FF03FBFD 4FCB4C7F 00A97FFE CFCB7F5C 00012800 .(..\.........L.O.....O....N...\@.\J 000040
7736EF9F FCADFDAF 9E8FABD7 FE398FAB 0104F1FC ADFDAF9E FCADFDAF 9EF3AB5C \.......................9...........6w 000060
008AB7FF 01FBFFFE 771EEF9F 60110219 5CA7AB51 5C505000 008A9FFF 01FBFFFE ..........PP\Q..\....`...w......... 000080
5128A97E 000085FC EF03FB28 A97F7E58 50FFFE76 91EF9F58 5CA7AB43 5C505000 .PP\C..\X....v..PX^..(........^.(Q 0000A0
CB4C7FFF FE79EBEF 9FFECFCB 7F5C0001 2800F3AB 0A000089 C5FF1650 FECFCB7E ^...P..........(..\..........y....L. 0000C0
04000089 A9FF16FC ADFDAF9E 000089D8 FF01FB06 5DCF9F00 00899FFF 03FBFD4F O..........]...................... 0000E0
000089DC FF01FBFF FE74E7EF 9F000089 C1FF01FB 00DDFCAD FDAF9EFC ADFDAF9E ..........................t.......... 000100
FFFEA42C EF02FBF8 A9DFF8A9 18D0FCA9 DFFCA900 00004D8F D0000089 BDFF00FB ..........N........................ 000120
FCADFDAF 9E000089 89FF00FB 000089A8 FF01FBFE AFCB7F00 00898BFF 01FB00DD .................................. 000140
EF9F0000 8956FF01 FB00DDFF FEA3F7EF 02FBF8A9 DFF8A905 D0FCA9DF FCA90AD0 ............................V..... 000160
FF27CB7E 52FFFE54 31EF9E51 00320000 8952FF00 FB000089 79FF01FB FFFE794C Ly......y.......R...2.Q..1T..R^.'. 000180
FE9FCB7E 51FE97CB 7EFFFEA8 59EF01FB FE97CB7F FCADFDAF 9E000088 E5FF1650 P.....................Y...^...Q^... 0001A0
7F000000 7F8FDDCE 110212FF FE53F7EF 0020FEA3 DBFE9FCB 2D000088 C9FF1650 P......-....... ...S.............. 0001C0
425C584E 58FF27CB 3C6B1204 B900A920 FEA3DBFE 9FCB2D00 0088AFFF 02FB00A9 ..........-.......  ......k<.'.XNX\B 0001E0

Virtual block number 227 (000000E3), 512 (0200) bytes

DD000088 B5FF01FB 00DD0000 8552EF03 FBFF27CB 7FFF27CB 7F5CDD5C 5C4A5C08 .\J\\.\..'...'....R.............. 000000
88C2FE01 FBFFFE74 D5EF9F00 0088CFFF 01FB08A9 7F000088 6DFF02FB 08A97F08 .......m.....................t........ 000020
```

```
31000088 85FF00FB 000088AC FF01FB00 A97F0000 884AFF02 FB00A97F 08DD0000 ..........J.....................1 000040
FE9FCB7F 331304B9 00A920FE A3DBFE9F CB2D0000 882AFF02 FB00A97F 0DDDFF45 E.........*........ .....3.... 000060
01FBFEFE 783AEF9F 0000883C FF01FB00 DD000087 F9FF03FB FF27CB7F FF27CB7F ..'...'..............<......!x.... 000080
530AEF00 20FF2BDB FF27CB2D FCADFDAF 9EFEF831 00008838 FF00FB00 00885FFF ._.......8...1.......-.'..+. ...S 0000A0
EF02FB28 A97F00A9 7F000084 91EF03FB 00A97FFF 27CB7F0A DDFE9431 0312FFFE ....1......'................(... 0000C0
028FAB01 19F18FAB D78FAB01 D0000087 9DFF1650 FF27CB7E 5128A97E FFFEA61C ....~.(Q~.'.P................... 0000E0
12FFFE8D 51EF4C0A 20FF2BDB FF27CB2D 5C000A19 008FAB0A FCADFDAF 9E2D1100 ..-............\-.'..+. .L.Q.... 000100
8FAB0AFC ADFDAF9E 008031FC ADFDAF9E 8FABD7B6 8FAB19F3 FCADFDAF 9E151102 ........................1......... 000120
8F98EF4C D05C0001 19008FAB 0A651102 15FFFE8F ABEF4CFF 6BCBD15C 00011900 ....\..k.L.........e.......\.L... 000140
09FF1650 FEB7CB7E 52FFFE8D FDEF4C9E 510F325C 000F1900 8FAB0AFF 6BCBFFFE ...k..........\2.Q.L......R~...P... 000160
00A97FFF FE774BEF 9F000086 F1FF03FB 00A97FFF FE7753EF 9FFEB7CB 7F000087 ..........Sw................Kw..... 000180
A90AD0FC ADFDAF9E 57110000 8716FF01 FB039BCF 9F000086 DDFF03FB FD57CB7F ..W.....................W........ 0001A0
FE770FEF 9F000086 F9FF01FB 00DDFFFE A19AEF02 FBF8A9DF F8A90AD0 FCA9DFFC ..............................w. 0001C0
FF1650FE B7CB7E52 FFFE51D4 EF9E5100 32000086 F5FF00FB 00008714 FF01FBFF ...............2.Q...Q..R~...P.. 0001E0
```

Virtual block number 228 (000000E4), 512 (0200) bytes

```
FCADFDAF 9E040000 868EFF16 FCADFDAF 9E000086 BDFF01FB 019ACF9F 00008688 ................................ 000000
324FAB5C D05CFF07 CB3C0Q00 8332EF03 FBFF07CB 7FFF07CB 7F0CDDFC ADFDAF9E ..................2...<...\.\.02 000020
8FAB010C F18FABD7 8FAB01D0 00008638 FF1650FF 2FCB7E52 FFFE5184 EF9E5100 .Q...Q..R~./.P..8............... 000040
50FE9FCB 7E52FFFE 502FEF9E 51013217 154FAB8F ABD1FCAD FDAF9E00 A3310003 ..1..........Q..2.Q../P..R~...P 000060
FE9FCB7F 000082E0 EF04FBFE 9FCB7FFF 07CB7F8F ABDD01DD 59110000 8606FF16 .........Y...................... 000080
115CD404 19345851 58F7AB4E F7AB504A 00008521 EF165050 4E000084 3DEF01FB ...=....NPP..!...JP..N..XQX4...\. 0000A0
1102135C D55C58C8 5801CE03 1158D404 14000043 648F5751 57F7AB4E 5C01CE03 ...\N..WQW.dC.....X.....X.X\.\... 0000C0
0CF1FCAD FDAF9E00 00858FFF 03FBFF2F CB7FFF2F CB7FFE9F CB7FFCAD FDAF9E3E >............/.../.............. 0000E0
9E771100 008573FF 1650FF07 CB7E51FF 2FCB7EFC ADFDAF9E 8FABD7FF 608FAB01 ...`.........~./.Q~...P..s.....w. 000100
FF00FB00 008597FF 01FB00DD 000085B0 FF00FB00 0085A7FF 01FB00DD FCADFDAF ................................ 000120
A1FF01FB 00A97F00 00826FEF 02FB00A9 7F0ADD00 008587FF 01FB00DD 000085A0 ........................u......... 000140
00854BFF 01FB28AF 9F000085 6DFF00FB 0000858C FF01FBFF FE758FEF 9F000085 ......u...............m......(...K.. 000160
008507FF 16FCADFD AF9E0000 84F6FF16 50FF07CB 7E52FFFE 5042EF9E 51003200 :2.Q..BP..R~...P.................. 000180
FE9FABEF 02FBF8A9 DFF8A918 D0FCA9DF FCA901D0 FCADFDAF 9EFCADFD AF9E0400 ................................ 0001A0
8522FF01 FB00A97F 000081CC EF03FB00 A97F28DD 20DD0000 850AFF01 FB00DDFF ........... .(..................'. 0001C0
00DDFFFE 9F6EEF02 FBF8A9DF F8A918D0 FCA9DFFC A929D000 0084FBFF 00FB0000 ...........)...................n...... 0001E0
```

Virtual block number 229 (000000E5), 512 (0200) bytes

```
FB000084 E5FF01FB 00A97F00 00818FEF 03FB00A9 7F24DD20 DD000084 CDFF01FB ........ .$...................... 000000
FF01FB00 DDFFFE9E 31EE02FB F8A9DFF8 A901D0FC A9DFFCA9 01D00000 84BEFF00 ...........................1....... 000020
FFFE9F0C EF02FBF8 A9DFF8A9 18D0FCA9 DFFCA905 D0000084 99FF00FB 00008490 ................................ 000040
FDAF9E00 008467FF 00FB0000 848EFF01 FBFFFE74 91EF9F00 00846BFF 01FB00DD ....k......t..............g....... 000060
7F0DDD00 0083F3FF 1650FF37 CB7E51FE 97CB7EFF FEA383EF 01FBFE97 CB7FFCAD ............~...Q~.7.P.......... 000080
FF16FCAD FDAF9EC4 11021304 B900A920 FF3BDBFF 37CB2D00 0083EFFF 02FB00A9 ..........-.7..;. ............... 0000A0
FE9EBBEF 02FBFF77 CBDFFCA9 DFFCA901 D0FCADFD AF9EFCAD FDAF9E04 000083E4 ..............................w.......... 0000C0
83FAFF01 FB00A97F 000080AC EF03FB00 A97F28DD 20DD0000 83EAFF01 FB00DDFF ........... .(.................. 0000E0
FF01FB00 DDFFFE9E 51EF02FB FF77CBDF FCA9DFFC A929D000 0083DBFF 00FB0000 ...........)........w....Q......... 000100
```

```
A1FF00FB 000083C0 FF01FB00 A97F0000 8072EF03 FB00A97F 28DD20DD 000083B0 .....  .(......P.................. 000120
FFFE92C4 EF4E7FAB 00EBCF9E FCADFDAF 9EFCADFD AF9E0400 00835FFF 16000083 ....._.....................N..... 000140
7BE3EF02 FB00A97F 00DD0000 835EFF01 FB02DD00 CA310312 00000000 8F5C515C \Q\......1.......^...........( 000160
FF01FBFD 57CB7F00 00836BFF 01FBFFFE 6F7EEF9F 00008378 FF01FB00 A97F0000 ........K......o......k.....W.... 000180
9E510032 5C000128 0053AB0A FCADFDAF 9E53AB08 4A000083 39FF00FB 00008358 X......9...J..S.......S.(..\2.Q.. 0001A0
53AB0A53 AB5C4A5C 08405C53 AB4E0000 82BAFF16 50FD4FCB 4C7E52FF FE4E07EF ..N..R"L.O.P......N.S\@.\J\.S..S 0001C0
D1FF01FB 02DD3D11 0212FFFE 4DD6EF00 2004BC6C 2D5CFD4F CB4C7E5C 00012800 .(..\"L.O.\-1.. ...N.....=...... 0001E0
```

Virtual block number 230 (000000E6), 512 (0200) bytes

```
00012800 53AB0A00 0082EBFF 01FB00A9 7F00007F B9EF02FB 00A97F0A DD000082 .........................S.(.. 000000
8266FF16 FCADFDAF 9EFE7831 000082B0 FF00FB00 0082CFFF 01FBFD4F CB4C7F5C \.L.O...............1x........?. 000020
FDAF9E00 008263FF 01FBE1AF 9FFFFE91 D1EF0000 0000BF4A FCADFDAF 9E040000 ........J................c....... 000040
01FB00DD FFFE9CF0 EF02FBF8 A9DFF8A9 18D0FCA9 DFFCA903 D0FCADFD AF9EFCAD ................................ 000060
FCA9DFFC A901D000 00824BFF 00FB0000 8272FF01 FBFFFE72 7DEF9F00 00824FFF .O....}r........r.....K.......... 000080
FF160000 8226FF00 FB000082 1DFF01FB 00DDFFFE 9CBEEF02 FBF8A9DF F8A901D0 ......................3..... 0000A0
000081EC FF01FB07 74CF9F57 ABFF73CB D0FCADFD AF9EFCAD FDAF9E04 000081E4 .................s..W..t........ 0000C0
000081CC FF01FB00 C1CF9F00 008197FF 1650FF3F CB7E52FF FE4522EF 9E510332 2.Q..'E..R".?.P................. 0000E0
FF1650FF 47CB7E51 28A97E00 007DBDEF 04FB28A9 7F7EFF73 CB6EFFFE 7062EF9F ..bp..n.s."..(....}..".(R".G.P.. 000100
47CB2C10 12000000 008F5C51 5C505000 0081F7FF 01FBFFFE 6D8EEF9F 0000816C 1........m.........PP\Q\........G 000120
9FFF73CB 504A0000 81CEFF01 FBFFFE70 ADEF9F37 11FFFE92 5EEF0320 FF4BDBFF ..K. ..^....7...p..........JP.s.. 000140
FF01FB3D AF9F0000 8116FF16 50FF3FCB 7E51FF47 CB7E0000 8162FF01 FB05E4CF ......b...".G.Q".?.P.......=... 000160
812AFF01 FB0716CF 9FFFFE92 15EF0320 FF4BDBFF 47CB2CFC ADFDAF9E 00008148 H.........G..K. ............*. 000180
9EFCADFD AF9E0400 0080EFFF 16000081 19FF01FB 059BCF9F FF73CB57 ABD00000 ....W.s.......................... 0001A0
08425C5B AB4E5BAB 5C4A5C80 0044998F 405C1444 5C08425C FF67CB4E FCADFDAF ....N.a.\B.\D.\@..D..\J\.[N.[\B. 0001C0
08A97F10 A97FFF3F CB7F0000 7D72EF03 FB10A97F FFFE6D0C EF9F5CDD 5C5C4A5C \J\\.\...m.........P}....?....... 0001E0
```

Virtual block number 231 (000000E7), 512 (0200) bytes

```
58584A58 800044A7 8F574357 5BAB4E5C 5C4A5C14 405C5BAB 4E000080 81FF03FB .......N.[\@.\J\\N.[WCW..D..XJXX 000000
EFFE6CB8 EF9F08A9 7F00A97F 00007D48 EF04FB00 A97FFFFE 6CCEEF9F 5CDD58DD ..X.\...l........H}...........l.. 000020
AF9EFCAD FDAF9E04 00008050 FF160000 807AFF01 FB0565CF 9F000080 41FF03FB ...A.....e.....z.....P........... 000040
5FABFF73 CBD0FF7B CB5C4A5C 80004499 8F405C14 445C0842 5CFF67CB 4EFCADFD ...N.a.\B.\D.\@..D..\J\.{...s... 000060
CBDD03DD 032F3103 13000000 008F5C51 5CFF6FCB 4E000080 41FF01FB 04C3CF9F .......A...N.o.\Q\........1/..... 000080
5CDD5C5C 4A5C0842 5CFF7BCB 4E00007C C9EF04FB FF4FCB7F FFFE6C50 EF9FFF7B {...P1....O.....l..N.{.\B.\J\\.\ 0000A0
A5FF03FB 08A97F10 A97FFFFE 703AEF9F 00007C98 EF03FB10 A97FFFFE 6C32EF9F ..21.........l....:p.............. 0000C0
58DD5858 4A588000 44A78F57 4357FF7B CB4E5C5C 4A5C1440 5CFF7BCB 4E00007F ...N.{.\@.\J\\N.{.WCW..D..XJXX.X 0000E0
03FBFFFE 6BDAEF9F 08A97F00 A97F0000 7C6AEF04 FB00A97F FFFE6BF0 EF9F5CDD .\...k........Jl...........k.... 000100
5C4A5C08 425CE3AB 4EE3AB5C 4A5C0840 5C10445C 08425CFF 67CB4E00 007F63FF .c...N.a.\B.\D.\@.\J\..N..\B.\J\ 000120
FB08A97F 10A97FFF FE6E17EF 9F00007C 15EF03FB 10A97FFF FE6BA7EF 9F5CDD5C \.\...k..........l.....n........ 000140
9F5CDD58 DD58584A 58235743 57E3AB4E 5C5C4A5C 10405CE3 AB4E0000 7F22FF03 ..'...N..\@.\J\\N..WCW#XJXX.X.\. 000160
7EE6FF03 FBFFFE6B 55EF9F08 A97F00A9 7F00007B EDEF04FB 00A97FFF FE6B6BEF .kk..........{...........Uk......" 000180
CF9FFFFE 750BEF0F 20FFFE4A 15EF002C 0E12FFFE 4251EFFF FE7535EF 0C290000 ..)..5u...QB.........J.. ...u..... 0001A0
01FB046F CF9F01F1 31031300 0000008F 5C515CFF 6FCB4E00 007F03FF 01FB03EE .........N.o.\Q\.........1....o... 0001C0
57CB7E52 FFFE44A8 EF9E5103 3201D831 0313E3AF 5C515CFF 6FCB4E00 007EE7FF ..~..N.o.\Q\....1..2.Q...D..R~.W 0001E0
```

```
Virtual block number 232 (000000E8), 512 (0200) bytes

125C5851 585FAB4E 5C505000 007F13FF 01FBFFFE 6AAAEF9F 00007E84 FF1650FF .F...".....J..........FF\N._XQX\. 000000
4A00007E E9FE01FB FFFE6A80 EF9E0116 31FFFE8F 7AEF0320 FF53DBFF 4FCB2C11 ...O..S. ..z...1......J.......".J 000020
00000000 8F5C515C FF6FCB4E 00007E78 FF01FB02 FACF9FFC ADFDAF9E FF73CB50 F.s..............x"..N.o.\Q\..... 000040
01FB00A9 7F00007B 01EF04FB 00A97FFF FE6A87EF 9FFF7BCB DD03DD01 66310313 ..1f.....{....J.........{........ 000060
CB6EFFFE 6CCAEF9F AC11FF73 CB63ABD0 08135FAB 63ABD163 AB504A00 007EA3FF ..".JF.c..c._....c.s.......1..n. 000080
FF7BCB4E 00007DD4 FF1650FF 57CB7E51 28A97E00 007A25EF 04FB28A9 7F7EFF73 s."..(...%z..".(Q".W.F....}..N.{. 0000A0
10A97FFF 4FCB7F00 007A8FEF 03FB10A9 7FFFFE6A 29EF9F5C DD5C5C4A 5C08425C \B.\J\\.\..)J..........z.....D.... 0000C0
0044A78F 574357FF 7BCB4E5C 5C4A5C14 405CFF7B CB4E0000 7D9EFF03 FB08A97F ........}..N.{.\@.\J\\N.{.WCW..D. 0000E0
9F08A97F 00A97F00 007A63EF 04FB00A9 7FFFFE69 E9EF9F5C DD58DD58 5R4A5880 .XJXX.X.\...i........cz......... 000100
008F5C51 5CFF6FCB 4E00007D 95FF01FB 0280CF9F 00007D5C FF03FBFF FE69D3EF ..i.....\}...........}..N.o.\Q\.. 000120
8F5C515C 50500000 7DCEFF01 FBFFFE69 65EF9FFC ADFDAF9E 00833103 13000000 ......1.........ei.......}..FF\Q\. 000140
5000007D A9FF01FB FFFE6C88 EF9FFFFE 8E37EFFF FE4337EF 03280C12 C0004579 yE....(..7C...7.......1.......}..F 000160
FBFFFE69 21EF9FFF FE8E13EF 0320FF5B DBFF57CB 2C0E1258 5C51585F AB4E5C50 F\N._XQ\X.....W..[. .........!i... 000180
FFFE8DEF EF0320FF 5BDBFF57 CB2C0E12 585C5158 5FAB4E5C 50500000 7D82FF01 ...}..FF\N._XQ\X.....W..[. ........ 0001A0
ADFDAF9E FCADFDAF 9E040000 7CD2FF16 FCADFDAF 9E00007D 01FF01FB 02EDCF9F .........}..........|............ 0001C0
7E000078 D3EF04FB 28A97F7E FE7FCB6E FFFE6B78 EF9FFF6F CB000000 008F4AFC .J.......o...xk..n...".(.....x..." 0001E0

Virtual block number 233 (000000E9), 512 (0200) bytes

007C67FF 03FBFD57 CB7FFFFE 6D02EF9F 00A97F00 007CB3FF 165000A9 7E5128A9 .(Q"..F...l.........m.....W.....gl. 000000
007CEBFE 01FBFFFE 6C16EF9F 00007C90 FF02FB04 DDFF7FCB DD7FAB03 25CF9E00 ...%..............l......l.......l. 000020
007C47FF 16FCADFD AF9E6BAB 50D00000 7CDAFF01 FBFFFE6B FDEF9F67 AB50D000 ..F.g...k.......l...F.k.........Gl. 000040
7EFF7FCB 6EFFFE6A EDEF9FFF 6FCB0000 00008F4A FCADFDAF 9EFCADFD AF9E0400 .............J.......o.....J..n...." 000060
FE6C7FEF 9F00A97F 00007BF8 FF165000 A97E5128 A97E0000 7848EF04 FB28A97F ..(...Hx..".(Q"..F....{..........1. 000080
FB28A97F 7E67AB6E FFFE68F0 EF9F7FAB 029ACF9E 00007BDC FF03FBFD 57CB7FFF ...W.....{..............h..n.g"..(. 0000A0
FB28A97F 7E6BAB6E FFFE6A90 EF9FFFFE 8CCCEF02 202CB928 A92C0000 780CEF04 ...x....(. ..........J..n.k"..(. 0000C0
CB7E52FF FE8B47EF 9E510163 8F32FFFE 8CAEEF03 202CB928 A92C0000 77ECEF04 ...w....(. ......2.c.Q..G...R". 0000E0
2C00007B 81FF01FB 04DD0000 7BAEFF02 FB04DDFF 7FCBDD00 007B83FF 1650FF5F _.F...{............{.........{... 000100
FCADFDAF 9E00007B B1FF02FB 04DDFF7F CBDDFFFE 8B16EFCB AF20FF63 DBFF5FCB ._..c; ..................{........ 000120
FFFE6A08 EF9FFF6F CB000000 008F4AFC ADFDAF9E FCADFDAF 9E040000 7B62FF16 ..b{...............J........o......J... 000140
00A97F00 007B13FF 165000A9 7E5128A9 7E000077 63EF04FB 28A97F7E FF73CB6E n.s."..(...cw..".(Q"..F...{...... 000160
FF02FB06 DDFF73CB DD7FAB01 B5CF9E00 007AF7FF 03FBFD57 CB7FFFFE 6BA2EF9F ...k....W......z..............s...... 000180
FF6FCB96 AF4AFCAD FDAF9EFC ADFDAF9E 0400007A F9FF16FC ADFDAF9E 00007B20 .{..........z..................J...o. 0001A0
ADFF1650 00A97E51 28A97E00 0076FDEF 04FB28A9 7F7EFF7F CB6EFFFE 69A2EF9F ...i..n...."..(....v..".(Q"..F... 0001C0
4E8F327F AB014FCF 9E00007A 91FF03FB FD57CB7F FFFE6B44 EF9F00A9 7F00007A z........Dk.....W......z.....O...2.N 0001E0

Virtual block number 234 (000000EA), 512 (0200) bytes

007AA3FF 02FB06DD FF73CBDD 00007A78 FF1650FF 5FCB7E52 FFFE6FB0 EF9F5101 .Q....o...R"._.F...xz.....s......(.z. 000000
FB06DDFF 73CBDDFF FE6F7FEF CBAF20FF 63DBFF5F CB2C0000 7A76FF01 FB06DD00 ......vz......c. .....o.....s..... 000020
FF6FCB00 0000008F 4AFCADFD AF9EFCAD FDAF9E04 00007A5C FF160000 7AA6FF02 ...z.....\z...................J........o. 000040
0DFF1650 00A97E51 28A97E00 00765DEF 04FB28A9 7F7EFF67 CB6EFFFE 6742EF9F ..Bg..n.g."..(...]v..".(Q"..F... 000060
67CBDD7F AB00AFCF 9E000079 F1FF03FB FD57CB7F FFFE6AAC EF9F00A9 7F00007A z.........J.....W.....y.............g 000080
6FCB9BAF 4AFCADFD AF9EFCAD FDAF9E04 000079F8 FF160000 7A1AFF02 FB07DDFF ........z.......y..............J....o 0000A0
```

```
FF165000 A97E5128 A97E0000 75FCEF04 FB28A97F 7EFF67CB 6EFFFE66 E1EF9FFF ....f..n.g.~..(....u..~.(Q~..F.. 0000C0
510A327F AB4FAF9E 00007990 FF03FBFD 37CB7FFF FE6A53EF 9F00A97F 000079AC .y.........SJ....W.....y...O..2.Q 0000E0
DD000079 A5FF02FB 07DDFF67 CBDD0000 797AFF16 50FF5FCB 7E52FFFE 8AA2EF9E ......R^._.F..zy....g.........y... 000100
A9FF02FB 07DDFF67 CBDDFFFE 8A72EF0A 20FF63DB FF5FCB2C 00007978 FF01FB07 ....xy..,._..c. ..r......g........ 000120
FF00FB00 007977FF 01FB00DD FCADFDAF 9EFCADFD AF9E0400 00795FFF 16000079 y....._y.....................wy...... 000140
00FB0000 790AFF03 FBFD57CB 7FFFFE69 D5EF9FFD 57CB7FFF 6FCB084A 00007980 .y..J..o...W....i....W......y.... 000160
7E5128A9 7E000075 37EF04FB 28A97F7E 5C6EFFFE 67DAEF9F 5C50D000 00792BFF .+y...F\....g..n\^..(...7u..~.(Q~ 000180
6996EF9F 000078CC FF03FB10 A97FFFFE 499EEF9F 18A97F00 0078E7FF 165018A9 ..F...x..........i...........x......i 0001A0
6EFFFE67 69EF9F5C 50D00000 78DEFF00 FB000078 B9FF03FB 08A97F10 A97FFFFE ...............x.........x...F\..ig,.n 0001C0
08A97F00 A97F0000 7896FF16 5000A97E 5130A97E 000074E6 EF04FB30 A97F7E5C \~..O.....t..~.OQ~..F...x.......... 0001E0
```

Virtual block number 235 (000000EB), 512 (0200) bytes

```
FB000078 DDFF01FB FD57CB7F 000078C0 FF01FB00 DD000078 7DFF03FB FD5FCB7F ..._.....}x..........x.....W.......x... 000000
0078A3FE 00FB0000 78C2FE01 FBFD5FCB 7F000078 A5FF01FB 00DD0000 78BEFF00 ...x............x....._......x..........x. 000020
00785FFF 01FB07AF 9F000078 75FF01FB F352CF9F 00007880 FF01FBF5 05CF9F00 ...........x.....R....ux............._x. 000040
0138CF9E FCADFDAF 9EFCADFD AF9EFCAD FDAF9E04 0000783C FF16FCAD FDAF9E00 .........<x..........................8. 000060
AE0BD008 AEFFFE68 C5EF9E37 DD000010 008FDD6E 2B006E00 2C5E2BC2 00DD7FAB .....+^,.n.+n.........7...h......... 0000B0
ADFDAF9E 04000077 EDFF166F AB000000 008F4A5E 37C00000 783EFF01 FB5EDD2C ,.^...>x...7^J........o...w......... 0000A0
0000781C FF01FBFE BFCB7F00 0077FFFF 01FB0BDD 7FAB00EE CF9EFCAD FDAF9EFC ......................w..............x.. 0000C0
9F0A1200 0042E88F 5C515C6F AB4E6FAB 5C4A5C08 405C6FAB 4E000077 FDFF00FB ....w..N.o\@.\J\.oN.o\Q\..B..... 0000E0
7FAB009A CF9EFCAD FDAF9EFC ADFDAF9E 04000077 99FF1600 0077C3FF 01FB0EAF .......w.......w......................... 000100
01D077AB 73ABD03E 15000000 008F5C51 5C73AB4E 73AB5C4A 5C2F5843 586FAB4E N.oXCX/\J\.sN.s\Q\........>...s.w.. 000120
FF00FB00 007777FF 01FB0BDD FCADFDAF 9E231100 026FAB01 77ABF16F ABD76FAB .o..o...w...o...#................ww..... 000140
7726FF16 6FABB9AF 4AFCADFD AF9E6FAB D7E06FAB 77ABF3FC ADFDAF9E 00007780 .w..............w.o....o.......J....o..3w 000160
6FCF9F00 00772FFF 01FBFF7A CF9F7FAB 28AF9EFC ADFDAF9E FCADFDAF 9F040000 ......................(....z..../w.....o 000180
FDAF9EFC ADFDAF9E 04000076 F1FF1600 0076EBFF 01FB0BDD 00007724 FF01FBFF .....$w.........v......v................ 0001A0
FFFE395F EF9E511F 32FF6FCB 084A0000 7712FF00 FB000077 09FF01FB 00DDFCAD ..........w.........w..J..o.2.Q.._9.. 0001C0
7F7E5C6E FFFE656C EF9F5C50 D0000076 BDFF00FB 000076A0 FF1650FD 57CB7E52 R~.W.F....v..........v....F\..le..n\~. 0001E0
```

Virtual block number 236 (000000EC), 512 (0200) bytes

```
FFFE6730 EF9F18A9 7F000076 79FF1650 18A97E51 28A97E00 0072C9EF 04FB28A9 .(.....r..~.(Q~..F..yv.........Oy.. 000000
FF00FB00 00764BFF 03FB08A9 7F10A97F FFFE6728 EF9F0000 765EFF03 FB10A97F .......^v.....(g...............Kv...... 000020
A97E5130 A97E0000 7278EF04 FB30A97F 7E5C6EFF FE64FBEF 9F5C50D0 00007670 rv...F\....d..n\~...O....xr..^.OQ~. 000040
7652FF01 FB00DD00 00760FFF 03FBFD5F CB7F08A9 7F00A97F 00007628 FF165000 .F.;(v................_......v..........Rv 000060
5FCB7F00 007637FF 01FB00DD 00007650 FF00FB00 00766FFF 01FBFD57 CB7F0000 ....W.....ov......Fv..........7v....._ 000080
01FBF0E4 CF9F0000 7612FF01 FBF297CF 9F000076 35FF00FB 00007654 FF01FBFD ....Tv......5v.................v......... 0000A0
FCADFDAF 9E040000 75CEFF16 FCADFDAF 9E000075 F1FF01FB 07AF9F00 007607FF ..v.............u.................u.......... 0000C0
EF9E52FB AF9ECEFC 00000450 01D00000 75B2FF16 50FFFE33 31EF9EFC ADFDAF9E ........13..F....u.....F..........R.. 0000E0
FDAF9EFC ADFDAF9E FCADFDAF 9EFCADFD AF9E0000 75BAFF16 5150D050 FFFE419C .A..F.FQ....u............................ 000100
D0000075 A5FF00FB 000075C4 FF01FBFF FE6637EF 9F000075 A9FF01FB 00DDFCAD ..........u.....7f.........u..........u.... 000120
007573FF 01FB00DD FFFE9014 EF02FBF8 A9DFF8A9 18D0FCA9 DFFCA900 00004DBF .M...............................su. 000140
F8A903D0 FCA9DFFC A91BD000 00736FFF 00FB0000 7596FF01 FBFFFE46 09EF9F00 .....f..........u.......ou.................. 000160
0000755C FF01FBFF FE65DFEF 9F000075 41FF01FB 00DDFFFE 8FE2EF02 FBF8A9DF ........................Au.......e.......\u.. 000180
01FB00DD FFFE8FB0 EF02FBF8 A9DFF8A9 05D0FCA9 DFFCA914 D0000075 3DFF00FB ....=u............................... 0001A0
```

```
65A6EF9F 00007528 FF01FB93 BB7F0000 7532FF01 FBFFFE65 B5EF9F00 00750FFF ..u.....e.....2u.........(u.....e 0001C0
97AB0100 00012C8F F197ABD7 97AB01D0 000074F4 FF00FB00 007513FF 01FBFFFE ......u.......t.................. 0001E0

Virtual block number 237 (000000ED), 512 (0200) bytes

0097AB0A F2BFCB4C 00000000 8F4A5C00 01EAAF00 97AB0AFC ADFDAF9E 36110002 ...6..............\J.....L........ 000000
9FFCADFD AF9E97AB D7CD97AB C5AFF3FC ADFDAF9E F773CB4C ECAF4A5C 000107AF ....\J..L.s....................... 000020
14445C08 425C8FBB 4E3F9931 0313C2AF 5C515C9B AB4E0000 7482FF01 FB3D93CF .......t..N..\Q\....1.?N..\B.\D. 000040
504A0000 74AAFF01 FBFFFE65 19EF9FA3 ABA5AF4A 9FAB5C4A 5C800044 998F405C \Q..D..\J\..J.......e.......t..JP 000060
01FBFFFE 64FAEF9F 5C01CE03 115CD404 1385AF58 515BA7AB 4EFCADFD AF9EA7AB .......N..XQX.....\.....\....d.... 000080
3103135C D55C58C8 5801CE03 1158D404 13000000 008F5851 58505000 007483FF ..t...PPXQX.........X....X.X\.\..1 0000A0
CBAF5C51 5C9BAB4E 000073F4 FF01FB3C 09CF9FA3 AB5C4A5C 08405CA3 AB4E0093 ..N..\@.\J\......<.....s..N..\Q\.. 0000C0
0001ECAF 00A3AB0A F2BFCB4C A7ABD05C 00010000 012C8F00 A3ABOA3F 0B310313 ..1.?...........\...L............ 0000E0
007407FF 01FBFFFE 647EEF9F F773CB4C 504A0000 741AFF01 FBFFFE64 99EF9F5C \...d.......t..JPL.s...^d.......t. 000100
EF04FB00 A97FFFFE 646EEF9F 9FABDD03 DD6B1102 125C5851 58A7AB4E 5C505000 .PP\N..XQX\....k.........nd........ 000120
A9DFFCA9 0AD0FCAD FDAF9EFF 2D31A7AB 504A0000 73DAFF01 FB00A97F 00007038 8r..........s...JP..1-............ 000140
01FBFFFE 6432EF9F 0000735C FF01FB00 DDFFFE8D FDEF02FB F8A9DFF8 A917D0FC .....................\s.....2d.... 000160
9EFCADFD AF9E3E56 31000073 35FF01FB 3234CF9F 00007358 FF00FB00 007377FF .ws......Xs.....42...5s..1V>...... 000180
00A97FFF FE6403EF 9F000072 D1FF03FB 00A97FFF FE640BEF 9F93BB7F FCADFDAF ..........d..........r......d..... 0001A0
AF4AABAB 00000000 8F4A0000 72F6FF01 FB339BCF 9F000072 BDFF03FB FC77CB7F ..w......1......3.....r..J........J. 0001C0
FE6367EF 9F000072 D9FF01FB 00DDFCAD FDAF9EB7 ABEDAF4A B3ABA3AB D0AFABF7 .........J......................r.....dc. 0001E0

Virtual block number 238 (000000EE), 512 (0200) bytes

A9DFF8A9 18D0FCA9 DFFCA900 00004DBF D0000072 D5FF00FB 000072F4 FF01FBFF .....r..........r....M............... 000000
00FB0000 72C6FF01 FBFFFE63 91EF9F00 0072A3FF 01FB00DD FFFE8D44 EF02FBF8 ....D.........r.......c.........r.... 000020
71FF01FB 00DDFFFE 8D12EF02 FBF8A9DF F8A903D0 FCA9DFFC A91BD000 00729FFF ..r.............................. 000040
05D0FCA9 DFFCA916 D0000072 6DFF00FB 0000728C FF01FBFF FE630FEF 9F000072 r.....c.........r.......mr.......... 000060
7262FF01 FBFFFE63 35EF9F00 00723FFF 01FB00DD FFFE8CE0 EF02FBF8 A9DFF8A9 ..................?r.....5c.....br 000080
00007224 FF00FB00 007243FF 01FBFFFE 62D6EF9F 00007258 FF01FB93 BB7F0000 .........Xr......b.....Cr.......$r.. 0000A0
EF9F0000 71F6FF01 FB00DDFF FE8C97EF 02FBF8A9 DFF8A908 D0FCA9DF FCA905D0 ................................. 0000C0
F8A9DFF8 A90AD0FC A9DFFCA9 05D00000 71F2FF00 FB000072 11FF01FB FFFE62F4 .b.......r.......q.................. 0000E0
FF00FB00 0071DFFF 01FBFFFE 62CAEF9F 000071C4 FF01FB00 DDFFFE8C 65EF02FB ...e...........q.....b.......q..... 000100
7192FF01 FB00DDFF FE8C33EF 02FBF8A9 DFF8A90C D0FCA9DF FCA93AD0 000071C0 .q...:..................3..........q 000120
A90ED0FC A9DFFCA9 3AD00000 71BEFF00 FB000071 ADFF01FB FFFE62A0 EF9F0000 .....b.......q........q...:........ 000140
00717BFF 01FBFFFE 6276EF9F 00007160 FF01FB00 DDFFFE8C 01EF02FB F8A9DFF8 ..................`q.....vb.....{q. 000160
FB00DDFF FE8BCFEF 02FBF8A9 DFF8A910 D0FCA9DF FCA93AD0 0000715C FF00FB00 ....\q...:......................... 000180
A9DFFCA9 2DD00000 712AFF00 FB000071 49FF01FB FFFE624C EF9F0000 712EFF01 ...q.....Lb.....Iq......*q...-.... 0001A0
01FBFFFE 6222EF9F 000070FC FF01FB00 DDFFFE8B 9DEF02FB F8A9DFF8 A914D0FC .......................p.....'b.... 0001C0
0232C3AB F2AF4ABF ABF7AF4A BBAB0000 00008F4A 000070F8 FF00FB00 00711FFF ..q.......p..J.........J....J....2. 0001E0

Virtual block number 239 (000000EF), 512 (0200) bytes

510232CB ABD3AF4A C7ABD8AF 4A000070 79FF1650 FDB7CB7E 52FFFE42 EFEF9E51 Q...B..R^...P..yp..J....J....2.Q 000000
9E510232 D3ABB4AE AACEABB9 AF4A0000 705AFF16 50FDBFCB 7E52FFFE 42D0EF9E ...B..R^...P..Zp..J.....J.....2.Q. 000020
504A0000 70CAFF01 FBFFFE61 39EF9F00 00703BFF 1650FDC7 CB7E52FF FE42B1EF ..B..R^...P..;p.....9a.......p..JP 000040
```

```
00B7AB0A 021C3103 15A3ABB7 ABD1B7AB 5C4A5C08 405CB7AB 4EFCADFD AF9EA7AB .......N..\@.\J\..........1...... 000060
01E2AF00 B7AB0AC9 11021200 0000008F 585158F2 BFCB4C4E 5C000100 00012CBF ......\NL...XRX................. 000080
2F310313 D5AF5C51 5C9BAB4E 00007018 FF01FB38 2DCF9FA7 ABF2BFCB 4CD05C00 .\.L.......-8.....N..\Q\....1/ 0000A0
9BAB4E00 006FEFFF 01FB369E CF9FD7AB 504A0000 705AFF01 FBFFFE60 D9EF9F3B ........Zp..JP.....6....o..N.. 0000C0
EF9F5CDD 02DD5C5C 4A5C0840 5C10445C 08425C8F BB4E3B06 310313AC AF5C515C \Q\....1.N..\B.\D.\@.\J\\...\... 0000E0
D0DFAB5C 4A5C5050 00007010 FF01FB00 A97F0000 6C6EEF04 FB00A97F FFFE6104 .a........nl..........FP\J\... 000100
52FFFE64 79EF9E51 0C32FCAD FDAF9E01 0F310003 DBAB01DF ABF1DBAB D7DBAB01 ...............1.......2.Q..yd..R 000120
DBFDD7CB 2D00006F 71FF01FB 0216CF9F FCADFDAF 9E00006F 41FF1650 FDCFCB7E ~...P..Ao...............ao..-.... 000140
4A110213 FFFE4176 EF0220FD DBDBFDD7 CB2D3A82 310312FF FE418BEF 0220FDDB .. ...A....1.!-....... ..vA.....J 000160
FFFEB9CC EF02FBF8 A9DFF8A9 18D0FCA9 DFFCA905 D000006F 41FF01FB 2F40CF9F ..@...Ao.......................... 000180
006F3BFF 01FB00A9 7F00006B EDEF03FB 00A97F28 DD20DD00 006F2BFF 01FB00DD .....+o.... .(.......k........o.. 0001A0
110213FF FE410DEF 0820FDDB DBFDD7CB 2DFCADFD AF9E8111 00006F1C FF00FB00 .....o..........-....... ...A..... 0001C0
08A97FFF FE6023EF 9F00006E 91FF03FB 08A97FFF FE602BEF 9FFFFE60 29EF9F4A J..)'....+'..........n....$'..... 0001E0
```

Virtual block number 240 (000000F0), 512 (0200) bytes

```
CF9F0000 6E6AFF03 FBFC77CB 7F00A97F FFFE6018 EF9F0000 6E7EFF03 FB00A97F ......^n.....`.......w....Jn.... 000000
DBABD7FE F4DBAB01 DFABF1FC ADFDAF9E FCADFDAF 9E1A1100 006EA3FF 01FB2F48 H/.....n......................... 000020
08405CAB AB4E1812 FFFE4077 EF0420FD DBDBFDD7 CB2DFCAD FDAF9EFC ADFDAF9E ...............-....... ..w@....N..\@. 000040
B3AB4EAF AB5C4A5C 08405CAF AB4E0B11 00006E5C FF01FB31 A3CF9FAB AB5C4A5C \J\.....1...\n....N..\@.\J\..N.. 000060
EF0C28FC ADFDAF9E FDCA3103 15000000 008F5C51 5CB3AB4E B3AB5C4A 5C08425C \B.\J\..R..\Q\........1........(.. 000080
7E52FFFE 7D86EF9E 510C32FF FE6303EF FFFE7D94 EF0C28FF FE7D9BEF FFFE401F .@....}..(...}.....c..2.Q...}..R~ 0000A0
52FFFE3F D7EF9E51 0932FFFE 630CEFFF FE3FEEEF 04280000 6DC2FF16 50FDCFCB ...P....m..(...T.....c..2.Q...T..R 0000C0
00006D8C FF1650FD E7CB7E52 FFFE3FC2 EF9E5109 3200006D A1FF1650 FDDFCB7E ~...P....m..2.Q...?..R~...P....m.. 0000E0
01FB2B75 CF9FFCAD FDAF9E00 006D77FF 1650FDEF CB7E52FF FE3FADEF 9F510932 2.Q...T..R~...P..wm...........u+.. 000100
0413FFFE 3FB6EF02 20FDDBDB FDD7CB2D 00006D9C FF01FB05 4FCF9F00 006DA7FF ..m.....O......m..-....... ...?.... 000120
58C85801 CE031158 D40413FF FE3F9DEF 0220FDDB DBFDD7CB 2D5C01CE 03115CD4 .\....\-....... ...?......X.....X.X 000140
6D4AFF01 FB245BCF 9FBBAB00 0000008F 4AFCADFD AF9EAB11 38883103 135CD55C \.\..1.8........J.........[$....Jm 000160
FB40A97F 7EBFAB6E FFFE5E98 EF9F0000 6D3AFF01 FB2B08CF 9FFCADFD AF9E0000 ...........+....:m......^..n..^..@. 000180
A97F7EC3 AB6EFFFE 5E7EEF9F 00006CDC FF165010 A97E5140 A97E0000 692CEF04 ...i..~.@Q~...P...1.....~^..n...~.. 0001A0
FB00A97F 10A97F08 A97F0000 6CBAFF16 5008A97E 5148A97E 0000690A EF04FB48 H....i...~.HQ~...P...1............. 0001C0
AB6EFFFE 5E32EF9F 00006C90 FF03FBFD DFCB7F00 A97FFDB7 CB7F0000 6CA2FF03 ...1......................1.....2^..n. 0001E0
```

Virtual block number 241 (000000F1), 512 (0200) bytes

```
FFFE5E18 EF9F0000 6C76FF16 5010A97E 5140A97E 000068C6 EF04FB40 A97F7EC7 .^..@....h..~.@Q~..P...vl......^.. 000000
7E08A97E 00006C54 FE165008 A97E5148 A97E0000 68A4EF04 FB48A97F 7ECBAB6E n..~..H.....h..~.HQ~...P...T1....... 000020
EF9F0000 6C2AFF03 FBFDE7CB 7F00A97F FDBFCB7F 00006C3C FF03FB00 A97F10A9 .........<l..................*l.... 000040
00006C10 FF165010 A97E5140 A97E0000 6860EF04 FB40A97F 7ECFAB6E FFFE5DCC .l...n..~..@...`h..~.@Q~..P...1... 000060
6BEEFF16 5008A97E 5148A97E 0000683E EF04FB48 A97F7ED3 AB6EFFFE 5DB2EF9F ...l..n..~..H...>h..~.HQ~..P....k 000080
FF03FBFD EFCB7F00 A97FFDC7 CB7F0000 6BD6FF03 FB00A97F 10A97F08 A97F0000 ...............k................ 0000A0
FFFE60D8 EF0C2800 006BAFFF 03FBFDEF CB7FFDEF CB7FFFFE 5D5EEF9F 00006BC4 .k....^]...............k...(...`.. 0000C0
F1EF0220 FDDBDBFD D7CB2DFC ADFDAF9E 00006BDC FF01FB03 8FCF9FFF FE7B5FEF ._(..........k........-....... .... 0000E0
DBFDD7CB 2D01FA31 0312FFFE 3DDCEF02 20FDDBDB FDD7CB2D 020D3103 12FFFE3D =....1..-........ ...=.....1..-..... 000100
FDDBDBFD D7CB2D00 78310000 6B96FF01 FB1E0DCF 9F0E12FF FE3DA6EF 0420FDDB .. ...=...............k...1x.-...... 000120
CB2D0000 6B2EFF16 50FDD7CB 7E52FFFE 3D98EF9E 51083215 12FFFE3D 60EF0820 ..'=.....2.Q...=...R~...P...k...-.. 000140
```

```
D7CB2D01 98310160 31031208 5C515CBB AB4E0F12 FFFE3D7E EF0820FD DBDBFDD7 ..........N..\Q\...1`.1..-.. 000160
DBFDD7CB 2DFDE731 00006B34 FF01FB01 90CF9F0E 12FFFE3D 16EF0620 FDDBDBFD .... ...............4k..1..-.... 000180
0000008F 5C515CBB AB4EFCAD FDAF9EFD B931012C 310312FF FE3CEFEF 0920FDDB .. ...<....1..1.......N..\Q\.... 0001A0
5C26EF9F E3ABDD02 DDE3AB5C 4A5C0840 5C10445C 08425C8F BB4E014F 31031200 ...10.N..\B.\D.\@.\J\.........&\ 0001C0
E7AB5C4A 5C08425C 50500000 6B32FF01 FB00A97F 00006790 EF04FB00 A97FFFFE .........g.........2k..PP\B.\J\.. 0001E0

Virtual block number 242 (000000F2), 512 (0200) bytes

5C1EEF9F 0000674C EF03FB18 A97FFFFE 5BF6EF9F 5CDD5C5C 4A5C0842 5CE3AB4E N..\B.\J\\.\...[.........Lg.....\ 000000
A97E0000 6A52FF16 5010A97E 5140A97E 000066A2 EF04FB40 A97F7EE7 AB6EFFFE ..n..~..Q....f..~.@Q~..P..RJ..... 000020
58235743 57E3AB4E 5C5C4A5C 10405CE3 AB4E0000 6A3AFF03 FB08A97F 18A97F10 ..........!J..N..\@.\J\\N..WCW#X 000040
85EF9F08 A97F00A9 7F000067 05EF04FB 00A97FFF FE5B9BEF 9F5CDD58 DD58584A JXX.X.\...[.........g..........j. 000060
01FB2D6E CF9FFCD0 31031500 0000008F 5C515CE7 AB4E0000 69FEFF03 FBFFFE5B [.......i..N..\Q\........1....n-.. 000080
4A5C0840 5CABAB4E F2BFCB4C DDAF4A5C 00010000 012C8F00 EBAB0A00 006A27FF .'J.............\J..L...N..\@.\J 0000A0
2CFCADFD AF9E3B11 0214BBAF 5C515CB3 AB4EB3AB 5C4A5C08 425CB3AB 4EABAB5C \..N..\B.\J\..N..\Q\.....;......, 0000C0
D9CF9FA7 ABF2BFCB 4CD05C00 01B7AF00 B7AB0AFF FE5ECBEF 0C20FDD3 DBFDCFCB ...... ...^...........\.L........ 0000E0
00006988 FF16FCAD FDAF9EFC 55310312 81AF5C51 5C9BAB4E 000069C4 FF01FB31 1....i..N..\Q\....1U..........i.. 000100
01EFABF1 97ABD797 ABB7ABD0 EFABA3AB D0BBAB08 4AFCADFD AF9EFCAD FDAF9E04 ...........J...................... 000120
0064BF00 F773CB4C 0A5C0001 0000012C 8F0097AB 0AFCADFD AF9E4011 000297AB .....@...................\.L.s...d. 000140
EFABF3FC ADFDAF9E 15110212 FFFE71EE EF4C0C20 FDFBDBFD F7CB2D5C 000C0000 ....\-...... .L..Q.............. 000160
5C0001B3 AF0097AB 0AEBAB97 ABD0FCAD FDAF9E5D 11FCADFD AF9E97AB D7C397AB ............J....................\ 000180
11021300 0000008F 5C515C9B AB4E0000 691AFF01 FB312FCF 9FA7ABF2 BFCB4CD0 .L......./1.....i..N..\Q\........ 0001A0
9BAB4E00 0068EFFF 01FB2F9E CF9FD7AB 504A0000 695AFF01 FBFFFE59 D9EF9F29 )...Y.....Zi..JP...../....h..N.. 0001C0
B9AF4AFF FE5DBBEF 0C20FDFB DBFDF7CB 2CFCADFD AF9E0082 310312D4 AF5C515C \Q\....1................ ...J..J.. 0001E0

Virtual block number 243 (000000F3), 512 (0200) bytes

4A000068 6DFF1650 FDB7CB7E 52FFFE3A 81EF9E51 0232C3AB 000043C8 BF4ABFAB ..J..C....2.Q....!..R~...P..mh..J 000000
8F4A0000 684EFF16 50FDBFCB 7E52FFFE 3A62EF9E 510232CB ABDDAF4A C7AB97AF ....J....2.Q..b!..R~...P..Nh..J. 000020
0000682C FF1650FD C7CB7E52 FFFE3A40 EF9E5102 32D3ABBB AE4ACFAB 00000000 ......J....2.Q..@!..R~...P...h.. 000040
FDAF9EFC ADFDAF9E 04000068 31FF16FC ADFDAF9E FFFE5D76 EFFFFE3A 58EF0428 (..X!...vJ.........1h............ 000060
510332FC ADFDAF9E 008C3103 12085C51 5CF3AB4E FCADFDAF 9EFCADFD AF9EFCAD ............N..\Q\...1........2.Q 000080
FE07CB7E 52FFFE39 D6EF9E51 03320000 67DAEF16 50FDFFCB 7E52FFFE 39EBEF9E ...9..R~...P...g..2.Q...9..R~... 0000A0
ADFDAF9E 000067B0 FF1650FE 0FCB7E52 FFFE39C1 EF9E5103 32000067 C5FF1650 P...g..2.Q...9..R~...P...g...... 0000C0
52FFFE39 8EEF9E51 04320000 6796FF16 50FE17CB 7E52FFFE 39A3EF9E 510432FC .2.Q...9..R~...P...g..2.Q...9..R 0000E0
0000676C FF1650FE 27CB7E52 FFFE3979 EF9E5104 32000067 81FF1650 FE1FCB7E ~...P...g..2.Q..g9..R~.'.P..1g.. 000100
00320000 674EFF16 50FDD7CB 7E52FFFE 395BEF9E 510032FC ADFDAF9E F3AB084A J........2.Q..[9..R~...P..Ng..2. 000120
CB2D0000 676EFF01 FB00F8CF 9F000067 39FF1650 FDF7CB7E 52FFFE39 46EF9E51 Q..F9..R~...P..9g...........ng..-. 000140
00674BFF 01FB07B3 CF9FFCAD FDAF9E00 D2310313 FFFE3921 EF0020FD DBDBFDD7 ..... ..!9....1..............Kg. 000160
FF01FB08 56CF9FFC ADFDAF9E 00AF3103 13FFFE38 FFEF0020 FDDBDBFD D7CB2D00 .-...... ....8....1..........V.... 000180
FE2FCB2D FCADFDAF 9E008C31 0313FFFE 38DBEF00 20FDDBDB FDD7CB2D 00006728 (g..-...... ...8....1.......-./. 0001A0
ADFF1650 FDFFCB7E 51FE2FCB 7EFCADFD AF9E6511 0212FFFE 39C9EF03 20FE33DB .3. ...9.....e.....~./.Q~...P... 0001C0
8DFF1650 FE07CB7E 51FE3FCB 7E000066 9DFF1650 FE17CB7E 51FE37CB 7E000066 f..~.7.Q~...P...f..~.?.Q~...P... 0001E0
```

Virtual block number 244 (000000F4), 512 (0200) bytes

```
6DFF1650 FE0FCB7E 51FE4FCB 7E000066 7DFF1650 FE1FCB7E 51FE47CB 7E000066 f..".C.Q"...P..}f..".D.Q"...P..m 000000
89FF01FB 087CCF9F FCADFDAF 9E000066 5DFF1650 FE27CB7E 51FE57CB 7E000066 f..".W.Q".'.P..]f.........1...... 000020
DFCB7F01 DD04DDFC ADFDAF9E FCADFDAF 9E040000 665AFF16 FCADFDAF 9E000066 f.........Zf.................... 000040
DD000062 FDEF04FB FE67CB7F FDE7CB7F 01DD04DD 00006310 EF04FBFE 5FCB7FFD ..._......c.............g.....b... 000060
EF04FB00 A97FFDDF CB7F05DD 03DD0000 62EAEF04 FBFE6FCB 7FFDEFCB 7F01DD04 ........o.....b................. 000080
FDE7CB7F 05DD03DD 000065D0 FF03FBFE 37CB7FFF FE579BEF 9F00A97F 000062D8 .b........W....7......e......... 0000A0
03DD0000 65AAFF03 FBFE47CB 7FFFFE57 75EF9F00 A97F0000 62B2EF04 FB00A97F .......b.......uW....G.....e.... 0000C0
FF03FBFE 57CB7FFF FE574FEF 9F00A97F 0000628C EF04FB00 A97FFDEF CB7F05DD .............b.......OW....W.... 0000E0
7FFFFE57 29EF9F00 A97F0000 6266EF04 FB00A97F FDDFCB7F 0BDD02DD 00006584 .e...................fb.......)W... 000100
9F00A97F 00006240 EF04FB00 A97FFDE7 CB7F08DD 02DD0000 655EFF03 FBFE2FCB ./....^e..................@b...... 000120
621AEF04 FB00A97F FDEFCB7F 08DD02DD 00006538 FF03FBFE 3FCB7FFF FE5703EF ..W....?....8e.................b 000140
CB7FFDEF CB7F0ADD 04DD0000 6512FF03 FBFE4FCB 7FFFFE56 DDEF9F00 A97F0000 ........V....O.....e............ 000160
36E9EF9E 51013242 12FFFE37 FCEF0320 FE33DBFE 2FCB2D00 0061F3EF 04FBFE77 w.....a..-./..3. ...7...B2.Q...6 000180
C9FF1650 FE87CB7E 52FFFE36 D4EF9E51 01320000 64DEFF16 50FE7FCB 7E52FFFE ..R"...P...d..2.Q...6..R"...P... 0001A0
FCADFDAF 9E03DD31 000064B4 FF1650FE 8FCB7E52 FFFE36BF EF9E5101 32000064 d..2.Q...6..R"...P...d..1....... 0001C0
FE2FCB7E 51FDFFCB 7E231200 0000008F 5C515C50 4E000065 41FF01FB FE5FCB7F .._....Ae..NP\Q\......#"...Q"./. 0001E0
```

Virtual block number 245 (000000F5), 512 (0200) bytes

```
7FFCADFD AF9E00A5 31000064 79FF1650 FE37CB7E 51FE17CB 7E000064 89FF1650 P...d..."...Q".7.P..y8..1........ 000000
FDD7CB7E 52FFFE36 6CEF9E51 08321518 2A5C515C 504E0000 6502FF01 FBFE5FCB ._......e..NP\Q\*..2.Q..16..R"... 000020
021293AF 5C515C50 4E000064 D5FF01FB FE37CB7F FCADFDAF 9E000064 45FF1650 P..Ed........7.....d..NP\Q\.... 000040
5CD40419 00004348 8F5C515C 504E0000 64BAFF01 FBFE37CB 7FFCADFD AF9E5D11 .J.......7.....d..NP\Q\.HC.....\ 000060
03115BD4 04140000 44968F58 5158504E 0000649C FF01FBFE 37CB7F5C 01CE0311 ....\..7.....d..NPXQX..D.....X... 000080
9E000063 CDFF1650 FDD7CB7E 52FFFE35 F4EF9E51 08321513 5CD55C58 C85801CE ..X.X\.\..2.Q...5..R"...P...c... 0000A0
51FE07CB 7E231200 0000008F 5C515C50 4E000064 5DFF01FB FE67CB7F FCADFDAF ......g....]d..NP\Q\......#"...Q 0000C0
AF9E00A5 31000063 95FF1650 FE47CB7E 51FE1FCB 7E000063 A5FF1650 FE3FCB7E ".?.P...c..."...Q".G.P...c..1.... 0000E0
52FFFE35 88EF9E51 08321518 2A5C515C 504E0000 641EFF01 FBFE67CB 7FFCADFD .....g.....d..NP\Q\*..2.Q...5..R 000100
5C515C50 4E000063 F1FF01FB FE47CB7F FCADFDAF 9E000063 61FF1650 FDD7CB7E "...P..ac.........G.....c..NP\Q\ 000120
00004348 8F5C515C 504E0000 63D6FF01 FBFE47CB 7FFCADFD AF9E5D11 021293AF .....J.......G.....c..NP\Q\.HC.. 000140
04140000 44968F58 5158504E 000063B8 FF01FBFE 47CB7F5C 01CE0311 5CD40419 ...\....\..G.....c..NPXQX..D.... 000160
E9FF1650 FDD7CB7E 52FFFE35 10EF9E51 08321513 5CD55C58 C85801CE 03115BD4 .X....X.X\.\..2.Q...5..R"...P... 000180
7E231200 0000008F 5C515C50 4E000063 79FF01FB FE6FCB7F FCADFDAF 9E000062 b.........o.....yc..NP\Q\......#" 0001A0
31000062 B1FF1650 FE57CB7E 51FE27CB 7E000062 C1FF1650 FE4FCB7E 51FE0FCB ...Q".O.P...b..".'.Q".W.P...b..1 0001C0
A4EF9E51 08321518 2A5C515C 504E0000 633AFF01 FBFE6FCB 7FFCADFD AF9E00A5 ...........o.....:c..NP\Q\*..2.Q... 0001E0
```

Virtual block number 246 (000000F6), 512 (0200) bytes

```
4E000063 0DFF01FB FE57CB7F FCADFDAF 9E000062 7DFF1650 FDD7CB7E 52FFFE34 4..R"...P..}b..........W.....c..N 000000
8F5C515C 504E0000 62F2FF01 FBFE57CB 7FFCADFD AF9E5D11 021293AF 5C515C50 P\Q\.....J........W.....b..NP\Q\. 000020
44968F58 5158504E 000062D4 FF01FBFE 57CB7F5C 01CE0311 5CD40419 00004348 HC.....\....\..W.....b..NPXQX..D 000040
FDD7CB7E 52FFFE34 2CEF9E51 08321513 5CD55C58 C85801CE 03115BD4 04140000 .....X....X.X\.\..2.Q...4..R"... 000060
01FBFE67 CB7F5C50 D0000062 95FF01FB FE5FCB7F FCADFDAF 9E000062 05FF1650 P...b..............b...P\..g.... 000080
515C5C4E 5C58C058 50D00000 6276FF01 FBFE6FCB 7F5C58C0 5850D000 006287FF ..b...PX.X\..o....vb...PX.X\N\\Q 0000A0
```

```
FDAF9E00 0061AFFF 1650FDD7 CB7E52FF FE33D6EF 9E510832 1515C000 465A8F5C \.ZF....2.Q...3..R^...P...a...... 0000C0
33DBFE2F CB2DFCAD FDAF9E02 2C310312 FFFE33B7 EF0820FD DBDBFDD7 CB2DFCAD ..-....... ...3....1.......-./..3 0000E0
11000061 6DFF1650 FE7FCB7E 52FFFE33 77EF9E51 01321712 FE03DBFD FFCB20FE -. .........2.Q..w3..R^...P..ma... 000100
DBFE3FCB 2DFCADFD AF9E0000 6156FF16 50FE7FCB 7E52FFFE 3361EF9E 51013215 .2.Q..a3..R^...P..Va.........-.?.. 000120
0000612C FF1650FE 87CB7E52 FFFE3336 EF9E5101 321712FE 0BDBFE07 CB20FE43 C. ..........2.Q..63..R^...P...a.. 000140
FE4FCB2D FCADFDAF 9E000061 15FF1650 FE87CB7E 52FFFE33 20EF9E51 01321511 ..2.Q.. 3..R^...P...a.........-.0. 000160
0060EBFF 1650FE8F CB7E52FF FE32F5EF 9E510132 1712FE13 DBFE0FCB 20FE53DB .S. ..........2.Q...2..R^...P...`. 000180
2FCB2DFC ADFDAF9E 000060D4 FF1650FE 8FCB7E52 FFFE32DF EF9E5101 32151100 ...2.Q...2..R^...P...`.........-./ 0001A0
60AAFF16 50FE77CB 7E52FFFE 32B0EF9E 51043215 12FFFE33 C8EF0320 FE33DBFE ..3. ...3....2.Q...2..R^.w.P...` 0001C0
4E58FE97 CB3C0000 5D6EEF03 FBFE97CB 7FFFFE52 21EF9F0C DDFCADFD AF9E0000 ..............!R...........n]..<...XN 0001E0
```

Virtual block number 247 (000000F7), 512 (0200) bytes

```
20DD0000 606AFF03 FB38A97F FFFE523C EF9FFE97 CB7FF7AB 584A5824 5C435C58 X\C\$XJX..........<R....8...J`...  000000
7FCB7F00 00604BFF 03EB28A9 7F38A97F 30A97F00 005D77EF 03FB30A9 7FF7ABDD ......0...w]....0..8..(...K`...... 000020
7F000060 29FF03FB 18A97F20 A97FFE2F CB7F0000 603AFF03 FB20A97F 28A97FFE ...(.. ...!`..../... .......)`... 000040
006007FF 03FB08A9 7F10A97F FE3FCB7F 00006018 FF03FB10 A97F18A9 7FFE87CB ................`....?.............`. 000060
FF03FBFE 9FCB7F00 A97FFE4F CB7F0000 5FF6FF03 FB00A97F 08A97FFE 8FCB7F00 ..................._.....0............. 000080
FE5197EF 9FFE5FCB 7F00005F D1FF03FB FE9FCB7F FE9FCB7F FE77CB7F 00005FE4 ._.....W.................._....._.....Q. 0000A0
FE6FCB7F 00005FAC FF03FB18 A97F20A9 7FFE67CB 7F00005F BDFF03FB 20A97FFF ... ......_.....g.... ........_.....o. 0000C0
CB7F0000 5F8AFF03 FB08A97F 10A97FFE 37CB7F00 005F9BFF 03FB10A9 7F18A97F ..............._.....7.............._.... 0000E0
005F67FF 03FBFEA7 CB7F00A9 7FFE57CB 7F00005F 79FF03FB 00A97F08 A97FFE47 G..............g_.....W...............g_.. 000100
0120FEB3 DBFEAFCB 2DFCADFD AF9EFCAD FDAF9E04 00005F7C FF16FCAD FDAF9E00 ...........|_..................-........ . 000120
ABCFFCAD FDAF9E00 005F73FF 01FB01EB CF9FFCAD FDAF9E2F 110212FF FE313EEF .>1....../..................s_.......... 000140
510132FC ADFDAF9E 00005F34 FF01FB3A DD008400 84FFCFFF CF008400 150501FB ......................:....4_.........2.Q 000160
FEAFCB7E 52FFFE30 F2EF9E51 00320000 5EFAFF16 50FEB7CB 7E52FFFE 30FCEF9E ...0..R^...P...^..2.Q...0..R^... 000180
5F0AFF01 FB049FCF 9F00005E D9FF1650 FEBFCB7E 51FE9FCB 7E00005E E5FF1650 P...^..^...Q^...P...^............_ 0001A0
FDD7CB7E 51FEC7CB 7E1013FF FE30ABEF 0220FECB DBFEC7CB 2DFCADFD AF9E0000 ........-....... ....0....^...Q^... 0001C0
3CCF9FFC ADFDAF9E FCADFDAF 9E040000 5EB6FF16 FCADFDAF 9E00005E A9FF1650 P...^...........^..................< 0001E0
```

Virtual block number 248 (000000F8), 512 (0200) bytes

```
4E31009A 009AFFE6 0040009A 000F0501 FBABCFFC ADFDAF9E 00005EC4 FF01FB01 ......^......................@........1N 000000
EF9E5101 3200005E 51FF1650 FDD7CB7E 52FFFE30 BBEF9E51 0832FCAD FDAF9EFF ........2.Q...0..R^...P..Q^..2.Q.. 000020
FFFE3022 EF9E5101 32FCADFD AF9E5A11 00005E3C FF1650FE AFCB7E52 FFFE303F ?0..R^...P..<^...Z.....2.Q..°0.. 000040
03DACF9F 00005E14 FF1650FE BFCB7E51 FEA7CB7E 00005E20 FF1650FE B7CB7E52 R^...P.. ^..^...Q^...P...^....... 000060
FEC7CB7E 1013FFFE 2FE6EF02 20FECBDB FEC7CB2D FCADFDAF 9E00005E 45FF01FB ...E^.........-....... .../.....^.... 000080
FDAF9EFC ADFDAF9E 0400005D F1FF16FC ADFDAF9E 00005DE4 FF1650FD D7CB7E51 Q^...P...]..............]............... 0000A0
5A0040FF E6005A00 0F0501FB ABCFFCAD FDAF9E00 005DFFFF 01FB0077 CF9FFCAD .....W.......]..................Z...@.Z 0000C0
00005D8C FF1650FD D7CB7E52 FFFE2FF6 EF9E5108 32FCADFD AF9EFE89 31005A00 .Z.1..........2.Q.../..R^...P...]... 0000E0
9E510432 FCADFDAF 9E1A1100 005D77FF 1650FEAF CB7E52FF FE2F7AEF 9E510132 2.Q..z/..R^...P..w]..............2.Q. 000100
FDAF9E04 00005D6C FF16FCAD FDAF9E00 005D5BFF 1650FDD7 CB7E52FF FE2FAAEF ../..R^...P..[]...............l]........ 000120
CB7E52FF FE2F22EF 9E510132 FFABF7AF 4AFBAB00 0000008F 4AFCADFD AF9EFCAD .........J...........J....2.Q.."/..R^. 000140
AF9E0000 5D0EFF16 50FEB7CB 7E52FFFE 2F11EF9E 51013200 005D23FF 1650FEBF ..P..#]..2.Q.../..R^...P...]..... 000160
FE2EDFEF 0220FECB DBFEC7CB 2DFCADFD AF9E0000 5D3EFF01 FB02D3CF 9FFCADFD .............>]........-........ ...... 000180
02DD0000 59BEEF04 FBFECFCB 7FFED7CB 7F05DD01 DDFCADFD AF9E026F 310313FF ...1...........................Y..... 0001A0
```

```
2E9CEF01 20FED3DB FECFCB2D FCADFDAF 9E000059 99EF03FB FEDFCB7F FED7CB7F ............Y.......-...... .... 0001C0
AB084A04 12FFFE2E 87EF0120 FED3DBFE CFCB2DFC ADFDAF9E FFAB084A 0412FFFE ....J........-...... .........J.. 0001E0

Virtual block number 249 (000000F9), 512 (0200) bytes

2DFCADFD AF9EFBAB 104A0412 FFFE2E69 EF0120FE D3DBFECF CB2DFCAD FDAF9EFB ......-...... ..i.....J........- 000000
20FED3DB FECFCB2D FCADFDAF 9EFBAB14 4A0412FF FE2E4FEF 0120FED3 DBFECFCB ...... ..O.....J.......-......... 000020
D25B01CE 03115BD4 04130857 5157FFAB 4E5C01CE 03115CD4 0413FFFE 2E46EF01 ..F.......\....\N..WQW....X.....X. 000040
CA5858D2 5801CE03 1158D404 13FFFE2E 07EF0220 FEE3DBFE DFCB2D5C 58CA5858 XX.X\-...... .........X.....X.XX. 000060
D40413FF FE2DEFEF 0120FED3 DBFECFCB 2DFCADFD AF9EFBAB 184A0413 5CD55C58 X\.\..J........-...... ...-........ 000080
FEDFCB2D 5C58CA58 58D25801 CE031158 D4041308 575157FF AB4E5C01 CE03115C \....\N..WQW....X....X.XX.X\-... 0000A0
AB1A4A04 135CD55C 58CA5858 D25801CE 031158D4 0412FFFE 2DB0EF02 20FEE3DB ... ...-......X....X.XX.X\.\..J.. 0000C0
DFCB2D5C 01CE0311 5CD40413 FFFE2D98 EF0120FE D3DBFECF CB2DFCAD FDAF9EFB ......-...... ...-.....\....\-.. 0000E0
1A4A0413 5CD55C58 CA5858D2 5801CE03 1158D404 13FFFE2D 6DEF0220 FEE3DBFE .... ..m-.....X....X.XX.X\.\..J. 000100
CB2D5C01 CE03115C D40413FF FE2D57EF 0120FED3 DBFECFCB 2DFCADFD AF9EFBAB .......-...... ..W-.....\....\-. 000120
4A04135C D55C58CA 5858D258 01CE0311 58D40413 FFFE2D2A EF0220FE E3DBFEDF ..... ..*-.....X....X.XX.X\.\..J 000140
2D5C01CE 03115CD4 0413FFFE 2D16EF01 20FED3DB FECFCB2D FCADFDAF 9EFBAB1A .......-...... ...-.....\....\- 000160
04135CD5 5C58CA58 58D25801 CE031158 D40413FF FE2CE7EF 0220FEE3 DBFEDFCB ...... .........X....X.XX.X\.\.. 000180
AB4EFCAD FDAF9EFD C5310312 00000000 8F5C515C FBAB4EFC ADFDAF9E FBAB1A4A J........N..\Q\.......1.......N. 0001A0
A9FF1650 FDD7CB7E 52FFFE2C CAEF9E51 0632FCAD FDAF9E42 11021310 5C515CFB .\Q\....B.....2.Q.......R"...P... 0001C0
52FFFE2C 84EF9E51 01320000 5786EF04 FBFDF7CB 7FFED7CB 7F06DD0C DD00005A Z..................W..2.Q.......R 0001E0

Virtual block number 250 (000000FA), 512 (0200) bytes

2C4DEF9E 51053215 121A5C51 5CFBAB4E FCADFDAF 9E00005A 81FF1650 FE4FCB7E "...P...Z.......N..\Q\...2.Q..M. 000000
CB7EFBAB 1C4AFCAD FDAF9E19 11FCADFD AF9E0000 5A5EFF16 50FDD7CB 7E52FFFE ..R"...P..^Z..............J...". 000020
9EFCADFD AF9E0400 005A4FFF 16FCADFD AF9E0000 5A42FF16 50FDD7CB 7E51FEC7 ..Q"...P..B7.........OZ......... 000040
FEE7CB7E 03AB5C4A 5C08405C 03AB4EFC ADFDAF9E 03AB0000 00008F4A FCADFDAF ....J............N..\Q.\J\.."... 000060
13FFFE2B E1EF0220 FECBDBFE C7CB2DFC ADFDAF9E 00005A04 FF1650FE C7CB7E51 Q"...P...Z.......-...... ...+.... 000080
13FFFE2B C1EF0220 FECBDBFE C7CB2DFC ADFDAF9E 00005A20 FF01FB01 C6CF9F0B ........ Z.......-...... ...+... 0000A0
FE2BA1EF 9E510132 000059F4 FF01FB02 E4CF9F07 AB084AFC ADFDAF9E 252C3103 .1.%.....J...........Y..2.Q...+. 0000C0
00F23103 13FFFE2B 85EF0220 FECBDBFE C7CB2D00 00599FFF 1650FEEF CB7E52FF .R"...P...Y..-...... ...+.....1.. 0000E0
0312FFFE 2BD6EF02 20FECBDB FEC7CB2D 000059BC FF01FB04 1ACF9FFC ADFDAF9E ............Y..-...... ...+..... 000100
00598BFF 01FB0541 CF9F00F4 310312FF FE2BC1EF 0220FECB DBFEC7CB 2D010731 1..-...... ...+.....1....A.....Y. 000120
4A5C0840 5C07AB4E FCADFDAF 9E1E1102 13FFFE2B 1BEF0520 FECBDBFE C7CB2D00 .-...... ...+...........N..\@.\J 000140
EF0220FE CBDBFEC7 CB2DFCAD FDAF9E00 81319211 02181A5C 515C07AB 4E07AB5C \..N..\Q\.....1.......-........ 000160
000055DC EF04FB00 A97FFEF7 CB7F04DD 01DDFCAD FDAF9E00 69310313 FFFE2AFC .*....1i.......................U.. 000180
C9FF1650 FEFFCB7E 52FFFE2A A6EF9E51 09324413 FFFE2ABD EF012004 B900A92D -.... ...*...D2.Q....*..R"...P... 0001A0
4A110212 FFFE2B18 EF0220FE CBDBFEC7 CB2D0000 58FEFF01 FB035CCF 9F000058 X....\.....X..-...... ...+.....J 0001C0
0220FECB DBFEC7CB 2DFCADFD AF9E3811 0212FFFE 2B04EF02 20FECBDB FEC7CB2D -...... ...+.....8....-...... . 0001E0

Virtual block number 251 (000000FB), 512 (0200) bytes

58CB5801 CE031158 D404141A 57515703 AB4E5C01 CE03115C D40413FF FE2A7BEF .{*.....\....\N..WQW....X.....X.X 000000
7E1012FF FE2A2DEF 0520FECB DBFEC7CB 2DFCADFD AF9EFE42 31031102 135CD55C \.\....1B.......-...... ..-*....". 000020
FF1650FE E7CB7E51 FEC7CB7E FCADFDAF 9E000058 41FF1650 FEC7CB7E 51FF07CB ...Q"...P..AX.......".....Q"...P.. 000040
```

```
0232FCAD FDAF9E0B AB084AFC ADFDAF9E FCADFDAF 9E040000 583EFF16 0000582C ,X....>X.............J.........2. 000060
A97FFFFE 49C2EF9F 0BABDD02 DD000057 F9FF1650 FEC7CB7E 52FFFE29 F9EF9E51 Q...)..R^...P...W..........I.... 000080
09C5CF9F 000057CC FF03FBFF 0FCB7FFF FE49B7EF 9F00A97F 000054D4 EF04FB00 .....T........I..........W...... 0000A0
7FFFFE49 91EF9F00 0057AFFF 03FB00A9 7FFF0FCB 7FFF17CB 7F000058 05FF01FB ....X...................W.....I... 0000C0
578AFF16 50FEEFCB 7E52FFFE 298CEF9E 51013200 00579BFF 03FBFEFF CB7F00A9 ..........W..2.Q...)..R^...P...W 0000E0
00893103 12FFFE29 D9EF0220 FECBDBFE C7CB2D00 0057BFFF 01FB021D CF9F0000 ..........W..-...... ...)....1.. 000100
89FF01FB 04AFCF9F FCADFDAF 9E007631 0312FFFE 29C4EF02 20FECBDB FEC7CB2D -...... ...)....1v............. 000120
CB7F04DD 01DD5C01 CE03115C D40413FF FE292FEF 0220FECB DBFEC7CB 2D000057 W..-...... ../)....\....\....... 000140
01CE0311 58D40413 FFFE28CE EF012004 B900A92D 00005410 EF04FB00 A97FFEF7 .........T..-.... ...(.....X.... 000160
0BAB4E0B AB5C4A5C 10405C0B AB4EFCAD FDAF9E1C 1102135C D55C58CA 5858D258 X.XX.X\.\..........N..\@.\J\..N.. 000180
32FCADFD AF9EFCAD FDAF9E04 000056F4 FF16FCAD FDAF9EFE D0310318 2A5C515C \Q\*..1.............V............2 0001A0
28A1EF01 20FEBBDB FEB7CB2D 000056B8 FF1650FF 1FCB7E52 FFFE287D EF9E5101 .Q..)(..R^...P...V..-...... ...( 0001C0
CB3CFCAD FDAF9E00 005693FF 1650FF1F CB7E52FF FE2857EF 9E510132 1512FFFE ....2.Q..W(..R^...P...V.......<. 0001E0
```

Virtual block number 252 (000000FC), 512 (0200) bytes

```
447F8F57 51570FAB 4E5C01CE 03115CD4 04190858 51580FAB 4E0FAB5C D05CFEBF ..\.\..N..XQX....\....\N..WQW..D 000000
EF9FFF1F CB7FFCAD FDAF9E00 C8310313 5CD55C58 C85801CE 031158D4 04140000 ....X....X.X\.\..1................ 000020
7E5140A9 7E00004C 09EF02FB 40A97F0F ABDF0000 563AFF03 FB10A97F FFFF4834 4H........!V.......@....L..^.@Q^ 000040
10A97F00 A97F0000 5302EF04 FB00A97F 08A97F03 DD02DD00 005627FF 165008A9 ..P..'V................S........ 000060
CB7FFF0F CB7FFF17 CB7F0000 5636FF01 FB07F6CF 9F000055 FDFF03FB FF0FCB7F ........U.........6V............ 000080
FF01FB07 C8CF9F00 0055D7FF 1650FF0F CB7E51FE BFCB7E00 0055DFFF 03FBFEFF ......U..^...Q^...P...U......... 0000A0
00A97F0B A97FFF17 CB7F0000 55B2FF03 FB08A97F FEFFCB7F FEBFCB7F 00005608 .V.................U............ 0000C0
FDAF9E1A 11000055 8DFF03FB FEFFCB7F 00A97FFF FE4783EF 9F000055 A1FF03FB ....U.....G..............U....... 0000E0
5586FF16 FCADFDAF 9E000055 75FF1650 FEC7CB7E 52FFFE27 2BEF9E51 0B32FCAD ..2.Q..+'..R^...P..uU..........U 000100
FFFE2743 EF0120FE F3DBFEEF CB2DFCAD FDAF9EFC ADFDAF9E FCADFDAF 9E040000 ..................-....... ..C'.. 000120
11000055 85FF00FB 000055AD FF01FBFF FE472FEF 9F000055 89FF01FB 09DD1F12 ........U..../G......U......U... 000140
ADFDAF9E 00005568 FF00FB00 00558FFF 01FBFEFF CB7F0000 556AFF01 FB09DD1B ......JU..........U.....hU...... 000160
13FFFE26 CAEF0120 04B900A9 2D000051 E9EF04FB 00A97FFE FFCB7F04 DD01DDFC ................Q..-..... ...&... 000180
27CB7F02 DDFCADFD AF9EFCAD FDAF9EFC ADFDAF9E 00004894 EF01FBFF 27CB7F0B ...'.....H........................' 0001A0
2712EF9E 5102322A 12FFFE27 1DEF0220 04B900A9 2D000051 9DEF03FB 00A97FFF ........Q..-..... ...'...*2.Q...' 0001C0
89FF1650 FF27CB7E 52FFFE26 96EF9E51 00320000 549EFF16 50FEC7CB 7E52FFFE ..R^...P...T..2.Q...&..R^.'.P... 0001E0
```

Virtual block number 253 (000000FD), 512 (0200) bytes

```
EF022004 B900A92D 00005150 EF03FB00 A97FFF27 CB7F02DD FCADFDAF 9E000054 T............'.......PQ..-..... .. 000000
EF9E5100 32000054 51FF1650 FEC7CB7E 52FFFE26 C3EF9E51 02322A12 FFFE26CE .&...*2.Q...&..R^...P..QT..2.Q.. 000020
7E52FFFE 2624EF9E 510132FC ADFDAF9E 0000543C FF1650FF 27CB7E52 FFFE2649 I&..R^.'.P..<T.......2.Q..$&..R^ 000040
FCADFDAF 9E040000 542EFF16 FCADFDAF 9EFCADFD AF9E0000 5422FF16 50FEEFCB ...P..'T...............T......... 000060
0212FFFE 25E2EF02 20FECBDB FEC7CB2D 0000543C FF01FB01 62CF9FFC ADFDAF9E .......b....<T..-....... ...%.... 000080
FEC7CB2D FCADFDAF 9E000053 D5FF1650 FED7CB7E 52FFFE25 E2EF9E51 00323011 .02.Q...%..R^...P...S.......-... 0000A0
7FFEF7CB 7F04DD01 DDFCADFD AF9E010D 3100CC31 0312FFFE 2559EF06 20FECBDB ... ..Y%....1..1.................. 0000C0
DDFCADFD AF9E00BB 310312FF FE252DEF 012004B9 00A92D00 005093EF 04FB00A9 ......P..-..... ..-%....1........ 0000E0
D40413FF FE254CEF 012004B9 00A92D00 00506BEF 04FB00A9 7FFEF7CB 7F04DD01 .............kP..-..... ..L%..... 000100
5858D258 01CE0311 58D40413 FFFE254E EF0120FE BBDBFEB7 CB2D5C01 CE03115C \....\-...... ..N%.....X....X.XX 000120
00501BEF 04FB00A9 7FFEF7CB 7F04DD01 DDFCADFD AF9E0095 3103135C D55C58CA .X\.\..1........................P. 000140
```

```
EF0120FE BBDBFEB7 CB2D5C01 CE03115C D40413FF FE24D8EF 012004B9 00A92D00 .-.... ...$.....\....\-...... .. 000160
FCADFDAF 9E1A1146 1102135C D55C58CA 5858D258 01CE0311 58D40413 FFFE24FF .$.....X....X.XX.X\.\...F....\.. 000180
7E51FEC7 CB7EFCAD FDAF9E00 0052D7FF 1650FEEF CB7E52FF FE24DAEF 9E510132 2.Q...$..R^...P...R.......^...Q^ 0001A0
9E000052 ADFF1650 FEC7CB7E 52FFFE24 97EF9E51 05320000 52C6FF16 50FF07CB ...P...R..2.Q...$..R^...P...R... 0001C0
093213AB 5CD05CFF 27CB3CFC ADFDAF9E FCADFDAF 9E040000 52BEFF16 FCADFDAF .......R............<.'.\.\..2. 0001E0
```

Virtual block number 254 (000000FE), 512 (0200) bytes

```
9E026A31 0318205C 515C13AB 4E000052 79FF1650 FFC7CB7E 52FFFE24 91EF9E51 Q...$..R^...P..yR..N..\Q\ ..1J.. 000000
5C1E425C 13AB4E00 005253FF 1650FEC7 CB7E52FF FE23ECEF 9E510932 FCADFDAF ....2.Q...$..R^...P..SR..N..\B.\ 000020
7F17ABDD 01DDFCAD FDAF9E3B 11000217 AB011BAB F117ABD7 17AB01D0 1BAB5C4A J\..................;........... 000040
FDAF9E1B 110212FF FE239FEF 012004B9 00A92D00 004F0FEF 04FB00A9 7FFF27CB .'........O..-.... ...$.......... 000060
DD08DDFC ADFDAF9E 01F131FC ADFDAF9E 17ABD7C8 17AB1BAB F3FCADFD AF9EFCAD ......................1.......... 000080
EF04FBFF 0FCB7FFE F7CB7F01 DD06DD00 004ECBEF 01FBFEF7 CB7FFF27 CB7F17AB ....'...........N................ 0000A0
FF1650FE C7CB7E52 FFFE2336 EF9E510A 32000051 FDFF01FB 03BDCF9F 00004EBB .R...........Q..2.Q..6#..R^...P.. 0000C0
00A920FF 1BDBFF17 CB2D0000 4E86EF04 FB00A97F FEF7CB7F 07DD02DD 000051A8 .Q................N..-...... .. 0000E0
00516BFF 1650FEC7 CB7E52FF FE22EDEF 9E510C32 FCADFDAF 9E018231 031304B9 ....1.......2.Q...'..R^...P..kQ. 000100
2304EF01 20FF23DB FF1FCB2D 00004E48 EF04FBFF 1FCB7FFE F7CB7F04 DD01DD00 ................HN..-....$. ...$ 000120
CE03115B D40413FF FE2310EF 0120FF23 DBFF1FCB 2D5C01CE 03115CD4 0413FFFE ....\....\-....$. ...$.....X... 000140
D55C58C8 5801CE03 1158D404 13FFFE22 AFEF0120 FF23DBFF 1FCB2D5C 58C85801 .X.X\-....$. ...".....X....X.X\. 000160
CE03115C D40412FF FE22ACEF 0120FF23 DBFF1FCB 2DFCADFD AF9E00F9 3103135C \..1........-....$. ...'.....\... 000180
D55C58CA 5858D258 01CE0311 58D40412 FFFE2294 EF0120FF 23DBFF1F CB2D5C01 .\-....$. ..."....X....X.XX.X\. 0001A0
CF9F0000 4D9EEF04 FBFF2FCB 7FFEF7CB 7F05DD02 DDFCADFD AF9E00C3 3103135C \..1................/.....M.... 0001C0
FF0FCB7F FF27CB7F 5CDD1FAB DD5C5C4A 5C20405C 17AB4E00 0050E3FF 01FB00B3 ......P..N..\@ \J\\....\..'..... 0001E0
```

Virtual block number 255 (000000FF), 512 (0200) bytes

```
FEC7CB7E 52FFFE22 08EF9E51 0A320000 50BAFF01 FB027ACF 9F00004D 75EF04FB ...uM....2.....P..2.Q..."..R^... 000000
FF27CB7F 5CDD02DD 5C584A58 5C40581F AB4E5C20 405C17AB 4E000050 65FF1650 P..eP..N..\@ \N..XPAXJX\...\..'. 000020
7EFCADFD AF9E2F11 021304B9 00A920FF 1BDBFF17 CB2D0000 4D32EF04 FB00A97F ......2M..-...... ......./.....^ 000040
CB7E52FF FE2203EF 9E510232 FCADFDAF 9E000050 21FF1650 FED7CB7E 51FF0FCB ..Q^...P..!P......2.Q...'..R^. 000060
DDFCADFD AF9EFCAD FDAF9E04 00005014 FF16FCAD FDAF9E00 005003FF 1650FEC7 ..P...P...........P............. 000080
23AB10C5 00005010 FF01FB40 AF9F0000 4CCAEF04 FBFF37CB 7FFF2FCB 7F01DD01 ....../...7.....L....@....P.....$ 0000A0
FF01FB18 AF9F0000 4CA2EF04 FBFF37CB 7FFF2FCB 7F02DD01 DDFCADFD AF9E1FAB ............./...7.....L........ 0000C0
00000000 8F4AFCAD FDAF9E04 00004FB4 FF16FCAD FDAF9E1F AB23ABC0 00004FE8 .O....$...........O........J..... 0000E0
FCADFDAF 9E23AB08 4A0412FF FE2176EF 0120FF3B DBFF37CB 2DFCADFD AF9E23AB .$......-.7..;. ..v!....J..$..... 000100
FF3BDBFF 37CB2DFC ADFDAF9E 23AB104A 0412FFFE 2118EF01 20FF3BDB FF37CB2D -.7..;. ...!....J..$......-.7..;. 000120
FFFE20C2 EF0120FF 3BDBFF37 CB2DFCAD FDAF9E23 AB144A04 12FFFE21 22EF0120 ..'!....J..$......-.7..;. ... .. 000140
9E23AB1A 4A0412FF FE20CCEF 0120FF3B DBFF37CB 2DFCADFD AF9E23AB 184A0412 ..J..$......-.7..;. ... .....J..$. 000160
37CB2DFC ADFDAF9E 23AB1C4A 0412FFFE 20B2EF01 20FF3BDB FF37CB2D FCADFDAF ....-.7..;. ... .....J..$......-.7 000180
EF0120FF 3BDBFF37 CB2DFCAD FDAF9E23 AB1E4A04 12FFFE20 54EF0120 FF3BDBFF ..;. ..V ....J..$......-.7..;. .. 0001A0
4A0412FF FE2022EF 0120FF3B DBFF37CB 2DFCADFD AF9E23AB 204A0412 FFFE203C < ....J .$......-.7..;. ..' ....J 0001C0
ADFDAF9E 23AB224A 0412FFFE 2008EF01 20FF3BDB FF37CB2D FCADFDAF 9E23AB21 !.$......-.7..;. ... ....J".$.... 0001E0
```

```
Virtual block number 256 (00000100), 512 (0200) bytes

3BDBFF37 CB2DFCAD FDAF9E23 AB234A04 12FFFE1F EEEF0120 FF3BDBFF 37CB2DFC .-.7..;. ;........J$.$......-.7..; 000000
EE1EBBEE 0120FE3B DBEE37CB 2DECADED AE9E23AB 244A0A12 FFFE205C EF0120FF ......\......J$.$.......7...;........ 000020
23AB264A 0412FFFE 1FA1EF01 20FF3BDB FF37CB2D FCADFDAF 9E23AB25 4A0412FF ...J%.$.....-.7..;. ........J&.$ 000040
FF16FCAD FDAF9E23 AB274A04 12FFFE1F 87EF0120 FF3BDBFF 37CB2DFC ADFDAF9E .....-.7..;. ........J'.$....... 000060
0FCB2C0F AB5CD05C FF0FCB3C FCADFDAF 9EFCADFD AF9EFCAD FDAF9E04 00004E24 $N.................<...\..\...... 000080
2BAB5C4A 5C08425C 0FAB4E27 AB000000 00SF4AFF FE61B3EF 00648F30 FF13DBFF .... .d...a..J......'N..\B.\J\.+ 0000A0
01000000 648F0097 AB0AFCAD FDAF9E2D 11000297 AB012BAB F197ABD7 97AB00D0 ........+.......-..........d.... 0000C0
AF9E97AB D7D697AB 2BABF3FC ADFDAF9E 27AB27AB 58C158FF FE6177EF 4C985C00 .\.L.wa..X.X.'.'.......+......... 0000E0
02DD0000 4D72FF16 5000A97E 5140A97E 00004354 EF02FB40 A97F27AB DFFCADFD ......'..@...TC..^.@Q^..P...M...( 000100
ADFDAF9E 0400004D 6DFF16FC ADFDAF9E 00004A4C EF04FBFF 17CB7F00 A97F03DB .............LJ.........mM....... 000120
2DEF9F00 004D2BFF 03FBFC77 CB7FFFFE 3F36EF9F FFFE3EC4 EF9FFCAD FDAF9EFC ..........>....6?.....w....+M...... 000140
FB00A97F 08A97FFF FE3F27EF 9F00004D 15FF03FB 08A97FFF FE3F2FEF 9FFFFE3F ?..../?..........M.....'?......... 000160
8F502FAB 144A0000 4CEEFF03 FBFC7FCB 7F00A97F FFFE3E9C EF9F0000 4B02FF03 ...M.....>...............L...J../P. 000180
5C97AB4E FCADFDAF 9E01D631 000397AB 011AF197 ABD797AB 01D033AB 00000000 .....3................1........N..\ 0001A0
499AEF04 FB00A97F FFFE3ED0 EF9F37AB DD02DD37 AB5C4A5C 08405C1C 445C0842 B.\D.\@.\J\.7....7...>..........I 0001C0
EF9F5CDD 04DD5C5C 4A5C1040 5C37AB4E 3BAB50D0 00004D40 FF01FB00 A97F0000 .........@M...P.;N.7\@.\J\\...\.. 0001E0

Virtual block number 257 (00000101), 512 (0200) bytes

8F3FAB51 3FAB5050 00004D10 FF01FB00 A97F0000 496EEF04 FB00A97F FFFE3EA4 .>.........nI..........K..PP.?Q.?. 000000
031158D4 0412FFFE 499AEE4C 3BABD15C 00011A00 97AB0A01 50310312 00000000 .......1P.........\..;L...I......X.. 000020
5857C857 01CE0311 57D40413 CCAFFFFE 4C76EF4C 515C0001 1A0097AB 0A5801CE ..X........\QL.vL........W.....W.WX 000040
C88F3FAB 516F1100 004C13FF 1650FF3F CB7E52FF FE1D5BEF 9E510432 171358D5 .X...2.Q...[...R^.?.P...L...oQ.?.. 000060
9E510432 15110000 4BF2FF16 50FF47CB 7E52FFFE 1D36EF9E 51043217 18000043 C....2.Q...6....R^.G.P....K.....2.Q. 000080
F5EF03FB 40A97F7E 3FAB50FF 47CB7F00 001BDBFF 1650FF47 CB7E52FF FE1E0DEF .......R^.G.P.....K.....G.P.?^...@.... 0000A0
FE4BE7EF 4C475C00 011A0097 AB0A0000 4BBEFF16 50FF3FCB 7E5140A9 7E000047 G..^.@Q^.?.P....K...........\GL..K. 0000C0
EF4C9EFF FE3DB3EF 9F5C0018 1A0097AB 0AFCADFD AF9E33AB 43AB4043 AB3FABFF ..?.C@.C.3.............\.......L. 0000E0
10A97FFF 3FCB7F00 004B6FFF 03FB10A9 7FFFFE3D A9EF9FFF FF3DB3EF FFFE493C <I.............=.........oK.....?..... 000100
97AB0A00 004B4BFF 03FB00A9 7F08A97F FFFE3D18 EF9F0000 4B5EFF03 FB08A97F .......^K....=............KK..... 000120
7FFFFE3D 61EF9FFF FE3D6BEF FFFE4BE0 EF4C9E58 00012B00 2FAB0A5C 00061A00 ....\../.(..X.L...K...k=......a=... 000140
AF9EFCAD FDAF9E2F AB5C4A5C 08405C2F AB4E0000 4B1AFF03 FBFC6FCB 487F00A9 ...H.o......K...N./\@.\J\./........ 000160
000397AB 0104F197 ABD797AB 01D0FCAD FDAF9E97 ABD7FE2D 97AB011A F1FCADFD .......-.......................... 000180
EF9F37AB DD02DD37 AB5C4A5C 08405C20 445C0842 5C97AB4E FCADFDAF 9E01AA31 1.........N..\B.\D \@.\J\.7....7.. 0001A0
5C37AB4E 47AB50D0 00004B54 FF01FB00 A97F0000 47AEEF04 FB00A97F FFFE3D04 .=..........G..........TK...P.GN.7\ 0001C0
FF01FB00 A97F0000 4782EF04 FB00A97F FFFE3CD8 EF9F5CDD 02DD5C5C 4A5C1040 @.\J\\...\...<............G......... 0001E0

Virtual block number 258 (00000102), 512 (0200) bytes

FB00A97F FFFE3CAC EF9F5CDD 04DD5C5C 4A5C1840 5C37AB4E 4BAB50D0 00004B28 (K...P.KN.7\@.\J\\...\...<....... 000000
F8310312 00000000 8F43AB51 43AB5050 00004AF8 FF01FB00 A97F0000 4756EF04 ..VG.........J..PP.CQ.C.........1. 000020
CB7E52FF FE1B6BEF 9E510432 1713FFFE 40B6EF4C 47ABD15C 00011300 4BAB0A00 ...K....\..CL..@.....2.Q..k....R^. 000040
EF03FB40 A97F7E43 AB50FFFE 3BBAEF9F 33AB43AB 40281100 004A23FF 1650FF4F O.P..$J...(@.C.3...;..P.C^..@... 000060
5C001213 004BAB0A FCADFDAF 9E000049 FDFF1650 FF4FCB7E 5140A97E 00004634 4F..^.@Q^.O.P....I...........K....\ 000080
49C6FF03 FB18A97F FFFE3C18 EF9FFFFE 3C22EFFF FE410FEF 4C9EFFFE 3BA2EF9F ...;...L..A...'<.....<..........I 0000A0
```

```
45D6EF03 FB40A97F 7EFFFE42 4DEF4C50 FFFE3C08 EF9F5C00 0113004B AB0A0000 ....K....\...<..PL.KB..^..@...;E 0000C0
00004988 FF03FB08 A97F18A9 7F10A97F 000049A0 FF165010 A97E5140 A97E0000 ..^.@Q^..P...I...............I.. 0000E0
7FFF4FCB 7F5C0001 28002FAB 0A000049 75FF03FB 00A97F08 A97FFFFE 3BDAEF9F ...;...........uI..../.(..\..O.. 000100
AF9EFCAD FDAF9E2F AB5C4A5C 08405C2F AB4E0000 495AFF03 FBFC6FCB 4C7F00A9 ...L.o....ZI..N./\@.\J\./....... 000120
50000049 C9FF01FB FFFE3B90 EF9FFCAD FDAF9E97 ABD7FE59 97AB0104 F1FCADFD .........Y...........;......I..P 000140
9F585C33 AB435C50 50000049 B1FF01FB FFFE3B78 EF9F6011 02195C33 AB515C50 P\Q.3\...`..x;......I..PP\C.3\X. 000160
0048EFFF 1650FF4F CB7E5140 A97E0000 4526EF03 FB40A97F 7E5850FF FF3AABEF ..!..PX^..@...&E..^.@Q^.O.P...H. 000180
9F000048 C9FF03FB FE6FCB4C 7FFFFE3B 3DEF9FFF 4FCB7F5C 00012800 2FAB0A00 ...(..\..O...=;...L.o.....H..... 0001A0
FCADFDAF 9EFCADFD AF9E0400 0048D3FF 16FCADFD AF9E0000 4902FF01 FB09A7CF .......I..........H............. 0001C0
AB4EFCAD FDAF9E00 FC310003 E3AB0104 F1E3ABD7 E3AB01D0 4FABQ000 00008F4A J.......O...............1.......N. 0001E0
```

Virtual block number 259 (00000103), 512 (0200) bytes

```
455AEFD4 FB00A97F FFFE3AB0 EF9F5CDD 04DD5C5C 4A5C1A40 5C20445C 08425CE3 .\B.\D \@.\J\\...\...:........ZE 000000
08425CE3 AB4EFC27 CB4C504A 000048F4 FF01FB00 A97F5C00 010500E3 AB0A0000 .........\........H..JPL.'.N..\B. 000020
AB0A0000 451EEF04 FB00A97F FFFE3A74 EF9F5CDD 02DD5C5C 4A5C1440 5C20445C \D \@.\J\\...\..t:.........E.... 000040
5C20445C 08425CE3 AB4EFC3F CB4C504A 000048B8 FF01FB00 A97F5C00 010500E3 .....\........H..JPL.?.N..\B.\D \ 000060
FF01FB00 A97F0000 44E2EF04 FB00A97F FFFE3A38 EF9F5CDD 02DD5C5C 4A5C0840 @.\J\\...\..8:.........D........ 000080
FE3E47EF 4CD15C00 0113Q0FC 3FCB4C0A 5C000105 00E3AB0A 53AB504A 00004884 .H..JP.S........\.L.?.....\.L.G>. 0000A0
C05C0001 0500E3AB 0AFC27CB 4C000000 008F4A5C 00010500 E3AB0A12 1353ABFF ..S..........\J.....L.'........\. 0000C0
ABD7E3AB 01D0FCAD FDAF9EE3 ABD7FF07 E3AB0104 F1FCADFD AF9E4FAB FC27CB4C L.'..O.......................... 0000E0
AFAFFFFE 47AAEF4C 515C0001 1A00E3AB 0AFCADFD AF9E6C11 0002E3AB 011AF1E3 ..........1............\QL..G.... 000100
00443BEF 04FB00A9 7FFF57CB 7F5CDD04 DD5C5C4A 5C1C445C 08425CE3 AB4E4713 .GN..\B.\D.\J\\...\..W.......GD. 000120
AB4E5CFF FE476BEF 48465800 011A00E3 AB0A5C50 50000047 DDFF01FB 00A97F00 ........G..PP\........XFH.kG..\N. 000140
0000008F 4AFCADFD AF9EE3AB D797E3AB 1AF3FCAD FDAF9E4F AB584A58 5C40584F OXO\XJX.O..................J.... 000160
45EF9F1C 185C5851 584FAB4E 5C505000 004797FF 01FBFFFE 395EEF9F FC3BCB00 ..;...^9.......G..PP\N.OXQX\....E 000180
E3ABD7E3 AB01D0FC 3BCB5C4A 5C584258 4FAB4E5C 50500000 477EFF01 FBFFFE39 9.....^G..PP\N.OXBX\J\.;........ 0001A0
182A5851 58FC27CB 4C4E5C00 010500E3 AB0AFCAD FDAF9E34 110002E3 AB0105F1 .........4............\NL.'.XQX*. 0001C0
FDAF9EE3 ABD7CFE3 AB05F3FC ADFDAF9E FC27CB4C 91AF4A5C 00010500 E3AB0A0F .........\J..L.'................ 0001E0
```

Virtual block number 260 (00000104), 512 (0200) bytes

```
00008F4A FCADFDAF 9E008531 0003E3AB FFFFFFFF 8F01F1E3 ABD6E3AB 05D0FCAD ......................1.......J... 000000
00010500 2FAB0AFC ADFDAF9E 38110002 2FAB0105 F12FABD7 2FAB01D0 57AB0000 ...W.../../..../...8......../.... 000020
9E57AB5C 4A5C0840 5C57AB4E 0B15FC27 CB4CFC27 CB4BD158 00010500 E3AB0A5C \........X.H.'.L.'...N.W\@.\J\.W. 000040
010500E3 AB0A0F18 105C515C 57AB4EFC ADFDAF9E 2FABD7CB 2FAB05F3 FCADFDAF ......./.../.....N.W\Q\......... 000060
ADFDAF9E E3ABD6FE 7EE3ABEF FFFFFF8F 01F1FCAD FDAF9EFC 27CB4C99 AF4A5C00 .\J..L.'...............^........ 000080
F197ABD7 97AB01D0 CFABF2AF 4AC7ABF7 AF4ABFAB 00000000 8F4AFCAD FDAF9EFC ......J.......J....J............ 0000A0
ADFDAF9E FC57CB4C D0AF4A5C 00010500 97AB0AFC ADFDAF9E 21110002 97AB0105 .......!.............\J..L.W..... 0000C0
0397AB01 04F197AB D797AB01 D0FCADFD AF9EFCAD FDAF9E97 ABD7E297 AB05F3FC ................................ 0000E0
00963103 128DAF58 5158FC27 CB4C4E5C 00010500 97AB0AFC ADFDAF9E 00C63100 .1..............\NL.'.XQX....1.. 000100
13FFFE17 44EFFFFE 424AEF4C 01295C00 011300FC 3FCB4C0A 5C000105 0097AB0A ........\.L.?.....\).L.JB...D.... Q00120
AB0AC3AB FFFE4188 EF4CD05C 00011300 FC3FCB4C 0A5C0001 050097AB 0A731102 ..s........\.L.?.....\.L..A...... 000140
A97F7EFF FE41B7EF 4C6EFFFE 36CAEF9F 5C000113 00FC3FCB 4C0A5C00 01050097 .....\.L.?.....\...6..nL..A..^.. 000160
D05C0001 050097AB 0A000044 F9FF1650 FDB7CB7E 5140A97E 0000414A EF04FB40 @...JA..^.@Q^...P...D.........\. 000180
FCADFDAF 9EFCADFD AF9E1911 FC57CB4C 084A5C00 01050097 AB0ABFAB FC27CB4C L.'..........\J.L.W............. 0001A0
```

```
97AB0104 F197ABD7 97AB01D0 FCADFDAF 9EFCADFD AF9E97AB D7FF3D97 AB0104F1 .....=.......................... 0001C0
13000000 008F5751 57FC27CB 4C4E5C00 01050097 AB0AFCAD FDAF9E00 F1310003 ..1...............\NL.'.WQW...... 0001E0
```

Virtual block number 261 (00000105), 512 (0200) bytes

```
CE031157 D4041308 565156FC 57CB4C4E 5C000105 0097AB0A 5801CE03 1158D404 ..X....X........\NL.W.VQV....W... 000000
01295C00 011300FC 3ECB4C0A 5C000105 0097AB0A 00963103 1358D558 57C85701 .W.WX.X..1..........\.L.?.....\.. 000020
00011300 FC3FCB4C 0A5C0001 050097AB 0A731102 13FFFE16 38EFFFFE 4152EF4C L.RA...B.........s.......\.L.?..... 000040
35BEEF9F 5C000113 00FC3FCB 4C0A5C00 01050097 AB0ACBAB FFFE407C EF4CD05C \.L.I@............\.L.?.....\...5 000060
EDFF1650 FDBFCB7E 5140A97E 0000403E EF04FB40 A97F7EFF FE40ABEF 4C6EFFFE ..nL..@..^..@...>@..^.@Q^...R... 000080
FC57CB4C 084A5C00 01050097 AB0AC7AB FC27CB4C D05C0001 050097AB 0A000043 C.........\.L.'...........\J.L.W. 0000A0
FCADFDAF 9EFCADFD AF9E97AB D7FF1297 AB0104F1 FCADFDAF 9EFCADFD AF9E1911 ................................ 0000C0
4C4E5C00 01050097 AB0AFCAD FDAF9E00 F2310003 97AB0104 F197ABD7 97AB01D0 ...............1..............\NL 0000E0
57CB4C4E 5C000105 0097AB0A 5801CE03 1158D40A 13000000 008F5751 57FC27CB .'.WQW........X....X........\NL.W 000100
5C000105 0097AB0A 00973103 1358D558 57C85701 CE031157 D4041308 565156FC .VQV....W....W.WX.X..1..........\ 000120
050097AB 0A741102 13FFFE15 2CEFFFFE 405AEF4C 01295C00 011300FC 3FCB4C0A .L.?.....\).L.Z@..............t..... 000140
4C0A5C00 01050097 AB0AD3AB FFFE3F70 EF4CD05C 00011300 FC3FCB4C 0A5C0001 ..\.L.?.....\.L.P?.............\.L 000160
00003F32 EF04FB40 A97F7EFF FE3F9FEF 4C6EFFFE 34B2EF9F 5C000113 00FC3FCB .?.....\...4..nL..?..^..@...2?.. 000180
AB0ACFAB FC27CB4C D05C0001 050097AB 0A000042 E1FF1650 FDC7CB7E 5140A97E ^.@Q^...P...B..........\.L.'..... 0001A0
FF1197AB 0104F1FC ADFDAF9E FCADFDAF 9E00B831 FC57CB4C 084A5C00 01050097 .....\J.L.W.1..................... 0001C0
AB4E0089 31031200 0000008F 5C515CFC 3BCB4EFC ADFDAF9E FCADFDAF 9E97ABD7 ..............N.;.\Q\........1..N. 0001E0
```

Virtual block number 262 (00000106), 512 (0200) bytes

```
FE1459EF 9E510232 C3AB0000 43C88F4A BFABFC3B CBD02511 0213EFAF 5C515CBF .\Q\.....%..;...J..C.....2.Q..Y.. 000000
22110213 B9AF5C51 5CCFAB4E FCADFDAF 9E581100 00425FFF 1650FDB7 CB7E52FF .R^...P..B...X.....N..\Q\......' 000020
0000422C FF1650FD C7CB7E52 FFFE1426 EF9E5102 32D3ABC9 AF4ACFAB FC3BCBD0 ..;...J....2.Q..&...R^...P..;B.. 000040
FDBFCB7E 52FFFE13 FFEF9E51 0232CBAB A2AF4AC7 ABFC3BCB D0FCADFD AF9E2511 .%.......;...J....2.Q......R^... 000060
A911D0FC ADFDAF9E FCADFDAF 9E040000 4216FF16 FCADFDAF 9E000042 05FF1650 P...B...........B................ 000080
FE334FEF 9F000042 19FF01FB 00DDFFFE 5CBAEF02 FBF8A9DF F8A908D0 FCA9DFFC ..............\........B....03. 0000A0
EF02FBF8 A9DFF8A9 0AD0FCA9 DFFCA911 D0000042 15FF00FB 00004234 FF01FBFF ....AB'.....B.................... 0000C0
D0000041 E5FF00FB 00004204 FF01FBFD CFCB7F00 0041E7FF 01FB00DD FFFE5C88 .\.........A...........B......A... 0000E0
00DDFFFE 331AEF9F FFFE5C54 EF02FBF8 A9DFF8A9 0CD0FCA9 DFFCA900 000458F .E....................[\.....3.... 000100
FCA9DFFC A9C6AFD0 000041AC FF00FB00 0041DFFF 01FBABAB DD000041 A9FF02FB ....A.........A.......A........... 000120
AFABDD00 004173FF 02FB00DD FFFE32E4 EF9FFFFE 5C1EEF02 FBF8A9DF F8A90ED0 ............\.....2........sA..... 000140
EF02FBF8 A9DFF8A9 10D0FCA9 DFFCA990 AFD00000 4176FF00 FB000041 A9FF01FB ....A.......vA..................... 000160
FF00FB00 004173FF 01FBB3AB DD000041 3DFF02FB 00DDFFFE 32AEEF9F FFFE5BE8 .[.....2.......=A.........sA...... 000180
E5FF16FF FE5BAFEF 02FBF8A9 DFF8A914 D0FCA9DF FCA90000 00458FD0 00004140 @A....E.....................[..... 0001A0
89EF02FB F8A9DFF8 A918D0FC A9DFFCA9 01D0FCAD FDAF9EFC ADFDAF9E 04000040 @................................. 0001C0
FF01FB00 A97F0000 3DAAEF03 FB00A97F 28DD20DD 000040E8 FF01FB00 DDFFFE5B [........@....(.......=......... 0001E0
```

Virtual block number 263 (00000107), 512 (0200) bytes

```
FFFE5B4C EF02FBF8 A9DFF8A9 18D0FCA9 DFFCA929 D0000040 D9FF00FB 00004100 .A.......@...)................L[.. 000000
0040C3FF 01FB00A9 7F00003D 6DEF03FB 00A97F24 DD20DD00 0040ABFF 01FB00DD .......@....$.......m=..........@. 000020
FB00DDFF FE5B0FEF 02FBF8A9 DFF8A901 D0FCA9DF FCA901D0 0000409C FFC0FB00 ......@.....................[..... 000040
```

```
5AEAEF02 FBF8A9DF F8A918D0 FCA9DFFC A905D000 001077FF 00FB0000 406EFF01 ..n@.....w@...................Z 000060
9E000040 45FF00FB 0000406C FF01FBFF FE3267EF 9F000040 49FF01FB 00DDFFFE .......I@....a2.....1@.....E@... 000080
DD00003F D1FF1650 FF67CB7E 51FF5FCB 7EFFFE5F 61EF01FB FF5FCB7F FCADFDAF ........a_..~._.Q~.a.P...?... 0000A0
FCADFDAF 9EC41102 1304B900 A920FF6B DBFF67CB 2D00003F CDFF02FB 00A97F0D ........?..-.a..k............... 0000C0
5A6AEF02 FB5BABDF FCA9DFFC A901D0FC ADFDAF9E FCADFDAF 9E040000 3FC2FF16 ...?.......................[...JZ 0000E0
D9FF01FB 00A97F00 003C8BEF 03FB00A9 7F28DD20 DD00003F C9FF01FB 00DDFFFE ........?....(.......<.......... 000100
FF01FB00 DDFFFE5A 31EF02FB 5BABDFFC A9DFFCA9 29D00000 3FBAFF00 FB00003F ?......?...).......[...1Z....... 000120
81FF00FB 00003FA0 FF01FB00 A97F0000 3C52EF03 FB00A97F 28DD20DD 00003F90 .?....(.......R<.........?...... 000140
FFFE4EA4 EF4E7FAB 00EBCF9E FCADFDAF 9EFCADFD AF9E0400 003F3FFF 1600003F ?....??..................N..N.. 000160
37C3EF02 FB00A97F 00DD0000 3F3EFF01 FB02DD00 CA310312 00000000 8F5C515C \0\.......1.......>?..........7 000180
FF01FBFC 77CB7F00 003F4BFF 01FBFFFE 3096EF9F 00003F58 FF01FB00 A97F0000 ........X?.....0.....K?....w..... 0001A0
9E510032 5C000128 005FAB08 FCADFDAF 9E5FAB08 4A00003F 19FF00FB 00003F38 8?......?..J.._........_(..\2.Q. 0001C0
5FAB0A5F AB5C4A5C 08405C5F AB4E0000 3E9AFF16 50FC6FCB 4C7E52FF FE10A8EF .....R^L.o.P...>..N._\@.\J\._... 0001E0
```

Virtual block number 264 (00000108), 512 (0200) bytes

```
B1FF01FB 02DD3D11 0212FFFE 1077EF00 2004BC6C 2D5CFC6F CB4C7E5C 00012800 .(..\^L.o.\-1....w.............. 000000
00012800 5FAB0A00 003ECBFF 01FB00A9 7F00003B 99EF02FB 00A97F0A DD00003E >...........;.........>....._.(.. 000020
3E46FF16 FCADFDAF 9EFF7831 00003E90 FF00FB00 003EAFFF 01FBFC6F CB4C7F5C \.L.o.....>......>..1x........F> 000040
FDAF9E00 003E43FF 01FBE1AF 9FFFFE4D B1EF0000 00008F4A FCADFDAF 9E040000 ........J.......M.........C>..... 000060
FFFE0EDD EF9E5103 3200003E 35FF01FB 0746CF9F 63ABA7AB D0FCADFD AF9EFCAD ..........c...F....5>..2.Q...... 000080
A7AB6EFF FE2F7BEF 9F00003E 15FF01FB 00BECF9F 00003DE0 FF1650FF 6FCB7E52 R^.o.P...=..........>....{/..n.. 0000A0
FFFE2EB0 EF9F0000 3DB6FF16 50FE77CB 7E5140A9 7E00003A 07EF04FB 40A97F7E ^..@....;..^.@Q^.w.P...=........ 0000C0
FE4EA8EF 0320FE7B DBFE77CB 2C101200 0000008F 5C515C50 5000003E 41FF01FB ...A>..PP\Q\........w..{....N. 0000E0
7E00003D ADFF01FB 05C2CF9F A7AB504A 00003E18 FF01FBFF FE2FF7EF 9F3611FF ..6..../......>..JP..........=..^ 000100
CB2CFCAD FDAF9E00 003D93FF 01FB3CAF 9F00003D 61FF1650 FF6FCB7E 51FE77CB .w.Q^.o.P..a=....<.....=........ 000120
057ACF9F A7AB63AB D000003D 75FF01FB 06E7CF9F FFFE4E60 EF0320FE 7BDBFE77 w..{. ..`N.........u=....c....z. 000140
445C0842 5C8FBB4E FCADFDAF 9EFCADFD AF9E0400 003D3BFF 1600003D 65FF01FB ...e=....;=..............N..\B.\D 000160
7FFFFE2E 09EF9F5C DD5C5C4A 5C08425C 67AB4E67 AB5C4A5C 80004499 BF405C14 .\@..D..\J\.gN.g\B.\J\\.\....... 000180
14405C67 AB4E0000 3CCEFF03 FB08A97F 10A97FFF 6FCB7F00 0039BFEF 03FB10A9 ......9....o............<..N.g\@. 0001A0
00A97FFF FE2DCBEF 9F5CDD58 DD58584A 58800044 A78F5743 5767AB4E 5C5C4A5C \J\\N.gWCW..D..XJXX.X.\...-.;... 0001C0
01FB0542 CF9F0000 3C8EFF03 FBFFFE2D B5EF9F08 A97F00A9 7F000039 95EF04FB ....9...........-.......<....B... 0001E0
```

Virtual block number 265 (00000109), 512 (0200) bytes

```
5C14445C 08425CBF BB4EFCAD FDAF9EFC ADFDAF9E 0400003C 9DFF1600 003CC7FF ..<.....<..............N..\B.\D.\ 000000
515C9BAB 4E00003C 91FF01FB 04A6CF9F 6BABA7AB D09FAB5C 4A5C8000 44998F40 @..D..\J\......k.........<..N..\Q 000020
00391BEF 04FBFF77 CB7FFFFE 2D52EF9F 9FABDD03 DD031D31 03130000 00008F5C \.......1.........R-....w.....9. 000040
85EF9F00 0038EBEF 03FB10A9 7FFFFE2D 35EF9F5C DD5C5C4A 5C08425C 9FAB4E00 .N..\B.\J\\.\..5-.........8..... 000060
5743579F AB4E5C5C 4A5C1440 5C9FAB4E 00003BF8 FF03FB08 A97F10A9 7FFFFE2E ..............;.N..\@.\J\\N..WCW 000080
00A97F00 0038BFEF 04FB00A9 7FFFFE2C F5EF9F5C DD58DD58 584A5880 0044A78F ..D..XJXX.X.\..............8..... 0000A0
AB5C4A5C 08405C10 445C0842 5C8FBB4E 00003BB8 FF03FBFF FE2CDFEF 9F08A97F ............;..N..\B.\D.\@.\J\. 0000C0
0DEF9F00 00386BEF 03FB10A9 7FFFFE2D 15EF9F5C DD5C5C4A 5C08425C E3AB4EE3 .N..\B.\J\\.\..-...........k8..... 0000E0
574357E3 AB4E5C5C 4A5C1040 5CE3AB4E 00003B78 FF03FB08 A97F10A9 7FFFFE2E ............x;..N..\@.\J\\N..WCW 000100
9F08A97F 00A97F00 003843EF 04FB00A9 7FFFFE2C D9EF9F5C DD58DD58 584A5823 XJXX.X.\..............C8......... 000120
FE0D2CEF 002C0E12 FFFE0C14 EFFFFE31 BBEF0C29 00003B3C FF03FBFF FE2CC3EF ........<;..)...1................ 000140
```

```
03130000 00008F5C 515C9BAB 4E00003B 59FF01FB 03D4CF9F FFFE3161 EF0F20FF . ..a1.........Y}..N..\Q\....... 000160
EF9E5103 3201CD31 0313E4AF 5C515C9B AB4E0000 3B3EFF01 FB044FCF 9F01E531 1....Q....>;..N..\Q\...,.1..2.Q.. 000180
5C505000 003B6BFF 01FBFFFE 2BDAEF9F 00003ADC FF1650FF 7FCB7E52 FFFE0BB6 .....R^...P...:.....+.....k;..PP\ 0001A0
FFFE2BB0 EF9F010D 31FFFE4B D2EF0320 FF7BDBFF 77CB2C11 125C5851 586BAB4E N.kXQX\...w..{. ...K..1.....+.. 0001C0
515C9BAB 4E00003A D1FF01FB 02E6CF9F FCADFDAF 9EA7AB50 4A00003B 41FF01FB ...A;..JP...............:..N..\Q 0001E0
```

Virtual block number 266 (0000010A), 512 (0200) bytes

```
0000375C EF04FB00 A97FFFFE 2B92EF9F 9FABDD03 DD015D31 03130000 00008F5C \.......1].........+.........\7.. 000000
2BF6EF9F AF11A7AB 6FABD007 136BAB6F ABD16FAB 504A0000 3AFEFF01 FB00A97F ........:..JP.o..o.k.....o.......+ 000020
4E00003A 31FF1650 FF7FCB7E 5140A97E 00003682 EF04FB40 A97F7EA7 AB6EFFFE ..n..^..@.....6..^.@Q^...P..1:..N 000040
7FFF77CB 7F000036 EDEF03FB 10A97FFF FE2B37EF 9F5CDD5C 5C4A5C08 425C9FAB ..\B,\J\\.\..7+.........6....W.. 000060
0044A78F 5743579F AB4E5C5C 4A5C1440 5C9FAB4E 000039FC FF03FB0B A97F10A9 .........9..N..\@.\J\\N..WCW..D. 000080
9F08A97F 00A97F00 0036C3EF 04FB00A9 7FFFFE2A F9EF9F5C DD58DD58 584A5880 .XJXX.X.\...*.........6......... 0000A0
00008F5C 515C9BAB 4E000039 F5FF01FB 0270CF9F 000039BC FF03FBFF FE2AE3EF ..*......9.....P.....9..N..\Q\... 0000C0
798F5C51 5C505000 003A2FFF 01FBFFFE 2A9EEF9F FCADFDAF 9E008131 03130000 ....1...........*...../:..PP\Q\.y 0000E0
50500000 3A0AFF01 FBFFFE2B E9EF9FFF FE4A98EF FFFE0A6E EF03280C 12C00045 E....(..n.....J......+......:..PP 000100
FF01FBFF FE2A5BEF 9FFFFE4A 75EF0320 83BBFF7F CB2C0D12 585C5158 6BAB4E5C \N.kXQ\X........ ..uJ....[*..... 000120
D6CF9FFF FE4A52EF 03208388 FF7FCB2C 0D12585C 51586BAB 4E5C5050 000039E4 .9..PP\N.kXQ\X........ ..RJ..... 000140
8F4AFCAD FDAF9EFC ADFDAF9E 04000039 35FF16FC ADFDAF9E 00003961 FF01FB02 ....d9..........59..............J. 000160
A97E5140 A97E0000 3538EF04 FB40A97F 7ED7AB6E FFFE2AAC EF9F9BAB 00000000 .........*..n..^..@...85..^.@Q^. 000180
0309CF9E 000038CC FF03FBFC 77CB7FFF FE2B67EF 9F00A97F 000038E8 FF165000 .P...8.......g+.....w.....8...... 0001A0
9F73AB50 D0000039 51FF01FB FFFE2B4C EF9F0000 38F6FF02 FB04DDD7 ABDD7FAB ............8.....L+.....Q9...P.s. 0001C0
ADFDAF9E 04000038 ADFF16FC ADFDAF9E 77AB50D0 00003940 FF01FBFF FE2B43EF .C+.....@9...P.w.........8....... 0001E0
```

Virtual block number 267 (0000010B), 512 (0200) bytes

```
34B0EF04 FB40A97F 7ED7AB6E FFFE2A24 EF9F9BAB 00000000 8F4AFCAD FDAF9EFC ......J..........$*..n..^..@....4 000000
FF03FBFC 77CB7FFF FE2AF7EF 9F00A97F 00003860 FF165000 A97E5140 A97E0000 ..^.@Q^..P..`8.........*......w..... 000020
A92C0000 3474EF04 FB40A97F 7E73AB6E FFFE29F0 EF9F7FAB 0281CF9E 00003B44 D8...........)..n.s^..@...t4..... 000040
A92C0000 3454EF04 FB40A97F 7E77AB6E FFFE29C8 EF9FFFFE 4934EF02 2044B940 @.D ..4I.....)..n.w^..@...T4..... 000060
000037EC FF165087 AB7E52FF FE47AFEF 9E510163 8F32FFFE 4916EF03 2044B940 @.D^...I..2.c.Q...G..R^..P...7.. 000080
4782EFCF AF208BBB 87AB2C00 0037EBFF 01FB04DD 00003818 FF02FB04 DDD7ABDD ...........8........7........ ....G 0000A0
9EFCADFD AF9E0400 0037CFFF 16FCADFD AF9E0000 381EFF02 FB04DDD7 ABDDFFFE ..........B..........7.......... 0000C0
000033D2 EF04FB40 A97F7EA7 AB6EFFFE 2946EF9F 9BAB0000 00008F4A FCADFDAF ....J..........F)..n..^..@....3.. 0000E0
3766FF03 FBFC77CB 7FFFFE2A 21EF9F00 A97F0000 3782FF16 5000A97E 5140A97E ^.@Q^..P...7........!*....w.....f7 000100
04000037 69FF16FC ADFDAF9E 00003790 FF02FB06 DDA7ABDD 7FAB01A3 CF9E0000 .................7..........i7... 000120
6FEF04FB 40A97F7E D7AB6EFF FE28E3EF 9F9BAB99 AF4AFCAD FDAF9EFC ADFDAF9E ..........J.........(..n..^..@...o 000140
03FBFC77 CB7FFFFE 29C6EF9F 00A97F00 00371FFF 165000A9 7E5140A9 7E000033 3..^.@Q^..P...7.........)....w... 000160
0036EBFF 165087AB 7E52FFFE 2C22EF9E 51014E8F 327FAB01 40CF9E00 003703FF ..7....@...2.N.Q..",..R^..P...6. 000180
F5EFCFAF 208BBB87 AB2C0000 36EAFF01 FB06DD00 003717FF 02FB06DD A7ABDD00 ..........7.........6............ .... 0001A0
FCADFDAF 9EFCADFD AF9E0400 0036D3FF 16000037 1DFF02FB 06DDA7AB DDFFFE2B +...........7.....6.............. 0001C0
5140A97E 000032D6 EF04FB40 A97F7E8F BB6EFFFE 2852EF9F 9BAB0000 00008F4A J.........R(..n..^..@....2..^.@Q 0001E0
```

```
Virtual block number 268 (0000010C), 512 (0200) bytes

 CF9E0000 366AFF03 FBFC77CB 7FFFFE29 35EF9F00 A97F0000 3686FF16 5000A97E ^..P...6.......5)....W....J6.... 000000
 ADFDAF9E FCADFDAF 9E040000 3672FF16 00003694 FF02FB07 DD8FBBDD 7FAB00A7 ..............6....r6........... 000020
 A97E5140 A97E0000 3278EF04 FB40A97F 7E8FBB6E FFFE27F4 EF9F9BAB 9EAF4AFC .J.......'.n..^..@...x2..^.@Q^. 000040
 AB4AAF9E 0000360C FF03FBFC 77CB7FFF FE28DFEF 9F00A97F 00003628 FF165000 .F..(6..........(....W.....6....J. 000060
 003623FF 02FB07DD 8FBBDD00 0035F7FF 165087AB 7E52FFFE 471EEF9E 510A327F .2.Q...C..R^..P...5..........#6. 000080
 362AFF02 FB07DD8F BBDDFFFE 46F2EF0A 208BBB87 AB2C0000 35F6FF01 FB07DD00 ......5.......  ...F..........*6 0000A0
 01FF00FB 000035F8 FF01FB00 DDFCADFD AF9EFCAD FDAF9E04 000035E0 FF160000 ....5....................5...... 0000C0
 ADFF00FB 0000358C FF03FBFC 77CB7FFF FE2867EF 9FFC77CB 7F9BAB08 4A000036 6..J.....W....g(....W.....5...... 0000E0
 18A97E51 40A97E00 0031B9EF 04FB40A9 7F7E5C6E FFFE272C EF9F5C50 D0000035 5...P\...'...n\^..@.....1..^.@Q^.. 000100
 FFFE2828 EF9F0000 354EFF03 FB10A97F FFFE2830 EF9F18A9 7F000035 69FF1650 P..i5.......0(.........N5....((.. 000120
 7E5C6EFF FE2813EF 9F5C50D0 00003560 FF00FB00 00353BFF 03FB08A9 7F10A97F .........(5.....`5...P\...(..n\^ 000140
 CB7F08A9 7F00A97F 00003518 FF165000 A97E5148 A97E0000 3168EF04 FB48A97F ..H...h1..^.HQ^..P...5.......... 000160
 FF00FB00 00355FFF 01FBFC77 CB7F0000 3542FF01 FB00DD00 0034FFFF 03FBFC7F .......4.........B5....W....._5..... 000180
 9F000035 25FF00FB 00003544 FF01FBFC 7FCB7F00 003527FF 01FB00DD 00003540 @5......'5.........D5.....%5... 0001A0
 9E000034 E1FF01FB 07AF9F00 0034F7FF 01FBF3F6 CF9F0000 3502FF01 FBF5A7CF .......5...........4.........4... 0001C0
 34A2FF16 50FFFE00 A5EF9EFC ADFDAF9E FCADFDAF 9E040000 34BEFF16 FCADFDAF .......4...................P...4 0001E0

Virtual block number 269 (0000010D), 512 (0200) bytes

 AF9E0000 34AAFF16 5150D050 FFFE07C0 EF9E52FB AF9ECFFC 00000450 01D00000 ....P........R......P.PQ...4.... 000000
 348AFF01 FB14EFCF 9FECADFD AF9EFCAD FDAF9EFC ADFDAF9E FCADFDAF 9EFCADFD ...............................4 000020
 003473FF 01FB00DD FCADFDAF 9E27D431 0312FFFE 0D02EF00 2097BB93 AB2D0000 ..-..............1.'.........s4. 000040
 FCA9DFFC A9000000 4D8FD000 00346FFF 00FB0000 348EFF01 FBFFFE27 11EF9F00 ....'......4.....o4....N........ 000060
 FF01FBFF FE26E3EF 9F000034 3DFF01FB 00DDFFFE 4EDEEF02 FBF8A9DF F8A918D0 ............N.......=4.....&...... 000080
 FFFE4EAC EF02FBF8 A9DFF8A9 05D0FCA9 DFFCA916 D0000034 39FF00FB 00003460 `4.....94.....................N.. 0000A0
 A919D000 003407FF 00FB0000 3426FF01 FBFFFE26 B9EF9F00 00340BFF 01FB00DD ......4......&.....&4.......4...... 0000C0
 FE268FEF 9E000033 D9FF01FB 00DDFFFE 4E7AEF02 FBF8A9DF F8A908D0 FCA9DFFC ................zN........3.....&. 0000E0
 EF02FBF8 A9DFF8A9 0BD0FCA9 DFFCA914 D0000033 D5FF00FB 000033F4 FF01FBFF .....3......3.................. 000100
 0033A3FF 00FB0000 33C2FF01 FBFFFE26 65EF9F00 0033A7FF 01FB00DD FFFE4E48 HN.........3.....e3........3.......3. 000120
 9F000033 75FF01FB 00DDFFFE 4E16EF02 FBF8A9DF F8A90CD0 FCA9DFFC A914D000 .....................N........u3.... 000140
 A9DFF8A9 10D0FCA9 DFFCA914 D0000033 71FF00FB 00003390 FF01FBFF FE263BEF .;&.......3......q3................ 000160
 00FB0000 335EFF01 FBFFFE26 11EF9F00 003343FF 01FB00DD FFFE4DE4 EF02FBF8 .....M........C3.....&.....^3.... 000180
 11FF01FB 00DDFFFE 4DB2EF02 FBF8A9DF F8A911D0 FCA9DFFC A914D000 00333FFF .?3.........................N......... 0001A0
 FCA914D0 FCADFDAF 9E000033 0DFF00FB 0000332C FF01FBFF FE25E7EF 9F000033 3.....%.......,3.......3.......... 0001C0
 FFFE25B8 EF9F0000 32DAFF01 FB00DDFF FE4D7BEF 02FBF8A9 DFF8A914 D0FCA9DF ..............{M.........2.....%.. 0001E0

Virtual block number 270 (0000010E), 512 (0200) bytes

 49EF02FB F8A9DFF8 A914D0FC A9DFFCA9 27D00000 32D6FF00 FB000032 F5FF01FB ....2.......2...'................I 000000
 00003250 FF1650A3 AB7E519B AB7EFFFE 51DEEF01 FB9BAB7F FCADFDAF 9EFFFE4D M..............Q..^..Q^..P..P2... 000020
 7F00002F 09EF03FB 00A97FA3 AB7F01DD D3110212 FFFE0B04 EF0020A7 BBA3AB2D -....  ........................./... 000040
 2DFCADFD AF9E0000 3216FF16 50A3AB7E 5120A97E FFFE5094 EF02FB20 A97F00A9 ....  ....P..^. Q^..P...2.......- 000060
 FCADFDAF 9EFDB831 00003234 FF01FB00 B8CF9F0E 12FFFE0A 57EF0120 A7BBA3AB ....  ..W..............42..1......... 000080
 ADFDAF9E FD973100 003213FF 01FB1267 CF9F0E12 FFFE0A35 EF0120A7 BBA3AB2D -....  ..5........g.....2..1...... 0000A0
```

```
09FDEF01 20A7BBA3 AB2D5C01 CE03115C D40413FF FE0A13EF 0120A7BB A3AB2DFC .-.... .........\....\-.... .... 0000C0
03115BD4 0413FFFE 09E4EF01 20A7BBA3 AB2D5C58 C85801CE 03115BD4 0413FFFE .....X....X.X\-.... .........X.. 0000E0
A97F0000 316EFF16 5000A97E 52FFFE09 C9EF9E51 02322113 5CD55C58 C85801CE ..X.X\.\.!2.Q......R^..F..n1.... 000100
E6310312 FFFE099F EF0120A7 BBA3AB2D FCADFDAF 9EFD2831 FFFE4D70 EF01FB00 ....pM..1(......-.... ........1. 000120
2416EF9F 00003178 FF01FB00 DDFCADFD AF9EFCAD FDAF9EFE BE31FCAD FDAF9E24 $.....1...................x1.....$ 000140
DFF8A918 D0FCA9DF FCA90000 004D8FD0 00003174 FF00FB00 003193FF 01FBFFFE ......1.....t1....M............. 000160
FB000031 65FF01FB FFFE23E8 EF9F0000 3142FF01 FB00DDFF FE4BE3EF 02FBF8A9 ......K.........B1.....#.....e1... 000180
FF01FB00 DDFFFE4B B1EF02FB F8A9DFF8 A905D0FC A9DFFCA9 16D00000 313EFF00 ..>1.....................K....... 0001A0
D0FCA9DF FCA914D0 0000310C FF00FB00 00312BFF 01FBFFFE 23F6EF9F 00003110 .1.....#.....+1......1.......... 0001C0
F9FF01FB FFFE23CC EF9F0000 30DEFF01 FB00DDFF FE4B7FEF 02FBF8A9 DFF8A90B ..........K........0.....#...... 0001E0
```

Virtual block number 271 (0000010F), 512 (0200) bytes

```
DDFFFE4B 4DEF02FB F8A9DFF8 A90CD0FC A9DFFCA9 14D00000 30DAFF00 FB000030 0......0.....................MK... 000000
ECA914D0 000030A8 FE00FB00 0030C7FE 01FBFFFE 23A2EF9E 000030AC FF01FB00 .....0.....#......0......0....... 000020
FFFE237B EF9F0000 307AFF01 FB00DDFF FE4B1BEF 02FBF8A9 DFF8A90D D0FCA9DF ..............K.......z0.....x#.. 000040
E9EF02FB F8A9DFF8 A90ED0FC A9DFFCA9 14D00000 3076FF00 FB000030 95FF01FB ....0.....v0..................... 000060
00003044 FE00FB00 003063FF 01FBFFFE 234EEF9F 00003048 FF01FB00 DDFFFE4A J.......H0.....N#.....c0.....D0... 000080
EF9F0000 3016FF01 FB00DDFF FE4AB7EF 02FBF8A9 DFF8A910 D0FCA9DF FCA914D0 ..................J.........0.... 0000A0
F8A9DFF8 A911D0FC A9DFFCA9 14D00000 3012FF00 FB000030 31FF01FB FFFE22E4 .'.....10......0................ 0000C0
FE00FB00 002FFFFF 01FBFFFE 22BAEF9F 00002FE4 FF01FB00 DDFFFE4A 85EF02FB ....J........./......".......J.. 0000E0
00DDFFFE 4A4EEF02 FBF8A9DF F8A914D0 FCA9DFFC A914D0FC ADFDAF9E 00002FE0 ./.......................NJ.... 000100
DFFCA92B D000002F A9FF00FB 00002FC8 FF01FBFF FE22BBEF 9F00002F ADFF01FB ..../......"....../......./...+... 000120
7EFFFE4E B1EF01FB 9BAB7FFC ADFDAF9E FFFE4A1C EF02FBFB A9DFF8A9 14D0FCA9 ..............J.............N..~ 000140
7F01DDD3 110212FF FE07D7EF 0020A7BB A3AB2D00 002F23FF 1650A3AB 7E519BAB ..Q^..P..B/..-.... ............ 000160
A3AB7E51 20A97EFF FE4D67EF 02FB20A9 7F00A97F 00002BDC EF03FB00 A97FA3AB .........+...... ....gM..^. Q^.. 000180
01FB00F9 CF9F0E12 FFFE072A EF0120A7 BBA3AB2D FCADFDAF 9E00002E E9FF1650 P..............-.... ..*.......... 0001A0
FB00E4CF 9F0E12FF FE0708EF 0120A7BB A3AB2DFC ADFDAF9E FDB13100 002F07FF ../..1.........-.... ............ 0001C0
02A6CF9F 0E12FFFE 0658EF01 20A7BBA3 AB2DFCAD FDAF9EFD 60310000 2EE6FF01 ......1`.........-.... ..X........ 0001E0
```

Virtual block number 272 (00000110), 512 (0200) bytes

```
96CF9F0E 12FFFE06 36EF0120 A7BBA3AB 2DFCADFD AF9EFD3F 3100002E C5FF01FB .......1?......-.... ..6........ 000000
5CD40413 FFFE06A4 EF0120A7 BBA3AB2D FCADFDAF 9EFD1E31 00002EA4 FF01FB00 ........1.......-..............\ 000020
A3AB2D5C 58C85801 CE031158 D40413FF FE068EEF 0120A7BB A3AB2D5C 01CE0311 ....\-.... .........X....X.X\-.. 000040
05CDEF9E 51023221 135CD55C 58C85801 CE031158 D40413FF FE0675EF 0120A7BB .. ..u......X....X.X\.\.!2.Q.... 000060
2DFCADFD AF9EFCAF 31FFFE4A 01EF01FB 00A97F00 002DFFFF 165000A9 7E52FFFE ..R^..P...-..........J..1......... 000080
2DE6FF16 FCADFDAF 9EFE4D31 FCADFDAF 9E081102 12FFFE06 30EF0120 A7BBA3AB .... ..0............1M.........- 0000A0
19FF01FB FFFE209C EF9F0000 2DFEFF01 FB00DDFC ADFDAF9E FCADFDAF 9F040000 ...........................-.... 0000C0
DDFFFE48 6DEF02FB F8A9DFF8 A90CD0FC A9DFFCA9 1AD00000 2DFAFF00 FB00002E ...........-.................mH.. 0000E0
ADFDAF9E 00002DC8 FF00FB00 002DE7FF 01FBFFFE 20E2EF9F 00002DCC FF01FB00 ....-.... ......-........-...... 000100
03DD03AB DDFCADFD AF9E015F 31000303 AB010000 00648FF1 03ABD703 AB01D0FC ..........d.........1_........... 000120
AF9E013C 3103120B 5C515C07 AB4E0000 2D7AFF01 FB1A59CF 9F00002D 7DFF02FB ...}-....Y....z-..N..\Q\...1<..... 000140
FFFE2080 EF9FFFFE 207EEF9F 00793103 12FFFE3C A5EFFFFE 3CDAEFCC 29FCADFD ...)...<.....<....1y...^ ./.... .. 000160
FF01FB00 DD00002D 49FF00FB 00002D40 FF01FB00 DD00002C FDFF03FB FE53CB7F ..S..............@-.....I-....... 000180
002D0BFF 01FB1389 CF9F0000 2D2EFF00 FB00002D 4DFF01FB FE53CB7F 00002D30 0-....S....M......-.............. 0001A0
```

```
002CBFFF 01FB03DD FFFE3C3C EFFFFE3C 71EF0C28 00002D00 FF01FB11 DDCF9F00 .........-..(..a<...<<.......... 0001C0
0C295C00 0C000000 648F0003 AB0AFCAD FDAF9E00 002CFFFF 02FB03DD 03ABDD00 ..........................d.....\). 0001E0

Virtual block number 273 (00000111), 512 (0200) bytes

FBFE53CB 7FFFFE1F EDEF9FFF FE1FE3EF 9F6E1102 12FFFE35 57EF4CFF FE3C3FFF .?<..L.W5.....n................S.. 000000
7F00002C 95FF01FB 00DD0000 2CAEFF00 FB00002C A5FF01FB 00DD0000 2C62FF03 ..b............................. 000020
1142CF9F 00002C70 FF01FB12 EECF9F00 002C93FF 00FB0000 2CB2FF01 FBFE53CB .S.........................B. 000040
FDAF9EFF FE34E5EF 4CFFFE3B CDEF0C28 5C000C8A AF0003AB 0A00002C 65FF01FB ...e...........\(.....L..4..... 000060
16FCADFD AF9EFCAD FDAF9E03 ABD7FEA4 03AB0100 0000648F F1FCADFD AF9EFCAD .........d...................... 000080
FBFFFE1E B9EF9F00 002C1BFF 01FB00DD FCADFDAF 9EFCADFD AF9E0400 002C03FF ................................ 0000A0
468AEF02 FBF8A9DF F8A90CD0 FCA9DFFC A91AD000 002C17FF 00FB0000 2C36FF01 ..6.............................F 0000C0
9E00002B E5FF00FB 00002C04 FF01FBFF FE1F1FEF 9F00002B E9FF01FB 00DDFFFE ........+...................+... 0000E0
FB05DD0B ABDDFCAD FDAF9E05 A9310003 0BAB0103 F10BABD7 0BAB01D0 FCADFDAF .................1............ 000100
5C000043 C68F425C 000043C8 8F445C0B AB4E0FAB 00000000 8F4A0000 2B9EFF02 ...+..J.......N..\D..C..\B..C..\ 000120
AF9E0532 31000313 AB0117AB F113ABD7 13AB5C4A 17AB584A 58EDAF44 580BAB4E N..XD..XJX..J\.............v12... 000140
085C515C 07AB4E00 002B53FF 01FB1933 CF9F0FAB 5C4A5C08 405C0FAB 4EFCADFD ...N..\@.\J\....3....S+..N..\@\. 000160
DD01DD02 63310313 FFFE03B8 EF0020FF FE2027EF 0C2DFCAD FDAF9E09 11310312 ..1......-..( .. .........1c.... 000180
0312FFFE 021FEF01 2004B900 A92D0000 27CAEF04 FB00A97F FFFE1E70 EF9F0FAB ...p...........'..-......p...... 0001A0
7FFFFE1E 51EF9F00 002AAFFF 03FB08A9 7FFFFE1E 59EF9FFF FE1E57EF 9F00DC31 1....W.....Y...........*....Q.... 0001C0
00002A88 FF03FBFE 53CB7F00 A97FFFFE 1E46EF9F 00002A9C FF03FB00 A97F08A9 .........*....F.........S.....*.. 0001E0

Virtual block number 274 (00000112), 512 (0200) bytes

FF01FBFE 53CB7F00 002ABBFF 01FB00DD 00002AD4 FF00FB00 002ACBFF 01FB00DD ......*......*.........*....S.... 000000
002ABBFF 01FB0F68 CF9F0000 2A94FF01 FB1114CF 9F00002A B9FF00FB 00002AD8 .*......*..........*....h......*. 000020
DDEF9F00 00270BEF 03FB10A9 7FFFFE1D C5EF9F5C DD5C5C4A 5C08425C 0FAB4E00 .N..\B.\J\\.\................'..... 000040
1D96EF9F 5CDD5C5C 4A5C0840 5C0FAB4E 00002A18 FF03FB08 A97F10A9 7FFFFE1D ............*..N..\@.\J\\.\.... 000060
9E000029 E9FF03FB FFFE1D80 EF9F08A9 7F00A97F 00002704 EF03FB00 A97FFFFE ........'...................)... 000080
FE1D8BEF FFFE3762 EF4C9E0F ABDD01DD 5C000000 00648F03 000BAB0A FCADFDAF ..........d....\.......L.b7...... 0000A0
310312FF FE0100EF 012004B9 00A92D00 0026ABEF 04FB00A9 7FFFFE1D 81EF9FFF ..............&..-.... .........1 0000C0
A97FFFFE 1D32EF9F 00002990 FF03FB08 A97FFFFE 1D62EF9F FFFE1D38 EF9F011E ....8.....b............)....2.... 0000E0
DD000029 69FF03FB FE53CB7F 00A97FFF FE1D27EF 9F000029 7DFF03FB 00A97F08 .......))....'.........S....i)... 000100
B9FF01FB FE53CB7F 0000299C FF01FB00 DD000029 B5FF00FB 000029AC FF01FB00 .....).......).........)....S.... 000120
0000296C FF01FB0E 49CF9F00 002977FF 01FB0FF5 CF9F0000 299AFF00 FB000029 )......)..........w)...I....1).. 000140
EFFFFE36 9FEF4C9E 58DD5858 4A580842 580FAB4E 5C000000 00648F03 000BAB0A ......d....\N..XB.XJXX.X.L..6.... 000160
08A97F10 A97FFFFE 1CA6EF9F 000025D4 EF03FB10 A97FFFFE 1CCEEF9F FFFE1CD8 ................%.............. 000180
5BEF4C9E 58DD5858 4A580840 580FAB4E 5C00B8AF 03000BAB 0A000028 E1FF03FB ....(...........\N..X@.XJXX.X.L.[ 0001A0
0087AF03 000BAB0A 000025B8 EF03FB00 A97FFFFE 1C92EF9F FFFE1C9C EFFFFE36 6.....................%.......... 0001C0
00002888 FF03FBFF FE1C6FEF 9FFFFE1C 79EFFFFE 3630EF4C 9E08A97F 00A97F5C \.......L.06...y.....o.......(.. 0001E0

Virtual block number 275 (00000113), 512 (0200) bytes

F5EF9F0F ABDD01DD 02633103 12FFFE01 3DEF0020 FFFE1DAC EF0C2DFC ADFDAF9E .....-...... ..=.....1c......... 000000
EF9F00DC 310312FF FDFF68EF 012004B9 00A92D00 00254FEF 04FB00A9 7FFFFE1B ..........0%..-.... ..h.....1.... 000020
00A97F08 A97FFFFE 1BD6EF9F 00002834 FF03FB08 A97FFFFE 1BDEEF9F FFFE1BDC .................4(.............. 000040
```

```
FF01FB00 DD000028 0DFF03FB FE53CB7F 00A97FFF FE1BCBEF 9F000028 21FF03FB ...!(..............S.....(....... 000060
FB000028 5DFF01FB FE53CB7E 00002840 FF01FB00 DD000028 59EF00FB 00002850 F(.....Y(.......@(....S....](... 000080
5C0FAB4E 00002810 FF01FB0C EDCF9F00 00281BFF 01FB0E99 CF9F0000 283EFF00 ..>(..........(...........(..N..\ 0000A0
A97FFFFE 1B92EF9F 00002490 EF03FB10 A97FFFFE 1B4AEF9F 5CDD5C5C 4A5C0842 B.\J\\.\..J...........$.......... 0000C0
00A97FEF FE1B1BEF 9F5CDD5C 5C4A5C08 405C0FAB 4E000027 9DFF03FB 08A97F10 ........'..N..\@.\J\\.\......... 0000E0
0AFCADFD AF9E0000 276EFF03 FBFFFE1B 05EF9F08 A97F00A9 7F000024 89EF03FB ...$.................n'......... 000100
1B36EF9F FFFE1B40 EFFFFE34 E7EF4C9E 0FABDD01 DD5C0000 0000648F 03000BAB ....d....\......L..4...@.....6. 000120
BDEF9F01 1E310312 FFFDFE49 EF012004 B900A92D 00002430 EF04FB00 A97FFFFE ........0$..-..... ..I.....1..... 000140
FB00A97F 08A97FFF FE1AB7EF 9F000027 15FF03FB 08A97FFF FE1AE7EF 9FFFFE1A ...............'............... 000160
31FF01FB 00DD0000 26EEFF03 FBFE53CB 7F00A97F FFFE1AAC EF9F0000 2702FF03 ...'............S.....&........1 000180
00FB0000 273EFF01 FBFE53CB 7F000027 21FF01FB 00DD0000 273AFF00 FB000027 '.....!'.......!'...S....>'.... 0001A0
03000BAB 0A000026 F1FF01FB 0BCECF9F 000026FC FF01FB0D 7ACF9F00 00271FFF ..'....&.....&..........&...... 0001C0
9FFFFE1A 85EFFFFE 3424EF4C 9E58DD58 584A5808 42580FAB 4E5C0000 0000648F .d....\N..XB.XJXX.X.L.$4........ 0001E0
Virtual block number 276 (00000114), 512 (0200) bytes
2666FF03 FB08A97F 10A97FFF FE1A5BEF 9F000023 59EF03FB 10A97FFF FE1A7BEF .f.........Y$....[...........!.f& 000000
49EFFFFE 33E0EF4C 9E58DD58 584A5808 40580FAB 4E5C00B8 AF03000B AB0A0000 ..........\N..X@.XJXX.X.L..3....I. 000020
7F00A97F 5C0087AF 03000BAB 0A000023 3DEF03FB 00A97FFF FE1A3FEF 9FFFFE1A .....?.........=#..........\..... 000040
FCADFDAF 9E000026 0DFF03FB FFFE1A1C EF9FFFFE 1A26EFFF FE33B5EF 4C9E08A9 ...L..3...&..............3....... 000060
ABDD0000 2602FF01 FB05DDEC ADFDAF9E 13ABD7FA D113AB01 17ABF1FC ADFDAF9E ......................&.... 000080
AF9E0BAB D7FA5A0B AB0103F1 FCADFDAF 9EFCADFD AF9E0000 2612FF02 FB05DD0B ......B&...............Z......... 0000A0
FDAF9E03 B4310003 03AB0100 0000648F F103ABD7 03AB01D0 FCADFDAF 9EFCADFD ...................d........1..... 0000C0
FFFE3544 EF0C2D03 9D310312 085C515C 07AB4E00 0025DFFF 01FB125E CF9FFCAD .........%..N..\Q\...1.-..D5.. 0000E0
FE2EEF00 2C441102 12FFFDFC 89EF0120 FFFE368E EF022D56 12FFFDFE 49EF0020 ..I....V-...6.........D,..... 000100
0220FFFD FC62EF01 2CFFFE36 69EF0320 FFFDFE20 EF002CFF FE351BEF 0C20FFFD .. ...b.,. ... ..i6.....b.... . 000120
9E031A31 033A3103 12085C51 5C07AB4E 0000257C FF01FB12 C1CF9FFF FE3659EF .Y6.........!%..N..\Q\...1!.1.... 000140
25A6FF01 FBFFFE19 25EF9F13 AB504A00 0025B7FF 01FBFFFE 192EEF9F FCADFDAF ............%..JP....%.......% 000160
FCADFDAF 9E00D331 00031BAB 011FABF1 1BABD71B AB01D01F AB5C4A5C 50500000 ..PP\J\...................1....... 000180
F5EF0C29 FCADFDAF 9E02DF31 0312085C 515C07AB 4E000025 21FF01FB 1301CF9F .......!%..N..\Q\...1.........)... 0001A0
D40412FF FE3473EF FFFE19EC EF1E295C 01CE0311 5CD40412 FFFE347C EFFFFE19 ....!4......\.....\).......s4..... 0001C0
56585156 03AB4E58 50500000 2532FF01 FBFFFE18 B9EF9F5C 58C85801 CE031158 X....X.X\..........2%..PPXN..VQXV 0001E0
Virtual block number 277 (00000115), 512 (0200) bytes
EF9F5C00 03000000 64BF001B AB0A6411 02135CD5 5C57C857 01CE0311 57D40412 !..W....W.W\.\..d.....d.....\.. 000000
FFFE1878 EF9F5C00 03E0AF00 1BAB0AF7 AFCB4C50 4A000024 FDFF01FB FFFE188C ........$..JPL...........\..x... 000020
AF9E13AB 504A0000 24CEFF01 FBFFFE18 5DEF9FF7 B3CB4C50 4A000024 E1FF01FB ....$..JPL.....]........$..JP.... 000040
FCCEEF00 2CFCADFD AF9E01E9 31FCADFD AF9E1BAB D7FF301B AB011FAB F1FCADFD .........0.........1............ 000060
FE17E7EF 9F000024 5DEF02FB FFFE180C EF7F1BAB DDFFFE19 2DEF014E 8F20FFFD .. .N..-....................]$....... 000080
31000323 AB0127AB F123ABD7 23AB1BAB D027AB5C 4A5C5050 00002480 FF01FBFF .....$..PP\J\.'....#..#..'..#..1 0000A0
04FB00A9 7F08A97F 01DD01DD 00002424 FF02FB08 A97F13AB DDFCADFD AF9E0125 %.................$$............ 0000C0
000023F8 FF02FB08 A97F13AB DD0BAB50 4A000024 39FF01FB 00A97F00 002097EF .. .........9$..JP............#.. 0000E0
DD0FAB50 4A000024 0DFF01FB 00A97F00 00206BEF 04FB00A9 7F08A97F 02DD02DD ...........k..........$..JP.... 000100
10A97FFF FE16DBEF 9F5CDD5C 5C4A5C08 425C0FAB 4E000023 99FF02FB 05DD0BAB .........#..N..\B.\J\\.\......... 000120
08405C0F AB4E0000 232EFF03 FB08A97F 10A97FFF FE16F3EF 9F000020 21EF03FB ...! ..................#..N..\@. 000140
1696EF9F 08A97F00 A97F0000 201AEF03 FB00A97F FFFE16AC EF9F5CDD 5C5C4A5C \J\\.\.......................... 000160
CF9F0000 234EFF02 FB05DD0B ABDD0000 230EFF01 FB05DD00 0022FFFF 03FBFFFE ......'.........#..........N#.... 000180
```

```
0000230C FF01FB10 51CF9F00 E1310312 085C515C 07AB4E00 002323FF 01FB1169 i....‡‡..N..\Q\...1....Q.....‡.. 0001A0
0127ABF1 FCADFDAF 9E13AB5C 4A5C0840 5C13AB4E 00CA3103 12085C51 5C07AB4E N..\Q\...1..N..\@.\J\.........'. 0001C0
2286FF03 FB08A97F FFFE1630 EF9FFFFE 162EEF9F FCADFDAF 9E23ABD7 FEDE23AB .‡....‡..............0.........' 0001E0
Virtual block number 278 (00000116), 512 (0200) bytes

CB7F00A9 7FFFFE16 1DEF9F00 002273FF 03FB00A9 7F08A97F FFFE1628 EF9F0000 ....(............s'............. 000000
2292FE01 EB00DD00 0022ABFF 00FB0000 22A2FF01 FB00DD00 00225FFF 03FBFE53 S...._'........'......'........' 000020
9E000022 6DFF01FB 08EBCF9F 00002290 FF00FB00 0022AFFF 01FBFE53 CB7F0000 ....S....'.....'........m'...... 000040
AF9EFCAD FDAF9E1D 11021208 5C515C07 AB4E0000 225EFF01 FB3BAF9F FCADFDAF ......;....^"..N..\Q\........... 000060
002207FF 16FCADFD AF9EFCAD FDAF9E03 ABD7FC4F 03AB0100 0000648F F1FCADFD .....d......D..................' 000080
BFCBF7BB CBD13711 0213085C 515C1BAB 4E2BAB00 0000008F 4AFCADFD AF9E0400 .......J......+N..\Q\....7...... 0000A0
15B6EF9F F7BBCB50 4A000022 51FF01FB FFFE15C8 EF9F2BAB 08440247 310312F7 ...1Q.J..+.........Q'..JP....... 0000C0
AB5C4A5C 08425C1B AB4EFCAD FDAF9E00 C931F7BF CB504A00 00223FFF 01FBFFFE .....?'..JP...1.......N..\B.\J\. 0000E0
5C5C4A5C 0833AB41 FCADFDAF 9E006F31 000323AB 012FABF1 23ABD723 AB01D02F /...‡..‡../..‡..1o......A.3.\J\\ 000100
F7AFCB4C F7AFCB48 D1580003 F0AF0058 0A5833AB 4A5C0003 00000064 8F005C0A .\..d.....\J.3X.X.....X.H...L... 000120
AF005C0A 580003CB AF00580A 5833AB4A 5C5C4A5C 0833AB41 2BAB084A 29110212 ...)J..+A.3.\J\\J.3X.X.....X.\.. 000140
D7FF9423 AB012FAB F1FCADFD AF9EFCAD FDAF9EF7 B3CB4CF7 AFCB48B0 5C0003C3 ...\.H...L.............../..‡... 000160
F7BFCBF7 AFCB4CD1 5C00038F AF005C0A 5C37AB4A FCADFDAF 9EFCADFD AF9E23AB .‡..........J.7\.\......\.L..... 000180
4EFCADFD AF9EF7BF CBF7AFCB 4CD05C00 03000000 648F001B AB0A2BAB 084A1813 ..J..+......d.....\.L..........N 0001A0
13AB504A 0000214C FF01FBFF FE14C3EF 9F013E31 03120000 00008F5C 515C2BAB .+\Q\.......1>..........L!..JP.. 0001C0
AB013BAB F11BABD7 1BAB01D0 3BAB5C4A 5C505000 00213BFF 01FBFFFE 11BAEF9F .........;!..PP\J\.;.........;.. 0001E0
Virtual block number 279 (00000117), 512 (0200) bytes

31031208 5C515C07 AB4E0000 20B6FF01 FB0E96CF 9FFCADFD AF9E008F 3100031B ..1...............N..\Q\...1 000000
1BAB0A00 0020B7FF 02FBFFFE 147AEF7F 7EFC6BCB 4C505C00 0B0A001B AB0A00FB .........\PL.k.~..z............. 000020
69FF01FB 0EAFCF9F 0000209C FF02FBFF FE1467EF 7F7EFC6F CB4C505C 000B0A00 ....\PL.o.~..g.................i 000040
13AB504A 000020AC FF01FBFF FE143BEF 9F009E31 0312085C 515C07AB 4E000020 ..N..\Q\...1....;.........JP.. 000060
FFFE1380 EF9FFCAD FDAF9E1B ABD7FF74 1BAB013B ABF1FCAD FDAF9EFC ADFDAF9E .............;....t............. 000080
C5FF03FB 00A97F08 A97FFFFE 137AEF9F 00001FD8 FF03FB08 A97FFFFE 1382EF9F ..................z............. 0000A0
00001FF4 FF01FB00 DD00001F B1FF03FB FE53CB7F 00A97FFF FE136FEF 9F00001F ......o.........S............... 0000C0
1FE2FF00 FB000020 01FF01FB FE53CB7F 00001FE4 FF01FB00 DD00001F FDFF00FB ................S............... 0000E0
AF9EFCAD FDAF9E04 00001F90 FF16FCAD FDAF9E00 001FBFFF 01FB063D CF9F0000 ....=........................... 000100
35EF9F00 001F97FF 01FB00DD FCADFDAF 9EFCADFD AF9E0400 001F7FFF 16FCADFD ...............................5 000120
FBA918D0 FCA9DFFC A9000000 4DBFD000 001F93FF 00FB0000 1FB2FF01 FBFFFE12 .....................M.......... 000140
FF00FB00 001F7FFF 01FBABAB 7F00001F 61FF01FB 00DDFFFE 3A02EF02 FBF8A9DF ........!......a................ 000160
00DDFFFE 39CEEF02 FBF8A9DF F8A905D0 FCA9DFFC A90ADFFC ADFDAF9E 00001F60 ...............................9.... 000180
EF9E5100 3200001F 29FF00FB 00001F50 FF01FBFF FE1313EF 9F00001F 2DFF01FB `................P......)...2.Q.. 0001A0
AB7EFFFE 3E32EF01 FB9BAB7F FCADFDAF 9E00001E BDFF1650 B3AB7E52 FFFDF78C ...-...........P.........2>..~. 0001C0
007F8FDD D3110212 FFFDF758 EF0020A7 BBA3AB2D 00001EA4 FF1650A3 AB7E519B ....R^..P.....................X.. 0001E0
Virtual block number 280 (00000118), 512 (0200) bytes

425C584E 58B3AB3C 681204B9 00A920A7 BBA3AB2D 00001E8C FF02FB00 A97F0000 .Q~..P.......-......h<..XNX\B 000000
7F08DD00 001E97FF 01FB00DD 00001B34 EF03FBB3 AB7FB3AB 7F5CDD5C 5C4A5C08 .\J\\.\.........4............... 000020
00001EA4 FF01FBFF FE11D7EF 9F00001E B1FF01FB 08A97F00 001E4FFF 02FB08A9 .....D.......................... 000040
FF4F3100 001E67FF 00FB0000 1E8EFF01 FB00A97F 00001E2C FF02FB00 A97F08DD ......................g....1O. 000060
AB7FB3AB 7FA3AB7F 301304B9 00A920A7 BBA3AB2D 00001E0C FF02FB00 A97F0DDD ...............-......0......... 000080
```

```
00FB0000 1E46FF01 FBFFFE12 11EF9F00 001E23FF 01FB00DD 00001DE0 FF03FBB3 .............$............F..... 0000A0
0ADDFEA6 310312FF FDF677EF 0020B7BB B3AB2DFC ADFDAF9E FF073100 001E1FFF .....1.......-......w.....1..... 0000C0
AB7E5120 A97EFFFE 3C06EF02 FB20A97F 00A97F00 001A7BEF 03FB00A9 7FB3AB7F ..........(..........<..^. Q^.. 0000E0
23AB0AFC ADFDAF9E 2B110002 23AB0119 F123ABD7 23AB01D0 00001D88 FF1650B3 .P.........$..$.....$...+.......$ 000100
D823AB19 F3FCADFD AF9E1511 0212FFFE 233EEF4C 0A20B7AB B3AB2D5C 000A1900 ....\-......L.>$...............$. 000120
FE2599EF 4C3FABD1 5C000119 0023AB0A FCADFDAF 9E007C31 FCADFDAF 9E23ABD7 ..$......1|.........$....\..?L..%. 000140
0F325C00 0F190023 AB0A3FAB FFFE2586 EF4CD05C 00011900 23AB0A62 110215FF ....b..$....\.L..%...?..$....\2. 000160
FB00A97F FFFE1134 EF9F93AB 7F00001C F9FF1650 93AB7E52 FFFE23EC EF4C9E51 Q.L..$..R^..P............4....... 000180
01FB0385 CF9F0000 1CCEFF03 FBFE53CB 7F00A97F FFFE112C EF9F0000 1CE2FF03 ..................S............... 0001A0
FE378BEF 02FBF8A9 DFF8A90A D0FCA9DF FCA90AD0 FCADFDAF 9E561100 001D07FF ......V....................7. 0001C0
00320000 1CE6FF00 FB00001D 05FF01FB FFFE10F0 EF9F0000 1CEAFF01 FB00DDFF ..............................2. 0001E0
Virtual block number 281 (00000119), 512 (0200) bytes

FDAF9E00 001CAFFF 01FB018C CF9F0000 1C7AFF16 5093AB7E 52FFFDF5 49EF9E51 Q..I...R^..P..z.................. 000000
1926EF03 FBBBAB7F BBAB7F0C DDFCADFD AF9EFCAD FDAF9E04 00001C80 FF16FCAD ..............................2. 000020
01D00000 1C2EFF16 50C3AB7E 52FFFDF4 FDEF9E51 003243AB 5CD05CBB AB3C0000 ..<..\.\.C2.Q......R^..P......... 000040
EF9E5101 32161543 AB23ABD1 FCADFDAF 9E009C31 000323AB 010CF123 ABD723AB .$..$....$..1..........$.C..2.Q.. 000060
D9EF04FB A3AB7FBB AB7F23AB DD01DD56 1100001B FDFF1650 A3AB7E52 FFFDF33C <...R^..P.......V....$........... 000080
58515847 AB4E47AB 504A0000 1B1BEF16 50504E00 001A37EF 01FBA3AB 7F000018 .........7...NPP......JP.GN.GXQX 0000A0
58C85801 CE03115B D4041400 0043648F 57515747 AB4E5C01 CE03115C D4041934 4...\....\N.CWQW.dC.....X....X.X 0000C0
ADFDAF9E 00001B8C FF03FBC3 AB7FC3AB 7FA3AB7F FCADFDAF 9E391102 135CD55C \.\...9......................... 0000E0
76110000 1B72FF16 50BBAB7E 51C3AB7E FCADFDAF 9E23ABD7 FF6723AB 010CF1FC .....$g...$.....^..Q^..P..r....v 000100
00FB0000 1B96FF01 FB00DD00 001BAFFF 00FB0000 1BA6FF01 FB00DDFC ADFDAF9E ................................ 000120
FF01FB00 A97F0000 1B6EEF02 FB00A97F 0ADD0000 1B86FF01 FB00DD00 001B9FFF ......................n......... 000140
1B4AFF01 FB27AF9F 00001B6C FF00FB00 001B8BFF 01FBFFFE 0F7EEF9F 00001BA0 ......^............1......'...J. 000160
001B07FF 16FCADFD AF9E0000 1AF6FF16 50BBAB7E 52FFFDF3 C5EF9E51 00320000 ..2.Q......R^..P................ 000180
FE35ABEF 02FBF8A9 DFF8A918 D0FCA9DF FCA901D0 FCADFDAF 9EFCADFD AF9E0400 ..............................5. 0001A0
1B22FF01 FB00A97F 000017CC EF03FB00 A97F28DD 20DD0000 1B0AFF01 FB00DDFF ............(...................° 0001C0
00DDFFFE 356EEF02 FBF8A9DF F8A918D0 FCA9DFFC A929D000 001AFBFF 00FB0000 ..........)...............n5.... 0001E0
Virtual block number 282 (0000011A), 512 (0200) bytes

FB00001A E5FF01FB 00A97F00 00178FEF 03FB00A9 7F24DD20 DD00001A CDFF01FB .........$...................... 000000
FF01FB00 DDFFFE35 31EF02FB F8A9DFF8 A901D0FC A9DFFCA9 01D00000 1ABEFF00 ..........................15...... 000020
FFFE350C EF02FBF8 A9DFF8A9 18D0FCA9 DFFCA905 D000001A 99FF00FB 00001A90 ..............................5.. 000040
FDAF9E00 001A67FF 00FB0000 1A8EFF01 FBFFFE0E 81EF9F00 001A6BFF 01FB00DD .....k...................g....... 000060
FB00A97F 0DDD0000 19F6FF16 50CBAB7E 519BAB7E FFFE3984 EF01FB9B AB7FFCAD .........9..^..Q^..P............. 000080
04000019 E9FF16FC ADFDAF9E C9110213 04B900A9 20CFBBCB AB2D0000 19F2FF02 ......-......................... 0000A0
FF01FB00 DDFFFE34 91EF02FB 4BABDFFC A9DFFCA9 01D0FCAD FDAF9EFC ADFDAF9E ....................K....4....... 0000C0
E1FF00FB 00001A00 FF01FB00 A97F0000 16B2EF03 FB00A97F 28DD20DD 000019F0 ......(......................... 0000E0
DD20DD00 0019B7FF 01FB00DD FFFE3458 EF02FB4B ABDFFCA9 DFFCA929 D0000019 ....).......K...X4............. 000100
1966FF16 000019A8 FF00FB00 0019C7FF 01FB00A9 7F000016 79EF03FB 00A97F28 (......y........................f. 000120
0000008F 5C515CFF FE28CBEF 4E7FAB00 EBCF9EFC ADFDAF9E FCADFDAF 9F040000 ....................N..(..\Q\.... 000140
01FB00A9 7F000011 EAEF02FB 00A97F00 DD000019 65FF01FB 02DD00CA 31031200 ...1.......e..................... 000160
FF00FB00 00195FFF 01FBFE53 CB7F0000 1972FF01 FBFFFE0C A5EF9F00 00197FFF ..................r.....S...-.... 000180
7E52FFFD F192EF9E 5100325C 00012800 4FAB0AFC ADFDAF9E 4FAB084A 00001940 Q...J..O.......O.(..\2.Q......R^ 0001A0
4C7E5C00 0128004F AB0A4FAB 5C4A5C08 405C4FAB 4E000018 C1FF1650 FE4BCB4C L.K.P......N.O\@.\J\.O..O.(..\^L 0001C0
A97F0ADD 000018D8 FF01FB02 DD3D1102 12FFFDF1 61EF0020 04BC6C2D 5CFE4BCB .K.\-1.....a.......=............ 0001E0
```

```
Virtual block number 283 (0000011B), 512 (0200) bytes

FBFE4BCB 4C7F5C00 0128004F AB0A0000 18F2FF01 FB00A97F 000015C0 EF02FB00 ..................D.(..\.L.K.. 000000
ADFDAF9E 04000018 6DFF16FC ADFDAF9E FF783100 0018B7FF 00FB0000 18D6FF01 ..............1x........m....... 000020
FCADFDAF 9EFCADFD AF9E0000 186AFF01 FBE1AF9F FFFE27D8 EF000000 008F4AFC .J.......'.......J.............. 000040
EF9F0000 1856FF01 FB00DDFF FE32F7EF 02FBF8A9 DFF8A918 D0FCA9DF FCA903D0 ................2.......V....... 000060
F8A9DFF8 A901D0FC A9DFFCA9 01D00000 1852FF00 FB000018 79FF01FB FFFE0C74 t.......y.....R................. 000080
AF9E0400 0017EBFF 16000018 2DFF00FB 00001824 FF01FB00 DDFFFE32 C5EF02FB ....2.......$.......-........... 0000A0
FDEE16EF 9E510332 000017F4 FF01FB06 D0CF9F53 AB13ABD0 FCADFDAF 9EFCADFD ............S...........2.Q...... 0000C0
13AB6EFF FE0C03EF 9F000017 D5FF01FB 00B7CF9F 000017A0 FF1650D3 AB7E52FF .R~..P.......................n.. 0000E0
FBFFFE0B E9EF9F00 001777FF 1650DBAB 7E5120A9 7E000013 C7EF04FB 20A97F7E ~.........~. Q~..P..w........... 000100
3411FFFE 286BEF03 20DFBBDB AB2C0E12 00000000 8F5C515C 50500000 1802FF01 ......PP\Q\...............k(...4 000120
51DBAB7E 00001770 FF01FB05 50CF9F13 AB504A00 0017DBFF 01FBFFFE 0BCAEF9F .................JP....P.....~..Q 000140
0320DFBB DBAB2CFC ADFDAF9E 00001758 FF01FB3A AF9F0000 1726FF16 50D3AB7E ~..P..:.......X................. 000160
0000172C FF01FB05 0CCF9F13 AB53ABD0 0000173C FF01FB06 79CF9FFF FE2827EF .'(.....y.....<......S.......... 000180
0044998F 405C1444 5C08425C 5BAB4EFC ADFDAF9E FCADFDAF 9E040000 1702FF16 ................N.[\B.\D.\@..D. 0001A0
1386EF03 FB10A97F FFFE0B40 EF9F5CDD 5C5C4A5C 08425C57 AB4E57AB 5C4A5C80 .\J\.WN.W\B.\J\\.\..@........... 0001C0
5757AB4E 5C5C4A5C 14405C57 AB4E0000 1696FF03 FB08A97F 10A97FD3 AB7F0000 .................N.W\@.\J\\N.WW 0001E0
Virtual block number 284 (0000011C), 512 (0200) bytes

7F000013 5DEF04FB 00A97FFF FE0B03EF 9F5CDD58 DD58584A 58800044 A78F5743 CW..D..XJXX.X.\.............]..... 000000
65EE1600 00168EFE 01FB04D5 CF9E0000 1656FF03 FBFFEE0A EDEF9F08 A97F00A9 .............V................... 000020
4A5C8000 44998F40 5C14445C 08425C5B AB4EFCAD FDAF9EFC ADFDAF9E 04000016 .............N.[\B.\D.\@..D..\J 000040
03130000 00008F5C 515C07AB 4E000016 59FF01FB 0439CF9F 63AB13AB D05FAB5C \._....c..9....Y....N..\Q\....... 000060
4A5C0842 5C5FAB4E 000012E4 EF04FBE3 AB7EFFFE 0ABAEF9F 5FABDD03 DD031531 1......................N._\B.\J 000080
08A97F10 A97FFFFE 0A66EF9F 000012B4 EF03FB10 A97FFFFE 0A6EEF9F 5CDD5C5C \\.\..n..............f.......... 0000A0
58584A58 B00044A7 8F574357 5FAB4E5C 5C4A5C14 405C5FAB 4E000015 C1FF03FB .......N._\@.\J\\N._WCW..D..XJXX 0000C0
FFFE0A18 EF9F08A9 7F00A97F 00001288 EF04FB00 A97FFFFE 0A2EEF9F 5CDD58DD .X.\............................ 0000E0
4A5C0842 5C67AB4E 67AB5C4A 5C08405C 10445C08 425C5BAB 4E000015 81FF03FB .......N.[\B.\D.\@.\J\.gN.g\B.\J 000100
08A97F10 A97FFFFE 09F6EF9F 00001234 EF03FB10 A97FFFFE 09FEEF9F 5CDD5C5C \\.\..............4............. 000120
5CDD58DD 58584A58 23574357 67AB4E5C 5C4A5C10 405C67AB 4E000015 41FF03FB ...A...N.g\@.\J\\N.gWCW#XJXX.X.\ 000140
05FF03FB FFFE09AC EF9F08A9 7F00A97F 0000120C EF04FB00 A97FFFFE 09C2EF9F ................................ 000160
9FFFFE0B 2AEF0F20 FFFDEDB8 EF002C0E 12FFFDEB 54EFFFFE 0B54EF0C 29000015 ...)..T....T..............*..... 000180
01FB03E3 CF9F01DE 31031300 0000008F 5C515C07 AB4E0000 1522FF01 FB0368CF .h....'....N..\Q\.......1........ 0001A0
50EBAB7E 52FFFDEB 16EF9E51 033201C6 310313E4 AF5C515C 07AB4E00 001507FF .....N..\Q\....1..2.Q......R~..P 0001C0
2C0F125C 58515863 AB4E5C50 50000015 35FF01FB FFFE091C EF9F0000 14A6FF16 ...............5...PP\N.cXQX\... 0001E0
Virtual block number 285 (0000011D), 512 (0200) bytes

9E13AB50 4A000015 0DFF01FB FFFE08F4 EF9F010B 31FFFE25 9EEF0320 E7BBE3AB .... ...%..1..............JP... 000000
DD015931 03130000 00008F5C 515C07AB 4E000014 9DFF01FB 027DCF9F FCADFDAF ......}........N..\Q\........1Y.. 000020
504A0000 14CAFF01 FB00A97F 00001128 EF04FB00 A97FFFFE 0BCEEF9F 5FABDD03 .....................(...........JP 000040
EF04FB20 A97F7E13 AB6EFFFE 088AEF9F AF1113AB 6BABD007 1363AB6B ABD16BAB ..-.......................n..~.. ... 000060
EF9F5CDD 5C5C4A5C 08425C5F AB4E0000 13FEFF16 50EBAB7E 5120A97E 0000104E .k..k.c....k...........N._\B.\J\\.\.. 000080
AB4E0000 13CAFF03 FB08A97F 10A97FE3 AB7F0000 10BAEF03 FB10A97F FFFE0874 N...~. Q~..P......N._\B.\J\\.\..........N. 0000A0
FE0837EF 9F5CDD58 DD58584A 58800044 A78F5743 575FAB4E 5C5C4A5C 14405C5F t............................... 0000C0
CF9F0000 138AFF03 FBFFFE08 21EF9F08 A97F00A9 7F000010 91EF04FB 00A97FFF _\@.\J\\N._WCW..D..XJXX.X.\..7.. 0000E0
EF9FFCAD FDAF9E00 7F310313 00000000 8F5C515C 07AB4E00 0013C3FF 01FB0209 .....................!.......... 000100
                                                                            .........N..\Q\.......1......... 
```

```
66EFFFFD E9B3EF03 280C12C0 0045798F 5C515C50 50000013 FDFF01FB FFFE07E4 ...............PP\Q\.sE....(........f 000120
BBEBAB2C 0C12585C 515863AB 4E5C5050 000013D8 FF01FBFF FE07C7EF 9FFFFE24 $.................PP\N.cXQ\X...,.... 000140
12585C51 5863AB4E 5C505000 0013B3FF 01FBFFFE 07CAEF9F FFFE2444 EF0320EF . ..D$...................PP\N.cXQ\X. 000160
05FF16FC ADFDAF9E 00001334 FF01FB02 71CF9FFF FE2422EF 0320EFBB EBAB2C0C .,..... ..°$....Q....4............. 000180
7E03AB6E FFFE0744 EF9F07AB 00000000 8F4AFCAD FDAF9EFC ADFDAF9E 04000013 ..................J..........D...n..~ 0001A0
FE075FEF 9F00A97F 000012B8 FF165000 A97E5120 A97E0000 0F08EF04 FB20A97F .. ........^. Q~..F..............._.. 0001C0
AF9E0000 12C6FF02 FB04DD03 ABDD7FAB 02A4CF9E 0000129C FF03FBFE 53CB7FFF ...S.............................. 0001E0
Virtual block number 286 (0000011E), 512 (0200) bytes

6EFFFE06 E1EF9F07 AB99AF4A FCADFDAF 9EFCADFD AF9E0400 00129FFF 16FCADFD .....................J.............n 000000
EF9E00A9 7E000012 55FF1650 00A97E51 20A97E00 000EA3EF 04FB20A9 7F7E03AB ..~.. ........~. Q~..F..U........... 000020
FFFE21E4 EF9E5101 638F327F AB0241CF 9E000012 39FF03FB FE53CB7F FFFE0704 .......S....9......A...2.c.Q...!.. 000040
00001220 FF01FB04 DD000012 4DFF02FB 04DD03AB DD000012 21FF1650 F3AB7E52 R~..F..!...............M......... ... 000060
FE16FCAD FDAF9E00 001253FF 02FB04DD 03ABDDFF FE21B7EF CFAF20F7 BBF3AB2C ..... ....!............S............ 000080
13AB6EFF FE0643EF 9F07AB00 0000008F 4AFCADFD AF9EFCAD FDAF9E04 00001204 ...................J..........C...n.. 0000A0
066EEF9F 00A97F00 0011B7FF 165000A9 7E5120A9 7E00000E 07EF04FB 20A97F7E ~.. .........~. Q~..F...............n. 0000C0
9E000011 C5FF02FB 06DD13AB DD7FAB01 A3CF9E00 00119BFF 03FBFE53 CB7FFFFE ....S............................ 0000E0
FFFE05E0 EF9F07AB 99AF4AFC ADFDAF9E FCADFDAF 9E040000 119EFF16 FCADFDAF ......................J............ 000100
9F00A97F 00001154 FF165000 A97E5120 A97E0000 0DA4EF04 FB20A97F 7E03AB6E n..~.. .........~. Q~..F..T........ 000120
FE0657EF 9E51014E 8F327FAB 0140CF9E 00001138 FF03FBFE 53CB7FFF FE0613EF .........S....B......@...2.N.Q..W.. 000140
00111FFF 01FB06DD 0000114C FF02FB06 DD13ABDD 00001120 FF1650F3 AB7E52FF .R~..F.. ..................L.......... 000160
0000110B FF160000 1152FF02 FB06DD13 ABDDFFFE 062AEFCF AF20F7BB F3AB2C00 ....... ...*..............R......... 000180
20A97F7E 5BAB6EFF FE05A7EF 9F07AB00 0000008F 4AFCADFD AF9EFCAD FDAF9E04 ...............J....................n.[~... 0001A0
CB7FFFFE 058AEF9F 00A97F00 0010BBFF 165000A9 7E5120A9 7E00000D 0BEF04FB .........~. Q~..F....................... 0001C0
0010A7FF 16000010 C9FF02FB 07DD5BAB DD7FAB00 A7CF9E00 00109FFF 03FBFE53 S..................[.................. 0001E0
Virtual block number 287 (0000011F), 512 (0200) bytes

04FB20A9 7F7E5BAB 6EFFFE05 49EF9F07 AB9EAF4A FCADFDAF 9EFCADFD AF9E0400 ..................J.......I...n.[~... .. 000000
FE53CB7F FFFE053A EE9E00A9 7F000010 5DFF1650 00A97E51 20A97E00 000CADEF ......~. Q~..F..]..........4......S. 000020
0000102C FF1650F3 AB7E52FF FE2153EF 9E510A32 7FAB4AAF 9E000010 41FF03FB ...A......J..2.Q..S!..R~..F...... 000040
FE2127EF 0A20F7BB F3AB2C00 00102BFF 01FB07DD 00001058 FF02FB07 DD5BABDD ..[......X.........+........ ..'!. 000060
00DDFCAD FDAF9EFC ADFDAF9E 04000010 15FF1600 00105FFF 02FB07DD 5BABDDFF ...[......_......................... 000080
FE53CB7F FFFE04BC EF9FFE53 CB7F07AB 084A0000 1036FF00 FB000010 2DFF01FB ...-.........6...J......S..........S. 0000A0
EF04FB20 A97F7E5C 6EFFFE04 29EF9F5C 50D00000 0FE2FF00 FB00000F C1FF03FB ....................F\..)...n\^.. ... 0000C0
03FB10A9 7FFFFE04 85EF9F18 A97F0000 0F9EFF16 5018A97E 5120A97E 00000BEE .....~. Q~..F....................... 0000E0
D000000F 95FF00FB 00000F70 FF03FB08 A97F10A9 7FFFFE04 7DEF9F00 000F83FF .........}.................P............ 000100
4DFF1650 00A97E51 28A97E00 000B9DEF 04FB28A9 7F7E5C6E FFFE0468 EF9F5C50 P\..n...n\^..(.........~.(Q~..F..M 000120
53CB7F00 000F77FF 01FB00DD 00000F34 FF03FBFE 5BCB7F08 A97F00A9 7F00000F ...............[....4..........w......S 000140
79FF01FB FE5BCB7F 00000F5C FF01FB00 DD00000F 75FF00FB 00000F94 FF01FBFE ...............u..........\......[....y 000160
00000F2C FF01FBF4 09CF9F00 000F37FF 01FBF5B5 CF9F0000 0F5AFF00 FB00000F .......Z...........7................. 000180
FCADFDAF 9EFCADFD AF9E0400 000EF3FF 16FCADFD AF9E0000 0F16FF01 FB07AF9F ................................... 0001A0
EF9E37DD 00001000 8FDD6E2B 006E002C 5E2BC200 DD7FAB01 37CF9EFC ADFDAF9E ........7.......+^,.n.+n.......7.. 0001C0
FF166FAB 00000000 8F4A5E37 C000000E F5FF01FB 5EDD2CAE 0BD008AE FFFE03B4 ............,.^..........7^J.......o.. 0001E0
Virtual block number 288 (00000120), 512 (0200) bytes

AB7F0000 0EB6FF01 FB0BDD7F AB00EDCF 9EFCADFD AF9EFCAD FDAF9E04 00000EA4 ................................ 000000
```

```
5C515C6F AB4E6FAB 5C4A5C08 405C6FAB 4E00000E B5FF00FB 00000ED4 FF01FBFB ...................N.o\@.\J\.oN.o\Q\ 000020
FDAF9EFC ADFDAF9E 0400000E 51FF1600 000E7BFF 01FB0EAF 9F0A1200 0042EBBF ..B...........{.....Q............. 000040
15000000 008F5C51 5C73AB4E 73AB5C4A 5C2F5843 586FAB4E 7FAB009A CF9EFCAD ,.........N.oXCX/\J\.sN.s\Q\...... 000060
01FB0BDD FCADFDAF 9E231100 026FAB01 77ABF16F ABD76FAB 01D077AB 73ABD03E >..s.w...o..o..w..o...#.......... 000080
4AFCADFD AF9E6FAB D7E06FAB 77ABF3FC ADFDAF9E 00000E38 FF00FB00 000E2FFF ./.......8.............w.o....o.....J 0000A0
01FBFF7A CF9F7FAB 28AF9EFC ADFDAF9E FCADFDAF 9E040000 0DDEFF16 6FABB9AF ...o.....................(....z... 0000C0
0400000D A9FF1600 000DA3FF 01FB0BDD 00000DDC FF01FBFF 6FCF9F00 000DE7FF ........o......................... 0000E0
1F3207AB 084A0000 0DCAFF00 FB00000D C1FF01FB 00DDFCAD FDAF9EFC ADFDAF9E ...........................J...2. 000100
BDEF9F5C 50D00000 0D76FF00 FB00000D 59FF1650 FE53CB7E 52FFFDE2 F5EF9E51 Q.......R~.S.P..Y........V....F\... 000120
A97F0000 0D32FF16 5018A97E 5120A97E 00000982 EF04FB20 A97F7E5C 6FFFFE01 ...n\^.. ........~. Q~..P..2..... 000140
FF03FB08 A97F10A9 7FFFFE02 11EF9F00 000D17FF 03FB10A9 7FFFFE02 19EF9F18 .................................. 000160
000931EF 04FB28A9 7F7E5C6E FFFE01FC EF9F5C50 D000000D 29FF00FB 00000D04 ........)....F\.....).n\~..(...1.. 000180
00000CC8 FF03FBFE 5BCB7F08 A97F00A9 7F00000C E1FF1650 00A97E51 28A97E00 .~.(Q~..P.................[........ 0001A0
FF01FB00 DD00000D 09FF00FB 00000D28 FF01FBFE 53CB7F00 000D0BFF 01FB00DD .............S....(................ 0001C0
000CCBFF 01FBF349 CF9F0000 0CEEFF00 FB00000D 0DFF01FB FE5BCB7F 00000CF0 .......[......................I........ 0001E0
Virtual block number 289 (00000121), 512 (0200) bytes

000C87FF 16FCADFD AF9E0000 0CAAFF01 FB07AF9F 00000CC0 FF01FBF1 9DCF9F00 ............................... 000000
00000004 5001D000 000C6BFF 1650EFFD DFA2EF9E FCADFDAF 9EFCADFD AF9E0400 ....................P..k......P.... 000020
FCADFDAF 9EFCADFD AF9E0000 0C72FF16 5150D050 FFFDE504 EF9E52FB AF9ECFFC .....R.......F.FQ..r.............. 000040
00000031 8FD067AB 00000080 8F5CC95C 00000040 8F000000 318FC9FC ADFDAF9E ........1....@...\.\.;......g..1... 000060
67ABDD4F AB3E00DD 00DDEEFD E76AEF9F 00000084 8FDD06DD 00DD00DD 00DD6BAB .k.....................j........T.D..g 000080
00DD00DD FCADFDAF 9E6FAB50 D07FFEDF C89F0CFB FFFE1B8A EFDDFFFE 1B98EFDD ......................F.o.......... 0000A0
1B58EFDD FFFE1B56 EFDD6BAB DD59AB3F 00DD00DD FFFDE7BB EF9F02DD 00DD00DD .....................T.Y..k..V.....X. 0000C0
7FFEE090 9E02FBFF FE1B3DEF DDFFFFFF FF8FDD6F AB50D07F FEDFC89F 0CFBFFFE .............F.o..........=.............. 0000E0
7FFFFE00 81EF9F00 AA310312 00000000 8F5C515C 5BAB4DFC ADFDAF9E 6FAB50D0 .F.o......K.[\Q\.........1.......... 000100
08A97FFF FE0063EF 9F02DDFF FDE74FEF 14201489 10A92CFF FE29D7EF 02FB10A9 .......)........ ..O.........c....... 000120
EF9F02DD 5C01CE03 115CD404 13FFFDE4 6FEF0220 0CB90BA9 2D000008 21EF03FB ...!....-..... ..o........\.....\.... 000140
031158D4 0413FFFD E446EF02 2004B900 A92D0000 07FAEF03 FB00A97F FFFE003C <...................-.... ..F......X.. 000160
EF9E5114 326FAB50 D07FFEDE 609F01FB FFFE1AAE EFDD2813 5CD55C58 C85801CF ..X.X\.\.(...........`.....F.o2.Q.. 000180
FFFDE6C4 EF1420FF FDE407EF 002C009B 3100000A DDFF1650 63BB7E52 FFFDE6E0 ....R~.eP.........1........ ....... 0001A0
E3DEEF9E 5100326F AB50D07F FEDE609F 01FBFFFE 1A64EFDD FCADFDAF 9EFEF431 1...........d........`....F.o2.Q..... 0001C0
D077AB51 AB325315 00000000 8F5C515C 53AB4D00 000A9FFF 165063BB 7E52FFFD ..R~.cP.......M.S\Q\.......S2.Q.w. 0001E0
Virtual block number 290 (00000122), 512 (0200) bytes

FFFDFF88 EF9F73AB DD01DDFC ADFDAF9E 38110002 73AB0177 ABF173AB D773AB01 ..s..s..w..s...B.........s...... 000000
E3FCADED AF9E0000 0A4EFE03 FB63BB7F 63BB7F00 A97F0000 0752EF04 FB00A97F .......R........c..c...N......... 000020
D000000A 45FF1650 FFFDE2F8 EF9EFCAD FDAF9EFC ADFDAF9E 73ABD7CB 73AB77AB .W.S...S..................F..E.... 000040
9EFCADFD AF9E0000 0A4EFF16 5150D050 FFFDE354 EF9E52FB AF9ECFFC 00015001 .F.........R..T...F.FQ..N......... 000060
5CF0AF44 5C63AB4E 63AB5C4A 5C000044 808F465C 5FBB4EFC ADFDAF9E FCADFDAF ..........N._\F..D..\J\.cN.c\D..\ 000080
63AB4E5C 28445C6B AB4E6BAB 5C4A5C28 465C63AB 4E67AB58 4A585C42 585FBB4E N._XB\XJX.sN.c\F(\J\.kN.k\D(\N.c 0000A0
5C425867 AB4E5C28 445C73AB 4E73AB5C 4A5C2846 5C67AB4E 6FAB584A 585C4258 XB\XJX.oN.s\F(\J\.sN.s\D(\N.sXB\ 0000C0
79EF04EB 28A97FFF FDFEB7EF 9F5CDD01 DD5C5C4A 5C08405C 6BAB4E77 AB584A58 XJX.wN.k\@.\J\\...\.........(...y 0000E0
00065BEF 04FB20A9 7FFFFDFE 99EF9F5C DD01DD5C 5C4A5C08 405C6FAB 4E000006 ...N.o\@.\J\\...\......... ...[.. 000100
9F5CDD01 DD5C5C4A 5C08405C 73AB4E00 000957FF 03FB18A9 7F28A97F 20A97F00 ... ..(......W...N.s\@.\J\\...\. 000120
4E000009 29FF03FB 08A97F18 A97F10A9 7F000006 2DEF04FB 10A97FFF FDFE6BEF .k..........................)...N 000140
```

```
00A97F00 0005FFEF 04FB00A9 7FFFFDFE 3DEF9F5C DD01DD5C 5C4A5C08 405C77AB .w\@.\J\\...\.................. 000160
04000009 05FF1650 FFFDE22C EF9EFCAD FDAF9E00 0008FBFF 03FB5BBB 7F08A97F .....[..................P....... 000180
44AE28AE 9E40AE01 0E00188F D0321254 08ACD05E B8AE9E55 7FFEDE58 9F9E003C <...X...U...^...T.2.......@..(.D 0001A0
9F2CAE20 208FA828 AE309004 122028AE 912FAE31 AEB00000 06E6EF01 FB40AE9F ..@.........1./..(....0.(..  ... 0001C0
8F7B7E00 54017A38 AE309034 AE302D58 588FD030 AE582D30 308FD001 6E3128AE .(1n...00-X.0..XX-0.4.0.8z.T.~(. 0001E0
Virtual block number 291 (00000123), 512 (0200) bytes

016E8F52 D1013531 031854D5 5307B2C0 9E505400 0003E88F C752528E 000003E8 .....RR......TP....S.T..15..R.n. 000000
4E418EB0 30AE4A2D 31308FD0 E41250D5 50508E04 7B7E0053 017A0E12 F4140000 ......z.S.~(..PP.P....01-J.0..AN 000020
7E005001 7A505300 000064BF C737AE50 30815053 000003E8 8FC736AE 2D9034AE .4.-.6......SP.OP.7..d...SPz.P.~ 000040
53017A39 AE503081 50508E0A 7B7E0050 017A5053 0AC738AE 50308150 508E0A7B (..PP.OP.8..SPz.P.~(..PP.OP.9z.S 000060
2E308FD0 3FAE303A 30308FD0 3BAE3A30 30208FD0 3AAE5030 8150508E 0A7B7E00 .~(..PP.OP.:.. 00:.;..00:0.?..0. 000080
30906502 FB2CAE9F 18AE9F2C AE30AE9E 28AE010E 00188FD0 47AE2090 43AE3030 00.C. .G.......(..0..........e.0 0000A0
510AC705 AE503081 50508E0A 7B7E0050 017A5051 00000064 8FC751FF A49E04AE .....Q..d...QPz.P.~(..PP.OP....Q 0000C0
D007AE50 30815050 8E0A7B7E 0051017A 06AE5030 8150508E 0A7B7E00 50017A50 Pz.P.~(..PP.OP..z.Q.~(..PP.OP... 0000E0
18AE9F0C AE9F5EDD 6E02D065 02FB24AE 9F10AE9F 24AE04AE 9E20AE01 0E00048F ...........$.....$..e..n.^...... 000100
37AE39AE B07FFEDE 489F04FB 7ED430AE 9F0CAE9F 7ED40000 063CEF04 FB24AE9F ..$...<.....~.....0.~...H.....9.7 000120
FF03FB04 ACDD04AE 9F04AE09 D030AE9F 34AE2020 8FA830AE 30900412 2030AE91 ..0 ...0.0..  .4..0.............. 000140
82310313 5308ACD0 5E24C255 00178014 8FD05600 000713FF 9E007C04 00000718 ......l........V......U.$^...S..1. 000160
8F9015AE 41208FB0 00000518 EF01FB1C AE9F20AE 04AE9E1C AE010E00 188FD000 ........................ A.... 000180
3D1110AE 32318FB0 081250FD F0C09E50 51C05111 AE9A500A C45010AE 9A17AE4D M.....P..P...Q.QP.....P.....12...= 0001A0
51308151 500AC750 0CC22214 1750D127 190D50D1 25130C50 D136150B 50D10515 ...P..6.P..%.P..'.P..'..P..PQ.0Q 0001C0
10AE9F66 01FB55DD 051116AE 508F9011 AE503081 50508E0A 7B7E0050 017A10AE ..z.P.~(..PP.OP....P.....U..f... 0001E0
Virtual block number 292 (00000124), 512 (0200) bytes

000005A0 8F53C300 00065FFF 01FB7EF9 8F9A0B15 000005A0 8F53D109 19009F31 1.....S..........~......S...... 000000
1D150B52 D1051524 11520CD0 051252D5 54418F9A 5350C250 523CC552 533CC753 S.<SR.<RP.PS..AT.R....R.$...R... 000020
520AC766 01FB55DD 05115450 8F9A520C C2091417 52D10E19 0D52D10D 130C52D1 .R....R....R......R..PT...U..?..R 000040
50308150 530AC71E AE3A901D AE503081 50508E0A 7B7E0052 017A1CAE 50308150 P.OP..z.R.~(..PP.OP...:....SP.OP 000060
AE9F23AE 4D8F9022 AE549021 AE209020 AE503081 50508E0A 7B7E0053 017A1FAE ..z.S.~(..PP.OP. . .!.T.°..M.#.. 000080
E0D89F9E 57000005 C9FF9E00 FC040000 05CAFF03 FB04ACDD 04AE9F04 AE08D01C ..........................W.... 0000A0
00D2007A 00180400 04ACCF5E ACAE9E54 000005B0 FF9E5500 0005CBFF 9E567FFE ..V.......U.......T...^........z.... 0000C0
9F50AE34 AE9E4CAE 010E0018 8FD001C2 31000005 89FF01FB 7EFA8F9A 01DA01DA ........~.......1..........L..4.P. 0000E0
5143AE9A 52FDF0C0 9E5051C0 5141AE9A 500AC450 40AE9A00 0003A7EF 01FB4CAE .L..........@P..P..AQ.QP....R..CQ 000100
F1C09E50 53C05347 AE9A500A C45046AE 9A51FDF0 C19E5150 C05044AE 9A510AC4 ..Q..DP.PQ.....Q..FP..P..GS.SP... 000120
AEDCAE9E 44AE0407 00048FD0 01593150 5200000E 108FC551 70419E51 3CC450FD .P.<Q.APQ......RP1Y.........D..... 000140
AEDD7E7C 50AE9F7E D47E7C64 01FB52DD 0552E852 50D06501 FB08AE9F 4CAE7C48 HI.L......d.PR.R..R..dI~.~..PI~.. 000160
6401FB52 DD0552E8 5250D067 01FB08AE 9F6401FB 52DD0552 E85250D0 6607FB20 ..f.PR.R..R..d......d.PR.R..R..d 000180
FB04AE9F 4CAE7C48 AE34AE9E 44AE0206 00088FD0 04505100 51504E50 0CAE0AC7 ....PNPQ.QP........D..4.HI.L.... 0001A0
E85250D0 6607FB1C AEDD7E7C 50AE9F7E D47E7C64 01FB52DD 0552E852 50D06501 .e.PR.R..R..dI~.~.:PI~.....f.PR. 0001C0
DF789F01 FB2CAE9F 6401FB52 DD0552E8 5250D067 01FB04AE 9F6401FB 52DD0552 R..R..d......d.PR.R..R..d.......x. 0001E0
Virtual block number 293 (00000125), 512 (0200) bytes

9E24AE01 0E00118F D0000003 4FEF04FB 40AE9F34 AE9F40AE 9F5EDD6E 02D07FFE ....n.^..@..4..@...O..........$. 000000
30900312 2010AE40 9150D47F FEDE489F 04FB7ED4 2CAE9F40 AE9F7ED4 28AE10AE ...(.~..@.....~...H....P.@.. ...0 000020
5051C051 00000064 8FC45111 AE9A5000 0003E88F C45010AE 9AF05003 F310AE40 @....P....P......P...Q..d...Q.QP 000040
```

```
9A510AC4 5115AE9A 52FFFF2F B0E09E50 51C05113 AE9A5051 C0510AC4 5112AE9A ...Q..Q.QP...Q.QP.../..R...Q..Q. 000060
3CC450FD F1C09E50 53C05319 AE9A500A C45018AE 9A51FDF0 C19E5150 C05016AE ..P.PQ....Q...P..P...S.SP....P.< 000080
DD5EDD5E 04C20000 000450D4 0450514E 5150C050 52000005 A08FC551 70419E51 Q.A~Q......RP.PQNQP..P......^.^. 0000A0
FF16500C A1D0515D D05E04C2 0FFC0400 00039FFF 05FB08AC 9F0CACDD 0ADD04AC ....................^.JQ...P.. 0000C0
04C20000 04000003 75FF06FB 08AC9F10 ACDD0BDD 04ACDD04 AE9F50DD 00000388 .....P.................u........ 0000E0
ACDD04AE 9F7ED45E 04C20000 04000003 5DFF05FB 7E08AC7D 0EDD04AC DD5EDD5E ^.^.....}..~...]........^.~..... 000100
1CDD04AC DD04AE9F 7ED45E04 C2000004 00000340 FF06FB08 AC9F10AC DD1BDD04 ............@.......^.~......... 000120
05FB7E08 AC7D15DD 04ACDD5E DD5E04C2 00000400 000323FF 06FB08AC 9F1BACDD .........#.......^.^......}..~.. 000140
AC9F0000 00000004 000002F0 FF03FB7E 04AC7D0C AC9F0000 00000400 00030BFF ................}..~............ 000160
000002C0 FF03FB7E 04AC7D0C AC9F0000 04000002 D5FF04FB 7E04AC7D 0CAC9F10 ....}..~...............}..~..... 000180
FB04ACDD 08AC9F5E DD6E2090 03116ECC AC900612 036C915E 04C20000 00000004 ........^.l.......n.... n.^...... 0001A0
0296FF01 FB7E628F 9A0B125B D5000002 81FF165E 04C20800 00040000 0296FF03 ...........^.......[....b~...... 0001C0
05116ED4 041908AC 50D10000 0262FF01 FB7EC6AB 3204117E D40418FE AB950000 ........~..2..~...b....P......n.. 0001E0
Virtual block number 294 (00000126), 512 (0200) bytes

7EB08F9A 0F1408AC D55E04C2 083C0400 00024BFF 02FB04AC DD5EDD6E 0BAC50C3 .P..n.^......K....<..^.........~ 000000
35FF01FB 7E628F9A 0B125BD5 00000220 FF1608AC D708AC01 D0000002 4DFF01FB ...H.............. ....[....b~...5 000020
017A50D4 AB3C5250 D0000002 01FF01FB 7EC6AB32 04117ED4 0418FEAB 95000002 .........~..2..~.........PR<..Pz. 000040
FEAB048A 000001D4 FF165006 D01E1508 AC52D108 AC50D050 508E507B 7E0008AC ...~{P.PP.P...R......P.......... 000060
6E08AC52 C305116E D4041208 AC52D152 D408AC50 D050D402 185008AC D0C8ABD4 ......P...P.P...R.R.......n....R..n 000080
04AE08AE 9E010E00 188FDD5E 30C2007C 00000004 000001B0 FF02FB04 ACDD5EDD .^..............|..0^........... 0000A0
0000016C FF16506E 3C5204AC D05108AE 9E7FFEDE 489F04FB 0CAE9F08 AE9F7E7C |^..........H.......Q...R<nP..l... 0000C0
0146FF16 0450619A 151B50B5 5004BC7D 0C1A0203 A0915004 ACD00001 00000004 ..........P......}..P.P....aP..F. 0000E0
1310ACD5 281A6C04 9151D750 017D0004 0450D404 50629A04 1B51B508 50E90000 ...P..Q...bP..P...}.P.Q..1.(.... 000100
D05208BC 41D85204 BC41D004 50001582 348FD02E 13191150 D7041550 10BCD023 $...P...P......4...P..A..R.A..R. 000120
0450018F 9A051D0C BC4152D8 0CBC4104 BC41D052 08BC41D0 ED5150F2 0CBC4152 RA...PQ..A..R.A...A....RA.......P. 000140
1150D704 155010BC D0231310 ACD5281A 6C049151 D750017D 00040450 047C8F3C <.|.P....}.P.Q..1.(....$...P...P. 000160
41D0ED51 50F20CBC 4152D052 08BC41D9 5204BC41 D0045000 1582348F D0D81319 .....4...P..A..R.A..R.RA...PQ..A 000180
50545004 BC500000 00000450 018F9AAF 1D0CBC41 52D90CBC 4104BC41 D05208BC ..R.A...A...RA.......P.....P..PTP 0001A0
03185153 07145051 42515108 00505404 50084203 18515307 14505142 51510800 ..QRBQP..SQ..B.P.TP..QRBQP..SQ.. 0001C0
00000000 00000000 00000000 00000000 00000000 00000000 00000000 05500812 B.P............................. 0001E0
Virtual block number 295 (00000127), 512 (0200) bytes

00000002 00000140 00000134 00000000 00000040 00000040 00000000 00000000 ........@...@........4...@....... 000000
00000000 00000000 00000000 00000000 00000000 00000000 00000000 00000000 ................................ 000020
00000850 00000B20 00000B80 00001600 00000588 00001488 00000001 0000003A :......................... ..P... 000040
00000810 00000BC0 00000BA8 00000BF0 00000BD8 00000828 00000830 00000848 H...0...(....................... 000060
00000A88 00000B48 00001470 00000C10 00000C18 00000800 00001468 000005D0 ....h.................P...H....... 000080
00000970 00000958 00000980 00000978 00000B50 00000950 00000938 00000AE0 ....8...P...P...x.......X...P... 0000A0
000009B0 000009A0 000009C0 000009C8 00000930 00000918 00000A98 00000968 h...........0.................... 0000C0
00000A50 000008C8 000008B8 00000B28 00000A80 00000A80 000009D0 000009B8 ................(...........P... 0000E0
000009F8 00000A00 00000A10 00000A08 00000A18 00000A20 00000A48 00000A58 X...H........................... 000100
000D0001 00026A00 00000001 00000000 00000900 00000908 000009E0 000009E8 ..........................J....... 000120
00000000 00000000 00000000 00000000 00000000 00000000 00000000 00000000 ................................ 000140
00000000 00000000 00000000 00000000 00000000 00000000 00000000 00000000 ................................ 000160
00000000 00000000 004C5452 534D5606 00000000 00000000 00000000 00000000 ..................VMSRTL......... 000180
```

```
00000000 00000000 00000000 00000000 00000000 00000000 00000000 00000000 ................................ 0001A0
00000000 00000000 00000000 00000000 00000000 00000000 00000000 00000000 ................................ 0001C0
00000000 00000000 00000000 00000000 00000000 00000000 00000000 00000000 ................................ 0001E0
Virtual block number 296 (00000128); 512 (0200) bytes

414D5453 480B0000 820000BE 124E4941 4D244E41 4D545348 0B000000 0400BC12 ........HSTMAN$MAIN........HSTMA 000000
00000007 00630208 FB000000 00000007 FB03E703 EA03E703 B9A24E49 414D244E N$MAIN......................c..... 000020
E3EBE3E7 DE070001 F30308F0 F1070001 8F0308FB 00000000 00000000 00000000 ................................ 000040
EB010208 E3E607E3 630208EA E3E7E3EA E3EAE3E7 E3EBE3EB E3EBE3EB E3EBE3EB .........................c...... 000060
310208FD F9ED0700 090208FD F9ED0700 090208FD F9ED0700 070208D6 F0F2F107 ...............................1 000080
E3EBDE07 CD630208 E907FBC7 02F8031F 03000902 08EB0700 090208FD E2B20700 ..........................c..... 0000A0
45544143 4F4C0600 00000400 BCODBD01 00000569 00BF06EA F7025703 08F7F7F0 .....W......i...........LOCATE 0000C0
F700DEDC F2070013 0208FB07 EA7D6303 B9194554 41434F4C 06000087 6C00BE0D ...1....LOCATE...c}............. 0000E0
0D504C48 54534806 00000004 00BC0DBD 01000001 2C00BF06 EAA84E02 0B00DEDC .....N...................HSTHLF. 000100
07000902 08FB0700 1D0208FB 07EA752F 03B96250 4C485453 48060000 889800BE .......HSTHLFb../u.............. 000120
F2E10700 310208EB D9E7E3D0 07003B02 08FB0000 00000000 00000000 00000000 .................;.........1.... 000140
07E72702 EF070208 F2E6CF07 FB010200 270208E9 07FD0402 08E3EB07 EF040208 ..............'..............'.. 000160
00000004 00BC0ABD 01000002 6600BF06 EFF207E6 260208F2 F107E309 0208EBFB ..........&.......f............. 000180
D7E4F8E7 07001302 08FB07EA 791703B9 19525055 0300008B 0000BE0A 52505503 .UPR.........UPR....y........... 0001A0
59454B54 53480600 00000400 BCODBD01 0000010D 00BF06ED F24E0208 EBE3F5D2 ......N..................HSTKEY 0001C0
08FB0000 00000007 FB03E703 EA4E1F03 B95C5945 4B545348 0600008C 1000BE0D .........HSTKEY\...N............. 0001E0
Virtual block number 297 (00000129), 512 (0200) bytes

08FDF2C1 07F56302 08FDF2D9 07006302 08E1DEF3 F5EBF200 FDF2ECC3 07006302 .c...............c........c...... 000000
07FD6302 08F9E6F4 EBE6F4EA E6F4EAE6 F4EAE6F4 EAE6F4EA E6F4EDED 07F56302 .c.............................. 000020
49545348 06000000 0400BC0D BD010000 03F600BF 06EAF901 BF030800 E1DFF3CE ............................HSTI 000040
00000007 00630208 FB07EA13 8703B9FA 544E4954 53480600 00900800 BE0D544E NT........HSTINT...........c..... 000060
FBE3E7E3 AA070003 1F0308FB 00000000 00000000 00000000 00000700 630208FB ...c............................ 000080
01E8D4EF EFD8D5D9 EBE707E3 03E70308 EAE3E7E3 EAE3EAE3 E7E3EBE3 EBE3EBFA ................................ 0000A0
EFE9E9EC EAD5EB07 EC090208 E3F507AA 6D0208CD F9EB0700 590208D8 F2E30088 ........Y......m................ 0000C0
08F10220 01F5E907 FB270208 F8FAECE9 E9E9E9EF ECEFEFEF EFEFEFEF ECEFEFEF ................................ 0000E0
FBFAECEF EFEFEFEC EFEFE9E9 EFE9ECEA D5EB07EC 090208E3 F507F209 02F82702 .'..............................  000100
E3E3E3E3 D5EB07EC 090208E3 F507F209 02F82702 08F50139 01F5E607 FB270208 ..'.....9....'.................. 000120
ED310208 EAF4E207 C5270208 EB07EC09 0208E3F5 07F20902 004F0208 E6E3E3E3 ......O................'.......1. 000140
07EE5902 08E5F4EB C5EB07EC 090208E3 F507C5B9 F7590208 EB07EC09 0208F507 ..........Y...................Y.. 000160
FB270208 FBFAEEEC E9E9EBD5 EB07EC09 0208E3F5 07C55902 08EB07EC 090208F5 .........Y....................'. 000180
0308EEB0 EBEC84E5 07C5BD02 08EB07EC 03330308 FAF207F8 270208F1 98F5E907 ........'.......3............... 0001A0
02FBFB08 02FBFB08 02FBFB08 02FBFB08 02FBFB08 02FBFB08 02FBFB63 02FD1387 ....c........................... 0001C0
1D02FB44 02FBFB08 02FBFB08 02FBFB08 02FBFB08 02FBFB08 02FBFB08 02FBFB08 .............................D... 0001E0
Virtual block number 298 (0000012A), 512 (0200) bytes

FBFBFBFB FBFBFBFB FBFBFBFB FBFBFBFB FBFB0202 FBFBFBFB 1602FBFB FBFBFBFB ................................ 000000
0308E8E6 E2E107E3 630208EB A6E607FB 0BB803FB 026003FB FBFBFBFB FBFBFBFB ..........`............c......... 000020
820308FB F0F0E5F0 F2F107E3 630208EB AAE60700 01F30308 F6F7FCEC 07F5018F ..........................c..... 000040
00A7E800 BE0D544E 45545348 06000000 0400BC0D BD010000 17E000BF 06EAC003 ........................HSTENT...... 000060
00630208 EB000000 00000007 00630208 FB07EA13 8703B98A 544E4554 53480600 ..HSTENT..........c.............c. 000080
```

```
E3EBE3E7 DE070063 0208FB07 00C70208 FB000000 00000000 00000000 00000007 ........................c....... 0000A0
630208D6 F0F2F107 EB090208 E3E607E3 630208EB E3EBE3EB E3EBE3EB E3EBE3EB ...............c...............c 0000C0
270208FD F9ED0700 090208FD F9ED0700 090208FD F9ED0700 090208FD F9ED0700 ................................ 0000E0
0400BC0D BD010000 03CB00BF 06EAF8BE 02000802 08EB0700 090208FD E2B20700 ................................ 000100
FB07EA17 6F03B9FA 50544554 53480600 00ABB400 BE0D5054 45545348 06000000 ....HSTETP.......HSTETP...o..... 000120
003B0208 FB000000 00000000 00000000 00000007 00090208 FB000007 00130208 ................................ 000140
EDD8EBE3 EBE3E607 E3310208 E7DE07ED 310208F5 FCEBF307 006D0208 FB000007 ......m.......1.....1........... 000160
02FD0257 0308F5D8 F5EDF3F5 F5D507F0 630208F5 EBEDE4E7 EBEDF5FD E2CBE3EF ..............c..........W...... 000180
FB0902F4 0902F503 C90308D6 F588F2EC EEF5E9F5 F0F007E3 090208E7 DE07FB09 ................................ 0001A0
F8CC02FD 01210308 F6C8F5F0 07F501DF 0308F4E9 F3F5EFEF F8E3E7DE 07E60902 ........................!....... 0001C0
D6EBD6E6 07FB0902 F0590208 F007FB09 02F41388 03F50302 08B0F5EF 88F2E607 .......................Y........ 0001E0
Virtual block number 292 (0000012B), 512 (0200) bytes

EB9AC7EB D6EBD6EB D6EBD6EB D6EBD6EB BCC9EBBC C9EBD6EB E3EBD6EB D6EBD6EB ................................ 000000
EBC9EBC0 D6EBD6EB D6E607B9 FAFB0902 F4013503 E34F0208 E3E1F0EB D6EB9AC7 ..........0..5.................. 000020
F5F0F5E9 07F52702 08E5F1F5 EBF8FCD6 EBD6EB9A C7EB9AC7 EBF5F2F5 F2F5F2C9 ...........................'.... 000040
C4F3ECE5 F3F1F5F3 F7FCF4F9 FCF9E307 E80402EE 090208FE D6E6EBF5 E4EAF8EE ................................ 000060
F60E0208 FCEBF6FC EBF6FCEB F5FCEBF5 E607FB09 02F40902 E70902CF 0E0208F5 ................................ 000080
EA07D709 0208FEFB EAD4DDF5 F3D4EA07 FB0902F9 130208F6 008801EA 07F40402 ................................ 0000A0
FCEBF6FC EBF6FCEB F5FCEBF5 E607FB09 02F91302 08F007E3 090208DD EDFEE3F6 ................................ 0000C0
E3C8E0CB EFD4DDF5 F3D4EA07 FB0902F9 130208F6 008801EA 07F40402 F60E0208 ................................ 0000E0
0208F6EE E5F3D3EB F5E607FB 0902F906 0208D3CF EA07FB02 02F91D02 08F6E3F6 ................................ 000100
EAEEF1EB FAFAFAF8 E607FB09 02FB0702 B9FAFBFB FBFBFBFB FBFBFBFB FBF4F909 ................................ 000120
E6E6BDB9 EAEED5E4 EBDFEBF0 E707E40E 0208E4E4 E4E4E4E4 E4E4E4E8 EACECECE ................................ 000140
07FB0902 F40402EC 090208F8 FCF7F5D5 D3ECF3EA FCFCE707 E6130208 E6E6E6E6 ................................ 000160
EDE1EBE9 F6E80700 040208CF 07000402 08DDEA07 FB0902F4 1302EE13 0208F5E6 ................................ 000180
FD630208 F007DA27 0208EFEF EFF4FCF2 07F70902 FB3102F9 1D0208E3 E5EDE9F6 ..........1............'.....c. 0001A0
C5CCEDF0 07F51D02 08F2EBFE EBF2FB07 ABC70208 E3C7F007 FD630208 B9C8F007 .....c.......................... 0001C0
07009201 1D0208DB 07FE012B 0308BE08 EBC5F2ED F5F5ED07 FD450208 C1D8EBD2 ......E.............+........... 0001E0
Virtual block number 300 (0000012C), 512 (0200) bytes

EBF8FDF8 F3F8F5F7 EFEFEFFC F207F704 02FB0902 F40902FD 3B0208F5 C9F5CBE8 ........;....................... 000000
040208F5 E807FD18 0208EBF5 F5E3EBED CFEDFDEF F0B9FAFD EFF0EFD4 F5F8F5E3 ................................ 000020
07FD0902 08EBF5F6 07E90902 08F5FBF0 07FE0402 08F5E9F5 EFFDF5E7 F5FB07ED ................................ 000040
F5FDF5CB C3C8E807 F5090208 F0F5F0F5 F0EC91EF EAE4F092 EFDB07FD 090208F0 ................................ 000060
DFF3DAF8 CBCEEDED EDF5FCF8 F007FC09 0208EDED E3EBF5F3 07FB0902 F4090208 ................................ 000080
08E80700 270208FD CDF3FEF5 C5CEEDED EDF5FCFC F007F709 02FD4F02 08F5CEF6 .....0....................'..... 0000A0
F3F0F5FB F5E2CEFB FB07FA09 0208FCF7 F5F8EA00 CD07F509 0208F5C6 07C80902 ................................ 0000C0
FCEFD907 FD090208 FCEFD907 E5090208 E0EDF5EF EFEA07F7 0902FD13 0208F5F5 ................................ 0000E0
07EE2702 08F4F5F5 CBCBE807 F50E0208 F5DAF8E5 07FC0402 08EFD907 FE090208 ............................'.. 000100
07F51D02 08F0E1EB E9F6F393 EFC0F1ED F5EFEFEA 07FD1302 08EBB9FA F5F8FBFB ................................ 000120
03F40902 08F6F5EF 07FE0902 08F1F6F8 F5F3FB07 ED130208 F0F5EDEE F5F0C8E8 ................................ 000140
ECEDF5E7 07FC0902 08FCF8EE C5EFF2EB E3EBF5F8 EBE80700 090208FB 07DE0199 ................................ 000160
FBF5F3F5 CCD2DFDD EFEAEA07 F4090208 F4F5F5CB EFEDE807 97270208 FEC9F3BD ......'......................... 000180
F307FB13 02F40402 ED0E0208 E707F504 0208F2F7 CD07008A 01040208 EAF0F5EF ................................ 0001A0
310208F5 F5E5D8EE CAFCF3F5 EBCF07FB 1302F4D1 02F54502 08F5E5D8 EEE7F5EB ..........E....................1 0001C0
F4950293 270208EF 00980107 FB0902F4 6D02F613 0208F8FC F0FCF0FC F0F707FE ............m.............'..... 0001E0
```

```
Virtual_block number 301 (0000012D), 512 (0200) bytes

FAF4F2F2 F2F2F2F2 F2F2FBF5 FBEBEBEB EBEBEBEB FBC5F7FD F5D9E0F5 07FB0902 ................................ 000000
F307FB09 02F96D02 08CDE607 F6060208 F107FB02 02F41D02 E5270208 C5F7F2B9 ..........................m..... 000020
F0F5F707 FB0902F4 028E03CD 04020BDB F707FE09 0208E707 A3130208 C9ECEAC7 ................................ 000040
E3EEEDF0 F007EC09 0208F0E6 07FB0902 08EB07FB 1302F959 0208F8F5 F0F5F0F5 .........Y...................... 000060
EE090208 F0F007FD 090208E5 EE07B009 0208F5FD DAF407FD 130208CA F5F0AEE3 ................................ 000080
E3E3EDFD F3007F01 E3F0F007 E3090208 F0E607EB 090208F8 EB07FB13 02F46D02 .m.............................. 0000A0
0208F0F0 07FD0402 08E5BFE3 EE07F004 0208D2F5 FDDAF407 FD130208 D2F5F0AE ................................ 0000C0
E7DE07EB 1D02F503 E10308BB EE07F404 02F10402 08F607AF 040208E3 EC07EE04 ................................ 0000E0
EBD4E807 B9FAFD09 0208E3ED E6FDB7E1 E2EEF0F0 07EB0402 08E3E607 E5090208 ................................ 000100
EA07FB13 02F41402 F5030208 EBE3E607 FE040208 F5D8E2EF E607FD0E 0208EEE5 ................................ 000120
F40902EB 090208F6 CDF0EB07 FE1D0208 F0ECE807 D31D0208 E8ECFEEB F9EAEBF7 ................................ 000140
EFD8EA07 FB0902F4 0902E409 0208F0F0 07E30902 08EBF0EB D8EBD8E6 07FB1302 ................................ 000160
0208F007 F40902FD 310208C6 E3F5DD07 FC090208 C2EDF507 FB1302F9 270208D8 ......................l......... 000180
0E0208FC F5F5E5F0 EBEDE4E7 F307FB0E 02F901E9 0308F0EB E3E607FB 0902F66D m............................... 0001A0
E0F2F7F4 FAC507FB 0902E501 0D0308F3 F5F3F5F8 F4F4F4F4 88F2F2F8 F2EB07FD ................................ 0001C0
F2EBF1DD E207FD09 0208FCF5 F5E5F0EB ECEDC5E7 E507FB13 02F40902 F44F0208 ..O............................. 0001E0
Virtual block number 302 (0000012E), 512 (0200) bytes

EFF4F3F5 F607E013 02B9F908 F2F0F2F3 F5F4F488 F2E0F4CD EB07F313 0208F5FB ................................ 000000
0208F607 F44F0208 E800B401 F7F4FAC5 07001302 08FBF007 F3130208 F5F2F0F5 ..........................O..... 000020
310208E0 F2F7F4FA C5070009 0208F8E5 F3F5F0E8 F3F5EA07 F30902FB 1302F909 ...............................1 000040
E0F3F5FB FDF8EBF5 F0EFEFF4 E8F7F400 B401EAE1 FACAF0F0 07FB1302 F40902F4 ................................ 000060
FEF4E7DE F5EBF007 FB1302F4 0902F509 0208FBE4 07F13B02 08F5E0F4 F5FBF3F5 ................................ 000080
E607FB13 02F91802 08F593E6 07FB0402 F91D0208 F5EFF5EF 07F61302 08F1F5EF ................................ 0000A0
08F593DE FEFBF9DD F0F007EF 130208FD F2E7ECF3 F5F0F5F2 F295EF91 EAF0F5FB ................................ 0000C0
6302EF4F 0208EFF4 FACAF307 FB1302F4 0902F51D 0208F4E7 F4E7F4E2 07F01302 ..............................O.c 0000E0
0208FACA F307FB13 02F46302 F44F02B9 5C08F3F7 F4EAE0E0 FACAF307 FB1302F4 ..............\..O..c........... 000100
1D0208F4 FACAF307 FB1302F9 4F0208F4 F3F7F4EA FACAF607 FB1302F4 6302F44F O..c...............O............ 000120
F6F5F5E5 E5008D01 EBFCEB07 FB0902F9 1D0208F4 F4F7F4EC FBCAF607 FB1302F9 ................................ 000140
54534806 00000004 00BC0DBD 0100006A A8003F06 EAFB0802 F4085B03 00270208 ..'..[..........J...........HST 000160
00000700 130208FB 07EA176F 03B9FA52 54455453 48060001 165C00BE 0D525445 ETR...\....HSTETR...o........... 000180
6D0208FB 00000700 3B0208FB 00000000 00000000 00000000 00000700 090208FB ...............................m 0001A0
004F0208 E3EBE3EB E3EBE3EB E3EBE3EB E3EBE3E7 DE07ED63 0208F5FC EBF30700 ........c......................O. 0001C0
EBFCF0FD EBFCEB07 00090208 D4EEF0F5 E607F313 0208E607 E3130208 EBE3E607 ................................ 0001E0
Virtual block number 303 (0000012F), 512 (0200) bytes

07FD1D02 08E80700 130208FD E2AC0700 130208FD EBFCF0FD EBFCF0FD EBFCF0FD ................................ 000000
F5D8E607 F3630208 EB07F5C7 0208F0F5 EFF5EECA F3F5F607 EF630208 FBE7F0F0 ......c..................c...... 000020
02F503C9 0308D6F5 88F2ECEE F5E9F5F0 F007E309 0208E7DE 07FB0902 FD630208 ..c............................. 000040
02430308 EDF5F5F5 E3E7E3C8 F5E9F5F4 F3F5EFF8 E3E7DE07 E60902FB 0902F409 ..............................C. 000060
EBF5F307 FB0902F4 F508EE00 EB07F502 0208B9FA B088F2E6 07F4CC02 F1BD02F5 ................................ 000080
02F05902 08F007FB 0902F412 5B03F501 210308B0 EEEBABD4 D8EBEEC5 EFF2EBE3 ..........!...[.........Y.. 0000A0
EBD6EBD6 EBD6EBD6 EBBCC9EB BCC9EBD6 EBE3EBD6 EBD6EBD6 EBD6EBD6 E607FB09 ................................ 0000C0
EBD6EBD6 E607FB09 02F40135 03E34F02 08E3E1F0 EBD6EB9A C7EB9AC7 EBD6EBD6 ...............O..5............. 0000E0
```

```
F5270208 E5F1F5EB F8FCD6EB D6EB9AC7 EB9AC7EB F5F2F5F2 F5F2C9EB C9EBC0D6 ..............................'. 000100
F1F5F3F7 FCF4F9FC F9E307E8 0402EE09 0208EED6 E6EBF5E4 EAF8EEF5 F0F5E907 ................................ 000120
EBF6FCEB F6FCEBF5 FGEBF5E6 07FB0902 F40902E7 0902CF0E 0208F5C4 F3ECE5F3 ................................ 000140
08FEFBEA D4DDF5F3 D4EA07FB 0902F913 0208F600 8801EA07 F40402F6 0E0208FC ................................ 000160
EBF5FCEB F5E607FB 0902F913 0208F007 E3090208 DDEDFEB9 FAE3F6EA 07D70902 ................................ 000180
F5F3D4EA 07FB0902 F9130208 F6008801 EA07F404 02F60E02 08FCEBF6 FCEBF6FC ................................ 0001A0
EBF5E607 FB0902F9 060208D3 CFEA07FB 0202F91D 0208F6E3 F6E3C8E0 CBEFD4DD ................................ 0001C0
FAFAF8E6 07FB0902 FB0702FB FBFBFBFB FBFBFBFB FBFBF4F9 090208F6 EEE6F3D4 ................................ 0001E0
Virtual block number 304 (00000130), 512 (0200) bytes

EED5E4EB DFEBF0E7 07E40E02 08E4E4E4 E4E4E4E4 E4E4E8EA CECECEEA EFF1EBFA ................................ 000000
02F40402 EE090208 F8ECE7F5 D5E3EBFC FCE707E6 130208E6 E6E6E6E6 E6BDB9EA ................................ 000020
EAF6E807 00040208 CF070004 0208DDEA 07FB0902 F41302EE 130208F5 E607FB09 ................................ 000040
08F007DA 270208EF EFEFF4FC F207F709 02FB3102 F91D0208 E3E6ECEA F6EDE2EC ............1.........'......... 000060
F51D0208 F2ECFEEC F2FB07B1 C70208E5 C9F007FD 630208BB C8F007FD B9FA6302 .c.......c...................... 000080
0208DD07 FE012B03 08BFD9EB C7F2EFF5 F5ED07FD 450208C2 D9EBD5C8 CCEFF007 ..........E...........+......... 0000A0
FBF5F7EF EFEFFCF2 07F70402 FB0902F4 0902FD3B 0208F5C9 F5CBE807 0091011D ...............;................ 0000C0
07FB0902 F4090208 F5FDF5CB C3C8E807 93090208 DE07F040 0208F5F5 F8FEF8F3 ........@....................... 0000E0
02FD4F02 08F5CEF6 DFF3DAF8 CBCEEFED EFF5FCF8 F007FC09 0208EDED E3EBF5F3 ..............................O. 000100
0208F5C6 07C80902 08E80700 270208FD CDF3FEF5 C5CEEFED EFF5FCFC F007F709 ...........'.................... 000120
0902FD13 0208F5F5 F3F0F5FB F5E2CEFB FB07FA09 0208FCF7 F5F8EA00 CD07F509 ................................ 000140
D9B9FA07 FE090208 FCEFD907 FD090208 FCEFD907 E5090208 E2EDF5EF EFEA07F7 ................................ 000160
08EBF5F8 FBFB07EE 270208F4 F5F5CBC8 E807F50E 0208F5DA F8E507FC 040208EF .........................'...... 000180
F0F5EDEE F5F0C8E8 07F51D02 08F0E2EC EAF6F374 EFC2F1EF F5EFEFEA 07FD1302 ................................ 0001A0
630208FB 07DE0199 03F40902 08F6F5EF 07FE0902 08F1F6F8 F5F3FB07 ED130208 ...............................c 0001C0
D8EECAFC F3F5EBCF 07FB1302 F4D102F5 450208F5 E5D8EEE7 F5EBF607 FB1302F9 ................E............... 0001E0
Virtual block number 305 (00000131), 512 (0200) bytes

08EF0097 0107FB09 02F46D02 F6130208 F8FCF0FC F0FCF0F7 07FE3102 08F5F5E5 .....1...............m.......... 000000
040208DB E707FE09 0208E707 A5130208 CDEEEAC9 F307FB09 02F4015D 03942702 .'..].......................... 000020
07FB0902 08EC07FB 1302F959 0208F8F5 F2F5F2F5 F2F5F707 FB0902F4 028E03CD ..........................Y..... 000040
B2090208 F5FDB9FA DAF407FD 130208CC F5F0AEE3 E3EEEDF0 F007EC09 0208F0E6 ................................ 000060
0208F0E6 07EC0902 08E8EC07 FB1302F4 6D02EE09 0208F0F0 07FD0902 08E6EE07 ...................m............ 000080
EE07F104 0208D4F5 FDDAF407 FD130208 D4F5F0AE E3E3EDFD F389E4F0 F007E309 ................................ 0000A0
EE07F404 02F20402 08F607B5 040208E5 EC07EE04 0208F0F0 07FD0402 08E6BFE5 ................................ 0000C0
E6EDB7E4 E2EEF0F0 07EC0402 08E3E607 E5090208 E7DE07FB 1D02F503 F10308BB ................................ 0000E0
0208EBE3 E607FE04 0208F5D8 E2EFE607 FD0E0208 EEE7EBD6 EA07FD09 0208E3EF ................................ 000100
EB07FE1D 0208F2EC EA07D31D 0208E8ED FEEBF9EA ECF8EC07 FB1302F4 1402F503 ................................ 000120
E6090208 F1F007E3 090208EB F0EBD8EB D8E607FB 1302F409 02EC0902 08E6CDF0 ................................ 000140
E3F5DD07 FC090208 C2EDF5B9 A007FB13 02F92702 08D8EFD8 EA07FB09 02F40902 .............'.................. 000160
F307FB13 02F905D1 0308F0EB E3E607FB 0902F66D 0208F007 F40902FD 310208C6 ...1........m................... 000180
02F46302 F44F0208 F3F7F4EA E0E0FACA F307FB13 02F46302 EF4F0208 EFF4FACA ......O..c...............O..c... 0001A0
FB1302F9 4F0208F4 F3F7F4EA FACAF607 FB1302F4 6302F44F 0208FACA F307FB13 ........O..c.........'.....O.... 0001C0
EBFCEB07 FB0902F9 1D0208F4 F4F7F4EC FBCAF607 FB1302F9 1D0208F4 FACAF307 ................................ 0001E0
```

```
Virtual block number 306 (00000132), 512 (0200) bytes

00BC0DBD 01000053 3400BF06 EAFB0802 F4085B03 00270208 F6F5F5E5 E5008D01 ..........'..[.........4S....... 000000
07EA2EDF 03B9FA4C 54455453 48060001 699000BE 0D4C5445 54534806 00000004 ....HSTETL....i...HSTETL........ 000020
09020BFB 00000000 00000000 00000000 00000700 40020BFB 00000700 180208FB ..........@..................... 000040
E7E207ED 090208DF EAE4D6E4 CCE0E007 00090208 EDF0D7E7 F5FBF307 FB090200 ................................ 000060
D4E3E0DA F0F5F7E3 07F59F02 08F7F500 9D01EDEF F5EAF5D6 EFF8E5F5 F0F5E1E6 ................................ 000080
EBE3E7DE 07FB0902 F9590208 F6F007FB 0902F86D 02F5012B 0308E3D4 E3E0DAE3 .......+..m.........Y........... 0000A0
0208F2F1 07E30902 08EBF0EB D8EBD8E6 07FB1302 F41C2903 FCB30208 F0CDAAF0 ........)....................... 0000C0
E3C7DAF7 B907EA09 0208F507 FB1302F9 270208D8 EFD8EA07 FB0902F4 0902E609 ............'................... 0000E0
07FB1302 F905D103 08F0EBE3 E607FB09 02F96D02 08F9F0EA 07F40902 EC310208 ..1.......m..................... 000100
02F44F02 08F3F7F4 EAE0B948 E0FACBF3 07FB1302 F46302EF 4F0208EF F4FACBF3 .......O..c..........H........O.. 000120
02F44F02 08F3F7F4 EAFBCBF6 07FB1302 F46302F4 4F0208FA CBF307FB 1302F463 c..........O..c............O.. 000140
00BF06EA FB0802F4 085B0300 270208F6 F5F5E6E6 008C01ED FCEB07FB 0902F463 c.....................'..[....... 000160
45545348 06000177 4400BE0D 44544554 53480600 00000400 BC0DBD01 00000DB2 ..............HSTETD...Dw...HSTE 000180
00000000 00000000 00070009 0208FB00 00070013 0208FB07 EA176F03 B9FA4454 TD.............................. 0001A0
E3E607E3 310208E7 DE07EF31 0208F5FC ECF307FB 6D02003B 0208FB00 00000000 ........1..m.........1.....1.... 0001C0
01F30308 F5DAF5EF F107FD63 0208F5CD EBEDE6E7 EFF5FDE2 CFE5F1EF D9EBE3EB ....................c........... 0001E0
Virtual block number 307 (00000133), 512 (0200) bytes

F0F5D6EF EFE5F0F2 F107E34F 0208EBF0 F007E309 0208E7DE 07FB0902 F86302FD ..c..................O.......... 000000
02F05902 08F007FB 0902F417 7903EC01 E90308F5 CDEBF5F3 07FD01SF 0308EDEF .....................y........Y.. 000020
EBD6EBD6 EBD6EBD6 EBBCC9EB BCC9EBD6 EBE3EBD6 EBD6EBD6 EBD6EBD6 E607FB09 ................................ 000040
090208E7 DE07FB1D 02F416B1 03E34F02 08E3E1F0 EBD6EB7A C7EB9AC7 EBD6EBD6 ....................O........... 000060
08B9FAEE E7EBD6EA 07FD0902 08E3F0E8 FDB7E4E4 F0F2F107 EC040208 E3E607E6 ................................ 000080
EAECF8EC 07FB1302 F41402F5 030208EC E3E607FE 040208F5 DAE3EFE6 07FD0E02 ................................ 0000A0
07FB1302 F40902EC 090208F6 CDEB07FE 1D0208F2 ECEB07D3 1D0208E9 EEFEECF9 ................................ 0000C0
270208D8 EFD8EA07 FB0902F4 0902E609 0208F2F1 07E30902 08EBF0EB D8EBD8E6 ...............................' 0000E0
0902F66D 0208F007 F40902FD 310208C7 E4F5DE07 FC090208 E3EDF507 FB1302F9 ....................1........m... 000100
07000902 08F8E5F3 F5F0E8F3 F5EA07F3 0902FB13 02F90441 0308F0EB E3E607FB ........A....................... 000120
EFEFF4E0 F7F400B4 01EAE1FA CBF0F007 FB1302F4 0902F431 0208E0F2 F7F4FAC6 ........1....................... 000140
1302F4D1 02F50902 08FBE407 F13B0208 F5E0F4F5 FBF3F5E0 F3F5FBFD F8EBF5F0 ................................ 000160
4F0208F3 F7F4B946 EAE0E0FA CBF307FB 1302F463 02EF4F02 08EFF4FA CBF607FB .........O..c...........F......O 000180
4F0208F3 F7F4EAFB CBF607FB 1302F463 02F44F02 08FACBF3 07FB1302 F46302F4 ..c..............O..c..............O 0001A0
06EAFB08 02F4085B 03002702 08F6F5F5 E6E6008C 01EDFCEB 07FB0902 F46302F4 ..c....................'..[....... 0001C0
53480600 01922C00 BE0D4D4F 43545348 06000000 0400BC0D BD010000 10E800BF ..................HSTCON........HS 0001E0
Virtual block number 308 (00000134), 512 (0200) bytes

00000000 00000000 00000000 00000007 001D0208 FB07EA13 8703B9FA 4D4F4354 TCOM............................ 000000
EBE3EBE3 EBE3EBE3 EBE3EBE3 EBE3E7DE 070003C9 0308FB00 00000000 00000000 ................................ 000020
EB070013 0208FDF5 EB070010 0208D4EE F0F007EB 020208E3 E607E313 0208EBE3 ................................ 000040
E8070013 0208FDE2 AC070013 0208FDF5 EB070013 0208FDF5 EB070013 0208FDF5 ................................ 000060
0E0208E3 EBE3EBE3 EBE3EBE3 EBE3EBE3 EBE3E7DE 07FB1302 F8034703 00130208 .....G.......................... 000080
FBF0FDEB FBEB0700 130208D4 EEF0F007 EB090208 E3E607E3 040208EB E3E60700 ................................ 0000A0
950208FE EB070004 0208FDE2 AC07000E 0208FDEB FBF0FDEB FBF0FDFB FBF0FDEB ................................ 0000C0
FAF7C5EE F2F5EFF5 D8EBE3E7 E3EDF007 ED090208 F5FBE607 FB0902F4 010303FD ................................ 0000E0
```

```
F5F6DCED F5B4F2F5 EEEFF007 E9090208 F5E3EBF5 F5D307FD 4F0208F5 E3EBF5B9 ........O....................... 000100
0208FBFB FBFBF8EE F1E607FB 0902F409 02F81802 F50E0208 F007FD27 0208FAB6 ....'........................... 000120
B9B9C507 F5090208 CFB6EFE7 07F51302 08CF9C84 E6EAF5CF EBDE07FB 0902F959 Y............................... 000140
C5F3D4DD EFEAF5EB F8F5EBF5 F5F5EBF5 D007FB63 02F99F02 08F5F5CF B9CAF5CF ...........c.................... 000160
F5EBF5E6 07E70902 F5130208 009F0107 DF1D0208 FBEBE9F9 EDDFEBE9 F6FDEBEB ................................ 000180
F5E5EBC9 E7E707F5 09020800 8201AD92 07DD1302 08FBFEEB EDF3E0D4 D4DDEFEA ................................ 0001A0
D507EB13 0208F5FE EBF5F6FE EBF5F6FD EBF5F6FD EBF5F6F5 ACF5D907 EF090208 ................................ 0001C0
99F007F5 B9FA0902 08EBDCF5 F5E607F5 090208FB F5EBD707 FB0902F5 4F0208F5 ...O............................ 0001E0

Virtual block number 309 (00000135), 512 (0200) bytes

0BEBF5EB F5EBD707 F56D0208 A6B7E7E4 DBF5EBF5 EBF5EBF5 E6070009 0208F5F5 ....................m........... 000000
E7E4F5EB F5F5EBF5 EBF5F599 F5F5EBF5 E9F5E9F5 F5D007FB 0902F01D 02F51302 ................................ 000020
E607FB09 02F95902 08F5E9F5 E9F5BE07 FB0902F9 950208F0 07002702 08F5A6B7 .....'..................Y....... 000040
0402F904 0208E707 F5040208 8507DF13 0208EBE9 F6FEEBC5 F3D4DDEF EAF5EBF5 ................................ 000060
D4DDEFEA EA07FD09 0208E707 F50E0208 9EDDE9ED D9C8D4D4 DDEFEAEF F5E607FB ................................ 000080
F40402F5 220208C9 F5C9F5B7 F007FD09 0208E707 F5130208 00A001DD E9EDF3D4 ............................'... 0000A0
F9040208 F5C9F5C9 F5C9F5C9 F5B7F5EB F5B6F5A5 A3F5A5A3 F5A5A3F0 07FB0402 ................................ 0000C0
E4090208 E4E4E4E4 E4B9FAE4 E4E4E4E8 EACECECE EAEEF1EB FAFAFAF3 07FB0402 ................................ 0000E0
EBF5F7E7 EFF007FB 0902F404 02E70902 E6130208 E6E6E6E6 E6E6BDB9 EAF0E707 ................................ 000100
02FD0902 08F5E3EB F5F7E8E9 F8FBEDED E207FD09 0208FBD6 EEF0F007 E3090208 ................................ 000120
F5EFD607 DA090208 E7EDEEB4 EAEBECB6 EBB8EAE1 FBEFF5FD F5ECF0EF F007E909 ................................ 000140
02EA0902 08F0F5F3 F5ECD7EB 07EF1302 08F5DFED F2F5F2F5 ECE5F3EF F5F4F4F4 ................................ 000160
090208F4 E5F4EEF5 D0EBF8E6 E707008F 01090208 E5E1EAE6 F007FB09 02F4F008 ................................ 000180
0208F207 F8270208 EDFCF5D5 F5DEFBEB FCEA07F5 090206FB EAFCE8E3 07008F01 ..........................'..... 0001A0
FB2702FB FBFBFBFB FBFBFBFB FBF92702 08F9EEEE D6EBE607 FB0902F4 0902EC09 .................'...........'. 0001C0
F0E5E807 FB0902F4 9502EB27 0208B9FA F7F5F6F7 FBFBECF5 ACEAF8DE 07FB0902 ..................'............. 0001E0

Virtual block number 310 (00000136), 512 (0200) bytes

F103C903 08EEF007 EE090208 F5FBE607 FB0902F9 01E90308 EEE8D5E5 EBE6DCE6 ................................ 000000
E3EBE3E7 E3FB07F3 3B0208F0 07F91302 08F0F5FB F307FB13 02F40FA4 03F90402 ................................ 000020
07E62C02 08EAE3DD E3DDE3DD F007F013 02F00902 08DF07E3 090208EB E3EBE3EB ................................ 000040
0308F5CB E607E613 02E70902 FD020208 F7ECF5E8 F5EF07E7 010208F5 D6C9C5D8 ................................ 000060
130208E9 07FE1302 08E907FD 130208E9 07E01302 00130208 F307FB13 02FD030B ................................ 000080
FB0902F4 031F03FC 130208F3 07FE1302 08E907FE 130208E9 07FE1302 08E907FE ................................ 0000A0
F0D3F5F0 07F90902 08F5CBEB F707F409 0208FAEF EFEE07F1 090208FB EBFBF307 ................................ 0000C0
08EBF5EC D6D6D6EA E9F707FB 1302F98B 0208F6B9 FA07F809 02F00402 DC040208 ................................ 0000E0
ED4F0208 F5FBE607 FB1302F9 02A70308 E7F5F1D6 D4EAE5F8 F707FB13 02F94F02 .O............................O. 000100
EED8E607 FD630208 F5CDEBEB E3E4EDF5 FDE2CBE3 EFEDD8EB E3EBE3FB E3E7DE07 ..........................c..... 000120
FBF0FDFB F0E3E5EB E3E607FD 630208F5 CDEBEBEE EEDCEDEB F0F2F3D5 EFEFF5DC .....................c.......... 000140
08F6C7F5 A1D8E607 FD310208 F5CDEBBE 07FD3102 08DAFEFB F0FEFBF0 FEFBF0FD ...........1........1........... 000160
EBE9F6FE EBC5F3D4 DDEFEAF8 FCC3E407 FB0902F4 0902FD01 E9030BF0 07006302 .c.............................. 000180
07DD1D02 08FBFEEB EDF3E0D4 D4DDEFEA E707F513 02080084 0107FB77 0208EDDF ...w............................ 0001A0
E607E509 0208E7DE 07FB1D02 F4031F03 F5090208 E2C9E8E7 07F50902 08009B01 ................................ 0001C0
FD0E0208 EEE5EBD4 E807FD09 0208E3ED E6FDB7E1 E2EEF0F0 B9F907EB 040208F3 ................................ 0001E0
```

```
Virtual block number 311 (00000137), 512 (0200) bytes

FEEBF9EA EBF7EA07 FB1302F4 1402F503 0208EBE3 E607FE04 0208F5D8 E2EFE507 ................................ 000000
D8E607FB 1302F409 02EB0902 08F6CDF0 EB07FE1D 0208F0EC E807D31D 0208E8EC ................................ 000020
02F92702 08D8EED8 E907FB09 02F40902 E4090208 F0F007E3 090208EB F0EBD8EB ................................ 000040
07FB0902 F66D0208 F007F409 02FD3102 08C6E3F5 DD07FC09 0208C2ED F507FB13 ................1.........m..... 000060
FAF5ED07 F6130208 F0F5EEFE F2E7DCF5 EBF5F507 FB1302F9 05090308 F0EBE3E6 ................................ 000080
EFF5F2F2 95EE8EE9 EFF5FAE4 07FB1302 F9180208 F593E507 FB0402F9 1D0208F5 ................................ 0000A0
08F2E7F2 E7F4E207 EF130208 F590DCFE FAF9DCEF F007EE13 0208FDF2 E7EBF2F5 ................................ 0000C0
E0FAC9F2 07FB1302 F46302EF 4F0208EF F3FAC9F2 07FB1302 F40902F5 1D02B9CC ..................0..c.......... 0000E0
C9F507FB 1302F463 02F34F02 08FAC9F2 07FB1302 F46302F3 4F0208F1 F7F3E9E0 .......0..c...........0..c...... 000100
F7F3EBFB C9F507FB 1302F91D 0208F3FA C9F207FB 1302F94F 0208F3F1 F7F3E9FA .......0........................ 000120
02FB6302 F4950200 270208F6 F5F5E5E5 008D01EB FBEB07FB 0902F91D 0208F3F2 ......................'.....c... 000140
F0E5F3F4 F507FB13 02F94F02 08F6F3F5 E5F507FB 1302F94F 0208F8D5 F507FB13 .......0..............0......... 000160
F5F5E5E5 008D01EB FBEB07FB 0902F94F 0208F7F5 F5F607FB 1302F94F 0208FBED ...0...........0................ 000180
53480600 00000400 BC0DBD01 000064CA 00BF06EA FB0802F4 059F0300 270208F6 ...'.............d............HS 0001A0
0007001D 0208FB07 EA138703 B9FA504B 41545348 060001F6 F800BE0D 504D4154 TAMP........HSTAMP.............. 0001C0
07FB0902 00136903 08FB0000 00000000 00000000 00000000 00000000 00000000 ..........................i..... 0001E0

Virtual block number 312 (00000138), 512 (0200) bytes

FD130208 DDE5E4ED F3F5F5C0 07EF1302 08FBEBF3 F5EDF0ED E7CCEBE3 EBE3E7DE ................................ 000000
E3EBCCEB E3EBE3E7 DE070013 0208FBFB FBF8F5D4 07FB0902 FD130208 F5E3E607 ................................ 000020
EFF3F5F0 E3F6F007 EF130208 EBFBFBEB FBFBEBFB FBFBE3EB E3EBE3EB E3EBE3EB ................................ 000040
F5EB07E6 0402FE04 0208F5C3 E907FE09 0208D8EB F5EEEDF0 07EB0902 08B4F3F5 ................................ 000060
090208F3 07001302 08C600F5 F007EB09 0208EBEB F4EBF4EF 07F01302 08F5F5F3 ................................ 000080
FD010D03 08EDFDF5 F0F100F0 EBF0FDF5 F0EDE807 F5130208 F4EB9A9A 9AF007F5 ................................ 0000A0
FB1302F4 1D02F327 0208F5F0 ED07F431 02B9FA08 F5F5EDF5 F0008A01 D7EFEB07 ...............1.......'........ 0000C0
EBFBF8EB FBFBEBF8 FBED07F3 3B0208F5 EFF1F5F0 F607003B 0208FEFD D3E4F707 ................................ 0000E0
08FCEBEB E607EB13 0208EBE6 07EF1302 FB1302FB 1302FB13 02F41302 F4130208 ................................ 000100
F0F0EB07 E91302ED 130208F0 07001302 08EDF007 00130208 EDF5EBE6 07001302 ................................ 000120
EBF0EDDA DADADADA DAEDEDE8 07FB1302 F4130200 130208F0 07001302 08F0F0F0 ................................ 000140
07001302 08EBB807 E51302EB 130208E8 07FD1302 08F0F0E4 07001302 08FDEBEB ................................ 000160
07FD1302 08F0F0E4 07001302 08EBB807 E51302EB 130208E8 07FD1302 08F0F0E4 ................................ 000180
0208E9EB 07001302 08E807EB 130208BF 07001302 08EBB807 E51302FB 130208E8 ................................ 0001A0
ED009A01 F0E807EB 130208EB 07001302 08EBE9EB 07EBB9FA 130208E9 EB07EB13 ................................ 0001C0
08F5F0EB E6070013 0208E107 00130208 F007E913 02FB1302 F4130200 13020896 ................................ 0001E0

Virtual block number 313 (00000139), 512 (0200) bytes

FEEBE607 00130208 E7070013 0208F007 FB1302F4 13020013 0208F0EB 07001302 ................................ 000000
07001302 08F007FB 1302F413 02001302 08F0EB07 00130208 F5F0E607 00130208 ................................ 000020
130208EB FBF307FB 1302F413 02001302 08E60700 130208FE EBE60700 130208E7 ................................ 000040
0208FCEB 07001302 08FCEB07 00130208 EFE80700 130208E8 07001302 08F007FB ................................ 000060
C3070013 0208FCAD 07001302 08FCAD07 00130208 FCEB0700 130208FC EB070013 ................................ 000080
130208ED E607F013 02001302 08EB0700 130208FC C307FC13 0208C307 FC130208 ................................ 0000A0
02FB4F02 00270208 F4070013 0208F0F7 07001302 08F907EB 130208B9 FAF207EB ............................0.. 0000C0
EDF007ED 130208EB F5F70700 130208E8 07F51302 08EB0700 130208F0 F007F313 ................................ 0000E0
```

```
130208C8 0007EE13 0208EEF5 EBDB07E8 13020013 0208F200 F007EE13 0208F5ED ................................ 000100
EDEDF5EB DAF5D7E6 07001302 08F707FB 1302F913 0208EB07 00130208 F0EB0700 ................................ 000120
00130208 EBF0E607 FB1302F4 13020013 0208F4F0 07001302 08B6F007 00130208 ................................ 000140
02FB1302 F4130200 130208E6 07001302 08FEC9F5 F0EDF5AA 07001302 08D2F207 ................................ 000160
07000402 08EBEBDD 07FB1302 FB130200 270208F5 DB070013 0208E5E1 EB07FB13 ................................ 000180
B9FA0007 00130208 EBEEF007 FB1302F4 1202FB00 130208E6 07000E02 08EBEBDD ................................ 0001A0
EB070013 0208E607 00130208 AF000700 130208B0 07001302 08D80700 130208E5 ................................ 0001C0
00130208 FDE807DD 130208DF E607F413 0208EBF2 07FB1302 F4130200 130208EB ................................ 0001E0
Virtual block number 314 (0000013A), 512 (0200) bytes

CD130208 EBF5E2F5 E8070013 0208C007 AE130208 EDE607DD 130208EB F5EDE707 ................................ 000000
130208E6 E8070013 0208EAF6 E807EB13 02F41302 00130208 E6070013 0208EB07 ................................ 000020
0208EB07 FC130208 EB07FC13 0208EB07 FC130208 EB07F313 02001302 08F407FB ................................ 000040
FC130208 EB07FC13 0208EB07 FC130208 EB07FC13 0208EB07 FC130208 EB07FC13 ................................ 000060
EB07FC13 0208EB07 FC130208 EB07FC13 0208EB07 FC130208 EB07FC13 0208EB07 ................................ 000080
9B03D313 02B9FA08 EDE6DFF8 F0F20700 130208FB 0007FB13 02F41302 FC130208 ................................ 0000A0
08008401 07FB7702 08EDDFEB E9F6FEEB C5F3D4DD EFEAF8FC C3E407FB 0902F413 ........................W....... 0000C0
E2C9E8E7 07F50902 08009B01 07DD1D02 08FBFEFB EDF3D4D4 DDEFEAE7 07F51302 ................................ 0000E0
E6EEF1ED EBE4E7F7 EEB9EDEB ECF1EEE3 CEC4C4EA F307FB09 02F40402 F5040208 ................................ 000100
090208F2 F1C7E5DD E9E507EE 090208F1 EBFBFBF3 07E85902 08F1F7EE F5E5EBF8 ..........Y..................... 000120
02FD0902 08F2F1C7 E5DDBEE5 07E70902 FE090208 F2F1C7E5 DDBEE507 E70902FE ................................ 000140
F4310200 1D0208EB FBF507FE 090208EB FBFAEF07 FE090208 EBF8FAF4 EA07E727 ..............................1. 000160
08EBF0EB D8EBD8E6 07FB1302 F902B603 08E7E0EA E0EAE0E7 E5EBE3E6 07FB0402 ................................ 000180
F507FB13 02F92702 08D8B9FA EFD8EA07 FB0902F4 0902E409 0208F0F0 07E30902 ................................ 0001A0
EBF5F607 FB1302F6 05810308 F007F409 02FD3102 08C6E3F5 DD07FC09 0208C2ED ..............1................. 0001C0
F9180208 F593E607 FB0402F9 1D0208F5 FBF5ED07 F6130208 F0F5EFFE F2E7DBF5 ................................ 0001E0
Virtual block number 315 (0000013B), 512 (0200) bytes

FBF9DDF0 F007EF13 0208FDF2 E7EBF3F5 F0F5F2F2 95EF91EA F0F5FBE6 07FB1302 ................................ 000000
08EFF4FA CAF307FB 1302F409 02F51D02 08F3E7F3 E7F4E207 F0130208 F593DDFE ................................ 000020
CAF307FB 1302F463 02F44F02 08F3F7F4 EAE0E0FA CAF307FB 1302F463 02EF4F02 .O..c...........O..c............ 000040
F4FACAF3 07FB1302 F94F0208 F4F3F7F4 EAFACAF6 07FB1302 F46302F4 4F0208FA ...O..c...........O............. 000060
E5E5008D 01EBFCEB 07FB0902 F91D0208 F4F4F7F4 ECFBCAF6 07FB1302 F91D0208 ................................ 000080
06000000 0400BC0D BD010000 410E00BF 06EAFB08 02F4085B 03002702 08F6F5F5 .......C..........A............. 0000A0
00630208 FB07EA13 8703B9FA 54505254 53480600 02380800 BE0D5450 52545348 HSTRPT....B...HSTRPT..........c. 0000C0
07FB0102 00C70208 FB000000 00000000 00000000 00000007 00630208 FB000007 ......c......................... 0000E0
020208E3 E607E313 0208EBE3 EBE3EBE3 EBE3EBE3 EBE3E7DE 07EF0255 0308F5FB ....U........................... 000100
0208FDE2 B207003B 0208FDF5 ED070013 0208FDF5 ED070010 0208D6F0 F2F107EB ................................ 000120
EBE3EBE3 EBE3EBE3 EBE3EBE3 EBE3E7DE 07FB0902 FB034703 00130208 EA070013 .........C...................... 000140
FDF5ED07 00130208 FDF5ED07 00100208 D6F0F2F1 07EB0202 08E3E607 E3090208 ................................ 000160
0208EB07 00130208 FDE2B207 00130208 FDF5ED07 00130208 FDF5ED07 00130208 ................................ 000180
E5F0E9EA 07F41D02 08F5F4E1 07E35902 08EBDE07 FB0902F4 025703F8 EF020013 ......W.........Y............... 0001A0
FB0902F4 05DB03E3 014903EA 130208B9 FAF5F5E5 F0E9DE07 F4130208 F7F4F5F5 ....................I........... 0001C0
07A20902 08F5F5E5 F0C3DAE8 07F40902 08F5F5CB F8F4E507 00590208 E3FBDE07 ......Y......................... 0001E0
```

```
Virtual block number 316 (0000013C), 512 (0200) bytes

08F5F5E5 F0C3BD07 A2090208 F5F5E5F0 C3DAE807 00A00113 0208F5F5 E5F0C3BD ................................ 000000
090208F4 F5F2F2F2 EEF0F4F5 E1070013 0208E707 F4130208 F7E60700 A0010702 ................................ 000020
F5F4F5F4 F7A2F4D4 D4D4F0EB 07FD1302 08EBEFE4 E1A507F4 090208F5 D5EA07FD ................................ 000040
EEFCF4F5 F3070031 0208F407 E301C103 F5F90208 F107F509 0208E5F0 C3EBF5F4 ........................1....... 000060
E5E5F4F5 D5EFEB07 003B0208 ECFCE507 E61302DB 090208FC D4D907FD 090208EE ................................ 000080
07FB1D02 F403E703 FB0F9F03 F40DAB03 F5018503 08E5F0C3 E607EF09 0208F4F5 ................................ 0000A0
EA07FD09 0208E3F0 E8FDB7E4 E4F0F2F1 07EC0402 B9FA08E3 E607E609 0208E7DE ................................ 0000C0
FB1302F4 1402F503 0208ECE3 E607FE04 0208F5D9 E3EFE607 FD0E0208 EEE7EBD6 ................................ 0000E0
02EC0902 08F6CDF0 EB07FE1D 0208F2EC EB07D31D 0208E9EE FEECF9EA ECF8EC07 ................................ 000100
EA07FB09 02F40902 E6090208 F2F107E3 090208EB F0EBD8EB D8E607FB 1302F409 ................................ 000120
F007F409 02FD3102 08C6E3F5 DD07FC09 0208C2ED F507FB13 02F92702 08D8EFD8 ....'...................1....... 000140
F2F5EFFE F4E7DEF5 ECF5F607 FB1302F9 05090308 F0EBE3E6 07FB0902 F66D0208 ..m............................. 000160
F0F5FBE6 07FB1302 F91B0208 F594E607 FB0402F9 1D0208F5 FBF5EF07 F6130208 ................................ 000180
F0130208 F594DEFE FBF9DDF0 F007EF13 0208FDF4 E7ECF3F5 F0F5F2F2 95EF91EB ................................ 0001A0
1302F463 02F44F02 08FACAF3 07FB1302 F40902F5 1D0208F4 E7B9CBF4 E7F4E207 .........................0..c... 0001C0
1302F463 02F44F02 08FACAF3 07FB1302 F46302F4 4F0208F3 F7F4EAFA CAF607FB ...........0..c...........0..c.. 0001E0
```

```
Virtual block number 317 (0000013D), 512 (0200) bytes

CAF607FB 1302F91D 0208F4FA CAF307FB 1302F94F 0208F4F3 F7F4EAFA CAF607FB ............0................... 000000
E4950200 270208F6 F5F5E5E5 008D01EB FCEB07FB 0902F91D 0208F4F4 F7F4ECFB ................................ 000020
F507FB13 02F94F02 08F6F3F5 E6F507FB 1302F94F 0208F8D5 F507FB13 02FB6302 .c..........0...........0....... 000040
008D01EB FCEB07FB 0902F94F 0208F7F5 F5F607FB 1302F94F 0208FBED F0E5F3F4 ........0...........0........... 000060
00000400 BC0DBD01 00002835 00BF06EA FB0802F4 059F0300 270208F6 F5F5E5E5 .......'............5(.......... 000080
FB03E703 EA4E1F03 B93E4D49 54545348 06000260 4000BE0D 4D495454 53480600 ..HSTTIN...@`...HSTTIN>...N..... 0000A0
EFABE4EB 07E96302 08CA07CB 630208F8 E6070063 0208FB00 00000000 00000007 ............c.....c.....c....... 0000C0
BC0ABD01 00000223 00BF06EA 00018F03 08EDDBE5 F3ECEA07 00C70208 FDF2FDEC ........................+....... 0000E0
00090208 FB07EA7C FF03B91C 58454803 00026264 00BE0A58 45480300 00000400 ......HEX...db...HEX....|....... 000100
00000000 0000BD01 0000013C 00BF06ED 00A80144 0208EEFD EEF5EDEC 07FB1302 ............D.......<........... 000120
00000000 00000000 00000000 00000000 00000000 00000000 00000000 00000000 ................................ 000140
00000000 00000000 00000000 00000000 00000000 00000000 00000000 00000000 ................................ 000160
00000000 00000000 00000000 00000000 00000000 00000000 00000000 00000000 ................................ 000180
00000000 00000000 00000000 00000000 00000000 00000000 00000000 00000000 ................................ 0001A0
00000000 00000000 00000000 00000000 00000000 00000000 00000000 00000000 ................................ 0001C0
00000000 00000000 00000000 00000000 00000000 00000000 00000000 00000000 ................................ 0001E0
```

EXHIBIT B - COMPOUNDER PROGRAM (FORMAT - INTEL HEX FORMAT)

COPYRIGHT 1984 BAXTER TRAVENOL LABORATORIES, INC.

:2000000040432031393833203D2054524156454E4F4C204C4142532C20494E432EFF302655
:20002000802C8034803C80420909802204801040002803460501103000AE03C805E801041A
:20004000000E805E0A0A804B8064020400128050806C1203001A805880740204001E000001
:200060000C0C8064000004040022E06C00001403002A807400000404002E00008040032C5
:200080000000008C400360000FFFF40050040070040040340060040050440070440040040EF
:2000A0000600400900400B004008FF400AFF40904400B04400B00400A0040110040130044
:2000C0004010BF40126040110440130440100040120040210040230040 20FF4022FF40212C
:2000E000044023044020004022005000035000950392AE00590100A895006E14006E0A8045
:200100000040800143800220800331 9FF6949FF9CC9FFA959FFB2C9FFC969FFD039FFE8243
:2001200009FFF1B1000118812041300142815281604170030 4A314A324A334A344A354A3669
:200140004A374A3806394A404A414A504A514A524A534A904991499249934994499549 96D5
:2001600049 9749E80000F808000000220000001280200013001000138806C0440030001482A
:2001800005000150040001588050046006000168080001700700017880340480090001 8846
:2001A000806408908048089880208009701101097D51018000010084030303254414343 56
:2001C0008403030333030434308403030343030434308403030343032434308403030 34FC
:2001E0003033434308403030353131434 30E4030303530344434350303031434 30E202020AF
:20020000202020202020202020434300810185028903 8D049105950699079D0F7F5000C600
:2002200022CE805AA602AE00360808085A26E57E6A39BD8241BD84447D003A27F8BD58208A
:20024000F4B6100084 07CE820BA100270908088C821B26F52012C603E75000E75000E75009
:2002600000A601B7500097A80E39B680B740108610B7400A973B8660B740128608BD99966B
:20028000D63AC197270BBD944CBD93B226034A26EC8620B740123996AA8A0497AA86F89794
:2002A0007BBD8334D790C5012721CE807AEE048197270DD6AAC501270797B87F003A206DCB
:2002C000A70386DAA702CE807A203E811626118601FE8024DF00EE04A701DE00EE0026F4EE
:2002E000C5042709CE807AEE046F016C01C502271BCE807AEE04E138260686AAA7032004C8
:20030000A70386BAA702CE807ABD908D9690D69084F0B7400A973B966D8A40976D8602C5B7
:200320000827028A01973CBD834BBD83C896AA84FB97AA39CE8123C620963AA1002604E689
:200340000120070808 5A26F3C64A39D63A663CC1152723C114271FC1132741BD9454BD9965
:2003600096BD93B226364A26F2BD83F6BD9996BD93B227F820268D282525BD9454BD99960E
:20038000BD93B226034A26EEBD83F6BD93B226FB8D0E250BBD9996BD93B227F47F003A39B5
:2003A00036BD93A5261CD63A7F003ABD91F9D73A963FD640BD92D24D260BC1142207B6168D
:2003C000973A0D20010C3239BD83F68D467F003C7F003B7F400ACE807AEE046F0186BAA155
:2003E00002270686DAA102260686FFA702A703CE807ABD908D39963C84FD973C96D84BE80
:20040000976DB7401239966D8A40976D963C8A02973C39FE80207D006B2703FE8024DF9298
:20042000EE046F01DE92BD908DDE92EE0026EFFE8022DF92EE046F01DE92BD908DDE92EE82
:200440000026EE397F00797F007A7D006B2605BD84F0200486F8977BBD99967D003A263F5D
:20046000BD84A0263A7D006B262DD67BC1F82727BD90F97D003A2627A60381102705BD91AA
:200480001320D1A60081002605BD97012011911026C2BD97D52008BD93A327B8BD990B394A
:2004A000BD91F9963A270A813626417F003ABD84F0BD93B27D006B2710963FD640BD92D2BD
:2004C0004D2629C11422258D27963FD640CE807AEE04E703F64004C5042704840F8AA0A78E
:2004E00027D006C2606CE807ABD908D7D003A394F976B97539754976DB74012B7400A9788
:200500003B7D003E270B4FC6FFBD90237F003E200EEE8020DF00BD908DDE00EE0026F539CD
:200520007D006B27066612973A200E7D003E260A96408105220486119 73A39CE0000DF460C
:20054000FE801EDF00EE0AA602E603BD92D2975FD760DE00EE12A602840FE603BD92D2978F
:2005600061D7628D26BD85FDBD8641DE00EE0A9663D664A704E7059665D666A706E707DE1B
:2005800000EE0026BE8D50BD868C39DE5F273B7D005F261296608113220C8610973ADE00F4
:2005A000EE0A8601A70196618100251222 06D662C131230A8101251222 04C12C230C861055
:2005C000973ADE00EE128601A701D660965FD847994 6D747974639964 6810D2208251DD631
:2005E00047C1AC23178610973A8601FE8020270CDF00EE04A701DE00EE0020F2394F976375
:2006000097649767DE00EE12A602840F810F26014FCE00018D12A603BD94C2CE000A8D082B
:20062000A603CE00648D0139840F9768DF69D660965F8D37DB649963D7649763DE00EE1201
:2006400039DE61DF67CE0064DF69C6144F8D1CD7669765D6649663D0669265250526075D43
:200660002604D6649663D766976539CE008BA701E7029667D668A703E704BD945DA601E6B6
:2006800002DE69DF8BCE008BBD9478397D003A261C7F003B7F003C8620976DB740127C00AE
:2006A0006BFE80248D0826FCCE807A8D0139DF00EE046F026F03DE00BD908DDE00EE003976
:2006C0008604B7400596AA8A0197AA865697B47F00A97F00537F0054963FD640BD92D297F1
:2006E00049D74AFE801EDF00BD87097D003A2606DE00EE0026F0862097B47F00A996AA8426
:20070000FC97AA8605B7400539EE0AEE0427457F00817F0082DE008D3C964B914D22082520
:2007200011D64CD14E230BDE4DDE4F8D567D003A2622DE4BDE4F86909789BD87CCD74A97A9

:2007400049D6549653DB569955D75497537D003A26028D1C39EE0AD64A9649EB05A904D7DD
:20076000402974BD64A9649EB07A906D74E974D29D64C964BCB0E8900D04A92492404863031
:2007800097 3A397E0076D6AACA02D7AABD8847262E3D9996963A2625DE00A602B74010B663
:2007A000401284082615BD93B2260CBD8847260FBD88C1250D20DA8613200285329 73ABDE8
:2007C00088D53D899CBD944CBD899C397E0076D6AAC4FDD7AABD8847264 6DE57DF87BD9982
:2007E00096963A2639DE00A603B74010B640128408262 9BD8EE0BD93B2261DBD944CBD946B
:20080000548D93B22612BD8847261 5BD88C12518BD89B73D8947 20C6861320028632973A8C
:20082000BD8ED5BD899C201E3637DE4FDF493637DE00EE0AA602E603BD92D2D782978 13323
:20084000 32BD89B73332397E0059BD91F9963A27058D85D520578D59241BBD56D5BD82970A
:20086000963A811526057E003A20DF811627 3E8613973A20389 63FD640BD92D29792D793E2
:20088000DE92DF573637BD63963A271F8D478114261 9BD8297963A8114270A8116270C86DB
:2008A00013973A20067E003A7F007633327D003A39360CB6401285802605861 5973A0D3206
:2008C00039914F220C2504D1502406BD89B70C20038D020D39367C00598680B74010 3239D9
:2008E000DE89092 6FD8680B74010397D007626117C00768678D6AAC50226028B509775208E
:20090000357D00752640D6729671CB018900D05892572506861 4973A2012D6729671CB961D
:200920008900D0589 257240486 33973AD6729671D05892572404DE57DF718678D6AAC50219
:200940002602835097753996 58D6579088D287250342602860136965090598103220331C1
:20096000203180032401 4FCE008B6F01A7026F039689A704BD945DCE008B33A700A601E712
:20098000001E602BD94784D2604C1A02302C6A0C1102202C610D789DE57DF8739963A8116DC
:2009A000271436BD91F9963FD640BD92D2BD89B7324D2702973A393637D04A924924025FDD
:2009C0004FD75297517F00567F0055D6529651C0FA82002513D7529751C6FA4F8D30DB567D
:2009E0009955D75697552 0E3D652965 18D20DB569955DB829981D7569755DE00EE14BD9055
:200A000068DB549953CE807ABD9068333239CE008BA701E7024FC664A703E704BD945DDEB4
:200A2000 00EE12A602E603BD92D2CE008BA700A601E701E602BD9478397E8A9D8E03FFBD99
:200A40008B357D003A26514FC6FFBD90238605B74005B74011BD8B537D003A263BBD8B6436
:200A60007D003A2633BD8E84B64012840581052707B64010854026099 6AA8A0897AABD8B00
:200A8000BB7E00A77E00AA7E00A97E00B8E6F8977B862097B47E8232 5D829720FE8655C6A5
:200AA000AACE03FEA701E700909 8CFFFE26F5CE03FEA1012674E1002670090 98CFFFE2635
:200AC000E186AAC655CE03FEA701E700090 98CFFFE26F5CE03FEA1012650E100264C09097A
:200AE0008CFFFE26E186FECE03FEA700098CFFFF26F8CE03FEA1002631095CFFFF26F6CE64
:200B000003FF6E00098CFFFF26F8CE03FF6D002619098CFFFF26F6C605CE80F0A602AE0029
:200B2000360E08085A26F57E8A3C8650973A8640F7401220FECE80FFC60CDF00A602EE0086
:200B4000A100260ADE00080 8085A26EE20048651973A39862897A68D2486189146 2204863E
:200B60005297 3A398605 7D0048260E8D104A26F67D0048260486 53973ABD943639CEFFFE6D
:200B8000092 6 5D39866 0B74012BD944CBD944C4FB74012 8601C6F0973CD73BF7400A860185
:200BA000C688BD902386 0ABD944C4A26FA4F973C973BB7400AC6FFBD9023397D003A27039 2
:200BC000BD82974FC6FEBD9023CE807AEE0486EAA702B6801DA703CE807ABD908DB6401044
:200BE00085 4026037E8C88BD93B226FBBD82415F86FF9790862097B4BD9996BD90F9A603FB
:200C000085012741BD916FA6015D2610BD94BD84F0979196908 40F9A915C200B840F97911F
:200C20009 69084F09A915FB10E2707810425035F86F09790CE807AEE04A70386FEA702CEC9
:200C4000807ABD908D86F8977BBD93B2262DBD93A327A5BD93A326FB9690810126 06BD8CEB
:200C60009C7E8BBB81022606BD8D6A7E8BBB810327037E8BEEBD8EF77E8BBB96AA84F797EE
:200C8000AA4FC6FFBD902339BD93B226EEBD93A327F6BD93A326FBBD8C9C20DF0F4FC6D7D4
:200CA000BD9023BD93B227037E8D68BD93A327F34FC6FFBD9023BD93A326FBFE8020EE04F0
:200CC00086F0F64004C50427028A01A7034FF64012C58027028A10C50827028A01A702FE76
:200CE0008020BD908DFE8020B64006BD8FA0BD94BDBD8FA0BD93B2266FBD93A327BD4FC677
:200D0000FFBD9023CE807AEE046F026F03CE807ABD908D7F00907F0091FE801EBD8FCC262C
:200D200036EE0026F7D6909691CB018900D7909791D75B975ABD9342CE807AEE04965EA7E7
:200D40003965DA702CE807ABD908D81092708BD944CBD944C20C2BD93B226FBBD93B22632
:200D60007BD93A326B320F40E394FC6FFBD9023C602BD8E9CBD8EC32532864E97B4860206
:200D800097A996AA8A1097AA8628978 0BD9996BD8E9CBD8EC325157D003A261096AA8580E6
:200DA000260DBD93B226057D008026E07E8E388614BD8E5425F67D003A267D5A2710865077
:200DC00097B496AA847E97AA860497A920BABD916F8680977D865697B496AA846F8A01974D
:200DE000AA7E00A98609B74010861 48D6725497D003A2644BD944CBD944C860AB740108617
:200E0000148D5125337D003A262EBD944CBD944C860CB74010861 48D3B2 51D7D003A261611
:200E2000862097B496AA847E97AA86148D2625087D003A26037E8D6A862097B47E00A99600
:200E4000A784BF97A796AA846E97AAB6400A840FB7400A39379780 96AA85012721BD91F987
:200E600963FD640CE807AEE04E703F64004C5042704840F8AA0A702CE807ABD908DBD9957

:200E800096BD8E9C7D003A260CBD93B20D26067D908026C30C8680B74010333937F6400ACF
:200EA000C44F96BA85102702CA1085202702CA2085402702CA2096A785802602CA80E740BC
:200EC0000A333937EF96A785802618B6400A8A80B7400AC6E5BD9996BD8E9CBD93B227E57C
:200EE0007F003A0D20075D2704B6649780B6400A847FB7400A33390FCE807AEE0486FFA717
:200F00002B603A703CE807ABD908DB6400A8410B7400ABD93B22675B65000858027E48517
:200F2000702718E65001C603F75000F75000F75000D6A8F750007E00A720DE850127E49615
:200F4000A7E650018504261 9C10326C7EA0497A7B6400A64EF8A20B7400ACE019EDF9C2038
:200F6000B2DE9C8C03922725C1042707E7000BDF9C20A00EBDEF99B6400A84DF8A90B74064
:200F80000ABDEF99BD019E7E00A77EBEF77E00A7B6400A640FB7400A39BD944CBD944C3977
:200FA000EE00DF00EE045F85802702CA1085402702CA01E7025F85202702CA108510270244
:200FC000CA01E703DE00BD908DDE0039DF00C614A602B74010868080D3E2705B740102037C9
:200FE000BD944C5A26E1B74010BD944CC6058D282625DE00A603B74010CE7FFF0926FD86E8
:2010000080B740108D12260EBD944C5A26E0BD944CBD944CDE004F3936BD9436B64012848F
:2010200043239FE8022BD903EEE0026F9FE8020BD903EEE0026F9CE807ABD903E39DF006B
:20104000EE04A70137C1FE2602C6FFE7023337C1FE2604C6FF2006C1FE2602C6F0E7033331
:20106000DE00BD908DDE00393637DF94975AD75BBD9342DE94EE04965ED65DA703E702DE10
:20108000947D006C26048D05DE943332393637A602EE04E6006C005D265CE601270A7D003A
:2010A0003D27056F00CE8086E603C40FB74008F7400A3684F0B74008328A20E603BD94C702
:2010C000B74008F7400A3684F0B74008328860E602C40FB74008F7400A3684F0B740083237
:2010E0008A20E602BD94C7DA3BB74008F7400A84F0B740086F0033323937967BCE8163E691
:2011000001127 0D080808088C81B726F28634973A3339BD90F9E603C5012710A601DE796D
:20112000274CD67EE10324468D51203FC50C2725EE01DF77DE792709EE046F01DE79BD906E
:201140006DDE77DF79EE048601A7017F007EDE79BD908D2016DE792715EE0486FFC6F0A769
:201160002E7037F007EDE79BD908DBD916F3936966D8A40976DB740123239EE047D007EE7
:201180002616C6FFD17F260ABD94BD8A0F1686FF2029C6FF8AF02023840F977CC6FFD17E06
:2011A0002605BD91CB2014E602A60381F0260286FF48594859485948599A7CE702A7037E5C
:2011C000007FDE79BD908D7C007E39D67EC101260AE602A603C4F0DA7C201DC1022611967E
:2011E0007CBD94BD977CE602A603840F9A7C2008E602A60384F09A7C393637DF8586FFC680
:20120000FFD7457A004526048631202D9741D7428D312627963FD640914126E7D14226E3E4
:201220008D212617963FD640914126D7D14226D3B64004850427048638973ADE857D003AA6
:2012400033239860897438D2D2627973F7400438D24261EBD94C29A3F973F7400438D16E3
:20126000261097407400438D0D2607BD94C29A4097407D003A39378D1826048D3D250D7FAE
:2012800003A8D0D26068D322502D73A337D003A39378D13260C8D0F26088D0B2604C635A4
:2012A000D73A337D003A39C6FF5A270CB64006439784954327F384F05D39D684C40FD8430A
:2012C0002704C636200AD684C4F0C1A02503C6370C398D3D97907F009117C40FBD94C227BF
:2012E0005CB0A4A20F90C9690840F270ACB6424037C00914A20F49690BD94C29790260470
:201300009691200C96910CCBE889037A009026F63936840F810F26043284F036323684F06E
:2013200081F0260432840F363237C40FC10F260433C4F0373337C4F0C1F0260433C40F378D
:2013400033394F975D975CD65BC40F1B19975ECE937CD65BC4F08D05CE9388D65A08080839
:2013600058240 28D045D26F539965EAB0019975E965DA90119975D965CA90219975C39284C
:2013800001006400003200001600006827038463019281009640004820002410001205008A
:2013A0005602003637BD94368D17B6401284023332393637BD94368D08B640128404333293
:2013C00039B600AA843C2634DF94B64012840116986C2726D76CC50127078D21FE80202050
:2013E000ECE807ABD908D7D006B270EFE8024DF96BD908DDE96EE0026F5DE94397F005A2E
:201400007F005BFE8020DF96EE04A602E603BD92D2DB5B995AD75E975ADE96EE0026E7BDC3
:201420009342CE8080EE04965ED65DA703E702CE8080BD908D39367D0048270E8602B740CD
:2014400004010101 7F40047F004832398DE8CE7FFF0926FD8DE0CE7FFF0926FD398610A748
:2014600004F5F660166022404EB04A9034656660166026A0026F0393736A600E6013736A1
:20148000343086016D012B0B4C680269012B04811126F5A700A603E6046F036F04E002A21E
:2014A00012407EB02A9010C20010D690469036401660 26A0026E6313131323339484848 0A
:2014C0004839444444444395454545439964 48A809744B6500097BAB65000858027 29857053
:2014E000261285012705BD9562201C85022705BD95332013E65001C603F75000F75000F712
:201500005000D6A8F75000E64005B64004C58027028D079644847F97443BE600AAC40426EE
:201520001184FB7D007D260A81FB2706977B860A977D3996A78508272885102624DE9EE605
:2015400002710C10D26026F0103E600F75001DF9E200EC603F75000D6A8F7500084F79726
:20156000A73996A7E6500185042617C14027047C00E7398404CE0100DF98DF9C37C628D75E
:20158000B333DE9CE70006DF9CC10D27077A00B32667202E7E00ABDE98E603C1332604C60F
:2015A00012025C1312604C604201DC1542604C6062015C1352604C620200DC1362604C686

```
:2015C0004020057C00B5202B0DBD9D8327057C00B62030C501261CC50427028A80D7AB8597
:2015E000802710C603F75000D6A8C41FF75000C60AD7A6C63CD7A484EB97A7398680B740BF
:201600001020F9BD9622BD96DB7A006F2607860A976FBD96657A006E26078614976EBD9693
:201620007E3B86AEB1039227033F2038B64010B64012B5102704B60197487D00A627037ABA
:2016400000A67D007527037A00757D007D27157A007D2610B600AA85042609966DE4BF9781
:201660006DF74012397D00A427037A00A47D00A527037A00A57D008027037A008039ED9A36
:201680003D8D013986019 63D973DEE80247D006B2603EE80208D34EE0026FAFE80228D2B9E
:2016A000EE0026FACE807ABD22963C8501270BD63B7D003D27015FF740048502270CD66DBB
:2016C0007D003D2702C4BFF7401239DE73EE046D012705DE73BD908DDE73399644858026 5A
:2016E0001F96A785102719C603F75000D6A8CA20C47FF75000DE9EE600F7500184EF97A75C
:20170000398614 97B0BD916F864E97B4860297A996AA8A1097AA4FC6FEBD902386F8977B0D
:20172000BD99967D003A27078655973E7E97D1D6A7C580260DD6B4C15027078690973A7E1E
:2017400097CBBD93B227037E97CBBD93A327197D0080261496B48150260EBD84A026728663
:2017600055973EBD990B2069F69113C1F827ADBD90F97D003A265AA60381042605BD996F93
:20178000209A81102696967B81002608BD9900248B7E97018118261EBD9900241696B4812E
:2017A0004E2610BD995D260BBD916FC650D7B4860497A97E971C811026F9BD990024F486C4
:2017C0002097B47F00497F00AA20094FC6FEBD9023BD993039861497B0BD916F862097B482
:2017E00096AA8A2097AA7F00A94FC6FEBD90237F007EFE8020DF7986F8977BBD99967D0027
:201800003A27078655973E7E98F9D6A7C580260DD6B4C15027078690973A7E98F3BD93B2F1
:2018200027037E98F3BD93A3271A7D0080261596B48150260FBD84A026078655973EBD99A5
:201840000B7E98F9F69113C1F827ACBD90F97D003A26EEA60381012777810426 05BD996FF9
:201860002095967B81102624BD993F276AD6B4C14D2784BD99002411D6B4C150270BBD9198
:201880006FC64DD7B4C601D7A97E97F78118261EBD99002416D6B4C14D2610BD995D260BC9
:2018A000BD916FC650D7B4C604D7A97E97F781002611BD990024F4862097B47F00A97F00B6
:2018C000AA203C8108262996B4812026237E97D5D6B4C120261AC6FFD77FBD9113DE792767
:2018E0000FD67EE10325097F007EDE79EE00DF797E97F74FC6FEBD90237F007FBD9930398C
:201900007D00802605C614D7B00D3996AA84CF97AABD85207D003A2616BD8413BD853B7DB1
:20192000003A260BBD86C07D003A2603BD826A3986F8977B862097B47F00A97F00AA39FE6E
:20194000B020DF92EE046D012612A60281FF260CA60381FF2606DE92EE0026E639FE8022EC
:20196000DF92EE046D012606DE92EE0026F239A60081782602200A81582602200481 3B26C6
:2019800014EE01DF92EE04A60127056F01BD916FDE92BD908D393637DFA2BD943696A78527
:2019A00080272C7D00A426057F00A720227D00AB271A7D00A62615D6ABC40C2703BD9B22E4
:2019C000D6ABC4602703BD9A8D7F00ABBD99D4DEA23332397D00B8271C96AA85042616D68F
:2019E000B8C19727048501260C7D003A264ED73A7F00B820477D00A5273596B581052506A0
:201A0000869197B8201696B681052506869297B8200A96B781322524869397B896AA850422
:201A2000261A8501261696B8973A7F00B8200D7F00B57F00B67F00B7862897A53996A7859D
:201A400040274996B92604860897B9CE807AEE04C6FFE702E7038508270486AF201D85047A
:201A6000270486FA20158502270486AF20118501270486FA20097F00B92006A7022002A744
:201A800003CE807ABD908D96B94797B93996A78540270484BF97A7CE0108DF9ACE0100A60F
:201AA0000381352642 96AA850827048A8097AAA608814A2605BD9B6120078143261 4BD9BE8
:201AC00061CE81C0BD9C38BD9D6196A78A1897A7204F814C263EBD9B61CE0182A600BD948C
:201AE000BDAA0197B82030813626 29A608814926 0BCE81EDBD9C38BD9D612010815126146C
:201B0000CE81E4BD9C38BD9C68BD9D6196A78A1897A7200D7C00B5C603F75000D6A8F75035
:201B2000003996A7D6ABC5042705CE81B72027C5082713C628D7ACCE015ADFADCE0132DF5F
:201B4000AEBD9C502016C639D7ACC603F75000D6A8F75000200ABD9C38BD9D618A1897A7BC
:201B600039D6AAC430274D36860FC61CCE0182A700085A26FACE0182DFA0DE9A08DF9AA6AE
:201B800000E602C10D272681202604860F2012812D2604860A200A813922F8813025F48000
:201BA00030DEA0A70008DFA0DE9A0820D032814C27028D0139BD8413CE0182DFA0FE802028
:201BC000DF928D4EA7028D4AA703DE92BD908DDE92EE0026EBFE8022DF92DEA0A60081011F
:201BE000260AC60FE700DE92EE04A7018D24A7028D20A703DE92BD908DDE92EE0026D9CEC9
:201C0000807ADF928D0CA7028D08A703DE92BD908D39DEA0A600BD94BDAA010808DFA0DE0B
:201C2000928C807A2603EE0439EE0481AA2608C601E701C617D73A393637E600D7AC08DF5A
:201C4000ADCE0132DFAFBD9C50860DA7003332393637D6ACDEADA60008DFADDEAFA70008D7
:201C6000DEAF5A26EF333239DEAF963ABD94C28B30A70008963A840F8B30A700088630A7C5
:201C8000007D005927026C00088630A7007D006B27026C000896B4A70008DEAFFE80248145
:201CA0005626022062812026022005CD6A9FE8020814D260FC101264296A78A4097A77F00D1
:201CC000B920448150260FC104262F96A78A4097A77F00B92031814E2620C102261C96A7A2
:201CE0008A4097A77F00B9CE81FCE600D7AC08DFADBD9C50860DA7002010DEAF098620A766
```

```
:201D0000008DEAFEE8024BD9D0E7F00A939DF92BD9D20DE92EE0026F5860DDEAFA702395C
:201D2000EE04A602E602BD9D35DE92EE04A603E603BD9D3539BD94C2C40FBB30CB30813F7A
:201D400026028620C13F2602C620813A2602862DC13A2602C62DDEAFA700E7010808DEAF41
:201D6000393637CE01320CBD9D83C628D7ACCE0132DEADCE015ADEAFBD9C50CE0132DF9EF7
:201D80003332393637073667F00B17F00B2C606A6009BB297B2085A26F6BD9DF93206362E
:201DA0000EA600E60191B1264CD1B22648200896B1D6B2A700E7010808A600810D27367F3D
:201DC00000B17F00B2C628A602810D270AA6009BB297B2085A26F0BD9DF93206362 40EA67F
:201DE00000E60191B1260ED1B2260A200896B1D6B2A700E7013233323996B284F0BD94C2AE
:201E00008B308139230 28B0797B196B2840F8B30813923028B0797B239FFFFFFFFFFFFFFCC
:201E2000FFFFFFFFFFFFFFFFFFFFFFFFFFFFFFFFFFFFFFFFFFFFFFFFFFFFFFFFFFFFFFFFC2
:201E4000FFFFFFFFFFFFFFFFFFFFFFFFFFFFFFFFFFFFFFFFFFFFFFFFFFFFFFFFFFFFFFFFA2
:201E6000FFFFFFFFFFFFFFFFFFFFFFFFFFFFFFFFFFFFFFFFFFFFFFFFFFFFFFFFFFFFFFFF82
:201E8000FFFFFFFFFFFFFFFFFFFFFFFFFFFFFFFFFFFFFFFFFFFFFFFFFFFFFFFFFFFFFFFF62
:201EA000FFFFFFFFFFFFFFFFFFFFFFFFFFFFFFFFFFFFFFFFFFFFFFFFFFFFFFFFFFFFFFFF42
:201EC000FFFFFFFFFFFFFFFFFFFFFFFFFFFFFFFFFFFFFFFFFFFFFFFFFFFFFFFFFFFFFFFF22
:201EE000FFFFFFFFFFFFFFFFFFFFFFFFFFFFFFFFFFFFFFFFFFFFFFFFFFFFFFFFFFFFFFFF02
:201F0000FFFFFFFFFFFFFFFFFFFFFFFFFFFFFFFFFFFFFFFFFFFFFFFFFFFFFFFFFFFFFFFFE1
:201F2000FFFFFFFFFFFFFFFFFFFFFFFFFFFFFFFFFFFFFFFFFFFFFFFFFFFFFFFFFFFFFFFFC1
:201F4000FFFFFFFFFFFFFFFFFFFFFFFFFFFFFFFFFFFFFFFFFFFFFFFFFFFFFFFFFFFFFFFFA1
:201F6000FFFFFFFFFFFFFFFFFFFFFFFFFFFFFFFFFFFFFFFFFFFFFFFFFFFFFFFFFFFFFFFF81
:201F8000FFFFFFFFFFFFFFFFFFFFFFFFFFFFFFFFFFFFFFFFFFFFFFFFFFFFFFFFFFFFFFFF61
:201FA000FFFFFFFFFFFFFFFFFFFFFFFFFFFFFFFFFFFFFFFFFFFFFFFFFFFFFFFFFFFFFFFF41
:201FC000FFFFFFFFFFFFFFFFFFFFFFFFFFFFFFFFFFFFFFFFFFFFFFFFFFFFFFFFFFFFFFFF21
:201FE000FFFFFFFFFFFFFFFFFFFFFFFFFFFFFFFFFFFFFFFFFFFFFFFF94CC95FC9603821BD2
:00000001FF
```

EXHIBIT C - DISPLAYS

```
Patient ID    :  12                                    Entered:  10-Sep-84
                                                       Updated:  10-Sep-84
Patient Name :  fred smith                                 By:  Fred Tech

Location      :  rm 1101                                  0    Active Bag(s)

Physician     :  Dr. J

Patient Type :  A                (Adult, Pediatric or Neonate)
Age           :  50
Weight        :   80.0 Kgm   176 lb
Height        :    180  cm    71 in

Diagnosis     :  drg #12
Disease State:  advanced hangnail
Allergies     :  none

Notes         :  note 1
              :  note 2

Billing Code :  12x
```

```
'Home'-back to top & reset, 'Pg Up'-back to top, 'Pg Dn'-done          111
Patient ID   :  12
Patient Name :  fred smith                                Entered: 10-Sep-84
Bag  # 1-1                      1 Active                  Updated: 10-Sep-84
Volume Ordered: 1000 ml Infusion Rate:   200 ml/hr Authorized:  By: Fred Tech

        Amino        100 ml          [Travasol           10.00 % ]   132b
        Dex          100 ml          [Dextrose           50.00 % ]
 132c   Lipid        100 ml          [Travamulsion       10.00 % ]
        Other          0 ml          [- - -               0.00 % ]
                             132a

Sodium Chloride ...........30.0 Meq     Trace Minerals ............ 0.0 Ml
Sodium Acetate ............ 0.0 Meq     Selenium .................. 0.0 Mcg
Sodium Phosphate .......... 0.0 Meq     Zinc ...................... 0.0 Mg
Potassium Chloride ........ 0.0 Meq     Multi-vitamin 12 .......... 1.0 Vial
Potassium Acetate ......... 0.0 Meq     Cimetidine ................ 0.0 Mg
Potassium Phosphate ....... 0.0 Meq     Albumin ................... 0.0 Gm
Calcium Gluconate ......... 0.0 Meq     Heparin ................... 0.0 Units
Magnesium Sulfate ......... 0.0 Meq     Reg.Insulin (/t-vol) ...... 0.0 Units
Iron ...................... 0.0 Mg      Folic Acid ................ 0.0 Mg
```

```
'C'oncentration, 'V'olumes, 'N'utrition, <space>-change component
'Home'-back to top & reset, 'Pg Up'-back to top, 'Pg Dn'-done              112

Patient ID    :  12                                   Entered: 10-Sep-84
Patient Name  :  fred smith                           Updated: 10-Sep-84
Bag  # 1-1                 1 Active                        By: Fred Tech
Volume Ordered: 1000 ml Infusion Rate:   200 ml/hr Authorized:

        Amino         1.00 %             [Travasol           10.00 %]
        Dex           5.00 %             [Dextrose           50.00 %]
        Lipid         1.00 %             [Travamulsion       10.00 %]
        Other         0.00 %             [- - -               0.00 %]

Sodium Chloride ..........30.0 Meq       Trace Minerals ............ 0.0 Ml
Sodium Acetate ........... 0.0 Meq       Selenium .................. 0.0 Mcg
Sodium Phosphate ......... 0.0 Meq       Zinc ...................... 0.0 Mg
Potassium Chloride ....... 0.0 Meq       Multi-vitamin 12 .......... 1.0 Vial
Potassium Acetate ........ 0.0 Meq       Cimetidine ................ 0.0 Mg
Potassium Phosphate ...... 0.0 Meq       Albumin ................... 0.0 Gm
Calcium Gluconate ........ 0.0 Meq       Heparin ................... 0.0 Units
Magnesium Sulfate ........ 0.0 Meq       Reg.Insulin (/t-vol) ...... 0.0 Units
Iron ..................... 0.0 Mg        Folic Acid ................ 0.0 Mg
```

132b

132a

```
'C'oncentration, 'V'olumes, 'N'utrition, <space>-change component
'Home'-back to top & reset, 'Pg Up'-back to top, 'Pg Dn'-done              112
Patient ID    :  12                                   Entered: 10-Sep-84
Patient Name  :  fred smith                           Updated: 10-Sep-84
Bag  # 1-1                 1 Active                        By: Fred Tech
Volume Ordered: 1000 ml Infusion Rate:   200 ml/hr Authorized:

Nitrogen:    1.7 gm  Calories-Protein:  41    NA+   30.0 Meq   CL-     30.0 Meq
                             Dextrose: 171    K+     0.0 Meq   PO4--    0.0 Mmol
                                Lipid:  40    CA++   0.0 Meq   AC-      0.0 Meq
                                Total: 252    MG++   0.0 Meq

Sodium Chloride ..........30.0 Meq       Trace Minerals ............ 0.0 Ml
Sodium Acetate ........... 0.0 Meq       Selenium .................. 0.0 Mcg
Sodium Phosphate ......... 0.0 Meq       Zinc ...................... 0.0 Mg
Potassium Chloride ....... 0.0 Meq       Multi-vitamin 12 .......... 1.0 Vial
Potassium Acetate ........ 0.0 Meq       Cimetidine ................ 0.0 Mg
Potassium Phosphate ...... 0.0 Meq       Albumin ................... 0.0 Gm
Calcium Gluconate ........ 0.0 Meq       Heparin ................... 0.0 Units
Magnesium Sulfate ........ 0.0 Meq       Reg.Insulin (/t-vol) ...... 0.0 Units
Iron ..................... 0.0 Mg        Folic Acid ................ 0.0 Mg
```

133b

```
Compound Time Slot - A- 0   B- 1   C- 0   D- 0   L- 0
 'Home'-back to top & reset, 'Pg Up'-back to top, 'Pg Dn'-done          112

                                          10-Sep-84
                 F O R M U L A
Id   : 12                                Bag #: 1-1
Name: fred smith
Loc  : rm 1101

Travasol              -   1.00 %
Dextrose              -   5.00 %
Travamulsion          -   1.00 %

--Additives--                          -Dose-        -ml-
Sodium Chloride                      30.0 Meq         7.5
Multi-vitamin 12                      1.0 Vial       10.0

--Base Component--          -Code-  -Spg-          -ml-
Travasol             10.00%   21     1.03           100
Dextrose             50.00%   15     1.17           100
Travamulsion         10.00%   32     0.99           100
Sterile Water                 00     1.00           683
                                                  -----
                                Total Volume      1000
                              (Use 1000ml Final Bag)

      CHD Test "Pharmacy"
        Round Lake, Il.
        Parenteral Nutrition Solution
Id   : 12                                 Bag #: 1-1
Name: fred smith
Loc  : rm 1101
advanced hangnail

Travasol              -   1.00 %
Dextrose              -   5.00 %
Travamulsion          -   1.00 %
                                 Total Volume 1000 ml
```

| --Additives-- | -Dose- |
|---|---|
| Sodium Chloride | 30.0 Meq |
| Multi-vitamin 12 | 1.0 Vial |

Prep. By:________ Date:______________ Time:_______

Solution Expires:________________________________

1000 ml at 200 ml/hr will run over 5 hours

LABEL PART 3

EXHIBIT D

10-Sep-84

Bag #: 1-1

Id : 12

Name: fred smith

Loc : rm 1101

Bag Prescription Entered by: Fred Tech

Authorized by: Fisler

Compounded by: Fisler

| | | |
|---|---|---|
| Travasol | - | 1.00 % |
| Dextrose | - | 5.00 % |
| Travamulsion | - | 1.00 % |

Total Volume 1000 ml

| --Additives-- | -Dose- |
|---|---|
| Sodium Chloride | 30.0 Meq |
| Multi-vitamin 12 | 1.0 Vial |

Approximate Electrolyte Totals

| | | | |
|---|---|---|---|
| NA+ | 30.0 Meq | CL- | 30.0 Meq |
| K+ | 0.0 Meq | PO4-- | 0.0 Mmol |
| CA++ | 0.0 Meq | AC- | 0.0 Meq |
| MG++ | 0.0 Meq | | |

Nitrogen Content 1.7 gm

```
Protein  Calories     41
Dextrose Calories    171
Lipid    Calories     40
Total    Calories    252


1000 ml at  200 ml/hr will run over  5 hours
```

EXHIBIT E - SUMMARY LABEL

```
--- Solution & Final Container Summaries ---
    Dextrose              50.00%     100 ml
    Travasol              10.00%     100 ml
    Travamulsion          10.00%     100 ml
    Sterile Water                    683 ml
  0 -  150ml        0 -  500ml       1 - 1000ml
  0 - 2000ml        0 - 3000ml
```

EXHIBIT F - AUDIT TRAIL

```
SYS$SYSDEVICE:[AUTOHOST]10SEP84.LOG;1

09:49 AM --- AUTOMIX PLUS Host version 1.0 Started ---
09:49 AM --- Date 10-Sep-84 ---
09:50 AM Patient 12           created  by Fred Tech
09:51 AM Patient Profile for 12          changed
09:57 AM Patient Bag for 12            Bag 1-1  changed
09:57 AM Patient 12           Bag 1-1  authorized by Fisler
09:58 AM Patient 12           accessed by Fred Tech
09:59 AM Labels for B printed by Fisler
09:59 AM Queue B compounded by Fisler
10:01 AM --- AUTOMIX PLUS Host version 1.0 Started ---
10:01 AM --- Date 10-Sep-84 ---
10:01 AM Pat 12            Bag 1-1  dequeued from B by Fisler
```

```
10:01 AM Manually Generated Compounding for Id 12
         Name - fred smith                          Bag # - 1-1
         Sodium Chloride                   30.0 Meq
         Multi-vitamin 12                   1.0 Vial
         Travasol            10.00%   100
         Dextrose            50.00%   100
         Travamulsion        10.00%   100
         Sterile Water                683
10:01 AM --- End of AUTOMIX PLUS Host Session ---
$
```

COPYRIGHT 1984 BAXTER TRAVENOL LABORATORIES, INC.

We claim:

1. A method of optimizing the compounding of a plurality of mixtures to produce individual doses of mixtures, comprising the steps of:

providing a plurality of sets of parameters of mixtures to be compounded from a selected group of base solutions, one set for each dose, each of said base solutions being contained in separate containers, each container having a discreet amount of a particular base solution;

sorting the sets of parameters in accordance with the particular base solutions included in each set and amount of each base solution included in each set to minimize the needed quantity of containers of base solution to produce said doses; and compounding the mixtures in said sorted order thereby minimizing the needed quantity of containers of base solution to produce said doses.

2. A method as defined in claim 1 including:

specifying parameters in a selected set as volumes to be added to the final mixture.

3. A method as defined in claim 2 including:

specifying parameters in a selected set alternately as a percent of the final mixture volume.

4. A method as defined in claim 3 including:

specifying parameters in a selected set alternately as a nutritional contribution to the final mixture.

5. A method as defined in claim 4 wherein:

the volumes, the percentages of the mixture volume and the nutritional contributions are three forms of a set of base solution parameters for a mixture and an unspecified form of base solution parameters may be determined from a specified form thereof.

6. A method as defined in claim 4 wherein:

changing one form of a set of base solution parameters produces a corresponding change in the alternate forms of said set of parameters.

7. A method as defined in claim 4 including: transmitting volume parameters of base solutions corresponding to an authorized set of parameters from a storage location to a compounding location to form the selected mixture.

8. A method as defined in claim 4 including printing an ordered sequence of labels corresponding to the sorted sequence of parameters in a selected group.

9. A method as defined in claim 8 including:

forming the sorted sets of parameters into a queue having a corresponding sorted order; and forming a print queue for labels having a corresponding sorted order.

10. A method as defined in claim 4 including the steps of:

forming groups of parameters; and compounding each corresponding group of mixtures in a predetermined time internal.

11. A method as defined in claim 10 including forming each group of parameters as a queue.

12. A method as defined in claim 10 including:

providing an authorizing indicia for each group of parameters; and checking each indicia to determine if compounding of said corresponding mixture has been authorized.

13. A method as defined in claim 12 including:

logging selected operations to form an audit trail.

14. A method as defined in claim 4 including;

forming a plurality of queues wherein sets of parameters are stored as members of a selected queue; and performing said sorting step on the members of a selected queue.

15. A method as defined in claim 14 including:

providing an operator settable authorization indicia for each member of a queue; and performing said sorting step on only queue members which have said authorization indicia set to a selected condition.

16. A method as defined in claim 15 including a second sorting step wherein authorized members of a queue are further sorted in accordance with the specified concentrations of corresponding base solutions.

17. A method as defined in claim 2 including:

prestoring standard combinations of base solution parameters for later use;

determining when at least a part of a selected mixture includes a prestored standard combination of parameters; and providing the corresponding prestored combination of parameters as said part of the set of parameters for the corresponding selected mixture.

18. A method as defined in claim 1 including:

authorizing selected sets of parameters for compounding; and providing an indication for each set of authorized parameters and performing said sorting step on only authorized sets of parameters.

19. A system for optimizing the compounding of a plurality of mixtures to produce individual doses of mixtures comprising:

means for storing a plurality of sets of parameters of mixtures to be compounded from a selected group of base solutions, said base solutions being contained in containers, each container having a discreet amount of base solution;

means for sorting said sets of parameters in accordance with the particular base solutions included in each set to minimize the required quantity of containers of base solution to produce said doses; and means for mixing the base solutions in said sorted order thereby minimizing the required quantity of containers of base solution to produce said doses.

20. A system as defined in claim 19 including control means for storing parameters of a selected mixture in the form of a volume to be added to said mixture.

21. A system as defined in claim 20 wherein said control means include means for storing the parameters of a selected mixture alternately as a percent of the final mixture volume.

22. A system as defined in claim 21 wherein said control means include means for storing the parameters of a selected mixture alternately as a nutritional contribution to the final mixture.

23. A system as defined in claim 22 wherein said control means include means for determining unspecified volumes, percentages of the mixture volume or the nutritional contributions from a specified form thereof.

24. A system as defined in claim 23 wherein said control means include means for changing a selected form of a set of parameters and means for making a corresponding change in the alternate forms of said set of parameters.

25. A system as defined in claim 24 including:

means for forming a plurality of queues wherein sets of parameters are stored as members of a selected queue; and means for sorting said members of said selected queue.

26. A system as defined in claim 20 including:

means for prestoring standard combinations of parameters;

means for identifying a said prestored standard combination to be included in a selected set; and means for including said prestored combination parameters in said set.

27. A system as defined in claim 19 including:

means for authorizing selected sets of parameters for compounding;

means for providing an indication for each said authorized set of parameters;

and means for sorting only authorized sets of parameters.

28. A system as defined in claim 27 including:

means for forming groups of sets of parameters of mixtures; and means for compounding each authorized member of a corresponding selected group in a predetermined time internal.

29. A system as defined in claim 28 wherein said means for forming groups include queuing means for forming each group as a queue.

30. A system as defined in claim 29 including means for sorting selected queue members.

31. A system as defined in claim 30 including means for printing an ordered sequence of labels corresponding to the sorted sequence of members in a selected queue.

32. A system as defined in claim 31 including:

audit means for recording selected operations.

33. A system as defined in claim 30 including library means for prestoring a plurality of standard combinations of parameters, means for associating a respective name therewith, means for retrieving a named prestored, standard combination of parameters and for associating said named, prestored combination of parameters with a named queue member.

34. A system as defined in claim 33 including means for modifying queue members.

35. A system as defined in claim 29 including:

means for authorizing selected members of a selected queue; and means for sorting only authorized queue members.

36. A system as defined in claim 35 including further means for sorting in accordance with the specified concentrations of corresponding base solutions.

37. A system as defined in claim 27 including:

means for transmitting volume parameters of base solutions corresponding to an authorized set of parameters from said storage means to said compounding means to form the selected mixture.

38. A system as defined in claim 27 including means for forming a queue of sets of authorized parameters having a corresponding sorted order; and including means for forming a print queue for labels having a corresponding sorted order.

39. A system as defined in claim 38 including:

means for setting an authorizing indicia for each member in a selected queue to a predetermined state; and means for checking each said indicia to determine if said corresponding indicia has been set to said state.

40. A system for compounding a plurality of selected mixtures to produce individual doses of mixture comprising:

means for receiving sets of parameters for a plurality of mixtures to be compounded from a group of base solutions, one set for each dose;

means for storing said sets and for selecting a set of parameters to be compounded;

means for compounding a selected mixture corresponding to a selected set of parameters to produce individual doses; and means for coupling said storing means to said compounding means.

41. A system as defined in claim 40 wherein:

said means for coupling include status means for sensing the status of said compounding means.

42. A system as defined in claim 40 wherein said storing means include:

means for forming said sets as a queue.

43. A system as defined in claim 42 including:

means for controlling the transfer of information from selected queue members in said storage means to said compounding means.

44. A system as defined in claim 43 wherein:

said receiving means includes manually operable means for entering a selected set of parameters in a first form into said queue.

45. A system as defined in claim 44 including:

means for converting said set of parameters from said first form to at least a second form.

46. A system as defined in claim 45 including:

means for converting said first or second forms of a set of parameters to a third form.

47. A system as defined in claim 45 including means for displaying a selected form of a set of parameters for a selected mixture.

48. A system as defined in claim 47 including:

library means for storing standard combinations of parameters for standard mixtures.

49. A system as defined in claim 48 including means for naming a stored combination of parameters in said library.

50. A system as defined in claim 49 wherein:

each said set of named library parameters is a member of a library queue.

51. A system as defined in claim 50 including means for manually entering a name and means for recalling a respective member of said library queue.

52. A system as defined in claim 40 wherein:

said compounding means include manually operable means for entering information into said compounding means.

53. A system as defined in claim 52 wherein:

said compounding means include a communications port for electrical connection to said coupling means.

54. A system as defined in claim 53 wherein said coupling means provide two-way communication between said storage means and said compounding means.

55. A system as defined in claim 54 wherein said manually operable means include means for requesting base solution information from a selected queue member for a mixture to be compounded.

56. A system as defined in claim 55 wherein:

said control means include request sensing means and means for sending base solution information from a said selected queue member to said means for compounding.

57. A system as defined in claim 56 wherein:

said compounding means include manually operable means for requesting base solution information from a selected queue member for immediate compounding.

58. A system as defined in claim 60 wherein:

said control means include means for sending base solution information for an ordered sequence of queue members to said means for compounding in the same order as said sequence of preprinted labels.

59. A system as defined in claim 58 wherein:

said control means include means for recording base solutions previously used by said compounding means, and means for transmitting a solution change command to said compounding means.

60. A system as defined in claim 59 wherein:

said control means include means for detecting a change in base solution to be sent to said compounding means.

61. A system as defined in claim 45 including:

means for authorizing compounding of a selected set of parameters.

62. A system in claim 61 including:

means for sorting authorized parameter sets.

63. A system as defined in claim 51 wherein:

said sorting means include means for sensing previously authorized parameter sets and said sorting means including means for arranging said parameter sets by base solutions used in each set.

64. A system as defined in claim 63 including concentration sensing means for arranging said parameter sets by concentration of base solution.

65. A system as defined in claim 63 including:

means for printing an ordered plurality of labels corresponding to authorized parameter sets.

66. A system in claim 65 wherein:

said means for coupling include means for transferring information for each said authorized parameter set from said storage means to said compounding means.

67. A method for compounding a plurality of selected mixtures to produce individual doses of mixtures comprising:

means for maintaining a plurality of base solutions, each base solution being contained in individual containers having a discreet amount of base solution;

providing a plurality of sets of parameters of mixtures to be compounded from a selected group of base solutions, one set of parameters for each dose to be produced;

storing said sets of parameters at a storing site and selecting a set to be compounded based on the particular base solution and amount required by a set to minimize the quantity of containers of base solution required;

transmitting said selected set of parameters from the storing site to a compounding site; and compounding said selected mixture in response thereto.

68. A method as defined in claim 67 wherein storing includes:

forming a queue with each said parameter set being a member thereof.

69. A method as defined in claim 68 further including:

sensing a selected set of parameters for a mixture entered in a first form; and inserting said entered set of parameters into said queue as a member thereof.

70. A method as defined in claim 69 including:

converting said entered set of parameters from said first form to at least a second form.

71. A method as defined in claim 70 including:

converting said first or second forms of a set of parameters to a third form.

72. A method as defined in claim 70 including displaying a selected form of a set of parameters.

73. A method as defined in claim 70 including:

forming a library of prestored standard combinations of parameters.

74. A method as defined in claim 73 including associating a unique name with each member of said library.

75. A method as defined in claim 74 including:

inserting into a selected queue member a prestored library member.

76. A method as defined in claim 75 including:

modifying parameters of a selected member of said queue.

77. A method as defined in claim 76 including authorizing compounding of a selected queue member.

78. A method as defined in claim 77 including sorting authorized queue members.

79. A method as defined in claim 78 wherein:

authorized queue members are sorted by type of base solution.

80. A method as defined in claim 79 including:

sorting authorized queue members by concentration of base solution.

81. A method as defined in claim 80 including:

transferring base solution information for an authorized queue member from a storing location to a compounding location.

82. A method as defined in claim 81 including:

transferring base solution information for an ordered plurality of queue members in an order corresponding to the order of said printed labels.

83. A method as defined in claim 82 including:

forming a plurality of mixtures of base solutions in the same order as said sequence of preprinted labels.

84. A method as defined in claim 79 including: printing an ordered plurality of labels corresponding to authorized and stored queue members.

85. A method as defined in claim 84 including: recording selected operations to form an audit trail.

86. A method as defined in claim 85 including: printing said recorded audit trail.

87. A method of optimizing the compounding of a plurality of mixtures comprising the steps of:

providing a plurality of sets of parameters of mixtures to be compounded from a group of base solutions in which each base solution is contained in a container having a discreet amount of base solution and each dose to be produced having a set of parameters associated therewith; and sorting the sets of parameters in accordance with the particular base solutions included in each of said sets; and the amount of each particular solution included in each set to minimize the quantity of containers of base solutions necessary to produce said mixtures; and printing a list of the sorted sets of parameters.

88. A method as defined in claim 87 including:

specifying parameters in a selected set as volumes to be added to the final mixture.

89. A method as defined in claim 88 including:

specifying parameters in a selected set alternately as a percent of the final mixture volume.

90. A method as defined in claim 89 including:

specifying parameters in a selected set alternately as a nutritional contribution to the final mixture.

91. A method as defined in claim 90 wherein:

changing one form of a set of base solution parameters produces a corresponding change in the alternate forms of said set of parameters.

92. A method as defined in claim 87 wherein the step of printing comprises printing an ordered list corresponding to the sorted order of the sets of parameters.

93. A system for optimizing the compounding of a plurality of mixtures to produce individual doses comprising:

means for receiving from a user of said system a plurality of sets of parameters for producing said doses using a plurality of base solutions, each base solution being contained in containers having discreet amounts of base solution therein;

means for storing said plurality of sets of parameters of mixtures to be compounded from said group of base solutions;

means for sorting said sets of parameters in accordance with the particular base solutions included in each said set and the amount of each base solution used to minimize the quantity of containers of base solutions needed to produce said doses; and means for printing an ordered list corresponding to the sorted sets of parameters.

94. A system as defined in claim 93 including control means for storing parameters of a each mixture in the form of a volume to be added to said mixture.

95. A system as defined in claim 94 wherein said control means include means for storing the parameters of each mixture alternately as a percent of the final mixture volume.

96. A system as defined in claim 95 wherein said control means include means for storing the parameters of each mixture alternately as a nutritional contribution to the final mixture.

97. A system as defined in claim 96 wherein said control means include means for determining any unspecified volumes, percentages of the mixture volume or the nutritional contributions from a specified form of said sets of parameters thereof.

* * * * *